United States Patent
Franchi et al.

(10) Patent No.: US 11,370,763 B2
(45) Date of Patent: Jun. 28, 2022

(54) COMPOUNDS AND COMPOSITIONS FOR TREATING CONDITIONS ASSOCIATED WITH NLRP ACTIVITY

(71) Applicant: Novartis AG, Basel (CH)

(72) Inventors: Luigi Franchi, Ann Arbor, MI (US); Shomir Ghosh, Brookline, MA (US); Gary Glick, Ann Arbor, MI (US); Jason Katz, Newton, MA (US); Anthony William Opipari, Jr., Dexter, MI (US); William Roush, Jupiter, FL (US); Hans Martin Seidel, Concord, MA (US); Dong-Ming Shen, Edison, NJ (US); Shankar Venkatraman, Lansdale, PA (US); David Guenther Winkler, Arlington, MA (US)

(73) Assignee: NOVARTIS AG, Basel (CH)

( * ) Notice: Subject to any disclaimer, the term of this patent is extended or adjusted under 35 U.S.C. 154(b) by 17 days.

(21) Appl. No.: 16/632,850

(22) PCT Filed: Jul. 23, 2018

(86) PCT No.: PCT/US2018/043330
§ 371 (c)(1),
(2) Date: Jan. 21, 2020

(87) PCT Pub. No.: WO2019/023145
PCT Pub. Date: Jan. 31, 2019

(65) Prior Publication Data
US 2021/0230129 A1    Jul. 29, 2021

Related U.S. Application Data

(60) Provisional application No. 62/573,935, filed on Oct. 18, 2017, provisional application No. 62/536,352, filed on Jul. 24, 2017.

(51) Int. Cl.
| | | |
|---|---|---|
| *C07D 265/30* | (2006.01) | |
| *A61P 1/00* | (2006.01) | |
| *A61P 11/00* | (2006.01) | |
| *A61P 19/08* | (2006.01) | |
| *A61P 35/00* | (2006.01) | |

(Continued)

(52) U.S. Cl.
CPC ............. *C07D 265/30* (2013.01); *A61P 1/00* (2018.01); *A61P 11/00* (2018.01); *A61P 19/08* (2018.01); *A61P 35/00* (2018.01); *C07C 381/10* (2013.01); *C07D 209/26* (2013.01); *C07D 211/78* (2013.01); *C07D 215/06* (2013.01); *C07D 231/12* (2013.01); *C07D 239/26* (2013.01); *C07D 239/36* (2013.01); *C07D 261/08* (2013.01); *C07D 263/46* (2013.01); *C07D 277/36* (2013.01); *C07D 317/50* (2013.01); *C07D 333/34* (2013.01);

(Continued)

(58) Field of Classification Search
CPC .... C07D 265/30; C07D 209/26; C07C 381/10
See application file for complete search history.

(56) References Cited

FOREIGN PATENT DOCUMENTS

| | | |
|---|---|---|
| WO | 2016/131098 A1 | 8/2016 |
| WO | 2017/184604 A1 | 10/2017 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802) (Year: 1995).*

(Continued)

*Primary Examiner* — Marcos L Sznaidman
(74) *Attorney, Agent, or Firm* — Asha K. Nadipuram

(57) ABSTRACT

In one aspect, compounds of Formula AA, or a pharmaceutically acceptable salt thereof, are featured. The variables shown in Formula AA are as defined in the claims. The compounds of formula AA are NLRP3 activity modulators and, as such, can be used in the treatment of metabolic disorders (e.g. Type 2 diabetes, atherosclerosis, obesity or gout), a disease of the central nervous system (e.g. Alzheimer's disease, multiple sclerosis, Amyotrophic Lateral Sclerosis or Parkinson's disease), lung disease (e.g. asthma, COPD or pulmonary idiopathic fibrosis), liver disease (e.g. NASH syndrome, viral hepatitis or cirrhosis), pancreatic disease (e.g. acute pancreatitis or chronic pancreatitis), kidney disease (e.g. acute kidney injury or chronic kidney injury), intestinal disease (e.g. Crohn's disease or Ulcerative Colitis), skin disease (e.g. psoriasis), musculoskeletal disease (e.g. scleroderma), a vessel disorder (e.g. giant cell arteritis), a disorder of the bones (e.g. osteoarthritis, osteoporosis or osteopetrosis disorders), eye disease (e.g. glaucoma or macular degeneration), a disease caused by viral infection (e.g. HIV or AIDS), an autoimmune disease (e.g. Rheumatoid Arthritis, Systemic Lupus Erythematosus or Autoimmune Thyroiditis), cancer or aging.

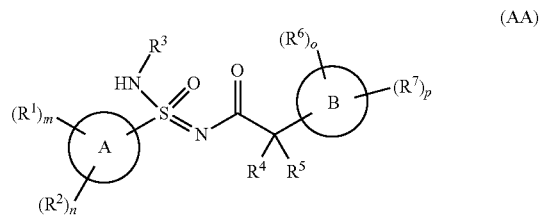

(AA)

13 Claims, 1 Drawing Sheet
Specification includes a Sequence Listing.

(51) Int. Cl.
  *C07C 381/10* (2006.01)
  *C07D 209/26* (2006.01)
  *C07D 211/78* (2006.01)
  *C07D 215/06* (2006.01)
  *C07D 231/12* (2006.01)
  *C07D 239/26* (2006.01)
  *C07D 239/36* (2006.01)
  *C07D 261/08* (2006.01)
  *C07D 263/46* (2006.01)
  *C07D 277/36* (2006.01)
  *C07D 317/50* (2006.01)
  *C07D 333/34* (2006.01)
  *C07D 401/12* (2006.01)
  *C07D 409/12* (2006.01)
  *C07D 417/12* (2006.01)
  *A61K 45/06* (2006.01)

(52) U.S. Cl.
  CPC ......... *C07D 401/12* (2013.01); *C07D 409/12* (2013.01); *C07D 417/12* (2013.01); *A61K 45/06* (2013.01)

(56) References Cited

FOREIGN PATENT DOCUMENTS

WO   2017/184623 A1   10/2017
WO   2017/184624 A1   10/2017

OTHER PUBLICATIONS

Nandi, G. C. et al.: "Direct Synthesis of N-Acyl Sulfonimidamides and N-Sulfonimidoyl Amidines from Sulfonimidoyl Azides", Advanced Synthesis & Catalysis, vol. 360, No. 13, Jul. 4, 2018, pp. 2465-2469.

\* cited by examiner

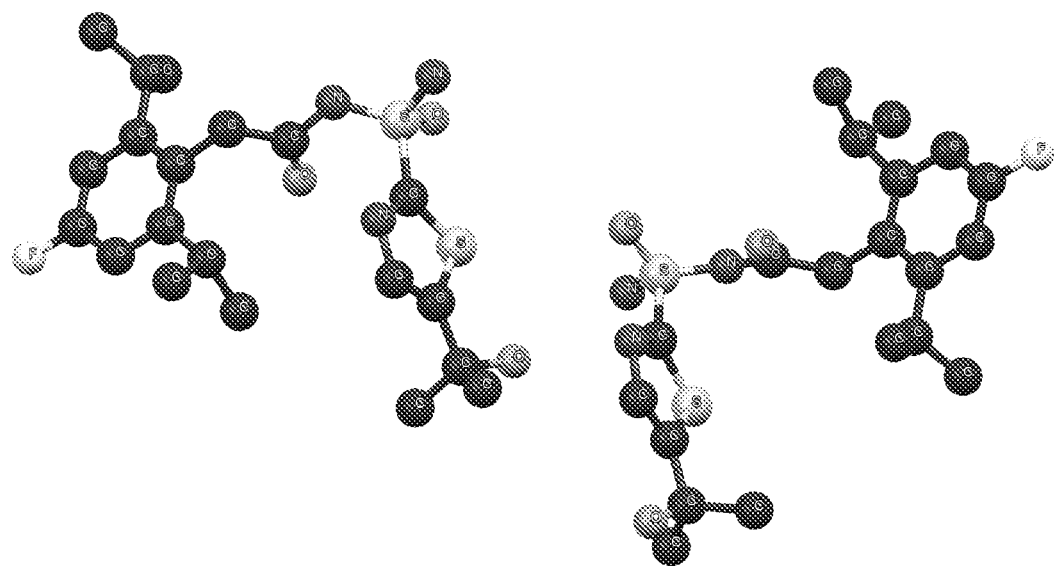

COMPOUNDS AND COMPOSITIONS FOR TREATING CONDITIONS ASSOCIATED WITH NLRP ACTIVITY

PRIORITY CLAIM

This application is a National Phase Entry of International Application No. PCT/US2018/043330, filed on Jul. 23, 2018, which claims the benefit of U.S. Provisional Application No. 62/536,352, filed on Jul. 24, 2017; and U.S. Provisional Application No. 62/573,935, filed on Oct. 18, 2017; which are incorporated herein by reference in their entirety.

TECHNICAL FIELD

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling) contributes to the pathology and/or symptoms and/or progression of the condition, disease or disorder in a subject (e.g., a human). This disclosure also features compositions as well as other methods of using and making the same.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

NLRP3 can form a complex and has been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In light of the above, it would be desirable to provide compounds that modulate (e.g., antagonize) NLRP3.

SUMMARY

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling) is implicated.

In some embodiments, provided herein is a compound of Formula AA

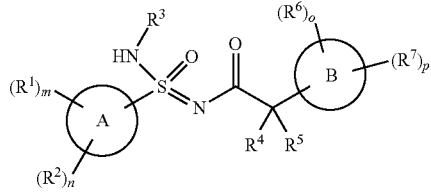

Formula AA or a pharmaceutically acceptable salt thereof, wherein the variables in Formula AA can be as defined anywhere herein.

This disclosure also features compositions as well as other methods of using and making the same.

An "antagonist" of NLRP3 includes compounds that inhibit the ability of NLRP3 to induce the production of IL-1β and/or IL-18 by directly binding to NLRP3, or by inactivating, destabilizing, altering distribution, of NLRP3 or otherwise.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating NLRP3 activity are featured that include contacting NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP3, as well as in vivo methods.

In a further aspect, methods of treatment of a disease in which NLRP3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune disease such as rheumatoid arthritis, systemic Lupus erythematosus, autoimmune thyroiditis; Addison's disease, pernicious anemia, cancer and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP3, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21*st ed.*; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation, 2nd ed.*; Gibson Ed.; CRC Press LLC: Boca Raton, Fla., 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, saturated or unsaturated, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocyclic rings include five-membered, six-membered, and seven-membered heterocyclic rings.

The term "cycloalkyl" as used herein includes a nonaromatic cyclic, bicyclic, fused, or spiro hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring fused or spiro system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "aryl" is intended to mean an aromatic ring radical containing 6 to 10 ring carbons. Examples include phenyl and naphthyl.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N. Examples include furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Examples also include carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "hydroxy" refers to an OH group.

The term "amino" refers to an NH$_2$ group.

The term "oxo" refers to O. By way of example, substitution of a CH$_2$ a group with oxo gives a C=O group.

As used herein, the terms "the ring A" or "A" are used interchangeably to denote

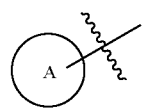

in formula AA, wherein the bond that is shown as being broken by the wavy line ∤ connects A to the S(O)(NHR$^3$)=N moiety of Formula AA.

As used herein, the terms "the ring B" or "B" are used interchangeably to denote

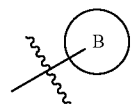

in formula AA wherein the bond that is shown as being broken by the wavy line ∤ connects B to the C(R$^4$R$^5$) group of Formula AA.

As used herein, the term "the substituted ring A" is used to denote

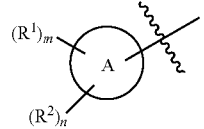

in formula AA, wherein the bond that is shown as being broken by the wavy line ∤ connects A to the S(O)(NHR$^3$)=N moiety of Formula AA.

As used herein, the term "the substituted ring B" is used to denote

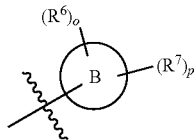

in formula AA, wherein the bond that is shown as being broken by the wavy line ∤ connects B to the C(R⁴R⁵) group of Formula AA.

As used herein, the recitation "S(O₂)", alone or as part of a larger recitation, refers to the group

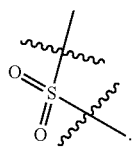

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The scope of the compounds disclosed herein includes tautomeric form of the compounds. Thus, by way of example, a compound that is represented as containing the moiety

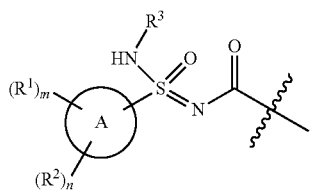

is also intended to include the tautomeric form containing the moiety

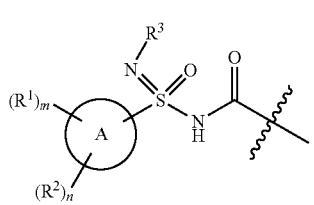

In addition, by way of example, a compound that is represented as containing the moiety

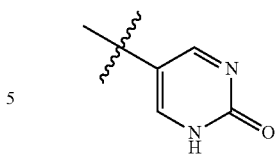

is also intended to include the tautomeric form containing the moiety

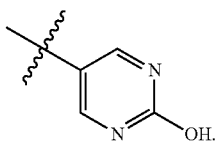

Non-limiting exemplified compounds of the formulae described herein include a stereogenic sulfur atom and optionally one or more stereogenic carbon atoms. This disclosure provides examples of stereoisomer mixtures (e.g., racemic mixture of enantiomers; mixture of diastereomers). This disclosure also describes and exemplifies methods for separating individual components of said stereoisomer mixtures (e.g., resolving the enantiomers of a racemic mixture). In cases of compounds containing only a stereogenic sulfur atom, resolved enantiomers are graphically depicted using one of the two following formats: formulas A/B (hashed and solid wedge three-dimensional representation); and formula C ("flat structures with *-labelled stereogenic sulfur).

Formula A

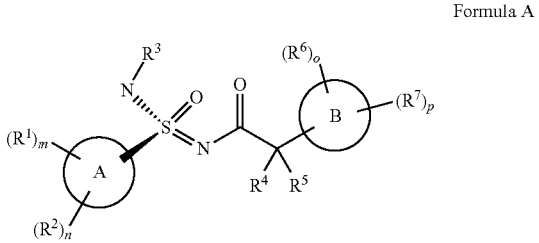

Formula B

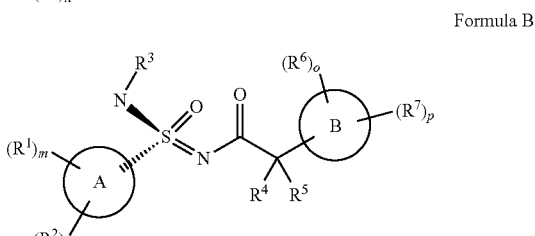

Formula C

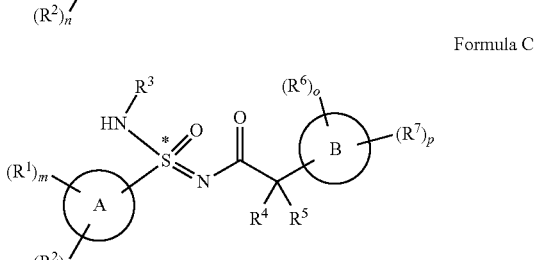

In reaction schemes showing resolution of a racemic mixture, Formulas A/B and C are intended only to convey that the constituent enantiomers were resolved in enantiopure pure form (about 98% ee or greater). The schemes that show resolution products using the formula A/B format are not intended to disclose or imply any correlation between absolute configuration and order of elution. Some of the compounds shown in the tables below are graphically represented using the formula A/B format. However, with the exception of compounds 132a and 132b, the depicted stereochemistry shown for each of the tabulated compounds drawn in the formula A/B format is a tentative assignment and based, by analogy, on the absolute stereochemistry assigned to compounds 132b (see, e.g., FIG. 1).

The details of one or more embodiments of the invention are set forth in the accompanying drawings and the description below. Other features and advantages of the invention will be apparent from the description and drawings, and from the claims.

DESCRIPTION OF DRAWINGS

FIG. 1 depicts ball-and-stick representations of two crystallographically independent molecules of compound 132b in the asymmetrical unit.

DETAILED DESCRIPTION

In some embodiments, provided herein is a compound of Formula AA

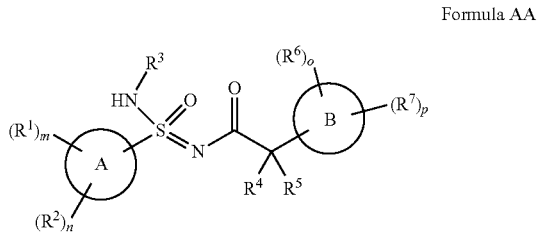

Formula AA wherein
m=0, 1, or 2
n=0, 1, or 2
o=1 or 2
p=0, 1, 2, or 3
wherein
A is a 5-10-membered monocyclic or bicyclic heteroaryl or a $C_6$-$C_{10}$ monocyclic or bicyclic aryl;
B is a 5-10-membered monocyclic or bicyclic heteroaryl or a $C_6$-$C_{10}$ monocyclic or bicyclic aryl;
wherein
at least one $R^6$ is ortho to the bond connecting the B ring to the $C(R^4R^5)$ group of Formula AA; $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, CO-5- to 10-membered heteroaryl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_{10}$ cycloalkyl and 3- to 10-membered heterocycloalkyl, and a $C_2$-$C_6$ alkenyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_7$ cycloalkyl and 3- to 7-membered heterocycloalkyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen and optionally substituted with one or more halo, OH, oxo, or $C_1$-$C_6$ alkyl;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 4- to 8-membered heterocyclic ring containing 1 or 2 heteroatoms independently selected from O, N, $NR^{20}$, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;
each of $R^4$ and $R^5$ is independently selected from hydrogen and $C_1$-$C_6$ alkyl;
$R^{10}$ is $C_1$-$C_6$ alkyl;
each of $R^8$ and $R^9$ at each occurrence is independently selected from hydrogen, $C_1$-$C_6$ alkyl, $NH-(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or
$R^8$ and $R^9$ taken together with the nitrogen they are attached to form a 3- to 7-membered ring optionally containing one or more heteroatoms in addition to the nitrogen they are attached to;
$R^{13}$ is $C_1$-$C_6$ alkyl, $C_6$-$C_{10}$ aryl, or 5- to 10-membered heteroaryl;
each of $R^{11}$ and $R^{12}$ at each occurrence is independently selected from hydrogen and $C_1$-$C_6$ alkyl;
$R^3$ is selected from hydrogen, cyano, hydroxy, $C_1$-$C_6$ alkoxy, $C_1$-$C_6$ alkyl, and

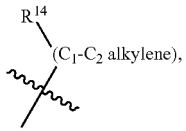

wherein the $C_1$-$C_2$ alkylene group is optionally substituted by oxo;
$R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$
or a pharmaceutically acceptable salt thereof.

In some embodiments, provided herein is a compound of Formula AA

Formula AA

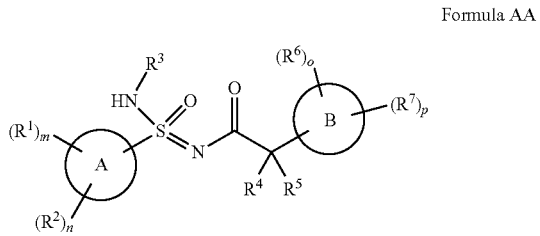

wherein
m=0, 1, or 2
n=0, 1, or 2
o=1 or 2
p=0, 1, 2, or 3 wherein
A is a 5-10-membered monocyclic or bicyclic heteroaryl or a $C_6$-$C_{10}$ monocyclic or bicyclic aryl;
B is a 5-10-membered monocyclic or bicyclic heteroaryl or a $C_6$-$C_{10}$ monocyclic or bicyclic aryl;
wherein
at least one $R^6$ is ortho to the bond connecting the B ring to the $C(R^4R^5)$ group of Formula AA;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO-C_6$-$C_{10}$ aryl, CO-5- to 10-membered heteroaryl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $NHCOOCC_1$-$C_6$ alkyl, $NH-(C=NR^{13})NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_{10}$ cycloalkyl and 3- to 10-membered heterocycloalkyl, and a $C_2$-$C_6$ alkenyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein R⁶ and R⁷ are each optionally substituted with one or more substituents independently selected from hydroxy, halo, CN, oxo, C₁-C₆ alkyl, C₁-C₆ alkoxy, NR⁸R⁹, =NR¹⁰, COOC₁-C₆ alkyl, CONR⁸R⁹, 3- to 7-membered heterocycloalkyl, C₆-C₁₀ aryl, 5- to 10-membered heteroaryl, OCOC₁-C₆ alkyl, OCOC₆-C₁₀ aryl, OCO (5- to 10-membered heteroaryl), OCO (3- to 7-membered heterocycloalkyl), NHCOC₁-C₆ alkyl, NHCOC₆-C₁₀ aryl, NHCO (5- to 10-membered heteroaryl), NHCO (3- to 7-membered heterocycloalkyl), NHCOC₂-C₆ alkynyl, C₆-C₁₀ aryloxy, and S(O₂)C₁-C₆ alkyl; and wherein the C₁-C₆ alkyl or C₁-C₆ alkoxy that R⁶ or R⁷ is substituted with is optionally substituted with one or more hydroxyl, C₆-C₁₀ aryl or NR⁸R⁹, or wherein R⁶ or R⁷ is optionally fused to a five-to-seven-membered carbocyclic ring or heterocyclic ring containing one or two heteroatoms independently selected from oxygen, sulfur and nitrogen and optionally substituted with one or more halo, OH, oxo, or C₁-C₆ alkyl;
  wherein the 3- to 7-membered heterocycloalkyl, C₆-C₁₀ aryl, 5- to 10-membered heteroaryl, NHCOC₆-C₁₀ aryl, NHCO (5- to 10-membered heteroaryl) and NHCO (3- to 7-membered heterocycloalkyl) are optionally substituted with one or more substituents independently selected from halo, C₁-C₆ alkyl, and OC₁-C₆ alkyl;
or at least one pair of R⁶ and R⁷ on adjacent atoms, taken together with the atoms connecting them, independently form at least one C₄-C₈ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C₁-C₆ alkyl, C₁-C₆ alkoxy, NR⁸R⁹, =NR¹⁰, COOC₁-C₆ alkyl, C₆-C₁₀ aryl, and CONR⁸R⁹, wherein the C₁-C₆ alkyl and C₁-C₆ alkoxy are optionally substituted with hydroxy, halo, oxo, NR⁸R⁹, =NR¹⁰, COOC₁-C₆ alkyl, C₆-C₁₀ aryl, and CONR⁸R⁹;
each of R⁴ and R⁵ is independently selected from hydrogen and C₁-C₆ alkyl;
R¹⁰, is C₁-C₆ alkyl;
each of R⁸ and R⁹ at each occurrence is independently selected from hydrogen, C₁-C₆ alkyl, NH—(C=NR¹³)NR¹¹R¹², S(O₂)C₁-C₆ alkyl, S(O₂)NR¹¹R¹², COR¹³, CO₂R¹³ and CONR¹¹R¹²; wherein the C₁-C₆ alkyl is optionally substituted with one or more hydroxy, halo, C₁-C₆ alkoxy, C₆-C₁₀ aryl, 5- to 10-membered heteroaryl, C₃-C₇ cycloalkyl or 3- to 7-membered heterocycloalkyl; or R⁸ and R⁹ taken together with the nitrogen they are attached to form a 3- to 7-membered ring optionally containing one or more heteroatoms in addition to the nitrogen they are attached to;
R¹³ is C₁-C₆ alkyl, C₆-C₁₀ aryl, or 5- to 10-membered heteroaryl;
each of R¹¹ and R¹² at each occurrence is independently selected from hydrogen and C₁-C₆ alkyl;
R³ is selected from hydrogen, cyano, hydroxy, C₁-C₆ alkoxy, C₁-C₆ alkyl, and

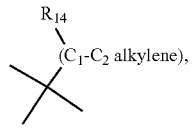

wherein the C₁-C₂ alkylene group is optionally substituted by oxo;

R¹⁴ is hydrogen, C₁-C₆ alkyl, 5-10-membered monocyclic or bicyclic heteroaryl or C₆-C₁₀ monocyclic or bicyclic aryl, wherein each C₁-C₆ alkyl, aryl or heteroaryl is optionally independently substituted with 1, 2, or 3 R⁶
or a pharmaceutically acceptable salt thereof.

In some embodiments, provided herein is a compound of Formula AA

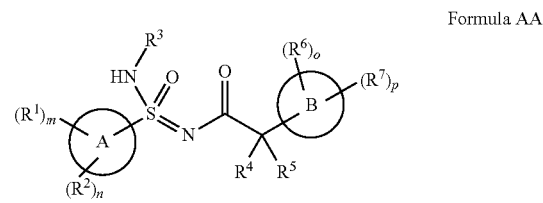

Formula AA wherein
m=0, 1, or 2
n=0, 1, or 2
o=1 or 2
p=0, 1, 2, or 3
wherein
A is a 5-10-membered monocyclic or bicyclic heteroaryl or a C₆-C₁₀ monocyclic or bicyclic aryl;
B is a 5-10-membered monocyclic or bicyclic heteroaryl or a C₆-C₁₀ monocyclic or bicyclic aryl;
wherein
at least one R⁶ is ortho to the bond connecting the B ring to the C(R⁴R⁵) group of Formula AA;
R¹ and R² are each independently selected from C₁-C₆ alkyl, C₁-C₆ haloalkyl, C₁-C₆ alkoxy, C₁-C₆ haloalkoxy, halo, CN, NO₂, COC₁-C₆ alkyl, CO₂C₁-C₆ alkyl, CO—C₆-C₁₀ aryl, CO-5- to 10-membered heteroaryl, CO₂C₃-C₈ cycloalkyl, OCOC₁-C₆ alkyl, OCOC₆-C₁₀ aryl, OCO (5- to 10-membered heteroaryl), OCO (3- to 7-membered heterocycloalkyl), C₆-C₁₀ aryl, 5- to 10-membered heteroaryl, NH₂, NHC₁-C₆ alkyl, N(C₁-C₆ alkyl)₂, NHCOC₁-C₆ alkyl, NHCOC₆-C₁₀ aryl, NHCO (5- to 10-membered heteroaryl), NHCO (3- to 7-membered heterocycloalkyl), NHCOC₂-C₆ alkynyl, NHCOOCC₁-C₆ alkyl, NH—(C=NR¹³)NR¹¹R¹², CONR⁸R⁹, SF₅, SC₁-C₆ alkyl, S(O₂)C₁-C₆ alkyl, S(O)C₁-C₆ alkyl, S(O₂)NR¹¹R¹², C₃-C₁₀ cycloalkyl and 3- to 10-membered heterocycloalkyl, and a C₂-C₆ alkenyl,
wherein the C₁-C₆ alkyl, C₁-C₆ haloalkyl, C₃-C₇ cycloalkyl and 3- to 7-membered heterocycloalkyl is optionally substituted with one or more substituents each independently selected from hydroxy, halo, CN, oxo, C₁-C₆ alkyl, C₁-C₆ alkoxy, NR⁸R⁹, =NR¹⁰, COOC₁-C₆ alkyl, CONR⁸R⁹, 3- to 7-membered heterocycloalkyl, C₆-C₁₀ aryl, 5- to 10-membered heteroaryl, OCOC₁-C₆ alkyl, OCOC₆-C₁₀ aryl, OCO (5- to 10-membered heteroaryl), OCO (3- to 7-membered heterocycloalkyl), NHCOC₁-C₆ alkyl, NHCOC₆-C₁₀ aryl, NHCO (5- to 10-membered heteroaryl), NHCO (3- to 7-membered heterocycloalkyl), and NHCOC₂-C₆ alkynyl;
  wherein each C₁-C₆ alkyl substituent and each C₁-C₆ alkoxy substituent of the R¹ or R² C₃-C₇ cycloalkyl or of the R¹ or R² 3- to 7-membered heterocycloalkyl is further optionally independently substituted with one to three hydroxy, halo, NR⁸R⁹, or oxo;
  wherein the 3- to 7-membered heterocycloalkyl, C₆-C₁₀ aryl, 5- to 10-membered heteroaryl, NHCOC₆-C₁₀ aryl, NHCO (5- to 10-membered heteroaryl) and NHCO (3- to 7-membered heterocycloalkyl) are optionally substituted with one or more substituents independently selected from halo, C₁-C₆ alkyl, and OC₁-C₆ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_7$ cycloalkyl and 3- to 7-membered heterocycloalkyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen and optionally substituted with one or more halo, OH, oxo, or $C_1$-$C_6$ alkyl;
  wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen and $C_1$-$C_6$ alkyl;

$R^{10}$, is $C_1$-$C_6$ alkyl;

each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, and

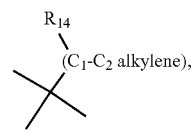

wherein the $C_1$-$C_2$ alkylene group is optionally substituted by oxo;

$R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$ or a pharmaceutically acceptable salt thereof.

In some embodiments, provided herein is a compound of Formula AA

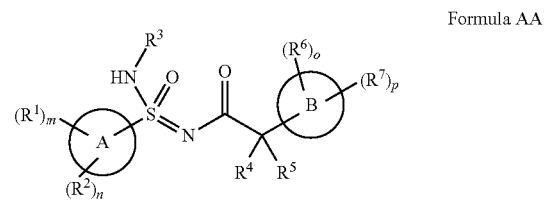

Formula AA wherein
m=0, 1 or 2
n=0, 1 or 2
o=1 or 2
p=0, 1, 2 or 3
wherein
A is a 5-10-membered monocyclic or bicyclic heteroaryl or a $C_6$-$C_{10}$ monocyclic or bicyclic aryl;
B is a 5-10-membered monocyclic or bicyclic heteroaryl or a $C_6$-$C_{10}$ monocyclic or bicyclic aryl;
wherein
at least one $R^6$ is ortho to the bond connecting the B ring to the $C(R^4R^5)$ group of Formula AA;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO$—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $NHCOOCC_1$-$C_6$ alkyl, NH—$(C=NR^{13})NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
  wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl,
  wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;
  wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;
each of $R^4$ and $R^5$ is independently selected from hydrogen and $C_1$-$C_6$ alkyl;
$R^{10}$, is $C_1$-$C_6$ alkyl;
each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or
$R^8$ and $R^9$ taken together with the nitrogen they are attached to form a 3- to 7-membered ring optionally containing one or more heteroatoms in addition to the nitrogen they are attached to;
$R^{13}$ is $C_1$-$C_6$ alkyl, $C_6$-$C_{10}$ aryl, or 5- to 10-membered heteroaryl;
each of $R^{11}$ and $R^{12}$ at each occurrence is independently selected from hydrogen and $C_1$-$C_6$ alkyl; and
$R^3$ is selected from hydrogen, cyano, hydroxy, $C_1$-$C_6$ alkoxy, $C_1$-$C_6$ alkyl, $CO_2C_1$-$C_6$ alkyl, and

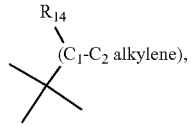

wherein the $C_1$-$C_2$ alkylene group is optionally substituted by oxo;
$R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$
or a pharmaceutically acceptable salt thereof.
  In some embodiments, provided herein is a compound of Formula AA

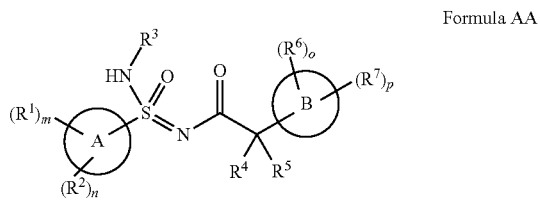

Formula AA wherein
m=0, 1, or 2;
n=0, 1, or 2;
o=1 or 2;
p=0, 1, 2, or 3;
wherein
A is a 5-10-membered heteroaryl or a $C_6$-$C_{10}$ aryl;
B is a 5-10-membered heteroaryl or a $C_6$-$C_{10}$ aryl;

wherein at least one $R^6$ is ortho to the bond connecting the B ring to the $C(R^4R^5)$ group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, CO-5- to 10-membered heteroaryl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $NHCOOCC_1$-$C_6$ alkyl, NH—$(C=NR^{13})NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_{10}$ cycloalkyl, 3- to 10-membered heterocycloalkyl, and $C_2$-$C_6$ alkenyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_7$ cycloalkyl, 3- to 7-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxy, halo, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen and $C_1$-$C_6$ alkyl;

$R^{10}$ is $C_1$-$C_6$ alkyl;

each of $R^8$ and $R^9$ at each occurrence is independently selected from hydrogen, $C_1$-$C_6$ alkyl, $(C=NR^{13})_{NR}^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, and $$\begin{array}{c} R_{14} \\ \diagdown \\ \diagup\!\!\!\!\diagdown (C_1\text{-}C_2 \text{ alkylene}), \\ \diagup \end{array}$$

wherein the $C_1$-$C_2$ alkylene group is optionally substituted by oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;
or a pharmaceutically acceptable salt thereof.

In some embodiments, provided herein is a compound of Formula AA

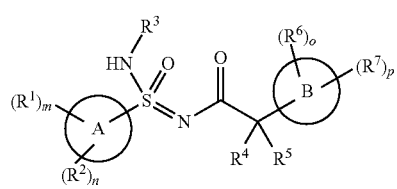

Fromula AA wherein
m=0, 1, or 2;
n=0, 1, or 2;
o=1 or 2;
p=0, 1, 2, or 3;
wherein
A is a 5-10-membered monocyclic or bicyclic heteroaryl or a $C_6$-$C_{10}$ monocyclic or bicyclic aryl;
B is a 5-10-membered monocyclic or bicyclic heteroaryl or a $C_6$-$C_{10}$ monocyclic or bicyclic aryl;
wherein
at least one $R^6$ is ortho to the bond connecting the B ring to the $C(R^4R^5)$ group of Formula AA;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_{10}$ cycloalkyl and 3- to 10-membered heterocycloalkyl, and $C_2$-$C_6$ alkenyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$;
each of $R^4$ and $R^5$ is independently selected from hydrogen and $C_1$-$C_6$ alkyl;
$R^{10}$, is $C_1$-$C_6$ alkyl;
each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or
$R^8$ and $R^9$ taken together with the nitrogen they are attached to form a 3- to 7-membered ring optionally containing one or more heteroatoms in addition to the nitrogen they are attached to;
$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl; and $R^3$ is selected from hydrogen, cyano, hydroxy, $C_1$-$C_6$ alkoxy, $C_1$-$C_6$ alkyl, $CO_2C_1$-$C_6$ alkyl, and

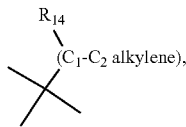

wherein the $C_1$-$C_2$ alkylene group is optionally substituted by oxo;

$R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

or a pharmaceutically acceptable salt thereof.

Provided herein is a compound of Formula AA

Formula AA

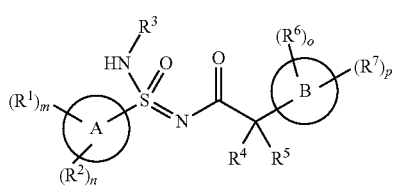

wherein
m=0, 1, or 2;
n=0, 1, or 2;
o=1 or 2;
p=0, 1, 2, or 3;
wherein
A is a 5-10-membered monocyclic or bicyclic heteroaryl or a $C_6$-$C_{10}$ monocyclic or bicyclic aryl;
B is a 5-10-membered monocyclic or bicyclic heteroaryl or a $C_6$-$C_{10}$ monocyclic or bicyclic aryl;
wherein
at least one $R^6$ is ortho to the bond connecting the B ring to the $C(R^4R^5)$ group of Formula AA;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and $C_2$-$C_6$ alkenyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$;

each of $R^4$ and $R^5$ is independently selected from hydrogen and $C_1$-$C_6$ alkyl;

$R^{10}$, is $C_1$-$C_6$ alkyl;

each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl; and $R^3$ is selected from hydrogen, cyano, hydroxy, $C_1$-$C_6$ alkoxy, $C_1$-$C_6$ alkyl, $CO_2C_1$-$C_6$ alkyl, and

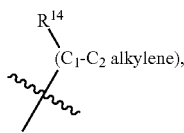

wherein the $C_1$-$C_2$ alkylene group is optionally substituted by oxo;

$R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

or a pharmaceutically acceptable salt thereof.

In some embodiments, provided herein is a compound of Formula AA

Formula AA

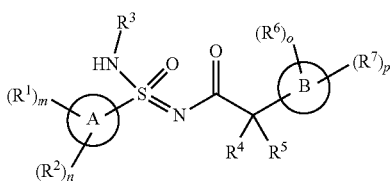

wherein
m=0, 1, or 2;
n=0, 1, or 2;
o=1 or 2;
p=0, 1, 2, or 3;
wherein
A is a 5-10-membered monocyclic or bicyclic heteroaryl or a $C_6$-$C_{10}$ monocyclic or bicyclic aryl;
B is a 5-10-membered monocyclic or bicyclic heteroaryl or a $C_6$-$C_{10}$ monocyclic or bicyclic aryl;

wherein
at least one $R^6$ is ortho to the bond connecting the B ring to the $C(R^4R^5)$ group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, CO-5- to 10-membered heteroaryl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_{10}$ cycloalkyl and 3- to 10-membered heterocycloalkyl, and a $C_2$-$C_6$ alkenyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), NHCOC$_1$-C$_6$ alkyl, NHCOC$_6$-C$_{10}$ aryl, NHCO (5- to 10-membered heteroaryl), NHCO (3- to 7-membered heterocycloalkyl), NHCO$_2$-C$_6$ alkynyl, C$_6$-C$_{10}$ aryloxy, and S(O$_2$)C$_1$-C$_6$ alkyl; and wherein the C$_1$-C$_6$ alkyl or C$_1$-C$_6$ alkoxy that R$^6$ or R$^7$ is substituted with is optionally substituted with one or more hydroxyl, C$_6$-C$_{10}$ aryl or NR$^8$R$^9$, or wherein R$^6$ or R$^7$ is optionally fused to a five-to-seven-membered carbocyclic ring or heterocyclic ring containing one or two heteroatoms independently selected from oxygen, sulfur and nitrogen;
wherein the 3- to 7-membered heterocycloalkyl, C$_6$-C$_{10}$ aryl, 5- to 10-membered heteroaryl, NHCOC$_6$-C$_{10}$ aryl, NHCO (5- to 10-membered heteroaryl) and NHCO (3- to 7-membered heterocycloalkyl) are optionally substituted with one or more substituents independently selected from halo, C$_1$-C$_6$ alkyl, and OC$_1$-C$_6$ alkyl; or at least one pair of R$^6$ and R$^7$ on adjacent atoms, taken together with the atoms connecting them, independently form at least one C$_4$-C$_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$, wherein the C$_1$-C$_6$ alkyl and C$_1$-C$_6$ alkoxy are optionally substituted with hydroxy, halo, oxo, NR$^8$R$^9$, =NR$^{10}$, COOC$_1$-C$_6$ alkyl, C$_6$-C$_{10}$ aryl, and CONR$^8$R$^9$;
each of R$^4$ and R$^5$ is independently selected from hydrogen and C$_1$-C$_6$ alkyl;
R$^{10}$, is C$_1$-C$_6$ alkyl;
each of R$^8$ and R$^9$ at each occurrence is independently selected from hydrogen, C$_1$-C$_6$ alkyl, (C=NR$^{13}$)NR$^{11}$R$^{12}$, S(O$_2$)C$_1$-C$_6$ alkyl, S(O$_2$)NR$^{11}$R$^{12}$, COR$^{13}$, CO$_2$R$^{13}$ and CONR$^{11}$R$^{12}$; wherein the C$_1$-C$_6$ alkyl is optionally substituted with one or more hydroxy, halo, C$_1$-C$_6$ alkoxy, C$_6$-C$_{10}$ aryl, 5- to 10-membered heteroaryl, C$_3$-C$_7$ cycloalkyl or 3- to 7-membered heterocycloalkyl; or
R$^8$ and R$^9$ taken together with the nitrogen they are attached to form a 3- to 7-membered ring optionally containing one or more heteroatoms in addition to the nitrogen they are attached to;
R$^{13}$ is C$_1$-C$_6$ alkyl, C$_6$-C$_{10}$ aryl, or 5- to 10-membered heteroaryl;
each of R$^{11}$ and R$^{12}$ at each occurrence is independently selected from hydrogen and C$_1$-C$_6$ alkyl;
R$^3$ is selected from hydrogen, cyano, hydroxy, C$_1$-C$_6$ alkoxy, C$_1$-C$_6$ alkyl, and

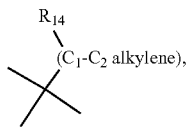

wherein the C$_1$-C$_2$ alkylene group is optionally substituted by oxo;
R$^{14}$ is hydrogen, C$_1$-C$_6$ alkyl, 5-10-membered monocyclic or bicyclic heteroaryl or C$_6$-C$_{10}$ monocyclic or bicyclic aryl, wherein each C$_1$-C$_6$ alkyl, aryl or heteroaryl is optionally independently substituted with 1, 2, or 3 R$^6$
or a pharmaceutically acceptable salt thereof.

In some embodiments the variables shown in the formulae herein are as follows:

The Variables m and n
  In some embodiments m=0, 1, or 2.
  In some embodiments m=0 or 1.
  In some embodiments m=1 or 2.
  In some embodiments m=0 or 2.
  In some embodiments m=0.
  In some embodiments m=1.
  In some embodiments m=2.
  In some embodiments n=0, 1, or 2.
  In some embodiments n=0 or 1.
  In some embodiments n=1 or 2.
  In some embodiments n=0 or 2.
  In some embodiments n=0.
  In some embodiments n=1.
  In some embodiments n=2.
  In some embodiments, m=0 and n=0.
  In some embodiments, m=1 and n=0.
  In some embodiments, m=1 and n=1.

The Ring A and Substitutions on the Ring A
  In some embodiments, A is a 5-10-membered (e.g., 5-6-membered) monocyclic or bicyclic heteroaryl or a C$_6$-C$_{10}$ monocyclic or bicyclic aryl, such as phenyl.
  In some embodiments, A is a 5-10-membered (e.g., 5-6-membered) monocyclic or bicyclic heteroaryl.
  In some embodiments, A is a 5-membered heteroaryl containing a sulfur and optionally one or more nitrogens.
  In some embodiments, A is a C$_6$-C$_{10}$ (e.g., C$_6$) monocyclic or bicyclic aryl.
  In some embodiments, A is phenyl optionally substituted with 1 or 2 R$^1$ and optionally substituted with 1 or 2 R$^2$.
  In some embodiments, A is furanyl optionally substituted with 1 or 2 R$^1$ and optionally substituted with 1 or 2 R$^2$.
  In some embodiments, A is thiophenyl optionally substituted with 1 or 2 R$^1$ and optionally substituted with 1 or 2 R$^2$.
  In some embodiments, A is oxazolyl optionally substituted with 1 or 2 R$^1$ and optionally substituted with 1 or 2 R$^2$.
  In some embodiments, A is thiazolyl optionally substituted with 1 or 2 R$^1$ and optionally substituted with 1 or 2 R$^2$.
  In some embodiments, A is pyrazolyl optionally substituted with 1 or 2 R$^1$ and optionally substituted with 1 or 2 R$^2$.
  In some embodiments, A is pyridyl optionally substituted with 1 or 2 R$^1$ and optionally substituted with 1 or 2 R$^2$.
  In some embodiments, A is phenyl substituted with 1 R$^1$ and optionally substituted with 1 R$^2$.
  In some embodiments, A is furanyl substituted with 1 R$^1$ and optionally substituted with 1 R$^2$.
  In some embodiments, A is thiophenyl substituted with 1 R$^1$ and optionally substituted with 1 R$^2$.
  In some embodiments, A is oxazolyl substituted with 1 R$^1$ and optionally substituted with 1 R$^2$.
  In some embodiments, A is thiazolyl substituted with 1 R$^1$ and optionally substituted with 1 R$^2$.
  In some embodiments, A is pyrazolyl substituted with 1 R$^1$ and optionally substituted with 1 R$^2$.
  In some embodiments, A is pyridyl substituted with 1 R$^1$ and optionally substituted with 1 R$^2$.
  In some embodiments, A is phenyl substituted with 1 R$^1$ and substituted with 1 R$^2$.
  In some embodiments, A is furanyl substituted with 1 R$^1$ and substituted with 1 R$^2$.
  In some embodiments, A is thiophenyl substituted with 1 R$^1$ and substituted with 1 R$^2$.
  In some embodiments, A is oxazolyl substituted with 1 R$^1$ and substituted with 1 R$^2$.

In some embodiments, A is thiazolyl substituted with 1 $R^1$ and substituted with 1 $R^2$.

In some embodiments, A is pyrazolyl substituted with 1 $R^1$ and substituted with 1 $R^2$.

In some embodiments, A is pyridyl substituted with 1 $R^1$ and substituted with 1 $R^2$.

In some embodiments, A is phenyl, m is 0, 1, or 2; and n is 0, 1, or 2.

In some embodiments, A is furanyl, m is 0, 1, or 2, and n is 0, 1, or 2.

In some embodiments, A is thiophenyl, m is 0, 1, or 2, and n is 0, 1, or 2.

In some embodiments, A is oxazolyl, m is 0, 1, or 2, and n is 0, 1, or 2.

In some embodiments, A is thiazolyl, m is 0, 1, or 2, and n is 0, 1, or 2.

In some embodiments, A is pyrazolyl, m is 0, 1, or 2, and n is 0, 1, or 2.

In some embodiments, A is pyridyl m is 0, 1, or 2, and n is 0, 1, or 2.

In some embodiments, A is phenyl, m is 0 or 1, and n is 0 or 1.

In some embodiments, A is furanyl, m is 0 or 1, and n is 0 or 1.

In some embodiments, A is thiophenyl, m is 1 and n is 0 or 1.

In some embodiments, A is oxazolyl, m is 1 and n is 0 or 1.

In some embodiments, A is thiazolyl, m is 1 and n is 0 or 1.

In some embodiments, A is pyrazolyl, m is 1 and n is 0 or 1.

In some embodiments, A is pyridyl, m is 1 and n is 0 or 1.

In some embodiments, A is phenyl, m is 1 and n is 1.

In some embodiments, A is furanyl, m is 1 and n is 1.

In some embodiments, A is thiophenyl, m is 1 and n is 1.

In some embodiments, A is oxazolyl, m is 1 and n is 1.

In some embodiments, A is thiazolyl, m is 1 and n is 1.

In some embodiments, A is pyrazolyl, m is 1 and n is 1.

In some embodiments, A is pyridyl, m is 1 and n is 1.

In some embodiments, A is phenyl, m is 0 or 1, and n is 0, 1, or 2.

In some embodiments, A is furanyl, m is 0 or 1, and n is 0, 1, or 2.

In some embodiments, A is thiophenyl, m is 0 or 1, and n is 0, 1, or 2.

In some embodiments, A is oxazolyl, m is 0 or 1, and n is 0, 1, or 2.

In some embodiments, A is thiazolyl, m is 0 or 1, and n is 0, 1, or 2.

In some embodiments, A is pyrazolyl, m is 0 or 1, and n is 0, 1, or 2.

In some embodiments, A is pyridyl, m is 0 or 1, and n is 0, 1, or 2.

In some embodiments, A is phenyl, m is 0, and n is 0 or 1.

In some embodiments, A is furanyl, m is 0, and n is 0 or 1.

In some embodiments, A is thiophenyl, m is 0, and n is 0 or 1.

In some embodiments, A is oxazolyl, m is 0, and n is 0 or 1.

In some embodiments, A is thiazolyl, m is 0, and n is 0 or 1.

In some embodiments, A is pyrazolyl, m is 0, and n is 0 or 1.

In some embodiments, A is pyridyl, m is 0, and n is 0 or 1.

In some embodiments, A is one of the rings disclosed hereinbelow optionally substituted as disclosed hereinbelow, wherein in each case the bond that is shown as being broken by the wavy line connects A to the $S(O)(NHR^3)$=N moiety of Formula AA.

In some embodiments, the optionally substituted ring A is

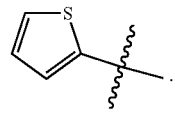 [SMILES: *c1cccs1]

In some embodiments, the optionally substituted ring A is

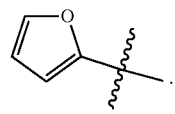

In some embodiments, the optionally substituted ring A is

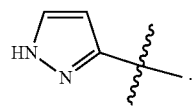

In some embodiments, the optionally substituted ring A is

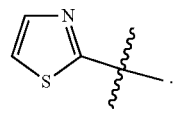 [SMILES: *c1nccs1]

In some embodiments, the optionally substituted ring A is

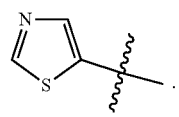 [SMILES: *c1cncs1]

In some embodiments, the optionally substituted ring A is

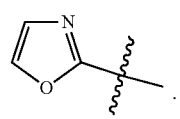

In some embodiments, the optionally substituted ring A is

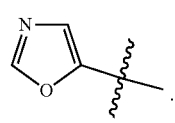 [SMILES: *c1cnco1]

In some embodiments, the optionally substituted ring A is

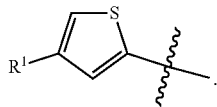

In some embodiments, the optionally substituted ring A is

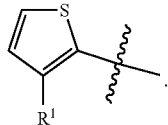

In some embodiments, the optionally substituted ring A is

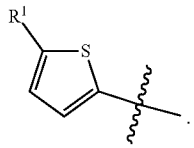

In some embodiments, the optionally substituted ring A is

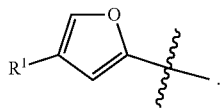

In some embodiments, the optionally substituted ring A is

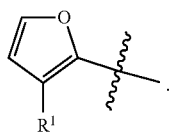

In some embodiments, the optionally substituted ring A is

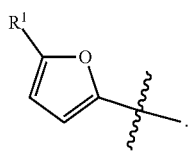

In some embodiments, the optionally substituted ring A is

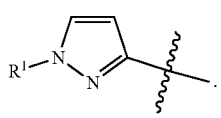

In some embodiments, the optionally substituted ring A is

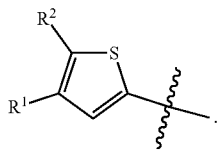

In some embodiments, the optionally substituted ring A is

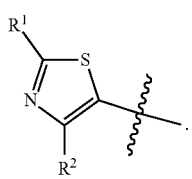

In some embodiments, the optionally substituted ring A is

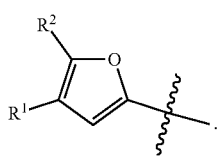

In some embodiments, the optionally substituted ring A is

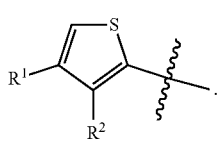

In some embodiments, the optionally substituted ring A is

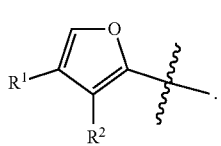

In some embodiments, the optionally substituted ring A is

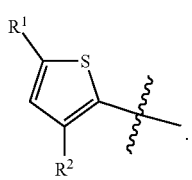

In some embodiments, the optionally substituted ring A is

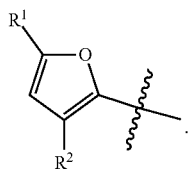

In some embodiments, the optionally substituted ring A is

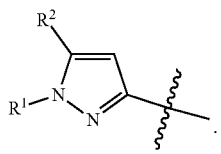

In some embodiments, the optionally substituted ring A is

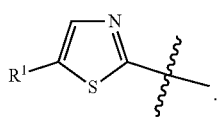

In some embodiments, the optionally substituted ring A is

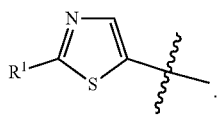

In some embodiments, the optionally substituted ring A is

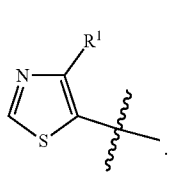

In some embodiments, the optionally substituted ring A is

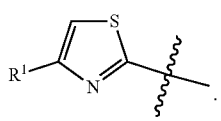

In some embodiments, the optionally substituted ring A is

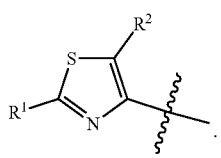

In some embodiments, the optionally substituted ring A is

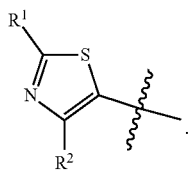

In some embodiments, the optionally substituted ring A is

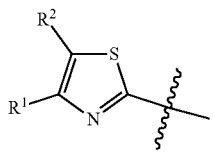

In some embodiments, the optionally substituted ring A is

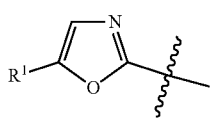

In some embodiments, the optionally substituted ring A is

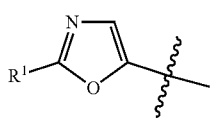

In some embodiments, the optionally substituted ring A is

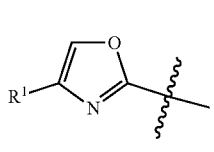

In some embodiments, the optionally substituted ring A is

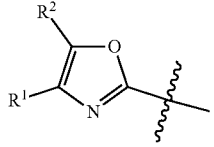

In some embodiments, the optionally substituted ring A is

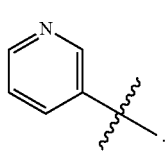

In some embodiments, the optionally substituted ring A is

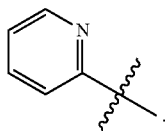 [SMILES: *c1ccccn1]

In some embodiments, the optionally substituted ring A is

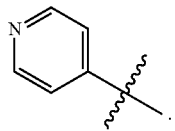 [SMILES: *c1ccncc1]

In some embodiments, the optionally substituted ring A is

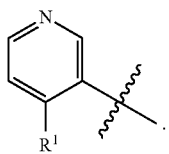

In some embodiments, the optionally substituted ring A is

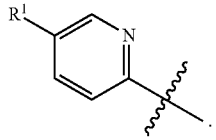

In some embodiments, the optionally substituted ring A is

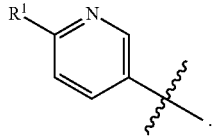

In some embodiments, the optionally substituted ring A is

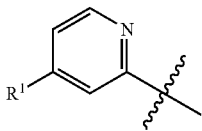

In some embodiments, the optionally substituted ring A is

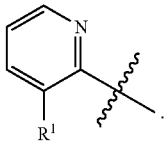

In some embodiments, the optionally substituted ring A is

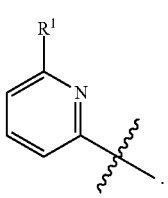

In some embodiments, the optionally substituted ring A is

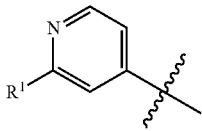

In some embodiments, the optionally substituted ring A is

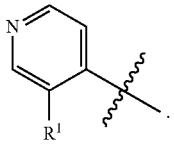

In some embodiments, the optionally substituted ring A is

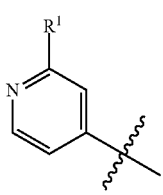

In some embodiments, the optionally substituted ring A is

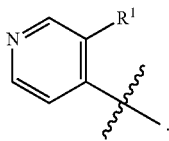

In some embodiments, the optionally substituted ring A is

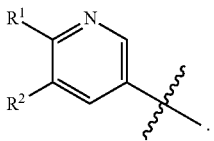

In some embodiments, the optionally substituted ring A is

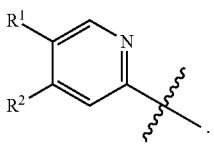

In some embodiments, the optionally substituted ring A is

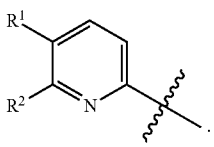

In some embodiments, the optionally substituted ring A is

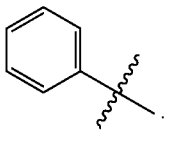

In some embodiments, the optionally substituted ring A is

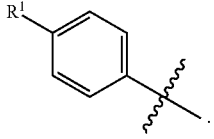

In some embodiments, the optionally substituted ring A is

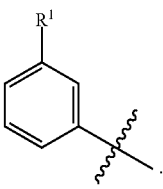

In some embodiments, the optionally substituted ring A is

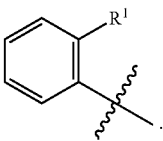

In some embodiments, the optionally substituted ring A is

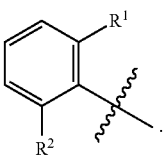

In some embodiments, the optionally substituted ring A is

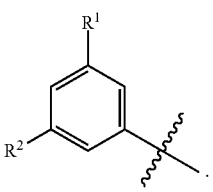

In some embodiments, the optionally substituted ring A is

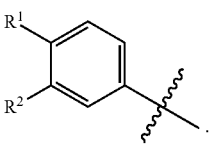

In some embodiments, the optionally substituted ring A is

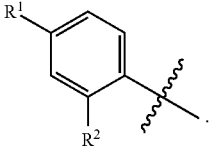

In some embodiments, the optionally substituted ring A is

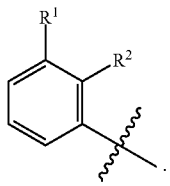

In some embodiments, the optionally substituted ring A is

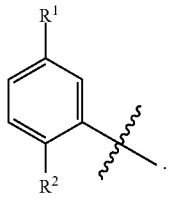

In some embodiments, the optionally substituted ring A is

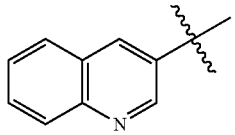

In some embodiments, the optionally substituted ring A is

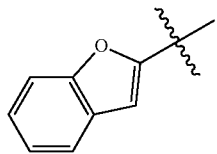

In some embodiments, the optionally substituted ring A is

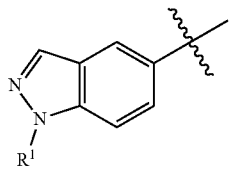

The Groups $R^1$ and $R^2$

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $SC_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is unsubstituted;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are unsubstituted;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl are each unsubstituted;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, $S(O)C_1$-$C_6$ alkyl, 5- to 10-membered heteroaryl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, each of $R^1$ and $R^2$ is independently selected from the group consisting of $C_1$-$C_6$ alkyl optionally substituted with one or more hydroxy, halo, oxo, $C_1$-$C_6$ alkoxy, or $NR^8R^9$; $C_3$-$C_7$ cycloalkyl optionally substituted with one or more hydroxy, halo, oxo, $C_1$-$C_6$ alkoxy, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; $S(O_2)CH_3$, and $S(O_2)NR^{11}R^{12}$.

In some embodiments, $R^2$ is selected from the group consisting of fluoro, chloro, cyano, methyl; methoxy; ethoxy; isopropyl; 1-hydroxy-2-methylpropan-2-yl; 2-hydroxy-2-propyl; hydroxymethyl; 1-hydroxyethyl; 2-hydroxyethyl; 1-hydroxy-2-propyl; 1-hydroxy-1-cyclopropyl; $COCH_3$; COPh; 2-methoxy-2-propyl; (dimethylamino)methyl; $S(O_2)CH_3$, and $S(O_2)NR^{11}R^{12}$.

In some embodiments, m=1; n=0; and
$R^1$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl.

In some embodiments, m=1; n=0; and,
$R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=0; and,
$R^1$ is selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, CO—$C_6$-$C_{10}$ aryl, CO-5- to 10-membered heteroaryl, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl.

In some embodiments, m=1; n=1; and,
$R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and
$R^1$ and $R^2$ are on adjacent atoms, and taken together with the atoms connecting them, form a $C_4$-$C_8$ carbocyclic ring or a 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and
$R^1$ and $R^2$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and
$R^1$ and $R^2$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and
$R^1$ and $R^2$ are on adjacent atoms, and taken together with the atoms connecting them, form a $C_5$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and
$R^1$ and $R^2$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is unsubstituted.

In some embodiments, m=1; n=1; and
$R^1$ and $R^2$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is unsubstituted.

Particular Embodiments Wherein m=1 and n=0:

In some embodiments, $R^1$ is $C_1$-$C_6$ alkyl optionally substituted with one or more hydroxy.

In some embodiments, $R^1$ is 1-hydroxy-2-methylpropan-2-yl.

In some embodiments, $R^1$ is $C_1$-$C_6$ alkyl.
In some embodiments, $R^1$ is methyl.
In some embodiments, $R^1$ is isopropyl.
In some embodiments, $R^1$ is $C_1$-$C_6$ alkyl substituted with hydroxy at the carbon directly connected to ring A.
In some embodiments, $R^1$ is 2-hydroxy-2-propyl.
In some embodiments, $R^1$ is hydroxymethyl.
In some embodiments, $R^1$ is 1-hydroxyethyl.
In some embodiments, $R^1$ is 2-hydroxyethyl.
In some embodiments, $R^1$ is 1-hydroxy-2-propyl.

In some embodiments, $R^1$ is $C_3$-$C_7$ cycloalkyl optionally substituted with one or more hydroxy.
In some embodiments, $R^1$ is $C_3$-$C_7$ cycloalkyl.
In some embodiments, $R^1$ is $C_3$-$C_7$ cycloalkyl substituted with hydroxy at the carbon directly connected to ring A.
In some embodiments, $R^1$ is 1-hydroxy-1-cyclopropyl.
In some embodiments, $R^1$ is 1-hydroxy-1-cyclobutyl.
In some embodiments, $R^1$ is 1-hydroxy-1-cyclopentyl.
In some embodiments, $R^1$ is 1-hydroxy-1-cyclohexyl.
In some embodiments, $R^1$ is 3- to 7-membered heterocycloalkyl optionally substituted with one or more hydroxy.
In some embodiments, $R^1$ is 3- to 7-membered heterocycloalkyl.
In some embodiments, $R^1$ is morpholinyl (e.g., 4-morpholinyl).
In some embodiments, $R^1$ is 1,3-dioxolan-2-yl.
In some embodiments, $R^1$ is 3- to 7-membered heterocycloalkyl substituted with hydroxy at the carbon directly connected to ring A.
In some embodiments, $R^1$ is $C_1$-$C_6$ alkyl optionally substituted with one or more oxo.
In some embodiments, $R^1$ is $COCH_3$.
In some embodiments, $R^1$ is $COCH_2CH_3$.
In some embodiments, $R^1$ is $C_3$-$C_7$ cycloalkyl optionally substituted with one or more oxo.
In some embodiments, $R^1$ is 3- to 7-membered heterocycloalkyl optionally substituted with one or more oxo.
In some embodiments, $R^1$ is $C_1$-$C_6$ alkyl optionally substituted with one or more $C_1$-$C_6$ alkoxy.
In some embodiments, $R^1$ is 2-methoxy-2-propyl.
In some embodiments, $R^1$ is $C_3$-$C_7$ cycloalkyl optionally substituted with one or more $C_1$-$C_6$ alkoxy.
In some embodiments, $R^1$ is 3- to 7-membered heterocycloalkyl optionally substituted with one or more $C_1$-$C_6$ alkoxy.
In some embodiments, $R^1$ is $C_1$-$C_6$ alkyl optionally substituted with one or more $NR^8R^9$.
In some embodiments, $R^1$ is (dimethylamino)methyl.
In some embodiments, $R^1$ is 2-(dimethylamino)prop-2-yl.
In some embodiments, $R^1$ is $C_3$-$C_7$ cycloalkyl optionally substituted with one or more $NR^8R^9$.
In some embodiments, $R^1$ is 3- to 7-membered heterocycloalkyl optionally substituted with one or more $NR^8R^9$.
In some embodiments, $R^1$ is $C_1$-$C_6$ alkyl optionally substituted with one or more hydroxy and one or more oxo.
In some embodiments, $R^1$ is $C(Me)_2C(O)OH$.
In some embodiments, $R^1$ is $C_1$-$C_6$ haloalkyl optionally substituted with one or more hydroxy.
In some embodiments, $R^1$ is $C_1$-$C_6$ alkoxy.
In some embodiments, $R^1$ is $C_1$-$C_6$ haloalkoxy.
In some embodiments, $R^1$ is halo.
In some embodiments, $R^1$ is fluoro.
In some embodiments, $R^1$ is chloro.
In some embodiments, $R^1$ is CN.
In some embodiments, $R^1$ is $NO_2$.
In some embodiments, $R^1$ is $COC_1$-$C_6$ alkyl.
In some embodiments, $R^1$ is $CO$—$C_6$-$C_{10}$ aryl.
In some embodiments, $R^1$ is CO-5- to 10-membered heteroaryl.
In some embodiments, $R^1$ is $CO_2C_1$-$C_6$ alkyl.
In some embodiments, $R^1$ is $CO_2C_3$-$C_8$ cycloalkyl.
In some embodiments, $R^1$ is $OCOC_1$-$C_6$ alkyl.
In some embodiments, $R^1$ is $OCOC_6$-$C_{10}$ aryl.
In some embodiments, $R^1$ is OCO (5- to 10-membered heteroaryl).
In some embodiments, $R^1$ is OCO (3- to 7-membered heterocycloalkyl).

In some embodiments, $R^1$ is $C_6$-$C_{10}$ aryl.
In some embodiments, $R^1$ is phenyl.
In some embodiments, $R^1$ is 5- to 10-membered heteroaryl.
In some embodiments, $R^1$ is pyridyl (e.g., 4-pyridyl).
In some embodiments, $R^1$ is pyrazolyl (e.g., 1-pyrazolyl).
In some embodiments, $R^1$ is $NH_2$.
In some embodiments, $R^1$ is $NHC_1$-$C_6$ alkyl.
In some embodiments, $R^1$ is $N(C_1$-$C_6$ alkyl$)_2$.
In some embodiments, $R^1$ is $CONR^8R^9$.
In some embodiments, $R^1$ is $SF_5$.
In some embodiments, $R^1$ is $SC_1$-$C_6$ alkyl,
In some embodiments, $R^1$ is $S(O_2)C_1$-$C_6$ alkyl.
In some embodiments, $R^1$ is $S(O_2)CH_3$.
In some embodiments, $R^1$ is $S(O_2)NR^{11}R^{12}$.
In some embodiments, $R^1$ is $S(O_2)N(CH_3)_2$.
In some embodiments, $R^1$ is $S(O)C_1$-$C_6$ alkyl.
In some embodiments, $R^1$ is $S(O)CH_3$.
In some embodiments, $R^1$ is attached to a carbon of an aryl ring A.
In some embodiments, $R^1$ is attached to a carbon of a heteroaryl ring A.
In some embodiments, $R^1$ is attached to a nitrogen of a heteroaryl ring A.
Particular embodiments wherein m=1 and n=1:
In some embodiments, $R^1$ is $C_1$-$C_6$ alkyl optionally substituted with one or more hydroxy, and $R^2$ is $C_1$-$C_6$ alkyl optionally substituted with one or more hydroxy.
In some embodiments, $R^1$ is 1-hydroxy-2-methylpropan-2-yl, and $R^2$ is methyl.
In some embodiments, $R^1$ is 2-hydroxy-2-propyl and $R^2$ is methyl.
In some embodiments, $R^1$ is 2-hydroxy-2-propyl and $R^2$ is isopropyl.
In some embodiments, $R^1$ is 2-hydroxy-2-propyl and $R^2$ is 2-hydroxy-2-propyl.
In some embodiments, $R^1$ is 2-hydroxy-2-propyl and $R^2$ is 1-hydroxyethyl.
In some embodiments, $R^1$ is hydroxymethyl and $R^2$ is methyl.
In some embodiments, $R^1$ is 1-hydroxyethyl and $R^2$ is methyl.
In some embodiments, $R^1$ is 2-hydroxyethyl and $R^2$ is methyl.
In some embodiments, $R^1$ is 1-hydroxy-2-propyl and $R^2$ is methyl.
In some embodiments, $R^1$ is $C_1$-$C_6$ alkyl optionally substituted with one or more hydroxy, and $R^2$ is $C_6$-$C_{10}$ aryl.
In some embodiments, $R^1$ is 2-hydroxy-2-propyl and $R^2$ is phenyl.
In some embodiments, $R^1$ is $C_1$-$C_6$ alkyl optionally substituted with one or more hydroxy, and $R^2$ is 5- to 10-membered heteroaryl.
In some embodiments, $R^1$ is 2-hydroxy-2-propyl and $R^2$ is pyridyl.
In some embodiments, $R^1$ is 2-hydroxy-2-propyl and $R^2$ is pyrazolyl.
In some embodiments, $R^1$ is $C_1$-$C_6$ alkyl optionally substituted with one or more hydroxy, and $R^2$ is $SF_5$.
In some embodiments, $R^1$ is $C_1$-$C_6$ alkyl optionally substituted with one or more hydroxy, and $R^2$ is $SC_1$-$C_6$ alkyl.
In some embodiments, $R^1$ is $C_1$-$C_6$ alkyl optionally substituted with one or more hydroxy, and $R^2$ is $S(O_2)C_1$-$C_6$ alkyl.
In some embodiments, $R^1$ is $C_1$-$C_6$ alkyl optionally substituted with one or more hydroxy, and $R^2$ is $S(O_2)CH_3$.

In some embodiments, $R^1$ is $C_1$-$C_6$ alkyl optionally substituted with one or more hydroxy, and $R^2$ is halo.
In some embodiments, $R^1$ is 2-hydroxy-2-propyl and $R^2$ is chloro.
In some embodiments, $R^1$ is 2-hydroxy-2-propyl and $R^2$ is fluoro.
In some embodiments, $R^1$ is $C_3$-$C_7$ cycloalkyl optionally substituted with one or more hydroxy, and $R^2$ is $C_1$-$C_6$ alkyl.
In some embodiments, $R^1$ is 1-hydroxy-1-cyclopropyl, and $R^2$ is methyl.
In some embodiments, $R^1$ is 1-hydroxy-1-cyclobutyl, and $R^2$ is methyl.
In some embodiments, $R^1$ is 1-hydroxy-1-cyclopentyl, and $R^2$ is methyl.
In some embodiments, $R^1$ is 1-hydroxy-1-cyclohexyl, and $R^2$ is methyl.
In some embodiments, $R^1$ is 3- to 7-membered heterocycloalkyl optionally substituted with one or more hydroxy, and $R^2$ is $C_1$-$C_6$ alkyl.
In some embodiments, $R^1$ is morpholinyl, and $R^2$ is methyl.
In some embodiments, $R^1$ is 1,3-dioxolan-2-yl, and $R^2$ is methyl.
In some embodiments, $R^1$ is 3- to 7-membered heterocycloalkyl optionally substituted with one or more hydroxy, and $R^2$ is halo.
In some embodiments, $R^1$ is 1,3-dioxolan-2-yl, and $R^2$ is fluoro.
In some embodiments, $R^1$ is 1,3-dioxolan-2-yl, and $R^2$ is chloro.
In some embodiments, $R^1$ is $C_1$-$C_6$ alkyl optionally substituted with one or more oxo, and $R^2$ is methyl.
In some embodiments, $R^1$ is $COCH_3$, and $R^2$ is methyl.
In some embodiments, $R^1$ is $C_1$-$C_6$ alkyl optionally substituted with one or more $C_1$-$C_6$ alkoxy, and $R^2$ is $C_1$-$C_6$ alkyl.
In some embodiments, $R^1$ is 2-methoxy-2-propyl, and $R^2$ is methyl.
In some embodiments, $R^1$ is $C_1$-$C_6$ alkyl optionally substituted with one or more $NR^8R^9$, and $R^2$ is $C_1$-$C_6$ alkyl.
In some embodiments, $R^1$ is (dimethylamino)methyl, and $R^2$ is methyl.
In some embodiments, $R^1$ is $C_1$-$C_6$ alkyl optionally substituted with one or more $NR^8R^9$, and $R^2$ is halo.
In some embodiments, $R^1$ is (dimethylamino)methyl, and $R^2$ is fluoro.
In some embodiments, $R^2$ is 1-hydroxy-2-methylpropan-2-yl, and $R^1$ is methyl.
In some embodiments, $R^2$ is 2-hydroxy-2-propyl and $R^1$ is methyl.
In some embodiments, $R^2$ is 2-hydroxy-2-propyl and $R^1$ is isopropyl.
In some embodiments, $R^2$ is 2-hydroxy-2-propyl and $R^1$ is 1-hydroxyethyl.
In some embodiments, $R^2$ is hydroxymethyl and $R^1$ is methyl.
In some embodiments, $R^2$ is 1-hydroxyethyl and $R^1$ is methyl.
In some embodiments, $R^2$ is 2-hydroxyethyl and $R^1$ is methyl.
In some embodiments, $R^2$ is 1-hydroxy-2-propyl and $R^1$ is methyl.
In some embodiments, $R^2$ is $C_1$-$C_6$ alkyl optionally substituted with one or more hydroxy, and $R^1$ is $C_6$-$C_{10}$ aryl.
In some embodiments, $R^2$ is 2-hydroxy-2-propyl and $R^7$ is phenyl.

In some embodiments, $R^2$ is $C_1$-$C_6$ alkyl optionally substituted with one or more hydroxy, and $R^1$ is 5- to 10-membered heteroaryl.

In some embodiments, $R^2$ is 2-hydroxy-2-propyl and $R^1$ is pyridyl.

In some embodiments, $R^2$ is 2-hydroxy-2-propyl and $R^1$ is pyrazolyl.

In some embodiments, $R^2$ is $C_1$-$C_6$ alkyl optionally substituted with one or more hydroxy, and $R^1$ is $SF_5$.

In some embodiments, $R^2$ is $C_1$-$C_6$ alkyl optionally substituted with one or more hydroxy, and $R^1$ is $SC_1$-$C_6$ alkyl.

In some embodiments, $R^2$ is $C_1$-$C_6$ alkyl optionally substituted with one or more hydroxy, and $R^1$ is $S(O_2)C_1$-$C_6$ alkyl.

In some embodiments, $R^2$ is $C_1$-$C_6$ alkyl optionally substituted with one or more hydroxy, and $R^1$ is $S(O_2)CH_3$.

In some embodiments, $R^2$ is $C_1$-$C_6$ alkyl optionally substituted with one or more hydroxy, and $R^1$ is halo.

In some embodiments, $R^2$ is 2-hydroxy-2-propyl and $R^1$ is chloro.

In some embodiments, $R^2$ is 2-hydroxy-2-propyl and $R^1$ is fluoro.

In some embodiments, $R^2$ is $C_3$-$C_7$ cycloalkyl optionally substituted with one or more hydroxy, and $R^1$ is $C_1$-$C_6$ alkyl.

In some embodiments, $R^2$ is 1-hydroxy-1-cyclopropyl, and $R^1$ is methyl.

In some embodiments, $R^2$ is 1-hydroxy-1-cyclobutyl, and $R^1$ is methyl.

In some embodiments, $R^2$ is 1-hydroxy-1-cyclopentyl, and $R^1$ is methyl.

In some embodiments, $R^2$ is 1-hydroxy-1-cyclohexyl, and $R^1$ is methyl.

In some embodiments, $R^2$ is 3- to 7-membered heterocycloalkyl optionally substituted with one or more hydroxy, and $R^1$ is $C_1$-$C_6$ alkyl.

In some embodiments, $R^2$ is morpholinyl, and $R^1$ is methyl.

In some embodiments, $R^2$ is 1,3-dioxolan-2-yl, and $R^1$ is methyl.

In some embodiments, $R^2$ is 3- to 7-membered heterocycloalkyl optionally substituted with one or more hydroxy, and $R^1$ is halo.

In some embodiments, $R^2$ is 1,3-dioxolan-2-yl, and $R^1$ is fluoro.

In some embodiments, $R^2$ is 1,3-dioxolan-2-yl, and $R^1$ is chloro.

In some embodiments, $R^2$ is $C_1$-$C_6$ alkyl optionally substituted with one or more oxo, and $R^1$ is methyl.

In some embodiments, $R^2$ is $COCH_3$, and $R^1$ is methyl.

In some embodiments, $R^2$ is $C_1$-$C_6$ alkyl optionally substituted with one or more $C_1$-$C_6$ alkoxy, and $R^1$ is $C_1$-$C_6$ alkyl.

In some embodiments, $R^2$ is 2-methoxy-2-propyl, and $R^1$ is methyl.

In some embodiments, $R^2$ is $C_1$-$C_6$ alkyl optionally substituted with one or more $NR^8R^9$, and $R^1$ is $C_1$-$C_6$ alkyl.

In some embodiments, $R^2$ is (dimethylamino)methyl, and $R^1$ is methyl.

In some embodiments, $R^2$ is $C_1$-$C_6$ alkyl optionally substituted with one or more $NR^8R^9$, and $R^1$ is halo.

In some embodiments, $R^2$ is (dimethylamino)methyl, and $R^1$ is fluoro.

In some embodiments, $R^1$ and $R^2$ are each attached to a carbon of an aryl ring A.

In some embodiments, $R^1$ and $R^2$ are each attached to a carbon of a heteroaryl ring A.

In some embodiments, $R^1$ is attached to a carbon and $R^2$ is attached to a nitrogen of a heteroaryl ring A.

In some embodiments, $R^2$ is attached to a carbon and $R^1$ is attached to a nitrogen of a heteroaryl ring A.

In some embodiments, $R^1$ and $R^2$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_5$ aliphatic carbocyclic ring.

In some embodiments, $R^1$ and $R^2$ are on adjacent atoms, and taken together with the atoms connecting them, form a $C_5$ saturated carbocyclic ring.

In some embodiments, $R^1$ and $R^2$ are on adjacent atoms, and taken together with the atoms connecting them, form a $C_6$ aromatic carbocyclic ring.

In some embodiments, $R^1$ and $R^2$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_6$ aliphatic carbocyclic ring.

In some embodiments, $R^1$ and $R^2$ are on adjacent atoms, and taken together with the atoms connecting them, form a $C_6$ saturated carbocyclic ring.

In some embodiments, $R^1$ and $R^2$ are on adjacent atoms, and taken together with the atoms connecting them, form a $C_6$ aromatic carbocyclic ring.

In some embodiments, $R^1$ and $R^2$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 5-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 5-membered heteroaromatic ring containing 1 or 2 heteroatoms independently selected from O, N, and S.

In some embodiments, $R^1$ and $R^2$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 6-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 6-membered heteroaromatic ring containing 1 or 2 heteroatoms independently selected from O, N, and S.

In some embodiments, $R^1$ and $R^2$ are different.

In some embodiments, $R^1$ and $R^2$ are different, and $R^2$ comprises a carbonyl group.

In some embodiments, $R^1$ and $R^2$ are different, and $R^2$ comprises 1 or 2 (e.g., 1) nitrogen atoms.

In some embodiments, $R^1$ and $R^2$ are different, and $R^2$ comprises 1 or 2 (e.g., 1) oxygen atoms.

In some embodiments, $R^1$ and $R^2$ are different, and $R^2$ comprises a sulfur atom.

In some embodiments, $R^2$ and $R^1$ are different, and $R^2$ comprises a carbonyl group.

In some embodiments, $R^2$ and $R^1$ are different, and $R^2$ comprises 1 or 2 (e.g., 1) nitrogen atoms.

In some embodiments, $R^2$ and $R^1$ are different, and $R^2$ comprises 1 or 2 (e.g., 1) oxygen atoms.

In some embodiments, $R^2$ and $R^1$ are different, and $R^2$ comprises a sulfur atom.

In some embodiments, $R^1$ and $R^2$ are the same.
In some embodiments, $R^1$ is para or meta to $R^2$.
In some embodiments, $R^1$ is para or ortho to $R^2$.
In some embodiments, $R^1$ is ortho or meta to $R^2$.
In some embodiments, $R^1$ is para to $R^2$.
In some embodiments, $R^1$ is meta to $R^2$.
In some embodiments, $R^1$ is ortho to $R^2$.

The Variables o and p
In some embodiments o=1 or 2.
In some embodiments o=1.
In some embodiments o=2.
In some embodiments p=0, 1, 2, or 3.
In some embodiments p=0.
In some embodiments p=1.
In some embodiments p=2.
In some embodiments, o=1 and p=0.
In some embodiments, o=2 and p=0.
In some embodiments, o=1 and p=1.
In some embodiments, o=1 and p=2.
In some embodiments, o=2 and p=1.
In some embodiments, o=2 and p=2.
In some embodiments, o=2 and p=3.

The ring B and substitutions on the ring B
In some embodiments, B is a 5-10-membered monocyclic or bicyclic heteroaryl or a $C_6$-$C_{10}$ monocyclic or bicyclic aryl, such as phenyl.

In some embodiments, B is a 5-6-membered monocyclic heteroaryl or a $C_6$ monocyclic aryl.

In some embodiments, B is a 5-10-membered monocyclic or bicyclic heteroaryl.

In some embodiments, B is a $C_6$-$C_{10}$ monocyclic or bicyclic aryl.

In some embodiments, B is a 5-membered monocyclic or bicyclic heteroaryl.

In some embodiments, B is a 7-10 membered monocyclic or bicyclic heteroaryl.

In some embodiments, B is a 6-membered bicyclic heteroaryl.

In some embodiments, B is a 6-membered monocyclic heteroaryl containing 2 or more N atoms.

In some embodiments, B is phenyl, o is 1 or 2, and p is 0, 1, 2, or 3.

In some embodiments, B is pyridyl, o is 1 or 2, and p is 0, 1, 2, or 3.

In some embodiments, B is 3-pyridyl, o is 1 or 2, and p is 0, 1, 2, or 3.

In some embodiments, B is phenyl, o is 1, or 2, and p is 0, 1, 2, or 3.

In some embodiments, B is pyridyl (e.g., 3-pyridyl), o is 1 or 2, and p is 0, 1, 2, or 3.

In some embodiments, B is phenyl, o is 1, and p is 1, 2, or 3.

In some embodiments, B is phenyl, o is 2, and p is 1, 2, or 3.

In some embodiments, B is pyridyl (e.g., 3-pyridyl), o is 1, and p is 0, 1, 2, or 3.

In some embodiments, B is pyridyl (e.g., 3-pyridyl), o is 2, and p is 0, 1, 2, or 3.

In some embodiments, B is phenyl, o is 1 or 2, and p is 0, 1, 2, or 3.

In some embodiments, B is pyridyl (e.g., 3-pyridyl), o is 1 or 2, and p is 0, 1, 2, or 3.

In some embodiments, B is phenyl, o is 1, and p is 0, 1, 2, or 3.

In some embodiments, B is phenyl, o is 2, and p is 0, 1, 2, or 3.

In some embodiments, B is pyridyl (e.g., 3-pyridyl), o is 1, and p is 0, 1, 2, or 3.

In some embodiments, B is pyridyl (e.g., 3-pyridyl), o is 2, and p is 0, 1, or 2.

In some embodiments, B is pyrimidinyl (e.g., pyrimidin-5-yl), o is 1, and p is 0, 1, or 2.

In some embodiments, B is pyrimidinyl (e.g., pyrimidin-5-yl), o is 2, and p is 0 or 1.

In some embodiments, B is one of the rings disclosed hereinbelow, substituted as disclosed hereinbelow, wherein in each case the bond that is shown as being broken by the wavy line ∫ connects B to the NH(CO) group of Formula AA.

In some embodiments, the substituted ring B

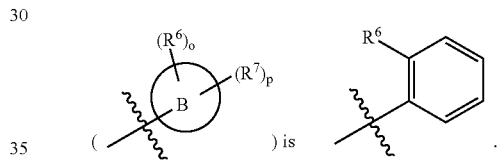

In some embodiments, the substituted ring B is

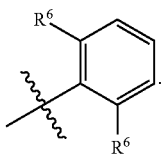

In some embodiments, the substituted ring B is

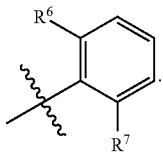

In some embodiments, the substituted ring B is

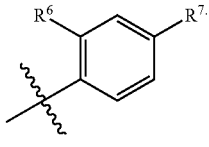

In some embodiments, the substituted ring B is

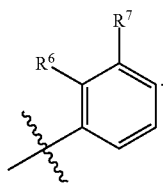

In some embodiments, the substituted ring B is

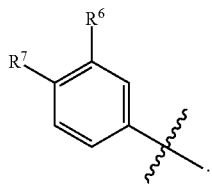

In some embodiments, the substituted ring B is

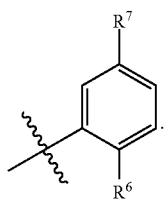

In some embodiments, the substituted ring B is

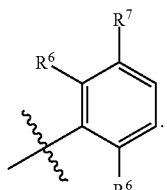

In some embodiments, the substituted ring B is

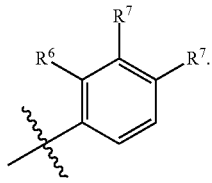

In some embodiments, the substituted ring B is

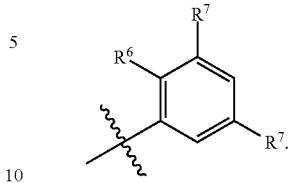

In some embodiments, the substituted ring B is

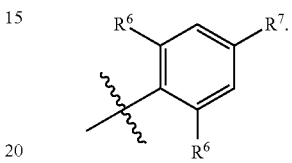

In some embodiments, the substituted ring B is

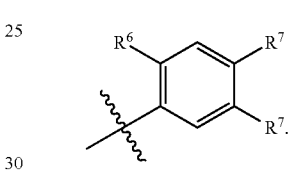

In some embodiments, the substituted ring B is

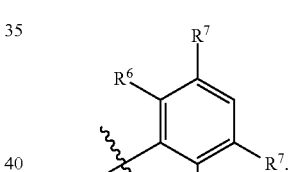

In some embodiments, the substituted ring B is

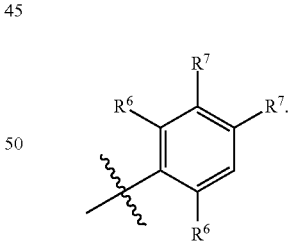

In some embodiments, the substituted ring B is

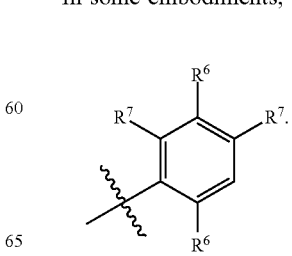

In some embodiments, the substituted ring B is

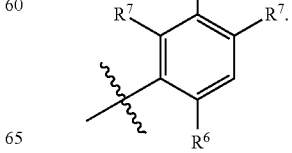

In some embodiments, the substituted ring B is

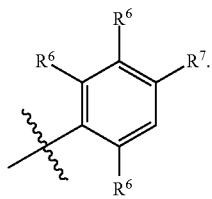

In some embodiments, the substituted ring B is

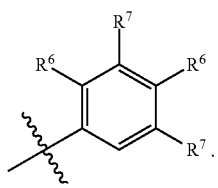

In some embodiments, the substituted ring B is

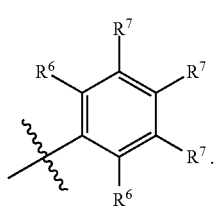

In some embodiments, the substituted ring B is

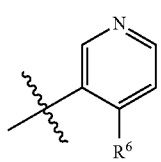

In some embodiments, the substituted ring B is

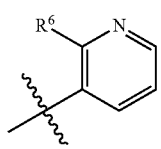

In some embodiments, the substituted ring B is

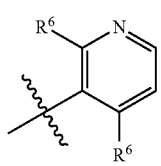

In some embodiments, the substituted ring B is

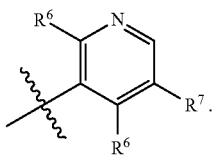

In some embodiments, the substituted ring B is

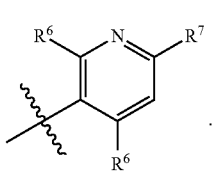

In some embodiments, the substituted ring B is

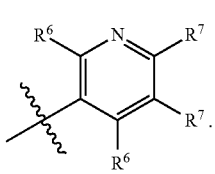

In some embodiments, the substituted ring B is

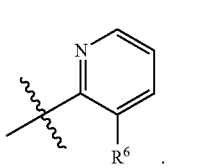

In some embodiments, the substituted ring B is

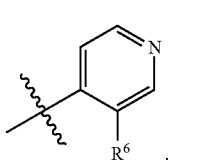

In some embodiments, the substituted ring B is

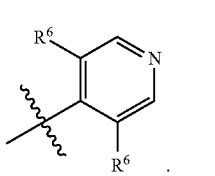

In some embodiments, the substituted ring B is

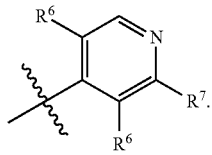

In some embodiments, the substituted ring B is

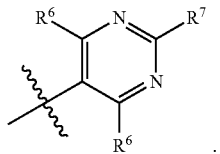

The Groups $R^6$ and $R^1$

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;
  wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$.

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from
hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;
  wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_6$ aliphatic carbocyclic ring or at least one 5- to 6-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, NHCOC$_6$-C$_{10}$ aryl, NHCO (5- to 10-membered heteroaryl), NHCO (3- to 7-membered heterocycloalkyl), and NHCOC$_2$-C$_6$ alkynyl;
  wherein the 3- to 7-membered heterocycloalkyl, C$_6$-C$_{10}$ aryl, 5- to 10-membered heteroaryl, NHCOC$_6$-C$_{10}$ aryl, NHCO (5- to 10-membered heteroaryl) and NHCO (3- to 7-membered heterocycloalkyl) are optionally substituted with one or more substituents independently selected from halo, C$_1$-C$_6$ alkyl, and OC$_1$-C$_6$ alkyl;
or at least one pair of R$^6$ and R$^7$ on adjacent atoms, taken together with the atoms connecting them, independently form at least one C$_5$-C$_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$.

In some embodiments,
R$^6$ and R$^7$ are each independently selected from C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO (5- to 10-membered heteroaryl), OCO (3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, S(O$_2$)C$_1$-C$_6$ alkyl, C$_3$-C$_7$ cycloalkyl and 3- to 7-membered heterocycloalkyl,
wherein the C$_3$-C$_7$ cycloalkyl, C$_1$-C$_6$ haloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO (3- to 7-membered heterocycloalkyl), NHCOC$_1$-C$_6$ alkyl, NHCOC$_6$-C$_{10}$ aryl, NHCO (5- to 10-membered heteroaryl), NHCO (3- to 7-membered heterocycloalkyl), and NHCOC$_2$-C$_6$ alkynyl;
  wherein the 3- to 7-membered heterocycloalkyl, C$_6$-C$_{10}$ aryl, 5- to 10-membered heteroaryl, NHCOC$_6$-C$_{10}$ aryl, NHCO (5- to 10-membered heteroaryl) and NHCO (3- to 7-membered heterocycloalkyl) are optionally substituted with one or more substituents independently selected from halo, C$_1$-C$_6$ alkyl, and OC$_1$-C$_6$ alkyl;
or at least one pair of R$^6$ and R$^7$ on adjacent atoms, taken together with the atoms connecting them, independently form at least one C$_5$-C$_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$.

In some embodiments,
R$^6$ and R$^7$ are each independently selected from C$_1$-C$_6$ alkyl, halo, CN, NO$_2$, COC$_1$-C$_6$ alkyl, CO$_2$C$_1$-C$_6$ alkyl, OCOC$_1$-C$_6$ alkyl, OCOC$_6$-C$_{10}$ aryl, OCO (5- to 10-membered heteroaryl), OCO (3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, S(O$_2$)C$_1$-C$_6$ alkyl, C$_3$-C$_7$ cycloalkyl and 3- to 7- membered heterocycloalkyl,
wherein the C$_1$-C$_6$ alkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO (3- to 7-membered heterocycloalkyl), NHCOC$_1$-C$_6$ alkyl, NHCOC$_6$-C$_{10}$ aryl, NHCO (5- to 10-membered heteroaryl), NHCO (3- to 7-membered heterocycloalkyl), and NHCOC$_2$-C$_6$ alkynyl;
  wherein the 3- to 7-membered heterocycloalkyl, C$_6$-C$_{10}$ aryl, 5- to 10-membered heteroaryl, NHCOC$_6$-C$_{10}$ aryl, NHCO (5- to 10-membered heteroaryl) and NHCO (3- to 7-membered heterocycloalkyl) are optionally substituted with one or more substituents independently selected from halo, C$_1$-C$_6$ alkyl, and OC$_1$-C$_6$ alkyl;
or at least one pair of R$^6$ and R$^7$ on adjacent atoms, taken together with the atoms connecting them, independently form at least one C$_5$-C$_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$.

In some embodiments,
R$^6$ and R$^7$ are each independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO (5- to 10-membered heteroaryl), OCO (3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, S(O$_2$)C$_1$-C$_6$ alkyl, C$_3$-C$_7$ cycloalkyl and 3- to 7-membered heterocycloalkyl,
wherein R$^6$ and R$^7$ are each optionally substituted with one or more substituents independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO (3- to 7-membered heterocycloalkyl), NHCOC$_1$-C$_6$ alkyl, NHCOC$_6$-C$_{10}$ aryl, NHCO (5- to 10-membered heteroaryl), NHCO (3- to 7-membered heterocycloalkyl), NHCOC$_2$-C$_6$ alkynyl, C$_6$-C$_{10}$ aryloxy, and S(O$_2$)C$_1$-C$_6$ alkyl; and wherein the C$_1$-C$_6$ alkyl or C$_1$-C$_6$ alkoxy that R$^6$ or R$^7$ is substituted with is optionally substituted with one or more hydroxyl, halo, C$_6$-C$_{10}$ aryl or NR$^8$R$^9$, or wherein R$^6$ or R$^7$ is optionally fused to a five-to-seven-membered carbocyclic ring or heterocyclic ring containing one or two heteroatoms independently selected from oxygen, sulfur and nitrogen;
  wherein the 3- to 7-membered heterocycloalkyl, C$_6$-C$_{10}$ aryl, 5- to 10-membered heteroaryl, NHCOC$_6$-C$_{10}$ aryl, NHCO (5- to 10-membered heteroaryl) and NHCO (3- to 7-membered heterocycloalkyl) are optionally substituted with one or more substituents independently selected from halo, C$_1$-C$_6$ alkyl, and OC$_1$-C$_6$ alkyl;
or at least one pair of R$^6$ and R$^7$ on adjacent atoms, taken together with the atoms connecting them, independently form at least one C$_4$-C$_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$, wherein the C$_1$-C$_6$ alkyl and C$_1$-C$_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, halo, CN, $NO_2$, $COC_1$-$C_6$ alkyl, $CO_2C_1$-$C_6$ alkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7- membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, halo, CN, $NO_2$, $COC_1$-$C_6$ alkyl, $CO_2C_1$-$C_6$ alkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7- membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are unsubstituted; or
at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_7$ cycloalkyl and 3- to 7-membered heterocycloalkyl,
wherein the $C_1$-$C_6$ alkyl, $C_3$-$C_7$ cycloalkyl and 3- to 7-membered heterocycloalkyl are each unsubstituted;
or at least one pair of $R^6$ and R' on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
$R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl;
$CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;
and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl,
wherein the $C_1$-$C_6$ alkyl is optionally substituted with one to two $C_1$-$C_6$ alkoxy;
or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
or at least one pair of $R^6$ and $R^7$ on adjacent atoms, taken together with the atoms connecting them, independently form at least one $C_5$-$C_8$ carbocyclic ring, wherein the carbocyclic ring is optionally independently substituted with one or more hydroxy or oxo.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
or at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocyloalkyl is optionally substituted with one or more substituents each independently selected from hydroxy or oxo,
or at least one pair of $R^6$ and $R^7$ on adjacent atoms, taken together with the atoms connecting them, independently form at least one 5- to 8-membered heterocyclic ring containing 1 or 2 heteroatoms independently selected from O, N, and S, wherein the heterocyclic ring is optionally independently substituted with one or more hydroxy or oxo.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocyloalkyl is optionally substituted with one or more substituents each independently selected from hydroxy or oxo,
or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more hydroxy or oxo.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocyloalkyl is optionally substituted with one or more substituents each independently selected from hydroxy or oxo,
or at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more $C_1$-$C_6$ alkyl.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocyloalkyl is optionally substituted with one or more substituents each independently selected from hydroxy or oxo,
or at least one pair of $R^6$ and $R^7$ on adjacent atoms, taken together with the atoms connecting them, independently form at least one 5- to 8-membered heterocyclic ring containing 1 or 2 heteroatoms independently selected from O, N, and S, wherein the heterocyclic ring is optionally independently substituted with one or more $C_1$-$C_6$ alkyl.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocyloalkyl is optionally substituted with one or more substituents each independently selected from $C_1$-$C_6$ alkyl.
or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more $C_1$-$C_6$ alkyl.

In some embodiments, o=1; p=0; and
$R^6$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
   wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl.

In some embodiments, o=1; p=1; and
$R^6$ is selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo,
or at least one pair of $R^6$ and $R^7$ on adjacent atoms, taken together with the atoms connecting them, independently form at least one $C_5$-$C_8$ carbocyclic ring, wherein the carbocyclic ring is optionally independently substituted with one or more hydroxy or oxo.

In some embodiments, o=1 or 2; p=1, 2, or 3; and
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (3- to 7-membered heterocycloalkyl), $NHCOC_1$-$C_6$ alkyl, $NHCOC_6$-$C_{10}$ aryl, NHCO (5- to 10-membered heteroaryl), NHCO (3- to 7-membered heterocycloalkyl), and $NHCOC_2$-$C_6$ alkynyl;
   wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl.

In some embodiments, o=2; p=1; and
each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl;
$CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;
   and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl,
   wherein the $C_1$-$C_6$ alkyl is optionally substituted with one to two $C_1$-$C_6$ alkoxy;
or $R^6$ and $R^7$, taken together with the atoms connecting them, independently form $C_4$-$C_7$ carbocyclic ring or 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl;
$CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ (e.g., $C_4$-$C_6$) carbocyclic ring (e.g., aliphatic carbocyclic ring) or at least one 5-to-7-membered (e.g., 5-to-6-membered) heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_5$-$C_5$ carbocyclic ring, wherein the carbocyclic ring is optionally independently substituted with one or more hydroxy or oxo.

In some embodiments, o=1 or 2; p=1, 2, or 3; and $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo.

In some embodiments, o=1 or 2; p=1, 2, or 3; and one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and one $R^6$ and one $R^7$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $NR^{10}$, $COOC_1$-$C_6$ alkyl, $C_6$-$C_{10}$ aryl, and $CONR^8R^9$.

In some embodiments, o=1 or 2; p=1, 2, or 3; and one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is unsubstituted.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms independently selected from O, N, and S, wherein each carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is unsubstituted.

Particular Embodiments Wherein o=1; p=0:

In some embodiments, $R^6$ is $C_1$-$C_6$ alkyl.
In some embodiments, $R^6$ is isopropyl.
In some embodiments, $R^6$ is ethyl.
In some embodiments, $R^6$ is methyl.
In some embodiments, $R^6$ is $C_1$-$C_6$ alkyl substituted with one or more halo.
In some embodiments, $R^6$ is $C_1$-$C_6$ alkyl (e.g., methyl) substituted with one or more (e.g., one) $C_1$-$C_6$ alkoxy (e.g., methoxy). In some embodiments, $R^6$ is methoxymethyl.
In some embodiments, $R^6$ is trifluoromethyl.
In some embodiments, $R^6$ is trifluoromethoxy.
In some embodiments, $R^6$ is $C_3$-$C_7$ cycloalkyl.
In some embodiments, $R^6$ is cyclopropyl.
In some embodiments, $R^6$ is halo.
In some embodiments, $R^6$ is chloro.
In some embodiments, $R^6$ is fluoro.
In some embodiments, $R^6$ is cyano.
In some embodiments, $R^6$ is attached to a carbon of an aryl ring B.
In some embodiments, $R^6$ is attached to a carbon of a heteroaryl ring B.
In some embodiments, $R^6$ is attached to a nitrogen of a heteroaryl ring B.

Particular Embodiments Wherein o=1 or 2; p=1, 2, or 3:

In some embodiments, at least one $R^6$ is $C_1$-$C_6$ alkyl, and at least one $R^7$ is $C_1$-$C_6$ alkyl optionally substituted with one or more halo.

In some embodiments, at least one $R^6$ is $C_1$-$C_6$ alkyl, and at least one $R^7$ is halo.

In some embodiments, at least one $R^6$ is $C_1$-$C_6$ alkyl and at least one $R^7$ is $C_1$-$C_6$ alkyl.

In some embodiments, at least one $R^6$ is isopropyl and at least one $R^7$ is methyl.

In some embodiments, at least one $R^6$ is isopropyl and at least one $R^7$ is isopropyl.

In some embodiments, o=1; p=1; $R^6$ is isopropyl; and $R^7$ is isopropyl.

In some embodiments, at least one $R^6$ is $C_1$-$C_6$ alkyl, and at least one $R^7$ is $C_1$-$C_6$ alkyl substituted with one or more halo.

In some embodiments, at least one $R^6$ is isopropyl and at least one $R^7$ is trifluoromethyl.

In some embodiments, at least one $R^6$ is $C_1$-$C_6$ alkyl, and at least one $R^7$ is $C_3$-$C_7$ cycloalkyl.

In some embodiments, at least one $R^6$ is isopropyl and at least one $R^7$ is cyclopropyl.

In some embodiments, o=1; p=1; $R^6$ is isopropyl; and $R^7$ is cyclopropyl.

In some embodiments, o=1; p=2; $R^6$ is isopropyl; one $R^7$ is cyclopropyl; and the other $R^7$ is fluoro.

In some embodiments, o=2; p=2; one $R^6$ is isopropyl; one $R^7$ is cyclopropyl; the other $R^6$ is cyano; and the other $R^7$ is fluoro.

In some embodiments, at least one $R^6$ is $C_1$-$C_6$ alkyl, and at least one $R^7$ is halo.

In some embodiments, at least one $R^6$ is isopropyl and at least one $R^7$ is halo.

In some embodiments, at least one $R^6$ is isopropyl and at least one $R^7$ is chloro.

In some embodiments, at least one $R^6$ is isopropyl and at least one $R^7$ is fluoro.

In some embodiments, o=1; p=1; $R^6$ is isopropyl; and $R^7$ is chloro.

In some embodiments, o=2; p=1; at least one $R^6$ is isopropyl; and $R^7$ is chloro.

In some embodiments, o=1; p=1; $R^6$ is isopropyl; and $R^7$ is fluoro.

In some embodiments, o=2; p=1; at least one $R^6$ is isopropyl, and $R^7$ is fluoro.

In some embodiments, o=2; p=1; each $R^6$ is isopropyl, and $R^7$ is fluoro.

In some embodiments, o=1; p=1; $R^6$ is isopropyl; and $R^7$ is fluoro.

In some embodiments, o=2; p=1; at least one $R^6$ is isopropyl; and $R^7$ is fluoro.

In some embodiments, o=2; p=2; at least one $R^6$ is isopropyl, one $R^7$ is fluoro, and one $R^7$ is phenyl substituted with trifluoromethyl (e.g., substituted at the meta position with trifluoromethyl).

In some embodiments, o=2; p=2; at least one $R^6$ is isopropyl; and $R^7$ is fluoro.

In some embodiments, o=2; p=2; at least one $R^6$ is isopropyl; one $R^7$ is fluoro; and the other $R^7$ is cyano.

In some embodiments, o=2; p=3; at least one $R^6$ is isopropyl; two $R^7$ are fluoro; and one $R^7$ is chloro.

In some embodiments, o=2; p=1; at least one $R^6$ is ethyl; and $R^7$ is fluoro.

In some embodiments, o=2; p=1; at least one $R^6$ is isopropyl; the other $R^6$ is trifluoromethyl; and $R^7$ is chloro.

In some embodiments, at least one $R^6$ is $C_1$-$C_6$ alkyl, and at least one $R^7$ is cyano.

In some embodiments, at least one $R^6$ is isopropyl and at least one $R^7$ is cyano.

In some embodiments, o=1; p=1; $R^6$ is isopropyl; and $R^7$ is cyano.

In some embodiments, o=2; p=1; at least one $R^6$ is isopropyl; and $R^7$ is cyano.

In some embodiments, at least one $R^6$ is $C_3$-$C_7$ cycloalkyl, and at least one $R^7$ is $C_3$-$C_7$ cycloalkyl.

In some embodiments, at least one $R^6$ is cyclopropyl, and at least one $R^7$ is cyclopropyl.

In some embodiments, at least one $R^6$ is $C_3$-$C_7$ cycloalkyl, and at least one $R^7$ is halo.

In some embodiments, at least one $R^6$ is cyclopropyl and at least one $R^7$ is halo.

In some embodiments, at least one $R^6$ is cyclopropyl and at least one $R^7$ is chloro.

In some embodiments, at least one $R^6$ is cyclopropyl and at least one $R^7$ is fluoro.

In some embodiments, o=1; p=1; $R^6$ is cyclopropyl; and $R^7$ is chloro.

In some embodiments, o=1; p=1; $R^6$ is cyclopropyl; and $R^7$ is fluoro.

In some embodiments, at least one $R^6$ is $C_1$-$C_6$ alkyl, and at least one $R^7$ is $C_1$-$C_6$ alkoxy optionally substituted with one or more halo.

In some embodiments, at least one $R^6$ is isopropyl, and at least one $R^7$ is $C_1$-$C_6$ alkoxy.

In some embodiments, at least one $R^6$ is isopropyl, and at least one $R^7$ is methoxy.

In some embodiments, o=1; p=1; $R^6$ is isopropyl, and $R^7$ is methoxy.

In some embodiments, o=2; p=1; at least one $R^6$ is isopropyl, and $R^7$ is methoxy.

In some embodiments, at least one $R^6$ is $C_1$-$C_6$ alkyl, and at least one $R^7$ is $C_1$-$C_6$ alkoxy substituted with one or more halo.

In some embodiments, at least one $R^6$ is isopropyl, and at least one $R^7$ is trifluoromethoxy.

In some embodiments, at least one $R^6$ is isopropyl, and at least one $R^7$ is difluoromethoxy.

In some embodiments, at least one $R^6$ is $C_1$-$C_6$ alkyl, and at least one $R^7$ is $C_1$-$C_6$ alkyl (e.g., methyl) substituted with one or more (e.g., one) $C_1$-$C_6$ alkoxy (e.g., methoxy).

In some embodiments, at least on $R^6$ is isopropyl, and at least one $R^7$ is methoxymethyl.

In some embodiments, o=2; p=1, each $R^6$ is isopropyl, and $R^7$ is methoxymethyl.

In some embodiments, at least one $R^6$ is halo, and at least one $R^7$ is $C_1$-$C_6$ haloalkyl optionally substituted with hydroxy.

In some embodiments, o=1; p=1; $R^6$ is chloro, and $R^7$ is trifluoromethyl.

In some embodiments, at least one $R^6$ is halo, and at least one $R^7$ is $C_1$-$C_6$ haloalkoxy.

In some embodiments, at least one $R^6$ is chloro, and at least one $R^7$ is trifluoromethoxy.

In some embodiments, o=1; p=1; $R^6$ is chloro, and $R^7$ is trifluoromethoxy.

In some embodiments, at least one $R^6$ is $C_1$-$C_6$ alkoxy; and at least one $R^7$ is halo.

In some embodiments, o=1; p=2; $R^6$ is $C_1$-$C_6$ alkoxy; and at least one $R^7$ is chloro.

In some embodiments, at least one $R^6$ is $C_3$-$C_7$ cycloalkyl; and at least one $R^7$ is $C_1$-$C_6$ haloalkyl optionally substituted with hydroxy.

In some embodiments, at least one $R^6$ is cyclopropyl; and at least one $R^7$ is trifluoromethyl.

In some embodiments, o=1; p=2; $R^6$ is cyclopropyl; one $R^7$ is trifluoromethyl; and the other $R^7$ is fluoro.

In some embodiments, at least one $R^6$ is $C_1$-$C_6$ alkyl, and at least one $R^7$ is $C_6$-$C_{10}$ aryl, wherein the $C_6$-$C_{10}$ aryl is optionally substituted or optionally fused as described elsewhere herein.

In some embodiments, at least one $R^6$ is isopropyl, and at least one $R^7$ is $C_6$-$C_{10}$ aryl, wherein the $C_6$-$C_{10}$ aryl is optionally substituted as described elsewhere herein.

In some embodiments, at least one $R^6$ is isopropyl, and at least one $R^7$ is dichlorophenyl (e.g., 3,4-dichlorophenyl).

In some embodiments, at least one $R^6$ is isopropyl, and at least one $R^7$ is dimethylphenyl (e.g., 3,4-dimethylphenyl).

In some embodiments, at least one $R^6$ is isopropyl, and at least one $R^7$ is naphthyl (e.g., napthyl substituted with one methoxy).

In some embodiments, at least one $R^6$ is isopropyl, and at least one $R^7$ is $C_6$-$C_{10}$ aryl, wherein the $C_6$-$C_{10}$ aryl is optionally fused to a five-to-seven-membered carbocyclic ring or heterocyclic ring containing one or two heteroatoms independently selected from oxygen, sulfur and nitrogen (e.g., $R^7$ is

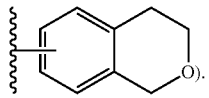

In some embodiments, o=2; p=1, each $R^6$ is isopropyl; and $R^7$ is $C_6$-$C_{10}$ aryl, wherein the $C_6$-$C_{10}$ aryl is optionally substituted as described elsewhere herein (e.g., $R^7$ is dimethylphenyl; or $R^7$ is dichlorophenyl; or $R^7$ is naphthyl).

In some embodiments, o=2; p=1, each $R^6$ is isopropyl; and $R^7$ is $C_6$-$C_{10}$ aryl, wherein the $C_6$-$C_{10}$ aryl is optionally fused to a five-to-seven-membered carbocyclic ring or heterocyclic ring containing one or two heteroatoms independently selected from oxygen, sulfur and nitrogen (e.g., $R^7$ is

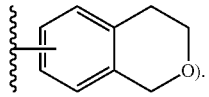

In some embodiments, at least one $R^6$ is $C_1$-$C_6$ alkyl, and at least one $R^7$ is 3- to 7-membered heterocycloalkyl, wherein the 3- to 7-membered heterocycloalkyl is optionally substituted or optionally fused as described elsewhere herein.

In some embodiments, at least one $R^6$ is isopropyl, and at least one $R^7$ is 3- to 7-membered heterocycloalkyl, wherein the 3- to 7-membered heterocycloalkyl is optionally substituted as described elsewhere herein.

In some embodiments, at least one $R^6$ is isopropyl, and at least one $R^7$ is tetrahydrofuranyl.

In some embodiments, at least one $R^6$ is isopropyl, and at least one $R^7$ is

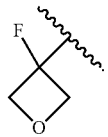

In some embodiments, at least one $R^6$ is $C_1$-$C_6$ alkyl, and at least one $R^7$ is 5- to 10-membered heteroaryl, wherein the 5- to 10-membered heteroaryl is optionally substituted or optionally fused as described elsewhere herein.

In some embodiments, at least one $R^6$ isopropyl, and at least one $R^7$ is 5- to 10-membered heteroaryl, wherein the 5- to 10-membered heteroaryl is optionally substituted or optionally fused as described elsewhere herein.

In some embodiments, at least one $R^6$ isopropyl, and at least one $R^7$ is pyrazolyl.

In some embodiments, at least one $R^7$ is $C_1$-$C_6$ alkyl, and at least one $R^6$ is $C_1$-$C_6$ alkyl optionally substituted with one or more halo.

In some embodiments, at least one $R^7$ is isopropyl and at least one $R^6$ is methyl.

In some embodiments, at least one $R^7$ is $C_1$-$C_6$ alkyl, and at least one $R^6$ is $C_1$-$C_6$ alkyl substituted with one or more halo.

In some embodiments, at least one $R^7$ is isopropyl and at least one $R^6$ is trifluoromethyl.

In some embodiments, at least one $R^7$ is $C_1$-$C_6$ alkyl, and at least one $R^6$ is $C_3$-$C_7$ cycloalkyl.

In some embodiments, at least one $R^7$ is isopropyl and at least one $R^6$ is cyclopropyl.

In some embodiments, o=1; p=1; $R^7$ is isopropyl; and $R^6$ is cyclopropyl.

In some embodiments, o=2; p=1; $R^7$ is isopropyl; one $R^6$ is cyclopropyl; and the other $R^6$ is fluoro.

In some embodiments, o=2; p=2; one $R^7$ is isopropyl; one $R^6$ is cyclopropyl; the other $R^7$ is cyano; and the other $R^6$ is fluoro.

In some embodiments, at least one $R^7$ is $C_1$-$C_6$ alkyl, and at least one $R^6$ is halo.

In some embodiments, at least one $R^7$ is isopropyl and at least one $R^6$ is halo.

In some embodiments, at least one $R^7$ is isopropyl and at least one $R^6$ is chloro.

In some embodiments, at least one $R^7$ is isopropyl and at least one $R^6$ is fluoro.

In some embodiments, o=1; p=1; $R^7$ is isopropyl; and $R^6$ is chloro.

In some embodiments, o=2; p=1; at least one $R^7$ is isopropyl; and at least one $R^6$ is chloro.

In some embodiments, o=1; p=1; $R^7$ is isopropyl; and $R^6$ is fluoro.

In some embodiments, o=2; p=1; $R^7$ is isopropyl; and at least one $R^6$ is fluoro.

In some embodiments, o=1; p=2; each $R^7$ is isopropyl, and $R^6$ is fluoro.

In some embodiments, o=2; p=2; at least one $R^7$ is isopropyl; and at least one $R^6$ is fluoro.

In some embodiments, o=2; p=2; at least one $R^7$ is isopropyl; one $R^6$ is fluoro; and the other $R^6$ is cyano.

In some embodiments, o=2; p=1; $R^7$ is ethyl; and at least one $R^6$ is fluoro.

In some embodiments, o=1; p=2; one $R^7$ is isopropyl; the other $R^7$ is trifluoromethyl; and $R^6$ is chloro.

In some embodiments, at least one $R^7$ is $C_1$-$C_6$ alkyl, and at least one $R^6$ is cyano.

In some embodiments, at least one $R^7$ is isopropyl and at least one $R^6$ is cyano.

In some embodiments, o=1; p=1; $R^7$ is isopropyl; and $R^6$ is cyano.

In some embodiments, o=2; p=1; $R^7$ is isopropyl; and at least one $R^6$ is cyano.

In some embodiments, at least one $R^7$ is $C_3$-$C_7$ cycloalkyl, and at least one $R^6$ is $C_3$-$C_7$ cycloalkyl.

In some embodiments, at least one $R^7$ is cyclopropyl, and at least one $R^6$ is cyclopropyl.

In some embodiments, at least one $R^7$ is $C_3$-$C_7$ cycloalkyl, and at least one $R^6$ is halo.

In some embodiments, at least one $R^7$ is cyclopropyl and at least one $R^6$ is halo.

In some embodiments, at least one $R^7$ is cyclopropyl and at least one $R^6$ is chloro.

In some embodiments, at least one $R^7$ is cyclopropyl and at least one $R^6$ is fluoro.

In some embodiments, o=1; p=1; $R^7$ is cyclopropyl; and $R^6$ is chloro.

In some embodiments, o=1; p=1; $R^7$ is cyclopropyl; and $R^6$ is fluoro.

In some embodiments, at least one $R^7$ is $C_1$-$C_6$ alkyl, and at least one $R^6$ is $C_1$-$C_6$ alkoxy optionally substituted with one or more halo.

In some embodiments, at least one $R^7$ is isopropyl, and at least one $R^6$ is $C_1$-$C_6$ alkoxy.

In some embodiments, at least one $R^7$ is isopropyl, and at least one $R^6$ is methoxy.

In some embodiments, o=1; p=1; $R^7$ is isopropyl, and $R^6$ is methoxy.

In some embodiments, o=2; p=1; $R^7$ is isopropyl, and at least one $R^6$ is methoxy.

In some embodiments, at least one $R^7$ is $C_1$-$C_6$ alkyl, and at least one $R^6$ is $C_1$-$C_6$ alkoxy substituted with one or more halo.

In some embodiments, at least one $R^7$ is isopropyl, and at least one $R^6$ is trifluoromethoxy.

In some embodiments, at least one $R^7$ is $C_1$-$C_6$ alkyl, and at least one $R^6$ is $C_1$-$C_6$ alkyl (e.g., methyl) substituted with one or more (e.g., one) $C_1$-$C_6$ alkoxy (e.g., methoxy).

In some embodiments, at least on $R^7$ is isopropyl, and at least one $R^6$ is methoxymethyl.

In some embodiments, o=2; p=1, each $R^7$ is isopropyl, and $R^6$ is methoxymethyl.

In some embodiments, at least one $R^7$ is halo, and at least one $R^6$ is $C_1$-$C_6$ haloalkyl optionally substituted with hydroxy.

In some embodiments, o=1; p=1; $R^7$ is chloro, and $R^6$ is trifluoromethyl.

In some embodiments, at least one $R^7$ is halo, and at least one $R^6$ is $C_1$-$C_6$ haloalkoxy.

In some embodiments, at least one $R^7$ is chloro, and at least one $R^6$ is trifluoromethoxy.

In some embodiments, o=1; p=1; $R^7$ is chloro, and $R^6$ is trifluoromethoxy.

In some embodiments, at least one $R^7$ is $C_1$-$C_6$ alkoxy; and at least one $R^6$ is halo.

In some embodiments, o=1; p=2; at least one $R^7$ is $C_1$-$C_6$ alkoxy; and $R^6$ is chloro.

In some embodiments, at least one $R^7$ is $C_3$-$C_7$ cycloalkyl; and at least one $R^6$ is $C_1$-$C_6$ haloalkyl optionally substituted with hydroxy.

In some embodiments, at least one $R^7$ is cyclopropyl; and at least one $R^6$ is trifluoromethyl.

In some embodiments, o=2; p=1; $R^7$ is cyclopropyl; one $R^6$ is trifluoromethyl; and the other $R^6$ is fluoro.

In some embodiments, at least one $R^6$ is $C_1$-$C_6$ alkyl, and at least one $R^7$ is $C_6$-$C_{10}$ aryl, wherein the $C_6$-$C_{10}$ aryl is optionally substituted or optionally fused as described elsewhere herein.

In some embodiments, at least one $R^6$ is isopropyl, and at least one $R^7$ is $C_6$-$C_{10}$ aryl, wherein the $C_6$-$C_{10}$ aryl is optionally substituted as described elsewhere herein.

In some embodiments, at least one $R^6$ is isopropyl, and at least one $R^7$ is dichlorophenyl (e.g., 3,4-dichlorophenyl).

In some embodiments, at least one $R^6$ is isopropyl, and at least one $R^7$ is dimethylphenyl (e.g., 3,4-dimethylphenyl).

In some embodiments, at least one $R^6$ is isopropyl, and at least one $R^7$ is naphthyl (e.g., napthyl substituted with one methoxy).

In some embodiments, at least one $R^7$ is isopropyl, and at least one $R^6$ is $C_6$-$C_{10}$ aryl, wherein the $C_6$-$C_{10}$ aryl is optionally fused to a five-to-seven-membered carbocyclic ring or heterocyclic ring containing one or two heteroatoms independently selected from oxygen, sulfur and nitrogen (e.g., $R^7$ is

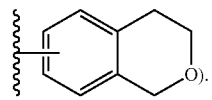).

In some embodiments, o=2; p=1, each $R^7$ is isopropyl; and $R^6$ is $C_6$-$C_{10}$ aryl, wherein the $C_6$-$C_{10}$ aryl is optionally substituted as described elsewhere herein (e.g., $R^6$ is dimethylphenyl; or $R^6$ is dichlorophenyl; or $R^6$ is naphthyl).

In some embodiments, o=2; p=1, each $R^7$ is isopropyl; and $R^6$ is $C_6$-$C_{10}$ aryl, wherein the $C_6$-$C_{10}$ aryl is optionally fused to a five-to-seven-membered carbocyclic ring or heterocyclic ring containing one or two heteroatoms independently selected from oxygen, sulfur and nitrogen (e.g., $R^7$ is

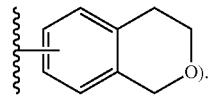).

In some embodiments, at least one $R^7$ is $C_1$-$C_6$ alkyl, and at least one $R^6$ is 3- to 7-membered heterocycloalkyl, wherein the 3- to 7-membered heterocycloalkyl is optionally substituted or optionally fused as described elsewhere herein.

In some embodiments, at least one $R^7$ is isopropyl, and at least one $R^6$ is 3- to 7-membered heterocycloalkyl, wherein the 3- to 7-membered heterocycloalkyl is optionally substituted as described elsewhere herein.

In some embodiments, at least one $R^7$ is isopropyl, and at least one $R^6$ is tetrahydrofuranyl.

In some embodiments, at least one $R^7$ is isopropyl, and at least one $R^6$ is

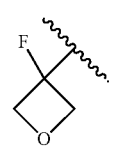 [SMILES: *C1(F)COC1]

In some embodiments, at least one $R^7$ is $C_1$-$C_6$ alkyl, and at least one $R^6$ is 5- to 10-membered heteroaryl, wherein the 5- to 10-membered heteroaryl is optionally substituted or optionally fused as described elsewhere herein.

In some embodiments, at least one $R^7$ isopropyl, and at least one $R^6$ is 5- to 10-membered heteroaryl, wherein the 5- to 10-membered heteroaryl is optionally substituted or optionally fused as described elsewhere herein.

In some embodiments, at least one $R^7$ isopropyl, and at least one $R^6$ is pyrazolyl.

In some embodiments, $R^6$ and $R^7$ are each attached to a carbon of an aryl ring B.

In some embodiments, $R^6$ and $R^7$ are each attached to a carbon of a heteroaryl ring B.

In some embodiments, $R^6$ is attached to a carbon and $R^7$ is attached to a nitrogen of a heteroaryl ring B.

In some embodiments, $R^7$ is attached to a carbon and $R^6$ is attached to a nitrogen of a heteroaryl ring B.

In some embodiments, one $R^6$ and one $R^7$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $=NR^{10}$, $COOC_1$-$C_6$ alkyl, $C_6$-$C_{10}$ aryl, and $CONR^8R^9$.

In some embodiments, $R^6$ and W are on adjacent atoms, and taken together with the atoms connecting them, form a $C_5$ aliphatic carbocyclic ring.

In some embodiments, $R^6$ and $R^7$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_6$ aliphatic carbocyclic ring.

In some embodiments, $R^6$ and W are on adjacent atoms, and taken together with the atoms connecting them, form a $C_6$ aromatic carbocyclic ring.

In some embodiments, $R^6$ and $R^7$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 5-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 5-membered heteroaromatic ring containing 1 or 2 heteroatoms independently selected from O, N, and S.

In some embodiments, $R^6$ and W are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and W are on adjacent atoms, and taken together with the atoms connecting them, form a 6-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 6-membered heteroaromatic ring containing 1 or 2 heteroatoms independently selected from O, N, and S.

In some embodiments, one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the ring is fused to the B ring at the ortho- and meta-positions relative to the bond connecting the B ring to the $C(R^4R^5)$ group.

In some embodiments, one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the ring is fused to the B ring at the meta- and para-positions relative to the bond connecting the B ring to the $C(R^4R^5)$ group.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aromatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered heteroaromatic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered heteroaromatic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms independently selected from O, N, and S,
wherein one of the two rings is fused to the B ring at the 2- and 3-positions relative to the bond connecting the B ring to the $C(R^4R^5)$ group, and the other of the two rings is fused to the B ring at the 5- and 6-positions relative to the bond connecting the B ring to the $C(R^4R^5)$ group.

In some embodiments, o=2; p=2; and two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is halo (e.g., Cl or F).

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is CN.

In some embodiments, one $R^7$ is pyrazolyl and is para to the bond connecting the B ring to the $C(R^4R^5)$ group of Formula AA.

In some embodiments, one $R^7$ is 3-pyrazolyl and is para to the bond connecting the B ring to the $C(R^4R^5)$ group of Formula AA.

In some embodiments, one $R^7$ is 4-pyrazolyl and is para to the bond connecting the B ring to the $C(R^4R^5)$ group of Formula AA.

In some embodiments, one $R^7$ is 5-pyrazolyl and is para to the bond connecting the B ring to the $C(R^4R^5)$ group of Formula AA.

In some embodiments, one $R^7$ is thiazolyl and is para to the bond connecting the B ring to the $C(R^4R^5)$ group of Formula AA.

In some embodiments, one $R^7$ is 4-thiazolyl and is para to the bond connecting the B ring to the $C(R^4R^5)$ group of Formula AA.

In some embodiments, one $R^7$ is 5-thiazolyl and is para to the bond connecting the B ring to the $C(R^4R^5)$ group of Formula AA.

In some embodiments, one $R^7$ is furyl and is para to the bond connecting the B ring to the $C(R^4R^5)$ group of Formula AA.

In some embodiments, one $R^7$ is 2-furyl and is para to the bond connecting the B ring to the $C(R^4R^5)$ group of Formula AA.

In some embodiments, one $R^7$ is thiophenyl and is para to the bond connecting the B ring to the $C(R^4R^5)$ group of Formula AA.

In some embodiments, one $R^7$ is 2-thiophenyl and is para to the bond connecting the B ring to the $C(R^4R^5)$ group of Formula AA.

In some embodiments, one $R^7$ is phenyl and is para to the bond connecting the B ring to the $C(R^4R^5)$ group of Formula AA.

In some embodiments, one $R^7$ is naphthyl (e.g., unsubstituted naphthyl or methoxynaphthyl) and is para to the bond connecting the B ring to the $C(R^4R^5)$ group of Formula AA.

In some embodiments, one $R^7$ is isochromanyl and is para to the bond connecting the B ring to the $C(R^4R^5)$ group of Formula AA.

In some embodiments, one $R^7$ is cycloalkenyl (e.g., cyclopentenyl, e.g., 1-cyclopentenyl) and is para to the bond connecting the B ring to the $C(R^4R^5)$ group of Formula AA.

In some embodiments, one $R^7$ is phenyl optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the $C(R^4R^5)$ group of Formula AA.

In some embodiments, one $R^7$ is phenyl optionally substituted with one or more $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the $C(R^4R^5)$ group of Formula AA.

In some embodiments, one $R^7$ is phenyl optionally substituted with one or more $C_6$-$C_{10}$ aryloxy (e.g., phenoxy) and is para to the bond connecting the B ring to the $C(R^4R^5)$ group of Formula AA.

In some embodiments, one $R^7$ is phenyl optionally substituted with one or more CN and is para to the bond connecting the B ring to the $C(R^4R^5)$ group of Formula AA.

In some embodiments, one $R^7$ is phenyl optionally substituted with one or more halo (e.g., F, Cl) and is para to the bond connecting the B ring to the $C(R^4R^5)$ group of Formula AA.

In some embodiments, one $R^7$ is phenyl optionally substituted with one or more $COOC_1$-$C_6$ alkyl (e.g., $CO_2$t-Bu) and is para to the bond connecting the B ring to the $C(R^4R^5)$ group of Formula AA.

In some embodiments, one $R^7$ is phenyl optionally substituted with one or more $S(O_2)C_1$-$C_6$ alkyl (e.g., $S(O_2)$ methyl) and is para to the bond connecting the B ring to the $C(R^4R^5)$ group of Formula AA.

In some embodiments, one $R^7$ is phenyl optionally substituted with one or more 3- to 7-membered heterocycloalkyl (e.g., morpholinyl) and is para to the bond connecting the B ring to the $C(R^4R^5)$ group of Formula AA.

In some embodiments, one $R^7$ is phenyl optionally substituted with one or more $CONR^8R^9$ (e.g., unsubstituted amido) and is para to the bond connecting the B ring to the $C(R^4R^5)$ group of Formula AA.

In some embodiments, one $R^7$ is phenyl optionally substituted with one or more $C_1$-$C_6$ alkyl (e.g., methyl or propyl, e.g., 2-propyl) and with one or more halo (e.g., F, Cl) and is para to the bond connecting the B ring to the $C(R^4R^5)$ group of Formula AA.

In some embodiments, one $R^7$ is phenyl optionally substituted with one or more $C_1$-$C_6$ alkyl (e.g., methyl or propyl, e.g., 2-propyl) optionally substituted with one or more (e.g., one) halo (e.g., fluoro) and is para to the bond connecting the B ring to the $C(R^4R^5)$ group of Formula AA.

In some embodiments, $R^6$ and $R^7$ are each attached to a carbon of an aryl ring B.

In some embodiments, $R^6$ and $R^7$ are each attached to a carbon of a heteroaryl ring B.

In some embodiments, $R^6$ is attached to a carbon and $R^7$ is attached to a nitrogen of a heteroaryl ring B.

In some embodiments, $R^7$ is attached to a carbon and $R^6$ is attached to a nitrogen of a heteroaryl ring B.

In some embodiments, the substituted ring B is

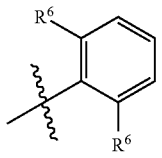

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl.

In some embodiments, the substituted ring B is

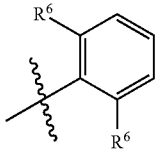

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, wherein the $C_1$-$C_6$ alkyl, $C_1$-$C_6$ haloalkyl, and $C_3$-$C_7$ cycloalkyl is optionally substituted with one or more substituents each independently selected from hydroxy, halo, CN, or oxo.

In some embodiments, the substituted ring B is

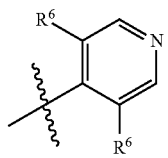

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl.

In some embodiments, the substituted ring B is

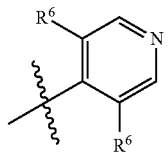

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, wherein the $C_1$-$C_6$ alkyl, $C_1$-$C_6$ haloalkyl, and $C_3$-$C_7$ cycloalkyl is optionally substituted with one or more substituents each independently selected from hydroxy, halo, CN, or oxo.

In some embodiments, the substituted ring B is

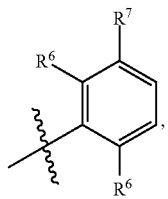

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and NHCOC$_2$-C$_6$ alkynyl;
  wherein R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO (5- to 10-membered heteroaryl), OCO (3- to 7-membered heterocycloalkyl), 6-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;
or R$^6$ and R$^7$, taken together with the atoms connecting them, independently form C$_4$-C$_7$ carbocyclic ring or 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments, the substituted ring B is

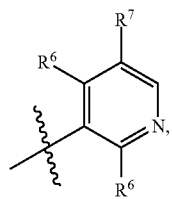

wherein each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl, CONR$^8$R$^9$, and 4- to 6-membered heterocycloalkyl,
  wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO (4- to 6-membered heterocycloalkyl), NHCOC$_1$-C$_6$ alkyl, NHCOC$_6$-C$_{10}$ aryl, NHCO (5- to 10-membered heteroaryl), NHCO (4- to 6-membered heterocycloalkyl), and NHCOC$_2$-C$_6$ alkynyl;
  wherein R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO (5- to 10-membered heteroaryl), OCO (3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;
or R$^6$ and R$^7$, taken together with the atoms connecting them, independently form C$_4$-C$_7$ carbocyclic ring or 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments, the substituted ring B is

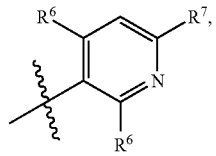

wherein each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl, CONR$^8$R$^9$, and 4- to 6-membered heterocycloalkyl,
  wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO (4- to 6-membered heterocycloalkyl), NHCOC$_1$-C$_6$ alkyl, NHCOC$_6$-C$_{10}$ aryl, NHCO (5- to 10-membered heteroaryl), NHCO (4- to 6-membered heterocycloalkyl), and NHCOC$_2$-C$_6$ alkynyl;
  wherein R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO (5- to 10-membered heteroaryl), OCO (3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy.

In some embodiments, the substituted ring B is

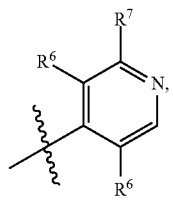

wherein each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl, CONR$^8$R$^9$, and 4- to 6-membered heterocycloalkyl,
  wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO (4- to 6-membered heterocycloalkyl), NHCOC$_1$-C$_6$ alkyl, NHCOC$_6$-C$_{10}$ aryl, NHCO (5- to 10-membered heteroaryl), NHCO (4- to 6-membered heterocycloalkyl), and NHCOC$_2$-C$_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

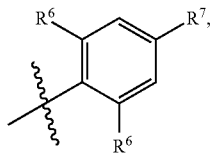

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

In some embodiments, the substituted ring B is

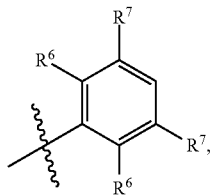

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

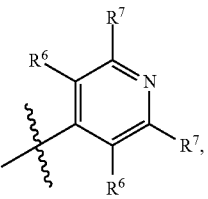

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

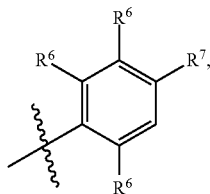

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

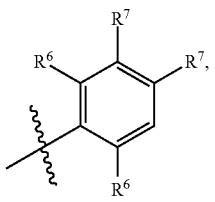

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

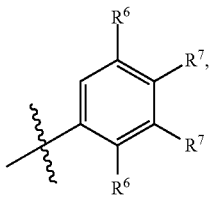

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, the substituted ring B is

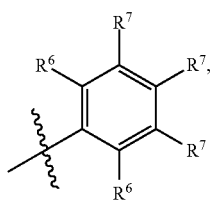

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, $CO$—$C_1$-$C_6$ alkyl, $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO (4- to 6-membered heterocycloalkyl), $NHCOC_1$-$C_6$ alkyl, $NHCOC_6$-$C_{10}$ aryl, NHCO (5- to 10-membered heteroaryl), NHCO (4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO (3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

The Groups $R^4$ and $R^5$

In some embodiments, each of $R^4$ and $R^5$ is independently selected from hydrogen and $C_1$-$C_6$ alkyl.

In some embodiments, $R^4$ is hydrogen.

In some embodiments, $R^5$ is hydrogen.

In some embodiments, each of $R^4$ and $R^5$ is hydrogen.

In some embodiments, $R^4$ is $C_1$-$C_6$ alkyl.

In some embodiments, $R^5$ is $C_1$-$C_6$ alkyl.

In some embodiments, each of $R^4$ and $R^5$ is $C_1$-$C_6$ alkyl,

In some embodiments, $R^4$ is hydrogen and $R^5$ is $C_1$-$C_6$ alkyl.

In some embodiments, $R^4$ is hydrogen; $R^5$ is $C_1$-$C_6$ alkyl; and the carbon bonded to $R^4$ and $R^5$ has (S) stereochemistry.

In some embodiments, $R^4$ is hydrogen; and $R^5$ is $C_1$-$C_6$ alkyl; and the carbon bonded to $R^4$ and $R^5$ has (R) stereochemistry.

The group $R^3$

In some embodiments, $R^3$ is selected from hydrogen, $C_1$-$C_6$ alkyl, and

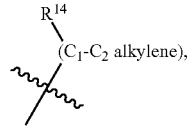

wherein the $C_1$-$C_2$ alkylene group is optionally substituted by oxo.

In some embodiments, $R^3$ is hydrogen.
In some embodiments, $R^3$ is cyano.
In some embodiments, $R^3$ is hydroxy.
In some embodiments, $R^3$ is $C_1$-$C_6$ alkoxy.
In some embodiments, $R^3$ is $C_1$-$C_6$ alkyl.
In some embodiments, $R^3$ is methyl.
In some embodiments, $R^3$ is

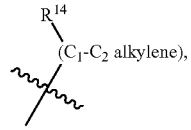

wherein the $C_1$-$C_2$ alkylene group is optionally substituted by oxo.

In some embodiments, $R^3$ is —$CH_2R^{14}$.
In some embodiments, $R^3$ is —$C(O)R^{14}$.
In some embodiments, $R^3$ is —$CH_2CH_2R^{14}$.
In some embodiments, $R^3$ is —$CHR^{14}CH_3$.
In some embodiments, $R^3$ is —$CH_2C(O)R^{14}$.
In some embodiments, $R^3$ is —$C(O)CH_2R^{14}$.

The group $R^{14}$

In some embodiments, $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$.

In some embodiments, $R^{14}$ is hydrogen or $C_1$-$C_6$ alkyl.

In some embodiments, $R^{14}$ is hydrogen, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$.

In some embodiments, $R^{14}$ is hydrogen.

In some embodiments, $R^{14}$ is $C_1$-$C_6$ alkyl.

In some embodiments, $R^{14}$ is methyl.

In some embodiments, $R^{14}$ is 5-10-membered monocyclic or bicyclic heteroaryl optionally independently substituted with 1 or 2 $R^6$.

In some embodiments, $R^{14}$ is $C_6$-$C_{10}$ monocyclic or bicyclic aryl optionally independently substituted with 1 or 2 $R^6$.

The moiety $S(=O)(NHR^3)=N—$

In some embodiments, the sulfur in the moiety $S(=O)(NHR^3)=N—$ has (S) stereochemistry.

In some embodiments, the sulfur in the moiety $S(=O)(NHR^3)=N—$ has (R) stereochemistry.

The group $R^{10}$

In some embodiments, $R^{10}$, is $C_1$-$C_6$ alkyl.

In some embodiments, $R^{10}$, is methyl.

In some embodiments, $R^{10}$, is ethyl.

The groups $R^8$ and $R^9$

In some embodiments, each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is hydrogen,

In some embodiments, each $R^8$ at each occurrence is hydrogen and each $R^9$ at each occurrence is $C_1$-$C_6$ alkyl.

In some embodiments, each $R^8$ at each occurrence is hydrogen and each $R^9$ at each occurrence is methyl.

In some embodiments, each $R^8$ at each occurrence is hydrogen and each $R^9$ at each occurrence is ethyl.

In some embodiments, each of $R^8$ and $R^9$ at each occurrence is methyl.

In some embodiments, each of $R^8$ and $R^9$ at each occurrence is ethyl.

In some embodiments, $R^8$ and $R^9$ taken together with the nitrogen they are attached to form a 3-membered ring.

In some embodiments, $R^8$ and $R^9$ taken together with the nitrogen they are attached to form a 4-membered ring.

In some embodiments, $R^8$ and $R^9$ taken together with the nitrogen they are attached to form a 5-membered ring.

In some embodiments, $R^8$ and $R^9$ taken together with the nitrogen they are attached to form a 6-membered ring optionally containing one or more oxygen atoms in addition to the nitrogen they are attached to.

In some embodiments, $R^8$ and $R^9$ taken together with the nitrogen they are attached to form a 6-membered ring optionally containing one or more nitrogen atoms in addition to the nitrogen they are attached to.

In some embodiments, $R^8$ and $R^9$ taken together with the nitrogen they are attached to form a 7-membered ring.

The Group $R^{13}$

In some embodiments, $R^{13}$ is $C_1$-$C_6$ alkyl.

In some embodiments, $R^{13}$ is methyl.

In some embodiments, $R^{13}$ is ethyl.

In some embodiments, $R^{13}$ is $C_6$-$C_{10}$ aryl.

In some embodiments, $R^{13}$ is phenyl.

In some embodiments, $R^{13}$ is 5- to 10-membered heteroaryl.

The Groups $R^{11}$ and $R^{12}$

In some embodiments, each of $R^{11}$ and $R^{12}$ at each occurrence is independently selected from hydrogen and $C_1$-$C_6$ alkyl.

In some embodiments, each of $R^{11}$ and $R^{12}$ at each occurrence is hydrogen, In some embodiments, each $R^{11}$ at each occurrence is hydrogen and each $R^{12}$ at each occurrence is $C_1$-$C_6$ alkyl.

In some embodiments, each $R^{11}$ at each occurrence is hydrogen and each $R^{12}$ at each occurrence is methyl.

In some embodiments, each $R^{11}$ at each occurrence is hydrogen and each $R^{12}$ at each occurrence is ethyl.

In some embodiments, each of $R^{11}$ and $R^{12}$ at each occurrence is methyl.

In some embodiments, each of $R^{11}$ and $R^{12}$ at each occurrence is ethyl.

In some embodiments of the compound of formula AA, the substituted ring A is

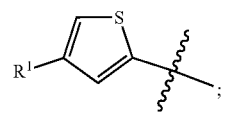

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; $CO—C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

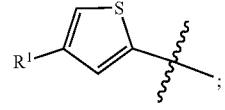

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

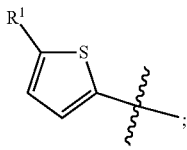

and $R^1$ is selected from:
 $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

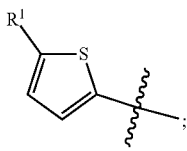

and $R^1$ is selected from:
 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

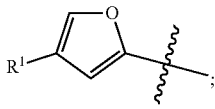

and $R^1$ is selected from:
 $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

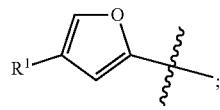

and $R^1$ is selected from:
 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

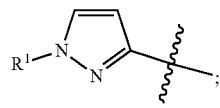

and $R^1$ is selected from:
 $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; and $S(O_2)C_1$-$C_6$ alkyl.

In some embodiments of the compound of formula AA, the substituted ring A is

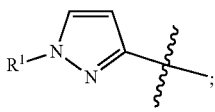

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; phenyl; pyridyl; pyrazolyl; and S(O₂)CH₃.

In some embodiments of the compound of formula AA, the substituted ring A is

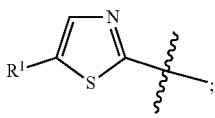

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO (5- to 10-membered heteroaryl); OCO (3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

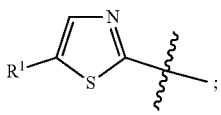

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

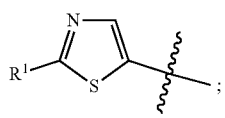

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO (5- to 10-membered heteroaryl); OCO (3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

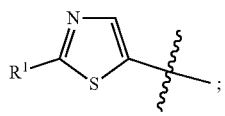

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

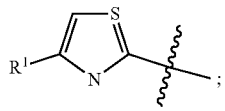

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

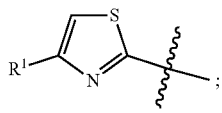

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

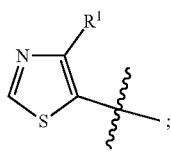

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

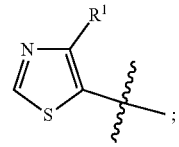

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

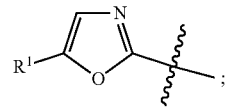

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

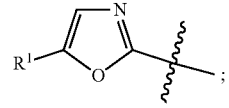

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy- 2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

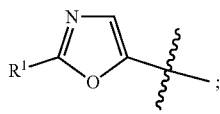

and R$^1$ is selected from:

C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO (5- to 10-membered heteroaryl); OCO (3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

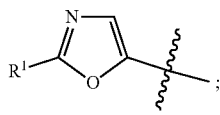

and R$^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

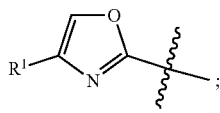

and R$^1$ is selected from:

C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO (5- to 10-membered heteroaryl); OCO (3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

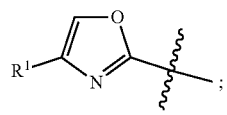

and R$^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

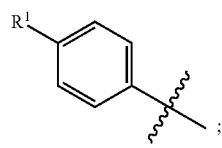

and R$^1$ is selected from:

C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO (5- to 10-membered heteroaryl); OCO (3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

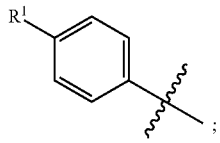

and $R^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO (5- to 10-membered heteroaryl); OCO (3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

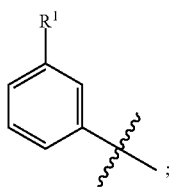

and $R^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO (5- to 10-membered heteroaryl); OCO (3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

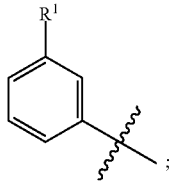

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

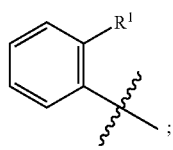

and $R^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO (5- to 10-membered heteroaryl); OCO (3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

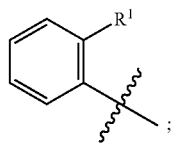

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, A is

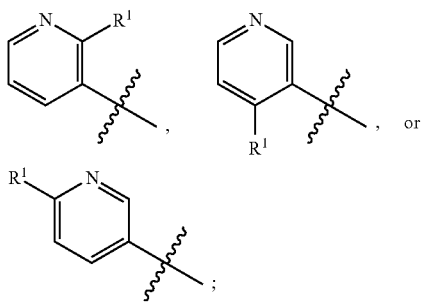

;

and R¹ is selected from:

C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO (5- to 10-membered heteroaryl); OCO (3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, A is

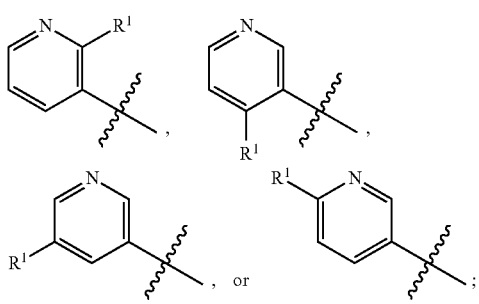

, or

;

and R¹ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

A is

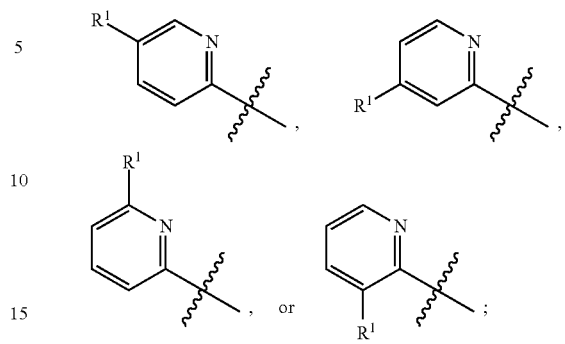

, or

;

and R¹ is selected from:

C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO (5- to 10-membered heteroaryl); OCO (3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, A is

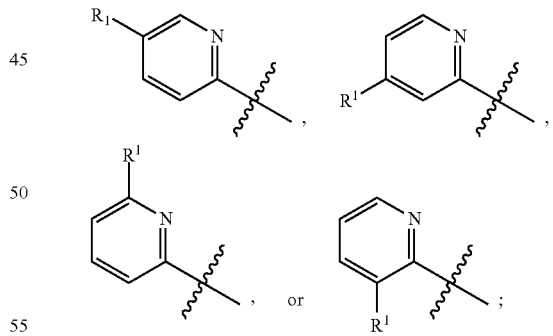

, or

;

and R¹ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

A is

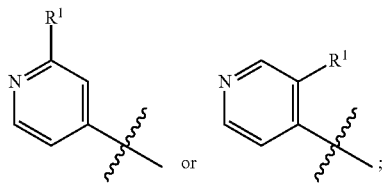

and R[1] is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, A is

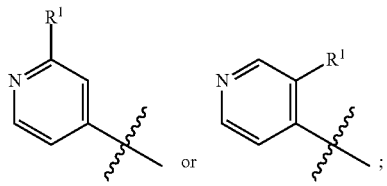

and R[1] is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

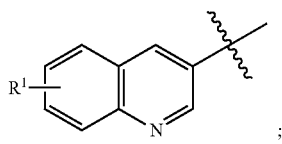

and R[1] is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

A is

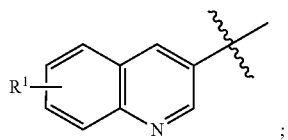

and R[1] is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

A is

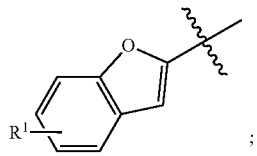

and R[1] is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO (5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

A is

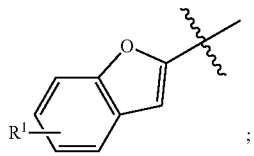

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

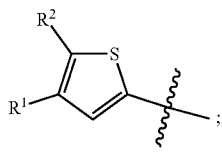

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.

(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl;
or
(xxv) $R^2$ is $C_1$-$C_6$ alkyl optionally substituted with one or more $NR^8R^9$, and $R^1$ is halo.

In some embodiments of the compound of formula AA, the substituted ring A is

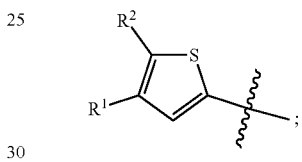

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;

(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro; (l) $R^2$ is 1,3-dioxolan-2-yl, and $R^1$ is chloro; (1i) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl;
or
(liv) $R^2$ is (dimethylamino)methyl, and $R^1$ is methyl.

In some embodiments, of the compound of formula AA, the substituted ring A is

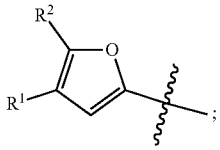

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl;
or
(xxv) $R^2$ is $C_1$-$C_6$ alkyl optionally substituted with one or more $NR^8R^9$, and $R^1$ is halo.

In some embodiments, of the compound of formula AA, the substituted ring A is

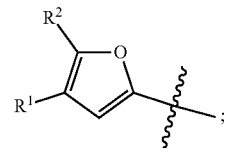

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;

(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

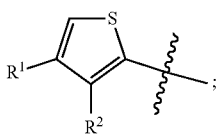

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

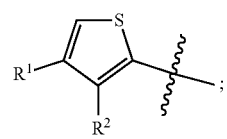

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;

(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

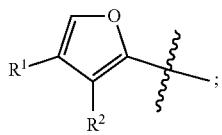

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

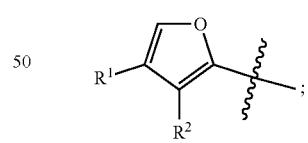

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;

(xi) R¹ is 2-hydroxy-2-propyl and R² is pyridyl;
(xii) R¹ is 2-hydroxy-2-propyl and R² is pyrazolyl;
(xiii) R¹ is 2-hydroxy-2-propyl, and R² is S(O₂)CH₃;
(xiv) R¹ is 2-hydroxy-2-propyl and R² is chloro;
(xv) R¹ is 2-hydroxy-2-propyl and R² is fluoro;
(xvi) R¹ is 1-hydroxy-1-cyclopropyl, and R² is methyl;
(xvii) R¹ is 1-hydroxy-1-cyclobutyl, and R² is methyl;
(xviii) R¹ is 1-hydroxy-1-cyclopentyl, and R² is methyl;
(xix) R¹ is 1-hydroxy-1-cyclohexyl, and R² is methyl;
(xx) R¹ is morpholinyl, and R² is methyl;
(xxi) R¹ is 1,3-dioxolan-2-yl, and R² is methyl;
(xxii) R¹ is 1,3-dioxolan-2-yl, and R² is fluoro;
(xxiii) R¹ is 1,3-dioxolan-2-yl, and R² is chloro;
(xxiv) R¹ is COCH₃, and R² is methyl;
(xxv) R¹ is 2-methoxy-2-propyl, and R² is methyl;
(xxvi) R¹ is (dimethylamino)methyl, and R² is methyl;
(xxvii) R² is 1-hydroxy-2-methylpropan-2-yl, and R¹ is methyl;
(xxviii) R² is 2-hydroxy-2-propyl and R¹ is methyl;
(xxix) R² is 2-hydroxy-2-propyl and R¹ is isopropyl;
(xxx) R² is 2-hydroxy-2-propyl and R¹ is 1-hydroxyethyl;
(xxxi) R² is hydroxymethyl and R¹ is methyl;
(xxxii) R² is 1-hydroxyethyl and R¹ is methyl;
(xxxiii) R² is 2-hydroxyethyl and R¹ is methyl;
(xxxiv) R² is 1-hydroxy-2-propyl and R¹ is methyl;
(xxxv) R² is 2-hydroxy-2-propyl and R¹ is phenyl;
(xxxvi) R² is C₁-C₆ alkyl optionally substituted with one or more hydroxy, and R¹ is 5- to 10-membered heteroaryl;
(xxxvii) R² is 2-hydroxy-2-propyl and R¹ is pyridyl;
(xxxviii) R² is 2-hydroxy-2-propyl and R¹ is pyrazolyl;
(xxxix) R² is C₁-C₆ alkyl optionally substituted with one or more hydroxy, and R¹ is S(O₂)CH₃;
(xl) R² is 2-hydroxy-2-propyl and R¹ is chloro;
(xli) R² is 2-hydroxy-2-propyl and R¹ is fluoro;
(xlii) R² is C₃-C₇ cycloalkyl optionally substituted with one or more hydroxy, and R¹ is C₁-C₆ alkyl;
(xliii) R² is 1-hydroxy-1-cyclopropyl, and R¹ is methyl;
(xliv) R² is 1-hydroxy-1-cyclobutyl, and R¹ is methyl;
(xlv) R² is 1-hydroxy-1-cyclopentyl, and R¹ is methyl;
(xlvi) R² is 1-hydroxy-1-cyclohexyl, and R¹ is methyl;
(xlvii) R² is morpholinyl, and R¹ is methyl;
(xlviii) R² is 1,3-dioxolan-2-yl, and R¹ is methyl;
(xlix) R² is 1,3-dioxolan-2-yl, and R¹ is fluoro;
(l) R² is 1,3-dioxolan-2-yl, and R¹ is chloro;
(li) R² is C₁-C₆ alkyl optionally substituted with one or more oxo, and R¹ is methyl;
(lii) R² is COCH₃, and R¹ is methyl;
(liii) R² is 2-methoxy-2-propyl, and R¹ is methyl; or
(liv) R² is (dimethylamino)methyl, and R¹ is methyl.

In some embodiments, of the compound of formula AA, the substituted ring A is

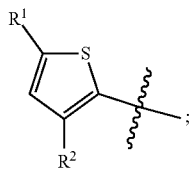

and R¹ and R² are one of the following combinations:
(i) R¹ is C₁-C₆ alkyl optionally substituted with one or more hydroxy, and R² is C₁-C₆ alkyl optionally substituted with one or more hydroxy;
(ii) R¹ is C₁-C₆ alkyl optionally substituted with one or more hydroxy, and R² is C₆-C₁₀ aryl;
(iii) R¹ is C₁-C₆ alkyl optionally substituted with one or more hydroxy, and R² is 5- to 10-membered heteroaryl;
(iv) R¹ is C₁-C₆ alkyl optionally substituted with one or more hydroxy, and R² is SF₅;
(v) R¹ is C₁-C₆ alkyl optionally substituted with one or more hydroxy, and R² is S(O₂)C₁-C₆ alkyl;
(vi) R¹ is C₁-C₆ alkyl optionally substituted with one or more hydroxy, and R² is halo;
(vii) R¹ is C₃-C₇ cycloalkyl optionally substituted with one or more hydroxy, and R² is C₁-C₆ alkyl;
(viii) R¹ is 3- to 7-membered heterocycloalkyl optionally substituted with one or more hydroxy, and R² is C₁-C₆ alkyl;
(ix) R¹ is 3- to 7-membered heterocycloalkyl optionally substituted with one or more hydroxy, and R² is halo;
(x) R¹ is C₁-C₆ alkyl optionally substituted with one or more oxo, and R² is methyl;
(xi) R¹ is C₁-C₆ alkyl optionally substituted with one or more C₁-C₆ alkoxy, and R² is C₁-C₆ alkyl;
(xii) R¹ is C₁-C₆ alkyl optionally substituted with one or more NR⁸R⁹, and R² is C₁-C₆ alkyl;
(xiii) R¹ is C₁-C₆ alkyl optionally substituted with one or more NR⁸R⁹, and R² is halo;
(xiv) R² is C₁-C₆ alkyl optionally substituted with one or more hydroxy, and R¹ is C₆-C₁₀ aryl;
(xv) R² is C₁-C₆ alkyl optionally substituted with one or more hydroxy, and R¹ is 5- to 10-membered heteroaryl;
(xvi) R² is C₁-C₆ alkyl optionally substituted with one or more hydroxy, and R¹ is SF₅.
(xvii) R² is C₁-C₆ alkyl optionally substituted with one or more hydroxy, and R¹ is S(O₂)C₁-C₆ alkyl;
(xviii) R² is C₁-C₆ alkyl optionally substituted with one or more hydroxy, and R¹ is halo;
(xix) R² is C₃-C₇ cycloalkyl optionally substituted with one or more hydroxy, and R¹ is C₁-C₆ alkyl;
(xx) R² is 3- to 7-membered heterocycloalkyl optionally substituted with one or more hydroxy, and R¹ is C₁-C₆ alkyl;
(xxi) R² is 3- to 7-membered heterocycloalkyl optionally substituted with one or more hydroxy, and R¹ is halo;
(xxii) R² is C₁-C₆ alkyl optionally substituted with one or more oxo, and R¹ is methyl;
(xxiii) R² is C₁-C₆ alkyl optionally substituted with one or more C₁-C₆ alkoxy, and R¹ is C₁-C₆ alkyl;
(xxiv) R² is C₁-C₆ alkyl optionally substituted with one or more NR⁸R⁹, and R¹ is C₁-C₆ alkyl; or
(xxv) R² is C₁-C₆ alkyl optionally substituted with one or more NR⁸R⁹, and R¹ is halo.

In some embodiments, of the compound of formula AA, the substituted ring A is

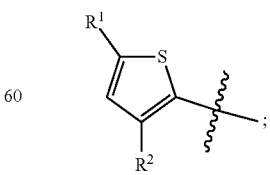

and R¹ and R² are one of the following combinations:
(i) R¹ is 1-hydroxy-2-methylpropan-2-yl, and R² is methyl;

(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

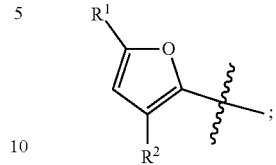

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl;
(xxv) or
(xxvi) $R^2$ is $C_1$-$C_6$ alkyl optionally substituted with one or more $NR^8R^9$, and $R^1$ is halo.

In some embodiments, of the compound of formula AA, the substituted ring A is

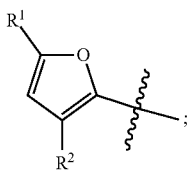

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

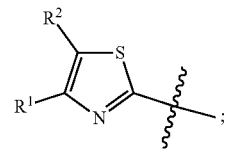

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$;
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;

(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

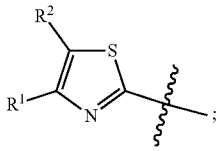

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

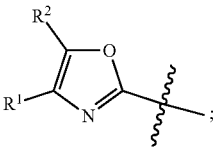

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;

(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

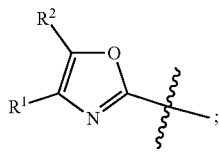

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

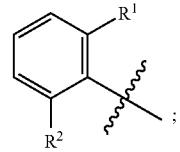

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;

(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

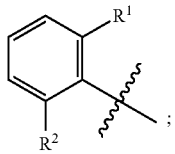

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

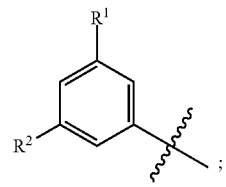

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;

(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

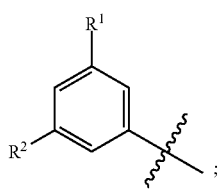

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

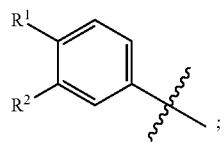

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;

(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

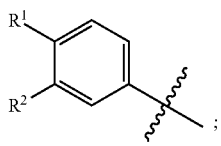

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

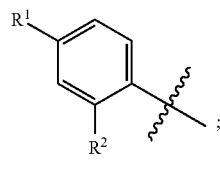

and $R^1$ and $R^2$ are one of the following combinations:
  (i) $R^1$ is $C_1$-$C_6$ alkyl optionally substituted with one or more hydroxy, and $R^2$ is $C_1$-$C_6$ alkyl optionally substituted with one or more hydroxy;
  (ii) $R^1$ is $C_1$-$C_6$ alkyl optionally substituted with one or more hydroxy, and $R^2$ is $C_6$-$C_{10}$ aryl;
  (iii) $R^1$ is $C_1$-$C_6$ alkyl optionally substituted with one or more hydroxy, and $R^2$ is 5- to 10-membered heteroaryl;
  (iv) $R^1$ is $C_1$-$C_6$ alkyl optionally substituted with one or more hydroxy, and $R^2$ is $SF_5$;
  (v) $R^1$ is $C_1$-$C_6$ alkyl optionally substituted with one or more hydroxy, and $R^2$ is $S(O_2)C_1$-$C_6$ alkyl;
  (vi) $R^1$ is $C_1$-$C_6$ alkyl optionally substituted with one or more hydroxy, and $R^2$ is halo;
  (vii) $R^1$ is $C_3$-$C_7$ cycloalkyl optionally substituted with one or more hydroxy, and $R^2$ is $C_1$-$C_6$ alkyl;
  (viii) $R^1$ is 3- to 7-membered heterocycloalkyl optionally substituted with one or more hydroxy, and $R^2$ is $C_1$-$C_6$ alkyl;
  (ix) $R^1$ is 3- to 7-membered heterocycloalkyl optionally substituted with one or more hydroxy, and $R^2$ is halo;
  (x) $R^1$ is $C_1$-$C_6$ alkyl optionally substituted with one or more oxo, and $R^2$ is methyl;
  (xi) $R^1$ is $C_1$-$C_6$ alkyl optionally substituted with one or more $C_1$-$C_6$ alkoxy, and $R^2$ is $C_1$-$C_6$ alkyl;
  (xii) $R^1$ is $C_1$-$C_6$ alkyl optionally substituted with one or more $NR^8R^9$, and $R^2$ is $C_1$-$C_6$ alkyl;
  (xiii) $R^1$ is $C_1$-$C_6$ alkyl optionally substituted with one or more $NR^8R^9$, and $R^2$ is halo;
  (xiv) $R^2$ is $C_1$-$C_6$ alkyl optionally substituted with one or more hydroxy, and $R^1$ is $C_6$-$C_{10}$ aryl;
  (xv) $R^2$ is $C_1$-$C_6$ alkyl optionally substituted with one or more hydroxy, and $R^1$ is 5- to 10-membered heteroaryl;
  (xvi) $R^2$ is $C_1$-$C_6$ alkyl optionally substituted with one or more hydroxy, and $R^1$ is $SF_5$.
  (xvii) $R^2$ is $C_1$-$C_6$ alkyl optionally substituted with one or more hydroxy, and $R^1$ is $S(O_2)C_1$-$C_6$ alkyl;
  (xviii) $R^2$ is $C_1$-$C_6$ alkyl optionally substituted with one or more hydroxy, and $R^1$ is halo;
  (xix) $R^2$ is $C_3$-$C_7$ cycloalkyl optionally substituted with one or more hydroxy, and $R^1$ is $C_1$-$C_6$ alkyl;
  (xx) $R^2$ is 3- to 7-membered heterocycloalkyl optionally substituted with one or more hydroxy, and $R^1$ is $C_1$-$C_6$ alkyl;
  (xxi) $R^2$ is 3- to 7-membered heterocycloalkyl optionally substituted with one or more hydroxy, and $R^1$ is halo;
  (xxii) $R^2$ is $C_1$-$C_6$ alkyl optionally substituted with one or more oxo, and $R^1$ is methyl;
  (xxiii) $R^2$ is $C_1$-$C_6$ alkyl optionally substituted with one or more $C_1$-$C_6$ alkoxy, and $R^1$ is $C_1$-$C_6$ alkyl;
  (xxiv) $R^2$ is $C_1$-$C_6$ alkyl optionally substituted with one or more $NR^8R^9$, and $R^1$ is $C_1$-$C_6$ alkyl; or
  (xxv) $R^2$ is $C_1$-$C_6$ alkyl optionally substituted with one or more $NR^8R^9$, and $R^1$ is halo.

In some embodiments, of the compound of formula AA, the substituted ring A is

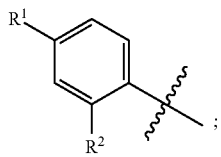

and $R^1$ and $R^2$ are one of the following combinations:
  (i) $R^1$ is 1-hydroxy-2-methylpropan-2-yl, and $R^2$ is methyl;
  (ii) $R^1$ is 2-hydroxy-2-propyl and $R^2$ is methyl;
  (iii) $R^1$ is 2-hydroxy-2-propyl and $R^2$ is isopropyl;
  (iv) $R^1$ is 2-hydroxy-2-propyl and $R^2$ is 2-hydroxy-2-propyl;
  (v) $R^1$ is 2-hydroxy-2-propyl and $R^2$ is 1-hydroxyethyl;
  (vi) $R^1$ is hydroxymethyl and $R^2$ is methyl;
  (vii) $R^1$ is 1-hydroxyethyl and $R^2$ is methyl;
  (viii) $R^1$ is 2-hydroxyethyl and $R^2$ is methyl;
  (ix) $R^1$ is 1-hydroxy-2-propyl and $R^2$ is methyl;
  (x) $R^1$ is 2-hydroxy-2-propyl and $R^2$ is phenyl;
  (xi) $R^1$ is 2-hydroxy-2-propyl and $R^2$ is pyridyl;
  (xii) $R^1$ is 2-hydroxy-2-propyl and $R^2$ is pyrazolyl;
  (xiii) $R^1$ is 2-hydroxy-2-propyl, and $R^2$ is $S(O_2)CH_3$;
  (xiv) $R^1$ is 2-hydroxy-2-propyl and $R^2$ is chloro;
  (xv) $R^1$ is 2-hydroxy-2-propyl and $R^2$ is fluoro;
  (xvi) $R^1$ is 1-hydroxy-1-cyclopropyl, and $R^2$ is methyl;
  (xvii) $R^1$ is 1-hydroxy-1-cyclobutyl, and $R^2$ is methyl;
  (xviii) $R^1$ is 1-hydroxy-1-cyclopentyl, and $R^2$ is methyl;
  (xix) $R^1$ is 1-hydroxy-1-cyclohexyl, and $R^2$ is methyl;
  (xx) $R^1$ is morpholinyl, and $R^2$ is methyl;
  (xxi) $R^1$ is 1,3-dioxolan-2-yl, and $R^2$ is methyl;
  (xxii) $R^1$ is 1,3-dioxolan-2-yl, and $R^2$ is fluoro;
  (xxiii) $R^1$ is 1,3-dioxolan-2-yl, and $R^2$ is chloro;
  (xxiv) $R^1$ is $COCH_3$, and $R^2$ is methyl;
  (xxv) $R^1$ is 2-methoxy-2-propyl, and $R^2$ is methyl;
  (xxvi) $R^1$ is (dimethylamino)methyl, and $R^2$ is methyl;
  (xxvii) $R^2$ is 1-hydroxy-2-methylpropan-2-yl, and $R^1$ is methyl;
  (xxviii) $R^2$ is 2-hydroxy-2-propyl and $R^1$ is methyl;
  (xxix) $R^2$ is 2-hydroxy-2-propyl and $R^1$ is isopropyl;
  (xxx) $R^2$ is 2-hydroxy-2-propyl and $R^1$ is 1-hydroxyethyl;
  (xxxi) $R^2$ is hydroxymethyl and $R^1$ is methyl;
  (xxxii) $R^2$ is 1-hydroxyethyl and $R^1$ is methyl;
  (xxxiii) $R^2$ is 2-hydroxyethyl and $R^1$ is methyl;
  (xxxiv) $R^2$ is 1-hydroxy-2-propyl and $R^1$ is methyl;
  (xxxv) $R^2$ is 2-hydroxy-2-propyl and $R^1$ is phenyl;
  (xxxvi) $R^2$ is $C_1$-$C_6$ alkyl optionally substituted with one or more hydroxy, and $R^1$ is 5- to 10-membered heteroaryl;
  (xxxvii) $R^2$ is 2-hydroxy-2-propyl and $R^1$ is pyridyl;
  (xxxviii) $R^2$ is 2-hydroxy-2-propyl and $R^1$ is pyrazolyl;
  (xxxix) $R^2$ is $C_1$-$C_6$ alkyl optionally substituted with one or more hydroxy, and $R^1$ is $S(O_2)CH_3$;
  (xl) $R^2$ is 2-hydroxy-2-propyl and $R^1$ is chloro;
  (xli) $R^2$ is 2-hydroxy-2-propyl and $R^1$ is fluoro;
  (xlii) $R^2$ is $C_3$-$C_7$ cycloalkyl optionally substituted with one or more hydroxy, and $R^1$ is $C_1$-$C_6$ alkyl;
  (xliii) $R^2$ is 1-hydroxy-1-cyclopropyl, and $R^1$ is methyl;
  (xliv) $R^2$ is 1-hydroxy-1-cyclobutyl, and $R^1$ is methyl;
  (xlv) $R^2$ is 1-hydroxy-1-cyclopentyl, and $R^1$ is methyl;
  (xlvi) $R^2$ is 1-hydroxy-1-cyclohexyl, and $R^1$ is methyl;
  (xlvii) $R^2$ is morpholinyl, and $R^1$ is methyl;
  (xlviii) $R^2$ is 1,3-dioxolan-2-yl, and $R^1$ is methyl;
  (xlix) $R^2$ is 1,3-dioxolan-2-yl, and $R^1$ is fluoro;
  (l) $R^2$ is 1,3-dioxolan-2-yl, and $R^1$ is chloro;
  (li) $R^2$ is $C_1$-$C_6$ alkyl optionally substituted with one or more oxo, and $R^1$ is methyl;
  (lii) $R^2$ is $COCH_3$, and $R^1$ is methyl;
  (liii) $R^2$ is 2-methoxy-2-propyl, and $R^1$ is methyl; or
  (liv) $R^2$ is (dimethylamino)methyl, and $R^1$ is methyl.

In some embodiments, of the compound of formula AA, the substituted ring A is

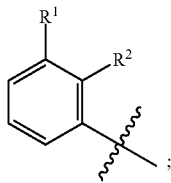

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

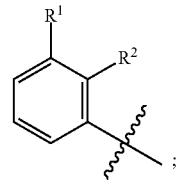

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;
(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;

(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments, of the compound of formula AA, the substituted ring A is

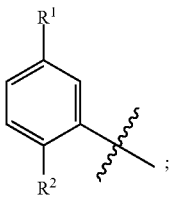

and $R^1$ and $R^2$ are one of the following combinations:
(i) $R^1$ is $C_1$-$C_6$ alkyl optionally substituted with one or more hydroxy, and $R^2$ is $C_1$-$C_6$ alkyl optionally substituted with one or more hydroxy;
(ii) $R^1$ is $C_1$-$C_6$ alkyl optionally substituted with one or more hydroxy, and $R^2$ is $C_6$-$C_{10}$ aryl;
(iii) $R^1$ is $C_1$-$C_6$ alkyl optionally substituted with one or more hydroxy, and $R^2$ is 5- to 10-membered heteroaryl;
(iv) $R^1$ is $C_1$-$C_6$ alkyl optionally substituted with one or more hydroxy, and $R^2$ is $SF_5$;
(v) $R^1$ is $C_1$-$C_6$ alkyl optionally substituted with one or more hydroxy, and $R^2$ is $S(O_2)C_1$-$C_6$ alkyl;
(vi) $R^1$ is $C_1$-$C_6$ alkyl optionally substituted with one or more hydroxy, and $R^2$ is halo;
(vii) $R^1$ is $C_3$-$C_7$ cycloalkyl optionally substituted with one or more hydroxy, and $R^2$ is $C_1$-$C_6$ alkyl;
(viii) $R^1$ is 3- to 7-membered heterocycloalkyl optionally substituted with one or more hydroxy, and $R^2$ is $C_1$-$C_6$ alkyl;
(ix) $R^1$ is 3- to 7-membered heterocycloalkyl optionally substituted with one or more hydroxy, and $R^2$ is halo;
(x) $R^1$ is $C_1$-$C_6$ alkyl optionally substituted with one or more oxo, and $R^2$ is methyl;
(xi) $R^1$ is $C_1$-$C_6$ alkyl optionally substituted with one or more $C_1$-$C_6$ alkoxy, and $R^2$ is $C_1$-$C_6$ alkyl;
(xii) $R^1$ is $C_1$-$C_6$ alkyl optionally substituted with one or more $NR^8R^9$, and $R^2$ is $C_1$-$C_6$ alkyl;
(xiii) $R^1$ is $C_1$-$C_6$ alkyl optionally substituted with one or more $NR^8R^9$, and $R^2$ is halo;
(xiv) $R^2$ is $C_1$-$C_6$ alkyl optionally substituted with one or more hydroxy, and $R^1$ is $C_6$-$C_{10}$ aryl;
(xv) $R^2$ is $C_1$-$C_6$ alkyl optionally substituted with one or more hydroxy, and $R^1$ is 5- to 10-membered heteroaryl;
(xvi) $R^2$ is $C_1$-$C_6$ alkyl optionally substituted with one or more hydroxy, and $R^1$ is $SF_5$.
(xvii) $R^2$ is $C_1$-$C_6$ alkyl optionally substituted with one or more hydroxy, and $R^1$ is $S(O_2)C_1$-$C_6$ alkyl;
(xviii) $R^2$ is $C_1$-$C_6$ alkyl optionally substituted with one or more hydroxy, and $R^1$ is halo;
(xix) $R^2$ is $C_3$-$C_7$ cycloalkyl optionally substituted with one or more hydroxy, and $R^1$ is $C_1$-$C_6$ alkyl;
(xx) $R^2$ is 3- to 7-membered heterocycloalkyl optionally substituted with one or more hydroxy, and $R^1$ is $C_1$-$C_6$ alkyl;
(xxi) $R^2$ is 3- to 7-membered heterocycloalkyl optionally substituted with one or more hydroxy, and $R^1$ is halo;
(xxii) $R^2$ is $C_1$-$C_6$ alkyl optionally substituted with one or more oxo, and $R^1$ is methyl;
(xxiii) $R^2$ is $C_1$-$C_6$ alkyl optionally substituted with one or more $C_1$-$C_6$ alkoxy, and $R^1$ is $C_1$-$C_6$ alkyl;
(xxiv) $R^2$ is $C_1$-$C_6$ alkyl optionally substituted with one or more $NR^8R^9$, and $R^1$ is $C_1$-$C_6$ alkyl; or
(xxv) $R^2$ is $C_1$-$C_6$ alkyl optionally substituted with one or more $NR^8R^9$, and $R^1$ is halo.

In some embodiments, of the compound of formula AA, the substituted ring A is

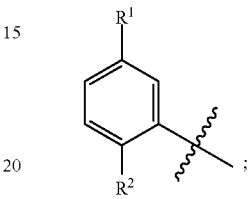

and $R^1$ and $R^2$ are one of the following combinations:
(i) $R^1$ is 1-hydroxy-2-methylpropan-2-yl, and $R^2$ is methyl;
(ii) $R^1$ is 2-hydroxy-2-propyl and $R^2$ is methyl;
(iii) $R^1$ is 2-hydroxy-2-propyl and $R^2$ is isopropyl;
(iv) $R^1$ is 2-hydroxy-2-propyl and $R^2$ is 2-hydroxy-2-propyl;
(v) $R^1$ is 2-hydroxy-2-propyl and $R^2$ is 1-hydroxyethyl;
(vi) $R^1$ is hydroxymethyl and $R^2$ is methyl;
(vii) $R^1$ is 1-hydroxyethyl and $R^2$ is methyl;
(viii) $R^1$ is 2-hydroxyethyl and $R^2$ is methyl;
(ix) $R^1$ is 1-hydroxy-2-propyl and $R^2$ is methyl;
(x) $R^1$ is 2-hydroxy-2-propyl and $R^2$ is phenyl;
(xi) $R^1$ is 2-hydroxy-2-propyl and $R^2$ is pyridyl;
(xii) $R^1$ is 2-hydroxy-2-propyl and $R^2$ is pyrazolyl;
(xiii) $R^1$ is 2-hydroxy-2-propyl, and $R^2$ is $S(O_2)CH_3$;
(xiv) $R^1$ is 2-hydroxy-2-propyl and $R^2$ is chloro;
(xv) $R^1$ is 2-hydroxy-2-propyl and $R^2$ is fluoro;
(xvi) $R^1$ is 1-hydroxy-1-cyclopropyl, and $R^2$ is methyl;
(xvii) $R^1$ is 1-hydroxy-1-cyclobutyl, and $R^2$ is methyl;
(xviii) $R^1$ is 1-hydroxy-1-cyclopentyl, and $R^2$ is methyl;
(xix) $R^1$ is 1-hydroxy-1-cyclohexyl, and $R^2$ is methyl;
(xx) $R^1$ is morpholinyl, and $R^2$ is methyl;
(xxi) $R^1$ is 1,3-dioxolan-2-yl, and $R^2$ is methyl;
(xxii) $R^1$ is 1,3-dioxolan-2-yl, and $R^2$ is fluoro;
(xxiii) $R^1$ is 1,3-dioxolan-2-yl, and $R^2$ is chloro;
(xxiv) $R^1$ is $COCH_3$, and $R^2$ is methyl;
(xxv) $R^1$ is 2-methoxy-2-propyl, and $R^2$ is methyl;
(xxvi) $R^1$ is (dimethylamino)methyl, and $R^2$ is methyl;
(xxvii) $R^2$ is 1-hydroxy-2-methylpropan-2-yl, and $R^1$ is methyl;
(xxviii) $R^2$ is 2-hydroxy-2-propyl and $R^1$ is methyl;
(xxix) $R^2$ is 2-hydroxy-2-propyl and $R^1$ is isopropyl;
(xxx) $R^2$ is 2-hydroxy-2-propyl and $R^1$ is 1-hydroxyethyl;
(xxxi) $R^2$ is hydroxymethyl and $R^1$ is methyl;
(xxxii) $R^2$ is 1-hydroxyethyl and $R^1$ is methyl;
(xxxiii) $R^2$ is 2-hydroxyethyl and $R^1$ is methyl;
(xxxiv) $R^2$ is 1-hydroxy-2-propyl and $R^1$ is methyl;
(xxxv) $R^2$ is 2-hydroxy-2-propyl and $R^1$ is phenyl;
(xxxvi) $R^2$ is $C_1$-$C_6$ alkyl optionally substituted with one or more hydroxy, and $R^1$ is 5- to 10-membered heteroaryl;
(xxxvii) $R^2$ is 2-hydroxy-2-propyl and $R^1$ is pyridyl;
(xxxviii) $R^2$ is 2-hydroxy-2-propyl and $R^1$ is pyrazolyl;

(xxxix) $R^2$ is $C_1$-$C_6$ alkyl optionally substituted with one or more hydroxy, and $R^1$ is $S(O_2)CH_3$;
(xl) $R^2$ is 2-hydroxy-2-propyl and $R^1$ is chloro;
(xli) $R^2$ is 2-hydroxy-2-propyl and $R^1$ is fluoro;
(xlii) $R^2$ is $C_3$-$C_7$ cycloalkyl optionally substituted with one or more hydroxy, and $R^1$ is $C_1$-$C_6$ alkyl;
(xliii) $R^2$ is 1-hydroxy-1-cyclopropyl, and $R^1$ is methyl;
(xliv) $R^2$ is 1-hydroxy-1-cyclobutyl, and $R^1$ is methyl;
(xlv) $R^2$ is 1-hydroxy-1-cyclopentyl, and $R^1$ is methyl;
(xlvi) $R^2$ is 1-hydroxy-1-cyclohexyl, and $R^1$ is methyl;
(xlvii) $R^2$ is morpholinyl, and $R^1$ is methyl;
(xlviii) $R^2$ is 1,3-dioxolan-2-yl, and $R^1$ is methyl;
(xlix) $R^2$ is 1,3-dioxolan-2-yl, and $R^1$ is fluoro;
(l) $R^2$ is 1,3-dioxolan-2-yl, and $R^1$ is chloro;
(li) $R^2$ is $C_1$-$C_6$ alkyl optionally substituted with one or more oxo, and $R^1$ is methyl;
(lii) $R^2$ is $COCH_3$, and $R^1$ is methyl;
(liii) $R^2$ is 2-methoxy-2-propyl, and $R^1$ is methyl; or
(liv) $R^2$ is (dimethylamino)methyl, and $R^1$ is methyl.

In some embodiments of the compound of formula AA, the substituted ring B is

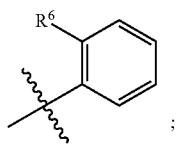

;

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

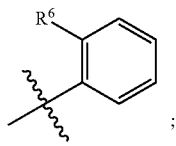

;

and $R^6$ is selected from:
isopropyl, ethyl, methyl, trifluoromethyl, trifluoromethoxy, cyclopropyl, halo, chloro, and fluoro.

In some embodiments of the compound of formula AA, the substituted ring B is

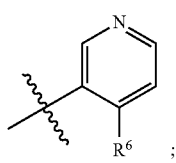

;

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

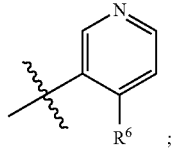

;

and $R^6$ is selected from:
isopropyl, ethyl, methyl, trifluoromethyl, trifluoromethoxy, cyclopropyl, halo, chloro, and fluoro.

In some embodiments of the compound of formula AA, the substituted ring B is

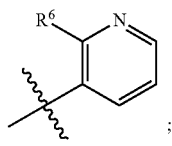

;

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

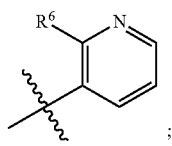

;

and $R^6$ is selected from:
isopropyl, ethyl, methyl, trifluoromethyl, trifluoromethoxy, cyclopropyl, halo, chloro, and fluoro.

In some embodiments of the compound of formula AA, the substituted ring B is

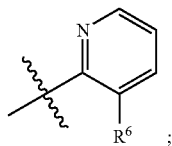

;

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

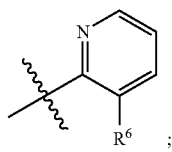

;

and R⁶ is selected from:
  isopropyl, ethyl, methyl, trifluoromethyl, trifluoromethoxy, cyclopropyl, halo, chloro, and fluoro.

In some embodiments of the compound of formula AA, the substituted ring B is

[structure: pyridine ring with R⁶ substituent]

and R⁶ is selected from:
  $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

[structure: pyridine ring with R⁶ substituent]

and R⁶ is selected from:
  isopropyl, ethyl, methyl, trifluoromethyl, trifluoromethoxy, cyclopropyl, halo, chloro, and fluoro.

In some embodiments, of the compound of formula AA, the substituted ring B is

[structure: benzene ring with two R⁶ substituents]

and the two R⁶ are one of the following combinations:
  One R⁶ is $C_1$-$C_6$ alkyl, and the other R⁶ is $C_1$-$C_6$ alkyl optionally substituted with one or more halo;
  One R⁶ is $C_1$-$C_6$ alkyl and the other R⁶ is $C_1$-$C_6$ alkyl;
  One R⁶ is $C_1$-$C_6$ alkyl, and the other R⁶ is $C_1$-$C_6$ alkyl substituted with one or more halo;
  One R⁶ is $C_1$-$C_6$ alkyl, and the other R⁶ is $C_3$-$C_7$ cycloalkyl;
  One R⁶ is $C_1$-$C_6$ alkyl, and the other R⁶ is halo;
  One R⁶ is $C_1$-$C_6$ alkyl, and the other R⁶ is cyano;
  One R⁶ is $C_3$-$C_7$ cycloalkyl, and the other R⁶ is $C_3$-$C_7$ cycloalkyl;
  One R⁶ is $C_3$-$C_7$ cycloalkyl, and the other R⁶ is halo;
  One R⁶ is cyclopropyl and the other R⁶ is halo;
  One R⁶ is $C_1$-$C_6$ alkyl, and the other R⁶ is $C_1$-$C_6$ alkoxy optionally substituted with one or more halo;
  One R⁶ is $C_1$-$C_6$ alkyl, and the other R⁶ is $C_1$-$C_6$ alkoxy;
  One R⁶ is $C_1$-$C_6$ alkyl, and the other R⁶ is $C_1$-$C_6$ alkoxy substituted with one or more halo;
  One R⁶ is halo, and the other R⁶ is $C_1$-$C_6$ haloalkyl;
  One R⁶ is halo, and the other R⁶ is $C_1$-$C_6$ haloalkoxy;
  One R⁶ is $C_1$-$C_6$ alkoxy; and the other R⁶ is halo;
  One R⁶ is $C_1$-$C_6$ alkoxy; and the other R⁶ is chloro.

In some embodiments, of the compound of formula AA, the substituted ring B is

[structure: benzene ring with two R⁶ substituents]

and the two R⁶ are one of the following combinations:
  One R⁶ is isopropyl; and the other R⁶ is methyl;
  One R⁶ is isopropyl; and the other R⁶ is n-propyl;
  One R⁶ is isopropyl; and the other R⁶ is isopropyl;
  One R⁶ is isopropyl; and the other R⁶ is trifluoromethyl;
  One R⁶ is isopropyl; and the other R⁶ is cyclopropyl;
  One R⁶ is isopropyl; and the other R⁶ is chloro;
  One R⁶ is isopropyl; and the other R⁶ is fluoro;
  One R⁶ is ethyl; and the other R⁶ is fluoro;
  One R⁶ is isopropyl; and the other R⁶ is cyano;
  One R⁶ is cyclopropyl; and the other R⁶ is cyclopropyl;
  One R⁶ is cyclopropyl; and the other R⁶ is chloro;
  One R⁶ is cyclopropyl; and the other R⁶ is fluoro;
  One R⁶ is isopropyl; and the other R⁶ is methoxy;
  One R⁶ is isopropyl; and the other R⁶ is trifluoromethoxy.

In some embodiments, of the compound of formula AA, the substituted ring B is

[structure: benzene ring with R⁶ and R⁷ substituents]

and R⁶ and R⁷ are one of the following combinations:
  R⁶ is $C_1$-$C_6$ alkyl, and R⁷ is $C_1$-$C_6$ alkyl optionally substituted with one or more halo;
  R⁶ is $C_1$-$C_6$ alkyl and R⁷ is $C_1$-$C_6$ alkyl;
  R⁶ is $C_1$-$C_6$ alkyl, and R⁷ is $C_1$-$C_6$ alkyl substituted with one or more halo;
  R⁶ is $C_1$-$C_6$ alkyl, and R⁷ is $C_3$-$C_7$ cycloalkyl;
  R⁶ is $C_1$-$C_6$ alkyl, and R⁷ is halo;
  R⁶ is $C_1$-$C_6$ alkyl, and R⁷ is cyano;
  R⁶ is $C_3$-$C_7$ cycloalkyl, and R⁷ is $C_3$-$C_7$ cycloalkyl;
  R⁶ is $C_3$-$C_7$ cycloalkyl, and R⁷ is halo;
  R⁶ is cyclopropyl and R⁷ is halo;
  R⁶ is $C_1$-$C_6$ alkyl, and R⁷ is $C_1$-$C_6$ alkoxy optionally substituted with one or more halo;
  R⁶ is $C_1$-$C_6$ alkyl, and R⁷ is $C_1$-$C_6$ alkoxy;
  R⁶ is $C_1$-$C_6$ alkyl, and R⁷ is $C_1$-$C_6$ alkoxy substituted with one or more halo;
  R⁶ is halo, and R⁷ is $C_1$-$C_6$ haloalkyl;
  R⁶ is halo, and R⁷ is $C_1$-$C_6$ haloalkoxy;
  R⁶ is $C_1$-$C_6$ alkoxy; and R⁷ is halo;
  R⁶ is $C_1$-$C_6$ alkoxy; and R⁷ is chloro;
  R⁷ is $C_1$-$C_6$ alkyl, and R⁶ is $C_1$-$C_6$ alkyl optionally substituted with one or more halo;
  R⁷ is $C_1$-$C_6$ alkyl, and R⁶ is $C_1$-$C_6$ alkyl substituted with one or more halo;
  R⁷ is $C_1$-$C_6$ alkyl, and R⁶ is $C_3$-$C_7$ cycloalkyl;
  R⁷ is $C_1$-$C_6$ alkyl, and R⁶ is halo;
  R⁷ is $C_1$-$C_6$ alkyl and R⁶ is halo;
  R⁷ is $C_1$-$C_6$ alkyl, and R⁶ is cyano;
  R⁷ is $C_3$-$C_7$ cycloalkyl, and R⁶ is $C_3$-$C_7$ cycloalkyl;

$R^7$ is $C_3$-$C_7$ cycloalkyl, and $R^6$ is halo;
$R^7$ is $C_3$-$C_7$ cycloalkyl and $R^6$ is halo;
$R^7$ is $C_1$-$C_6$ alkyl, and $R^6$ is $C_1$-$C_6$ alkoxy optionally substituted with one or more halo;
$R^7$ is $C_1$-$C_6$ alkyl, and $R^6$ is $C_1$-$C_6$ alkoxy;
$R^7$ is $C_1$-$C_6$ alkyl, and $R^6$ is $C_1$-$C_6$ alkoxy substituted with one or more halo;
$R^7$ is halo, and $R^6$ is $C_1$-$C_6$ haloalkyl;
$R^7$ is halo, and $R^6$ is $C_1$-$C_6$ haloalkoxy;
$R^7$ is $C_1$-$C_6$ alkoxy; and $R^6$ is halo;
$R^7$ is $C_1$-$C_6$ alkoxy; and $R^6$ is chloro;

In some embodiments, of the compound of formula AA, the substituted ring B is

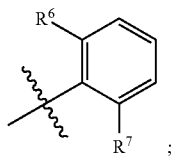
;

and $R^6$ and $R^7$ are one of the following combinations:
$R^6$ is isopropyl; and $R^7$ is methyl;
$R^6$ is isopropyl; and $R^7$ is isopropyl;
$R^6$ is isopropyl; and $R^7$ is trifluoromethyl;
$R^6$ is isopropyl; and $R^7$ is cyclopropyl;
$R^6$ is isopropyl; and $R^7$ is chloro;
$R^6$ is isopropyl; and $R^7$ is fluoro;
$R^6$ is ethyl; and $R^7$ is fluoro;
$R^6$ is isopropyl; and $R^7$ is cyano;
$R^6$ is cyclopropyl; and $R^7$ is cyclopropyl;
$R^6$ is cyclopropyl; and $R^7$ is chloro;
$R^6$ is cyclopropyl; and $R^7$ is fluoro;
$R^6$ is isopropyl; and $R^7$ is methoxy;
$R^6$ is isopropyl; and $R^7$ is trifluoromethoxy;
$R^6$ is chloro; and $R^7$ is trifluoromethyl;
$R^6$ is chloro; and $R^7$ is trifluoromethoxy;
$R^7$ is isopropyl; and $R^6$ is methyl;
$R^7$ is isopropyl; and $R^6$ is trifluoromethyl;
$R^7$ is isopropyl; and $R^6$ is cyclopropyl;
$R^7$ is isopropyl; and $R^6$ is chloro;
$R^7$ is ethyl; and $R^6$ is fluoro;
$R^7$ is isopropyl; and $R^6$ is cyano;
$R^7$ is cyclopropyl; and $R^6$ is cyclopropyl;
$R^7$ is cyclopropyl; and $R^6$ is chloro;
$R^7$ is cyclopropyl; and $R^6$ is fluoro;
$R^7$ is isopropyl; and $R^6$ is methoxy;
$R^7$ is isopropyl; and $R^6$ is trifluoromethoxy;
$R^7$ is chloro; and $R^6$ is trifluoromethyl;
$R^7$ is chloro; and $R^6$ is trifluoromethoxy.

In some embodiments, of the compound of formula AA, the substituted ring B is

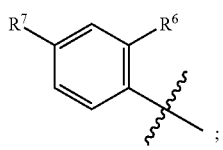
;

and $R^6$ and $R^7$ are one of the following combinations:
$R^6$ is $C_1$-$C_6$ alkyl, and $R^7$ is $C_1$-$C_6$ alkyl optionally substituted with one or more halo;
$R^6$ is $C_1$-$C_6$ alkyl and $R^7$ is $C_1$-$C_6$ alkyl;
$R^6$ is $C_1$-$C_6$ alkyl, and $R^7$ is $C_1$-$C_6$ alkyl substituted with one or more halo;
$R^6$ is $C_1$-$C_6$ alkyl, and $R^7$ is $C_3$-$C_7$ cycloalkyl;
$R^6$ is $C_1$-$C_6$ alkyl, and $R^7$ is halo;
$R^6$ is $C_1$-$C_6$ alkyl, and $R^7$ is cyano;
$R^6$ is $C_3$-$C_7$ cycloalkyl, and $R^7$ is $C_3$-$C_7$ cycloalkyl;
$R^6$ is $C_3$-$C_7$ cycloalkyl, and $R^7$ is halo;
$R^6$ is cyclopropyl and $R^7$ is halo;
$R^6$ is $C_1$-$C_6$ alkyl, and $R^7$ is $C_1$-$C_6$ alkoxy optionally substituted with one or more halo;
$R^6$ is $C_1$-$C_6$ alkyl, and $R^7$ is $C_1$-$C_6$ alkoxy;
$R^6$ is $C_1$-$C_6$ alkyl, and $R^7$ is $C_1$-$C_6$ alkoxy substituted with one or more halo;
$R^6$ is halo, and $R^7$ is $C_1$-$C_6$ haloalkyl;
$R^6$ is halo, and $R^7$ is $C_1$-$C_6$ haloalkoxy;
$R^6$ is $C_1$-$C_6$ alkoxy; and $R^7$ is halo;
$R^6$ is $C_1$-$C_6$ alkoxy; and $R^7$ is chloro;
$R^7$ is $C_1$-$C_6$ alkyl, and $R^6$ is $C_1$-$C_6$ alkyl optionally substituted with one or more halo;
$R^7$ is $C_1$-$C_6$ alkyl, and $R^6$ is $C_1$-$C_6$ alkyl substituted with one or more halo;
$R^7$ is $C_1$-$C_6$ alkyl, and $R^6$ is $C_3$-$C_7$ cycloalkyl;
$R^7$ is $C_1$-$C_6$ alkyl, and $R^6$ is halo;
$R^7$ is $C_1$-$C_6$ alkyl and $R^6$ is halo;
$R^7$ is $C_1$-$C_6$ alkyl, and $R^6$ is cyano;
$R^7$ is $C_3$-$C_7$ cycloalkyl, and $R^6$ is $C_3$-$C_7$ cycloalkyl;
$R^7$ is $C_3$-$C_7$ cycloalkyl, and $R^6$ is halo;
$R^7$ is $C_3$-$C_7$ cycloalkyl and $R^6$ is halo;
$R^7$ is $C_1$-$C_6$ alkyl, and $R^6$ is $C_1$-$C_6$ alkoxy optionally substituted with one or more halo;
$R^7$ is $C_1$-$C_6$ alkyl, and $R^6$ is $C_1$-$C_6$ alkoxy;
$R^7$ is $C_1$-$C_6$ alkyl, and $R^6$ is $C_1$-$C_6$ alkoxy substituted with one or more halo;
$R^7$ is halo, and $R^6$ is $C_1$-$C_6$ haloalkyl;
$R^7$ is halo, and $R^6$ is $C_1$-$C_6$ haloalkoxy;
$R^7$ is $C_1$-$C_6$ alkoxy; and $R^6$ is halo;
$R^7$ is $C_1$-$C_6$ alkoxy; and $R^6$ is chloro.

In some embodiments, of the compound of formula AA, the substituted ring B is

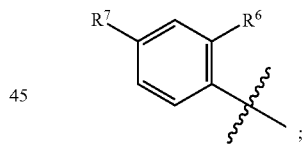
;

and $R^6$ and $R^7$ are one of the following combinations:
$R^6$ is isopropyl; and $R^7$ is methyl;
$R^6$ is isopropyl; and $R^7$ is isopropyl;
$R^6$ is isopropyl; and $R^7$ is trifluoromethyl;
$R^6$ is isopropyl; and $R^7$ is cyclopropyl;
$R^6$ is isopropyl; and $R^7$ is chloro;
$R^6$ is isopropyl; and $R^7$ is fluoro;
$R^6$ is ethyl; and $R^7$ is fluoro;
$R^6$ is isopropyl; and $R^7$ is cyano;
$R^6$ is cyclopropyl; and $R^7$ is cyclopropyl;
$R^6$ is cyclopropyl; and $R^7$ is chloro;
$R^6$ is cyclopropyl; and $R^7$ is fluoro;
$R^6$ is isopropyl; and $R^7$ is methoxy;
$R^6$ is isopropyl; and $R^7$ is trifluoromethoxy;
$R^6$ is chloro; and $R^7$ is trifluoromethyl;
$R^6$ is chloro; and $R^7$ is trifluoromethoxy;
$R^7$ is isopropyl; and $R^6$ is methyl;
$R^7$ is isopropyl; and $R^6$ is trifluoromethyl;
$R^7$ is isopropyl; and $R^6$ is cyclopropyl;

R⁷ is isopropyl; and R⁶ is chloro;
R⁷ is ethyl; and R⁶ is fluoro;
R⁷ is isopropyl; and R⁶ is cyano;
R⁷ is cyclopropyl; and R⁶ is cyclopropyl;
R⁷ is cyclopropyl; and R⁶ is chloro;
R⁷ is cyclopropyl; and R⁶ is fluoro;
R⁷ is isopropyl; and R⁶ is methoxy;
R⁷ is isopropyl; and R⁶ is trifluoromethoxy;
R⁷ is chloro; and R⁶ is trifluoromethyl;
R⁷ is chloro; and R⁶ is trifluoromethoxy.

In some embodiments, of the compound of formula AA, the substituted ring B is

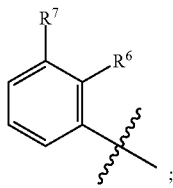
;

and R⁶ and R⁷ are one of the following combinations:
R⁶ is C₁-C₆ alkyl, and R⁷ is C₁-C₆ alkyl optionally substituted with one or more halo;
R⁶ is C₁-C₆ alkyl and R⁷ is C₁-C₆ alkyl;
R⁶ is C₁-C₆ alkyl, and R⁷ is C₁-C₆ alkyl substituted with one or more halo;
R⁶ is C₁-C₆ alkyl, and R⁷ is C₃-C₇ cycloalkyl;
R⁶ is C₁-C₆ alkyl, and R⁷ is halo;
R⁶ is C₁-C₆ alkyl, and R⁷ is cyano;
R⁶ is C₃-C₇ cycloalkyl, and R⁷ is C₃-C₇ cycloalkyl;
R⁶ is C₃-C₇ cycloalkyl, and R⁷ is halo;
R⁶ is cyclopropyl and R⁷ is halo;
R⁶ is C₁-C₆ alkyl, and R⁷ is C₁-C₆ alkoxy optionally substituted with one or more halo;
R⁶ is C₁-C₆ alkyl, and R⁷ is C₁-C₆ alkoxy;
R⁶ is C₁-C₆ alkyl, and R⁷ is C₁-C₆ alkoxy substituted with one or more halo;
R⁶ is halo, and R⁷ is C₁-C₆ haloalkyl;
R⁶ is halo, and R⁷ is C₁-C₆ haloalkoxy;
R⁶ is C₁-C₆ alkoxy; and R⁷ is halo;
R⁶ is C₁-C₆ alkoxy; and R⁷ is chloro;
R⁷ is C₁-C₆ alkyl, and R⁶ is C₁-C₆ alkyl optionally substituted with one or more halo;
R⁷ is C₁-C₆ alkyl, and R⁶ is C₁-C₆ alkyl substituted with one or more halo;
R⁷ is C₁-C₆ alkyl, and R⁶ is C₃-C₇ cycloalkyl;
R⁷ is C₁-C₆ alkyl, and R⁶ is halo;
R⁷ is C₁-C₆ alkyl and R⁶ is halo;
R⁷ is C₁-C₆ alkyl, and R⁶ is cyano;
R⁷ is C₃-C₇ cycloalkyl, and R⁶ is C₃-C₇ cycloalkyl;
R⁷ is C₃-C₇ cycloalkyl, and R⁶ is halo;
R⁷ is C₃-C₇ cycloalkyl and R⁶ is halo;
R⁷ is C₁-C₆ alkyl, and R⁶ is C₁-C₆ alkoxy optionally substituted with one or more halo;
R⁷ is C₁-C₆ alkyl, and R⁶ is C₁-C₆ alkoxy;
R⁷ is C₁-C₆ alkyl, and R⁶ is C₁-C₆ alkoxy substituted with one or more halo;
R⁷ is halo, and R⁶ is C₁-C₆ haloalkyl;
R⁷ is halo, and R⁶ is C₁-C₆ haloalkoxy;
R⁷ is C₁-C₆ alkoxy; and R⁶ is halo;
R⁷ is C₁-C₆ alkoxy; and R⁶ is chloro
R⁶ and R⁷ on adjacent atoms taken together with the atoms connecting them form a C₄-C₆ aliphatic carbocyclic ring optionally substituted with one or more hydroxy, oxo, or C₁-C₆ alkyl; or
R⁶ and R⁷ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or C₁-C₆ alkyl.

In some embodiments, of the compound of formula AA, the substituted ring B is

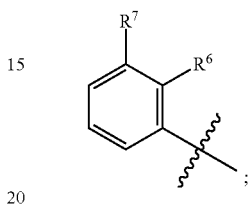
;

and R⁶ and R⁷ are one of the following combinations:
R⁶ is isopropyl; and R⁷ is methyl;
R⁶ is isopropyl; and R⁷ is isopropyl;
R⁶ is isopropyl; and R⁷ is trifluoromethyl;
R⁶ is isopropyl; and R⁷ is cyclopropyl;
R⁶ is isopropyl; and R⁷ is chloro;
R⁶ is isopropyl; and R⁷ is fluoro;
R⁶ is ethyl; and R⁷ is fluoro;
R⁶ is isopropyl; and R⁷ is cyano;
R⁶ is cyclopropyl; and R⁷ is cyclopropyl;
R⁶ is cyclopropyl; and R⁷ is chloro;
R⁶ is cyclopropyl; and R⁷ is fluoro;
R⁶ is isopropyl; and R⁷ is methoxy;
R⁶ is isopropyl; and R⁷ is trifluoromethoxy;
R⁶ is chloro; and R⁷ is trifluoromethyl;
R⁶ is chloro; and R⁷ is trifluoromethoxy;
R⁷ is isopropyl; and R⁶ is methyl;
R⁷ is isopropyl; and R⁶ is trifluoromethyl;
R⁷ is isopropyl; and R⁶ is cyclopropyl;
R⁷ is isopropyl; and R⁶ is chloro;
R⁷ is ethyl; and R⁶ is fluoro;
R⁷ is isopropyl; and R⁶ is cyano;
R⁷ is cyclopropyl; and R⁶ is cyclopropyl;
R⁷ is cyclopropyl; and R⁶ is chloro;
R⁷ is cyclopropyl; and R⁶ is fluoro;
R⁷ is isopropyl; and R⁶ is methoxy;
R⁷ is isopropyl; and R⁶ is trifluoromethoxy;
R⁷ is chloro; and R⁶ is trifluoromethyl;
R⁷ is chloro; and R⁶ is trifluoromethoxy;
R⁶ and R⁷ on adjacent atoms taken together with the atoms connecting them form a C₄ aliphatic carbocyclic ring;
R⁶ and R⁷ on adjacent atoms taken together with the atoms connecting them form a C₅ aliphatic carbocyclic ring;
R⁶ and R⁷ on adjacent atoms taken together with the atoms connecting them form a C₆ aliphatic carbocyclic ring;
R⁶ and R⁷ on adjacent atoms taken together with the atoms connecting them form a 5-membered heterocyclic ring containing 1 heteroatoms independently selected from O, N, and S;
R⁶ and R⁷ on adjacent atoms taken together with the atoms connecting them form a 6-membered heterocyclic ring containing 1 heteroatoms independently selected from O, N, and S; or $R^6$ and $R^7$ on adjacent atoms taken together with the atoms connecting them form a $C_5$ aliphatic carbocyclic ring.

In some embodiments, of the compound of formula AA, the substituted ring B is

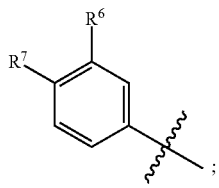

and $R^6$ and $R^7$ are one of the following combinations:
- $R^6$ is $C_1$-$C_6$ alkyl, and $R^7$ is $C_1$-$C_6$ alkyl optionally substituted with one or more halo;
- $R^6$ is $C_1$-$C_6$ alkyl and $R^7$ is $C_1$-$C_6$ alkyl;
- $R^6$ is $C_1$-$C_6$ alkyl, and $R^7$ is $C_1$-$C_6$ alkyl substituted with one or more halo;
- $R^6$ is $C_1$-$C_6$ alkyl, and $R^7$ is $C_3$-$C_7$ cycloalkyl;
- $R^6$ is $C_1$-$C_6$ alkyl, and $R^7$ is halo;
- $R^6$ is $C_1$-$C_6$ alkyl, and $R^7$ is cyano;
- $R^6$ is $C_3$-$C_7$ cycloalkyl, and $R^7$ is $C_3$-$C_7$ cycloalkyl;
- $R^6$ is $C_3$-$C_7$ cycloalkyl, and $R^7$ is halo;
- $R^6$ is cyclopropyl and $R^7$ is halo;
- $R^6$ is $C_1$-$C_6$ alkyl, and $R^7$ is $C_1$-$C_6$ alkoxy optionally substituted with one or more halo;
- $R^6$ is $C_1$-$C_6$ alkyl, and $R^7$ is $C_1$-$C_6$ alkoxy;
- $R^6$ is $C_1$-$C_6$ alkyl, and $R^7$ is $C_1$-$C_6$ alkoxy substituted with one or more halo;
- $R^6$ is halo, and $R^7$ is $C_1$-$C_6$ haloalkyl;
- $R^6$ is halo, and $R^7$ is $C_1$-$C_6$ haloalkoxy;
- $R^6$ is $C_1$-$C_6$ alkoxy; and $R^7$ is halo;
- $R^6$ is $C_1$-$C_6$ alkoxy; and $R^7$ is chloro;
- $R^7$ is $C_1$-$C_6$ alkyl, and $R^6$ is $C_1$-$C_6$ alkyl optionally substituted with one or more halo;
- $R^7$ is $C_1$-$C_6$ alkyl, and $R^6$ is $C_1$-$C_6$ alkyl substituted with one or more halo;
- $R^7$ is $C_1$-$C_6$ alkyl, and $R^6$ is $C_3$-$C_7$ cycloalkyl;
- $R^7$ is $C_1$-$C_6$ alkyl, and $R^6$ is halo;
- $R^7$ is $C_1$-$C_6$ alkyl and $R^6$ is halo;
- $R^7$ is $C_1$-$C_6$ alkyl, and $R^6$ is cyano;
- $R^7$ is $C_3$-$C_7$ cycloalkyl, and $R^6$ is $C_3$-$C_7$ cycloalkyl;
- $R^7$ is $C_3$-$C_7$ cycloalkyl, and $R^6$ is halo;
- $R^7$ is $C_3$-$C_7$ cycloalkyl and $R^6$ is halo;
- $R^7$ is $C_1$-$C_6$ alkyl, and $R^6$ is $C_1$-$C_6$ alkoxy optionally substituted with one or more halo;
- $R^7$ is $C_1$-$C_6$ alkyl, and $R^6$ is $C_1$-$C_6$ alkoxy;
- $R^7$ is $C_1$-$C_6$ alkyl, and $R^6$ is $C_1$-$C_6$ alkoxy substituted with one or more halo;
- $R^7$ is halo, and $R^6$ is $C_1$-$C_6$ haloalkyl;
- $R^7$ is halo, and $R^6$ is $C_1$-$C_6$ haloalkoxy;
- $R^7$ is $C_1$-$C_6$ alkoxy; and $R^6$ is halo;
- $R^7$ is $C_1$-$C_6$ alkoxy; and $R^6$ is chloro;
- $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
- $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

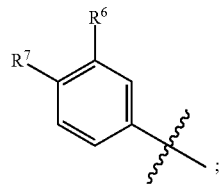

and $R^6$ and $R^7$ are one of the following combinations:
- $R^6$ is isopropyl; and $R^7$ is methyl;
- $R^6$ is isopropyl; and $R^7$ is isopropyl;
- $R^6$ is isopropyl; and $R^7$ is trifluoromethyl;
- $R^6$ is isopropyl; and $R^7$ is cyclopropyl;
- $R^6$ is isopropyl; and $R^7$ is chloro;
- $R^6$ is isopropyl; and $R^7$ is fluoro;
- $R^6$ is ethyl; and $R^7$ is fluoro;
- $R^6$ is isopropyl; and $R^7$ is cyano;
- $R^6$ is cyclopropyl; and $R^7$ is cyclopropyl;
- $R^6$ is cyclopropyl; and $R^7$ is chloro;
- $R^6$ is cyclopropyl; and $R^7$ is fluoro;
- $R^6$ is isopropyl; and $R^7$ is methoxy;
- $R^6$ is isopropyl; and $R^7$ is trifluoromethoxy;
- $R^6$ is chloro; and $R^7$ is trifluoromethyl;
- $R^6$ is chloro; and $R^7$ is trifluoromethoxy;
- $R^7$ is isopropyl; and $R^6$ is methyl;
- $R^7$ is isopropyl; and $R^6$ is trifluoromethyl;
- $R^7$ is isopropyl; and $R^6$ is cyclopropyl;
- $R^7$ is isopropyl; and $R^6$ is chloro;
- $R^7$ is ethyl; and $R^6$ is fluoro;
- $R^7$ is isopropyl; and $R^6$ is cyano;
- $R^7$ is cyclopropyl; and $R^6$ is cyclopropyl;
- $R^7$ is cyclopropyl; and $R^6$ is chloro;
- $R^7$ is cyclopropyl; and $R^6$ is fluoro;
- $R^7$ is isopropyl; and $R^6$ is methoxy;
- $R^7$ is isopropyl; and $R^6$ is trifluoromethoxy;
- $R^7$ is chloro; and $R^6$ is trifluoromethyl;
- $R^7$ is chloro; and $R^6$ is trifluoromethoxy;
- $R^6$ and $R^7$ on adjacent atoms taken together with the atoms connecting them form a $C_4$ aliphatic carbocyclic ring;
- $R^6$ and $R^7$ on adjacent atoms taken together with the atoms connecting them form a $C_5$ aliphatic carbocyclic ring;
- $R^6$ and $R^7$ on adjacent atoms taken together with the atoms connecting them form a $C_6$ aliphatic carbocyclic ring;
- $R^6$ and $R^7$ on adjacent atoms taken together with the atoms connecting them form a 5-membered heterocyclic ring containing 1 heteroatoms independently selected from O, N, and S;
- $R^6$ and $R^7$ on adjacent atoms taken together with the atoms connecting them form a 6-membered heterocyclic ring containing 1 heteroatoms independently selected from O, N, and S; or
- $R^6$ and $R^7$ on adjacent atoms taken together with the atoms connecting them form a $C_5$ aliphatic carbocyclic ring.

In some embodiments, of the compound of formula AA, the substituted ring B is

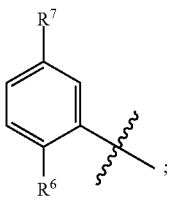

and R$^6$ and R$^7$ are one of the following combinations:
- R$^6$ is C$_1$-C$_6$ alkyl, and R$^7$ is C$_1$-C$_6$ alkyl optionally substituted with one or more halo;
- R$^6$ is C$_1$-C$_6$ alkyl and R$^7$ is C$_1$-C$_6$ alkyl;
- R$^6$ is C$_1$-C$_6$ alkyl, and R$^7$ is C$_1$-C$_6$ alkyl substituted with one or more halo;
- R$^6$ is C$_1$-C$_6$ alkyl, and R$^7$ is C$_3$-C$_7$ cycloalkyl;
- R$^6$ is C$_1$-C$_6$ alkyl, and R$^7$ is halo;
- R$^6$ is C$_1$-C$_6$ alkyl, and R$^7$ is cyano;
- R$^6$ is C$_3$-C$_7$ cycloalkyl, and R$^7$ is C$_3$-C$_7$ cycloalkyl;
- R$^6$ is C$_3$-C$_7$ cycloalkyl, and R$^7$ is halo;
- R$^6$ is cyclopropyl and R$^7$ is halo;
- R$^6$ is C$_1$-C$_6$ alkyl, and R$^7$ is C$_1$-C$_6$ alkoxy optionally substituted with one or more halo;
- R$^6$ is C$_1$-C$_6$ alkyl, and R$^7$ is C$_1$-C$_6$ alkoxy;
- R$^6$ is C$_1$-C$_6$ alkyl, and R$^7$ is C$_1$-C$_6$ alkoxy substituted with one or more halo;
- R$^6$ is halo, and R$^7$ is C$_1$-C$_6$ haloalkyl;
- R$^6$ is halo, and R$^7$ is C$_1$-C$_6$ haloalkoxy;
- R$^6$ is C$_1$-C$_6$ alkoxy; and R$^7$ is halo;
- R$^6$ is C$_1$-C$_6$ alkoxy; and R$^7$ is chloro;
- R$^7$ is C$_1$-C$_6$ alkyl, and R$^6$ is C$_1$-C$_6$ alkyl optionally substituted with one or more halo;
- R$^7$ is C$_1$-C$_6$ alkyl, and R$^6$ is C$_1$-C$_6$ alkyl substituted with one or more halo;
- R$^7$ is C$_1$-C$_6$ alkyl, and R$^6$ is C$_3$-C$_7$ cycloalkyl;
- R$^7$ is C$_1$-C$_6$ alkyl, and R$^6$ is halo;
- R$^7$ is C$_1$-C$_6$ alkyl and R$^6$ is halo;
- R$^7$ is C$_1$-C$_6$ alkyl, and R$^6$ is cyano;
- R$^7$ is C$_3$-C$_7$ cycloalkyl, and R$^6$ is C$_3$-C$_7$ cycloalkyl;
- R$^7$ is C$_3$-C$_7$ cycloalkyl, and R$^6$ is halo;
- R$^7$ is C$_3$-C$_7$ cycloalkyl and R$^6$ is halo;
- R$^7$ is C$_1$-C$_6$ alkyl, and R$^6$ is C$_1$-C$_6$ alkoxy optionally substituted with one or more halo;
- R$^7$ is C$_1$-C$_6$ alkyl, and R$^6$ is C$_1$-C$_6$ alkoxy;
- R$^7$ is C$_1$-C$_6$ alkyl, and R$^6$ is C$_1$-C$_6$ alkoxy substituted with one or more halo;
- R$^7$ is halo, and R$^6$ is C$_1$-C$_6$ haloalkyl;
- R$^7$ is halo, and R$^6$ is C$_1$-C$_6$ haloalkoxy;
- R$^7$ is C$_1$-C$_6$ alkoxy; and R$^6$ is halo;
- R$^7$ is C$_1$-C$_6$ alkoxy; and R$^6$ is chloro.

In some embodiments, of the compound of formula AA, the substituted ring B is

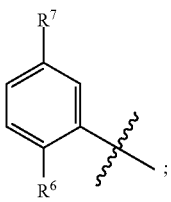

and R$^6$ and R$^7$ are one of the following combinations:
- R$^6$ is isopropyl; and R$^7$ is methyl;
- R$^6$ is isopropyl; and R$^7$ is isopropyl;
- R$^6$ is isopropyl; and R$^7$ is trifluoromethyl;
- R$^6$ is isopropyl; and R$^7$ is cyclopropyl;
- R$^6$ is isopropyl; and R$^7$ is chloro;
- R$^6$ is isopropyl; and R$^7$ is fluoro;
- R$^6$ is ethyl; and R$^7$ is fluoro;
- R$^6$ is isopropyl; and R$^7$ is cyano;
- R$^6$ is cyclopropyl; and R$^7$ is cyclopropyl;
- R$^6$ is cyclopropyl; and R$^7$ is chloro;
- R$^6$ is cyclopropyl; and R$^7$ is fluoro;
- R$^6$ is isopropyl; and R$^7$ is methoxy;
- R$^6$ is isopropyl; and R$^7$ is trifluoromethoxy;
- R$^6$ is chloro; and R$^7$ is trifluoromethyl;
- R$^6$ is chloro; and R$^7$ is trifluoromethoxy;
- R$^7$ is isopropyl; and R$^6$ is methyl;
- R$^7$ is isopropyl; and R$^6$ is trifluoromethyl;
- R$^7$ is isopropyl; and R$^6$ is cyclopropyl;
- R$^7$ is isopropyl; and R$^6$ is chloro;
- R$^7$ is ethyl; and R$^6$ is fluoro;
- R$^7$ is isopropyl; and R$^6$ is cyano;
- R$^7$ is cyclopropyl; and R$^6$ is cyclopropyl;
- R$^7$ is cyclopropyl; and R$^6$ is chloro;
- R$^7$ is cyclopropyl; and R$^6$ is fluoro;
- R$^7$ is isopropyl; and R$^6$ is methoxy;
- R$^7$ is isopropyl; and R$^6$ is trifluoromethoxy;
- R$^7$ is chloro; and R$^6$ is trifluoromethyl;
- R$^7$ is chloro; and R$^6$ is trifluoromethoxy.

In some embodiments, of the compound of formula AA, the substituted ring B is

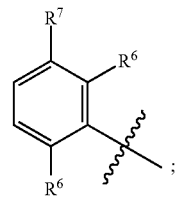

and R$^6$ and R$^7$ are one of the following combinations:
- each R$^6$ is independently C$_1$-C$_6$ alkyl, and R$^7$ is C$_1$-C$_6$ alkyl optionally substituted with one or more halo;
- each R$^6$ is independently C$_1$-C$_6$ alkyl and R$^7$ is C$_1$-C$_6$ alkyl; each R$^6$ is independently C$_1$-C$_6$ alkyl, and R$^7$ is C$_1$-C$_6$ alkyl substituted with one or more halo;
- each R$^6$ is independently C$_1$-C$_6$ alkyl, and R$^7$ is C$_3$-C$_7$ cycloalkyl;
- each R$^6$ is independently C$_1$-C$_6$ alkyl, and R$^7$ is halo;
- each R$^6$ is independently C$_1$-C$_6$ alkyl, and R$^7$ is cyano;
- each R$^6$ is independently C$_3$-C$_7$ cycloalkyl, and R$^7$ is C$_3$-C$_7$ cycloalkyl;
- each R$^6$ is independently C$_3$-C$_7$ cycloalkyl, and R$^7$ is halo;
- each R$^6$ is independently cyclopropyl and R$^7$ is halo;
- each R$^6$ is independently C$_1$-C$_6$ alkyl, and R$^7$ is C$_1$-C$_6$ alkoxy optionally substituted with one or more halo;
- each R$^6$ is independently C$_1$-C$_6$ alkyl, and R$^7$ is C$_1$-C$_6$ alkoxy;
- each R$^6$ is independently C$_1$-C$_6$ alkyl, and R$^7$ is C$_1$-C$_6$ alkoxy substituted with one or more halo;
- each R$^6$ is independently halo, and R$^7$ is C$_1$-C$_6$ haloalkyl;
- each R$^6$ is independently halo, and R$^7$ is C$_1$-C$_6$ haloalkoxy;
- each R$^6$ is independently C$_1$-C$_6$ alkoxy; and R$^7$ is halo;
- each R$^6$ is independently C$_1$-C$_6$ alkoxy; and R$^7$ is chloro;
- R$^7$ is C$_1$-C$_6$ alkyl, and each R$^6$ is independently C$_1$-C$_6$ alkyl optionally substituted with one or more halo;

$R^7$ is $C_1$-$C_6$ alkyl, and each $R^6$ is independently $C_1$-$C_6$ alkyl substituted with one or more halo;
$R^7$ is $C_1$-$C_6$ alkyl, and each $R^6$ is independently $C_3$-$C_7$ cycloalkyl;
$R^7$ is $C_1$-$C_6$ alkyl, and each $R^6$ is independently halo;
$R^7$ is $C_1$-$C_6$ alkyl and each $R^6$ is independently halo;
$R^7$ is $C_1$-$C_6$ alkyl, and each $R^6$ is cyano;
$R^7$ is $C_3$-$C_7$ cycloalkyl, and each $R^6$ is independently $C_3$-$C_7$ cycloalkyl;
$R^7$ is $C_3$-$C_7$ cycloalkyl, and each $R^6$ is independently halo;
$R^7$ is $C_3$-$C_7$ cycloalkyl and each $R^6$ is independently halo;
$R^7$ is $C_1$-$C_6$ alkyl, and each $R^6$ is independently $C_1$-$C_6$ alkoxy optionally substituted with one or more halo;
$R^7$ is $C_1$-$C_6$ alkyl, and each $R^6$ is independently $C_1$-$C_6$ alkoxy;
$R^7$ is $C_1$-$C_6$ alkyl, and each $R^6$ is independently $C_1$-$C_6$ alkoxy substituted with one or more halo;
$R^7$ is halo, and each $R^6$ is independently $C_1$-$C_6$ haloalkyl;
$R^7$ is halo, and each $R^6$ is independently $C_1$-$C_6$ haloalkoxy;
$R^7$ is $C_1$-$C_6$ alkoxy; and each $R^6$ is independently halo;
$R^7$ is $C_1$-$C_6$ alkoxy; and each $R^6$ is chloro;
$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

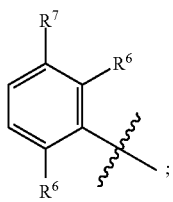

and $R^6$ and $R^7$ are one of the following combinations:
each $R^6$ is isopropyl; and $R^7$ is methyl;
each $R^6$ is isopropyl; and $R^7$ is isopropyl;
each $R^6$ is isopropyl; and $R^7$ is trifluoromethyl;
each $R^6$ is isopropyl; and $R^7$ is cyclopropyl;
each $R^6$ is isopropyl; and $R^7$ is chloro;
each $R^6$ is isopropyl; and $R^7$ is fluoro;
each $R^6$ is ethyl; and $R^7$ is fluoro;
each $R^6$ is isopropyl; and $R^7$ is cyano;
each $R^6$ is cyclopropyl; and $R^7$ is cyclopropyl;
each $R^6$ is cyclopropyl; and $R^7$ is chloro;
each $R^6$ is cyclopropyl; and $R^7$ is fluoro;
each $R^6$ is isopropyl; and $R^7$ is methoxy;
each $R^6$ is isopropyl; and $R^7$ is trifluoromethoxy;
each $R^6$ is chloro; and $R^7$ is trifluoromethyl;
each $R^6$ is chloro; and $R^7$ is trifluoromethoxy;
$R^7$ is isopropyl; and each $R^6$ is methyl;
$R^7$ is isopropyl; and each $R^6$ is trifluoromethyl;
$R^7$ is isopropyl; and each $R^6$ is cyclopropyl;
$R^7$ is isopropyl; and each $R^6$ is chloro;
$R^7$ is ethyl; and each $R^6$ is fluoro;
$R^7$ is isopropyl; and each $R^6$ is cyano;
$R^7$ is cyclopropyl; and each $R^6$ is cyclopropyl;
$R^7$ is cyclopropyl; and each $R^6$ is chloro;
$R^7$ is cyclopropyl; and each $R^6$ is fluoro;
$R^7$ is isopropyl; and each $R^6$ is methoxy;
$R^7$ is isopropyl; and each $R^6$ is trifluoromethoxy;
$R^7$ is chloro; and each $R^6$ is trifluoromethyl;
$R^7$ is chloro; and each $R^6$ is trifluoromethoxy;
one $R^6$ is isopropyl; the other $R^6$ is trifluoromethyl; and $R^7$ is chloro;
$R^6$ and $R^7$ on adjacent atoms taken together with the atoms connecting them form a $C_4$ aliphatic carbocyclic ring; and one $R^6$ is chloro, fluoro, or cyano;
$R^6$ and $R^7$ on adjacent atoms taken together with the atoms connecting them form a $C_5$ aliphatic carbocyclic ring; and one $R^6$ is chloro, fluoro, or cyano;
$R^6$ and $R^7$ on adjacent atoms taken together with the atoms connecting them form a $C_6$ aliphatic carbocyclic ring; and one $R^6$ is chloro, fluoro, or cyano;
$R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano;
$R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or
$R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

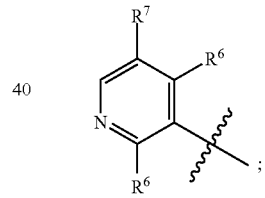

and $R^6$ and $R^7$ are one of the following combinations:
each $R^6$ is independently $C_1$-$C_6$ alkyl, and $R^7$ is $C_1$-$C_6$ alkyl optionally substituted with one or more halo;
each $R^6$ is independently $C_1$-$C_6$ alkyl and $R^7$ is $C_1$-$C_6$ alkyl;
each $R^6$ is independently $C_1$-$C_6$ alkyl, and $R^7$ is $C_1$-$C_6$ alkyl substituted with one or more halo;
each $R^6$ is independently $C_1$-$C_6$ alkyl, and $R^7$ is $C_3$-$C_7$ cycloalkyl;
each $R^6$ is independently $C_1$-$C_6$ alkyl, and $R^7$ is halo;
each $R^6$ is independently $C_1$-$C_6$ alkyl, and $R^7$ is cyano;
each $R^6$ is independently $C_3$-$C_7$ cycloalkyl, and $R^7$ is $C_3$-$C_7$ cycloalkyl;
each $R^6$ is independently $C_3$-$C_7$ cycloalkyl, and $R^7$ is halo;
each $R^6$ is independently cyclopropyl and $R^7$ is halo;
ach $R^6$ is independently $C_1$-$C_6$ alkyl, and $R^7$ is $C_1$-$C_6$ alkoxy optionally substituted with one or more halo;
each $R^6$ is independently $C_1$-$C_6$ alkyl, and $R^7$ is $C_1$-$C_6$ alkoxy;
each $R^6$ is independently $C_1$-$C_6$ alkyl, and $R^7$ is $C_1$-$C_6$ alkoxy substituted with one or more halo;
each $R^6$ is independently halo, and $R^7$ is $C_1$-$C_6$ haloalkyl;

each $R^6$ is independently halo, and $R^7$ is $C_1$-$C_6$ haloalkoxy;
each $R^6$ is independently $C_1$-$C_6$ alkoxy; and $R^7$ is halo;
each $R^6$ is independently $C_1$-$C_6$ alkoxy; and $R^7$ is chloro;
$R^7$ is $C_1$-$C_6$ alkyl, and each $R^6$ is independently $C_1$-$C_6$ alkyl optionally substituted with one or more halo;
$R^7$ is $C_1$-$C_6$ alkyl, and each $R^6$ is independently $C_1$-$C_6$ alkyl substituted with one or more halo;
$R^7$ is $C_1$-$C_6$ alkyl, and each $R^6$ is independently $C_3$-$C_7$ cycloalkyl;
$R^7$ is $C_1$-$C_6$ alkyl, and each $R^6$ is independently halo;
$R^7$ is $C_1$-$C_6$ alkyl and each $R^6$ is independently halo;
$R^7$ is $C_1$-$C_6$ alkyl, and each $R^6$ is cyano;
$R^7$ is $C_3$-$C_7$ cycloalkyl, and each $R^6$ is independently $C_3$-$C_7$ cycloalkyl;
$R^7$ is $C_3$-$C_7$ cycloalkyl, and each $R^6$ is independently halo;
$R^7$ is $C_3$-$C_7$ cycloalkyl and each $R^6$ is independently halo;
$R^7$ is $C_1$-$C_6$ alkyl, and each $R^6$ is independently $C_1$-$C_6$ alkoxy optionally substituted with one or more halo;
$R^7$ is $C_1$-$C_6$ alkyl, and each $R^6$ is independently $C_1$-$C_6$ alkoxy;
$R^7$ is $C_1$-$C_6$ alkyl, and each $R^6$ is independently $C_1$-$C_6$ alkoxy substituted with one or more halo;
$R^7$ is halo, and each $R^6$ is independently $C_1$-$C_6$ haloalkyl;
$R^7$ is halo, and each $R^6$ is independently $C_1$-$C_6$ haloalkoxy;
$R^7$ is $C_1$-$C_6$ alkoxy; and each $R^6$ is independently halo;
$R^7$ is $C_1$-$C_6$ alkoxy; and each $R^6$ is chloro;
$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

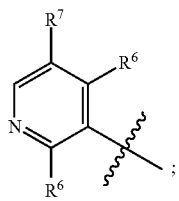

and $R^6$ and $R^7$ are one of the following combinations:
each $R^6$ is isopropyl; and $R^7$ is methyl;
each $R^6$ is isopropyl; and $R^7$ is isopropyl;
each $R^6$ is isopropyl; and $R^7$ is trifluoromethyl;
each $R^6$ is isopropyl; and $R^7$ is cyclopropyl;
each $R^6$ is isopropyl; and $R^7$ is chloro;
each $R^6$ is isopropyl; and $R^7$ is fluoro;
each $R^6$ is ethyl; and $R^7$ is fluoro;
each $R^6$ is isopropyl; and $R^7$ is cyano;
each $R^6$ is cyclopropyl; and $R^7$ is cyclopropyl;
each $R^6$ is cyclopropyl; and $R^7$ is chloro;
each $R^6$ is cyclopropyl; and $R^7$ is fluoro;
each $R^6$ is isopropyl; and $R^7$ is methoxy;
each $R^6$ is isopropyl; and $R^7$ is trifluoromethoxy;
each $R^6$ is chloro; and $R^7$ is trifluoromethyl;
each $R^6$ is chloro; and $R^7$ is trifluoromethoxy;
$R^7$ is isopropyl; and each $R^6$ is methyl;
$R^7$ is isopropyl; and each $R^6$ is trifluoromethyl;
$R^7$ is isopropyl; and each $R^6$ is cyclopropyl;
$R^7$ is isopropyl; and each $R^6$ is chloro;
$R^7$ is ethyl; and each $R^6$ is fluoro;
$R^7$ is isopropyl; and each $R^6$ is cyano;
$R^7$ is cyclopropyl; and each $R^6$ is cyclopropyl;
$R^7$ is cyclopropyl; and each $R^6$ is chloro;
$R^7$ is cyclopropyl; and each $R^6$ is fluoro;
$R^7$ is isopropyl; and each $R^6$ is methoxy;
$R^7$ is isopropyl; and each $R^6$ is trifluoromethoxy;
$R^7$ is chloro; and each $R^6$ is trifluoromethyl;
$R^7$ is chloro; and each $R^6$ is trifluoromethoxy;
one $R^6$ is isopropyl; the other $R^6$ is trifluoromethyl; and $R^7$ is chloro;
$R^6$ and $R^7$ on adjacent atoms taken together with the atoms connecting them form a $C_4$ aliphatic carbocyclic ring; and one $R^6$ is chloro, fluoro, or cyano;
$R^6$ and $R^7$ on adjacent atoms taken together with the atoms connecting them form a $C_5$ aliphatic carbocyclic ring; and one $R^6$ is chloro, fluoro, or cyano;
$R^6$ and $R^7$ on adjacent atoms taken together with the atoms connecting them form a $C_6$ aliphatic carbocyclic ring; and one $R^6$ is chloro, fluoro, or cyano;
$R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano;
$R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or
$R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

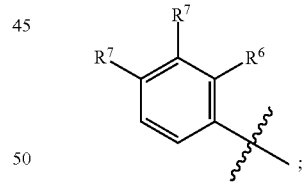

and $R^6$ and $R^7$ are one of the following combinations:
$R^6$ is $C_1$-$C_6$ alkyl, and each $R^7$ is independently $C_1$-$C_6$ alkyl optionally substituted with one or more halo;
$R^6$ is $C_1$-$C_6$ alkyl and each $R^7$ is independently $C_1$-$C_6$ alkyl;
$R^6$ is $C_1$-$C_6$ alkyl, and each $R^7$ is independently $C_1$-$C_6$ alkyl substituted with one or more halo;
$R^6$ is $C_1$-$C_6$ alkyl, and each $R^7$ is independently $C_3$-$C_7$ cycloalkyl;
$R^6$ is $C_1$-$C_6$ alkyl, and each $R^7$ is independently halo;
$R^6$ is $C_1$-$C_6$ alkyl, and each $R^7$ is cyano;
$R^6$ is $C_3$-$C_7$ cycloalkyl, and each $R^7$ is independently $C_3$-$C_7$ cycloalkyl;
$R^6$ is $C_3$-$C_7$ cycloalkyl, and each $R^7$ is independently halo;
$R^6$ is cyclopropyl and each $R^7$ is independently halo;

$R^6$ is $C_1$-$C_6$ alkyl, and each $R^7$ is independently $C_1$-$C_6$ alkoxy optionally substituted with one or more halo;
$R^6$ is $C_1$-$C_6$ alkyl, and each $R^7$ is independently $C_1$-$C_6$ alkoxy;
$R^6$ is $C_1$-$C_6$ alkyl, and each $R^7$ is independently $C_1$-$C_6$ alkoxy substituted with one or more halo;
$R^6$ is halo, and each $R^7$ is independently $C_1$-$C_6$ haloalkyl;
$R^6$ is halo, and each $R^7$ is independently $C_1$-$C_6$ haloalkoxy;
$R^6$ is $C_1$-$C_6$ alkoxy; and each $R^7$ is independently halo;
$R^6$ is $C_1$-$C_6$ alkoxy; and each $R^7$ is chloro;
each $R^7$ is independently $C_1$-$C_6$ alkyl, and $R^6$ is $C_1$-$C_6$ alkyl optionally substituted with one or more halo;
each $R^7$ is independently $C_1$-$C_6$ alkyl, and $R^6$ is $C_1$-$C_6$ alkyl substituted with one or more halo;
each $R^7$ is independently $C_1$-$C_6$ alkyl, and $R^6$ is $C_3$-$C_7$ cycloalkyl;
each $R^7$ is independently $C_1$-$C_6$ alkyl, and $R^6$ is halo;
each $R^7$ is independently $C_1$-$C_6$ alkyl and $R^6$ is halo;
each $R^7$ is independently $C_1$-$C_6$ alkyl, and $R^6$ is cyano;
each $R^7$ is independently $C_3$-$C_7$ cycloalkyl, and $R^6$ is $C_3$-$C_7$ cycloalkyl;
each $R^7$ is independently $C_3$-$C_7$ cycloalkyl, and $R^6$ is halo;
each $R^7$ is independently $C_3$-$C_7$ cycloalkyl and $R^6$ is halo;
each $R^7$ is independently $C_1$-$C_6$ alkyl, and $R^6$ is $C_1$-$C_6$ alkoxy optionally substituted with one or more halo;
each $R^7$ is independently $C_1$-$C_6$ alkyl, and $R^6$ is $C_1$-$C_6$ alkoxy;
each $R^7$ is independently $C_1$-$C_6$ alkyl, and $R^6$ is $C_1$-$C_6$ alkoxy substituted with one or more halo;
each $R^7$ is independently halo, and $R^6$ is $C_1$-$C_6$ haloalkyl;
each $R^7$ is independently halo, and $R^6$ is $C_1$-$C_6$ haloalkoxy;
each $R^7$ is independently $C_1$-$C_6$ alkoxy; and $R^6$ is halo;
each $R^7$ is independently $C_1$-$C_6$ alkoxy; and $R^6$ is chloro.

In some embodiments, of the compound of formula AA, the substituted ring B is

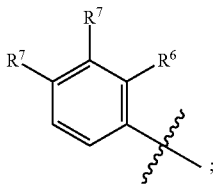

and $R^6$ and W are one of the following combinations:
each $R^7$ is isopropyl; and $R^6$ is methyl;
each $R^7$ is isopropyl; and $R^6$ is isopropyl;
each $R^7$ is isopropyl; and $R^6$ is trifluoromethyl;
each $R^7$ is isopropyl; and $R^6$ is cyclopropyl;
each $R^7$ is isopropyl; and $R^6$ is chloro;
each $R^7$ is isopropyl; and $R^6$ is fluoro;
each $R^7$ is ethyl; and $R^6$ is fluoro;
each $R^7$ is isopropyl; and $R^6$ is cyano;
each $R^7$ is cyclopropyl; and $R^6$ is cyclopropyl;
each $R^7$ is cyclopropyl; and $R^6$ is chloro;
each $R^7$ is cyclopropyl; and $R^6$ is fluoro;
each $R^7$ is isopropyl; and $R^6$ is methoxy;
each $R^7$ is isopropyl; and $R^6$ is trifluoromethoxy;
each $R^7$ is chloro; and $R^6$ is trifluoromethyl;
each $R^7$ is chloro; and $R^6$ is trifluoromethoxy;
$R^7$ is isopropyl; and each $R^6$ is methyl;
$R^7$ is isopropyl; and each $R^6$ is trifluoromethyl;
$R^7$ is isopropyl; and each $R^6$ is cyclopropyl;
$R^7$ is isopropyl; and each $R^6$ is chloro;
$R^7$ is ethyl; and each $R^6$ is fluoro;
$R^7$ is isopropyl; and each $R^6$ is cyano;
$R^7$ is cyclopropyl; and each $R^6$ is cyclopropyl;
$R^7$ is cyclopropyl; and each $R^6$ is chloro;
$R^7$ is cyclopropyl; and each $R^6$ is fluoro;
$R^7$ is isopropyl; and each $R^6$ is methoxy;
$R^7$ is isopropyl; and each $R^6$ is trifluoromethoxy;
$R^7$ is chloro; and each $R^6$ is trifluoromethyl;
$R^7$ is chloro; and each $R^6$ is trifluoromethoxy.

In some embodiments, of the compound of formula AA, the substituted ring B is

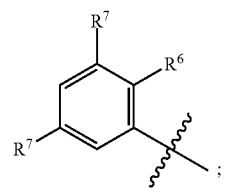

and $R^6$ and $R^7$ are one of the following combinations:
$R^6$ is $C_1$-$C_6$ alkyl, and each $R^7$ is independently $C_1$-$C_6$ alkyl optionally substituted with one or more halo;
$R^6$ is $C_1$-$C_6$ alkyl and each $R^7$ is independently $C_1$-$C_6$ alkyl;
$R^6$ is $C_1$-$C_6$ alkyl, and each $R^7$ is independently $C_1$-$C_6$ alkyl substituted with one or more halo;
$R^6$ is $C_1$-$C_6$ alkyl, and each $R^7$ is independently $C_3$-$C_7$ cycloalkyl;
$R^6$ is $C_1$-$C_6$ alkyl, and each $R^7$ is independently halo;
$R^6$ is $C_1$-$C_6$ alkyl, and each $R^7$ is cyano;
$R^6$ is $C_3$-$C_7$ cycloalkyl, and each $R^7$ is independently $C_3$-$C_7$ cycloalkyl;
$R^6$ is $C_3$-$C_7$ cycloalkyl, and each $R^7$ is independently halo;
$R^6$ is cyclopropyl and each $R^7$ is independently halo;
$R^6$ is $C_1$-$C_6$ alkyl, and each $R^7$ is independently $C_1$-$C_6$ alkoxy optionally substituted with one or more halo;
$R^6$ is $C_1$-$C_6$ alkyl, and each $R^7$ is independently $C_1$-$C_6$ alkoxy;
$R^6$ is $C_1$-$C_6$ alkyl, and each $R^7$ is independently $C_1$-$C_6$ alkoxy substituted with one or more halo;
$R^6$ is halo, and each $R^7$ is independently $C_1$-$C_6$ haloalkyl;
$R^6$ is halo, and each $R^7$ is independently $C_1$-$C_6$ haloalkoxy;
$R^6$ is $C_1$-$C_6$ alkoxy; and each $R^7$ is independently halo;
$R^6$ is $C_1$-$C_6$ alkoxy; and each $R^7$ is chloro;
each $R^7$ is independently $C_1$-$C_6$ alkyl, and $R^6$ is $C_1$-$C_6$ alkyl optionally substituted with one or more halo;
each $R^7$ is independently $C_1$-$C_6$ alkyl, and $R^6$ is $C_1$-$C_6$ alkyl substituted with one or more halo;
each $R^7$ is independently $C_1$-$C_6$ alkyl, and $R^6$ is $C_3$-$C_7$ cycloalkyl;
each $R^7$ is independently $C_1$-$C_6$ alkyl, and $R^6$ is halo;
each $R^7$ is independently $C_1$-$C_6$ alkyl and $R^6$ is halo;
each $R^7$ is independently $C_1$-$C_6$ alkyl, and $R^6$ is cyano;
each $R^7$ is independently $C_3$-$C_7$ cycloalkyl, and $R^6$ is $C_3$-$C_7$ cycloalkyl;
each $R^7$ is independently $C_3$-$C_7$ cycloalkyl, and $R^6$ is halo;
each $R^7$ is independently $C_3$-$C_7$ cycloalkyl and $R^6$ is halo;
each $R^7$ is independently $C_1$-$C_6$ alkyl, and $R^6$ is $C_1$-$C_6$ alkoxy optionally substituted with one or more halo;
each $R^7$ is independently $C_1$-$C_6$ alkyl, and $R^6$ is $C_1$-$C_6$ alkoxy;

each $R^7$ is independently $C_1$-$C_6$ alkyl, and $R^6$ is $C_1$-$C_6$ alkoxy substituted with one or more halo;
each $R^7$ is independently halo, and $R^6$ is $C_1$-$C_6$ haloalkyl;
each $R^7$ is independently halo, and $R^6$ is $C_1$-$C_6$ haloalkoxy;
each $R^7$ is independently $C_1$-$C_6$ alkoxy; and $R^6$ is halo;
each $R^6$ is independently $C_1$-$C_6$ alkoxy; and $R^6$ is chloro.

In some embodiments, of the compound of formula AA, the substituted ring B is

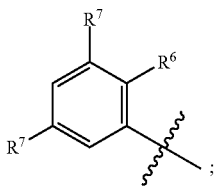

and $R^6$ and $R^7$ are one of the following combinations:
$R^6$ is isopropyl; and each $R^7$ is methyl;
$R^6$ is isopropyl; and each $R^7$ is isopropyl;
$R^6$ is isopropyl; and each $R^7$ is trifluoromethyl;
$R^6$ is isopropyl; and each $R^7$ is cyclopropyl;
$R^6$ is isopropyl; and each $R^7$ is chloro;
$R^6$ is isopropyl; and each $R^7$ is fluoro;
$R^6$ is ethyl; and each $R^7$ is fluoro;
$R^6$ is isopropyl; and each $R^7$ is cyano;
$R^6$ is cyclopropyl; and each $R^7$ is cyclopropyl;
$R^6$ is cyclopropyl; and each $R^7$ is chloro;
$R^6$ is cyclopropyl; and each $R^7$ is fluoro;
$R^6$ is isopropyl; and each $R^7$ is methoxy;
$R^6$ is isopropyl; and $R^7$ is trifluoromethoxy;
$R^6$ is chloro; and each $R^7$ is trifluoromethyl;
$R^6$ is chloro; and each $R^7$ is trifluoromethoxy;
each $R^7$ is isopropyl; and $R^6$ is methyl;
each $R^7$ is isopropyl; and $R^6$ is trifluoromethyl;
each $R^7$ is isopropyl; and $R^6$ is cyclopropyl;
each $R^7$ is isopropyl; and $R^6$ is chloro;
each $R^7$ is ethyl; and $R^6$ is fluoro;
each $R^7$ is isopropyl; and $R^6$ is cyano;
each $R^7$ is cyclopropyl; and $R^6$ is cyclopropyl;
each $R^7$ is cyclopropyl; and $R^6$ is chloro;
each $R^7$ is cyclopropyl; and $R^6$ is fluoro;
each $R^7$ is isopropyl; and $R^6$ is methoxy;
each $R^7$ is isopropyl; and $R^6$ is trifluoromethoxy;
each $R^7$ is chloro; and $R^6$ is trifluoromethyl;
each $R^7$ is chloro; and $R^6$ is trifluoromethoxy.

In some embodiments, of the compound of formula AA, the substituted ring B is

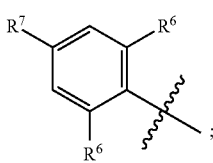

and $R^6$ and $R^7$ are one of the following combinations:
each $R^6$ is independently $C_1$-$C_6$ alkyl, and $R^7$ is $C_1$-$C_6$ alkyl optionally substituted with one or more halo;
each $R^6$ is independently $C_1$-$C_6$ alkyl and $R^7$ is $C_1$-$C_6$ alkyl;
each $R^6$ is independently $C_1$-$C_6$ alkyl, and $R^7$ is $C_1$-$C_6$ alkyl substituted with one or more halo;
each $R^6$ is independently $C_1$-$C_6$ alkyl, and $R^7$ is $C_3$-$C_7$ cycloalkyl;
each $R^6$ is independently $C_1$-$C_6$ alkyl, and $R^7$ is halo;
each $R^6$ is independently $C_1$-$C_6$ alkyl, and $R^7$ is cyano;
each $R^6$ is independently $C_3$-$C_7$ cycloalkyl, and $R^7$ is $C_3$-$C_7$ cycloalkyl;
each $R^6$ is independently $C_3$-$C_7$ cycloalkyl, and $R^7$ is halo;
each $R^6$ is independently cyclopropyl and $R^7$ is halo;
each $R^6$ is independently $C_1$-$C_6$ alkyl, and $R^7$ is $C_1$-$C_6$ alkoxy optionally substituted with one or more halo;
each $R^6$ is independently $C_1$-$C_6$ alkyl, and $R^7$ is $C_1$-$C_6$ alkoxy;
each $R^6$ is independently $C_1$-$C_6$ alkyl, and $R^7$ is $C_1$-$C_6$ alkoxy substituted with one or more halo;
each $R^6$ is independently halo, and $R^7$ is $C_1$-$C_6$ haloalkyl;
each $R^6$ is independently halo, and $R^7$ is $C_1$-$C_6$ haloalkoxy;
each $R^6$ is independently $C_1$-$C_6$ alkoxy; and $R^7$ is halo;
each $R^6$ is independently $C_1$-$C_6$ alkoxy; and $R^7$ is chloro;
$R^7$ is $C_1$-$C_6$ alkyl, and each $R^6$ is independently $C_1$-$C_6$ alkyl optionally substituted with one or more halo;
$R^7$ is $C_1$-$C_6$ alkyl, and each $R^6$ is independently $C_1$-$C_6$ alkyl substituted with one or more halo;
$R^7$ is $C_1$-$C_6$ alkyl, and each $R^6$ is independently $C_3$-$C_7$ cycloalkyl;
$R^7$ is $C_1$-$C_6$ alkyl, and each $R^6$ is independently halo;
$R^7$ is $C_1$-$C_6$ alkyl and each $R^6$ is independently halo;
$R^7$ is $C_1$-$C_6$ alkyl, and each $R^6$ is cyano;
$R^7$ is $C_3$-$C_7$ cycloalkyl, and each $R^6$ is independently $C_3$-$C_7$ cycloalkyl;
$R^7$ is $C_3$-$C_7$ cycloalkyl, and each $R^6$ is independently halo;
$R^7$ is $C_3$-$C_7$ cycloalkyl and each $R^6$ is independently halo;
$R^7$ is $C_1$-$C_6$ alkyl, and each $R^6$ is independently $C_1$-$C_6$ alkoxy optionally substituted with one or more halo;
$R^7$ is $C_1$-$C_6$ alkyl, and each $R^6$ is independently $C_1$-$C_6$ alkoxy;
$R^7$ is $C_1$-$C_6$ alkyl, and each $R^6$ is independently $C_1$-$C_6$ alkoxy substituted with one or more halo;
$R^7$ is halo, and each $R^6$ is independently $C_1$-$C_6$ haloalkyl;
$R^7$ is halo, and each $R^6$ is independently $C_1$-$C_6$ haloalkoxy;
$R^7$ is $C_1$-$C_6$ alkoxy; and each $R^6$ is independently halo;
$R^7$ is $C_1$-$C_6$ alkoxy; and each $R^6$ is chloro.

In some embodiments, of the compound of formula AA, the substituted ring B is

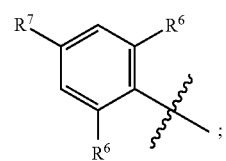

and $R^6$ and W are one of the following combinations:
each $R^6$ is isopropyl; and $R^7$ is methyl;
each $R^6$ is isopropyl; and $R^7$ is isopropyl;
each $R^6$ is isopropyl; and $R^7$ is trifluoromethyl;
each $R^6$ is isopropyl; and $R^7$ is cyclopropyl;
each $R^6$ is isopropyl; and $R^7$ is chloro;
each $R^6$ is isopropyl; and $R^7$ is fluoro;
each $R^6$ is ethyl; and $R^7$ is fluoro;
each $R^6$ is isopropyl; and $R^7$ is cyano;
each $R^6$ is cyclopropyl; and $R^7$ is cyclopropyl;
each $R^6$ is cyclopropyl; and $R^7$ is chloro;
each $R^6$ is cyclopropyl; and $R^7$ is fluoro;

each $R^6$ is isopropyl; and $R^7$ is methoxy;
each $R^6$ is isopropyl; and $R^7$ is trifluoromethoxy;
each $R^6$ is chloro; and $R^7$ is trifluoromethyl;
each $R^6$ is chloro; and $R^7$ is trifluoromethoxy;
$R^7$ is isopropyl; and each $R^6$ is methyl;
$R^7$ is isopropyl; and each $R^6$ is trifluoromethyl;
$R^7$ is isopropyl; and each $R^6$ is cyclopropyl;
$R^7$ is isopropyl; and each $R^6$ is chloro;
$R^7$ is ethyl; and each $R^6$ is fluoro;
$R^7$ is isopropyl; and each $R^6$ is cyano;
$R^7$ is cyclopropyl; and each $R^6$ is cyclopropyl;
$R^7$ is cyclopropyl; and each $R^6$ is chloro;
$R^7$ is cyclopropyl; and each $R^6$ is fluoro;
$R^7$ is isopropyl; and each $R^6$ is methoxy;
$R^7$ is isopropyl; and each $R^6$ is trifluoromethoxy;
$R^7$ is chloro; and each $R^6$ is trifluoromethyl;
$R^7$ is chloro; and each $R^6$ is trifluoromethoxy;
one $R^6$ is isopropyl; the other $R^6$ is trifluoromethyl; and $R^7$ is chloro.

In some embodiments, of the compound of formula AA, the substituted ring B is

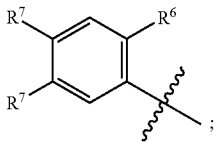

and $R^6$ and $R^7$ are one of the following combinations:
$R^6$ is $C_1$-$C_6$ alkyl, and each $R^7$ is independently $C_1$-$C_6$ alkyl optionally substituted with one or more halo;
$R^6$ is $C_1$-$C_6$ alkyl and each $R^7$ is independently $C_1$-$C_6$ alkyl;
$R^6$ is $C_1$-$C_6$ alkyl, and each $R^7$ is independently $C_1$-$C_6$ alkyl substituted with one or more halo;
$R^6$ is $C_1$-$C_6$ alkyl, and each $R^7$ is independently $C_3$-$C_7$ cycloalkyl;
$R^6$ is $C_1$-$C_6$ alkyl, and each $R^7$ is independently halo;
$R^6$ is $C_1$-$C_6$ alkyl, and each $R^7$ is cyano;
$R^6$ is $C_3$-$C_7$ cycloalkyl, and each $R^7$ is independently $C_3$-$C_7$ cycloalkyl;
$R^6$ is $C_3$-$C_7$ cycloalkyl, and each $R^7$ is independently halo;
$R^6$ is cyclopropyl and each $R^7$ is independently halo;
$R^6$ is $C_1$-$C_6$ alkyl, and each $R^7$ is independently $C_1$-$C_6$ alkoxy optionally substituted with one or more halo;
$R^6$ is $C_1$-$C_6$ alkyl, and each $R^7$ is independently $C_1$-$C_6$ alkoxy;
$R^6$ is $C_1$-$C_6$ alkyl, and each $R^7$ is independently $C_1$-$C_6$ alkoxy substituted with one or more halo;
$R^6$ is halo, and each $R^7$ is independently $C_1$-$C_6$ haloalkyl;
$R^6$ is halo, and each $R^7$ is independently $C_1$-$C_6$ haloalkoxy;
$R^6$ is $C_1$-$C_6$ alkoxy; and each $R^7$ is independently halo;
$R^6$ is $C_1$-$C_6$ alkoxy; and each $R^7$ is chloro;
each $R^7$ is independently $C_1$-$C_6$ alkyl, and $R^6$ is $C_1$-$C_6$ alkyl optionally substituted with one or more halo;
each $R^7$ is independently $C_1$-$C_6$ alkyl, and $R^6$ is $C_1$-$C_6$ alkyl substituted with one or more halo;
each $R^7$ is independently $C_1$-$C_6$ alkyl, and $R^6$ is $C_3$-$C_7$ cycloalkyl;
each $R^7$ is independently $C_1$-$C_6$ alkyl, and $R^6$ is halo;
each $R^7$ is independently $C_1$-$C_6$ alkyl and $R^6$ is halo;
each $R^7$ is independently $C_1$-$C_6$ alkyl, and $R^6$ is cyano;
each $R^7$ is independently $C_3$-$C_7$ cycloalkyl, and $R^6$ is $C_3$-$C_7$ cycloalkyl;
each $R^7$ is independently $C_3$-$C_7$ cycloalkyl, and $R^6$ is halo;
each $R^7$ is independently $C_3$-$C_7$ cycloalkyl and $R^6$ is halo;
each $R^7$ is independently $C_1$-$C_6$ alkyl, and $R^6$ is $C_1$-$C_6$ alkoxy optionally substituted with one or more halo;
each $R^7$ is independently $C_1$-$C_6$ alkyl, and $R^6$ is $C_1$-$C_6$ alkoxy;
each $R^7$ is independently $C_1$-$C_6$ alkyl, and $R^6$ is $C_1$-$C_6$ alkoxy substituted with one or more halo;
each $R^7$ is independently halo, and $R^6$ is $C_1$-$C_6$ haloalkyl;
each $R^7$ is independently halo, and $R^6$ is $C_1$-$C_6$ haloalkoxy;
each $R^7$ is independently $C_1$-$C_6$ alkoxy; and $R^6$ is halo;
each $R^7$ is independently $C_1$-$C_6$ alkoxy; and $R^6$ is chloro.

In some embodiments, of the compound of formula AA, the substituted ring B is

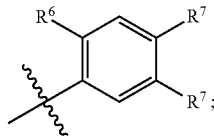

and $R^6$ and $R^7$ are one of the following combinations:
$R^6$ is isopropyl; and each $R^7$ is methyl;
$R^6$ is isopropyl; and each $R^7$ is isopropyl;
$R^6$ is isopropyl; and each $R^7$ is trifluoromethyl;
$R^6$ is isopropyl; and each $R^7$ is cyclopropyl;
$R^6$ is isopropyl; and each $R^7$ is chloro;
$R^6$ is isopropyl; and each $R^7$ is fluoro;
$R^6$ is ethyl; and each $R^7$ is fluoro;
$R^6$ is isopropyl; and each $R^7$ is cyano;
$R^6$ is cyclopropyl; and each $R^7$ is cyclopropyl;
$R^6$ is cyclopropyl; and each $R^7$ is chloro;
$R^6$ is cyclopropyl; and each $R^7$ is fluoro;
$R^6$ is isopropyl; and each $R^7$ is methoxy;
$R^6$ is isopropyl; and each $R^7$ is trifluoromethoxy;
$R^6$ is chloro; and each $R^7$ is trifluoromethyl;
$R^6$ is chloro; and each $R^7$ is trifluoromethoxy;
each $R^7$ is isopropyl; and $R^6$ is methyl;
each $R^7$ is isopropyl; and $R^6$ is trifluoromethyl;
each $R^7$ is isopropyl; and $R^6$ is cyclopropyl;
each $R^7$ is isopropyl; and $R^6$ is chloro;
each $R^7$ is ethyl; and $R^6$ is fluoro;
each $R^7$ is isopropyl; and $R^6$ is cyano;
each $R^7$ is cyclopropyl; and $R^6$ is cyclopropyl;
each $R^7$ is cyclopropyl; and $R^6$ is chloro;
each $R^7$ is cyclopropyl; and $R^6$ is fluoro;
each $R^7$ is isopropyl; and $R^6$ is methoxy;
each $R^7$ is isopropyl; and $R^6$ is trifluoromethoxy;
each $R^7$ is chloro; and $R^6$ is trifluoromethyl;
each $R^7$ is chloro; and $R^6$ is trifluoromethoxy.

In some embodiments, of the compound of formula AA, the substituted ring B is

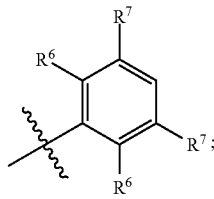

and R⁶ and R⁷ are one of the following combinations:
  each R⁶ is independently $C_1$-$C_6$ alkyl, and each R⁷ is independently $C_1$-$C_6$ alkyl optionally substituted with one or more halo;
  each R⁶ is independently $C_1$-$C_6$ alkyl and each R⁷ is independently $C_1$-$C_6$ alkyl;
  each R⁶ is independently $C_1$-$C_6$ alkyl, and each R⁷ is independently $C_1$-$C_6$ alkyl substituted with one or more halo;
  each R⁶ is independently $C_1$-$C_6$ alkyl, and each R⁷ is independently $C_3$-$C_7$ cycloalkyl;
  each R⁶ is independently $C_1$-$C_6$ alkyl, and each R⁷ is independently halo;
  each R⁶ is independently $C_1$-$C_6$ alkyl, and each R⁷ is cyano;
  each R⁶ is independently $C_3$-$C_7$ cycloalkyl, and each R⁷ is independently $C_3$-$C_7$ cycloalkyl;
  each R⁶ is independently $C_3$-$C_7$ cycloalkyl, and each R⁷ is independently halo;
  each R⁶ is independently cyclopropyl and each R⁷ is independently halo;
  each R⁶ is independently $C_1$-$C_6$ alkyl, and each R⁷ is independently $C_1$-$C_6$ alkoxy optionally substituted with one or more halo;
  each R⁶ is independently $C_1$-$C_6$ alkyl, and each R⁷ is independently $C_1$-$C_6$ alkoxy;
  each R⁶ is independently $C_1$-$C_6$ alkyl, and each R⁷ is independently $C_1$-$C_6$ alkoxy substituted with one or more halo;
  each R⁶ is independently halo, and each R⁷ is independently $C_1$-$C_6$ haloalkyl;
  each R⁶ is independently halo, and each R⁷ is independently $C_1$-$C_6$ haloalkoxy;
  each R⁶ is independently $C_1$-$C_6$ alkoxy; and each R⁷ is independently halo;
  each R⁶ is independently $C_1$-$C_6$ alkoxy; and each R⁷ is chloro;
  each R⁷ is independently $C_1$-$C_6$ alkyl, and each R⁶ is independently $C_1$-$C_6$ alkyl optionally substituted with one or more halo;
  each R⁷ is independently $C_1$-$C_6$ alkyl, and each R⁶ is independently $C_1$-$C_6$ alkyl substituted with one or more halo;
  each R⁷ is independently $C_1$-$C_6$ alkyl, and each R⁶ is independently $C_3$-$C_7$ cycloalkyl;
  each R⁷ is independently $C_1$-$C_6$ alkyl, and each R⁶ is independently halo;
  each R⁷ is independently $C_1$-$C_6$ alkyl and each R⁶ is independently halo;
  each R⁷ is independently $C_1$-$C_6$ alkyl, and each R⁶ is cyano;
  each R⁷ is independently $C_3$-$C_7$ cycloalkyl, and each R⁶ is independently $C_3$-$C_7$ cycloalkyl;
  each R⁷ is independently $C_3$-$C_7$ cycloalkyl, and each R⁶ is independently halo;
  each R⁷ is independently $C_3$-$C_7$ cycloalkyl and each R⁶ is independently halo;
  each R⁷ is independently $C_1$-$C_6$ alkyl, and each R⁶ is independently $C_1$-$C_6$ alkoxy optionally substituted with one or more halo;
  each R⁷ is independently $C_1$-$C_6$ alkyl, and each R⁶ is independently $C_1$-$C_6$ alkoxy;
  each R⁷ is independently $C_1$-$C_6$ alkyl, and each R⁶ is independently $C_1$-$C_6$ alkoxy substituted with one or more halo;
  each R⁷ is independently halo, and each R⁶ is independently $C_1$-$C_6$ haloalkyl;
  each R⁷ is independently halo, and each R⁶ is independently $C_1$-$C_6$ haloalkoxy;
  each R⁷ is independently $C_1$-$C_6$ alkoxy; and each R⁶ is independently halo;
  each R⁷ is independently $C_1$-$C_6$ alkoxy; and each R⁶ is chloro; two pairs, each of one R⁶ and one R⁷, are on adjacent atoms, and each pair of one R⁶ and one R⁷ taken together with the atoms connecting them form a $C_4$-$C_8$ aliphatic carbocyclic ring; two pairs, each of one R⁶ and one R⁷, are on adjacent atoms, and each pair of one R⁶ and one R⁷ taken together with the atoms connecting them form a $C_4$-$C_6$ aliphatic carbocyclic ring optionally substituted with one or more hydroxy, oxo, or $C_1$-$C_6$ alkyl; or two pairs, each of one R⁶ and one R⁷, are on adjacent atoms, and each pair of one R⁶ and one R⁷ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

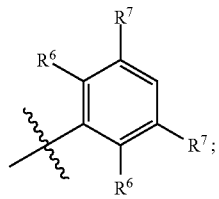

and R⁶ and R⁷ are one of the following combinations:
  each R⁶ is isopropyl; and each R⁷ is methyl;
  each R⁶ is isopropyl; and each R⁷ is isopropyl;
  each R⁶ is isopropyl; and each R⁷ is trifluoromethyl;
  each R⁶ is isopropyl; and each R⁷ is cyclopropyl;
  each R⁶ is isopropyl; and each R⁷ is chloro;
  each R⁶ is isopropyl; and each R⁷ is fluoro;
  each R⁶ is ethyl; and each R⁷ is fluoro;
  each R⁶ is isopropyl; and each R⁷ is cyano;
  each R⁶ is cyclopropyl; and each R⁷ is cyclopropyl;
  each R⁶ is cyclopropyl; and each R⁷ is chloro;
  each R⁶ is cyclopropyl; and each R⁷ is fluoro;
  each R⁶ is isopropyl; and each R⁷ is methoxy;
  each R⁶ is isopropyl; and each R⁷ is trifluoromethoxy;
  each R⁶ is chloro; and each R⁷ is trifluoromethyl;
  each R⁶ is chloro; and each R⁷ is trifluoromethoxy;
  each R⁷ is isopropyl; and each R⁶ is methyl;
  each R⁷ is isopropyl; and each R⁶ is trifluoromethyl;
  each R⁷ is isopropyl; and each R⁶ is cyclopropyl;
  each R⁷ is isopropyl; and each R⁶ is chloro;
  each R⁷ is ethyl; and each R⁶ is fluoro;
  each R⁷ is isopropyl; and each R⁶ is cyano;
  each R⁷ is cyclopropyl; and each R⁶ is cyclopropyl;
  each R⁷ is cyclopropyl; and each R⁶ is chloro;
  each R⁷ is cyclopropyl; and each R⁶ is fluoro;
  each R⁷ is isopropyl; and each R⁶ is methoxy;
  each R⁷ is isopropyl; and each R⁶ is trifluoromethoxy;
  each R⁷ is chloro; and each R⁶ is trifluoromethyl;
  each R⁷ is chloro; and each R⁶ is trifluoromethoxy;
  one R⁶ is isopropyl; the other R⁶ is trifluoromethyl; and each R⁷ is chloro;
  each R⁶ is isopropyl; one R⁷ is fluoro; and the other R⁷ is cyano;

two pairs, each of one $R^6$ and one $R^7$, are on adjacent atoms, and each pair of one $R^6$ and one $R^7$ taken together with the atoms connecting them form a $C_5$ aliphatic carbocyclic ring;
two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;
two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl; or
two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl.

In some embodiments, of the compound of formula AA, the substituted ring B is

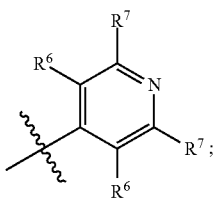

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl, and each $R^7$ is independently $C_3$-$C_7$ cycloalkyl;
each $R^6$ is independently $C_1$-$C_6$ alkyl, and each $R^7$ is independently halo;
each $R^6$ is independently $C_1$-$C_6$ alkyl, and each $R^7$ is cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and each $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and each $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and each $R^6$ is chloro;
two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;
two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; or
two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

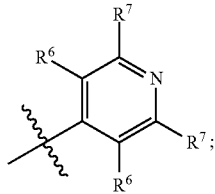

and $R^6$ and $R^7$ are one of the following combinations:
- each $R^6$ is isopropyl; and each $R^7$ is methyl;
- each $R^6$ is isopropyl; and each $R^7$ is isopropyl;
- each $R^6$ is isopropyl; and each $R^7$ is trifluoromethyl;
- each $R^6$ is isopropyl; and each $R^7$ is cyclopropyl;
- each $R^6$ is isopropyl; and each $R^7$ is chloro;
- each $R^6$ is isopropyl; and each $R^7$ is fluoro;
- each $R^6$ is ethyl; and each $R^7$ is fluoro;
- each $R^6$ is isopropyl; and each $R^7$ is cyano;
- each $R^6$ is cyclopropyl; and each $R^7$ is cyclopropyl;
- each $R^6$ is cyclopropyl; and each $R^7$ is chloro;
- each $R^6$ is cyclopropyl; and each $R^7$ is fluoro;
- each $R^6$ is isopropyl; and each $R^7$ is methoxy;
- each $R^6$ is isopropyl; and each $R^7$ is trifluoromethoxy;
- each $R^6$ is chloro; and each $R^7$ is trifluoromethyl;
- each $R^6$ is chloro; and each $R^7$ is trifluoromethoxy;
- each $R^7$ is isopropyl; and each $R^6$ is methyl;
- each $R^7$ is isopropyl; and each $R^6$ is trifluoromethyl;
- each $R^7$ is isopropyl; and each $R^6$ is cyclopropyl;
- each $R^7$ is isopropyl; and each $R^6$ is chloro;
- each $R^7$ is ethyl; and each $R^6$ is fluoro;
- each $R^7$ is isopropyl; and each $R^6$ is cyano;
- each $R^7$ is cyclopropyl; and each $R^6$ is cyclopropyl;
- each $R^7$ is cyclopropyl; and each $R^6$ is chloro;
- each $R^7$ is cyclopropyl; and each $R^6$ is fluoro;
- each $R^7$ is isopropyl; and each $R^6$ is methoxy;
- each $R^7$ is isopropyl; and each $R^6$ is trifluoromethoxy;
- each $R^7$ is chloro; and each $R^6$ is trifluoromethyl;
- each $R^7$ is chloro; and each $R^6$ is trifluoromethoxy;
- one $R^6$ is isopropyl; the other $R^6$ is trifluoromethyl; and each $R^7$ is chloro;
- each $R^6$ is isopropyl; one $R^7$ is fluoro; and the other $R^7$ is cyano;
- two pairs, each of one $R^6$ and one $R^7$, are on adjacent atoms, and each pair of one $R^6$ and one $R^7$ taken together with the atoms connecting them form a $C_5$ aliphatic carbocyclic ring;
- two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;
- two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
- two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
- two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl; or
- two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl.

In some embodiments, of the compound of formula AA, the substituted ring B is

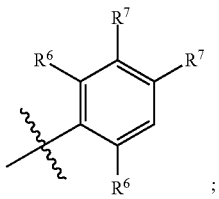

and $R^6$ and $R^7$ are one of the following combinations:
- each $R^6$ is independently $C_1$-$C_6$ alkyl, and each $R^7$ is independently $C_1$-$C_6$ alkyl optionally substituted with one or more halo;
- each $R^6$ is independently $C_1$-$C_6$ alkyl and each $R^7$ is independently $C_1$-$C_6$ alkyl;
- each $R^6$ is independently $C_1$-$C_6$ alkyl, and each $R^7$ is independently $C_1$-$C_6$ alkyl substituted with one or more halo;
- each $R^6$ is independently $C_1$-$C_6$ alkyl, and each $R^7$ is independently $C_3$-$C_7$ cycloalkyl;
- each $R^6$ is independently $C_1$-$C_6$ alkyl, and each $R^7$ is independently halo;
- each $R^6$ is independently $C_1$-$C_6$ alkyl, and each $R^7$ is cyano;
- each $R^6$ is independently $C_3$-$C_7$ cycloalkyl, and each $R^7$ is independently $C_3$-$C_7$ cycloalkyl;
- each $R^6$ is independently $C_3$-$C_7$ cycloalkyl, and each $R^7$ is independently halo;
- each $R^6$ is independently cyclopropyl and each $R^7$ is independently halo;
- each $R^6$ is independently $C_1$-$C_6$ alkyl, and each $R^7$ is independently $C_1$-$C_6$ alkoxy optionally substituted with one or more halo;
- each $R^6$ is independently $C_1$-$C_6$ alkyl, and each $R^7$ is independently $C_1$-$C_6$ alkoxy;
- each $R^6$ is independently $C_1$-$C_6$ alkyl, and each $R^7$ is independently $C_1$-$C_6$ alkoxy substituted with one or more halo;
- each $R^6$ is independently halo, and each $R^7$ is independently $C_1$-$C_6$ haloalkyl;
- each $R^6$ is independently halo, and each $R^7$ is independently $C_1$-$C_6$ haloalkoxy;
- each $R^6$ is independently $C_1$-$C_6$ alkoxy; and each $R^7$ is independently halo;
- each $R^6$ is independently $C_1$-$C_6$ alkoxy; and each $R^7$ is chloro;
- each $R^7$ is independently $C_1$-$C_6$ alkyl, and each $R^6$ is independently $C_1$-$C_6$ alkyl optionally substituted with one or more halo;

each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and each $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and each $R^6$ is chloro.

In some embodiments, of the compound of formula AA, the substituted ring B is

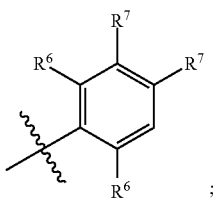

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano.

In some embodiments, of the compound of formula AA, the substituted ring B is

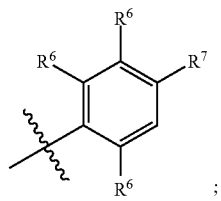

and $R^6$ and W are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl, and each $R^7$ is independently $C_3$-$C_7$ cycloalkyl;
each $R^6$ is independently $C_1$-$C_6$ alkyl, and each $R^7$ is independently halo;
each $R^6$ is independently $C_1$-$C_6$ alkyl, and each $R^7$ is independently cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and each $R^7$ is chloro;
each $R^7$ is independently $C_1$-$C_6$ alkyl, and each $R^6$ is independently $C_1$-$C_6$ alkyl optionally substituted with one or more halo;

each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and each $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and each $R^6$ is chloro;
$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

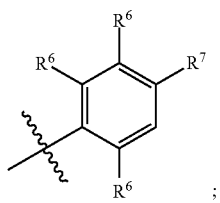
;

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano;
$R^6$ and $R^7$ on adjacent atoms taken together with the atoms connecting them form a $C_4$ aliphatic carbocyclic ring; and one $R^6$ is chloro, fluoro, or cyano;
$R^6$ and $R^7$ on adjacent atoms taken together with the atoms connecting them form a $C_5$ aliphatic carbocyclic ring; and one $R^6$ is chloro, fluoro, or cyano;
$R^6$ and $R^7$ on adjacent atoms taken together with the atoms connecting them form a $C_6$ aliphatic carbocyclic ring; and one $R^6$ is chloro, fluoro, or cyano;
$R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano;
$R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or
$R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

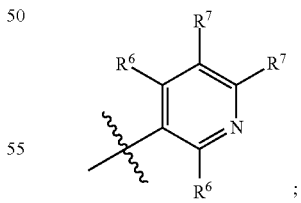
;

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;

each $R^6$ is independently $C_1$-$C_6$ alkyl, and each $R^7$ is independently $C_3$-$C_7$ cycloalkyl;
each $R^6$ is independently $C_1$-$C_6$ alkyl, and each $R^7$ is independently halo;
each $R^6$ is independently $C_1$-$C_6$ alkyl, and each $R^7$ is cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and $R^6$ is chloro.

In some embodiments, of the compound of formula AA, the substituted ring B is

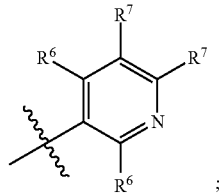

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano.

In some embodiments, of the compound of formula AA, the substituted ring B is

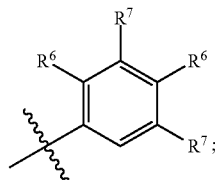

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl, and each $R^7$ is independently $C_3$-$C_7$ cycloalkyl;

each $R^6$ is independently $C_1$-$C_6$ alkyl, and each $R^7$ is independently halo;
each $R^6$ is independently $C_1$-$C_6$ alkyl, and each $R^7$ is cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and each $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and each $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and each $R^6$ is chloro;
Two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;

$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

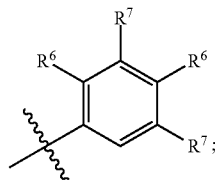

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano;
two pairs, each of one $R^6$ and one $R^7$, are on adjacent atoms, and each pair of one $R^6$ and one $R^7$ taken together with the atoms connecting them form a $C_5$ aliphatic carbocyclic ring;
$R^6$ and $R^7$ on adjacent atoms taken together with the atoms connecting them form a $C_4$ aliphatic carbocyclic ring; and one $R^6$ is chloro, fluoro, or cyano;
$R^6$ and $R^7$ on adjacent atoms taken together with the atoms connecting them form a $C_5$ aliphatic carbocyclic ring; and one $R^6$ is chloro, fluoro, or cyano;

$R^6$ and $R^7$ on adjacent atoms taken together with the atoms connecting them form a $C_6$ aliphatic carbocyclic ring; and one $R^6$ is chloro, fluoro, or cyano;

$R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano;

$R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or $R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

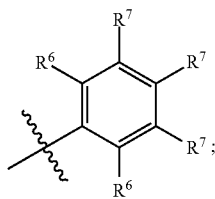

and $R^6$ and $R^7$ are one of the following combinations:
- each $R^6$ is independently $C_1$-$C_6$ alkyl, and each $R^7$ is $C_1$-$C_6$ alkyl optionally substituted with one or more halo;
- each $R^6$ is independently $C_1$-$C_6$ alkyl and $R^7$ is $C_1$-$C_6$ alkyl;
- each $R^6$ is independently $C_1$-$C_6$ alkyl, and $R^7$ is $C_1$-$C_6$ alkyl substituted with one or more halo;
- each $R^6$ is independently $C_1$-$C_6$ alkyl, and $R^7$ is $C_3$-$C_7$ cycloalkyl;
- each $R^6$ is independently $C_1$-$C_6$ alkyl, and $R^7$ is halo;
- each $R^6$ is independently $C_1$-$C_6$ alkyl, and $R^7$ is cyano;
- each $R^6$ is independently $C_3$-$C_7$ cycloalkyl, and $R^7$ is $C_3$-$C_7$ cycloalkyl;
- each $R^6$ is independently $C_3$-$C_7$ cycloalkyl, and $R^7$ is halo;
- each $R^6$ is independently cyclopropyl and $R^7$ is halo;
- each $R^6$ is independently $C_1$-$C_6$ alkyl, and $R^7$ is $C_1$-$C_6$ alkoxy optionally substituted with one or more halo;
- each $R^6$ is independently $C_1$-$C_6$ alkyl, and $R^7$ is $C_1$-$C_6$ alkoxy;
- each $R^6$ is independently $C_1$-$C_6$ alkyl, and $R^7$ is $C_1$-$C_6$ alkoxy substituted with one or more halo;
- each $R^6$ is independently halo, and $R^7$ is $C_1$-$C_6$ haloalkyl;
- each $R^6$ is independently halo, and $R^7$ is $C_1$-$C_6$ haloalkoxy;
- each $R^6$ is independently $C_1$-$C_6$ alkoxy; and $R^7$ is halo;
- each $R^6$ is independently $C_1$-$C_6$ alkoxy; and $R^7$ is chloro;
- $R^7$ is $C_1$-$C_6$ alkyl, and each $R^6$ is independently $C_1$-$C_6$ alkyl optionally substituted with one or more halo;
- $R^7$ is $C_1$-$C_6$ alkyl, and each $R^6$ is independently $C_1$-$C_6$ alkyl substituted with one or more halo;
- $R^7$ is $C_1$-$C_6$ alkyl, and each $R^6$ is independently $C_3$-$C_7$ cycloalkyl;
- $R^7$ is $C_1$-$C_6$ alkyl, and each $R^6$ is independently halo;
- $R^7$ is $C_1$-$C_6$ alkyl and each $R^6$ is independently halo;
- $R^7$ is $C_1$-$C_6$ alkyl, and $R^6$ is cyano;
- $R^7$ is $C_3$-$C_7$ cycloalkyl, and each $R^6$ is independently $C_3$-$C_7$ cycloalkyl;
- $R^7$ is $C_3$-$C_7$ cycloalkyl, and each $R^6$ is independently halo;
- $R^7$ is $C_3$-$C_7$ cycloalkyl and each $R^6$ is independently halo;
- $R^7$ is $C_1$-$C_6$ alkyl, and each $R^6$ is independently $C_1$-$C_6$ alkoxy optionally substituted with one or more halo;
- $R^7$ is $C_1$-$C_6$ alkyl, and each $R^6$ is independently $C_1$-$C_6$ alkoxy;
- $R^7$ is $C_1$-$C_6$ alkyl, and each $R^6$ is independently $C_1$-$C_6$ alkoxy substituted with one or more halo;
- $R^7$ is halo, and each $R^6$ is independently $C_1$-$C_6$ haloalkyl;
- $R^7$ is halo, and each $R^6$ is independently $C_1$-$C_6$ haloalkoxy;
- $R^7$ is $C_1$-$C_6$ alkoxy; and each $R^6$ is independently halo;
- $R^7$ is $C_1$-$C_6$ alkoxy; and $R^6$ is chloro;
- two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;
- and one $R^7$ is halo and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; and one $R^7$ is halo or cyano; or
- two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano.

In some embodiments, of the compound of formula AA, the substituted ring B is

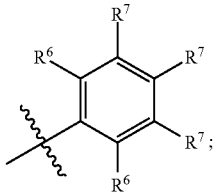

and $R^6$ and $R^7$ are one of the following combinations:
- each $R^6$ is isopropyl; and each $R^7$ is methyl;
- each $R^6$ is isopropyl; and each $R^7$ is isopropyl;
- each $R^6$ is isopropyl; and each $R^7$ is trifluoromethyl;
- each $R^6$ is isopropyl; and each $R^7$ is cyclopropyl;
- each $R^6$ is isopropyl; and each $R^7$ is chloro;
- each $R^6$ is isopropyl; and each $R^7$ is fluoro;
- each $R^6$ is ethyl; and each $R^7$ is fluoro;
- each $R^6$ is isopropyl; and each $R^7$ is cyano;
- each $R^6$ is cyclopropyl; and each $R^7$ is cyclopropyl;
- each $R^6$ is cyclopropyl; and each $R^7$ is chloro;
- each $R^6$ is cyclopropyl; and each $R^7$ is fluoro;
- each $R^6$ is isopropyl; and each $R^7$ is methoxy;
- each $R^6$ is isopropyl; and each $R^7$ is trifluoromethoxy;
- each $R^6$ is chloro; and each $R^7$ is trifluoromethyl;
- each $R^6$ is chloro; and each $R^7$ is trifluoromethoxy;
- each $R^7$ is isopropyl; and each $R^6$ is methyl;
- each $R^7$ is isopropyl; and each $R^6$ is trifluoromethyl;
- each $R^7$ is isopropyl; and each $R^6$ is cyclopropyl;
- each $R^7$ is isopropyl; and each $R^6$ is chloro;
- each $R^7$ is ethyl; and each $R^6$ is fluoro;
- each $R^7$ is isopropyl; and each $R^6$ is cyano;
- each $R^7$ is cyclopropyl; and each $R^6$ is cyclopropyl;
- each $R^7$ is cyclopropyl; and each $R^6$ is chloro;

each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
each $R^6$ is isopropyl; two $R^7$ are fluoro; and one $R^7$ is chloro;
two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is chloro;
(i) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl; and one $R^7$ is fluoro or chloro;
(ii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro;
(iii) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl; and one $R^7$ is fluoro or chloro;
(iv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl; and one $R^7$ is fluoro or chloro or
two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; and one $R^7$ is fluoro or chloro.

Unless otherwise indicated, when a disclosed compound is named or depicted by a structure without specifying the stereochemistry and has one or more chiral centers, it is understood to represent all possible stereoisomers of the compound.

It is understood that the combination of variables in the formulae herein is such that the compounds are stable.

In some embodiments, provided herein is a compound that is selected from the group consisting of the compounds in Table 1:

TABLE 1

| Compound | Structure |
| --- | --- |
| 101 | 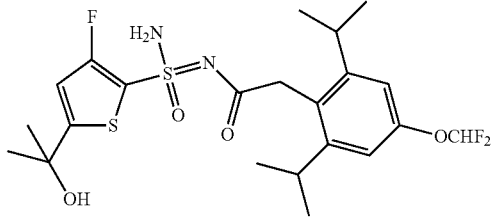 [SMILES: CC(C)c1cc(OC(F)F)cc(C(C)C)c1CC(=O)N=S(N)(=O)c1sc(C(C)(C)O)cc1F] |
| 101a | 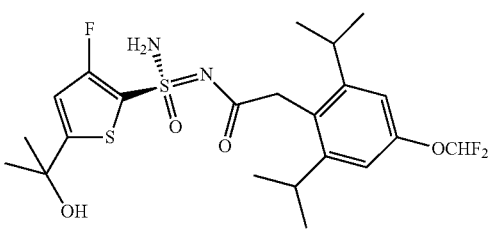 (R) |
| 101b | 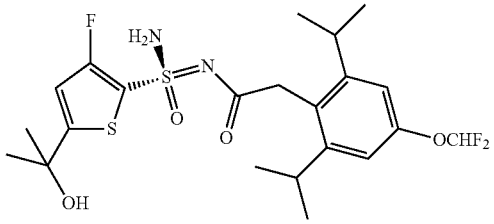 (S) |

TABLE 1-continued

| Compound | Structure |
|---|---|
| 102 | (structure) |
| 103 | (structure) |
| 104 | (structure) |
| 104a | (structure) (R) |
| 104b | (structure) (S) |
| 105 | (structure) |

TABLE 1-continued

| Compound | Structure |
|---|---|
| 106 | (structure) |
| 106a | (structure) (R) |
| 106b | (structure) (S) |
| 107 | (structure) |
| 107a | (structure) (R) |
| 107b | (structure) (S) |

TABLE 1-continued

| Compound | Structure |
|---|---|
| 108 | (structure) |
| 109 | (structure) |
| 110 | (structure) |
| 110a' | (structure) |
| 110b' | (structure) |
| 110a | (structure) |

TABLE 1-continued
| Compound | Structure |
|---|---|
| 110b | 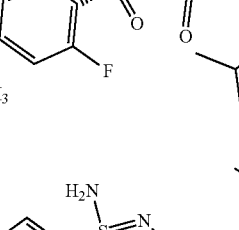 |
| 111 | 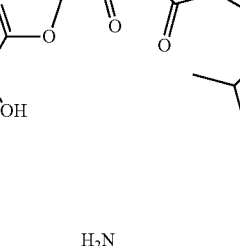 |
| 112 | 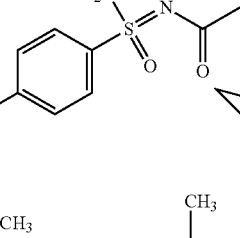 |
| 112a | 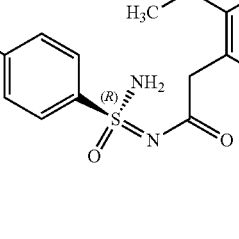 (R) |
| 112b | 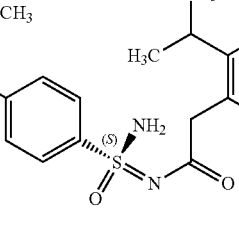 (S) |
| 113 | 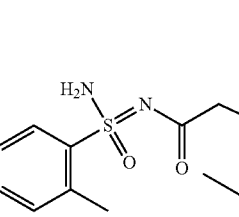 |

TABLE 1-continued

| Compound | Structure |
|---|---|
| 114 | 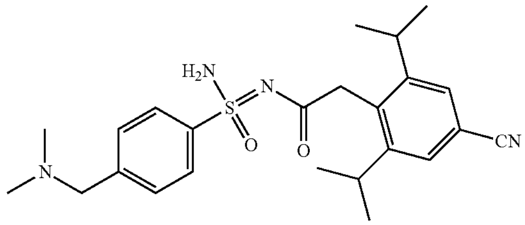 [SMILES: CC(C)c1cc(C#N)cc(C(C)C)c1CC(=O)N=S(N)(=O)c1ccc(CN(C)C)cc1] |
| 114a | (R) |
| 114b | (S) |
| 115 | 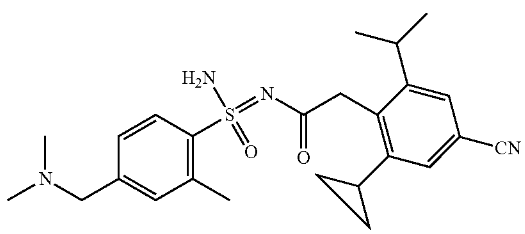 [SMILES: Cc1cc(CN(C)C)ccc1S(N)(=O)=NC(=O)Cc1c(C(C)C)cc(C#N)cc1C1CC1] |
| 116 | 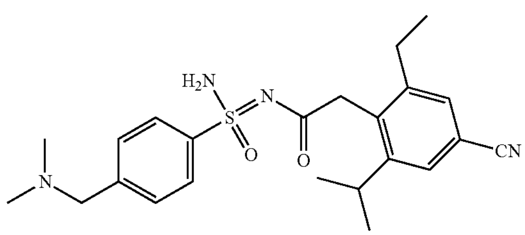 [SMILES: CCc1cc(C#N)cc(C(C)C)c1CC(=O)N=S(N)(=O)c1ccc(CN(C)C)cc1] |
| 116a | (R) |

TABLE 1-continued
| Compound | Structure |
|---|---|
| 116b | 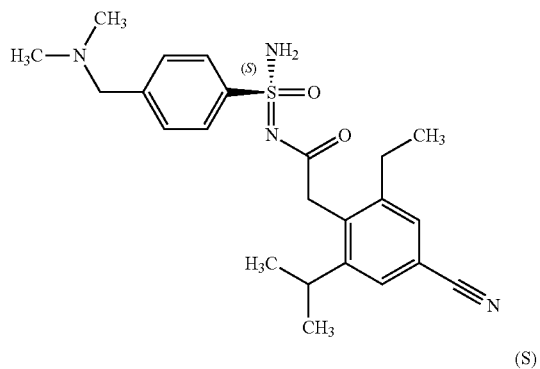 (S) |
| 117 | 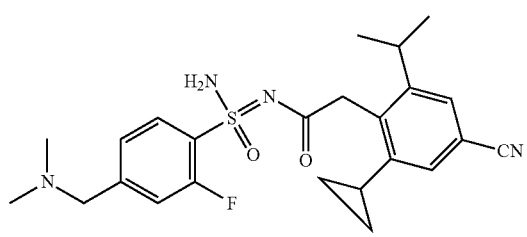 |
| 117a | 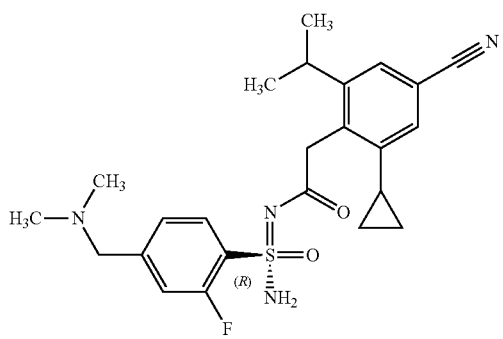 (R) |
| 117b | 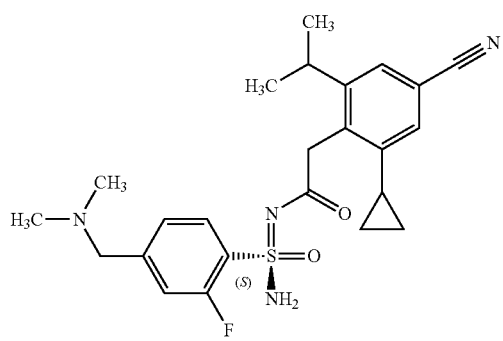 (S) |
| 118 | 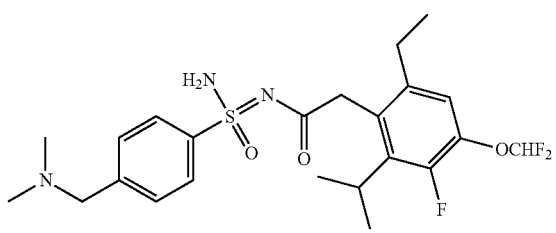 |

TABLE 1-continued

| Compound | Structure |
|---|---|
| 119 | 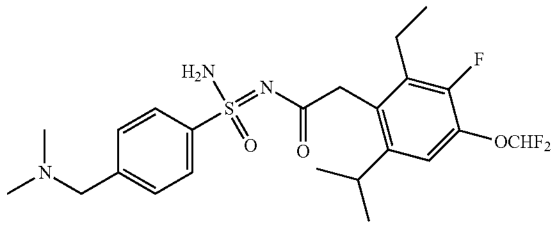 [SMILES: CCc1c(F)c(OC(F)F)cc(C(C)C)c1CC(=O)N=S(N)(=O)c1ccc(CN(C)C)cc1] |
| 120 | 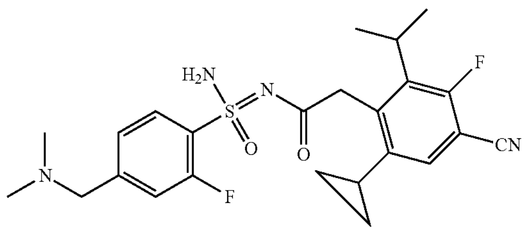 |
| 121 | 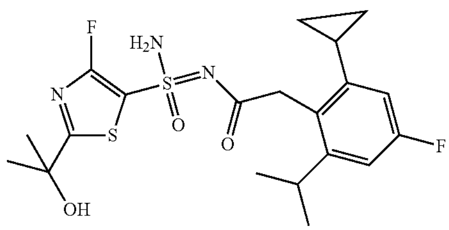 [SMILES: CC(C)c1cc(F)cc(C2CC2)c1CC(=O)N=S(N)(=O)c1sc(C(C)(C)O)nc1F] |
| 122 | 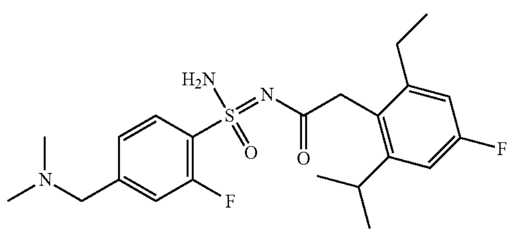 [SMILES: CCc1cc(F)cc(C(C)C)c1CC(=O)N=S(N)(=O)c1ccc(CN(C)C)cc1F] |
| 123 | 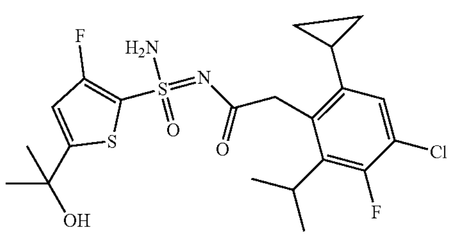 [SMILES: CC(C)c1c(F)c(Cl)cc(C2CC2)c1CC(=O)N=S(N)(=O)c1sc(C(C)(C)O)cc1F] |
| 123a | (R) |

TABLE 1-continued

| Compound | Structure |
|---|---|
| 123b | (S) |
| 124 | 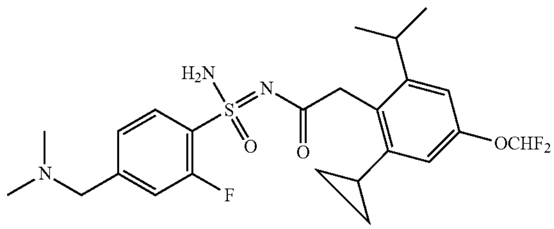 |
| 125 | 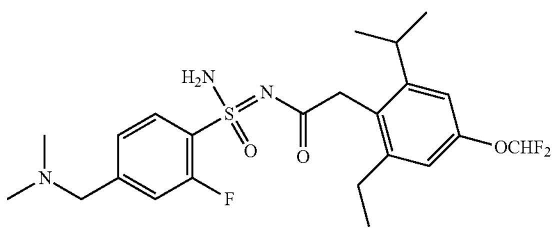 |
| 126 | 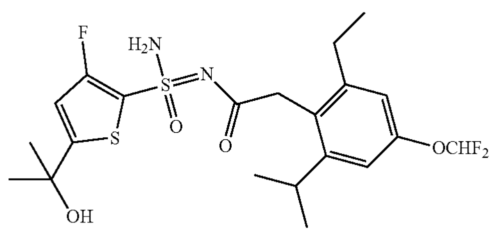 |
| 126a | (R) |
| 126b | (S) |

TABLE 1-continued

| Compound | Structure |
|---|---|
| 127 | *(chemical structure)* |
| 128 | *(chemical structure)* |
| 129 | *(chemical structure)* |
| 129a | *(chemical structure)* |
| 129b | *(chemical structure)* |
| 130 | *(chemical structure)* |
| 130a | *(chemical structure)* (S) |

TABLE 1-continued

| Compound | Structure |
|---|---|
| 130b | (R) |
| 131 | 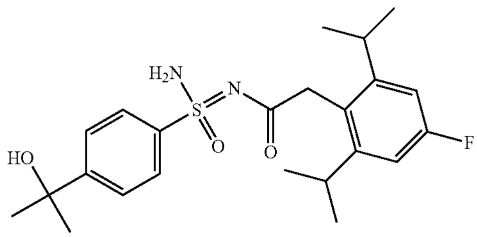 |
| 131a | (R) |
| 131b | (S) |
| 132 | 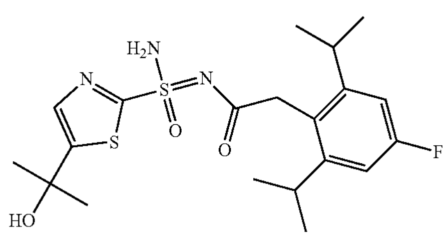 |
| 132a | (R) |

TABLE 1-continued

| Compound | Structure |
|---|---|
| 132b | (S) |
| 133 | 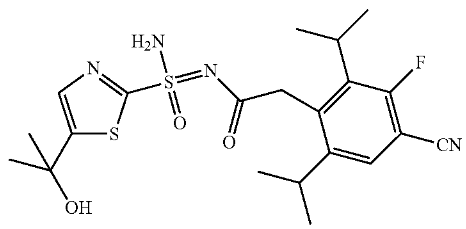 |
| 133a | (R) |
| 133b | (S) |
| 134 | 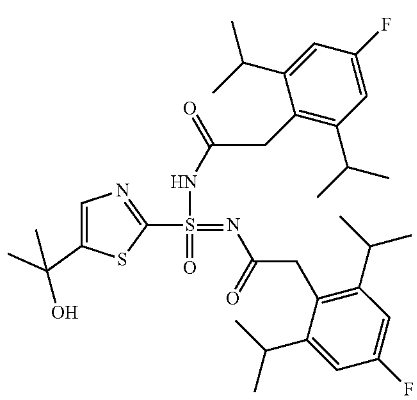 |

TABLE 1-continued

| Compound | Structure |
|---|---|
| 135 | (structure) |
| 136 | (structure) |
| 137 | (structure) |
| 138 | (structure) |
| 138a | (structure) |
| 138b | (structure) |

TABLE 1-continued

| Compound | Structure |
|---|---|
| 139 | 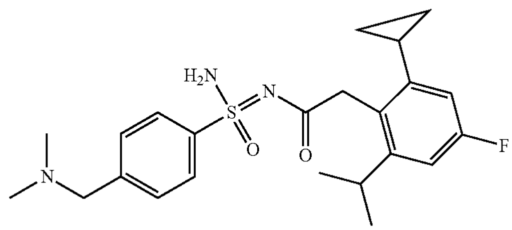 [SMILES: CC(C)c1cc(F)cc(C2CC2)c1CC(=O)N=S(N)(=O)c1ccc(CN(C)C)cc1] |
| 139a | 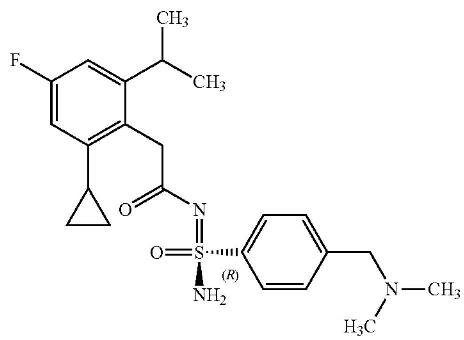 |
| 139b | 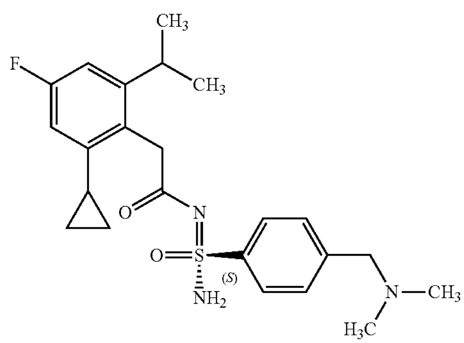 |
| 140 | 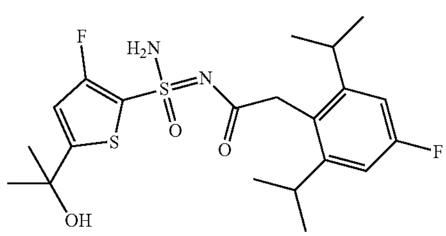 [SMILES: CC(C)c1cc(F)cc(C(C)C)c1CC(=O)N=S(N)(=O)c1sc(C(C)(C)O)cc1F] |
| 140a | 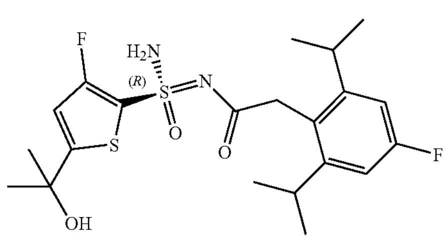 |

TABLE 1-continued

| Compound | Structure |
|---|---|
| 140b | (structure shown) |
| 141 | (structure shown) |
| 141a | (structure shown) |
| 141b | (structure shown) |
| 142 | (structure shown) |
| 143 | (structure shown) |

TABLE 1-continued

| Compound | Structure |
|---|---|
| 144 | 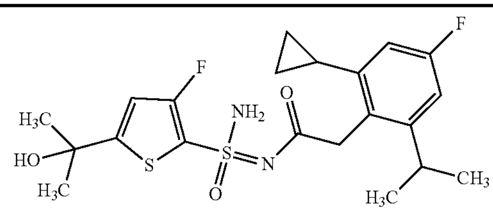 |
| 144a | (R) |
| 144b | (S) |
| 145 | 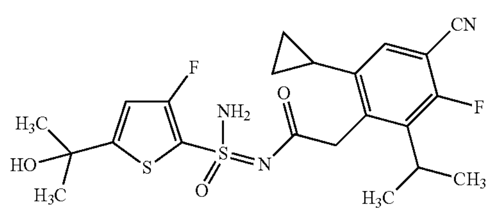 [SMILES: CC(C)c1c(F)c(C#N)cc(C2CC2)c1CC(=O)N=S(N)(=O)c1sc(C(C)(C)O)cc1F] |
| 145a | (R) |

TABLE 1-continued
| Compound | Structure |
|---|---|
| 145b | 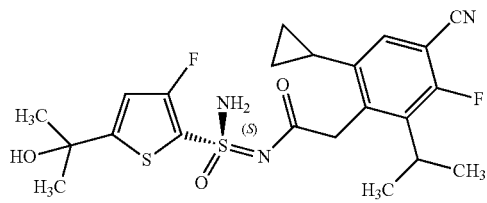 (S) |
| 146 | 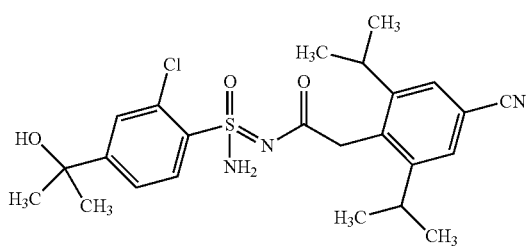 |
| 147 | 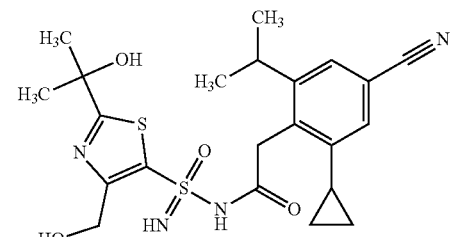 |
| 147a | 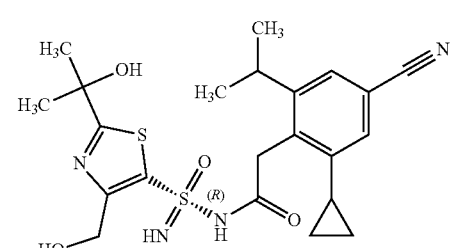 |
| 147b | 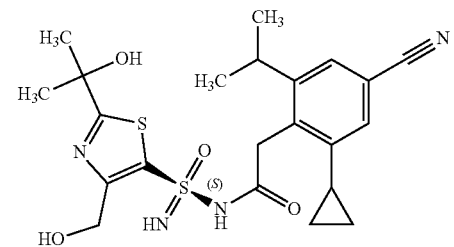 |

TABLE 1-continued

| Compound | Structure |
|---|---|
| 148 | (structure) |
| 148a | (structure) |
| 148b | (structure) |
| 149a | (structure) |
| 149b | (structure) |

TABLE 1-continued
| Compound | Structure |
|---|---|
| 150 | 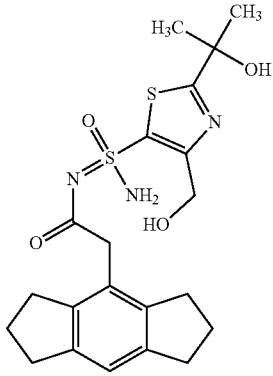 [SMILES: CC(C)(O)c1nc(CO)c(S(N)(=O)=NC(=O)Cc2c3c(cc4c2CCC4)CCC3)s1] |
| 150a | 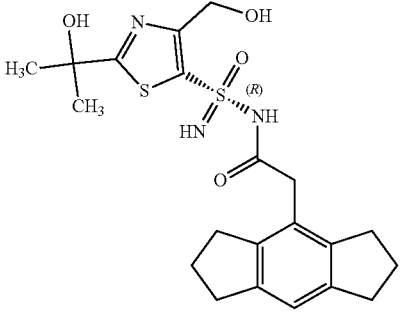 |
| 150b | 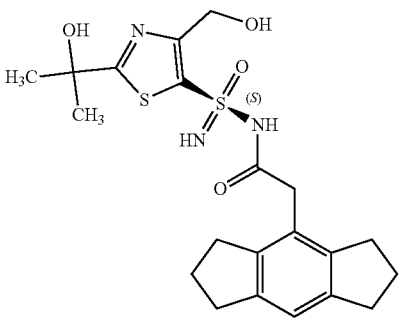 |
| 151 | 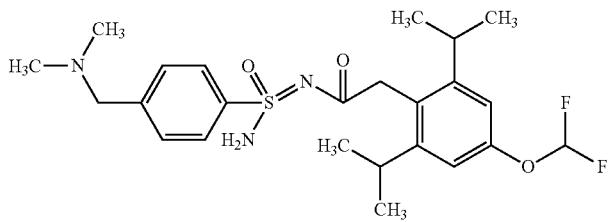 [SMILES: CC(C)c1cc(OC(F)F)cc(C(C)C)c1CC(=O)N=S(N)(=O)c1ccc(CN(C)C)cc1] |

TABLE 1-continued

| Compound | Structure |
|---|---|
| 152 | (chemical structure) |
| 152a | (chemical structure, R) |
| 152b | (chemical structure, S) |
| 153 | (chemical structure) |

TABLE 1-continued
| Compound | Structure |
|---|---|
| 154 | 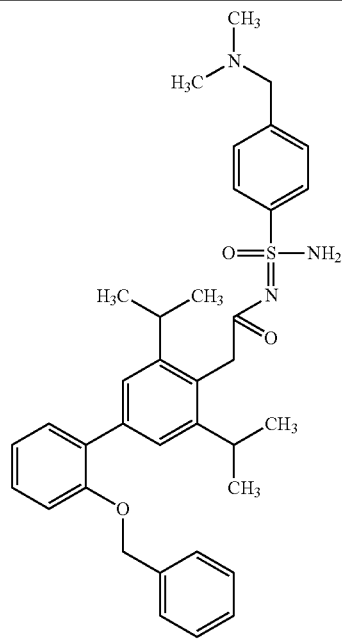 |
| 155 | 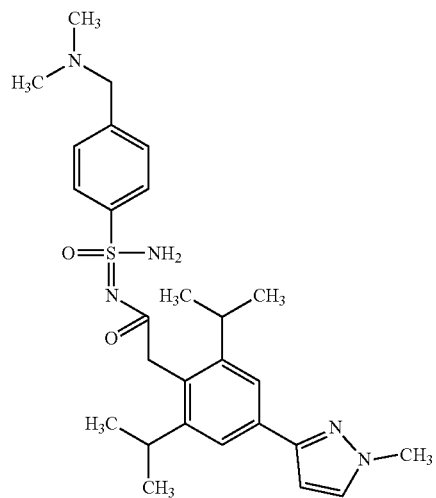 |

TABLE 1-continued
| Compound | Structure |
|---|---|
| 156 | 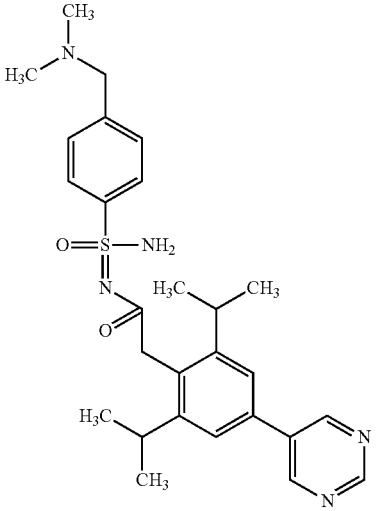 [SMILES: CC(C)c1cc(-c2cncnc2)cc(C(C)C)c1CC(=O)N=S(N)(=O)c1ccc(CN(C)C)cc1] |
| 157 | 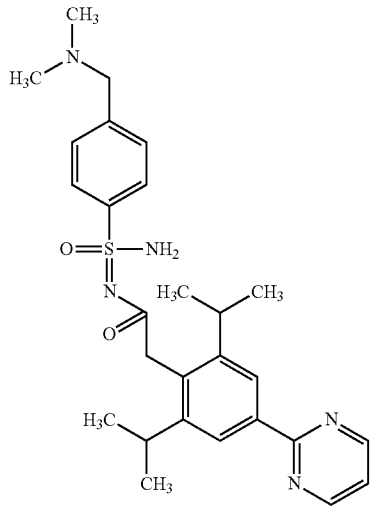 [SMILES: CC(C)c1cc(-c2ncccn2)cc(C(C)C)c1CC(=O)N=S(N)(=O)c1ccc(CN(C)C)cc1] |
| 158 | 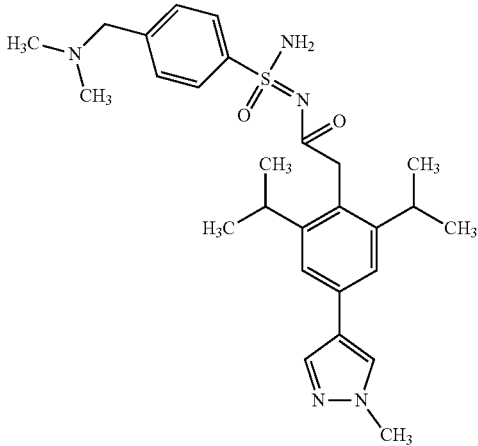 [SMILES: CC(C)c1cc(-c2cnn(C)c2)cc(C(C)C)c1CC(=O)N=S(N)(=O)c1ccc(CN(C)C)cc1] |

| Compound | Structure |
|---|---|
| 159 | 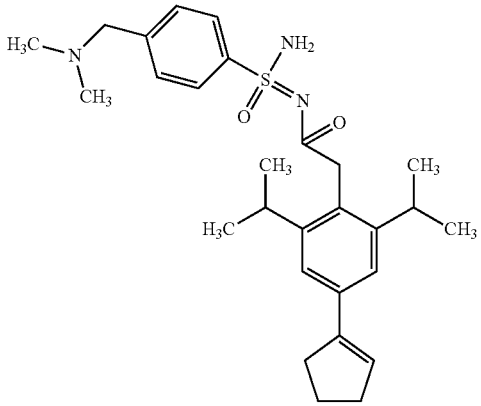 [SMILES: CC(C)c1cc(C2=CCCC2)cc(C(C)C)c1CC(=O)N=S(N)(=O)c1ccc(CN(C)C)cc1] |
| 160 | 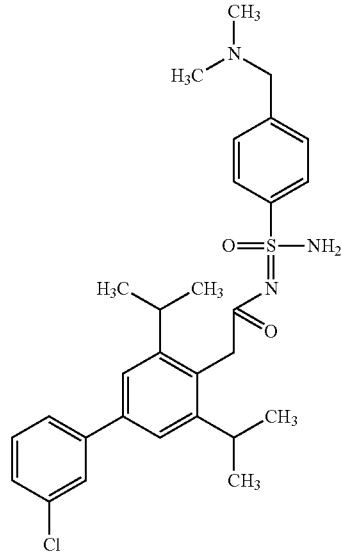 [SMILES: CC(C)c1cc(-c2cccc(Cl)c2)cc(C(C)C)c1CC(=O)N=S(N)(=O)c1ccc(CN(C)C)cc1] |
| 161 | 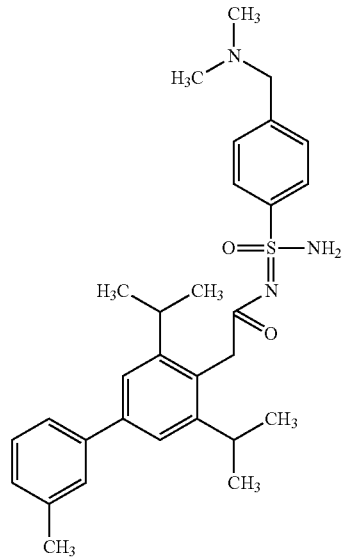 [SMILES: Cc1cccc(-c2cc(C(C)C)c(CC(=O)N=S(N)(=O)c3ccc(CN(C)C)cc3)c(C(C)C)c2)c1] |

TABLE 1-continued
| Compound | Structure |
|---|---|
| 162 | 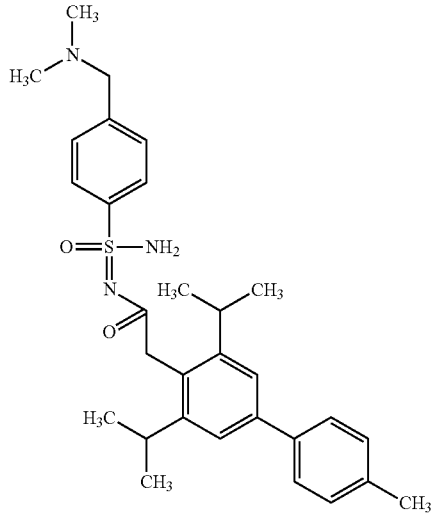 |
| 163 | 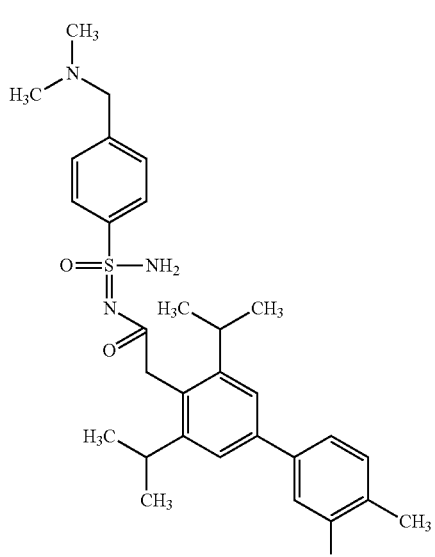 |

TABLE 1-continued
| Compound | Structure |
|---|---|
| 164 | 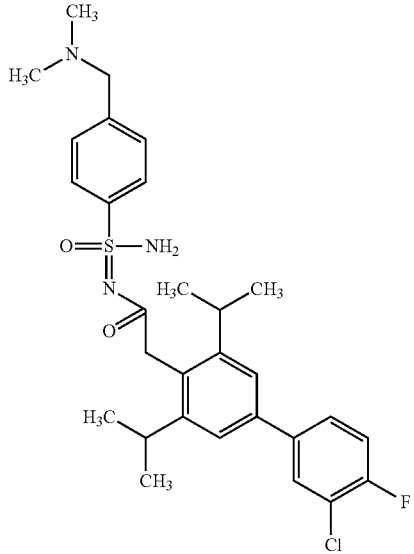 [SMILES: CC(C)c1cc(-c2ccc(F)c(Cl)c2)cc(C(C)C)c1CC(=O)N=S(N)(=O)c1ccc(CN(C)C)cc1] |
| 165 | 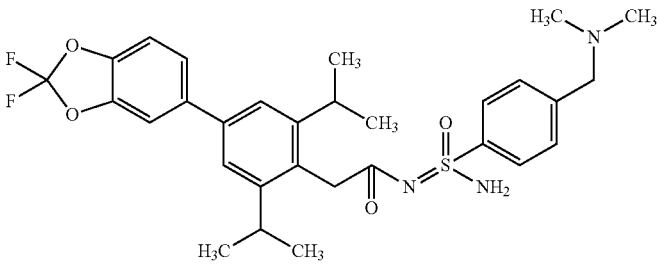 [SMILES: CC(C)c1cc(-c2ccc3c(c2)OC(F)(F)O3)cc(C(C)C)c1CC(=O)N=S(N)(=O)c1ccc(CN(C)C)cc1] |
| 166 | 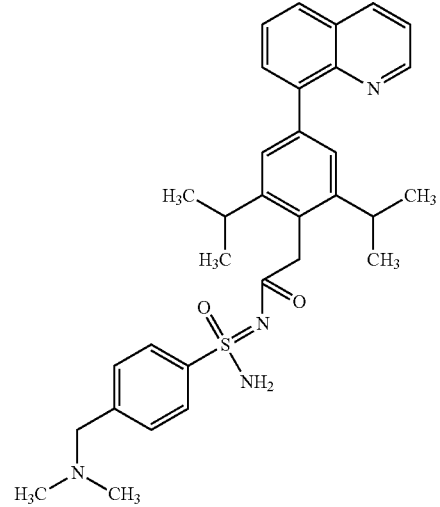 [SMILES: CC(C)c1cc(-c2cccc3cccnc23)cc(C(C)C)c1CC(=O)N=S(N)(=O)c1ccc(CN(C)C)cc1] |

TABLE 1-continued
| Compound | Structure |
|---|---|
| 167 | 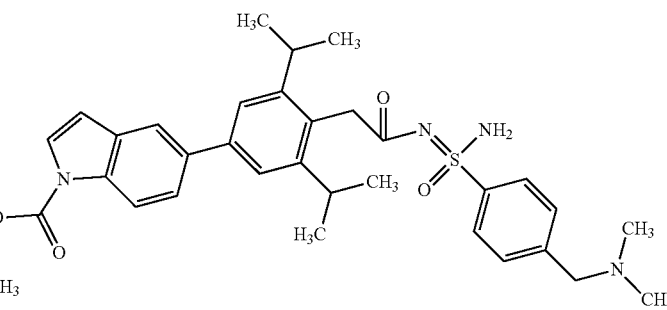 |
| 168 | 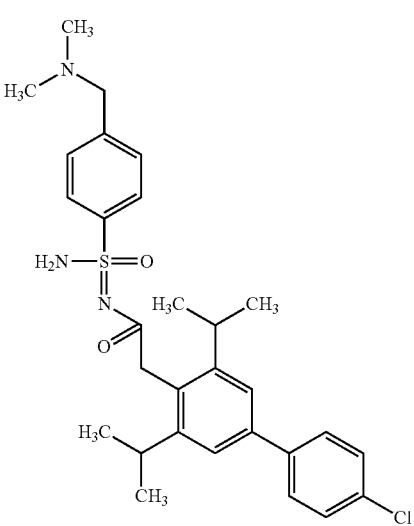 [SMILES: CC(C)c1cc(-c2ccc(Cl)cc2)cc(C(C)C)c1CC(=O)N=S(N)(=O)c1ccc(CN(C)C)cc1] |
| 169 | 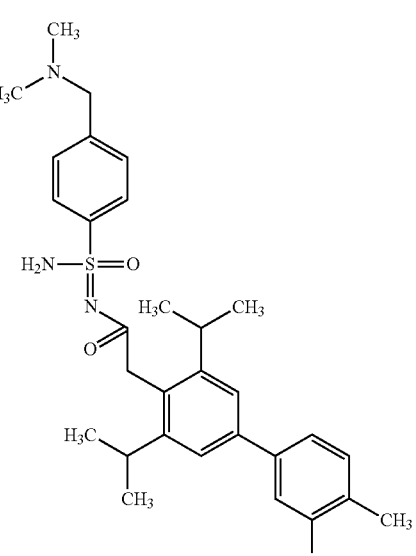 |

TABLE 1-continued
| Compound | Structure |
|---|---|
| 170 | 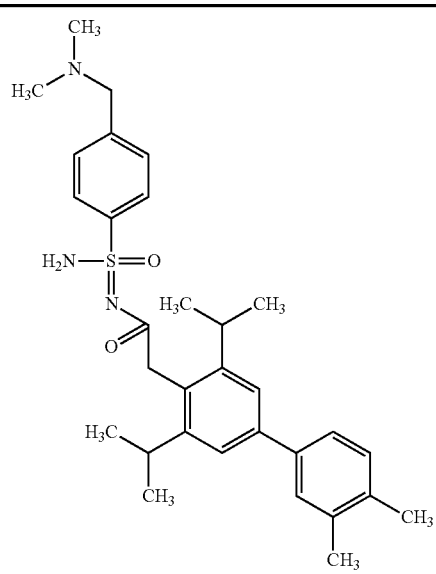 |
| 171 | 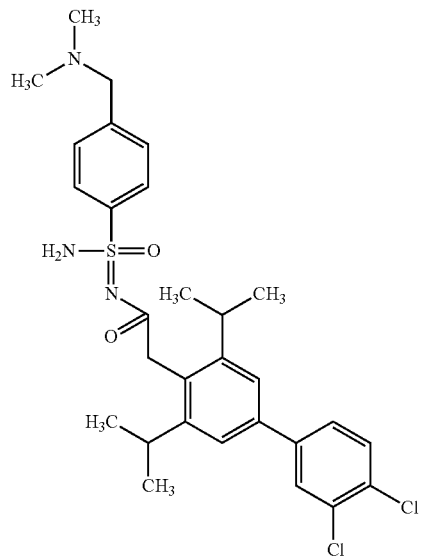 [SMILES: CC(C)c1cc(-c2ccc(Cl)c(Cl)c2)cc(C(C)C)c1CC(=O)N=S(N)(=O)c1ccc(CN(C)C)cc1] |

TABLE 1-continued
| Compound | Structure |
|---|---|
| 172 | 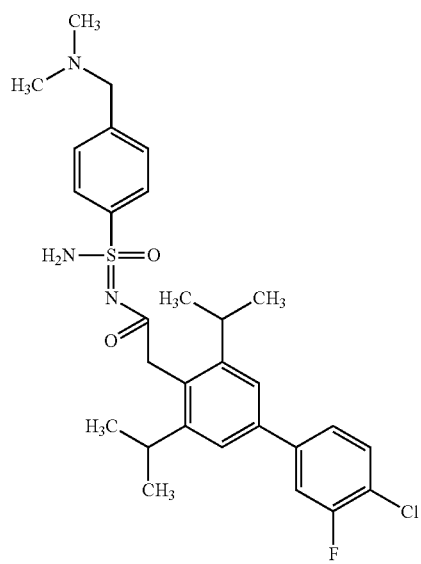 [SMILES: CC(C)c1cc(-c2ccc(Cl)c(F)c2)cc(C(C)C)c1CC(=O)N=S(N)(=O)c1ccc(CN(C)C)cc1] |
| 173 | 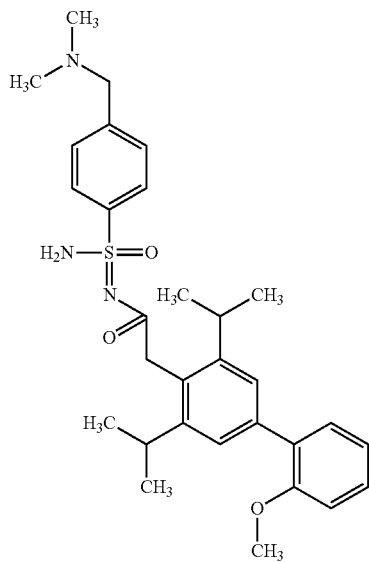 [SMILES: COc1ccccc1-c1cc(C(C)C)c(CC(=O)N=S(N)(=O)c2ccc(CN(C)C)cc2)c(C(C)C)c1] |

TABLE 1-continued
| Compound | Structure |
|---|---|
| 174 | 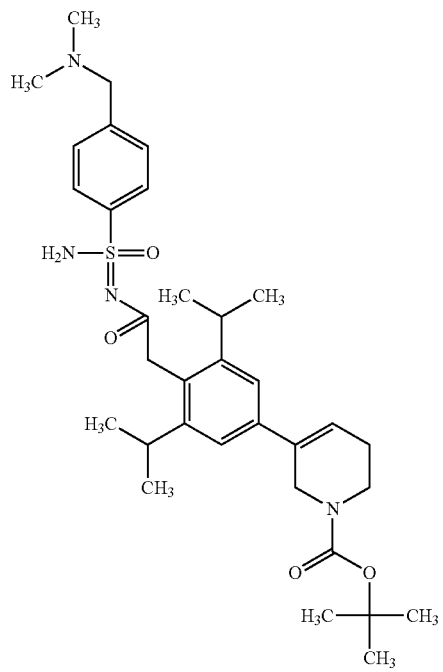 [SMILES: CC(C)c1cc(C2=CCCN(C(=O)OC(C)(C)C)C2)cc(C(C)C)c1CC(=O)N=S(N)(=O)c1ccc(CN(C)C)cc1] |
| 175 | 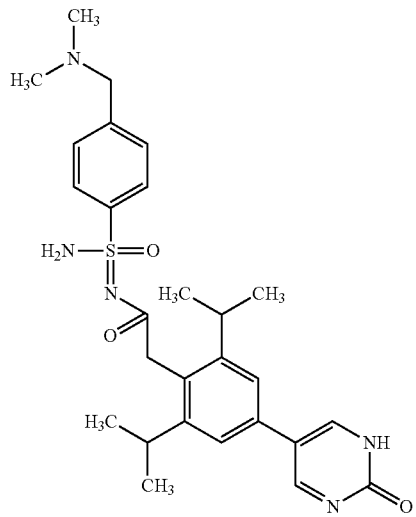 [SMILES: CC(C)c1cc(-c2cnc(=O)[nH]c2)cc(C(C)C)c1CC(=O)N=S(N)(=O)c1ccc(CN(C)C)cc1] |

TABLE 1-continued
| Compound | Structure |
|---|---|
| 176 | 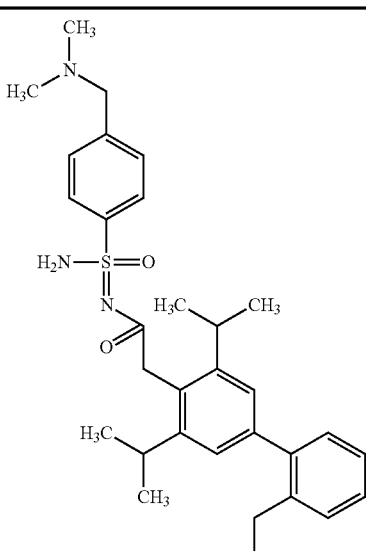 |
| 177 | 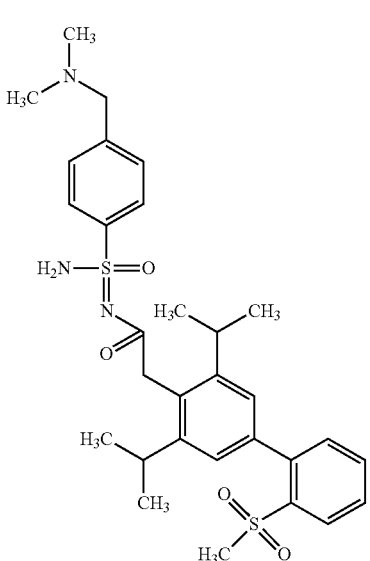 |
| 178 | 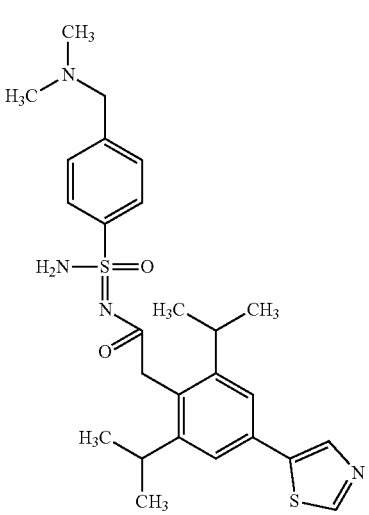 [SMILES: CC(C)c1cc(-c2cncs2)cc(C(C)C)c1CC(=O)N=S(N)(=O)c1ccc(CN(C)C)cc1] |

TABLE 1-continued
| Compound | Structure |
|---|---|
| 179 | 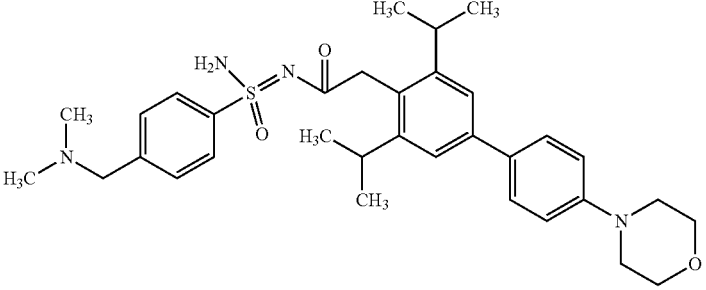 [SMILES: CC(C)c1cc(-c2ccc(N3CCOCC3)cc2)cc(C(C)C)c1CC(=O)N=S(N)(=O)c1ccc(CN(C)C)cc1] |
| 180 | 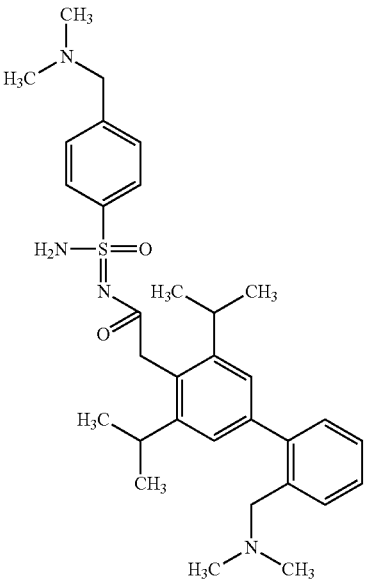 [SMILES: CC(C)c1cc(-c2ccccc2CN(C)C)cc(C(C)C)c1CC(=O)N=S(N)(=O)c1ccc(CN(C)C)cc1] |
| 181 | 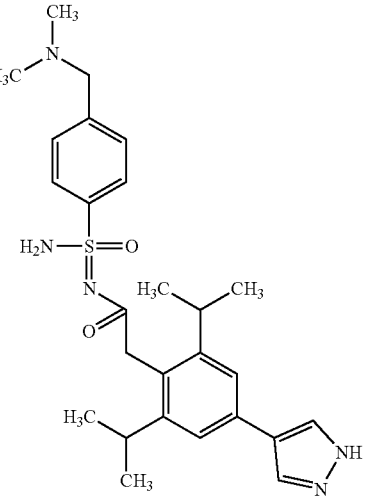 |

TABLE 1-continued
| Compound | Structure |
|---|---|
| 182 | 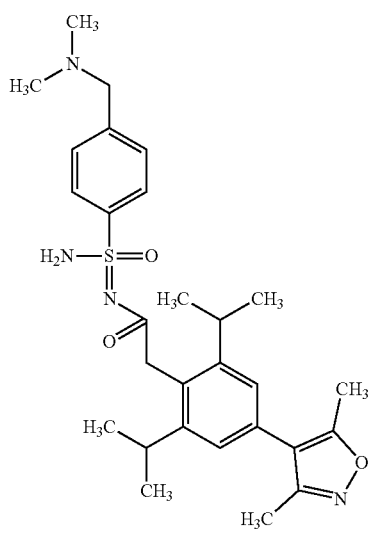 [SMILES: Cc1noc(C)c1-c1cc(C(C)C)c(CC(=O)N=S(N)(=O)c2ccc(CN(C)C)cc2)c(C(C)C)c1] |
| 183 | 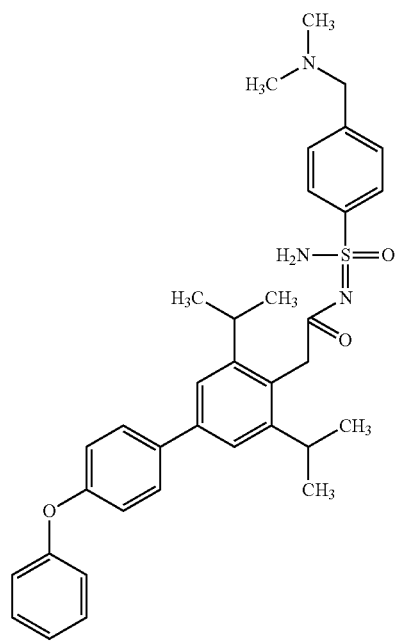 [SMILES: CC(C)c1cc(-c2ccc(Oc3ccccc3)cc2)cc(C(C)C)c1CC(=O)N=S(N)(=O)c1ccc(CN(C)C)cc1] |

TABLE 1-continued
| Compound | Structure |
|---|---|
| 184 | 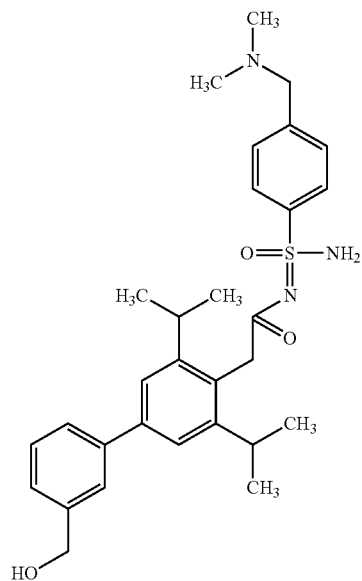 [SMILES: CC(C)c1cc(-c2cccc(CO)c2)cc(C(C)C)c1CC(=O)N=S(N)(=O)c1ccc(CN(C)C)cc1] |
| 185 | 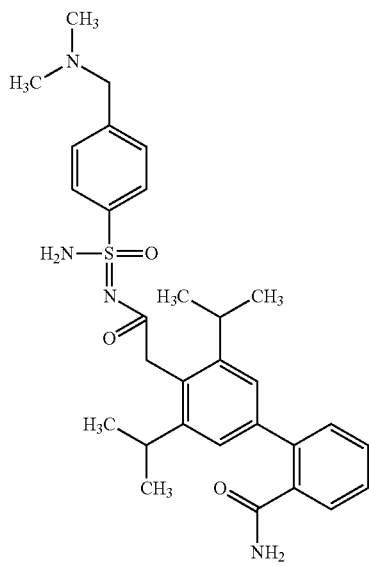 [SMILES: CC(C)c1cc(-c2ccccc2C(N)=O)cc(C(C)C)c1CC(=O)N=S(N)(=O)c1ccc(CN(C)C)cc1] |

TABLE 1-continued

| Compound | Structure |
|---|---|
| 186 | 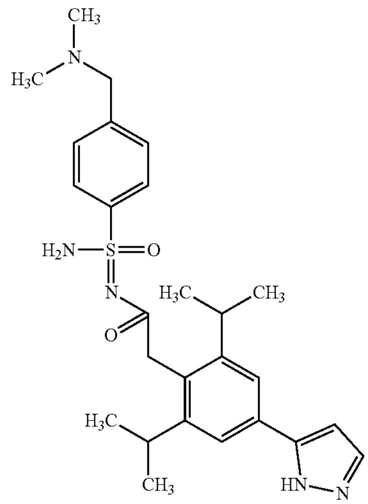 [SMILES: CC(C)c1cc(-c2ccn[nH]2)cc(C(C)C)c1CC(=O)N=S(N)(=O)c1ccc(CN(C)C)cc1] |
| 187 | 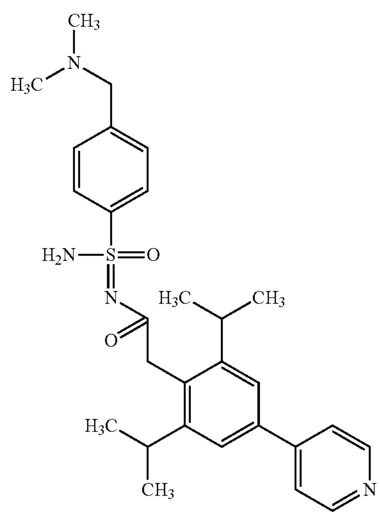 [SMILES: CC(C)c1cc(-c2ccncc2)cc(C(C)C)c1CC(=O)N=S(N)(=O)c1ccc(CN(C)C)cc1] |
| 188 | 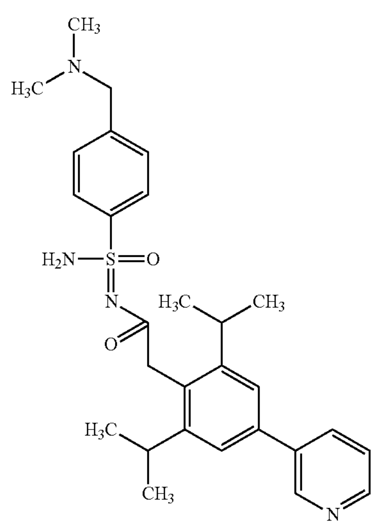 [SMILES: CC(C)c1cc(-c2cccnc2)cc(C(C)C)c1CC(=O)N=S(N)(=O)c1ccc(CN(C)C)cc1] |

| Compound | Structure |
|---|---|
| 189 | 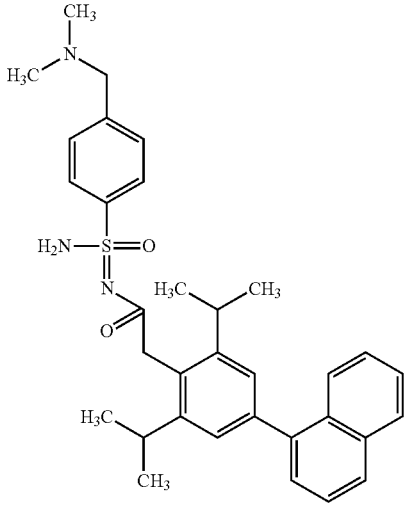 [SMILES: CC(C)c1cc(-c2cccc3ccccc23)cc(C(C)C)c1CC(=O)N=S(N)(=O)c1ccc(CN(C)C)cc1] |
| 190 | 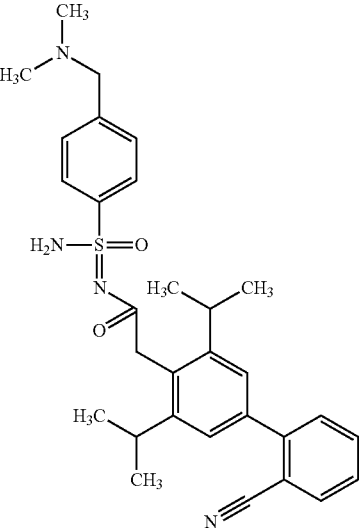 [SMILES: CC(C)c1cc(-c2ccccc2C#N)cc(C(C)C)c1CC(=O)N=S(N)(=O)c1ccc(CN(C)C)cc1] |
| 191 | 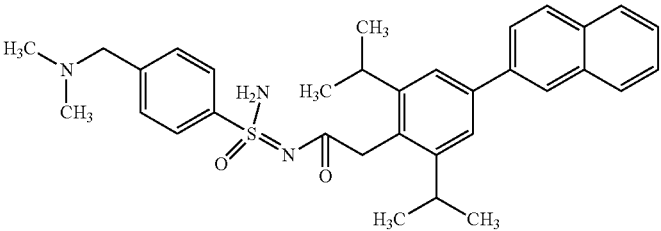 [SMILES: CC(C)c1cc(-c2ccc3ccccc3c2)cc(C(C)C)c1CC(=O)N=S(N)(=O)c1ccc(CN(C)C)cc1] |

TABLE 1-continued

| Compound | Structure |
|---|---|
| 192 | 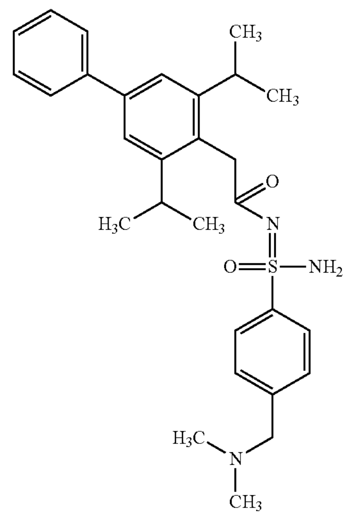 [SMILES: CC(C)c1cc(-c2ccccc2)cc(C(C)C)c1CC(=O)N=S(N)(=O)c1ccc(CN(C)C)cc1] |
| 193 | 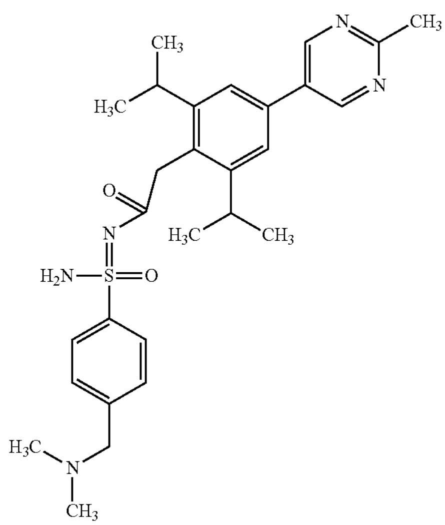 |
| 194 | 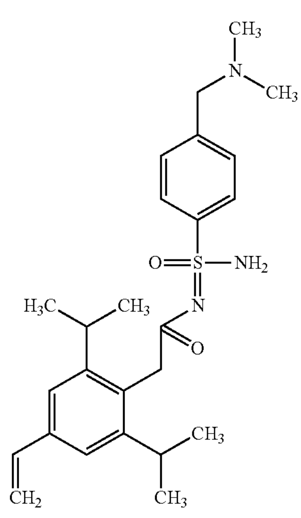 [SMILES: C=Cc1cc(C(C)C)c(CC(=O)N=S(N)(=O)c2ccc(CN(C)C)cc2)c(C(C)C)c1] |

TABLE 1-continued
| Compound | Structure |
|---|---|
| 195 | 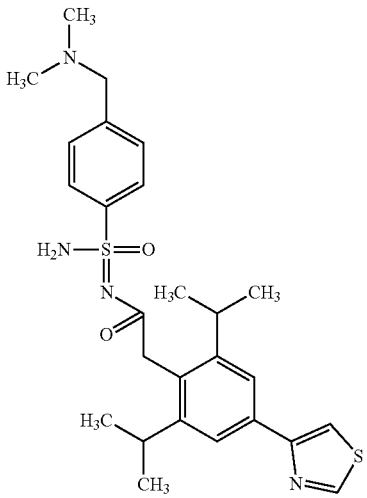 [SMILES: CC(C)c1cc(-c2cscn2)cc(C(C)C)c1CC(=O)N=S(N)(=O)c1ccc(CN(C)C)cc1] |
| 196 | 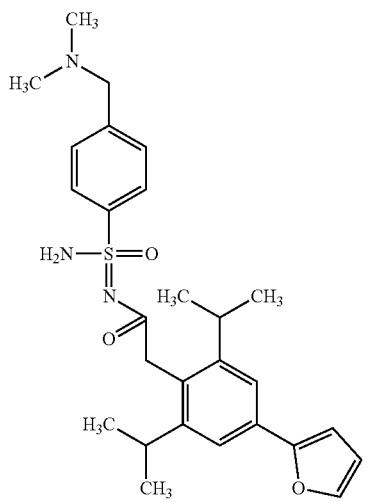 [SMILES: CC(C)c1cc(-c2ccco2)cc(C(C)C)c1CC(=O)N=S(N)(=O)c1ccc(CN(C)C)cc1] |
| 197 | 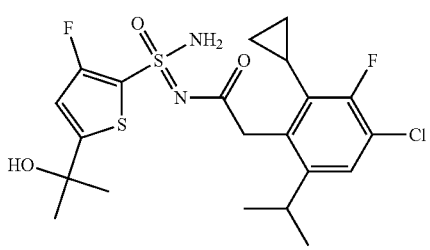 [SMILES: CC(C)c1cc(Cl)c(F)c(C2CC2)c1CC(=O)N=S(N)(=O)c1sc(C(C)(C)O)cc1F] |
| 197a | 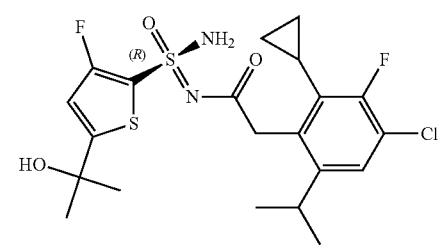 |

TABLE 1-continued

| Compound | Structure |
|---|---|
| 197b | (S) |
| 198 | 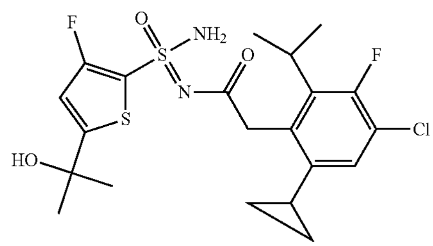 |
| 198a | (R) |
| 198b | (S) |
| 201 | 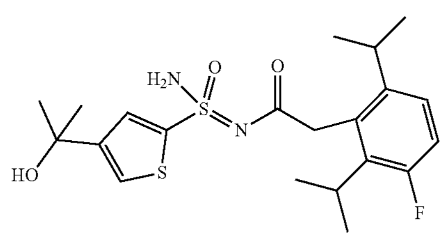 |
| 201b | 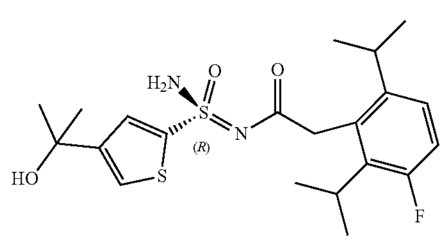 |

TABLE 1-continued

| Compound | Structure |
|---|---|
| 201a | 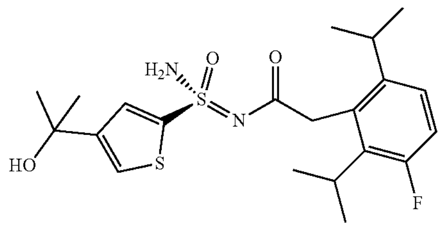 [SMILES: CC(C)c1ccc(F)c(C(C)C)c1CC(=O)N=[S@](N)(=O)c1cc(C(C)(C)O)cs1] |
| 202 | 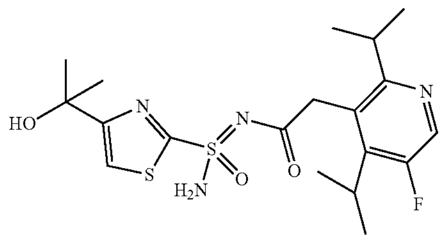 [SMILES: CC(C)c1ncc(F)c(C(C)C)c1CC(=O)N=S(N)(=O)c1nc(C(C)(C)O)cs1] |
| 202b | 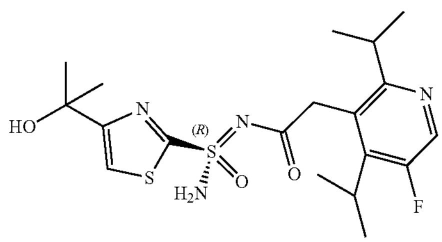 |
| 202a | 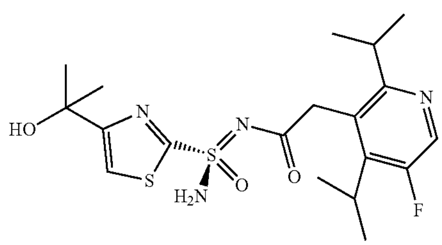 [SMILES: CC(C)c1ncc(F)c(C(C)C)c1CC(=O)N=[S@](N)(=O)c1nc(C(C)(C)O)cs1] |
| 203 | 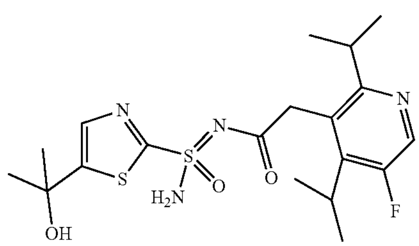 [SMILES: CC(C)c1ncc(F)c(C(C)C)c1CC(=O)N=S(N)(=O)c1ncc(C(C)(C)O)s1] |
| 203b | 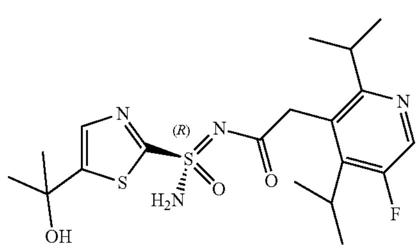 |

TABLE 1-continued

| Compound | Structure |
|---|---|
| 203a | 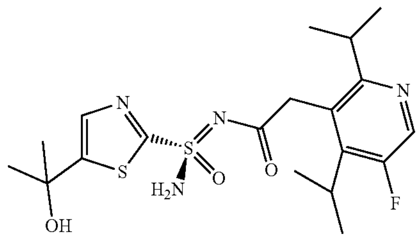 [SMILES: CC(C)c1ncc(F)c(C(C)C)c1CC(=O)N=[S@](N)(=O)c1ncc(C(C)(C)O)s1] |
| 204 | 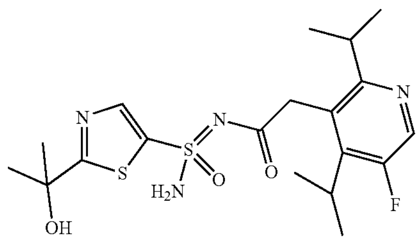 [SMILES: CC(C)c1ncc(F)c(C(C)C)c1CC(=O)N=S(N)(=O)c1cnc(C(C)(C)O)s1] |
| 204b | 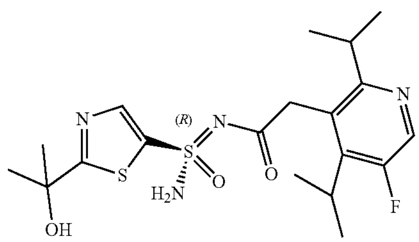 |
| 204a | 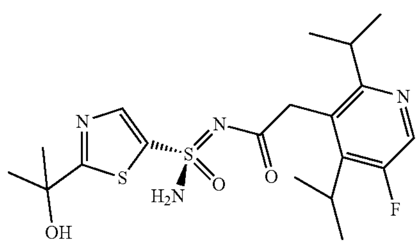 [SMILES: CC(C)c1ncc(F)c(C(C)C)c1CC(=O)N=[S@](N)(=O)c1cnc(C(C)(C)O)s1] |
| 205 | 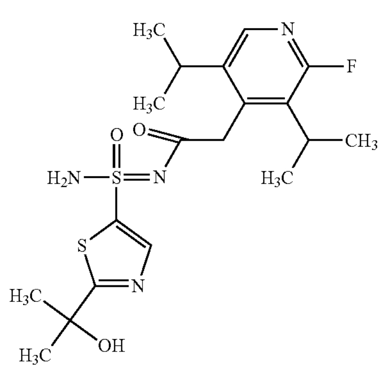 |

TABLE 1-continued

| Compound | Structure |
|---|---|
| 206 | 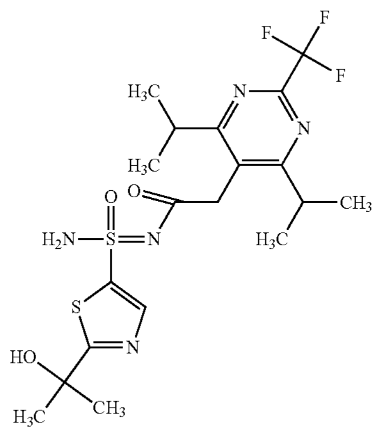 [SMILES: CC(C)c1nc(C(F)(F)F)nc(C(C)C)c1CC(=O)N=S(N)(=O)c1cnc(C(C)(C)O)s1] |
| 207 | 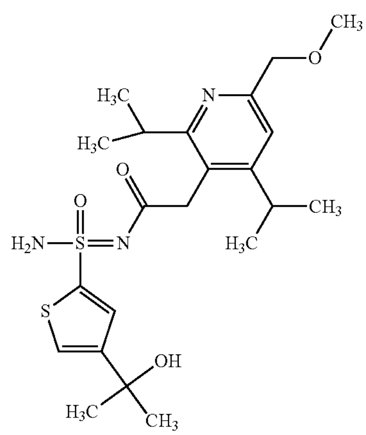 [SMILES: COCc1cc(C(C)C)c(CC(=O)N=S(N)(=O)c2cc(C(C)(C)O)cs2)c(C(C)C)n1] |
| 208 | 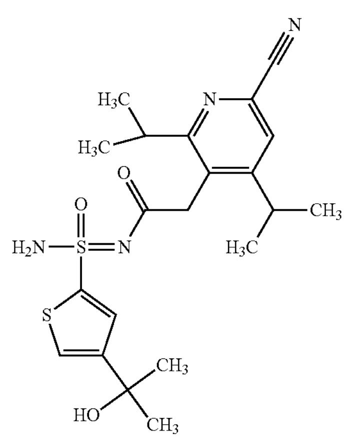 [SMILES: CC(C)c1cc(C#N)nc(C(C)C)c1CC(=O)N=S(N)(=O)c1cc(C(C)(C)O)cs1] |

TABLE 1-continued

| Compound | Structure |
|---|---|
| 209 | 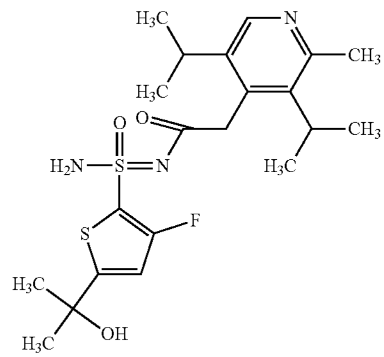 [SMILES: Cc1ncc(C(C)C)c(CC(=O)N=S(N)(=O)c2sc(C(C)(C)O)cc2F)c1C(C)C] |
| 210 | 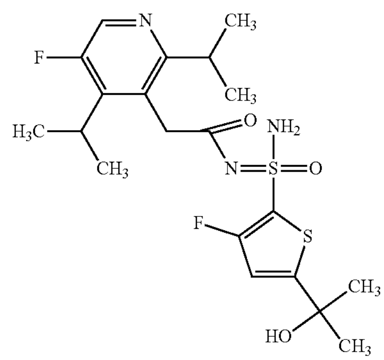 [SMILES: CC(C)c1ncc(F)c(C(C)C)c1CC(=O)N=S(N)(=O)c1sc(C(C)(C)O)cc1F] |
| 210a | 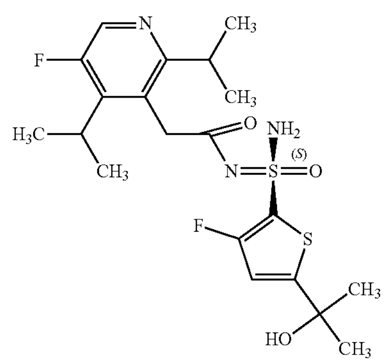 |
| 210b | 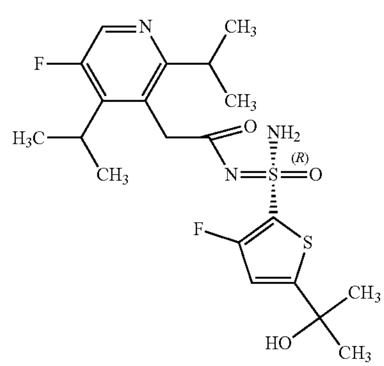 |

TABLE 1-continued
| Compound | Structure |
|---|---|
| 211 | 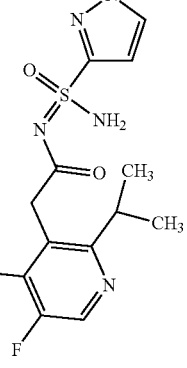 |
| 212 | 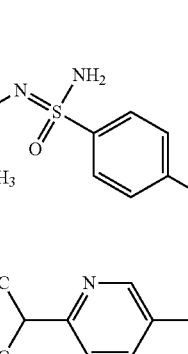 |
| 213 | 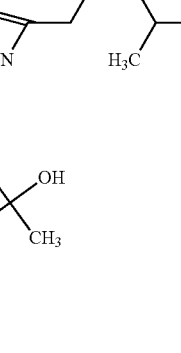 |
| 213a | 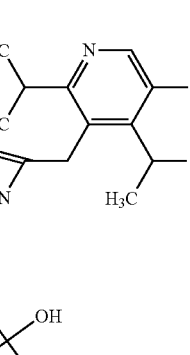 |

TABLE 1-continued

| Compound | Structure |
|---|---|
| 213b | (structure image) |
| 214 | (structure image) |
| 215 | (structure image) |
| 216 | (structure image) |
| 216a | (structure image) |

TABLE 1-continued

| Compound | Structure |
|---|---|
| 216b | (structure) |
| 217 | (structure) |
| 217a | (structure) |
| 217b | (structure) |
| 218 | (structure) |
| 218a | (structure) |
| 218b | (structure) |

TABLE 1-continued

| Compound | Structure |
|---|---|
| 219 | 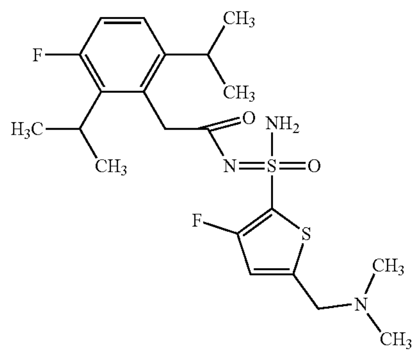 [SMILES: CC(C)c1ccc(F)c(C(C)C)c1CC(=O)N=S(N)(=O)c1sc(CN(C)C)cc1F] |
| 220 | 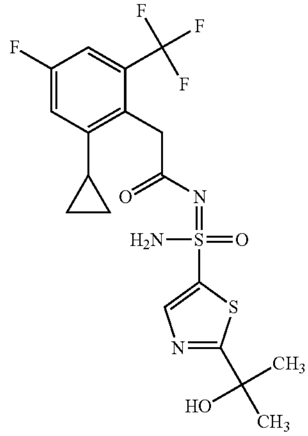 [SMILES: CC(C)(O)c1ncc(S(N)(=O)=NC(=O)Cc2c(C3CC3)cc(F)cc2C(F)(F)F)s1] |
| 220a | 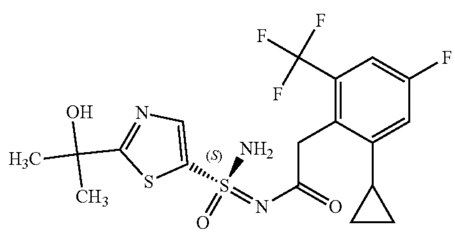 |
| 220b | 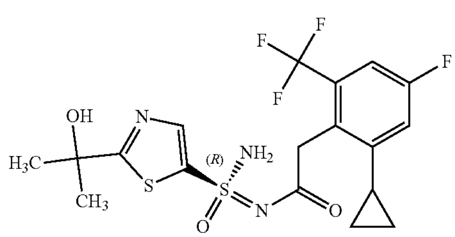 |
| 221 | 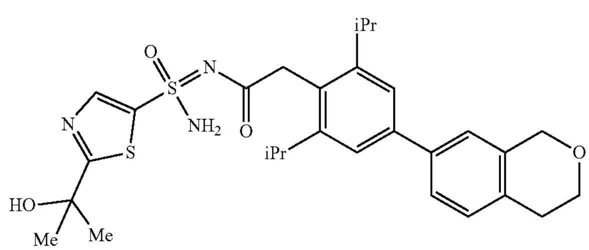 [SMILES: CC(C)c1cc(-c2ccc3c(c2)COCC3)cc(C(C)C)c1CC(=O)N=S(N)(=O)c1cnc(C(C)(C)O)s1] |

TABLE 1-continued
| Compound | Structure |
|---|---|
| 221a | 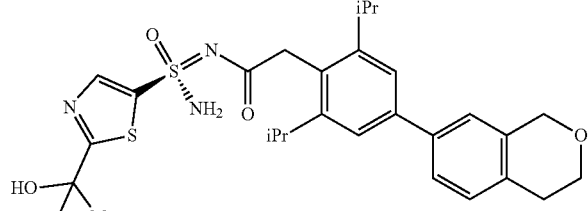 |
| 221b | 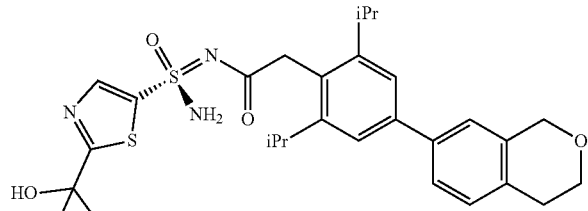 |
| 222 | 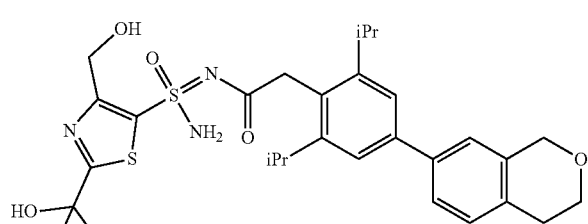 |
| 224 | 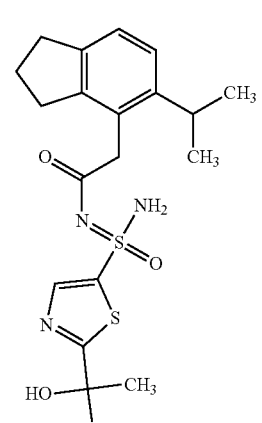 |
| 224b | 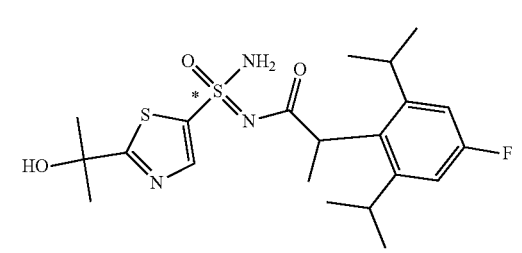 [SMILES: CC(C)c1cc(F)cc(C(C)C)c1C(C)C(=O)N=S(N)(=O)c1cnc(C(C)(C)O)s1] |

TABLE 1-continued

| Compound | Structure |
| --- | --- |
| 224ba | 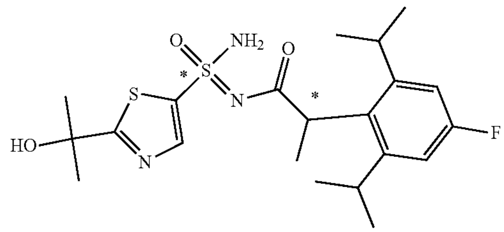 [SMILES: CC(C)c1cc(F)cc(C(C)C)c1C(C)C(=O)N=S(N)(=O)c1cnc(C(C)(C)O)s1] |
| 224aa | 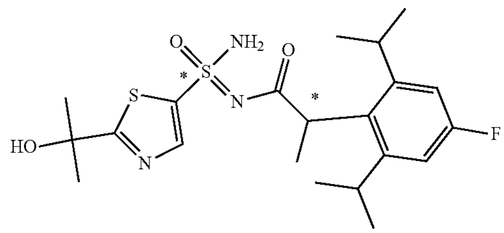 [SMILES: CC(C)c1cc(F)cc(C(C)C)c1C(C)C(=O)N=S(N)(=O)c1cnc(C(C)(C)O)s1] |
| 225 | 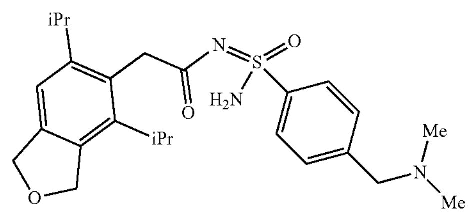 [SMILES: CC(C)c1cc2c(c(C(C)C)c1CC(=O)N=S(N)(=O)c1ccc(CN(C)C)cc1)COC2] |
| 225a | 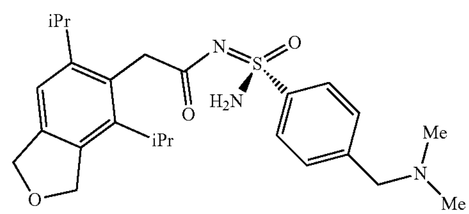 [SMILES: CC(C)c1cc2c(c(C(C)C)c1CC(=O)N=[S@](N)(=O)c1ccc(CN(C)C)cc1)COC2] |
| 225b | 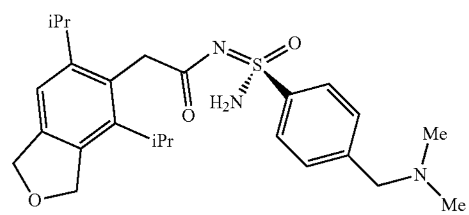 [SMILES: CC(C)c1cc2c(c(C(C)C)c1CC(=O)N=[S@@](N)(=O)c1ccc(CN(C)C)cc1)COC2] |
| 226 | 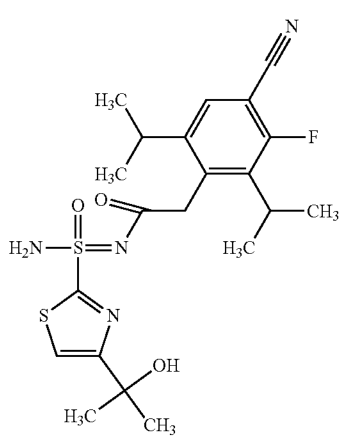 [SMILES: CC(C)c1cc(C#N)c(F)c(C(C)C)c1CC(=O)N=S(N)(=O)c1nc(C(C)(C)O)cs1] |

TABLE 1-continued

| Compound | Structure |
|---|---|
| 226a | 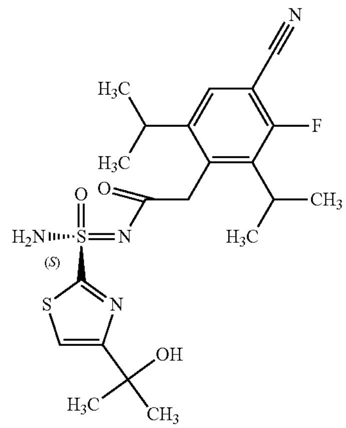 |
| 226b | 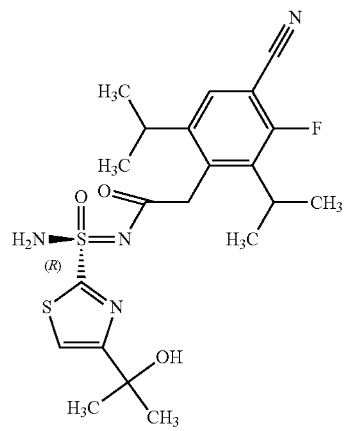 |
| 227 | 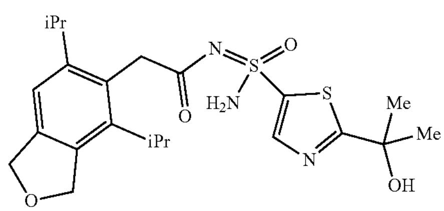 [SMILES: CC(C)c1cc2c(c(C(C)C)c1CC(=O)N=S(N)(=O)c1cnc(C(C)(C)O)s1)COC2] |
| 227a | 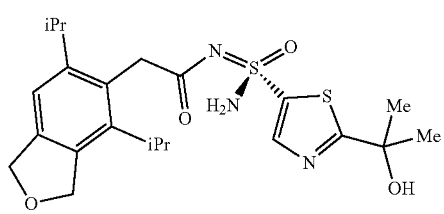 [SMILES: CC(C)c1cc2c(c(C(C)C)c1CC(=O)N=[S@](N)(=O)c1cnc(C(C)(C)O)s1)COC2] |
| 227b | 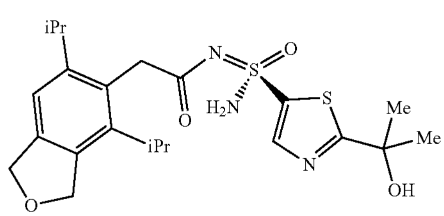 [SMILES: CC(C)c1cc2c(c(C(C)C)c1CC(=O)N=[S@@](N)(=O)c1cnc(C(C)(C)O)s1)COC2] |

TABLE 1-continued

| Compound | Structure |
| --- | --- |
| 228 | (chemical structure) |
| 228a | (chemical structure, (S)) |
| 228b | (chemical structure, (R)) |
| 229 | (chemical structure) |

TABLE 1-continued

| Compound | Structure |
|---|---|
| 229a | (structure) |
| 229b | (structure) |
| 230 | (structure) |
| 231 | (structure) |
| 232 | (structure) |

TABLE 1-continued

| Compound | Structure |
|---|---|
| 233 | 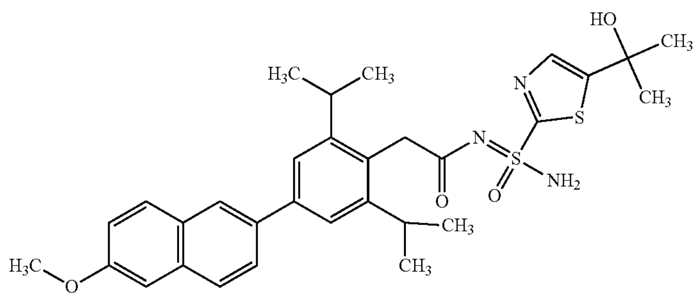 [SMILES: COc1ccc2cc(-c3cc(C(C)C)c(CC(=O)N=S(N)(=O)c4ncc(C(C)(C)O)s4)c(C(C)C)c3)ccc2c1] |
| 234 | 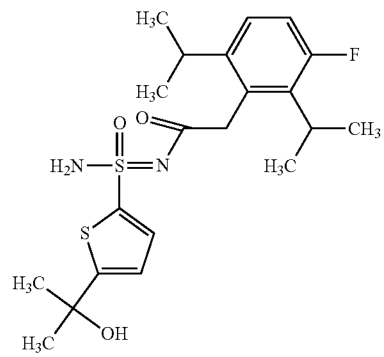 [SMILES: CC(C)c1ccc(F)c(C(C)C)c1CC(=O)N=S(N)(=O)c1ccc(C(C)(C)O)s1] |
| 234a | 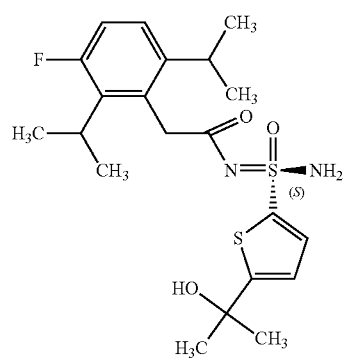 |
| 234b | 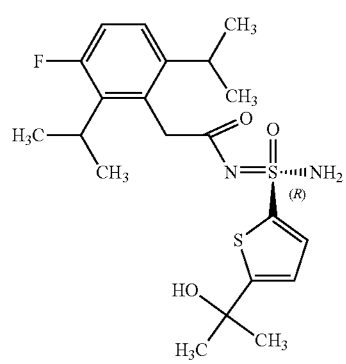 |
| 235 | 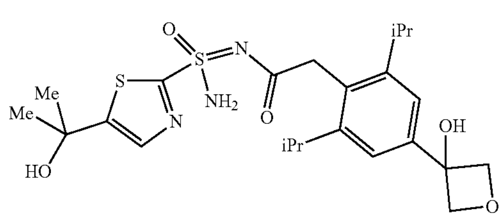 [SMILES: CC(C)c1cc(C2(O)COC2)cc(C(C)C)c1CC(=O)N=S(N)(=O)c1ncc(C(C)(C)O)s1] |

TABLE 1-continued

| Compound | Structure |
|---|---|
| 236 | 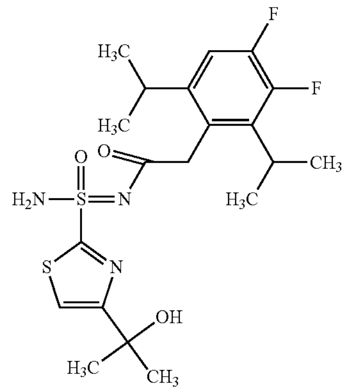 [SMILES: CC(C)c1cc(F)c(F)c(C(C)C)c1CC(=O)N=S(N)(=O)c1nc(C(C)(C)O)cs1] |
| 236a | 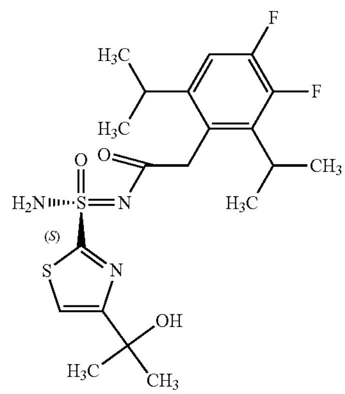 |
| 236b | 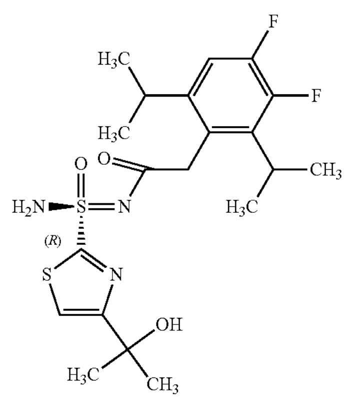 |
| 237 | 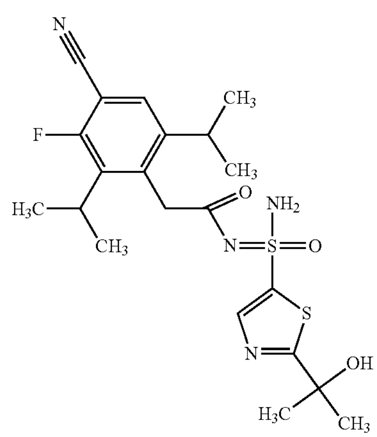 [SMILES: CC(C)c1cc(C#N)c(F)c(C(C)C)c1CC(=O)N=S(N)(=O)c1cnc(C(C)(C)O)s1] |

TABLE 1-continued
| Compound | Structure |
|---|---|
| 238 | 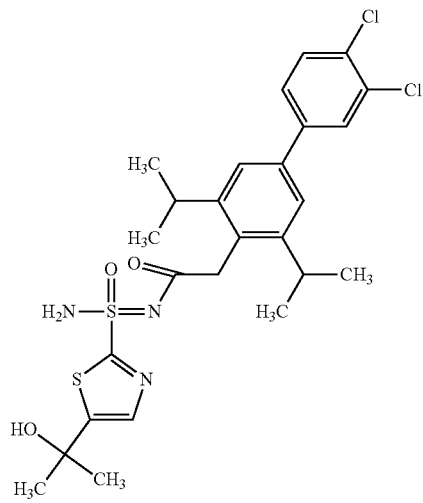 [SMILES: CC(C)c1cc(-c2ccc(Cl)c(Cl)c2)cc(C(C)C)c1CC(=O)N=S(N)(=O)c1ncc(C(C)(C)O)s1] |
| 238a | 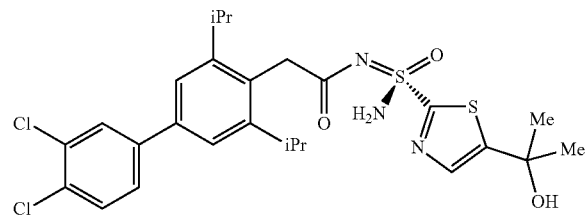 [SMILES: CC(C)c1cc(-c2ccc(Cl)c(Cl)c2)cc(C(C)C)c1CC(=O)N=[S@](N)(=O)c1ncc(C(C)(C)O)s1] |
| 238b | 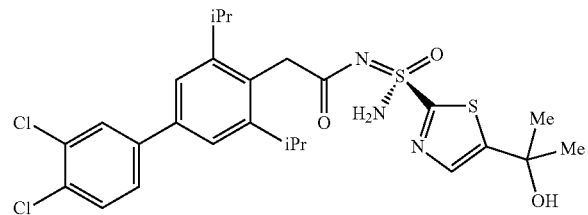 [SMILES: CC(C)c1cc(-c2ccc(Cl)c(Cl)c2)cc(C(C)C)c1CC(=O)N=[S@@](N)(=O)c1ncc(C(C)(C)O)s1] |
| 239 | 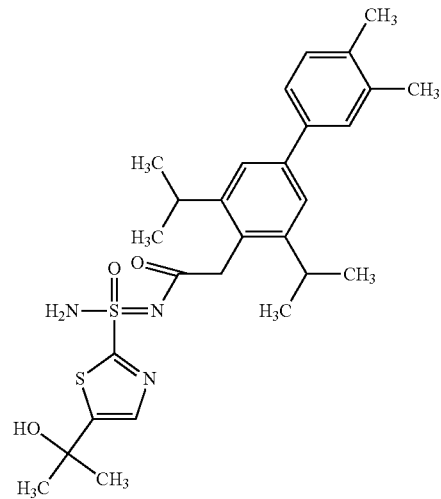 [SMILES: Cc1ccc(-c2cc(C(C)C)c(CC(=O)N=S(N)(=O)c3ncc(C(C)(C)O)s3)c(C(C)C)c2)cc1C] |

TABLE 1-continued

| Compound | Structure |
|---|---|
| 239a | 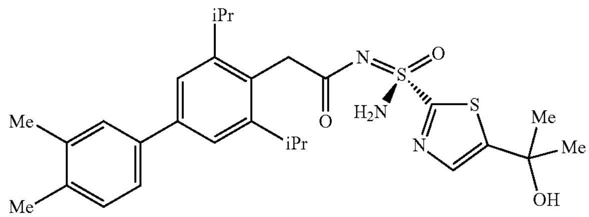 [SMILES: Cc1ccc(-c2cc(C(C)C)c(CC(=O)N=[S@](N)(=O)c3ncc(C(C)(C)O)s3)c(C(C)C)c2)cc1C] |
| 239b | 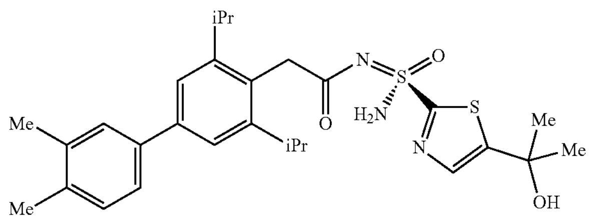 [SMILES: Cc1ccc(-c2cc(C(C)C)c(CC(=O)N=[S@@](N)(=O)c3ncc(C(C)(C)O)s3)c(C(C)C)c2)cc1C] |
| 240 | 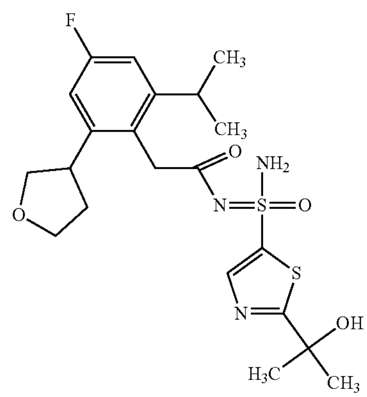 [SMILES: CC(C)c1cc(F)cc(C2CCOC2)c1CC(=O)N=S(N)(=O)c1cnc(C(C)(C)O)s1] |
| 241 | 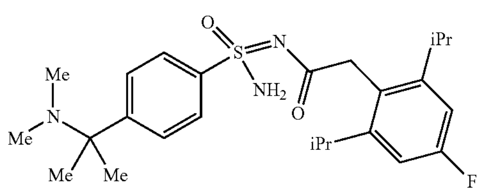 [SMILES: CC(C)c1cc(F)cc(C(C)C)c1CC(=O)N=S(N)(=O)c1ccc(C(C)(C)N(C)C)cc1] |
| 242 | 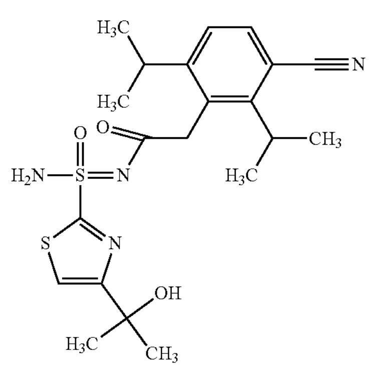 [SMILES: CC(C)c1ccc(C#N)c(C(C)C)c1CC(=O)N=S(N)(=O)c1nc(C(C)(C)O)cs1] |

TABLE 1-continued

| Compound | Structure |
|---|---|
| 242a | (structure) |
| 242b | (structure) |
| 243 | (structure) |
| 243a | (structure) |

TABLE 1-continued

| Compound | Structure |
|---|---|
| 243b | 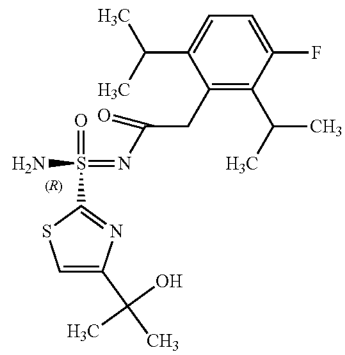 |
| 244 | 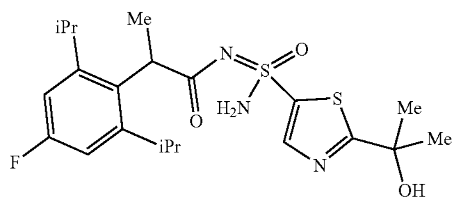 [SMILES: CC(C)c1cc(F)cc(C(C)C)c1C(C)C(=O)N=S(N)(=O)c1cnc(C(C)(C)O)s1] |
| 244aa | 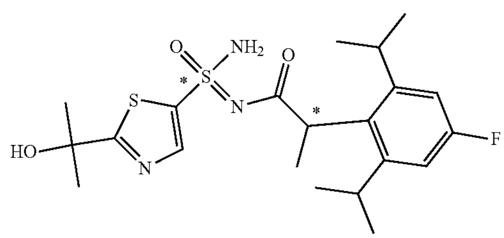 [SMILES: CC(C)c1cc(F)cc(C(C)C)c1C(C)C(=O)N=S(N)(=O)c1cnc(C(C)(C)O)s1] |
| 244b | 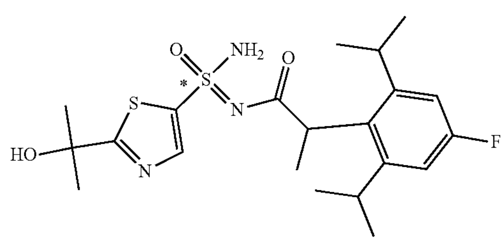 [SMILES: CC(C)c1cc(F)cc(C(C)C)c1C(C)C(=O)N=S(N)(=O)c1cnc(C(C)(C)O)s1] |
| 244ba | 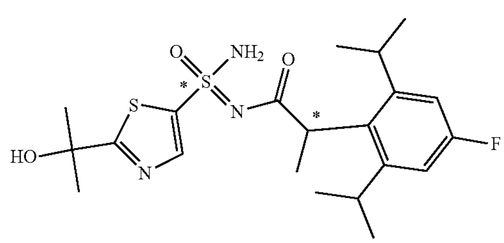 [SMILES: CC(C)c1cc(F)cc(C(C)C)c1C(C)C(=O)N=S(N)(=O)c1cnc(C(C)(C)O)s1] |

TABLE 1-continued

| Compound | Structure |
|---|---|
| 245 | 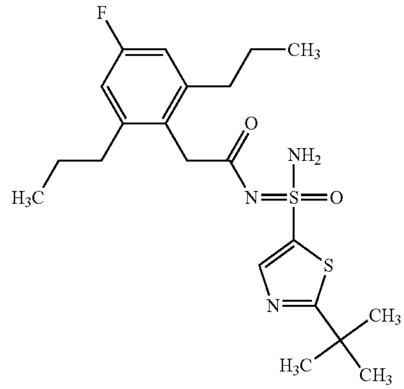 [SMILES: CCCc1cc(F)cc(CCC)c1CC(=O)N=S(N)(=O)c1cnc(C(C)(C)C)s1] |
| 246 | 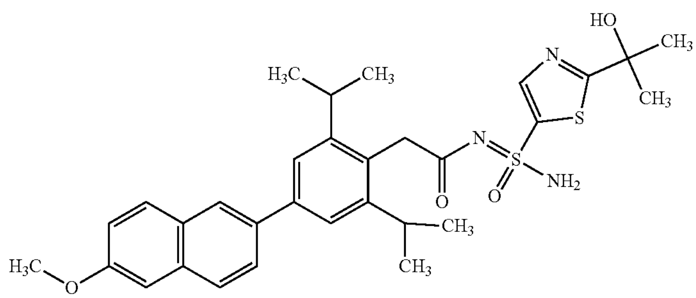 [SMILES: COc1ccc2cc(-c3cc(C(C)C)c(CC(=O)N=S(N)(=O)c4cnc(C(C)(C)O)s4)c(C(C)C)c3)ccc2c1] |
| 247 | 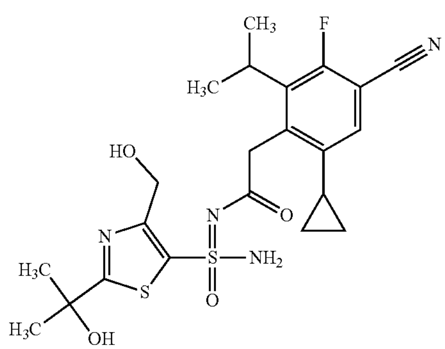 [SMILES: CC(C)c1c(F)c(C#N)cc(C2CC2)c1CC(=O)N=S(N)(=O)c1sc(C(C)(C)O)nc1CO] |
| 248 | 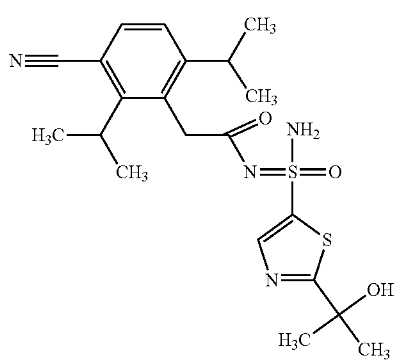 [SMILES: CC(C)c1ccc(C#N)c(C(C)C)c1CC(=O)N=S(N)(=O)c1cnc(C(C)(C)O)s1] |

TABLE 1-continued
| Compound | Structure |
|---|---|
| 249 | 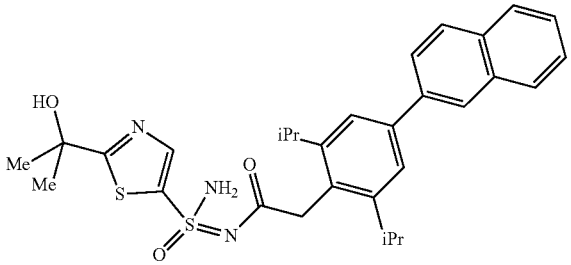 [SMILES: CC(C)c1cc(-c2ccc3ccccc3c2)cc(C(C)C)c1CC(=O)N=S(N)(=O)c1cnc(C(C)(C)O)s1] |
| 249a | 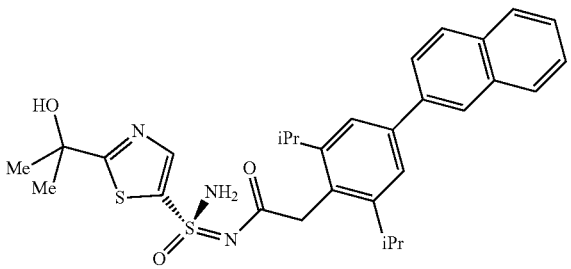 [SMILES: CC(C)c1cc(-c2ccc3ccccc3c2)cc(C(C)C)c1CC(=O)N=[S@](N)(=O)c1cnc(C(C)(C)O)s1] |
| 249b | 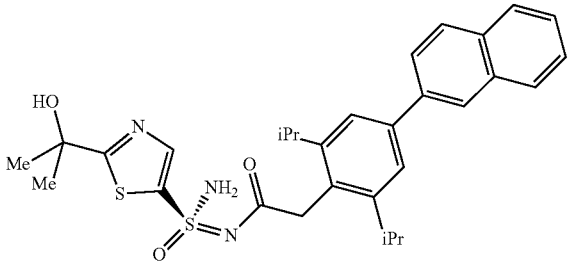 [SMILES: CC(C)c1cc(-c2ccc3ccccc3c2)cc(C(C)C)c1CC(=O)N=[S@@](N)(=O)c1cnc(C(C)(C)O)s1] |
| 250 | 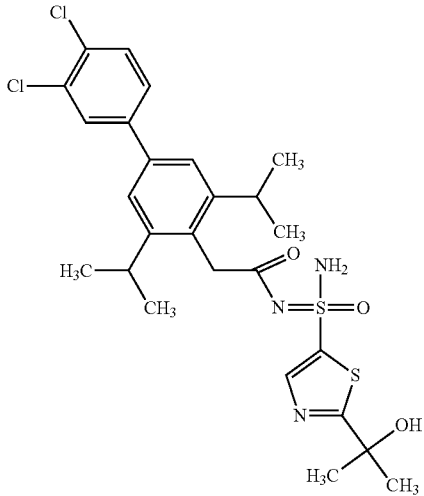 [SMILES: CC(C)c1cc(-c2ccc(Cl)c(Cl)c2)cc(C(C)C)c1CC(=O)N=S(N)(=O)c1cnc(C(C)(C)O)s1] |

TABLE 1-continued
| Compound | Structure |
|---|---|
| 251 | 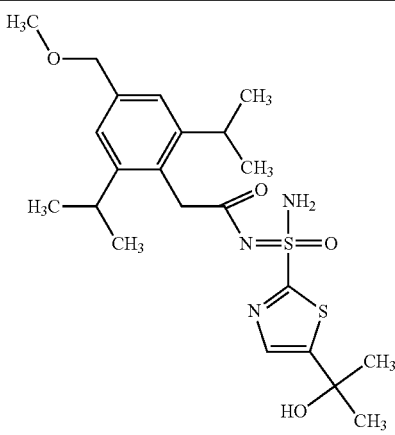 |
| 251a | 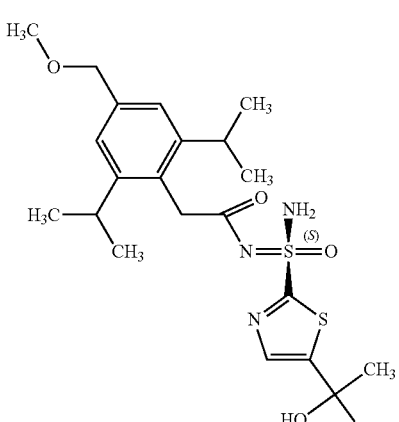 |
| 251b | 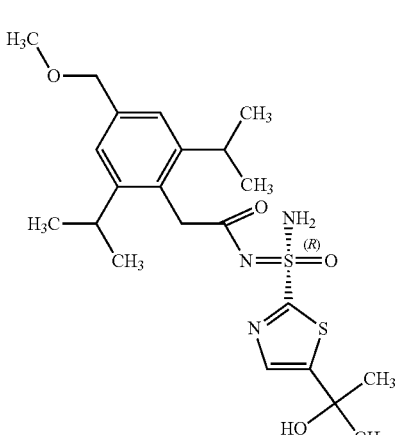 |
| 252 | 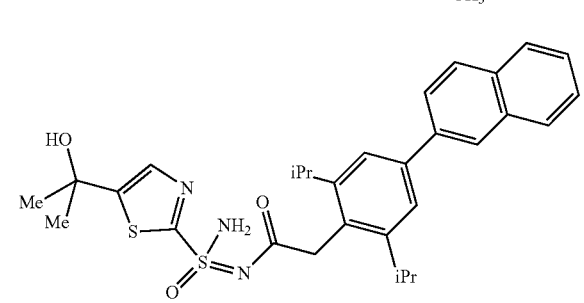 |

TABLE 1-continued
| Compound | Structure |
|---|---|
| 253 | 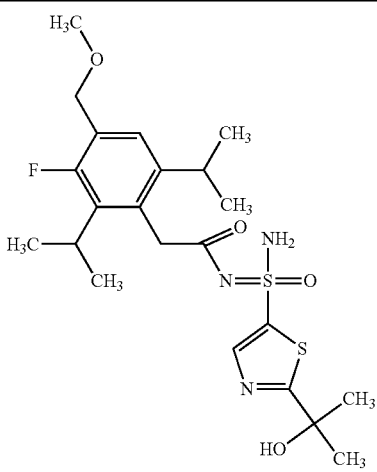 |
| 254 | 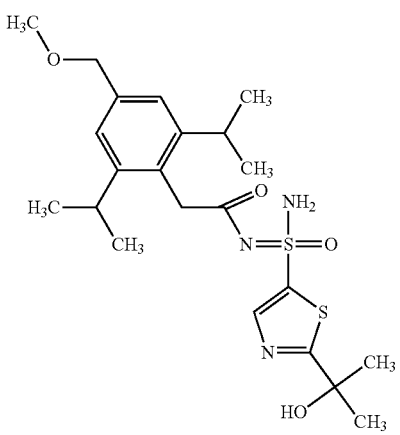 [SMILES: COCc1cc(C(C)C)c(CC(=O)N=S(N)(=O)c2cnc(C(C)(C)O)s2)c(C(C)C)c1] |
| 255 | 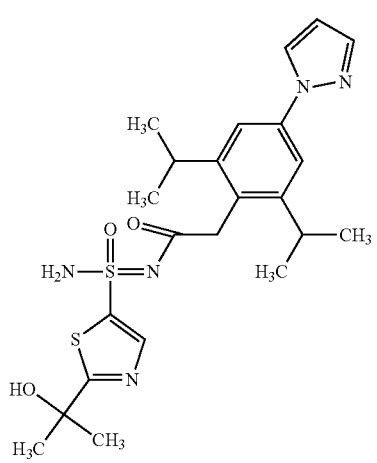 [SMILES: CC(C)c1cc(-n2cccn2)cc(C(C)C)c1CC(=O)N=S(N)(=O)c1cnc(C(C)(C)O)s1] |

TABLE 1-continued

| Compound | Structure |
|---|---|
| 256 | (chemical structure) |
| 256a | (chemical structure, S configuration) |
| 256b | (chemical structure, R configuration) |

TABLE 1-continued

| Compound | Structure |
|---|---|
| 257 | 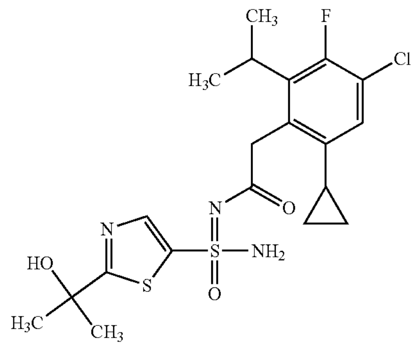 [SMILES: CC(C)c1c(F)c(Cl)cc(C2CC2)c1CC(=O)N=S(N)(=O)c1cnc(C(C)(C)O)s1] |
| 258 | 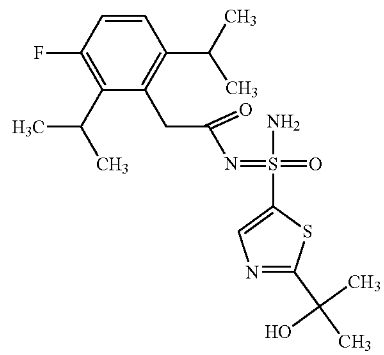 [SMILES: CC(C)c1ccc(F)c(C(C)C)c1CC(=O)N=S(N)(=O)c1cnc(C(C)(C)O)s1] |
| 258a | 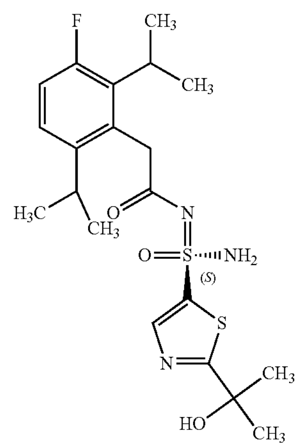 |
| 258b | 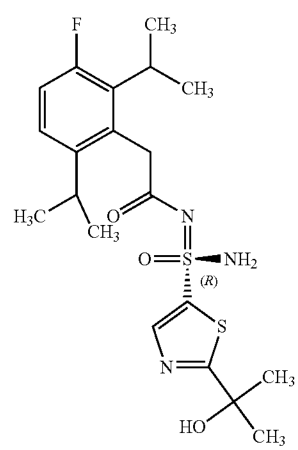 |

TABLE 1-continued
| Compound | Structure |
|---|---|
| 259 | 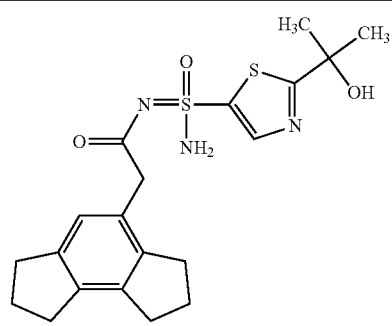 |
| 259a | 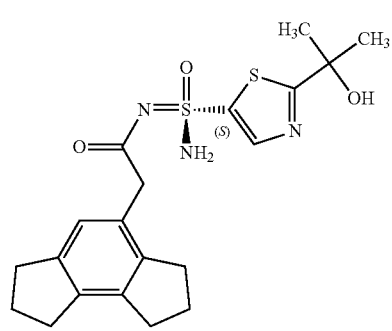 |
| 259b | 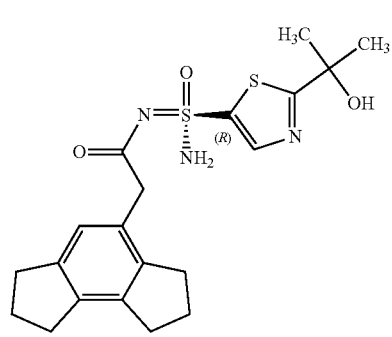 |
| 260 | 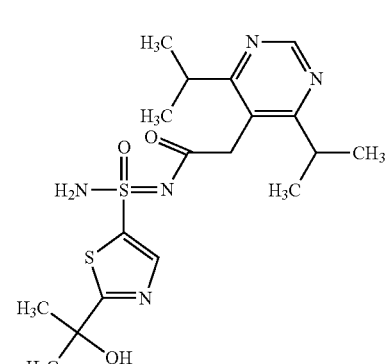 |
| 261a | 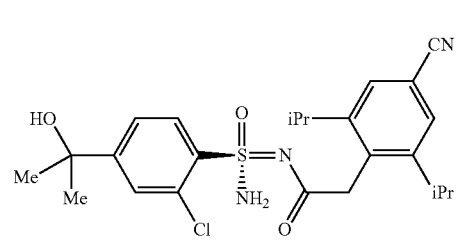 [SMILES: CC(C)c1cc(C#N)cc(C(C)C)c1CC(=O)N=[S@](N)(=O)c1ccc(C(C)(C)O)cc1Cl] |

TABLE 1-continued

| Compound | Structure |
|---|---|
| 261b | 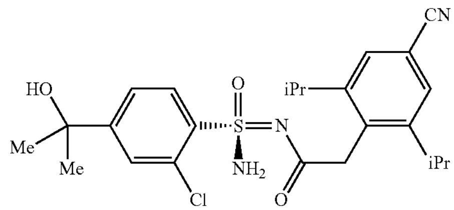 [SMILES: CC(C)c1cc(C#N)cc(C(C)C)c1CC(=O)N=[S@@](N)(=O)c1ccc(C(C)(C)O)cc1Cl] |
| 262a | 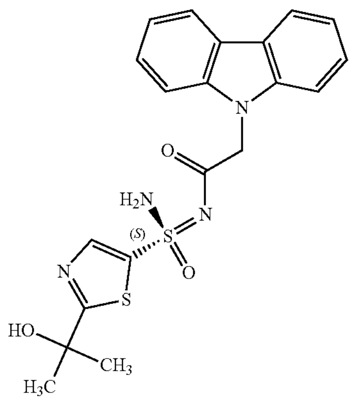 |
| 262b | 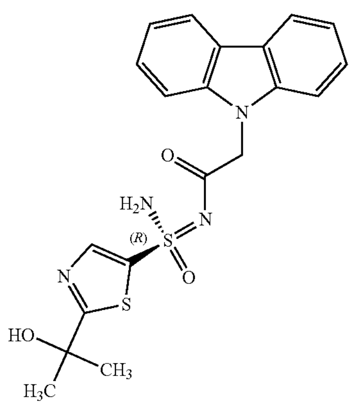 |
| 263 | 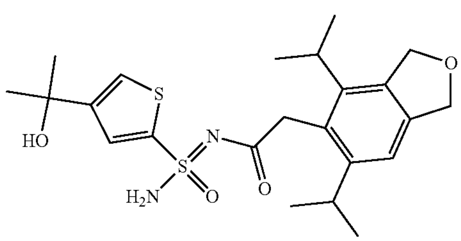 [SMILES: CC(C)c1cc2c(c(C(C)C)c1CC(=O)N=S(N)(=O)c1cc(C(C)(C)O)cs1)COC2] |
| 263a | 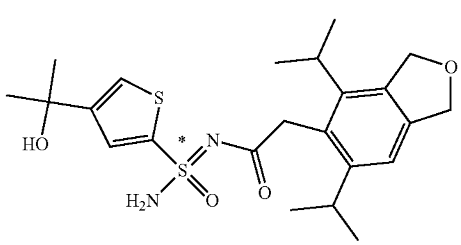 [SMILES: CC(C)c1cc2c(c(C(C)C)c1CC(=O)N=S(N)(=O)c1cc(C(C)(C)O)cs1)COC2] |

TABLE 1-continued

| Compound | Structure |
|---|---|
| 263b | |
| 264 | |
| 264a | |
| 264b | | and pharmaceutically acceptable salts thereof.

In some embodiments, provided herein is a compound that is selected from the group consisting of the compounds in Table 1-3:

TABLE 1-3

| 301 | |
|---|---|
| 302 | |

TABLE 1-3-continued
| 303 | 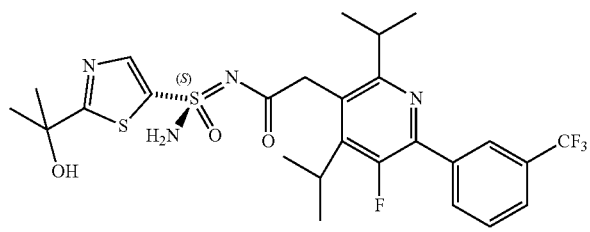 |
| --- | --- |
| 304 | 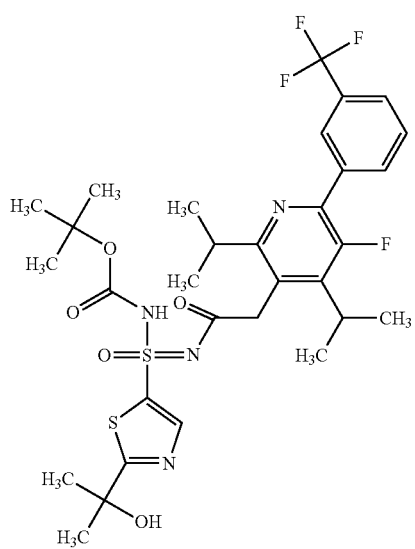 [SMILES: CC(C)c1nc(-c2cccc(C(F)(F)F)c2)c(F)c(C(C)C)c1CC(=O)N=S(=O)(NC(=O)OC(C)(C)C)c1cnc(C(C)(C)O)s1] |
| 305 | 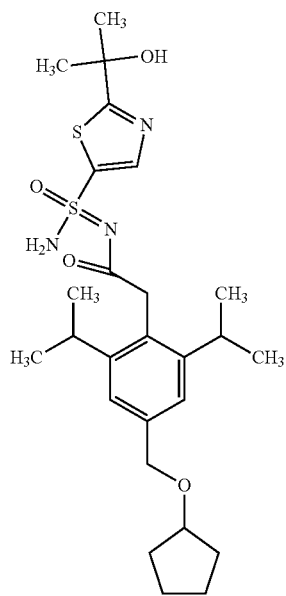 [SMILES: CC(C)c1cc(COC2CCCC2)cc(C(C)C)c1CC(=O)N=S(N)(=O)c1cnc(C(C)(C)O)s1] |

TABLE 1-3-continued
| | |
|---|---|
| 306 | 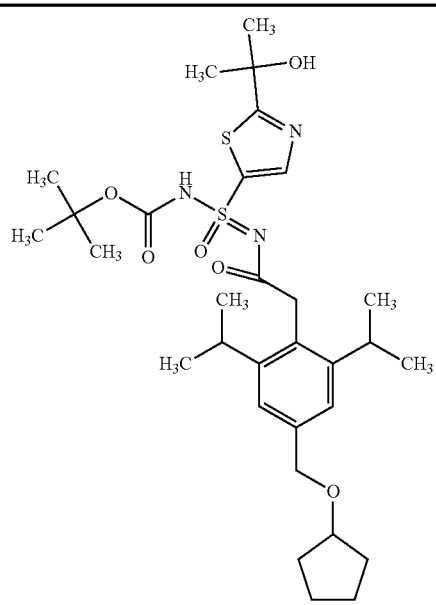 |
| 307 | 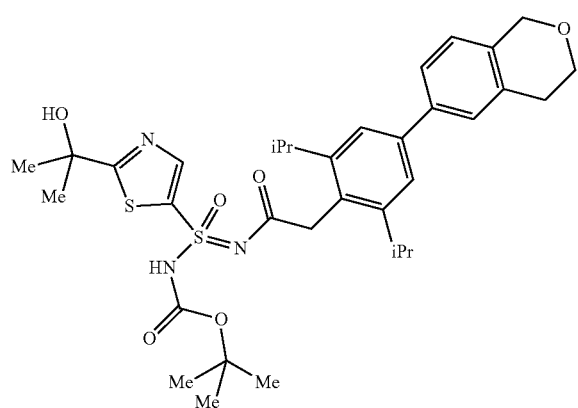 [SMILES: CC(C)c1cc(-c2ccc3c(c2)CCOC3)cc(C(C)C)c1CC(=O)N=S(=O)(NC(=O)OC(C)(C)C)c1cnc(C(C)(C)O)s1] |
| 309 | 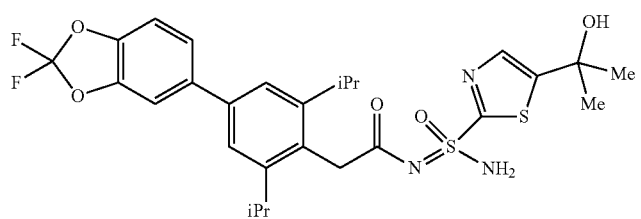 [SMILES: CC(C)c1cc(-c2ccc3c(c2)OC(F)(F)O3)cc(C(C)C)c1CC(=O)N=S(N)(=O)c1ncc(C(C)(C)O)s1] |
| 309a | 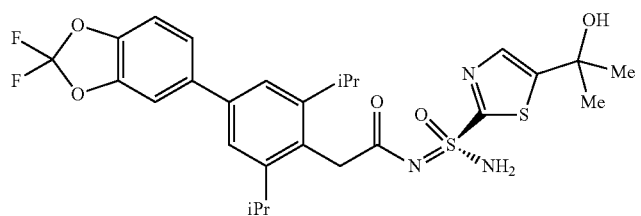 [SMILES: CC(C)c1cc(-c2ccc3c(c2)OC(F)(F)O3)cc(C(C)C)c1CC(=O)N=[S@@](N)(=O)c1ncc(C(C)(C)O)s1] |
| 309b | 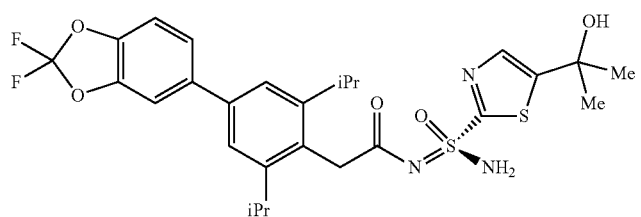 [SMILES: CC(C)c1cc(-c2ccc3c(c2)OC(F)(F)O3)cc(C(C)C)c1CC(=O)N=[S@](N)(=O)c1ncc(C(C)(C)O)s1] |

TABLE 1-3-continued

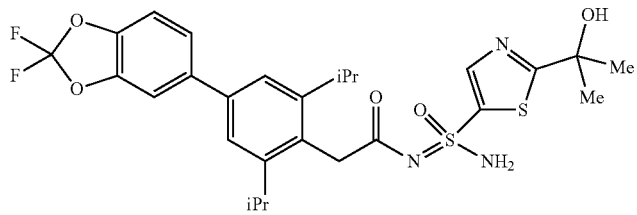 [SMILES: CC(C)c1cc(-c2ccc3c(c2)OC(F)(F)O3)cc(C(C)C)c1CC(=O)N=S(N)(=O)c1cnc(C(C)(C)O)s1]

or a pharmaceutically acceptable salt thereof.

Pharmaceutical Compositions and Administration

General

In some embodiments, a chemical entity (e.g., a compound that modulates (e.g., antagonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%400% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22nd Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

In certain embodiments, the chemical entities described herein or a pharmaceutical composition thereof are suitable for local, topical administration to the digestive or GI tract, e.g., rectal administration. Rectal compositions include, without limitation, enemas, rectal gels, rectal foams, rectal aerosols, suppositories, jelly suppositories, and enemas (e.g., retention enemas).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Enema Formulations

In some embodiments, enema formulations containing the chemical entities described herein are provided in "ready-to-use" form.

In some embodiments, enema formulations containing the chemical entities described herein are provided in one or more kits or packs. In certain embodiments, the kit or pack includes two or more separately contained/packaged components, e.g. two components, which when mixed together, provide the desired formulation (e.g., as a suspension). In certain of these embodiments, the two component system includes a first component and a second component, in which: (1) the first component (e.g., contained in a sachet) includes the chemical entity (as described anywhere herein) and optionally one or more pharmaceutically acceptable excipients (e.g., together formulated as a solid preparation, e.g., together formulated as a wet granulated solid preparation); and (ii) the second component (e.g., contained in a vial or bottle) includes one or more liquids and optionally one or more other pharmaceutically acceptable excipients together forming a liquid carrier. Prior to use (e.g., immediately prior to use), the contents of (1) and (ii) are combined to form the desired enema formulation, e.g., as a suspension. In other embodiments, each of component (1) and (ii) is provided in its own separate kit or pack.

In some embodiments, each of the one or more liquids is water, or a physiologically acceptable solvent, or a mixture of water and one or more physiologically acceptable solvents. Typical such solvents include, without limitation, glycerol, ethylene glycol, propylene glycol, polyethylene glycol and polypropylene glycol. In certain embodiments, each of the one or more liquids is water. In other embodiments, each of the one or more liquids is an oil, e.g. natural and/or synthetic oils that are commonly used in pharmaceutical preparations.

Further pharmaceutical excipients and carriers that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

In some embodiments, each of the one or more pharmaceutically acceptable excipients can be independently selelcted from thickeners, viscosity enhancing agents, bulking agents, mucoadhesive agents, penetration enhanceers, buffers, preservatives, diluents, binders, lubricants, glidants, disintegrants, fillers, solubilizing agents, pH modifying agents, preservatives, stabilizing agents, anti-oxidants, wetting or emulsifying agents, suspending agents, pigments, colorants, isotonic agents, chelating agents, emulsifiers, and diagnostic agents.

In certain embodiments, each of the one or more pharmaceutically acceptable excipients can be independently selelcted from thickeners, viscosity enhancing agents, mucoadhesive agents, buffers, preservatives, diluents, binders, lubricants, glidants, disintegrants, and fillers.

In certain embodiments, each of the one or more pharmaceutically acceptable excipients can be independently selelcted from thickeners, viscosity enhancing agents, bulking agents, mucoadhesive agents, buffers, preservatives, and fillers.

In certain embodiments, each of the one or more pharmaceutically acceptable excipients can be independently selelcted from diluents, binders, lubricants, glidants, and disintegrants.

Examples of thickeners, viscosity enhancing agents, and mucoadhesive agents include without limitation: gums, e.g. xanthan gum, guar gum, locust bean gum, tragacanth gums, karaya gum, ghatti gum, cholla gum, psyllium seed gum and gum arabic; poly(carboxylic acid-containing) based polymers, such as poly (acrylic, maleic, itaconic, citraconic, hydroxyethyl methacrylic or methacrylic) acid which have strong hydrogen-bonding groups, or derivatives thereof such as salts and esters; cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof; clays such as manomorillonite clays, e.g. Veegun, attapulgite clay; polysaccharides such as dextran, pectin, amylopectin, agar, mannan or polygalactonic acid or starches such as hydroxypropyl starch or carboxymethyl starch; polypeptides such as casein, gluten, gelatin, fibrin glue; chitosan, e.g. lactate or glutamate or carboxymethyl chitin; glycosaminoglycans such as hyaluronic acid; metals or water soluble salts of alginic acid such as sodium alginate or magnesium alginate; schleroglucan; adhesives containing bismuth oxide or aluminium oxide; atherocollagen; polyvinyl polymers such as carboxyvinyl polymers; polyvinylpyrrolidone (povidone); polyvinyl alcohol; polyvinyl acetates, polyvinylmethyl ethers, polyvinyl chlorides, polyvinylidenes, and/or the like; polycarboxylated vinyl polymers such as polyacrylic acid as mentioned above; polysiloxanes; polyethers; polyethylene oxides and glycols; polyalkoxys and polyacrylamides and derivatives and salts thereof. Preferred examples can include cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof (e.g., methyl cellulose); and polyvinyl polymers such as polyvinylpyrrolidone (povidone).

Examples of preservatives include without limitation: benzalkonium chloride, benzoxonium chloride, benzethonium chloride, cetrimide, sepazonium chloride, cetylpyridinium chloride, domiphen bromide (Bradosol®), thiomersal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, Purite®), Polyquart®), and sodium perborate tetrahydrate and the like.

In certain embodiments, the preservative is a paraben, or a pharmaceutically acceptable salt thereof. In some embodiments, the paraben is an alkyl substituted 4-hydroxybenzoate, or a pharmaceutically acceptable salt or ester thereof. In certain embodiments, the alkyl is a C1-C4 alkyl. In certain embodiments, the preservative is methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof.

Examples of buffers include without limitation: phosphate buffer system (sodium dihydrogen phospahate dehydrate, disodium phosphate dodecahydrate, bibasic sodium phosphate, anhydrous monobasic sodium phosphate), bicarbonate buffer system, and bisulfate buffer system.

Examples of disintegrants include, without limitation: carmellose calcium, low substituted hydroxypropyl cellulose (L-HPC), carmellose, croscarmellose sodium, partially pregelatinized starch, dry starch, carboxymethyl starch sodium, crospovidone, polysorbate 80 (polyoxyethylenesorbitan oleate), starch, sodium starch glycolate, hydroxypropyl cellulose pregelatinized starch, clays, cellulose, alginine, gums or cross linked polymers, such as cross-linked PVP (Polyplasdone XL from GAF Chemical Corp). In certain embodiments, the disintegrant is crospovidone.

Examples of glidants and lubricants (aggregation inhibitors) include without limitation: talc, magnesium stearate, calcium stearate, colloidal silica, stearic acid, aqueous silicon dioxide, synthetic magnesium silicate, fine granulated silicon oxide, starch, sodium laurylsulfate, boric acid, magnesium oxide, waxes, hydrogenated oil, polyethylene glycol, sodium benzoate, stearic acid glycerol behenate, polyethylene glycol, and mineral oil. In certain embodiments, the glidant/lubricant is magnesium stearate, talc, and/or colloidal silica; e.g., magnesium stearate and/or talc.

Examples of diluents, also referred to as "fillers" or "bulking agents" include without limitation: dicalcium phosphate dihydrate, calcium sulfate, lactose (e.g., lactose monohydrate), sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. In certain embodiments, the diluent is lactose (e.g., lactose monohydrate).

Examples of binders include without limitation: starch, pregelatinized starch, gelatin, sugars (including sucrose, glucose, dextrose, lactose and sorbitol), polyethylene glycol, waxes, natural and synthetic gums such as acacia tragacanth, sodium alginate cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (povidone). In certain embodiments, the binder is polyvinylpyrrolidone (povidone).

In some embodiments, enema formulations containing the chemical entities described herein include water and one or more (e.g., all) of the following excipients:
  One or more (e.g., one, two, or three) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);
  One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof;
  One or more (e.g., one or two; e.g., two) buffers, such as phosphate buffer system (e.g., sodium dihydrogen phospahate dehydrate, disodium phosphate dodecahydrate);
  One or more (e.g., one or two, e.g., two) glidants and/or lubricants, such as magnesium stearate and/or talc;
  One or more (e.g., one or two; e.g., one) disintegrants, such as crospovidone; and
  One or more (e.g., one or two; e.g., one) diluents, such as lactose (e.g., lactose monohydrate).

In certain of these embodiments, the chemical entity is a compound of Formula AA, or a pharmaceutically acceptable salt and/or hydrate and/or cocrystal thereof.

In certain embodiments, enema formulations containing the chemical entities described herein include water, methyl cellulose, povidone, methylparaben, propylparaben, sodium dihydrogen phospahate dehydrate, disodium phosphate dodecahydrate, crospovidone, lactose monohydrate, magnesium stearate, and talc. In certain of these embodiments, the chemical entity is a compound of Formula AA, or a pharmaceutically acceptable salt and/or hydrate and/or cocrystal thereof.

In certain embodiments, enema formulations containing the chemical entities described herein are provided in one or more kits or packs. In certain embodiments, the kit or pack includes two separately contained/packaged components, which when mixed together, provide the desired formulation (e.g., as a suspension). In certain of these embodiments, the two component system includes a first component and a second component, in which: (1) the first component (e.g., contained in a sachet) includes the chemical entity (as described anywhere herein) and one or more pharmaceutically acceptable excipients (e.g., together formulated as a solid preparation, e.g., together formulated as a wet granulated solid preparation); and (ii) the second component (e.g., contained in a vial or bottle) includes one or more liquids and one or more one or more other pharmaceutically acceptable excipients together forming a liquid carrier. In other embodiments, each of component (1) and (ii) is provided in its own separate kit or pack.

In certain of these embodiments, component (i) includes the chemical entity (e.g., a compound of Formula AA, or a pharmaceutically acceptable salt and/or hydrate and/or cocrystal thereof; e.g., a compound of Formula AA) and one or more (e.g., all) of the following excipients:
  (a) One or more (e.g., one) binders (e.g., a polyvinyl polymer, such as polyvinylpyrrolidone (povidone);
  (b) One or more (e.g., one or two, e.g., two) glidants and/or lubricants, such as magnesium stearate and/or talc;

(c) One or more (e.g., one or two; e.g., one) disintegrants, such as crospovidone; and (d) One or more (e.g., one or two; e.g., one) diluents, such as lactose (e.g., lactose monohydrate).

In certain embodiments, component (i) includes from about 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) of the chemical entity (e.g., a compound of Formula AA, or a pharmaceutically acceptable salt and/or hydrate and/or cocrystal thereof).

In certain embodiments, component (i) includes from about 0.5 weight percent to about 5 weight percent (e.g., from about 1.5 weight percent to about 4.5 weight percent, from about 2 weight percent to about 3.5 weight percent; e.g., about 2.76 weight percent) of the binder (e.g., povidone).

In certain embodiments, component (i) includes from about 0.5 weight percent to about 5 weight percent (e.g., from about 0.5 weight percent to about 3 weight percent, from about 1 weight percent to about 3 weight percent; about 2 weight percent e.g., about 1.9 weight percent) of the disintegrant (e.g., crospovidone).

In certain embodiments, component (i) includes from about 10 weight percent to about 50 weight percent (e.g., from about 20 weight percent to about 40 weight percent, from about 25 weight percent to about 35 weight percent; e.g., about 31.03 weight percent) of the diluent (e.g., lactose, e.g., lactose monohydrate).

In certain embodiments, component (i) includes from about 0.05 weight percent to about 5 weight percent (e.g., from about 0.05 weight percent to about 3 weight percent) of the glidants and/or lubricants.

In certain embodiments (e.g., when component (i) includes one or more lubricants, such as magnesium stearate), component (i) includes from about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent) of the lubricant (e.g., magnesium stearate).

In certain embodiments (when component (i) includes one or more lubricants, such as talc), component (i) includes from about 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; about 1.93 weight percent) of the lubricant (e.g., talc).

In certain of these embodiments, each of (a), (b), (c), and (d) above is present.

In certain embodiments, component (i) includes the ingredients and amounts as shown in Table A.

TABLE A

| Ingredient | Weight Percent |
| --- | --- |
| A compound of Formula AA | 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) |

TABLE A-continued

| Ingredient | Weight Percent |
| --- | --- |
| Crospovidone (Kollidon CL) | 0.5 weight percent to about 5 weight percent (e.g., from about 0.5 weight percent to about 3 weight percent, from about 1 weight percent to about 3 weight percent; about 1.93 weight percent |
| lactose monohydrate (Pharmatose 200M) | about 10 weight percent to about 50 weight percent (e.g., from about 20 weight percent to about 40 weight percent, from about 25 weight percent to about 35 weight percent; e.g., about 31.03 weight percent |
| Povidone (Kollidon K30) | about 0.5 weight percent to about 5 weight percent (e.g., from about 1.5 weight percent to about 4.5 weight percent, from about 2 weight percent to about 3.5 weight percent; e.g., about 2.76 weight percent |
| talc | 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; e.g., about 1.93 weight percent |
| Magnesium stearate | about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent |

In certain embodiments, component (1) includes the ingredients and amounts as shown in Table B.

TABLE B

| Ingredient | Weight Percent |
| --- | --- |
| A compound of Formula AA | About 62.1 weight percent) |
| Crospovidone (Kollidon CL) | About 1.93 weight percent |
| lactose monohydrate (Pharmatose 200M) | About 31.03 weight percent |
| Povidone (Kollidon K30) | About 2.76 weight percent |
| talc | About 1.93 weight percent |
| Magnesium stearate | About 0.27 weight percent |

In certain embodiments, component (1) is formulated as a wet granulated solid preparation. In certain of these embodiments an internal phase of ingredients (the chemical entity, disintegrant, and diluent) are combined and mixed in a high-shear granulator. A binder (e.g., povidone) is dissolved in water to form a granulating solution. This solution is added to the Inner Phase mixture resulting in the development of granules. While not wishing to be bound by theory, granule development is believed to be facilitated by the interaction of the polymeric binder with the materials of the internal phase. Once the granulation is formed and dried, an external phase (e.g., one or more lubricants—not an intrinsic component of the dried granulation), is added to the dry granulation. It is believed that lubrication of the granulation is important to the flowability of the granulation, in particular for packaging.

In certain of the foregoing embodiments, component (ii) includes water and one or more (e.g., all) of the following excipients:

(a') One or more (e.g., one, two; e.g., two) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

(b') One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof; and (c') One or more (e.g., one or two; e.g., two) buffers, such as phosphate buffer system (e.g., sodium dihydrogen phospahate dihydrate, disodium phosphate dodecahydrate);

In certain of the foregoing embodiments, component (ii) includes water and one or more (e.g., all) of the following excipients:

(a") a first thickener, viscosity enhancing agent, binder, and/or mucoadhesive agent (e.g., a cellulose or cellulose ester or ether or derivative or salt thereof (e.g., methyl cellulose));

(a''') a second thickener, viscosity enhancing agent, binder, and/or mucoadhesive agent (e.g., a polyvinyl polymer, such as polyvinylpyrrolidone (povidone));

(b") a first preservative, such as a paraben, e.g., propyl 4-hydroxybenzoate (propylparaben), or a pharmaceutically acceptable salt or ester thereof;

(b''') a second preservative, such as a paraben, e.g., methyl 4-hydroxybenzoate (methylparaben), or a pharmaceutically acceptable salt or ester thereof, (c") a first buffer, such as phosphate buffer system (e.g., disodium phosphate dodecahydrate);

(c''') a second buffer, such as phosphate buffer system (e.g., sodium dihydrogen phospahate dehydrate), In certain embodiments, component (ii) includes from about 0.05 weight percent to about 5 weight percent (e.g., from about 0.05 weight percent to about 3 weight percent, from about 0.1 weight percent to about 3 weight percent; e.g., about 1.4 weight percent) of (a').

In certain embodiments, component (ii) includes from about 0.05 weight percent to about 5 weight percent (e.g., from about 0.05 weight percent to about 3 weight percent, from about 0.1 weight percent to about 2 weight percent; e.g., about 1.0 weight percent) of (a''').

In certain embodiments, component (ii) includes from about 0.005 weight percent to about 0.1 weight percent (e.g., from about 0.005 weight percent to about 0.05 weight percent; e.g., about 0.02 weight percent) of (b").

In certain embodiments, component (ii) includes from about 0.05 weight percent to about 1 weight percent (e.g., from about 0.05 weight percent to about 0.5 weight percent; e.g., about 0.20 weight percent) of (b''').

In certain embodiments, component (ii) includes from about 0.05 weight percent to about 1 weight percent (e.g., from about 0.05 weight percent to about 0.5 weight percent; e.g., about 0.15 weight percent) of (c").

In certain embodiments, component (ii) includes from about 0.005 weight percent to about 0.5 weight percent (e.g., from about 0.005 weight percent to about 0.3 weight percent; e.g., about 0.15 weight percent) of (c''').

In certain of these embodiments, each of (a")-(c''') is present.

In certain embodiments, component (ii) includes water (up to 100%) and the ingredients and amounts as shown in Table C.

TABLE C

| Ingredient | Weight Percent |
| --- | --- |
| methyl cellulose (Methocel A15C premium) | 0.05 weight percent to about 5 weight percent (e.g., from about 0.05 weight percent to about 3 weight percent, from about 0.1 weight percent to about 3 weight percent; e.g., about 1.4 weight percent |
| Povidone (Kollidon K30) | 0.05 weight percent to about 5 weight percent (e.g., from about 0.05 weight percent to about 3 weight percent, from about 0.1 weight percent to about 2 weight percent; e.g., about 1.0 weight percent |
| propyl 4-hydroxybenzoate | about 0.005 weight percent to about 0.1 weight percent (e.g., from about 0.005 weight percent to about 0.05 weight percent; e.g., about 0.02 weight percent) |
| methyl 4-hydroxybenzoate | about 0.05 weight percent to about 1 weight percent (e.g., from about 0.05 weight percent to about 0.5 weight percent; e.g., about 0.20 weight percent) |
| disodium phosphate dodecahydrate | about 0.05 weight percent to about 1 weight percent (e.g., from about 0.05 weight percent to about 0.5 weight percent; e.g., about 0.15 weight percent) |
| sodium dihydrogen phospahate dihydrate | about 0.005 weight percent to about 0.5 weight percent (e.g., from about 0.005 weight percent to about 0.3 weight percent; e.g., about 0.15 weight percent) |

In certain embodiments, component (ii) includes water (up to 100%) and the ingredients and amounts as shown in Table D.

TABLE D

| Ingredient | Weight Percent |
| --- | --- |
| methyl cellulose (Methocel A15C premium) | about 1.4 weight percent |
| Povidone (Kollidon K30) | about 1.0 weight percent |
| propyl 4-hydroxybenzoate | about 0.02 weight percent |
| methyl 4-hydroxybenzoate | about 0.20 weight percent |
| disodium phosphate dodecahydrate | about 0.15 weight percent |
| sodium dihydrogen phospahate dihydrate | about 0.15 weight percent |

Ready-to-use" enemas are generally be provided in a "single-use" sealed disposable container of plastic or glass. Those formed of a polymeric material preferably have sufficient flexibility for ease of use by an unassisted patient. Typical plastic containers can be made of polyethylene. These containers may comprise a tip for direct introduction into the rectum. Such containers may also comprise a tube between the container and the tip. The tip is preferably provided with a protective shield which is removed before use. Optionally the tip has a lubricant to improve patient compliance.

In some embodiments, the enema formulation (e.g., suspension) is poured into a bottle for delivery after it has been prepared in a separate container. In certain embodiments, the bottle is a plastic bottle (e.g., flexible to allow for delivery by squeezing the bottle), which can be a polyethylene bottle (e.g., white in color). In some embodiments, the bottle is a single chamber bottle, which contains the suspension or solution. In other embodiments, the bottle is a multichamber bottle, where each chamber contains a separate mixture or solution. In still other embodiments, the bottle can further include a tip or rectal cannula for direct introduction into the rectum. In some embodiments, the enema formulation can be delivered in the device shown in FIGS. 3A-3C, which includes a plastic bottle, a breakable capsule, and a rectal cannula and single flow pack.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

In some embodiments, enema formulations include from about 0.5 mg to about 2500 mg (e.g., from about 0.5 mg to about 2000 mg, from about 0.5 mg to about 1000 mg, from about 0.5 mg to about 750 mg, from about 0.5 mg to about 600 mg, from about 0.5 mg to about 500 mg, from about 0.5 mg to about 400 mg, from about 0.5 mg to about 300 mg, from about 0.5 mg to about 200 mg; e.g., from about 5 mg to about 2500 mg, from about 5 mg to about 2000 mg, from about 5 mg to about 1000 mg; from about 5 mg to about 750 mg; from about 5 mg to about 600 mg; from about 5 mg to about 500 mg; from about 5 mg to about 400 mg; from about 5 mg to about 300 mg; from about 5 mg to about 200 mg; e.g., from about 50 mg to about 2000 mg, from about 50 mg to about 1000 mg, from about 50 mg to about 750 mg, from about 50 mg to about 600 mg, from about 50 mg to about 500 mg, from about 50 mg to about 400 mg, from about 50 mg to about 300 mg, from about 50 mg to about 200 mg; e.g., from about 100 mg to about 2500 mg, from about 100 mg to about 2000 mg, from about 100 mg to about 1000 mg, from about 100 mg to about 750 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg; e.g., from about 150 mg to about 2500 mg, from about 150 mg to about 2000 mg, from about 150 mg to about 1000 mg, from about 150 mg to about 750 mg, from about 150 mg to about 700 mg, from about 150 mg to about 600 mg, from about 150 mg to about 500 mg, from about 150 mg to about 400 mg, from about 150 mg to about 300 mg, from about 150 mg to about 200 mg; e.g., from about 150 mg to about 500 mg; e.g., from about 300 mg to about 2500 mg, from about 300 mg to about 2000 mg, from about 300 mg to about 1000 mg, from about 300 mg to about 750 mg, from about 300 mg to about 700 mg, from about 300 mg to about 600 mg; e.g., from about 400 mg to about 2500 mg, from about 400 mg to about 2000 mg, from about 400 mg to about 1000 mg, from about 400 mg to about 750 mg, from about 400 mg to about 700 mg, from about 400 mg to about 600 from about 400 mg to about 500 mg; e.g., 150 mg or 450 mg) of the chemical entity in from about 1 mL to about 3000 mL (e.g., from about 1 mL to about 2000 mL, from about 1 mL to about 1000 mL, from about 1 mL to about 500 mL, from about 1 mL to about 250 mL, from about 1 mL to about 100 mL, from about 10 mL to about 1000 mL, from about 10 mL to about 500 mL, from about 10 mL to about 250 mL, from about 10 mL to about 100 mL, from about 30 mL to about 90 mL, from about 40 mL to about 80 mL; from about 50 mL to about 70 mL; e.g., about 1 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 100 mL, about 250 mL, or about 500 mL, or about 1000 mL, or about 2000 mL, or about 3000 mL; e.g., 60 mL) of liquid carrier.

In certain embodiments, enema formulations include from about 50 mg to about 250 mg (e.g., from about 100 mg to about 200; e.g., about 150 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 150 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 150 mg of a compound of Formula AA in about 60 mL of the liquid carrier.

In certain embodiments, enema formulations include from about 350 mg to about 550 mg (e.g., from about 400 mg to about 500; e.g., about 450 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 450 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 450 mg of a compound of Formula AA in about 60 mL of the liquid carrier.

In some embodiments, enema formulations include from about from about 0.01 mg/mL to about 50 mg/mL (e.g., from about 0.01 mg/mL to about 25 mg/mL; from about 0.01 mg/mL to about 10 mg/mL; from about 0.01 mg/mL to about 5 mg/mL; from about 0.1 mg/mL to about 50 mg/mL; from about 0.01 mg/mL to about 25 mg/mL; from about 0.1 mg/mL to about 10 mg/mL; from about 0.1 mg/mL to about 5 mg/mL; from about 1 mg/mL to about 10 mg/mL; from about 1 mg/mL to about 5 mg/mL; from about 5 mg/mL to about 10 mg/mL; e.g., about 2.5 mg/mL or about 7.5 mg/mL) of the chemical entity in liquid carrier. In certain of these embodiments, the chemical entity is a compound of Formula AA, or a pharmaceutically acceptable salt and/or hydrate and/or cocrystal thereof. For example, enema formulations can include about 2.5 mg/mL or about 7.5 mg/mL of a compound of Formula AA in liquid carrier.

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP3 activity (e.g., an increase, e.g., NLRP3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from major adverse cardiovascular events such as cardiovascular death, non-fatal myocardial infarction and non-fatal stroke in patients with a prior hear attack and inflammatory atherosclerosis (see for example, NCT01327846).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In some embodiments, the condition, disease or disorder is a cardiovascular indication. In some embodiments, the condition, disease or disorder is myocardial infraction. In some embodiments, the condition, disease or disorder is stroke.

In some embodiments, the condition, disease or disorder is obesity.

In some embodiments, the condition, disease or disorder is Type 2 Diabetes.

In some embodiments, the condition, disease or disorder is NASH.

In some embodiments, the condition, disease or disorder is Alzheimer's disease.

In some embodiments, the condition, disease or disorder is gout.

In some embodiments, the condition, disease or disorder is SLE.

In some embodiments, the condition, disease or disorder is rheumatoid arthritis.

In some embodiments, the condition, disease or disorder is IBD.

In some embodiments, the condition, disease or disorder is multiple sclerosis.

In some embodiments, the condition, disease or disorder is COPD.

In some embodiments, the condition, disease or disorder is asthma.

In some embodiments, the condition, disease or disorder is scleroderma.

In some embodiments, the condition, disease or disorder is pulmonary fibrosis.

In some embodiments, the condition, disease or disorder is age related macular degeneration (AMD).

In some embodiments, the condition, disease or disorder is cystic fibrosis.

In some embodiments, the condition, disease or disorder is Muckle Wells syndrome.

In some embodiments, the condition, disease or disorder is familial cold autoinflammatory syndrome (FCAS).

In some embodiments, the condition, disease or disorder is chronic neurologic cutaneous and articular syndrome.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; acute myeloid leukemia (AML) chronic myeloid leukemia (CIVIL); gastric cancer; and lung cancer metastasis.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; gastric cancer; and lung cancer metastasis.

In some embodiments, the indication is MDS.

In some embodiments, the indication is non-small lung cancer in patients carrying mutation or overexpression of NLRP3.

In some embodiments, the indication is ALL in patients resistant to glucocorticoids treatment.

In some embodiments, the indication is LCH.

In some embodiments, the indication is multiple myeloma.

In some embodiments, the indication is promyelocytic leukemia.

In some embodiments, the indication is gastric cancer.

In some embodiments, the indication is lung cancer metastasis.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR 014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http://www.uniprot.org/uniprot/Q96P20.

In some embodiments, the methods described herein further include the step of identifying a subject (e.g., a patient) in need of treatment for an indication related to NLRP3 activity, such as an indication related to point mutation of NLRP3 signaling.

Anti-TNFα Agents

The term "anti-TNFα agent" refers to an agent which directly or indirectly blocks, down-regulates, impairs, inhibits, impairs, or reduces TNFα activity and/or expression. In some embodiments, an anti-TNFα agent is an antibody or an antigen-binding fragment thereof, a fusion protein, a soluble TNFα receptor (a soluble tumor necrosis factor receptor superfamily member 1A (TNFR1) or a soluble tumor necrosis factor receptor superfamily 1B (TNFR2)), an inhibitory nucleic acid, or a small molecule TNFα antagonist. In some embodiments, the inhibitory nucleic acid is a ribozyme, small hairpin RNA, a small interfering RNA, an antisense nucleic acid, or an aptamer.

Exemplary anti-TNFα agents that directly block, down-regulate, impair, inhibit, or reduce TNFα activity and/or expression can, e.g., inhibit or decrease the expression level of TNFα or a receptor of TNFα (TNFR1 or TNFR2) in a cell (e.g., a cell obtained from a subject, a mammalian cell), or inhibit or reduce binding of TNFα to its receptor (TNFR1 and/or TNFR2) and/or. Non-limiting examples of anti-TNFα agents that directly block, down-regulate, impair, inhibit, or reduce TNFα activity and/or expression include an antibody or fragment thereof, a fusion protein, a soluble TNFα receptor (e.g., a soluble TNFR1 or soluble TNFR2), inhibitory nucleic acids (e.g., any of the examples of inhibitory nucleic acids described herein), and a small molecule TNFα antagonist.

Exemplary anti-TNFα agents that can indirectly block, down-regulate, impair, inhibit reduce TNFα activity and/or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: AP-1, mitogen-activated protein kinase kinase kinase 5 (ASK1), inhibitor of nuclear factor kappa B (IKK), mitogen-activated protein kinase 8 (JNK), mitogen-activated protein kinase (MAPK), MEKK 1/4, MEKK 4/7, MEKK 3/6, nuclear factor kappa B (NF-κB), mitogen-activated protein kinase kinase kinase 14 (NIK), receptor interacting serine/threonine kinase 1 (RIP), TNFRSF1A associated via death domain (TRADD), and TNF receptor associated factor 2 (TRAF2), in a cell), and/or decrease the level of TNFα-induced gene expression in a mammalian cell (e.g., decrease the transcription of genes regulated by, e.g., one or more transcription factors selected from the group of activating transcription factor 2 (ATF2), c-Jun, and NF-κB). A description of downstream signaling of a TNFα receptor is provided in Wajant et al., *Cell Death Differentiation* 10:45-65, 2003 (incorporated herein by reference). For example, such indirect anti-TNFα agents can be an inhibitory nucleic acid that targets (decreases the expression) a signaling component downstream of a TNFα-induced gene (e.g., any TNFα-induced gene known in the art), a TNFα receptor (e.g., any one or more of the signaling components downstream of a TNFα receptor described herein or known in the art), or a transcription factor selected from the group of NF-κB, c-Jun, and ATF2.

In other examples, such indirect anti-TNFα agents can be a small molecule inhibitor of a protein encoded by a TNFα-induced gene (e.g., any protein encoded by a TNFα-induced gene known in the art), a small molecule inhibitor of a signaling component downstream of a TNFα receptor (e.g., any of the signaling components downstream of a TNFα receptor described herein or known in the art), and a small molecule inhibitor of a transcription factor selected from the group of ATF2, c-Jun, and NF-κB.

In other embodiments, anti-TNFα agents that can indirectly block, down-regulate, impair, or reduce one or more components in a cell (e.g., a cell obtained from a subject, a mammalian cell) that are involved in the signaling pathway that results in TNFα mRNA transcription, TNFα mRNA stabilization, and TNFα mRNA translation (e.g., one or more components selected from the group of CD14, c-Jun, ERK1/2, IKK, IκB, interleukin 1 receptor associated kinase 1 (IRAK), JNK, lipopolysaccharide binding protein (LBP), MEK1/2, MEK3/6, MEK4/7, MK2, MyD88, NF-κB, NIK, PKR, p38, AKT serine/threonine kinase 1 (rac), raf kinase (raf), ras, TRAF6, TTP). For example, such indirect anti-TNFα agents can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, LBP, MEK1/2, MEK3/6, MEK4/7, MK2, MyD88, NF-κB, NIK, IRAK, lipopolysaccharide binding protein (LBP), PKR, p38, rac, raf, ras, TRAF6, TTP). In other examples, an indirect anti-TNFα agents is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, lipopolysaccharide binding protein (LBP), MEK1/2, MEK3/6, MEK4/7, MK2, MyD88, NF-κB, NIK, IRAK, lipopolysaccharide binding protein (LBP), PKR, p38, rac, raf, ras, TRAF6, TTP).

Antibodies

In some embodiments, the anti-TNFα agent is an antibody or an antigen-binding fragment thereof (e.g., a Fab or a scFv). In some embodiments, an antibody or antigen-binding fragment of an antibody described herein can bind specifically to TNFα. In some embodiments, an antibody or antigen-binding fragment described herein binds specifically to any one of TNFα, TNFR1, or TNFR2. In some embodiments, an antibody or antigen-binding fragment of an antibody described herein can bind specifically to a TNFα receptor (TNFR1 or TNFR2).

In some embodiments, the antibody can be a humanized antibody, a chimeric antibody, a multivalent antibody, or a fragment thereof. In some embodiments, an antibody can be a scFv-Fc, a VHH domain, a VNAR domain, a $(scFv)_2$, a minibody, or a BiTE.

In some embodiments, an antibody can be a crossmab, a diabody, a scDiabody, a scDiabody-$CH_3$, a Diabody-$CH_3$, a DutaMab, a DT-IgG, a diabody-Fc, a scDiabody-HAS, a charge pair antibody, a Fab-arm exchange antibody, a SEEDbody, a Triomab, a LUZ-Y, a Fcab, a kλ-body, an orthogonal Fab, a DVD-IgG, an IgG(H)-scFv, a scFv-(H) IgG, an IgG(L)-scFv, a scFv-(L)-IgG, an IgG (L,H)-Fc, an IgG(H)-V, a V(H)-IgG, an IgG(L)-V, a V(L)-IgG, an KIH IgG-scFab, a 2scFv-IgG, an IgG-2scFv, a scFv4-Ig, a Zybody, a DVI-IgG, a nanobody, a nanobody-HSA, a DVD-Ig, a dual-affinity re-targeting antibody (DART), a triomab, a kih IgG with a common LC, an ortho-Fab IgG, a 2-in-1-IgG, IgG-ScFv, scFv2-Fc, a bi-nanobody, tanden antibody, a DART-Fc, a scFv-HAS-scFv, a DAF (two-in-one or four-in-one), a DNL-Fab3, knobs-in-holes common LC, knobs-in-holes assembly, a TandAb, a Triple Body, a miniantibody, a minibody, a TriBi minibody, a scFv-$CH_3$ KIH, a Fab-scFv, a scFv-CH-CL-scFv, a F(ab')2-scFV2, a scFv-KIH, a Fab-scFv-Fc, a tetravalent HCAb, a scDiabody-Fc, a tandem scFv-Fc, an intrabody, a dock and lock bispecific antibody, an ImmTAC, a HSAbody, a tandem scFv, an IgG-IgG, a Cov-X-Body, and a scFv1-PEG-scFv2.

Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); or an antigen-binding fragment of an IgM (e.g., an antigen-binding fragment of a human or humanized IgM).

Non-limiting examples of anti-TNFα agents that are antibodies that specifically bind to TNFα are described in Ben-Horin et al., *Autoimmunity Rev.* 13(1):24-30, 2014; Bongartz et al., *JAMA* 295(19):2275-2285, 2006; Butler et al., *Eur. Cytokine Network* 6(4):225-230, 1994; Cohen et al., *Canadian J Gastroenterol. Hepatol.* 15(6):376-384, 2001; Elliott et al., *Lancet* 1994; 344: 1125-1127, 1994; Feldmann et al., *Ann. Rev. Immunol.* 19(1):163-196, 2001; Rankin et al., *Br. J Rheumatol.* 2:334-342, 1995; Knight et al., *Molecular Immunol.* 30(16):1443-1453, 1993; Lorenz et al., *J. Immunol.* 156(4):1646-1653, 1996; Hinshaw et al., *Circulatory Shock* 30(3):279-292, 1990; Ordas et al., *Clin. Pharmacol. Therapeutics* 91(4):635-646, 2012; Feldman, *Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Wanner et al., *Shock* 11(6):391-395, 1999; and U.S. Pat. Nos. 6,090,382; 6,258,562; and 6,509,015).

In certain embodiments, the anti-TNFα agent can include or is golimumab (Golimumab™), adalimumab (Humira™), infliximab (Remicade™), CDP571, CDP 870, or certolizumab pegol (Cimzia™). In certain embodiments, the anti-TNFα agent can be a TNFα inhibitor biosimilar. Examples of approved and late-phase TNFα inhibitor biosimilars include, but are not limited to, infliximab biosimilars such as Flixabi™ (SB2) from Samsung Bioepis, Inflectra® (CT-P13) from Celltrion/Pfizer, GS071 from Aprogen, Remsima™, PF-06438179 from Pfizer/Sandoz, NI-071 from Nichi-Iko Pharmaceutical Co., and ABP 710 from Amgen; adalimumab biosimilars such as Amgevita® (ABP 501) from Amgen and Exemptia™ from Zydus Cadila, BMO-2 or MYL-1401-A from Biocon/Mylan, CHS-1420 from Coherus, FKB327 from Kyowa Kirin, and BI 695501 from Boehringer Ingelheim; Solymbic®, SB5 from Samsung Bioepis, GP-2017 from Sandoz, ONS-3010 from Oncobiologics, M923 from Momenta, PF-06410293 from Pfizer, and etanercept biosimilars such as Erelzi™ from Sandoz/Novartis, Brenzys™ (SB4) from Samsung Bioepis, GP2015 from Sandoz, TuNEX® from Mycenax, LBEC0101 from LG Life, and CHS-0214 from Coherus.

In some embodiments of any of the methods described herein, the anti-TNFα agent is selected from the group consisting of: adalimumab, certolizumab, etanercept, golimumab, infliximabm, CDP571, and CDP 870.

In some embodiments, any of the antibodies or antigen-binding fragments described herein has a dissociation constant ($K_D$) of less than $1 \times 10^{-5}$M (e.g., less than $0.5 \times 10^{-5}$ M, less than $1 \times 10^{-6}$M, less than $0.5 \times 10^{-6}$M, less than $1 \times 10^{-7}$M, less than $0.5 \times 10^{-7}$M, less than $1 \times 10^{-8}$M, less than $0.5 \times 10^{-8}$M, less than $1 \times 10^{-9}$M, less than $0.5 \times 10^{-9}$M, less than $1 \times 10^{-10}$M, less than $0.5 \times 10^{-10}$ M, less than $1 \times 10^{-11}$M, less than $0.5 \times 10^{-11}$M, or less than $1 \times 10^{-12}$M), e.g., as measured in phosphate buffered saline using surface plasmon resonance (SPR).

In some embodiments, any of the antibodies or antigen-binding fragments described herein has a $K_D$ of about $1 \times 10^{-12}$ M to about $1 \times 10^{-5}$M, about $0.5 \times 10^{-5}$M, about $1 \times 10^{-6}$ M, about $0.5 \times 10^{-6}$M, about $1 \times 10^{-7}$M, about $0.5 \times 10^{-7}$M, about $1 \times 10^{-8}$M, about $0.5 \times 10^{-8}$M, about $1 \times 10^{-9}$M, about $0.5 \times 10^{-9}$M, about $1 \times 10^{-10}$M, about $0.5 \times 10^{-10}$M, about $1 \times 10^{-11}$M, or about $0.5 \times 10^{-11}$M (inclusive); about $0.5 \times 10^{-11}$M to about $1 \times 10^{-5}$M, about $0.5 \times 10^{-5}$M, about $1 \times 10^{-6}$M, about $0.5 \times 10^{-6}$ M, about $1 \times 10^{-7}$M, about $0.5 \times 10^{-7}$M, about $1 \times 10^{-8}$M, about $0.5 \times 10^{-8}$M, about $1 \times 10^{-9}$M, about $0.5 \times 10^{-9}$M, about $1 \times 10^{-10}$ M, about $0.5 \times 10^{-10}$ M, or about $1 \times 10^{-11}$M (inclusive); about $1 \times 10^{-11}$M to about $1 \times 10^{-5}$M, about $0.5 \times 10^{-5}$M, about $1 \times 10^{-6}$M, about $0.5 \times 10^{-6}$M, about $1 \times 10^{-7}$M, about $0.5 \times 10^{-7}$M, about $1 \times 10^{-8}$M, about $0.5 \times 10^{-8}$M, about $1 \times 10^{-9}$M, about $0.5 \times 10^{-9}$M, about $1 \times 10^{-10}$ M, or about $0.5 \times 10^{-10}$ M (inclusive); about $0.5 \times 10^{-10}$ M to about $1 \times 10^{-5}$M, about $0.5 \times 10^{-5}$M, about $1 \times 10^{-6}$ M, about $0.5 \times 10^{-6}$ M, about $1 \times 10^{-7}$M, about $0.5 \times 10^{-7}$M, about $1 \times 10^{-8}$M, about $0.5 \times 10^{-8}$M, about $1 \times 10^{-9}$M, about $0.5 \times 10^{-9}$M, or about $1 \times 10^{-10}$ M (inclusive); about $1 \times 10^{-10}$ M to about $1 \times 10^{-5}$M, about $0.5 \times 10^{-5}$ M, about $1 \times 10^{-6}$M, about $0.5 \times 10^{-6}$M, about $1 \times 10^{-7}$M, about $0.5 \times 10^{-7}$M, about $1 \times 10^{-8}$M, about $0.5 \times 10^{-8}$M, about $1 \times 10^{-9}$M, or about $0.5 \times 10^{-9}$M (inclusive); about $0.5 \times 10^{-9}$M to about $1 \times 10^{-5}$M, about $0.5 \times 10^{-5}$M, about $1 \times 10^{-6}$M, about $0.5 \times 10^{-6}$M, about $1 \times 10^{-7}$M, about $0.5 \times 10^{-7}$M, about $1 \times 10^{-8}$M, about $0.5 \times 10^{-8}$M, or about $1 \times 10^{-9}$M (inclusive); about $1 \times 10^{-9}$M to about $1 \times 10^{-5}$M, about $0.5 \times 10^{-5}$M, about $1 \times 10^{-6}$M, about $0.5 \times 10^{-6}$M, about $1 \times 10^{-7}$M, about $0.5 \times 10^{-7}$M, about $1 \times 10^{-8}$M, or about $0.5 \times 10^{-8}$M (inclusive); about $0.5 \times 10^{-8}$ M to about $1 \times 10^{-5}$M, about $0.5 \times 10^{-5}$M, about $1 \times 10^{-6}$M, about $0.5 \times 10^{-6}$M, about $1 \times 10^{-7}$ M, about $0.5 \times 10^{-7}$M, or about $1 \times 10^{-8}$M (inclusive); about $1 \times 10^{-8}$M to about $1 \times 10^{-5}$M, about $0.5 \times 10^{-5}$M, about $1 \times 10^{-6}$M, about $0.5 \times 10^{-6}$M, about $1 \times 10^{-7}$M, or about $0.5 \times 10^{-7}$M (inclusive); about $0.5 \times 10^{-7}$M to about $1 \times 10^{-5}$M, about $0.5 \times 10^{-5}$M, about $1 \times 10^{-6}$M, about $0.5 \times 10^{-6}$M, or about $1 \times 10^{-7}$M (inclusive); about $1 \times 10^{-7}$M to about $1 \times 10^{-5}$M, about $0.5 \times 10^{-5}$M, about $1 \times 10^{-6}$M, or about $0.5 \times 10^{-6}$M (inclusive); about $0.5 \times 10^{-6}$M to about $1 \times 10^{-5}$ M, about $0.5 \times 10^{-5}$M, or about $1 \times 10^{-6}$M (inclusive); about $1 \times 10^{-6}$M to about $1 \times 10^{-5}$M or about $0.5 \times 10^{-5}$M (inclusive); or about $0.5 \times 10^{-5}$M to about $1 \times 10^{-5}$M (inclusive), e.g., as measured in phosphate buffered saline using surface plasmon resonance (SPR).

In some embodiments, any of the antibodies or antigen-binding fragments described herein has a $K_{off}$ of about $1 \times 10^{-6}$ s$^{-1}$ to about $1 \times 10^{-3}$ s$^{-1}$, about $0.5 \times 10^{-3}$ s$^{-1}$, about $1 \times 10^{-4}$ s$^{-1}$, about $0.5 \times 10^{-4}$ s$^{-1}$, about $1 \times 10^{-5}$ s$^{-1}$, or about $0.5 \times 10^{-5}$ s$^{-1}$ (inclusive); about $0.5 \times 10^{-5}$ s$^{-1}$ to about $1 \times 10^{-3}$ s$^{-1}$, about $0.5 \times 10^{-3}$ s$^{-1}$, about $1 \times 10$ s$^{-1}$, about $0.5 \times 10$ s$^{-1}$, or about $1 \times 10^{-5}$ s$^{-1}$ (inclusive); about $1 \times 10^{-5}$ s$^{-1}$ to about $1 \times 10^{-3}$ s$^{-1}$, about $0.5 \times 10^{-3}$ s$^{-1}$, about $1 \times 10$ s$^{-1}$, or about $0.5 \times 10^{-4}$ s$^{-1}$ (inclusive); about $0.5 \times 10^{-4}$ s$^{-1}$ to about $1 \times 10^{-3}$ s$^{-1}$, about $0.5 \times 10^{-3}$ s$^{-1}$, or about $1 \times 10^{-4}$ s$^{-1}$ (inclusive); about $1 \times 10^{-4}$ s$^{-1}$ to about $1 \times 10^{-3}$ s$^{-1}$, or about $0.5 \times 10^{-3}$ s$^{-1}$ (inclusive); or about $0.5 \times 10^{-5}$ s$^{1}$ to about $1 \times 10^{-3}$ s$^{1}$ (inclusive), e.g., as measured in phosphate buffered saline using surface plasmon resonance (SPR).

In some embodiments, any of the antibodies or antigen-binding fragments described herein has a $K_{on}$ of about $1 \times 10^{2}$M$^{-1}$ s$^{-1}$ to about $1 \times 10^{6}$M$^{-1}$ s$^{-1}$, about $0.5 \times 10^{6}$ M$^{-1}$ s$^{-1}$, about $1 \times 10^{5}$M$^{-1}$ s$^{-1}$, about $0.5 \times 10^{5}$ M$^{-1}$ s$^{-1}$, about $1 \times 10^{4}$M$^{-1}$ s$^{-1}$, about $0.5 \times 10^{4}$ M$^{-1}$ s$^{-1}$, about $1 \times 10^{3}$M$^{-1}$ s$^{-1}$, or about $0.5 \times 10^{3}$ M$^{-1}$ s$^{-1}$ (inclusive); about $0.5 \times 10^{3}$M$^{-1}$ s$^{-1}$ to about $1 \times 10^{6}$M$^{-1}$ s$^{-1}$, about $0.5 \times 10^{6}$ M$^{-1}$ s$^{-1}$, about $1 \times 10^{5}$M$^{-1}$ s$^{-1}$, about $0.5 \times 10^{5}$ M$^{-1}$ s$^{-1}$, about $1 \times 10^{4}$ M$^{-1}$ s$^{-1}$, about $0.5 \times 10^{4}$ M$^{-1}$ s$^{-1}$, or about $1 \times 10^{3}$ M$^{-1}$ s$^{-1}$ (inclusive); about $1 \times 10^{3}$ M$^{-1}$ s$^{-1}$ to about $1 \times 10^{6}$M$^{-1}$ s$^{-1}$, about $0.5 \times 10^{6}$M$^{-1}$ s$^{-1}$, about $1 \times 10^{5}$M$^{-1}$ s$^{-1}$, about $0.5 \times 10^{5}$ M$^{-1}$ s$^{-1}$, about $1 \times 10^{4}$ M$^{-1}$ s$^{-1}$, or about $0.5 \times 10^{4}$ M$^{-1}$ s$^{-1}$ (inclusive); about $0.5 \times 10^{4}$ M$^{-1}$ s$^{-1}$ to about $1 \times 10^{6}$M$^{-1}$ s$^{-1}$, about $0.5 \times 10^{6}$ M$^{-1}$ s$^{-1}$, about $1 \times 10^{5}$M$^{-1}$ s$^{-1}$, about $0.5 \times 10^{5}$ M$^{-1}$ s$^{-1}$, or about $1 \times 10^{4}$ M$^{-1}$ s$^{-1}$ (inclusive); about $1 \times 10^{4}$ M$^{-1}$ s$^{-1}$ to about $1 \times 10^{6}$ M$^{-1}$ s$^{-1}$, about $0.5 \times 10^{6}$ M$^{-1}$ s$^{-1}$, about $1 \times 10^{5}$M$^{-1}$ s$^{-1}$, or about $0.5 \times 10^{5}$M$^{-1}$ s$^{-1}$ (inclusive); about $0.5 \times 10^{5}$M$^{-1}$ s$^{-1}$ to about $1 \times 10^{6}$M$^{-1}$ s$^{-1}$, about $0.5 \times 10^{6}$ M$^{-1}$ $s^{-1}$, or about $1\times10^5$ $M^{-1}$ $s^{-1}$ (inclusive); about $1\times10^5 M^{-1}$ $s^{-1}$ to about $1\times10^6$ $M^{-1}$ $s^{-1}$, or about $0.5\times10^6 M^{-1}$ $s^{-1}$ (inclusive); or about $0.5\times10^6 M^{-1}$ $s^{-1}$ to about $1\times10^6 M^{-1}$ $s^{-1}$ (inclusive), e.g., as measured in phosphate buffered saline using surface plasmon resonance (SPR).

Fusion Proteins

In some embodiments, the anti-TNFα agent is a fusion protein (e.g., an extracellular domain of a TNFR fused to a partner peptide, e.g., an Fc region of an immunoglobulin, e.g., human IgG) (see, e.g., Deeg et al., *Leukemia* 16(2):162, 2002; Peppel et al., *J Exp. Med.* 174(6):1483-1489, 1991) or a soluble TNFR (e.g., TNFR1 or TNFR2) that binds specifically to TNFα. In some embodiments, the anti-TNFα agent includes or is a soluble TNFα receptor (e.g., Bjornberg et al., *Lymphokine Cytokine Res.* 13(3):203-211, 1994; Kozak et al., *Am. J. Physiol. Reg. Integrative Comparative Physiol.* 269(1):R23-R29, 1995; Tsao et al., *Eur Respir J.* 14(3):490-495, 1999; Watt et al., *J Leukoc Biol.* 66(6):1005-1013, 1999; Mohler et al., *J. Immunol.* 151(3):1548-1561, 1993; Nophar et al., *EMBO J.* 9(10):3269, 1990; Piguet et al., *Eur. Respiratory J.* 7(3):515-518, 1994; and Gray et al., *Proc. Natl. Acad. Sci. U.S.A.* 87(19):7380-7384, 1990). In some embodiments, the anti-TNFα agent includes or is etanercept (Enbrel™) (see, e.g., WO 91/03553 and WO 09/406,476, incorporated by reference herein). In some embodiments, the anti-TNFα agent inhibitor includes or is r-TBP-I (e.g., Gradstein et al., *J. Acquir. Immune Defic. Syndr.* 26(2): 111-117, 2001).

Inhibitory Nucleic Acids

Inhibitory nucleic acids that can decrease the expression of AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA expression in a mammalian cell include antisense nucleic acid molecules, i.e., nucleic acid molecules whose nucleotide sequence is complementary to all or part of a AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (e.g., complementary to all or a part of any one of SEQ ID NOs: 1-37).

Human TNFα CDS (SEQ ID NO: 1)
ATGAGCACTGAAAGCATGATCCGGGACGTGGAGCTGGCCGAGGAGGCGC

TCCCCAAGAAGACAGGGGGGCCCCAGGGCTCCAGGCGGTGCTTGTTCCT

CAGCCTCTTCTCCTTCCTGATCGTGGCAGGCGCCACCACGCTCTTCTGC

CTGCTGCACTTTGGAGTGATCGGCCCCAGAGGGAAGAGTTCCCCAGGG

ACCTCTCTCTAATCAGCCCTCTGGCCCAGGCAGTCAGATCATCTTCTCG

AACCCCGAGTGACAAGCCTGTAGCCCATGTTGTAGCAAACCCTCAAGCT

GAGGGGCAGCTCCAGTGGCTGAACCGCCGGGCCAATGCCCTCCTGGCCA

ATGGCGTGGAGCTGAGAGATAACCAGCTGGTGGTGCCATCAGAGGGCCT

GTACCTCATCTACTCCCAGGTCCTCTTCAAGGGCCAAGGCTGCCCCTCC

ACCCATGTGCTCCTCACCCACACCATCAGCCGCATCGCCGTCTCCTACC

AGACCAAGGTCAACCTCCTCTCTGCCATCAAGAGCCCCTGCCAGAGGGA

GACCCCAGAGGGGGCTGAGGCCAAGCCCTGGTATGAGCCCATCTATCTG

GGAGGGGTCTTCCAGCTGGAGAAGGGTGACCGACTCAGCGCTGAGATCA

ATCGGCCCGACTATCTCGACTTTGCCGAGTCTGGGCAGGTCTACTTTGG

GATCATTGCCCTGTGA.

Human TNFR1 CDS (SEQ ID NO: 2)
ATGGGCCTCTCCACCGTGCCTGACCTGCTGCTGCCACTGGTGCTCCTGG

AGCTGTTGGTGGGAATATACCCCTCAGGGGTTATTGGACTGGTCCCTCA

CCTAGGGGACAGGGAGAAGAGAGATAGTGTGTGTCCCCAAGGAAAATAT

ATCCACCCTCAAAATAATTCGATTTGCTGTACCAAGTGCCACAAAGGAA

CCTACTTGTACAATGACTGTCCAGGCCCGGGGCAGGATACGGACTGCAG

GGAGTGTGAGAGCGGCTCCTTCACCGCTTCAGAAAACCACCTCAGACAC

TGCCTCAGCTGCTCCAAATGCCGAAAGGAAATGGGTCAGGTGGAGATCT

CTTCTTGCACAGTGGACCGGGACACCGTGTGTGGCTGCAGGAAGAACCA

GTACCGGCATTATTGGAGTGAAAACCTTTTCCAGTGCTTCAATTGCAGC

CTCTGCCTCAATGGGACCGTGCACCTCTCCTGCCAGGAGAAACAGAACA

CCGTGTGCACCTGCCATGCAGGTTTCTTTCTAAGAGAAAACGAGTGTGT

CTCCTGTAGTAACTGTAAGAAAAGCCTGGAGTGCACGAAGTTGTGCCTA

CCCCAGATTGAGAATGTTAAGGGCACTGAGGACTCAGGCACCACAGTGC

TGTTGCCCCTGGTCATTTTCTTTGGTCTTTGCCTTTTATCCCTCCTCTT

CATTGGTTTAATGTATCGCTACCAACGGTGGAAGTCCAAGCTCTACTCC

ATTGTTTGTGGGAAATCGACACCTGAAAAAGAGGGGGAGCTTGAAGGAA

CTACTACTAAGCCCCTGGCCCCAAACCCAAGCTTCAGTCCCACTCCAGG

CTTCACCCCCACCCTGGGCTTCAGTCCCGTGCCCAGTTCCACCTTCACC

TCCAGCTCCACCTATACCCCCGGTGACTGTCCCAACTTTGCGGCTCCCC

GCAGAGAGGTGGCACCACCCTATCAGGGGCTGACCCCATCCTTGCGAC

AGCCCTCGCCTCCGACCCCATCCCCAACCCCCTTCAGAAGTGGGAGGAC

AGCGCCCACAAGCCACAGAGCCTAGACACTGATGACCCCGCGACGCTGT

ACGCCGTGGTGGAGAACGTGCCCCCGTTGCGCTGGAAGGAATTCGTGCG

GCGCCTAGGGCTGAGCGACCACGAGATCGATCGGCTGGAGCTGCAGAAC

GGGCGCTGCCTGCGCGAGGCGCAATACAGCATGCTGGCGACCTGGAGGC

GGCGCACGCCGCGGCGCGAGGCCACGCTGGAGCTGCTGGGACGCGTGCT

CCGCGACATGGACCTGCTGGGCTGCCTGGAGGACATCGAGGAGGCGCTT

TGCGGCCCCGCCGCCCTCCCGCCCGCGCCCAGTCTTCTCAGATGA.

Human TNFR2 CDS (SEQ ID NO: 3)
ATTCTTCCCCTGGTGGCCATGGGACCCAGGTCAATGTCACCTGCATCGT

GAACGTCTGTAGCAGCTCTGACCACAGCTCACAGTGCTCCTCCCAAGCC

AGCTCCACAATGGGAGACACAGATTCCAGCCCCTCGGAGTCCCCGAAGG

ACGAGCAGGTCCCCTTCTCCAAGGAGGAATGTGCCTTTCGGTCACAGCT

GGAGACGCCAGAGACCTGCTGGGGAGCACCGAAGAGAAGCCCTGCCC

CTTGGAGTGCCTGATGCTGGGATGAAGCCCAGTTAA.

Human TRADD CDS (SEQ ID NO: 4)
ATGGCAGCTGGGCAAAATGGGCACGAAGAGTGGGTGGGCAGCGCATACC

TGTTTGTGGAGTCCTCGCTGGACAAGGTGGTCCTGTCGGATGCCTACGC

GCACCCCCAGCAGAAGGTGGCAGTGTACAGGGCTCTGCAGGCTGCCTTG

GCAGAGAGCGGCGGGAGCCCGGACGTGCTGCAGATGCTGAAGATCCACC

GCAGCGACCCGCAGCTGATCGTGCAGCTGCGATTCTGCGGGCGGCAGCC

CTGTGGCCGCTTCCTCCGCGCCTACCGCGAGGGGGCGCTGCGCGCCGCG

CTGCAGAGGAGCCTGGCGGCCGCGCTCGCCCAGCACTCGGTGCCGCTGC

AACTGGAGCTGCGCGCCGGCGCCGAGCGGCTGGACGCTTTGCTGGCGGA

CGAGGAGCGCTGTTTGAGTTGCATCCTAGCCCAGCAGCCCGACCGGCTC

CGGGATGAAGAACTGGCTGAGCTGGAGGATGCGCTGCGAAATCTGAAGT

GCGGCTCGGGGCCCGGGGTGGCGACGGGGAGGTCGCTTCGGCCCCCTT

GCAGCCCCGGTGCCCTCTCTGTCGGAGGTGAAGCCGCCGCCGCCGCCG

CCACCTGCCCAGACTTTTCTGTTCCAGGGTCAGCCTGTAGTGAATCGGC

CGCTGAGCCTGAAGGACCAACAGACGTTCGCGCGCTCTGTGGGTCTCAA

ATGGCGCAAGGTGGGGCGCTCACTGCAGCGAGGCTGCCGGGCGCTGCGG

GACCCGGCGCTGGACTCGCTGGCCTACGAGTACGAGCGCGAGGGACTGT

ACGAGCAGGCCTTCCAGCTGCTGCGGCGCTTCGTGCAGGCCGAGGGCCG

CCGCGCCACGCTGCAGCGCCTGGTGGAGGCACTCGAGGAGAACGAGCTC

ACCAGCCTGGCAGAGGACTTGCTGGGCCTGACCGATCCCAATGGCGGCC

TGGCCTAG.

Human TRAF2 CDS (SEQ ID NO: 5)
ATGGCTGCAGCTAGCGTGACCCCCCCTGGCTCCCTGGAGTTGCTACAGC

CCGGCTTCTCCAAGACCCTCCTGGGGACCAAGCTGGAAGCCAAGTACCT

GTGCTCCGCCTGCAGAAACGTCCTCCGCAGGCCCTTCCAGGCGCAGTGT

GGCCACCGGTACTGCTCCTTCTGCCTGGCCAGCATCCTCAGCTCTGGGC

CTCAGAACTGTGCTGCCTGTGTTCACGAGGGCATATATGAAGAAGGCAT

TTCTATTTTAGAAAGCAGTTCGGCCTTCCCAGATAATGCTGCCCGCAGG

GAGGTGGAGAGCCTGCCGGCCGTCTGTCCCAGTGATGGATGCACCTGGA

AGGGGACCCTGAAAGAATACGAGAGCTGCCACGAAGGCCGCTGCCCGCT

CATGCTGACCGAATGTCCCGCGTGCAAAGGCCTGGTCCGCCTTGGTGAA

AAGGAGCGCCACCTGGAGCACGAGTGCCCGGAGAGAAGCCTGAGCTGCC

GGCATTGCCGGGCACCCTGCTGCGGAGCAGACGTGAAGGCGCACCACGA

GGTCTGCCCCAAGTTCCCCTTAACTTGTGACGGCTGCGGCAAGAAGAAG

ATCCCCCGGGAGAAGTTTCAGGACCACGTCAAGACTTGTGGCAAGTGTC

GAGTCCCTTGCAGATTCCACGCCATCGGCTGCCTCGAGACGGTAGAGGG

TGAGAAACAGCAGGAGCACGAGGTGCAGTGGCTGCGGGAGCACCTGGCC

ATGCTACTGAGCTCGGTGCTGGAGGCAAAGCCCCTCTTGGGAGACCAGA

GCCACGCGGGGTCAGAGCTCCTGCAGAGGTGCGAGAGCCTGGAGAAGAA

GACGGCCACTTTTGAGAACATTGTCTGCGTCCTGAACCGGGAGGTGGAG

AGGGTGGCCATGACTGCCGAGGCCTGCAGCCGGCAGCACCGGCTGGACC

AAGACAAGATTGAAGCCCTGAGTAGCAAGGTGCAGCAGCTGGAGAGGAG

CATTGGCCTCAAGGACCTGGCTGATGGCTGACTTGGAGCAGAAGGTCTTG

GAGATGGAGGCATCCACCTACGATGGGGTCTTCATCTGGAAGATCTCAG

ACTTCGCCAGGAAGCGCCAGGAAGCTGTGGCTGGCCGCATACCCGCCAT

CTTCTCCCCAGCCTTCTACACCAGCAGGTACGGCTACAAGATGTGTCTG

CGTATCTACCTGAACGGCGACGGCACCGGGCGAGGAACACACCTGTCCC

TCTTCTTTGTGGTGATGAAGGGCCCGAATGACGCCCTGCTGCGGTGGCC

CTTCAACCAGAAGGTGACCTTAATGCTGCTCGACCAGAATAACCGGGAG

CACGTGATTGACGCCTTCAGGCCCGACGTGACTTCATCCTCTTTTCAGA

GGCCAGTCAACGACATGAACATCGCAAGCGGCTGCCCCCTCTTCTGCCC

CGTCTCCAAGATGGAGGCAAAGAATTCCTACGTGCGGGACGATGCCATC

TTCATCAAGGCCATTGTGGACCTGACAGGGCTCTAA.

Human AP-1 CDS (SEQ ID NO: 6)
ATGGAAACACCCTTCTACGGCGATGAGGCGCTGAGCGGCCTGGGCGGCG

GCGCCAGTGGCAGCGGCGGCAGCTTCGCGTCCCCGGGCCGCTTGTTCCC

CGGGGCGCCCCCGACGGCCGCGGCCGGCAGCATGATGAAGAAGGACGCG

CTGACGCTGAGCCTGAGTGAGCAGGTGGCGGCAGCGCTCAAGCCTGCGG

CCGCGCCGCCTCCTACCCCCTGCGCGCCGACGGCGCCCCAGCGCGGC

ACCCCCCGACGGCCTGCTCGCCTCTCCCGACCTGGGGCTGCTGAAGCTG

GCCTCCCCCGAGCTCGAGCGCCTCATCATCCAGTCCAACGGGCTGGTCA

CCACCACGCCGACGAGCTCACAGTTCCTCTACCCCAAGGTGGCGGCCAG

CGAGGAGCAGGAGTTCGCCGAGGGCTTCGTCAAGGCCCTGGAGGATTTA

CACAAGCAGAACCAGCTCGGCGCGGGCGCGGCCGCTGCCGCCGCCGCCG

CCGCCGCCGGGGGCCCTCGGGCACGGCCACGGGCTCCGCGCCCCCGG

CGAGCTGGCCCCGGCGGCGGCCGCGCCCAAGCGCCTGTCTACGCGAAC

CTGAGCAGCTACGCGGGCGGCGCCGGGGCGCGGGGGGCGCCGCGACGG

TCGCCTTCGCTGCCGAACCTGTGCCCTTCCCGCCGCCGCCACCCCCAGG

CGCGTTGGGCCGCCGCGCCTGGCTGCGCTCAAGGACGAGCCACAGACG

GTGCCCGACGTGCCGAGCTTCGGCGAGAGCCCGCCGTTGTCGCCCATCG

ACATGGACACGCAGGAGCGCATCAAGGCGGAGCGCAAGCGGCTGCGCAA

CCGCATCGCCGCCTCCAAGTGCCGCAAGCGCAAGCTGGAGCGCATCTCG

CGCCTGGAAGAGAAAGTGAAGACCCTCAAGAGTCAGAACACGGAGCTGG

CGTCCACGGCGAGCCTGCTGCGCGAGCAGGTGGCGCAGCTCAAGCAGAA

AGTCCTCAGCCACGTCAACAGCGGCTGCCAGCTGCTGCCCCAGCACCAG

GTGCCCGCGTACTGA.

Human ASK1 CDS (SEQ ID NO: 7)
ATGAGCACGGAGGCGGACGAGGGCATCACTTTCTCTGTGCCACCCTTCG

CCCCCTCGGGCTTCTGCACCATCCCCGAGGGCGGCATCTGCAGGAGGGG

AGGAGCGGCGGCGGTGGGCGAGGGCGAGGAGCACCAGCTGCCACCGCCG

CCGCCGGGCAGTTTCTGGAACGTGGAGAGCGCCGCTGCCCCTGGCATCG

GTTGTCCGGCGCCACCTCCTCGAGCAGTGCCACCCGAGGCCGGGGCAG

CTCTGTTGGCGGGGCAGCCGACGGACCACGGTGGCATATGTGATCAAC

GAAGCGAGCCAAGGGCAACTGGTGGTGGCCGAGAGCGAGGCCCTGCAGA

GCTTGCGGGAGGCGTGCGAGACAGTGGGCGCCACCCTGGAACCCTGCAT

TTTGGGAAACTCGACTTTGGAGAAACCACCGTGCTGGACCGCTTTTACA

ATGCAGATATTGCGGTGGTGGAGATGAGCGATGCCTTCCGGCAGCCGTC
CTTGTTTTACCACCTTGGGGTGAGAGAAAGTTTCAGCATGGCCAACAAC
ATCATCCTCTACTGCGATACTAACTCGGACTCTCTGCAGTCACTGAAGG
AAATCATTTGCCAGAAGAATACTATGTGCACTGGGAACTACACCTTTGT
TCCTTACATGATAACTCCACATAACAAAGTCTACTGCTGTGACAGCAGC
TTCATGAAGGGGTTGACAGAGCTCATGCAACCGAACTTCGAGCTGCTTC
TTGGACCCATCTGCTTACCTCTTGTGGATCGTTTTATTCAACTTTTGAA
GGTGGCACAAGCAAGTTCTAGCCAGTACTTCCGGGAATCTATACTCAAT
GACATCAGGAAAGCTCGTAATTTATACACTGGTAAAGAATTGGCAGCTG
AGTTGGCAAGAATTCGGCAGCGAGTAGATAATATCGAAGTCTTGACAGC
AGATATTGTCATAAATCTGTTACTTTCCTACAGAGATATCCAGGACTAT
GATTCTATTGTGAAGCTGGTAGAGACTTTAGAAAAACTGCCAACCTTTG
ATTTGGCCTCCCATCACCATGTGAAGTTTCATTATGCATTTGCACTGAA
TAGGAGAAATCTCCCTGGTGACAGAGCAAAAGCTCTTGATATTATGATT
CCCATGGTGCAAAGCGAAGGACAAGTTGCTTCAGATATGTATTGCCTAG
TTGGTCGAATCTACAAAGATATGTTTTTGGACTCTAATTTCACGGACAC
TGAAAGCAGAGACCATGGAGCTTCTTGGTCAAAAAGGCATTTGAATCT
GAGCCAACACTACAGTCAGGAATTAATTATGCGGTCCTCCTCCTGGCAG
CTGGACACCAGTTTGAATCTTCCTTTGAGCTCCGGAAAGTTGGGGTGAA
GCTAAGTAGTCTTCTTGGTAAAAAGGGAAACTTGGAAAAACTCCAGAGC
TACTGGGAAGTTGGATTTTTTCTGGGGGCCAGCGTCCTAGCCAATGACC
ACATGAGAGTCATTCAAGCATCTGAAAAGCTTTTTAAACTGAAGACACC
AGCATGGTACCTCAAGTCTATTGTAGAGACAATTTTGATATATAAGCAT
TTTGTGAAACTGACCACAGAACAGCCTGTGGCCAAGCAAGAACTTGTGG
ACTTTTGGATGGATTTCCTGGTCGAGGCCACAAAGACAGATGTTACTGT
GGTTAGGTTTCCAGTATTAATATTAGAACCAACCAAAATCTATCAACCT
TCTTATTTGTCTATCAACAATGAAGTTGAGGAAAAGACAATCTCTATTT
GGCACGTGCTTCCTGATGACAAGAAAGGTATACATGAGTGGAATTTTAG
TGCCTCTTCTGTCAGGGGAGTGAGTATTTCTAAATTTGAAGAAAGATGC
TGCTTTCTTTATGTGCTTCACAATTCTGATGATTTCCAAATCTATTTCT
GTACAGAACTTCATTGTAAAAAGTTTTTTGAGATGGTGAACACCATTAC
CGAAGAGAAGGGGAGAAGCACAGAGGAAGGAGACTGTGAAAGTGACTTG
CTGGAGTATGACTATGAATATGATGAAAATGGTGACAGAGTCGTTTTAG
GAAAAGGCACTTATGGGATAGTCTACGCAGGTCGGGACTTGAGCAACCA
AGTCAGAATTGCTATTAAGGAAATCCCAGAGAGAGACAGCAGATACTCT
CAGCCCCTGCATGAAGAAATAGCATTGCATAAACACCTGAAGCACAAAA
ATATTGTCCAGTATCTGGGCTCTTTCAGTGAGAATGGTTTCATTAAAAT
CTTCATGGAGCAGGTCCCTGGAGGAAGTCTTTCTGCTCTCCTTCGTTCC
AAATGGGGTCCATTAAAAGACAATGAGCAAACAATTGGCTTTTATACAA
AGCAAATACTGGAAGGATTAAAAATATCTCCATGACAATCAGATAGTTCA
CCGGGACATAAAGGGTGACAATGTGTTGATTAATACCTACAGTGGTGTT

CTCAAGATCTCTGACTTCGGAACATCAAAGAGGCTTGCTGGCATAAACC
CCTGTACTGAAACTTTTACTGGTACCCTCCAGTATATGGCACCAGAAAT
AATAGATAAAGGACCAAGAGGCTACGGAAAAGCAGCAGACATCTGGTCT
CTGGGCTGTACAATCATTGAAATGGCCACAGGGAAAACCCCCATTTTATG
AACTGGGAGAACCACAAGCAGCTATGTTCAAGGTGGGAATGTTTAAAGT
CCACCCTGAGATCCCAGAGTCCATGTCTGCAGAGGCCAAGGCATTCATA
CTGAAATGTTTTGAACCAGATCCTGACAAGAGAGCCTGTGCTAACGACT
TGCTTGTTGATGAGTTTTTAAAAGTTTCAAGCAAAAAGAAAAAGACACA
ACCTAAGCTTTCAGCTCTTTCAGCTGGATCAAATGAATATCTCAGGAGT
ATATCCTTGCCGGTACCTGTGCTGGTGGAGGACACCAGCAGCAGCAGTG
AGTACGGCTCAGTTTCACCCGACACGGAGTTGAAAGTGGACCCCTTCTC
TTTCAAACAAGAGCCAAGTCCTGCGGAGAAAGAGATGTCAAGGGAATT
CGGACACTCTTTTTGGGCATTCCAGATGAGAATTTTGAAGATCACAGTG
CTCCTCCTTCCCCTGAAGAAAAGATTCTGGATTCTTCATGCTGAGGAA
GGACAGTGAGAGGCGAGCTACCCTTCACAGGATCCTGACGGAAGACCAA
GACAAAATTGTGAGAAACCTAATGGAATCTTTAGCTCAGGGGGCTGAAG
AACCGAAACTAAATGGGAACACATCACAACCCTCATTGCAAGCCTCAG
AGAATTTGTGAGATCCACTGACCGAAAAATCATAGCCACCACACTGTCA
AAGCTGAAACTGGAGCTGGACTTCGACAGCCATGGCATTAGCCAAGTCC
AGGTGGTACTCTTTGGTTTTCAAGATGCTGTCAATAAAGTTCTTCGGAA
TCATAACATCAAGCCGCACTGGATGTTTGCCTTAGACAGTATCATTCGG
AAGGCGGTACAGACAGCCATTACCATCCTGGTTCCAGAACTAAGGCCAC
ATTTCAGCCTTGCATCTGAGAGTGATACTGCTGATCAAGAAGACTTGGA
TGTAGAAGATGACCATGAGGAACAGCCTTCAAATCAAACTGTCCGAAGA
CCTCAGGCTGTCATTGAAGATGCTGTGGCTACCTCAGGCGTGAGCACGC
TCAGTTCTACTGTGTCTCATGATTCCCAGAGTGCTCACCGGTCACTGAA
TGTACAGCTTGGAAGGATGAAAATAGAAACCAATAGATTACTGGAAGAA
TTGGTTCGGAAAGAGAAAGAATTACAAGCACTCCTTCATCGAGCTATTG
AAGAAAAAGACCAAGAAATTAAACACCTGAAGCTTAAGTCCCAACCCAT
AGAAATTCCTGAATTGCCTGTATTTCATCTAAATTCTTCTGGCACAAAT
ACTGAAGATTCTGAACTTACCGACTGGCTGAGAGTGAATGGAGCTGATG
AAGACACTATAAGCCGGTTTTTGGCTGAAGATTATACACTATTGGATGT
TCTCTACTATGTTACACGTGATGACTTAAAATGCTTGAGACTAAGGGGA
GGGATGCTGTGCACACTGTGGAAGGCTATCATTGACTTTCGAAACAAAC
AGACTTGA.
Human CD14 CDS (SEQ ID NO: 8)
ATGGAGCGCGCGTCCTGCTTGTTGCTGCTGCTGCTGCCGCTGGTGCACG
TCTCTGCGACCACGCCAGAACCTTGTGAGCTGGACGATGAAGATTTCCG
CTGCGTCTGCAACTTCTCCGAACCTCAGCCCGACTGGTCCGAAGCCTTC
CAGTGTGTGTCTGCAGTAGAGGTGGAGATCCATGCCGGCGGTCTCAACC
TAGAGCCGTTTCTAAAGCGCGTCGATGCGGACGCCGACCCGCGGCAGTA TGCTGACACGGTCAAGGCTCTCCGCGTGCGGCGGCTCACAGTGGGAGCC
GCACAGGTTCCTGCTCAGCTACTGGTAGGCGCCCTGCGTGTGCTAGCGT
ACTCCCGCCTCAAGGAACTGACGCTCGAGGACCTAAAGATAACCGGCAC
CATGCCTCCGCTGCCTCTGGAAGCACAGGACTTGCACTTTCCAGCTTG
CGCCTACGCAACGTGTCGTGGGCGACAGGGCGTTCTTGGCTCGCCGAGC
TGCAGCAGTGGCTCAAGCCAGGCCTCAAGGTACTGAGCATTGCCCAAGC
ACACTCGCCTGCCTTTTCCTGCGAACAGGTTCGCGCCTTCCCGGCCCTT
ACCAGCCTAGACCTGTCTGACAATCCTGGACTGGGCGAACGCGGACTGA
TGGCGGCTCTCTGTCCCCACAAGTTCCCGGCCATCCAGAATCTAGCGCT
GCGCAACACAGGAATGGAGACGCCCACAGGCGTGTGCGCCGCACTGGCG
GCGGCAGGTGTGCAGCCCCACAGCCTAGACCTCAGCCACAACTCGCTGC
GCGCCACCGTAAACCCTAGCGCTCCGAGATGCATGTGGTCCAGCGCCCT
GAACTCCCTCAATCTGTCGTTCGCTGGGCTGGAACAGGTGCCTAAAGGA
CTGCCAGCCAAGCTCAGAGTGCTCGATCTCAGCTGCAACAGACTGAACA
GGGCGCCGCAGCCTGACGAGCTGCCCGAGGTGGATAACCTGACACTGGA
CGGGAATCCCTTCCTGGTCCCTGGAACTGCCCTCCCCCACGAGGGCTCA
ATGAACTCCGGCGTGGTCCCAGCCTGTGCACGTTCGACCCTGTCGGTGG
GGGTGTCGGGAACCCTGGTGCTGCTCCAAGGGGCCCGGGGCTTTGCCTA
A.

Human ERK1 CDS (SEQ ID NO: 9)
ATGGCGGCGGCGGCGGCTCAGGGGGGCGGGGGCGGGGAGCCCCGTAGAA
CCGAGGGGGTCGGCCCGGGGGTCCCGGGGGAGGTGGAGATGGTGAAGGG
GCAGCCGTTCGACGTGGGCCCGCGCTACACGCAGTTGCAGTACATCGGC
GAGGGCGCGTACGGCATGGTCAGCTCGGCCTATGACCACGTGCGCAAGA
CTCGCGTGGCCATCAAGAAGATCAGCCCCTTCGAACATCAGACCTACTG
CCAGCGCACGCTCCGGGAGATCCAGATCCTGCTGCGCTTCCGCCATGAG
AATGTCATCGGCATCCGAGACATTCTGCGGGCGTCCACCCTGGAAGCCA
TGAGAGATGTCTACATTGTGCAGGACCTGATGGAGACTGACCTGTACAA
GTTGCTGAAAAGCCAGCAGCTGAGCAATGACCATATCTGCTACTTCCTC
TACCAGATCCTGCGGGGCCTCAAGTACATCCACTCCGCCAACGTGCTCC
ACCGAGATCTAAAGCCCTCCAACCTGCTCATCAACACCACCTGCGACCT
TAAGATTTGTGATTTCGGCCTGGCCCGGATTGCCGATCCTGAGCATGAC
CACACCGGCTTCCTGACGGAGTATGTGGCTACGCGCTGGTACCGGGCCC
CAGAGATCATGCTGAACTCCAAGGGCTATACCAAGTCCATCGACATCTG
GTCTGTGGGCTGCATTCTGGCTGAGATGCTCTCTAACCGGCCCATCTTC
CCTGGCAAGCACTACCTGGATCAGCTCAACCACATTCTGGGCATCCTGG
GCTCCCCATCCCAGGAGGACCTGAATTGTATCATCAACATGAAGGCCCG
AAACTACCTACAGTCTCTGCCCTCCAAGACCAAGGTGGCTTGGGCCAAG
CTTTTCCCCAAGTCAGACTCCAAAGCCCTTGACCTGCTGGACCGGATGT
TAACCTTTAACCCCAATAAACGGATCACAGTGGAGGAAGCGCTGGCTCA
CCCCTACCTGGAGCAGTACTATGACCCGACGGATGAGCCAGTGGCCGAG GAGCCCTTCACCTTCGCCATGGAGCTGGATGACCTACCTAAGGAGCGGC
TGAAGGAGCTCATCTTCCAGGAGACAGCACGCTTCCAGCCCGGAGTGCT
GGAGGCCCCCTAG.

Human ERK2 CDS (SEQ ID NO: 10)
ATGGCGGCGGCGGCGGCGGGGGCGGGGCCCGAGATGGTCCGCGGGC
AGGTGTTCGACGTGGGGCCGCGCTACACCAACCTCTCGTACATCGGCGA
GGGCGCCTACGGCATGGTGTGCTCTGCTTATGATAATGTCAACAAAGTT
CGAGTAGCTATCAAGAAAATCAGCCCCTTTGAGCACCAGACCTACTGCC
AGAGAACCCTGAGGGAGATAAAAATCTTACTGCGCTTCAGACATGAGAA
CATCATTGGAATCAATGACATTATTCGAGCACCAACCATCGAGCAAATG
AAAGATGTATATATAGTACAGGACCTCATGGAAACAGATCTTTACAAGC
TCTTGAAGACACAACACCTCAGCAATGACCATATCTGCTATTTTCTCTA
CCAGATCCTCAGAGGGTTAAAATATATCCATTCAGCTAACGTTCTGCAC
CGTGACCTCAAGCCTTCCAACCTGCTGCTCAACACCACCTGTGATCTCA
AGATCTGTGACTTTGGCCTGGCCCGTGTTGCAGATCCAGACCATGATCA
CACAGGGTTCCTGACAGAATATGTGGCCACACGTTGGTACAGGGCTCCA
GAAATTATGTTGAATTCCAAGGGCTACACCAAGTCCATTGATATTTGGT
CTGTAGGCTGCATTCTGGCAGAAATGCTTTCTAACAGGCCCATCTTTCC
AGGGAAGCATTATCTTGACCAGCTGAACCACATTTTGGGTATTCTTGGA
TCCCCATCACAAGAAGACCTGAATTGTATAATAAATTTAAAAGCTAGGA
ACTATTTGCTTTCTCTTCCACACAAAAATAAGGTGCCATGGAACAGGCT
GTTCCCAAATGCTGACTCCAAAGCTCTGGACTTATTGGACAAAATGTTG
ACATTCAACCCACACAAGAGGATTGAAGTAGAACAGGCTCTGGCCCACC
CATATCTGGAGCAGTATTACGACCCGAGTGACGAGCCCATCGCCGAAGC
ACCATTCAAGTTCGACATGGAATTGGATGACTTGCCTAAGGAAAAGCTC
AAAGAACTAATTTTTGAAGAGACTGCTAGATTCCAGCCAGGATACAGAT
CTTAA.

Human IKK CDS (SEQ ID NO: 11)
ATGTTTTCAGGGGGGTGTCATAGCCCCGGGTTTGGCCGCCCCAGCCCCG
CCTTCCCCGCCCCGGGGAGCCCGCCCCCTGCCCCGCGTCCCTGCCGACA
GGAAACAGGTGAGCAGATTGCCATCAAGCAGTGCCGGCAGGAGCTCAGC
CCCCGGAACCGAGAGCGGTGGTGCCTGGAGATCCAGATCATGAGAAGGC
TGACCCACCCCAATGTGGTGGCTGCCCGAGATGTCCCTGAGGGGATGCA
GAACTTGGCGCCCAATGACCTGCCCCTGCTGGCCATGGAGTACTGCCAA
GGAGGAGATCTCCGGAAGTACCTGAACCAGTTTGAGAACTGCTGTGGTC
TGCGGGAAGGTGCCATCCTCACCTTGCTGAGTGACATTGCCTCTGCGCT
TAGATACCTTCATGAAAACAGAATCATCCATCGGGATCTAAAGCCAGAA
AACATCGTCCTGCAGCAAGGAGAACAGAGGTTAATACACAAATTATTG
ACCTAGGATATGCCAAGGAGCTGGATCAGGGCAGTCTTTGCACATCATT
CGTGGGACCCTGCAGTACCTGGCCCAGAGCTACTGGAGCAGCAGAAG
TACACAGTGACCGTCGACTACTGGAGCTTCGGCACCCTGGCCTTTGAGT

```
GCATCACGGGCTTCCGGCCCTTCCTCCCCAACTGGCAGCCCGTGCAGTG

GCATTCAAAAGTGCGGCAGAAGAGTGAGGTGGACATTGTTGTTAGCAA

GACTTGAATGGAACGGTGAAGTTTTCAAGCTCTTTACCCTACCCCAATA

ATCTTAACAGTGTCCTGGCTGAGCGACTGGAGAAGTGGCTGCAACTGAT

GCTGATGTGGCACCCCCGACAGAGGGGCACGGATCCCACGTATGGGCCC

AATGGCTGCTTCAAGGCCCTGGATGACATCTTAAACTTAAAGCTGGTTC

ATATCTTGAACATGGTCACGGGCACCATCCACACCTACCCTGTGACAGA

GGATGAGAGTCTGCAGAGCTTGAAGGCCAGAATCCAACAGGACACGGGC

ATCCCAGAGGAGGACCAGGAGCTGCTGCAGGAAGCGGGCCTGGCGTTGA

TCCCCGATAAGCCTGCCACTCAGTGTATTTCAGACGGCAAGTTAAATGA

GGGCCACACATTGGACATGGATCTTGTTTTTCTCTTTGACAACAGTAAA

ATCACCTATGAGACTCAGATCTCCCCACGGCCCCAACCTGAAAGTGTCA

GCTGTATCCTTCAAGAGCCCAAGAGGAATCTCGCCTTCTTCCAGCTGAG

GAAGGTGTGGGGCCAGGTCTGGCACAGCATCCAGACCCTGAAGGAAGAT

TGCAACCGGCTGCAGCAGGGACAGCGAGCCGCCATGATGAATCTCCTCC

GAAACAACAGCTGCCTCTCCAAAATGAAGAATTCCATGGCTTCCATGTC

TCAGCAGCTCAAGGCCAAGTTGGATTTCTTCAAAACCAGCATCCAGATT

GACCTGGAGAAGTACAGCGAGCAAACCGAGTTTGGGATCACATCAGATA

AACTGCTGCTGGCCTGGAGGGAAATGGAGCAGGCTGTGGAGCTCTGTGG

GCGGGAGAACGAAGTGAAACTCCTGGTAGAACGGATGATGGCTCTGCAG

ACCGACATTGTGGACTTACAGAGGAGCCCCATGGGCCGGAAGCAGGGG

GAACGCTGGACGACCTAGAGGAGCAAGCAAGGGAGCTGTACAGGAGACT

AAGGGAAAAACCTCGAGACCAGCGAACTGAGGGTGACAGTCAGGAAATG

GTACGGCTGCTGCTTCAGGCAATTCAGAGCTTCGAGAAGAAAGTGCGAG

TGATCTATACGCAGCTCAGTAAAACTGTGGTTTGCAAGCAGAAGGCGCT

GGAACTGTTGCCCAAGGTGGAAGAGGTGGTGAGCTTAATGAATGAGGAT

GAGAAGACTGTTGTCCGGCTGCAGGAGAAGCGGCAGAAGGAGCTCTGGA

ATCTCCTGAAGATTGCTTGTAGCAAGGTCCGTGGTCCTGTCAGTGGAAG

CCCCGGATAGCATGAATGCCTCTCGACTTAGCCAGCCTGGGCAGCTGATG

TCTCAGCCCTCCACGGCCTCCAACAGCTTACCTGAGCCAGCCAAGAAGA

GTGAAGAACTGGTGGCTGAAGCACATAACCTCTGCACCCTGCTAGAAAA

TGCCATACAGGACACTGTGAGGGAACAAGACCAGAGTTTCACGGCCCTA

GACTGGAGCTGGTTACAGACGGAAGAAGAAGAGCACAGCTGCCTGGAGC

AGGCCTCATGA.

Human IκB CDS (SEQ ID NO: 12)
ATGTTCCAGGCGGCCGAGCGCCCCCAGGAGTGGGCCATGGAGGGCCCCC

GCGACGGGCTGAAGAAGGAGCGGCTACTGGACGACCGCCACGACAGCGG

CCTGGACTCCATGAAAGACGAGGAGTACGAGCAGATGGTCAAGGAGCTG

CAGGAGATCCGCCTCGAGCCGCAGGAGGTGCCGCGCGGCTCGGAGCCCT

GGAAGCAGCAGCTCACCGAGGACGGGACTCGTTCCTGCACTTGGCCAT

CATCCATGAAGAAAAGGCACTGACCATGGAAGTGATCCGCCAGGTGAAG
```

```
GGAGACCTGGCCTTCCTCAACTTCCAGAACAACCTGCAGCAGACTCCAC

TCCACTTGGCTGTGATCACCAACCAGCCAGAAATTGCTGAGGCACTTCT

GGGAGCTGGCTGTGATCCTGAGCTCCGAGACTTTCGAGGAAATACCCCC

CTACACCTTGCCTGTGAGCAGGGCTGCCTGGCCAGCGTGGGAGTCCTGA

CTCAGTCCTGCACCACCCCGCACCTCCACTCCATCCTGAAGGCTACCAA

CTACAATGGCCACACGTGTCTACACTTAGCCTCTATCCATGGCTACCTG

GGCATCGTGGAGCTTTTGGTGTCCTTGGGTGCTGATGTCAATGCTCAGG

AGCCCTGTAATGGCCGACTGCCCTTCACCTCGCAGTGGACCTGCAAAA

TCCTGACCTGGTGTCACTCCTGTTGAAGTGTGGGGCTGATGTCAACAGA

GTTACCTACCAGGGCTATTCTCCCTACCAGCTCACCTGGGGCCGCCCAA

GCACCCGGATACAGCAGCAGCTGGGCAGCTGACACTAGAAAACCTTCA

GATGCTGCCAGAGAGTGAGGATGAGGAGAGCTATGACACAGAGTCAGAG

TTCACGGAGTTCACAGAGGACGAGCTGCCCTATGATGACTGTGTGTTTG

GAGGCCAGCGTCTGACGTTATGA

Human IRAK CDS (SEQ ID NO: 13)
ATGGCCGGGGGCCGGGCCCGGGGGAGCCCGCAGCCCCCGGCGCCCAGC

ACTTCTTGTACGAGGTGCCGCCCTGGGTCATGTGCCGCTTCTACAAAGT

GATGGACGCCCTGGAGCCCGCCGACTGGTGCCAGTTCGCCGCCCTGATC

GTGCGCGACCAGACCGAGCTGCGGCTGTGCGAGCGCTCCGGGCAGCGCA

CGGCCAGCGTCCTGTGGCCCTGGATCAACCGCAACGCCCGTGTGGCCGA

CCTCGTGCACATCCTCACGCACCTGCAGCTGCTCCGTGCGCGGGACATC

ATCACAGCCTGGCACCCTCCCGCCCCGCTTCCGTCCCCAGGCACCACTG

CCCCGAGGCCCAGCAGCATCCCTGCACCCGCCGAGGCCGAGGCCTGGAG

CCCCCGGAAGTTGCCATCCTCAGCCTCCACCTTCCTCTCCCCAGCTTTT

CCAGGCTCCCAGACCCATTCAGGGCCTGAGCTCGGCCTGGTCCCAAGCC

CTGCTTCCCTGTGGCCTCCACCGCCATCTCCAGCCCCTTCTTCTACCAA

GCCAGGCCCAGAGAGCTCAGTGTCCCTCCTGCAGGGAGCCCGCCCCTTT

CCGTTTTGCTGGCCCCTCTGTGAGATTTCCCGGGGCACCCACAACTTCT

CGGAGGAGCTCAAGATCGGGGAGGGTGGCTTTGGGTGCGTGTACCGGGC

GGTGATGAGGAACACGGTGTATGCTGTGAAGAGGCTGAAGGAGAACGCT

GACCTGGAGTGGACTGCAGTGAAGCAGAGCTTCCTGACCGAGGTGGAGC

AGCTGTCCAGGTTTCGTCACCCAAACATTGTGGACTTTGCTGGCTACTG

TGCTCAGAACGGCTTCTACTGCCTGGTGTACGGCTTCCTGCCCAACGGC

TCCCTGGAGGACCGTCTCCACTGCCAGACCCAGGCCTGCCCACCTCTCT

CCTGGCCTCAGCGACTGGACATCCTTCTGGGTACAGCCCGGGCAATTCA

GTTTCTACATCAGGACAGCCCCAGCCTCATCCATGGAGACATCAAGAGT

TCCAACGTCCTTCTGGATGAGAGGCTGACACCCAAGCTGGGAGACTTTG

GCCTGGCCCGGTTCAGCCGCTTTGCCGGGTCCAGCCCCAGCCAGAGCAG

CATGGTGGCCCGGACACAGACAGTGCGGGGCACCCTGGCCTACCTGCCC

GAGGAGTACATCAAGACGGGAAGGCTGGCTGTGACACGGACACCTTCA

GCTTTGGGGTGGTAGTGCTAGAGACCTTGGCTGGTCAGAGGGCTGTGAA
```

```
GACGCACGGTGCCAGGACCAAGTATCTGAAAGACCTGGTGGAAGAGGAG
GCTGAGGAGGCTGGAGTGGCTTTGAGAAGCACCCAGAGCACACTGCAAG
CAGGTCTGGCTGCAGATGCCTGGGCTGCTCCCATCGCCATGCAGATCTA
CAAGAAGCACCTGGACCCCAGGCCCGGGCCCTGCCCACCTGAGCTGGGC
CTGGGCCTGGGCCAGCTGGCCTGCTGCTGCCTGCACCGCCGGGCCAAAA
GGAGGCCTCCTATGACCCAGGTGTACGAGAGGCTAGAGAAGCTGCAGGC
AGTGGTGGCGGGGGTGCCCGGGCATTCGGAGGCCGCCAGCTGCATCCCC
CCTTCCCCGCAGGAGAACTCCTACGTGTCCAGCACTGGCAGAGCCCACA
GTGGGGCTGCTCCATGGCAGCCCCTGGCAGCGCCATCAGGAGCCAGTGC
CCAGGCAGCAGAGCAGCTGCAGAGAGGCCCCAACCAGCCCGTGGAGAGT
GACGAGAGCCTAGGCGGCCTCTCTGCTGCCCTGCGCTCCTGGCACTTGA
CTCCAAGCTGCCCTCTGGACCCAGCACCCCTCAGGGAGGCCGGCTGTCC
TCAGGGGACACGGCAGGAGAATCGAGCTGGGGGAGTGGCCCAGGATCC
CGGCCCACAGCCGTGGAAGGACTGGCCCTTGGCAGCTCTGCATCATCGT
CGTCAGAGCCACCGCAGATTATCATCAACCCTGCCCGACAGAAGATGGT
CCAGAAGCTGGCCCTGTACGAGGATGGGGCCCTGGACAGCCTGCAGCTG
CTGTCGTCCAGCTCCCTCCCAGGCTTGGGCCTGGAACAGGACAGGCAGG
GGCCCGAAGAAAGTGATGAATTTCAGAGCTGA.
Human JNK CDS (SEQ ID NO: 14)
ATGAGCAGAAGCAAGCGTGACAACAATTTTTATAGTGTAGAGATTGGAG
ATTCTACATTCACAGTCCTGAAACGATATCAGAATTTAAAACCTATAGG
CTCAGGAGCTCAAGGAATAGTATGCGCAGCTTATGATGCCATTCTTGAA
AGAAATGTTGCAATCAAGAAGCTAAGCCGACCATTTCAGAATCAGACTC
ATGCCAAGCGGGCCTACAGAGAGCTAGTTCTTATGAAATGTGTTAATCA
CAAAAATATAATTGGCCTTTTGAATGTTTTCACACCACAGAAATCCCTA
GAAGAATTTCAAGATGTTTACATAGTCATGGAGCTCATGGATGCAAATC
TTTGCCAAGTGATTCAGATGGAGCTAGATCATGAAAGAATGTCCTACCT
TCTCTATCAGATGCTGTGTGGAATCAAGCACCTTCATTCTGCTGGAATT
ATTCATCGGGACTTAAAGCCCAGTAATATAGTAGTAAAATCTGATTGCA
CTTTGAAGATTCTTGACTTCGGTCTGGCCAGGACTGCAGGAACGAGTTT
TATGATGACGCCTTATGTAGTGACTCGCTACTACAGAGCACCCGAGGTC
ATCCTTGGCATGGGCTACAAGGAAAACGTTGACATTTGGTCAGTTGGGT
GCATCATGGGAGAAATGATCAAAGGTGGTGTTTTGTTCCCAGGTACAGA
TCATATTGATCAGTGGAATAAAGTTATTGAACAGCTTGGAACACCATGT
CCTGAATTCATGAAGAAACTGCAACCAACAGTAAGGACTTACGTTGAAA
ACAGACCTAAATATGCTGGATATAGCTTTGAGAAACTCTTCCCTGATGT
CCTTTTCCCAGCTGACTCAGAACACAACAAACTTAAAGCCAGTCAGGCA
AGGGATTTGTTATCCAAATGCTGGTAATAGATGCATCTAAAAGGATCT
CTGTAGATGAAGCTCTCCAACACCCGTACATCAATGTCTGGTATGATCC
TTCTGAAGCAGAAGCTCCACCACCAAAGATCCCTGACAAGCAGTTAGAT
GAAAGGGAACACACAATAGAAGAGTGGAAAGAATTGATATATAAGGAAG
```

```
TTATGGACTTGGAGGAGAGAACCAAGAATGGAGTTATACGGGGCAGCC
CTCTCCTTTAGGTGCAGCAGTGATCAATGGCTCTCAGCATCCATCATCA
TCGTCGTCTGTCAATGATGTGTCTTCAATGTCAACAGATCCGACTTTGG
CCTCTGATACAGACAGCAGTCTAGAAGCAGCAGCTGGGCCTCTGGGCTG
CTGTAGATGA.
Human LBP CDS (SEQ ID NO: 15)
ATGGGGGCCTTGGCCAGAGCCCTGCCGTCCATACTGCTGGCATTGCTGC
TTACGTCCACCCCAGAGGCTCTGGGTGCCAACCCCGGCTTGGTCGCCAG
GATCACCGACAAGGGACTGCAGTATGCGGCCCAGGAGGGGCTATTAGCT
CTGCAGAGTGAGCTGCTCAGGATCACGCTGCCTGACTTCACCGGGGACT
TGAGGATCCCCCACGTCGGCCGTGGGCGCTATGAGTTCCACAGCCTGAA
CATCCACAGCTGTGAGCTGCTTCACTCTGCGCTGAGGCCTGTCCCTGGC
CAGGGCCTGAGTCTCAGCATCTCCGACTCCTCCATCCGGGTCCAGGGCA
GGTGGAAGGTGCGCAAGTCATTCTTCAAACTACAGGGCTCCTTTGATGT
CAGTGTCAAGGGCATCAGCATTTCGGTCAACCTCCTGTTGGGCAGCGAG
TCCTCCGGGAGGCCCACAGTTACTGCCTCCAGCTGCAGCAGTGACATCG
CTGACGTGGAGGTGGACATGTCGGGAGACTTGGGGTGGCTGTTGAACCT
CTTCCACAACCAGATTGAGTCCAAGTTCCAGAAAGTACTGGAGAGCAGG
ATTTGCGAAATGATCCAGAAATCGGTGTCCTCCGATCTACAGCCTTATC
TCCAAACTCTGCCAGTTACAACAGAGATTGACAGTTTCGCCGACATTGA
TTATAGCTTAGTGGAAGCCCCTCGGGCAACAGCCCAGATGTGGAGGTG
ATGTTTAAGGGTGAAATCTTTCATCGTAACCACCGTTCTCCAGTTACCC
TCCTTGCTGCAGTCATGAGCCTTCCTGAGGAACACAACAAAATGGTCTA
CTTTGCCATCTCGGATTATGTCTTCAACACGGCCAGCCTGGTTTATCAT
GAGGAAGGATATCTGAACTTCTCCATCACAGATGACATGATACCGCCTG
ACTCTAATATCCGACTGACCACCAAGTCCTTCCGACCCTTCGTCCCACG
GTTAGCCAGGCTCTACCCCAACATGAACCTGGAACTCCAGGGATCAGTG
CCCTCTGCTCCGCTCCTGAACTTCAGCCCTGGGAATCTGTCTGTGGACC
CCTATATGGAGATAGATGCCTTTGTGCTCCTGCCCAGCTCCAGCAAGGA
GCCTGTCTTCCGGCTCAGTGTGGCCACTAATGTGTCCGCCACCTTGACC
TTCAATACCAGCAAGATCACTGGGTTCCTGAAGCCAGGAAAGGTAAAAG
TGGAACTGAAAGAATCCAAAGTTGGACTATTCAATGCAGAGCTGTTGGA
AGCGCTCCTCAACTATTACATCCTTAACACCCTCTACCCCAAGTTCAAT
GATAAGTTGGCCGAAGGCTTCCCCCTTCCTCTGCTGAAGCGTGTTCAGC
TCTACGACCTTGGGCTGCAGATCCATAAGGACTTCCTGTTCTTGGGTGC
CAATGTCCAATACATGAGAGTTTGA.
Human MEK1 CDS (SEQ ID NO: 16)
ATGCCCAAGAAGAAGCCGACGCCCATCCAGCTGAACCCGGCCCCCGACG
GCTCTGCAGTTAACGGGACCAGCTCTGCGGAGACCAACTTGGAGGCCTT
GCAGAAGAAGCTGGAGGAGCTAGAGCTTGATGAGCAGCAGCGAAAGCGC
CTTGAGGCCTTTCTTACCCAGAAGCAGAAGGTGGGAGAACTGAAGGATG
ACGACTTTGAGAAGATCAGTGAGCTGGGGGCTGGCAATGGCGGTGTGGT
```

GTTCAAGGTCTCCCACAAGCCTTCTGGCCTGGTCATGGCCAGAAAGCTA
ATTCATCTGGAGATCAAACCCGCAATCCGGAACCAGATCATAAGGGAGC
TGCAGGTTCTGCATGAGTGCAACTCTCCGTACATCGTGGGCTTCTATGG
TGCGTTCTACAGCGATGGCGAGATCAGTATCTGCATGGAGCACATGGAT
GGAGGTTCTCTGGATCAAGTCCTGAAGAAAGCTGGAAGAATTCCTGAAC
AAATTTTAGGAAAAGTTAGCATTGCTGTAATAAAAGGCCTGACATATCT
GAGGGAGAAGCACAAGATCATGCACAGAGATGTCAAGCCCTCCAACATC
CTAGTCAACTCCCGTGGGGAGATCAAGCTCTGTGACTTTGGGGTCAGCG
GGCAGCTCATCGACTCCATGGCCAACTCCTTCGTGGGCACAAGGTCCTA
CATGTCGCCAGAAAGACTCCAGGGGACTCATTACTCTGTGCAGTCAGAC
ATCTGGAGCATGGGACTGTCTCTGGTAGAGATGGCGGTTGGGAGGTATC
CCATCCCTCCTCCAGATGCCAAGGAGCTGGAGCTGATGTTTGGGTGCCA
GGTGGAAGGAGATGCGGCTGAGACCCCACCCAGGCCAAGGACCCCCGGG
AGGCCCCTTAGCTCATACGAATGGACAGCCGACCTCCCATGGCAATTT
TTGAGTTGTTGGATTACATAGTCAACGAGCCTCCTCCAAAACTGCCCAG
TGGAGTGTTCAGTCTGGAATTTCAAGATTTTGTGAATAAATGCTTAATA
AAAAACCCCGCAGAGAGCAGATTTGAAGCAACTCATGGTTCATGCTT
TTATCAAGAGATCTGATGCTGAGGAAGTGGATTTTGCAGGTTGGCTCTG
CTCCACCATCGGCCTTAACCAGCCCAGCACACCAACCCATGCTGCTGGC
GTCTAA.
Human MEK2 CDS (SEQ ID NO: 17)
ATGCTGGCCCGGAGGAAGCCGGTGCTGCCGGCGCTCACCATCAACCCTA
CCATCGCCGAGGGCCCATCCCCTACCAGCGAGGGCGCCTCCGAGGCAAA
CCTGGTGGACCTGCAGAAGAAGCTGGAGGAGCTGGAACTTGACGAGCAG
CAGAAGAAGCGGCTGGAAGCCTTTCTCACCCAGAAAGCCAAGGTCGGCG
AACTCAAAGACGATGACTTCGAAAGGATCTCAGAGCTGGGCGCGGGCAA
CGGCGGGGTGGTCACCAAAGTCCAGCACAGACCCTCGGGCCTCATCATG
GCCAGGAAGCTGATCCACCTTGAGATCAAGCCGGCCATCCGGAACCAGA
TCATCCGCGAGCTGCAGGTCCTGCACGAATGCAACTCGCCGTACATCGT
GGGCTTCTACGGGGCCTTCTACAGTGACGGGGAGATCAGCATTTGCATG
GAACACATGGACGGCGGCTCCCTGGACCAGGTGCTGAAAGAGGCCAAGA
GGATTCCCGAGGAGATCCTGGGGAAAGTCAGCATCGCGGTTCTCCGGGG
CTTGGCGTACCTCCGAGAGAAGCACCAGATCATGCACCGAGATGTGAAG
CCCTCCAACATCCTCGTGAACTCTAGAGGGGAGATCAAGCTGTGTGACT
TCGGGGTGAGCGGCCAGCTCATCGACTCCATGGCCAACTCCTTCGTGGG
CACGCGCTCCTACATGGCTCCGGAGCGGTTGCAGGGCACACATTACTCG
GTGCAGTCGGACATCTGGAGCATGGGCCTGTCCCTGGTGGAGCTGGCCG
TCGGAAGGTACCCCATCCCCCCGCCCGACGCCAAAGAGCTGGAGGCCAT
CTTTGGCCGGCCCGTGGTCGACGGGGAAGAAGGAGAGCCTCACAGCATC
TCGCCTCGGCCGAGGCCCCCGGGCGCCCCGTCAGCGGTCACGGGATGG
ATAGCCGGCCTGCCATGGCCATCTTTGAACTCCTGGACTATATTGTGAA CGAGCCACCTCCTAAGCTGCCCAACGGTGTGTTCACCCCCGACTTCCAG
GAGTTTGTCAATAAATGCCTCATCAAGAACCCAGCGGAGCGGGCGGACC
TGAAGATGCTCACAAACCACACCTTCATCAAGCGGTCCGAGGTGGAAGA
AGTGGATTTTGCCGGCTGGTTGTGTAAAACCCTGCGGCTGAACCAGCCC
GGCACACCCACGCGCACCGCCGTGTGA.
Human MEK3 CDS (SEQ ID NO: 18)
ATGTCCAAGCCACCCGCACCCAACCCCACACCCCCCGGAACCTGGACT
CCCGGACCTTCATCACCATTGGAGACAGAAACTTTGAGGTGGAGGCTGA
TGACTTGGTGACCATCTCAGAACTGGGCCGTGGAGCCTATGGGGTGGTA
GAGAAGGTGCGGCACGCCCAGAGCGGCACCATCATGGCCGTGAAGCGGA
TCCGGGCCACCGTGAACTCACAGGAGCAGAAGCGGCTGCTCATGGACCT
GGACATCAACATGCGCACGGTCGACTGTTTCTACACTGTCACCTTCTAC
GGGGCACTATTCAGAGAGGGAGACGTGTGGATCTGCATGGAGCTCATGG
ACACATCCTTGGACAAGTTCTACCGGAAGGTGCTGGATAAAAACATGAC
AATTCCAGAGGACATCCTTGGGGAGATTGCTGTGTCTATCGTGCGGGCC
CTGGAGCATCTGCACAGCAAGCTGTCGGTGATCCACAGAGATGTGAAGC
CCTCCAATGTCCTTATCAACAAGGAGGGCCATGTGAAGATGTGTGACTT
TGGCATCAGTGGCTACTTGGTGGACTCTGTGGCCAAGACGATGGATGCC
GGCTGCAAGCCCTACATGGCCCCTGAGAGGATCAACCCAGAGCTGAACC
AGAAGGGCTACAATGTCAAGTCCGACGTCTGGAGCCTGGGCATCACCAT
GATTGAGATGGCCATCCTGCGGTTCCCTTACGAGTCCTGGGGGACCCCG
TTCCAGCAGCTGAAGCAGGTGGTGGAGGAGCCGTCCCCCCAGCTCCCAG
CCGACCGTTTCTCCCCCGAGTTTGTGGACTTCACTGCTCAGTGCCTGAG
GAAGAACCCCGCAGAGCGTATGAGCTACCTGGAGCTGATGGAGCACCCC
TTCTTCACCTTGCACAAAACCAAGAAGACGGACATTGCTGCCTTCGTGA
AGGAGATCCTGGGAGAAGACTCATAG.
Human MEK6 CDS (SEQ ID NO: 19)
ATGTCTCAGTCGAAAGGCAAGAAGCGAAACCCTGGCCTTAAAATTCCAA
AAGAAGCATTTGAACAACCTCAGACCAGTTCCACACCACCTCGAGATTT
AGACTCCAAGGCTTGCATTTCTATTGGAAATCAGAACTTTGAGGTGAAG
GCAGATGACCTGGAGCCTATAATGGAACTGGGACGAGGTGCGTACGGGG
TGGTGGAGAAGATGCGGCACGTGCCCAGCGGGCAGATCATGGCAGTGAA
GCGGATCCGAGCCACAGTAAATAGCCAGGAACAGAAACGGCTACTGATG
GATTTGGATATTTCCATGAGGACGGTGGACTGTCCATTCACTGTCACCT
TTTATGGCGCACTGTTTCGGGAGGGTGATGTGTGGATCTGCATGGAGCT
CATGGACACATCACTAGATAAATTCTACAAACAAGTTATTGATAAAGGC
CAGACAATTCCAGAGGACATCTTAGGGAAAATAGCAGTTTCTATTGTAA
AAGCATTAGAACATTTACATAGTAAGCTGTCTGTCATTCACAGAGACGT
CAAGCCTTCTAATGTACTCATCAATGCTCTCGGTCAAGTGAAGATGTGC
GATTTTGGAATCAGTGGCTACTTGGTGGACTCTGTTGCTAAAACAATTG
ATGCAGGTTGCAAACCATACATGGCCCCTGAAAGAATAAACCCAGAGCT -continued
CAACCAGAAGGGATACAGTGTGAAGTCTGACATTTGGAGTCTGGGCATC

ACGATGATTGAGTTGGCCATCCTTCGATTTCCCTATGATTCATGGGAA

CTCCATTTCAGCAGCTCAAACAGGTGGTAGAGGAGCCATCGCCACAACT

CCCAGCAGACAAGTTCTCTGCAGAGTTTGTTGACTTTACCTCACAGTGC

TTAAAGAAGAATTCCAAAGAACGGCCTACATACCCAGAGCTAATGCAAC

ATCCATTTTTCACCCTACATGAATCCAAAGGAACAGATGTGGCATCTTT

TGTAAAACTGATTCTTGGAGACTAA.

Human MEKK1 CDS (SEQ ID NO: 20)
ATGGCGGCGGCGGCGGGGAATCGCGCCTCGTCGTCGGGATTCCCGGGCG

CCAGGGCTACGAGCCCTGAGGCAGGCGGCGGCGGAGGAGCCCTCAAGGC

GAGCAGCGCGCCCGCGGCTGCCGCGGGACTGCTGCGGGAGGCGGGCAGC

GGGGGCCGCGAGCGGGCGGACTGGCGGCGGCGGCAGCTGCGCAAAGTGC

GGAGTGTGGAGCTGGACCAGCTGCCTGAGCAGCCGCTCTTCCTTGCCGC

CTCACCGCCGGCCTCCTCGACTTCCCCGTCGCCGGAGCCCGCGGACGCA

GCGGGGAGTGGGACCGGCTTCCAGCCTGTGGCGGTGCCGCCGCCCCACG

GAGCCGCGAGCCGCGGCGGCGCCCACCTTACCGAGTCGGTGGCGGCGCC

GGACAGCGGCGCCTCGAGTCCCGCAGCGGCCGAGCCCGGGGAGAAGCGG

GCGCCCGCCGCCGAGCCGTCTCCTGCAGCGGCCCCCGCCGGTCGTGAGA

TGGAGAATAAAGAAACTCTCAAAGGGTTGCACAAGATGGATGATCGTCC

AGAGGAACGAATGATCAGGGAGAAACTGAAGGCAACCTGTATGCCAGCC

TGGAAGCACGAATGGTTGGAAAGGAGAAATAGGCGAGGGCCTGTGGTGG

TAAAACCAATCCCAGTTAAAGGAGATGGATCTGAAATGAATCACTTAGC

AGCTGAGTCTCAGGAGAGGTCCAGGCAAGTGCGGCTTCACCAGCTTCC

AAAGGCCGACGCAGTCCTTCTCCTGGCAACTCCCCATCAGGTCGCACAG

TGAAATCAGAATCTCCAGGAGTAAGGAGAAAAAGAGTTTCCCCAGTGCC

TTTTCAGAGTGGCAGAATCACACCACCCCGAAGAGCCCCTTCACCAGAT

GGCTTCTCACCATATAGCCCTGAGGAAACAAACCGCCGTGTTAACAAAG

TGATGCGGGCCAGACTGTACTTACTGCAGCAGATAGGGCCTAACTCTTT

CCTGATTGGAGGAGACAGCCCAGACAATAAATACCGGGTGTTTATTGGG

CCTCAGAACTGCAGCTGTGCACGTGGAACATTCTGTATTCATCTGCTAT

TTGTGATGCTCCGGGTGTTTCAACTAGAACCTTCAGACCCAATGTTATG

GAGAAAAACTTTAAAGAATTTTGAGGTTGAGAGTTTGTTCCAGAAATAT

CACAGTAGGCGTAGCTCAAGGATCAAAGCTCCATCTCGTAACACCATCC

AGAAGTTTGTTTCACGCATGTCAAATTCTCATACATTGTCATCATCTAG

TACTTCTACGTCTAGTTCAGAAAACAGCATAAAGGATGAAGAGGAACAG

ATGTGTCCTATTTGCTTGTTGGGCATGCTTGATGAAGAAAGTCTTACAG

TGTGTGAAGACGGCTGCAGGAACAAGCTGCACCACCACTGCATGTCAAT

TTGGGCAGAAGAGTGTAGAAGAAATAGAGAACCTTTAATATGTCCCCTT

TGTAGATCTAAGTGGAGATCTCATGATTTCTACAGCCACGAGTTGTCAA

GTCCTGTGGATTCCCCTTCTTCCCTCAGAGCTGCACAGCAGCAAACCGT

ACAGCAGCAGCCTTTGGCTGGATCACGAAGGAATCAAGAGAGCAATTTT

-continued
AACCTTACTCATTATGGAACTCAGCAAATCCCTCCTGCTTACAAAGATT

TAGCTGAGCCATGGATTCAGGTGTTTGGAATGGAACTCGTTGGCTGCTT

ATTTTCTAGAAACTGGAATGTGAGAGAGATGGCCCTCAGGCGTCTTTCC

CATGATGTCAGTGGGCCCTGCTGTTGGCAAATGGGGAGAGCACTGGAA

ATTCTGGGGCAGCAGTGGAAGCAGCCCGAGTGGGGGAGCCACCAGTGG

GTCTTCCCAGACCAGTATCTCAGGAGATGTGGTGGAGGCATGCTGCAGC

GTTCTGTCAATGGTCTGTGCTGACCCTGTCTACAAAGTGTACGTTGCTG

CTTTAAAAACATTGAGAGCCATGCTGGTATATACTCCTTGCCACAGTTT

AGCGGAAAGAATCAAACTTCAGAGACTTCTCCAGCCAGTTGTAGACACC

ATCCTAGTCAAATGTGCAGATGCCAATAGCCGCACAAGTCAGCTGTCCA

TATCAACACTGTTGGAACTGTGCAAAGGCCAAGCAGGAGAGTTGGCAGT

TGGCAGAGAAATACTAAAAGCTGGATCCATTGGTATTGGTGGTGTTGAT

TATGTCTTAAATTGTATTCTTGGAAACCAAACTGAATCAAACAATTGGC

AAGAACTTCTTGGCCGCCTTTGTCTTATAGATAGACTGTTGTTGGAATT

TCCTGCTGAATTTTATCCTCATATTGTCAGTACTGATGTTTCACAAGCT

GAGCCTGTTGAAATCAGGTATAAGAAGCTGCTGTCCCTCTTAACCTTTG

CTTTGCAGTCCATTGATAATTCCCACTCAATGGTTGGCAAACTTTCCAG

AAGGATCTACTTGAGTTCTGCAAGAATGGTTACTACAGTACCCCATGTG

TTTTCAAAACTGTTAGAAATGCTGAGTGTTTCCAGTTCCACTCACTTCA

CCAGGATGCGTCGCCGTTTGATGGCTATTGCAGATGAGGTGGAAATTGC

CGAAGCCATCCAGTTGGGCGTAGAAGACACTTTGGATGGTCAACAGGAC

AGCTTCTTGCAGGCATCTGTTCCCAACAACTATCTGGAAACCACAGAGA

ACAGTTCCCTGAGTGCACAGTCCATTTAGAGAAAACTGGAAAAGGATT

ATGTGCTACAAAATTGAGTGCCAGTTCAGAGGACATTTCTGAGAGACTG

GCCAGCATTTCAGTAGGACCTTCTAGTTCAACAACAACAACAACAACAA

CAACAGAGCAACCAAAGCCAATGGTTCAAACAAAAGGCAGACCCCACAG

TCAGTGTTTGAACTCCTCTCCTTTATCTCATCATTCCCAATTAATGTTT

CCAGCCTTGTCAACCCCTTCTTCTTCTACCCCATCTGTACCAGCTGGCA

CTGCAACAGATGTCTCTAAGCATAGACTTCAGGGATTCATTCCCTGCAG

AATACCTTCTGCATCTCCTCAAACACAGCGCAAGTTTTCTCTACAATTC

CACAGAAACTGTCCTGAAAACAAAGACTCAGATAAACTTTCCCCAGTCT

TTACTCAGTCAAGACCCTTGCCCTCCAGTAACATACACAGGCCAAAGCC

ATCTAGACCTACCCCAGGTAATACAAGTAAACAGGGAGATCCCTCAAAA

AATAGCATGACACTTGATCTGAACAGTAGTTCCAAATGTGATGACAGCT

TTGGCTGTAGCAGCAATAGTAGTAATGCTGTTATACCCAGTGACGAGAC

AGTGTTCACCCCAGTAGAGGAGAAATGCAGATTAGATGTCAATACAGAG

CTCAACTCCAGTATTGAGGACCTTCTTGAAGCATCTATGCCTTCAAGTG

ATACAACAGTAACTTTTAAGTCAGAAGTTGCTGTCCTGTCTCCTGAAAA

GGCTGAAAATGATGATACCTACAAAGATGATGTGAATCATAATCAAAAG

TGCAAAGAGAAGATGGAAGCTGAAGAAGAAGAAGCTTTAGCAATTGCCA

TGGCAATGTCAGCGTCTCAGGATGCCCTCCCCATAGTTCCTCAGCTGCA

GGTTGAAAATGGAGAAGATATCATCATTATTCAACAGGATACACCAGAG
ACTCTACCAGGACATACCAAAGCAAAACAACCGTATAGAGAAGACACTG
AATGGCTGAAAGGTCAACAGATAGGCCTTGGAGCATTTTCTTCTTGTTA
TCAGGCTCAAGATGTGGGAACTGGAACTTTAATGGCTGTTAAACAGGTG
ACTTATGTCAGAAACACATCTTCTGAGCAAGAAGAAGTAGTAGAAGCAC
TAAGAGAAGAGATAAGAATGATGAGCCATCTGAATCATCCAAACATCAT
TAGGATGTTGGGAGCCACGTGTGAGAAGAGCAATTACAATCTCTTCATT
GAATGGATGGCAGGGGGATCGGTGGCTCATTTGCTGAGTAAATATGGAG
CCTTCAAAGAATCAGTAGTTATTAACTACACTGAACAGTTACTCCGTGG
CCTTTCGTATCTCCATGAAAACCAAATCATTCACAGAGATGTCAAAGGT
GCCAATTTGCTAATTGACAGCACTGGTCAGAGACTAAGAATTGCAGATT
TTGGAGCTGCAGCCAGGTTGGCATCAAAAGGAACTGGTGCAGGAGAGTT
TCAGGGACAATTACTGGGGACAATTGCATTTATGGCACCTGAGGTACTA
AGAGGTCAACAGTATGGAAGGAGCTGTGATGTATGGAGTGTTGGCTGTG
CTATTATAGAAATGGCTTGTGCAAAACCACCATGGAATGCAGAAAAACA
CTCCAATCATCTTGCTTTGATATTTAAGATTGCTAGTGCAACTACTGCT
CCATCGATCCCTTCACATTTGTCTCCTGGTTTACGAGATGTGGCTCTTC
GTTGTTTAGAACTTCAACCTCAGGACAGACCTCCATCAAGAGAGCTACT
GAAGCATCCAGTCTTTCGTACTACATGGTAG.

Human MEKK 3 CDS (SEQ ID NO: 21)
ATGGACGAACAGGAGGCATTGAACTCAATCATGAACGATCTGGTGGCCC
TCCAGATGAACCGACGTCACCGGATGCCTGGATATGAGACCATGAAGAA
CAAAGACACAGGTCACTCAAATAGGCAGAAAAAACACAACAGCAGCAGC
TCAGCCCTTCTGAACAGCCCCACAGTAACAACAAGCTCATGTGCAGGGG
CCAGTGAGAAAAAGAAATTTTTGAGTGACGTCAGAATCAAGTTCGAGCA
CAACGGGGAGAGGCGAATTATAGCGTTCAGCCGGCCTGTGAAATATGAA
GATGTGGAGCACAAGGTGACAACAGTATTGGACAACCTCTTGATCTAC
ATTACATGAACAATGAGCTCTCCATCCTGCTGAAAAACCAAGATGATCT
TGATAAAGCAATTGACATTTTAGATAGAAGCTCAAGCATGAAAAGCCTT
AGGATATTGCTGTTGTCCCAGGACAGAAACCATAACAGTTCCTCTCCCC
ACTCTGGGGTGTCCAGACAGGTGCGGATCAAGGCTTCCCAGTCCGCAGG
GGATATAAATACTATCTACCAGCCCCCCGAGCCCAGAAGCAGGCACCTC
TCTGTCAGCTCCCAGAACCCTGGCCGAAGCTCACCTCCCCCTGGCTATG
TTCCTGAGCGGCAGCAGCACATTGCCCGGCAGGGGTCCTACACCAGCAT
CAACAGTGAGGGGAGTTCATCCCAGAGACCAGCGAGCAGTGCATGCTG
GATCCCCTGAGCAGTGCAGAAAATTCCTTGTCTGGAAGCTGCCAATCCT
TGGACAGGTCAGCAGACAGCCCATCCTTCCGGAAATCACGAATGTCCCG
TGCCCAGAGCTTCCCTGACAACAGACAGGAATACTCAGATCGGGAAACT
CAGCTTTATGACAAAGGGGTCAAAGGTGGAACCTACCCCCGGCGCTACC
ACGTGTCTGTGCACCACAAGGACTACAGTGATGGCAGAAGAACATTTCC
CCGAATACGGCGTCATCAAGGCAACTTGTTCACCCTGGTGCCCTCCAGC CGCTCCCTGAGCACAAATGGCGAGAACATGGGTCTGGCTGTGCAATACC
TGGACCCCCGTGGGCGCCTGCGGAGTGCGGACAGCGAGAATGCCCTCTC
TGTGCAGGAGAGGAATGTGCCAACCAAGTCTCCCAGTGCCCCCATCAAC
TGGCGCCGGGGAAAGCTCCTGGGCCAGGGTGCCTTCGGCAGGGTCTATT
TGTGCTATGACGTGGACACGGGACGTGAACTTGCTTCCAAGCAGGTCCA
ATTTGATCCAGACAGTCCTGAGACAAGCAAGGAGGTGAGTGCTCTGGAG
TGCGAGATCCAGTTGCTAAAGAACTTGCAGCATGAGCGCATCGTGCAGT
ACTATGGCTGTCTGCGGGACCGCGCTGAGAAGACCCTGACCATCTTCAT
GGAGTACATGCCAGGGGGCTCGGTGAAAGACCAGTTGAAGGCTTACGGT
GCTCTGACAGAGAGCGTGACCCGAAAGTACACGCGGCAGATCCTGGAGG
GCATGTCCTACCTGCACAGCAACATGATTGTTCACCGGGACATTAAGGG
AGCCAACATCCTCCGAGACTCTGCTGGGAATGTAAAGCTGGGGGACTTT
GGGGCCAGCAAACGCCTGCAGACGATCTGTATGTCGGGGACGGGCATGC
GCTCCGTCACTGGCACACCCTACTGGATGAGCCCTGAGGTGATCAGCGG
CGAGGGCTATGGAAGGAAAGCAGACGTGTGGAGCCTGGGCTGCACTGTG
GTGGAGATGCTGACAGAGAAACCACCGTGGGCAGAGTATGAAGCTATGG
CCGCCATCTTCAAGATTGCCACCCAGCCCACCAATCCTCAGCTGCCCTC
CCACATCTCTGAACATGGCCGGGACTTCCTGAGGCGCATTTTTGTGGAG
GCTCGCCAGAGACCTTCAGCTGAGGAGCTGCTCACACACCACTTTGCAC
AGCTCATGTACTGA.

Human MEKK4 CDS (SEQ ID NO: 22)
ATGAGAGAAGCCGCTGCCGCGCTGGTCCCTCCTCCCGCCTTTGCCGTCA
CGCCTGCCGCCGCCATGGAGGAGCCGCCGCCACCGCCGCCGCCGCCACC
ACCGCCACCGGAACCCGAGACCGAGTCAGAACCCGAGTGCTGCTTGGCG
GCGAGGCAAGAGGGCACATTGGGAGATTCAGCTTGCAAGAGTCCTGAAT
CTGATCTAGAAGACTTCTCCGATGAAACAAATACAGAGAATCTTTATGG
TACCTCTCCCCCCAGCACACCTCGACAGATGAAACGCATGTCAACCAAA
CATCAGAGGAATAATGTGGGGAGGCCAGCCAGTCGGTCTAATTTGAAAG
AAAAAATGAATGCACCAAATCAGCCTCCACATATAAAGACACTGGAAAAAC
AGTGGAGAATGTGGAAGAATACAGCTATAAGCAGGAGAAAAAGATCCGA
GCAGCTCTTAGAACAACAGAGCGTGATCATAAAAAAAAATGTACAGTGCT
CATTCATGTTAGACTCAGTGGGTGGATCTTTGCCAAAAAAATCAATTCC
AGATGTGGATCTCAATAAGCCTTACCTCAGCCTTGGCTGTAGCAATGCT
AAGCTTCCAGTATCTGTGCCCATGCCTATAGCCAGACCTGCACGCCAGA
CTTCTAGGACTGACTGTCAGCAGATCGTTTAAAGTTTTTTGAAACTTT
ACGACTTTTGCTAAAGCTTACCTCAGTCTCAAAGAAAAAGACAGGGAG
CAAAGAGGACAAGAAAATACGTCTGGTTTCTGGCTTAACCGATCTAACG
AACTGATCTGGTTAGAGCTACAAGCCTGGCATGCAGGACGGACAATTAA
CGACCAGGACTTCTTTTTATATACAGCCCGTCAAGCCATCCCAGATATT
ATTAATGAAATCCTTACTTTCAAAGTCGACTATGGGAGCTTCGCCTTTG
TTAGAGATAGAGCTGGTTTTAATGGTACTTCAGTAGAAGGGCAGTGCAA

```
AGCCACTCCTGGAACAAAGATTGTAGGTTACTCAACACATCATGAGCAT

CTCCAACGCCAGAGGGTCTCATTTGAGCAGGTAAAACGGATAATGGAGC

TGCTAGAGTACATAGAAGCACTTTATCCATCATTGCAGGCTCTTCAGAA

GGACTATGAAAAATATGCTGCAAAAGACTTCCAGGACAGGGTGCAGGCA

CTCTGTTTGTGGTTAAACATCACAAAAGACTTAAATCAGAAATTAAGGA

TTATGGGCACTGTTTTGGGCATCAAGAATTTATCAGACATTGGCTGGCC

AGTGTTTGAAATCCCTTCCCCTCGACCATCCAAAGGTAATGAGCCGGAG

TATGAGGGTGATGACACAGAAGGAGAATTAAAGGAGTTGGAAAGTAGTA

CGGATGAGAGTGAAGAAGAACAAATCTCTGATCCTAGGGTACCGGAAAT

CAGACAGCCCATAGATAACAGCTTCGACATCCAGTCGCGGGACTGCATA

TCCAAGAAGCTTGAGAGGCTCGAATCTGAGGATGATTCTCTTGGCTGGG

GAGCACCAGACTGGAGCACAGAAGCAGGCTTTAGTAGACATTGTCTGAC

TTCTATTTATAGACCATTTGTAGACAAAGCACTGAAGCAGATGGGGTTA

AGAAAGTTAATTTTAAGACTTCACAAGCTAATGGATGGTTCCTTGCAAA

GGGCACGTATAGCATTGGTAAAGAACGATCGTCCAGTGGAGTTTTCTGA

ATTTCCAGATCCCATGTGGGGTTCAGATTATGTGCAGTTGTCAAGGACA

CCACCTTCATCTGAGGAGAAATGCAGTGCTGTGTCGTGGGAGGAGCTGA

AGGCCATGGATTTACCTTCATTCGAACCTGCCTTCCTAGTTCTCTGCCG

AGTCCTTCTGAATGTCATACATGAGTGTCTGAAGTTAAGATTGGAGCAG

AGACCTGCTGGAGAACCATCTCTCTTGAGTATTAAGCAGCTGGTGAGAG

AGTGTAAGGAGGTCCTGAAGGGCGGCCTGCTGATGAAGCAGTACTACCA

GTTCATGCTGCAGGAGGTTCTGGAGGACTTGGAGAAGCCCGACTGCAAC

ATTGACGCTTTTGAAGAGGATCTACATAAAATGCTTATGGTGTATTTTG

ATTACATGAGAAGCTGGATCCAAATGCTACAGCAATTACCTCAAGCATC

GCATAGTTTAAAAAATCTGTTAGAAGAAGAATGGAATTTCACCAAAGAA

ATAACTCATTACATACGGGGAGGAGAAGCACAGGCCGGGAAGCTTTTCT

GTGACATTGCAGGAATGCTGCTGAAATCTACAGGAAGTTTTTTAGAATT

TGGCTTACAGGAGAGCTGTGCTGAATTTTGGACTAGTGCGGATGACAGC

AGTGCTTCCGACGAAATCAGGAGGTCTGTTATAGAGATCAGTCGAGCCC

TGAAGGAGCTCTTCCATGAAGCCAGAGAAAGGGCTTCCAAAGCACTTGG

ATTTGCTAAAATGTTGAGAAAGGACCTGGAAATAGCAGCAGAATTCAGG

CTTTCAGCCCCAGTTAGAGACCTCCTGGATGTTCTGAAATCAAAACAGT

ATGTCAAGGTGCAAATTCCTGGGTTAGAAAACTTGCAAATGTTTGTTCC

AGACACTCTTGCTGAGGAGAAGAGTATTATTTTGCAGTTACTCAATGCA

GCTGCAGGAAAGGACTGTTCAAAAGATTCAGATGACGTACTCATCGATG

CCTATCTGCTTCTGACCAAGCACGGTGATCGAGCCCGTGATTCAGAGGA

CAGCTGGGGCACCTGGGAGGCACAGCCTGTCAAAGTCGTGCCTCAGGTG

GAGACTGTTGACACCCTGAGAAGCATGCAGGTGGATAATCTTTTACTAG

TTGTCATGCAGTCTGCGCATCTCACAATTCAGAGAAAAGCTTTCCAGCA

GTCCATTGAGGGACTTATGACTCTGTGCCAGGAGCAGACATCCAGTCAG

CCGGTCATCGCCAAAGCTTTGCAGCAGCTGAAGAATGATGCATTGGAGC

TATGCAACAGGATAAGCAATGCCATTGACCGCGTGGACCACATGTTCAC

ATCAGAATTTGATGCTGAGGTTGATGAATCTGAATCTGTCACCTTGCAA

CAGTACTACCGAGAAGCAATGATTCAGGGGTACAATTTTGGATTTGAGT

ATCATAAAGAAGTTGTTCGTTTGATGTCTGGGGAGTTTAGACAGAAGAT

AGGAGACAAATATATAAGCTTTGCCCGGAAGTGGATGAATTATGTCCTG

ACTAAATGTGAGAGTGGTAGAGGTACAAGACCCAGGTGGGCGACTCAAG

GATTTGATTTTCTACAAGCAATTGAACCTGCCTTTATTTCAGCTTTACC

AGAAGATGACTTCTTGAGTTTACAAGCCTTGATGAATGAATGCATTGGC

CATGTCATAGGAAAACCACACAGTCCTGTTACAGGTTTGTACCTTGCCA

TTCATCGGAACAGCCCCCGTCCTATGAAGGTACCTCGATGCCATAGTGA

CCCTCCTAACCCACACCTCATTATCCCCACTCCAGAGGGATTCAGCACT

CGGAGCATGCCTTCCGACGCGCGGAGCCATGGCAGCCCTGCTGCTGCTG

CTGCTGCTGCTGCTGCTGTTGCTGCCAGTCGGCCCAGCCCCTCTGG

TGGTGACTCTGTGCTGCCCAAATCCATCAGCAGTGCCCATGATACCAGG

GGTTCCAGCGTTCCTGAAAATGATCGATTGGCTTCCATAGCTGCTGAAT

TGCAGTTTAGGTCCCTGAGTCGTCACTCAAGCCCCACGGAGGAGCGAGA

TGAACCAGCATATCCAAGAGGAGATTCAAGTGGGTCCACAAGAAGAAGT

TGGGAACTTCGGACACTAATCAGCCAGAGTAAAGATACTGCTTCTAAAC

TAGGACCCATAGAAGCTATCCAGAAGTCAGTCCGATTGTTTGAAGAAAA

GAGGTACCGAGAAATGAGGAGAAAGAATATCATTGGTCAAGTTTGTGAT

ACGCCTAAGTCCTATGATAATGTTATGCACGTTGGCTTGAGGAAGGTGA

CCTTCAAATGGCAAAGAGGAAACAAAATTGGAGAAGGCCAGTATGGGAA

GGTGTACACCTGCATCAGCGTCGACACCGGGGAGCTGATGGCCATGAAA

GAGATTCGATTTCAACCTAATGACCATAAGACTATCAAGGAAACTGCAG

ACGAATTGAAAATATTCGAAGGCATCAAACACCCCAATCTGGTTCGGTA

TTTTGGTGTGGAGCTCCATAGAGAAGAAATGTACATCTTCATGGAGTAC

TGCGATGAGGGGACTTTAGAAGAGGTGTCAAGGCTGGGACTTCAGGAAC

ATGTGATTAGGCTGTATTCAAAGCAGATCACCATTGCGATCAACGTCCT

CCATGAGCATGGCATAGTCCACCGTGACATTAAAGGTGCCAATATCTTC

CTTACCTCATCTGGATTAATCAAACTGGGAGATTTTGGATGTTCAGTAA

AGCTCAAAAACAATGCCCAGACCATGCCTGGTGAAGTGAACAGCACCCT

GGGGACAGCAGCATACATGGCACCTGAAGTCATCACTCGTGCCAAAGGA

GAGGGCCATGGGCGTGCGGCCGACATCTGGAGTCTGGGGTGTGTTGTCA

TAGAGATGGTGACTGGCAAGAGGCCTTGGCATGAGTATGAGCACAACTT

TCAAATTATGTATAAAGTGGGGATGGGACATAAGCCACCAATCCCTGAA

AGATTAAGCCCTGAAGGAAAGGACTTCCTTTCTCACTGCCTTGAGAGTG

ACCCAAAGATGAGATGGACCGCCAGCCAGCTCCTCGACCATTCGTTTGT

CAAGGTTTGCACAGATGAAGAATG.
```

Human MEKK 6 CDS (SEQ ID NO: 23)
ATGGCGGGGCCGTGTCCCCGGTCCGGGGCGGAGCGCGCCGGCAGCTGCT
GGCAGGACCCGCTGGCCGTGGCGCTGAGCCGGGGCCGGCAGCTCGCGGC
GCCCCCGGGCCGGGGCTGCGCGCGGAGCCGGCCGCTCAGCGTGGTCTAC
GTGCTGACCCGGGAGCCGCAGCCCGGGCTCGAGCCTCGGGAGGGAACCG
AGGCGGAGCCGCTGCCCCTGCGCTGCCTGCGCGAGGCTTGCGCGCAGGT
CCCCCGGCCGCGGCCGCCCCGCAGCTGCGCAGCCTGCCCTTCGGGACG
CTGGAGCTAGGCGACACCGCGGCTCTGGATGCCTTCTACAACGCGGATG
TGGTGGTGCTGGAGGTGAGCAGCTCGCTGGTACAGCCCTCCCTGTTCTA
CCACCTTGGTGTGCGTGAGAGCTTCAGCATGACCAACAATGTGCTCCTC
TGCTCCCAGGCCGACCTCCCTGACCTGCAGGCCCTGCGGGAGGATGTTT
TCCAGAAGAACTCGGATTGCGTTGGCAGCTACACACTGATCCCCTATGT
GGTGACGGCCACTGGTCGGTGCTGTGTGGTGATGCAGGCCTTCTGCGG
GGCCTGGCTGATGGGCTGGTACAGGCTGGAGTGGGGACCGAGGCCCTGC
TCACTCCCTGGTGGGCGGCTTGCCCGCCTGCTGGAGGCCACACCCAC
AGACTCTTGTGGCTATTTCCGGGAGACCATTCGGCGGGACATCCGGCAG
GCGCGGGAGCGGTTCAGTGGGCACAGCTGCGGCAGGAGCTGGCTCGCC
TGCAGCGGAGACTGGACAGCGTGGAGCTGCTGAGCCCCGACATCATCAT
GAACTTGCTGCTCTCCTACCGCGATGTGCAGGACTACTCGGCCATCATT
GAGCTGGTGGAGACGCTGCAGGCCTTGCCCACCTGTGATGTGGCCGAGC
AGCATAATGTCTGCTTCCACTACACTTTTGCCCTCAACCGGAGGAACAG
GCCTGGGGACCGGGCGAAGGCCCTGTCTGTGCTGCTGCCGCTGGTACAG
CTTGAGGGCTCTGTGGCGCCCGATCTGTACTGCATGTGTGGCCTATCT
ACAAGGACATGTTCTTCAGCTCGGGTTTCCAGGATGCTGGGCACCGGGA
GCAGGCCTATCACTGGTATCGCAAGGCTTTTGACGTAGAGCCCAGCCTT
CACTCAGGCATCAATGCAGCTGTGCTCCTCATTGCTGCCGGGCAGCACT
TTGAGGATTCCAAAGAGCTCCGGCTAATAGGCATGAAGCTGGGCTGCCT
GCTGGCCCGCAAAGGCTGCGTGGAGAAGATGCAGTATTACTGGGATGTG
GGTTTCTACCTGGGAGCCCAGATCCTCGCCAATGACCCCACCCAGGTGG
TGCTGGCTGCAGAGCAGCTGTATAAGCTCAATGCCCCCATATGGTACCT
GGTGTCCGTGATGGAGACCTTCCTGCTCTACCAGCACTTCAGGCCCACG
CCAGAGCCCCTGGAGGGCACCACGCCGTGCCCACTTCTGGCTCCACT
TCTTGCTACAGTCCTGCCAACCATTCAAGACAGCCTGTGCCCAGGGCGA
CCAGTGCTTGGTGCTGGTCCTGGAGATGAACAAGGTGCTGCTGCCTGCA
AAGCTCGAGGTTCGGGGTACTGACCCAGTAAGCACAGTGACCCTGAGCC
TGCTGGAGCCTGAGACCCAGGACATTCCCTCCAGCTGGACCTTCCCAGT
CGCCTCCATATGCGGAGTCAGCGCCTCAAAGCGCGACGAGCGCTGCTGC
TTCCTCTATGCACTCCCCCCGGCTCAGGACGTCCAGCTGTGCTTCCCCA
GCGTAGGGCACTGCCAGTGGTTCTGCGGCCTGATCCAGGCCTGGGTGAC
GAACCCCGGATTCCACGCGCCCGCGGAGGAGGCGGAGGGCGCGGGGGAG
ATGTTGGAGTTTGATTATGAGTACACGGAGACGGGCGAGCGGCTGGTGC TGGGCAAGGGCACGTATGGGGTGGTGTACGCGGGCCGCGATCGCCACAC
GAGGGTGCGCATCGCCATCAAGGAGATCCCGGAGCGGGACAGCAGGTTC
TCTCAGCCCCTGCATGAAGAGATCGCTCTTCACAGACGCCTGCGCCACA
AGAACATAGTGCGCTATCTGGGCTCAGCTAGCCAGGGCGGCTACCTTAA
GATCTTCATGGAGGAAGTGCCTGGAGGCAGCCTGTCCTCCTTGCTGCGG
TCGGTGTGGGGACCCCTGAAGGACAACGAGAGCACCATCAGTTTCTACA
CCCGCCAGATCCTGCAGGGACTTGGCTACTTGCACGACAACCACATCGT
GCACAGGGACATAAAAGGGGACAATGTGCTGATCAACACCTTCAGTGGG
CTGCTCAAGATTTCTGACTTCGGCACCTCCAAGCGGCTGGCAGGCATCA
CACCTTGCACTGAGACCTTCACAGGAACTCTGCAGTATATGGCCCCAGA
AATCATTGACCAGGGCCCACGCGGGTATGGGAAAGCAGCTGACATCTGG
TCACTGGGCTGCACTGTCATTGAGATGGCCACAGGTCGCCCCCCCTTCC
ACGAGCTCGGGAGCCCACAGGCTGCCATGTTTCAGGTGGGTATGTACAA
GGTCCATCCGCCAATGCCCAGCTCTCTGTCGGCCGAGGCCCAAGCCTTT
CTCCTCCGAACTTTTGAGCCAGACCCCCGCCTCCGAGCCAGCGCCCAGA
CACTGCTGGGGACCCCTTCCTGCAGCCTGGGAAAAGGAGCCGCAGCCC
CAGCTCCCCACGACATGCTCCACGGCCCTCAGATGCCCCTTCTGCCAGT
CCCACTCCTTCAGCCAACTCAACCACCCAGTCTCAGACATTCCCGTGCC
CTCAGGCACCCTCTCAGCACCCACCCAGCCCCCCGAAGCGCTGCCTCAG
TTATGGGGGCACCAGCCAGCTCCGGGTGCCCGAGGAGCCTGCGGCCGAG
GAGCCTGCGTCTCCGGAGGAGAGTTCGGGGCTGAGCCTGCTGCACCAGG
AGAGCAAGCGTCGGGCCATGCTGGCCGCAGTATTGGAGCAGGAGCTGCC
AGCGCTGGCGGAGAATCTGCACCAGGAGCAGAAGCAAGAGCAGGGGGCC
CGTCTGGGCAGAAACCATGTGGAAGAGCTGCTGCGCTGCCTCGGGGCAC
ACATCCACACTCCCAACCGCCGGCAGCTCGCCCAGGAGCTGCGGGCGCT
GCAAGGACGGCTGAGGGCCCAGGGCCTTGGGCCTGCGCTTCTGCACAGA
CCGCTGTTTGCCTTCCCGGATGCGGTGAAGCAGATCCTCCGCAAGCGCC
AGATCCGTCCACACTGGATGTTCGTTCTGGACTCACTGCTCAGCCGTGC
TGTGCGGGCAGCCCTGGGTGTGCTAGGACCGGAGGTGGAGAAGGAGGCG
GTCTCACCGAGGTCAGAGGAGCTGAGTAATGAAGGGGACTCCCAGCAGA
GCCCAGGCCAGCAGAGCCCGCTTCCGGTGGAGCCCGAGCAGGGCCCCGC
TCCTCTGATGGTGCAGCTGAGCCTCTTGAGGGCAGAGACTGATCGGCTG
CGCGAAATCCTGGCGGGGAAGGAACGGGAGTACCAGGCCCTGGTGCAGC
GGGCTCTACAGCGGCTGAATGAGGAAGCCCGGACCTATGTCCTGGCCCC
AGAGCCTCCAACTGCTCTTTCAACGGACCAGGGCCTGGTGCAGTGGCTA
CAGGAACTGAATGTGGATTCAGGCACCATCCAAATGCTGTTGAACCATA
GCTTCACCCTCCACACTCTGCTCACCTATGCCACTCGAGATGACCTCAT
CTACACCCGCATCAGGGGAGGGATGGTATGCCGCATCTGGAGGGCCATC
TTGGCACAGCGAGCAGGATCCACACCAGTCACCTCTGGACCCTGA.

Human MEKK7 CDS (SEQ ID NO: 24)
ATGTCTACAGCCTCTGCCGCCTCCTCCTCCTCCTCGTCTTCGGCCGGTG
AGATGATCGAAGCCCCTTCCCAGGTCCTCAACTTTGAAGAGATCGACTA
CAAGGAGATCGAGGTGGAAGAGGTTGTTGGAAGAGGAGCCTTTGGAGTT
GTTTGCAAAGCTAAGTGGAGAGCAAAAGATGTTGCTATTAAACAAATAG
AAAGTGAATCTGAGAGGAAAGCGTTTATTGTAGAGCTTCGGCAGTTATC
CCGTGTGAACCATCCTAATATTGTAAAGCTTTATGGAGCCTGCTTGAAT
CCAGTGTGTCTTGTGATGGAATATGCTGAAGGGGGCTCTTTATATAATG
TGCTGCATGGTGCTGAACCATTGCCATATTATACTGCTGCCCACGCAAT
GAGTTGGTGTTTACAGTGTTCCCAAGGAGTGGCTTATCTTCACAGCATG
CAACCCAAAGCGCTAATTCACAGGGACCTGAAACCACCAAACTTACTGC
TGGTTGCAGGGGGACAGTTCTAAAAATTTGTGATTTTGGTACAGCCTG
TGACATTCAGACACACATGACCAATAACAAGGGGAGTGCTGCTTGGATG
GCACCTGAAGTTTTTGAAGGTAGTAATTACAGTGAAAAATGTGACGTCT
TCAGCTGGGGTATTATTCTTTGGGAAGTGATAACGCGTCGGAAACCCTT
TGATGAGATTGGTGGCCCAGCTTTCCGAATCATGTGGGCTGTTCATAAT
GGTACTCGACCACCACTGATAAAAAATTTACCTAAGCCCATTGAGAGCC
TGATGACTCGTTGTTGGTCTAAAGATCCTTCCCAGCGCCCTTCAATGGA
GGAAATTGTGAAAATAATGACTCACTTGATGCGGTACTTTCCAGGAGCA
GATGAGCCATTACAGTATCCTTGTCAGTATTCAGATGAAGGACAGAGCA
ACTCTGCCACCAGTACAGGCTCATTCATGGACATTGCTTCTACAAATAC
GAGTAACAAAAGTGACACTAATATGGAGCAAGTTCCTGCCACAAATGAT
ACTATTAAGCGCTTAGAATCAAAATTGTTGAAAAATCAGGCAAAGCAAC
AGAGTGAATCTGGACGTTTAAGCTTGGGAGCCTCCCGTGGGAGCAGTGT
GGAGAGCTTGCCCCCAACCTCTGAGGGCAAGAGGATGAGTGCTGACATG
TCTGAAATAGAAGCTAGGATCGCCGCAACCACAGGCAACGGACAGCCAA
GACGTAGATCCATCCAAGACTTGACTGTAACTGGAACAGAACCTGGTCA
GGTGAGCAGTAGGTCATCCAGTCCCAGTGTCAGAATGATTACTACCTCA
GGACCAACCTCAGAAAAGCCAACTCGAAGTCATCCATGGACCCCTGATG
ATTCCACAGATACCAATGGATCAGATAACTCCATCCCAATGGCTTATCT
TACACTGGATCACCAACTACAGCCTCTAGCACCGTGCCCAAACTCCAAA
GAATCTATGGCAGTGTTTGAACAGCATTGTAAAATGGCACAAGAATATA
TGAAAGTTCAAACAGAAATTGCATTGTTATTACAGAGAAAGCAAGAACT
AGTTGCAGAACTGGACCAGGATGAAAAGGACCAGCAAAATACATCTCGC
CTGGTACAGGAACATAAAAAGCTTTAGATGAAAACAAAAGCCTTTCTAC
TTACTACCAGCAATGCAAAAAACAACTAGAGGTCATCAGAAGTCAGCAG
CAGAAACGACAAGGCACTTCATGA.

Human MK2 CDS (SEQ ID NO: 25)
ATGCTGTCCAACTCCCAGGGCCAGAGCCCGCCGGTGCCGTTCCCCGCCC
CGGCCCCGCCGCCGCAGCCCCCCACCCCTGCCCTGCCGCACCCCCCGGC
GCAGCCGCCGCCGCCGCCCCCGCAGCAGTTCCCGCAGTTCCACGTCAAG TCCGGCCTGCAGATCAAGAAGAACGCCATCATCGATGACTACAAGGTCA
CCAGCCAGGTCCTGGGGCTGGGCATCAACGGCAAAGTTTTGCAGATCTT
CAACAAGAGGACCCAGGAGAAATTCGCCCTCAAAATGCTTCAGGACTGC
CCCAAGGCCCGCAGGGAGGTGGAGCTGCACTGGCGGGCCTCCCAGTGCC
CGCACATCGTACGGATCGTGGATGTGTACGAGAATCTGTACGCAGGGAG
GAAGTGCCTGCTGATTGTCATGGAATGTTTGGACGGTGGAGAACTCTTT
AGCCGAATCCAGGATCGAGGAGACCAGGCATTCACAGAAAGAGAAGCAT
CCGAAATCATGAAGAGCATCGGTGAGGCCATCCAGTATCTGCATTCAAT
CAACATTGCCCATCGGGATGTCAAGCCTGAGAATCTCTTATACACCTCC
AAAAGGCCCAACGCCATCCTGAAACTCACTGACTTTGGCTTTGCCAAGG
AAACCACCAGCCACAACTCTTTGACCACTCCTTGTTATACACCGTACTA
TGTGGCTCCAGAAGTGCTGGGTCAGAGAAGTATGACAAGTCCTGTGAC
ATGTGGTCCCTGGGTGTCATCATGTACATCCTGCTGTGTGGGTATCCCC
CCTTCTACTCCAACCACGGCCTTGCCATCTCTCCGGGCATGAAGACTCG
CATCCGAATGGGCCAGTATGAATTTCCCAACCCAGAATGGTCAGAAGTA
TCAGAGGAAGTGAAGATGCTCATTCGGAATCTGCTGAAAACAGAGCCCA
CCCAGAGAATGACCATCACCGAGTTTATGAACCACCCTTGGATCATGCA
ATCAACAAAGGTCCCTCAAACCCCACTGCACACCAGCCGGGTCCTGAAG
GAGGACAAGGAGCGGTGGAGGATGTCAAGGGGTGTCTTCATGACAAGA
ACAGCGACCAGGCCACTTGGCTGACCAGGTTGTGA.

Human MyD88 CDS (SEQ ID NO: 26)
ATGGCGACCCGACCGCGCTGAGGCTCCAGGACCGCCCGCCATGGCTGCAG
GAGGTCCCGGCGCGGGGTCTGCGGCCCCGGTCTCCTCCACATCCTCCCT
TCCCCTGGCTGCTCTCAACATGCGAGTGCGGCGCCGCCTGTCTCTGTTC
TTGAACGTGCGGACACAGGTGGCGGCCGACTGGACCGCGCTGGCGGAGG
AGATGGACTTTGAGTACTTGGAGATCCGGCAACTGGAGACACAAGCGGA
CCCCACTGGCAGGCTGCTGGACGCCTGGCAGGGACGCCCTGGCGCCTCT
GTAGGCCGACTGCTCGAGCTGCTTACCAAGCTGGGCCGCGACGACGTGC
TGCTGGAGCTGGGACCCAGCATTGAGGAGGATTGCCAAAAGTATATCTT
GAAGCAGCAGCAGGAGGAGGCTGAGAAGCCTTTACAGGTGGCCGCTGTA
GACAGCAGTGTCCCACGGACAGCAGAGCTGGCGGGCATCACCACACTTG
ATGACCCCCTGGGGCATATGCCTGAGCGTTTCGATGCCTTCATCTGCTA
TTGCCCCAGCGACATCCAGTTTGTGCAGGAGATGATCCGGCAACTGGAA
CAGACAAACTATCGACTGAAGTTGTGTGTGTCTGACCGCGATGTCCTGC
CTGGCACCTGTGTCTGGTCTATTGCTAGTGAGCTCATCGAAAAGAGGTT
GGCTAGAAGGCCACGGGGTGGTGCCGCCGGATGGTGGTGGTTGTCTCT
GATGATTACCTGCAGAGCAAGGAATGTGACTTCCAGACCAAATTTGCAC
TCAGCCTCTCTCCAGGTGCCCATCAGAAGCGACTGATCCCCATCAAGTA
CAAGGCAATGAAGAAAGAGTTCCCCAGCATCCTGAGGTTCATCACTGTC
TGCGACTACACCAACCCCTGCACCAAATCTTGGTTCTGGACTCGCCTTG
CCAAGGCCTTGTCCCTGCCCTGA.

Human NF-κB CDS (SEQ ID NO: 27)
ATGGCAGAAGATGATCCATATTTGGGAAGGCCTGAACAAATGTTTCATT

TGGATCCTTCTTTGACTCATACAATATTTAATCCAGAAGTATTTCAACC

ACAGATGGCACTGCCAACAGATGGCCCATACCTTCAAATATTAGAGCAA

CCTAAACAGAGAGGATTTCGTTTCCGTTATGTATGTGAAGGCCCATCCC

ATGGTGGACTACCTGGTGCCTCTAGTGAAAAGAACAAGAAGTCTTACCC

TCAGGTCAAAATCTGCAACTATGTGGGACCAGCAAAGGTTATTGTTCAG

TTGGTCACAAATGGAAAAAATATCCACCTGCATGCCCACAGCCTGGTGG

GAAAACACTGTGAGGATGGGATCTGCACTGTAACTGCTGGACCCAAGGA

CATGGTGGTCGGCTTCGCAAACCTGGGTATACTTCATGTGACAAAGAAA

AAAGTATTTGAAACACTGGAAGCACGAATGACAGAGGCGTGTATAAGGG

GCTATAATCCTGGACTCTTGGTGCACCCTGACCTTGCCTATTTGCAAGC

AGAAGGTGGAGGGGACCGGCAGCTGGGAGATCGGGAAAAAGAGCTAATC

CGCCAAGCAGCTCTGCAGCAGACCAAGGAGATGGACCTCAGCGTGGTGC

GGCTCATGTTTACAGCTTTCTTCCGGATAGCACTGGCAGCTTCACAAG

GCGCCTGGAACCCGTGGTATCAGACGCCATCTATGACAGTAAAGCCCCC

AATGCATCCAACTTGAAAATTGTAAGAATGGACAGGACAGCTGGATGTG

TGACTGGAGGGGAGGAAATTTATCTTCTTTGTGACAAAGTTCAGAAAGA

TGACATCCAGATTCGATTTTATGAAGAGGAAGAAAATGGTGGAGTCTGG

GAAGGATTTGGAGATTTTTCCCCCACAGATGTTCATAGACAATTTGCCA

TTGTCTTCAAAACTCCAAAGTATAAAGATATTAATATTACAAAACCAGC

CTCTGTGTTTGTCCAGCTTCGGAGGAAATCTGACTTGGAAACTAGTGAA

CCAAAACCTTTCCTCTACTATCCTGAAATCAAAGATAAGAAGAAGTGC

AGAGGAAACGTCAGAAGCTCATGCCCAATTTTTCGGATAGTTTCGGCGG

TGGTAGTGGTGCTGGAGCTGGAGGCGGAGGCATGTTTGGTAGTGGCGGT

GGAGGAGGGGGCACTGGAAGTACAGGTCCAGGGTATAGCTTCCCACACT

ATGGATTTCCTACTTATGGTGGGATTACTTTCCATCCTGGAACTACTAA

ATCTAATGCTGGGATGAAGCATGGAACCATGGACACTGAATCTAAAAAG

GACCCTGAAGGTTGTGACAAAAGTGATGACAAAAACACTGTAAACCTCT

TTGGGAAAGTTATTGAAACCACAGAGCAAGATCAGGAGCCCAGCGAGGC

CACCGTTGGGAATGGTGAGGTCACTCTAACGTATGCAACAGGAACAAAA

GAAGAGAGTGCTGGAGTTCAGGATAACCTCTTTCTAGAGAAGGCTATGC

AGCTTGCAAAGAGGCATGCCAATGCCCTTTTCGACTACGCGGTGACAGG

AGACGTGAAGATGCTGCTGGCCGTCCAGCGCCATCTCACTGCTGTGCAG

GATGAGAATGGGACAGTGTCTTACACTTAGCAATCATCCACCTTCATT

CTCAACTTGTGAGGGATCTACTAGAAGTCACATCTGGTTTGATTTCTGA

TGACATTATCAACATGAGAAATGATCTGTACCAGACGCCCTTGCACTTG

GCAGTGATCACTAAGCAGGAAGATGTGGTGGAGGATTTGCTGAGGGCTG

GGGCCGACCTGAGCCTTCTGGACCGCTTGGGTAACTCTGTTTTGCACCT

AGCTGCCAAAGAAGGACATGATAAAGTTCTCAGTATCTTACTCAAGCAC

AAAAAGGCAGCACTACTTCTTGACCACCCCAACGGGGACGGTCTGAATG

CCATTCATCTAGCCATGATGAGCAATAGCCTGCCATGTTTGCTGCTGCT

GGTGGCCGCTGGGGCTGACGTCAATGCTCAGGAGCAGAAGTCCGGGCGC

ACAGCACTGCACCTGGCTGTGGAGCACGACAACATCTCATTGGCAGGCT

GCCTGCTCCTGGAGGGTGATGCCCATGTGGACAGTACTACCTACGATGG

AACCACACCCCTGCATATAGCAGCTGGGAGAGGGTCCACCAGGCTGGCA

GCTCTTCTCAAAGCAGCAGGAGCAGATCCCCTGGTGGAGAACTTTGAGC

CTCTCTATGACCTGGATGACTCTTGGGAAAATGCAGGAGAGGATGAAGG

AGTTGTGCCTGGAACCACGCCTCTAGATATGGCCACCAGCTGGCAGGTA

TTTGACATATTAAATGGGAAACCATATGAGCCAGAGTTTACATCTGATG

ATTTACTAGCACAAGGAGACATGAAAGCTGGCTGAAGATGTGAAGCT

GCAGCTGTATAAGTTACTAGAAATTCCTGATCCAGACAAAAACTGGGCT

ACTCTGGCGCAGAAATTAGGTCTGGGGATACTTAATAATGCCTTCCGGC

TGAGTCCTGCTCCTTCCAAAACACTTATGGACAACTATGAGGTCTCTGG

GGGTACAGTCAGAGAGCTGGTGGAGGCCCTGAGACAAATGGGCTACACC

GAAGCAATTGAAGTGATCCAGGCAGCCTCCAGCCCAGTGAAGACCACCT

CTCAGGCCCACTCGCTGCCTCTCTCGCCTGCCTCCACAAGGCAGCAAAT

AGACGAGCTCCGAGACAGTGACAGTGTCTGCGACAGCGGCGTGGAGACA

TCCTTCCGCAAACTCAGCTTTACCGAGTCTCTGACCAGTGGTGCCTCAC

TGCTAACTCTCAACAAAATGCCCCATGATTATGGGCAGGAAGGACCTCT

AGAAGGCAAAATTTAG.

Human NIK CDS (SEQ ID NO: 28)
ATGGCAGTGATGGAAATGGCCTGCCCAGGTGCCCCTGGCTCAGCAGTGG

GGCAGCAGAAGGAACTCCCCAAAGCCAAGGAGAAGACGCCGCCACTGGG

GAAGAAACAGAGCTCCGTCTACAAGCTTGAGGCCGTGGAGAAGAGCCCT

GTGTTCTGCGGAAAGTGGGAGATCCTGAATGACGTGATTACCAAGGGCA

CAGCCAAGGAAGGCTCCGAGGCAGGGCCAGCTGCCATCTCTATCATCGC

CCAGGCTGAGTGTGAGAATAGCCAAGAGTTCAGCCCCACCTTTTCAGAA

CGCATTTTCATCGCTGGGTCCAAACAGTACAGCCAGTCCGAGAGTCTTG

ATCAGATCCCCAACAATGTGGCCCATGCTACAGAGGGCAAAATGGCCCG

TGTGTGTTGGAAGGGAAAGCGTCGCAGCAAAGCCCGGAAGAAACGGAAG

AAGAAGAGCTCAAAGTCCCTGGCTCATGCAGGAGTGGCCTTGGCCAAAC

CCCTCCCCAGGACCCCTGAGCAGGAGAGCTGCACCATCCCAGTGCAGGA

GGATGAGTCTCCACTCGGCGCCCCATATGTTAGAAACACCCCGCAGTTC

ACCAAGCCTCTGAAGGAACCAGGCCTTGGGCAACTCTGTTTTAAGCAGC

TTGGCGAGGGCCTACGGCCGGCTCTGCCTCGATCAGAACTCCACAAACT

GATCAGCCCCTTGCAATGTCTGAACCACGTGTGGAAACTGCACCACCCC

CAGGACGGAGGCCCCCTGCCCCTGCCCACGCACCCCTTCCCCTATAGCA

GACTGCCTCATCCCTTCCCATTCCACCCTCTCCAGCCCTGGAAACCTCA

CCCTCTGGAGTCCTTCCTGGGCAAACTGGCCTGTGTAGACAGCCAGAAA

CCCTTGCCTGACCCACACCTGAGCAAACTGGCCTGTGTAGACAGTCCAA

AGCCCCTGCCTGGCCCACACCTGGAGCCCAGCTGCCTGTCTCGTGGTGC

-continued

CCATGAGAAGTTTTCTGTGGAGGAATACCTAGTGCATGCTCTGCAAGGC
AGCGTGAGCTCAGGCCAGGCCCACAGCCTGACCAGCCTGGCCAAGACCT
GGGCAGCAAGGGGCTCCAGATCCCGGGAGCCCAGCCCCAAAACTGAGGA
CAACGAGGGTGTCCTGCTCACTGAGAAACTCAAGCCAGTGGATTATGAG
TACCGAGAAGAAGTCCACTGGGCCACGCACCAGCTCCGCCTGGGCAGAG
GCTCCTTCGGAGAGGTGCACAGGATGGAGGACAAGCAGACTGGCTTCCA
GTGCGCTGTCAAAAAGGTGCGGCTGGAAGTATTTCGGGCAGAGGAGCTG
ATGGCATGTGCAGGATTGACCTCACCCAGAATTGTCCCTTTGTATGGAG
CTGTGAGAGAAGGGCCTTGGGTCAACATCTTCATGGAGCTGCTGGAAGG
TGGCTCCCTGGGCCAGCTGGTCAAGGAGCAGGGCTGTCTCCCAGAGGAC
CGGGCCCTGTACTACCTGGGCCAGGCCCTGGAGGGTCTGGAATACCTCC
ACTCACGAAGGATTCTGCATGGGGACGTCAAAGCTGACAACGTGCTCCT
GTCCAGCGATGGGAGCCACGCAGCCCTCTGTGACTTTGGCCATGCTGTG
TGTCTTCAACCTGATGGCCTGGGAAAGTCCTTGCTCACAGGGGACTACA
TCCCTGGCACAGAGACCCACATGGCTCCGGAGGTGGTGCTGGGCAGGAG
CTGCGACGCCAAGGTGGATGTCTGGAGCAGCTGCTGTATGATGCTGCAC
ATGCTCAACGGCTGCCACCCCTGGACTCAGTTCTTCCGAGGGCCGCTCT
GCCTCAAGATTGCCAGCGAGCCTCCGCCTGTGAGGGAGATCCCACCCTC
CTGCGCCCCTCTCACAGCCCAGGCCATCCAAGAGGGGCTGAGGAAAGAG
CCCATCCACCGCGTGTCTGCAGCGGAGCTGGGAGGGAAGGTGAACCGGG
CACTACAGCAAGTGGGAGGTCTGAAGAGCCCTTGGAGGGGAGAATATAA
AGAACCAAGACATCCACCGCCAAATCAAGCCAATTACCACCAGACCCTC
CATGCCCAGCCGAGAGAGCTTTCGCCAAGGGCCCCAGGGCCCCGGCCAG
CTGAGGAGACAACAGGCAGAGCCCCTAAGCTCCAGCCTCCTCTCCCACC
AGAGCCCCCAGAGCCAAACAAGTCTCCTCCCTTGACTTTGAGCAAGGAG
GAGTCTGGGATGTGGGAACCCTTACCTCTGTCCTCCCTGGAGCCAGCCC
CTGCCAGAAACCCCAGCTCACCAGAGCGGAAAGCAACCGTCCCGGAGCA
GGAACTGCAGCAGCTGGAAATAGAATTATTCCTCAACAGCCTGTCCCAG
CCATTTTCTCTGGAGGAGCAGGAGCAAATTCTCTCGTGCCTCAGCATCG
ACAGCCTCTCCCTGTCGGATGACAGTGAGAAGAACCCATCAAAGGCCTC
TCAAAGCTCGCGGGACACCCTGAGCTCAGGCGTACACTCCTGGAGCAGC
CAGGCCGAGGCTCGAAGCTCCAGCTGGAACATGGTGCTGGCCCGGGGGC
GGCCCACCGACACCCCAAGCTATTTCAATGGTGTGAAAGTCCAAATACA
GTCTCTTAATGGTGAACACCTGCACATCCGGGAGTTCCACCGGGTCAAA
GTGGGAGACATCGCCACTGGCATCAGCAGCCAGATCCCAGCTGCAGCCT
TCAGCTTGGTCACCAAAGACGGGCAGCCTGTTCGCTACGACATGGAGGT
GCCAGACTCGGGCATCGACCTGCAGTGCACACTGGCCCCTGATGGCAGC
TTCGCCTGGAGCTGGAGGGTCAAGCATGGCCAGCTGGAGAACAGGCCCT
AA.

-continued

Human p38 CDS (SEQ ID NO: 29)
ATGTCTCAGGAGAGGCCCACGTTCTACCGGCAGGAGCTGAACAAGACAA
TCTGGGAGGTGCCCGAGCGTTACCAGAACCTGTCTCCAGTGGGCTCTGG
CGCCTATGGCTCTGTGTGTGCTGCTTTTGACACAAAAACGGGGTTACGT
GTGGCAGTGAAGAAGCTCTCCAGACCATTTCAGTCCATCATTCATGCGA
AAAGAACCTACAGAGAACTGCGGTTACTTAAACATATGAAACATGAAAA
TGTGATTGGTCTGTTGGACGTTTTTACACCTGCAAGGTCTCTGGAGGAA
TTCAATGATGTGTATCTGGTGACCCATCTCATGGGGGCAGATCTGAACA
ACATTGTGAAATGTCAGAAGCTTACAGATGACCATGTTCAGTTCCTTAT
CTACCAAATTCTCCGAGGTCTAAAGTATATACATTCAGCTGACATAATT
CACAGGGACCTAAAACCTAGTAATCTAGCTGTGAATGAAGACTGTGAGC
TGAAGATTCTGGATTTTGGACTGGCTCGGCACACAGATGATGAAATGAC
AGGCTACGTGGCCACTAGGTGGTACAGGGCTCCTGAGATCATGCTGAAC
TGGATGCATTACAACCAGACAGTTGATATTTGGTCAGTGGGATGCATAA
TGGCCGAGCTGTTGACTGGAAGAACATTGTTTCCTGGTACAGACCATAT
TAACCAGCTTCAGCAGATTATGCGTCTGACAGGAACACCCCCCGCTTAT
CTCATTAACAGGATGCCAAGCCATGAGGCAAGAAACTATATTCAGTCTT
TGACTCAGATGCCGAAGATGAACTTTGCGAATGTATTTATTGGTGCCAA
TCCCCTGGCTGTCGACTTGCTGGAGAAGATGCTTGTATTGGACTCAGAT
AAGAGAATTACAGCGGCCCAAGCCCTTGCACATGCCTACTTTGCTCAGT
ACCACGATCCTGATGATGAACCAGTGGCCGATCCTTATGATCAGTCCTT
TGAAAGCAGGGACCTCCTTATAGATGAGTGGAAAAGCCTGACCTATGAT
GAAGTCATCAGCTTTGTGCCACCACCCCTTGACCAAGAAGAGATGGAGT
CCTGA.

Human PKR CDS (SEQ ID NO: 30)
ATGGCTGGTGATCTTTCAGCAGGTTTCTTCATGGAGGAACTTAATACAT
ACCGTCAGAAGCAGGGAGTAGTACTTAAATATCAAGAACTGCCTAATTC
AGGACCTCCACATGATAGGAGGTTTACATTTCAAGTTATAATAGATGGA
AGAGAATTTCCAGAAGGTGAAGGTAGATCAAAGAAGGAAGCAAAAAATG
CCGCAGCCAAATTAGCTGTTGAGATACTTAATAAGGAAAAGAAGGCAGT
TAGTCCTTTATTATTGACAACAACGAATTCTTCAGAAGGATTATCCATG
GGGAATTACATAGGCCTTATCAATAGAATTGCCCAGAAGAAAAGACTAA
CTGTAAATTATGAACAGTGTGCATCGGGGGTGCATGGGCCAGAAGGATT
TCATTATAAATGCAAAATGGGACAGAAAGAATATAGTATTGGTACAGGT
TCTACTAAACAGGAAGCAAAACAATTGGCCGCTAAACTTGCATATCTTC
AGATATTATCAGAAGAAACCTCAGTGAAATCTGACTACCTGTCCTCTGG
TTCTTTTGCTACTACGTGTGAGTCCCAAAGCAACTCTTTAGTGACCAGC
ACACTCGCTTCTGAATCATCATCTGAAGGTGACTTCTCAGCAGATACAT
CAGAGATAAATTCTAACAGTGACAGTTTAAACAGTTCTTCGTTGCTTAT
GAATGGTCTCAGAAATAATCAAAGGAAGGCAAAAAGATCTTTGGCACCC
AGATTTGACCTTCCTGACATGAAAGAAACAAAGTATACTGTGGACAAGA

```
GGTTTGGCATGGATTTTAAAGAAATAGAATTAATTGGCTCAGGTGGATT
TGGCCAAGTTTTCAAAGCAAAACACAGAATTGACGGAAAGACTTACGTT
ATTAAACGTGTTAAATATAATAACGAGAAGGCGGAGCGTGAAGTAAAAG
CATTGGCAAAACTTGATCATGTAAATATTGTTCACTACAATGGCTGTTG
GGATGGATTTGATTATGATCCTGAGACCAGTGATGATTCTCTTGAGAGC
AGTGATTATGATCCTGAGAACAGCAAAAATAGTTCAAGGTCAAAGACTA
AGTGCCTTTTCATCCAAATGGAATTCTGTGATAAAGGGACCTTGGAACA
ATGGATTGAAAAAGAAGAGGCGAGAAACTAGACAAAGTTTTGGCTTTG
GAACTCTTTGAACAAATAACAAAAGGGGTGGATTATATACATTCAAAAA
AATTAATTCATAGAGATCTTAAGCCAAGTAATATATTCTTAGTAGATAC
AAAACAAGTAAAGATTGGAGACTTTGGACTTGTAACATCTCTGAAAAAT
GATGGAAAGCGAACAAGGAGTAAGGGAACTTTGCGATACATGAGCCCAG
AACAGATTTCTTCGCAAGACTATGGAAAGGAAGTGGACCTCTACGCTTT
GGGGCTAATTCTTGCTGAACTTCTTCATGTATGTGACACTGCTTTTGAA
ACATCAAAGTTTTTCACAGACCTACGGATGGCATCATCTCAGATATAT
TTGATAAAAAGAAAAAACTCTTCTACAGAAATTACTCTCAAAGAAACC
TGAGGATCGACCTAACACATCTGAAATACTAAGGACCTTGACTGTGTGG
AAGAAAAGCCCAGAGAAAAATGAACGACACACATGTTAG.

Human Rae CDS (SEQ ID NO: 31)
ATGAGCGACGTGGCTATTGTGAAGGAGGGTTGGCTGCACAAACGAGGGG
AGTACATCAAGACCTGGCGGCCACGCTACTTCCTCCTCAAGAATGATGG
CACCTTCATTGGCTACAAGGAGCGGCCGCAGGATGTGGACCAACGTGAG
GCTCCCCTCAACAACTTCTCTGTGGCGCAGTGCCAGCTGATGAAGACGG
AGCGGCCCCGGCCCAACACCTTCATCATCCGCTGCCTGCAGTGGACCAC
TGTCATCGAACGCACCTTCCATGTGGAGACTCCTGAGGAGCGGGAGGAG
TGGACAACCGCCATCCAGACTGTGGCTGACGGCCTCAAGAAGCAGGAGG
AGGAGGAGATGGACTTCCGGTCGGGCTCACCCAGTGACAACTCAGGGGC
TGAAGAGATGGAGGTGTCCCTGGCCAAGCCCAAGCACCGCGTGACCATG
AACGAGTTTGAGTACCTGAAGCTGCTGGGCAAGGGCACTTTCGGCAAGG
TGATCCTGGTGAAGGAGAAGGCCACAGGCCGCTACTACGCCATGAAGAT
CCTCAAGAAGGAAGTCATCGTGGCCAAGGACGAGGTGGCCCACACACTC
ACCGAGAACCGCGTCCTGCAGAACTCCAGGCACCCCTTCCTCACAGCCC
TGAAGTACTCTTTCCAGACCCACGACCGCCTCTGCTTTGTCATGGAGTA
CGCCAACGGGGGCGAGCTGTTCTTCCACCTGTCCCGGGAGCGTGTGTTC
TCCGAGGACCGGGCCCGCTTCTATGGCGCTGAGATTGTGTCAGCCCTGG
ACTACCTGCACTCGGAGAAGAACGTGGTGTACCGGGACCTCAAGCTGGA
GAACCTCATGCTGGACAAGGACGGGCACATTAAGATCACAGACTTCGGG
CTGTGCAAGGAGGGGATCAAGGACGGTGCCACCATGAAGACCTTTTGCG
GCACACCTGAGTACCTGGCCCCCGAGGTGCTGGAGGACAATGACTACGG
CCGTGCAGTGGACTGGTGGGGCTGGCGTGGTCATGTACGAGATGATG
TGCGGTCGCCTGCCCTTCTACAACCAGGACCATGAGAAGCTTTTTGAGC
```
```
TCATCCTCATGGAGGAGATCCGCTTCCCGCGCACGCTTGGTCCCGAGGC
CAAGTCCTTGCTTTCAGGGCTGCTCAAGAAGGACCCCAAGCAGAGGCTT
GGCGGGGGCTCCGAGGACGCCAAGGAGATCATGCAGCATCGCTTCTTTG
CCGGTATCGTGTGGCAGCACGTGTACGAGAAGAAGCTCAGCCCACCCTT
CAAGCCCCAGGTCACGTCGGAGACTGACACCAGGTATTTTGATGAGGAG
TTCACGGCCCAGATGATCACCATCACACCACCTGACCAAGATGACAGCA
TGGAGTGTGTGGACAGCGAGCGCAGGCCCCACTTCCCCCAGTTCTCCTA
CTCGGCCAGCGGCACGGCCTGA.

Human Raf CDS (SEQ ID NO: 32)
ATGGCTAGCAAACGAAAATCTACAACTCCATGCATGGTTCGGACATCAC
AAGTAGTAGAACAAGATGTGCCCGAGGAAGTAGACAGGGCCAAAGAGAA
AGGAATCGGCACACCACAGCCTGACGTGGCCAAGGACAGTTGGGCAGCA
GAACTTGAAAACTCTTCCAAAGAAAACGAAGTGATAGAGGTGAAATCTA
TGGGGGAAAGCCAGTCCAAAAAACTCCAAGGTGGTTATGAGTGCAAATA
CTGCCCCTACTCCACGCAAAACCTGAACGAGTTCACGGAGCATGTCGAC
ATGCAGCATCCCAACGTGATTCTCAACCCCCTCTACGTGTGTGCAGAAT
GTAACTTCACAACCAAAAAGTACGACTCCCTATCCGACCACAACTCCAA
GTTCCATCCCGGGGAGGCCAACTTCAAGCTGAAGTTAATTAAACGCAAT
AATCAAACTGTCTTGGAACAGTCCATCGAAACCACCAACCATGTCGTGT
CCATCACCACCAGTGGCCCTGGAACTGGTGACAGTGATTCTGGGATCTC
GGTGAGTAAAACCCCCATCATGAAGCCTGGAAAACCAAAAGCGGATGCC
AAGAAGGTGCCCAAGAAGCCCGAGGAGATCACCCCCGAGAACCACGTGG
AAGGGACCGCCCGCCTGGTGACAGACACAGCTGAGATCCTCTCGAGACT
CGGCGGGGTGGAGCTCCTCCAAGACACATTAGGACACGTCATGCCTTCT
GTACAGCTGCCACCAAATATCAACCTTGTGCCCAAGGTCCCTGTCCCAC
TAAATACTACCAAATACAACTCTGCCCTGGATACAAATGCCACGATGAT
CAACTCTTTCAACAAGTTTCCTTACCCGACCCAGGCTGAGTTGTCCTGG
CTGACAGCTGCCTCCAAACACCCAGAGGAGCACATCAGAATCTGGTTTG
CCACCCAGCGCTTAAAGCATGGCATCAGCTGGTCCCCAGAAGAGGTGGA
GGAGGCCCGGAAGAAGATGTTCAACGGCACCATCCAGTCAGTACCCCCG
ACCATCACTGTGCTGCCCGCCCAGTTGGCCCCCACAAAGGTGACGCAGC
CCATCCTCCAGACGGCTCTACCGTGCCAGATCCTCGGCCAGACTAGCCT
GGTGCTGACTCAGGTGACCAGCGGGTCAACAACCGTCTCTTGCTCCCCC
ATCACACTTGCCGTGGCAGGAGTCACCAACCATGGCCAGAAGAGACCCT
TGGTGACTCCCCAAGCTGCCCCCGAACCCAAGCGTCCACACATCGCTCA
GGTGCCAGAGCCCCACCCAAGGTGGCCAACCCCCCGCTCACACCAGCC
AGTGACCGCAAGAAGACAAAGGAGCAGATAGCACATCTCAAGGCCAGCT
TCTCCAGAGCCAGTTCCCTGACGATGCCGAGGTTTACCGGCTCATCGA
GGTGACTGGCCTTGCCAGGAGCGAGATCAAGAAGTGGTTCAGTGACCAC
CGATATCGGTGTCAAAGGGGCATCGTCCACATCACCAGCGAATCCCTTG
CCAAAGACCAGTTGGCCATCGCGGCCTCCCGACACGGTCGCACGTATCA
```

-continued
TGCGTACCCAGACTTTGCCCCCCAGAAGTTCAAAGAGAAAACACAGGGT
CAGGTTAAAATCTTGGAAGACAGCTTTTTGAAAAGTTCTTTTCCTACCC
AAGCAGAACTGGATCGGCTAAGGGTGGAGACCAAGCTGAGCAGGAGAGA
GATCGACTCCTGGTTCTCGGAGAGGCGGAAGCTTCGAGACAGCATGGAA
CAAGCTGTCTTGGATTCCATGGGGTCTGGCAAAAAAGGCCAAGATGTGG
GAGCCCCCAATGGTGCTCTGTCTCGACTCGACCAGCTCTCCGGTGCCCA
GTTAACAAGTTCTCTGCCCAGCCCTTCGCCAGCAATTGCAAAAGTCAA
GAACAGGTTCATCTCCTGAGGAGCACGTTTGCAAGAACCCAGTGGCCTA
CTCCCCAGGAGTACGACCAGTTAGCGGCCAAGACTGGCCTGGTCCGAAC
TGAGATTGTGCGTTGGTTCAAGGAGAACAGATGCTTGCTGAAAACGGGA
ACCGTGAAGTGGATGGAGCAGTACCAGCACCAGCCCATGGCAGATGATC
ACGGCTACGATGCCGTAGCAAGGAAAGCAACAAAACCCATGGCCGAGAG
CCCAAAGAACGGGGGTGATGTGGTTCCACAATATTACAAGGACCCCAAA
AAGCTCTGCGAAGAGGACTTGGAGAAGTTGGTGACCAGGGTAAAAGTAG
GCAGCGAGCCAGCAAAAGACTGTTTGCCAGCAAAGCCCTCAGAGGCCAC
CTCAGACCGGTCAGAGGGCAGCAGCCGGGACGGCCAGGGTAGCGACGAG
AACGAGGAGTCGAGCGTTGTGGATTACGTGGAGGTGACGGTCGGGGAGG
AGGATGCGATCTCAGATAGATCAGATAGCTGGAGTCAGGCTGCGGCAGA
GGTGTGTCGGAACTGGCTGAATCAGACTCCGACTGCGTCCCTGCAGAGG
CTGGCCAGGCCTAG.

Human K-Ras CDS (SEQ ID NO: 33)
ATGACTGAATATAAACTTGTGGTAGTTGGAGCTGGTGGCGTAGGCAAGA
GTGCCTTGACGATACAGCTAATTCAGAATCATTTTGTGGACGAATATGA
TCCAACAATAGAGGATTCCTACAGGAAGCAAGTAGTAATTGATGGAGAA
ACCTGTCTCTTGGATATTCTCGACACAGCAGGTCAAGAGGAGTACAGTG
CAATGAGGGACCAGTACATGAGGACTGGGGAGGGCTTTCTTTGTGTATT
TGCCATAAATAATACTAAATCATTTGAAGATATTCACCATTATAGAGAA
CAAATTAAAAGAGTTAAGGACTCTGAAGATGTACCTATGGTCCTAGTAG
GAAATAAATGTGATTTGCCTTCTAGAACAGTAGACACAAAACAGGCTCA
GGACTTAGCAAGAAGTTATGGAATTCCTTTTATTGAAACATCAGCAAAG
ACAAGACAGGGTGTTGATGATGCCTTCTATACATTAGTTCGAGAAATTC
GAAAACATAAAGAAAAGATGAGCAAAGATGGTAAAAAGAAGAAAAAGAA
GTCAAAGACAAAGTGTGTAATTATGTAA.

Human N-Ras CDS (SEQ ID NO: 34)
ATGACTGAGTACAAACTGGTGGTGGTTGGAGCAGGTGGTGTTGGGAAAA
GCGCACTGACAATCCAGCTAATCCAGAACCACTTTGTAGATGAATATGA
TCCCACCATAGAGGATTCTTACAGAAAACAAGTGGTTATAGATGGTGAA
ACCTGTTTGTTGGACATACTGGATACAGCTGGACAAGAAGAGTACAGTG
CCATGAGAGACCAATACATGAGGACAGGCGAAGGCTTCCTCTGTGTATT
TGCCATCAATAATAGCAAGTCATTTGCGGATATTAACCTCTACAGGGAG
CAGATTAAGCGAGTAAAAGACTCGGATGATGTACCTATGGTGCTAGTGG
GAAACAAGTGTGATTTGCCAACAAGGACAGTTGATACAAAACAAGCCCA -continued
CGAACTGGCCAAGAGTTACGGGATTCCATTCATTGAAACCTCAGCCAAG
ACCAGACAGGGTGTTGAAGATGCTTTTTACACACTGGTAAGAGAAATAC
GCCAGTACCGAATGAAAAAACTCAACAGCAGTGATGATGGGACTCAGGG
TTGTATGGGATTGCCATGTGTGGTGATGTAA.

Human RIP CDS (SEQ ID NO: 35)
ATGCAACCAGACATGTCCTTGAATGTCATTAAGATGAAATCCAGTGACT
TCCTGGAGAGTGCAGAACTGGACAGCGGAGGCTTTGGGAAGGTGTCTCT
GTGTTTCCACAGAACCCAGGGACTCATGATCATGAAAACAGTGTACAAG
GGGCCCAACTGCATTGAGCACAACGAGGCCCTCTTGGAGGAGGCGAAGA
TGATGAACAGACTGAGACACAGCCGGGTGGTGAAGCTCCTGGGCGTCAT
CATAGAGGAAGGGAAGTACTCCCTGGTGATGGAGTACATGGAGAAGGGC
AACCTGATGCACGTGCTGAAAGCCGAGATGAGTACTCCGCTTTCTGTAA
AAGGAAGGATAATTTTGGAAATCATTGAAGGAATGTGCTACTTACATGG
AAAAGGCGTGATACACAAGGACCTGAAGCCTGAAAATATCCTTGTTGAT
AATGACTTCCACATTAAGATCGCAGACCTCGGCCTTGCCTCCTTTAAGA
TGTGGAGCAAACTGAATAATGAAGAGCACAATGAGCTGAGGGAAGTGGA
CGGCACCGCTAAGAAGAATGCGGCACCCCTCTACTACATGGCGCCCGAG
CACCTGAATGACGTCAACGCAAAGCCCACAGAGAAGTCGGATGTGTACA
GCTTTGCTGTAGTACTCTGGGCGATATTTGCAAATAAGGAGCCATATGA
AAATGCTATCTGTGAGCAGCAGTTGATAATGTGCATAAAATCTGGGAAC
AGGCCAGATGTGGATGACATCACTGAGTACTGCCCAAGAGAAATTATCA
GTCTCATGAAGCTCTGCTGGGAAGCGAATCCGGAAGCTCGGCCGACATT
TCCTGGCATTGAAGAAAAATTTAGGCCTTTTTATTTAAGTCAATTAGAA
GAAAGTGTAGAAGAGGACGTGAAGAGTTTAAAGAAAGAGTATTCAAACG
AAAATGCAGTTGTGAAGAGAATGCAGTCTCTTCAACTTGATTGTGTGGC
AGTACCTTCAAGCCGGTCAAATTCAGCCACAGAACAGCCTGGTTCACTG
CACAGTTCCCAGGGACTTGGGATGGGTCCTGTGAGGAGTCCTGGTTTG
CTCCTTCCCTGGAGCACCCACAAGAAGAGAATGAGCCCAGCCTGCAGAG
TAAACTCCAAGACGAAGCCAACTACCATCTTTATGCAGCCGCATGGAC
AGGCAGACGAAACAGCAGCCCAGACAGAATGTGGCTTACAACAGAGAGG
AGGAAAGGAGACGCAGGGTCTCCCATGACCCTTTTGCACAGCAAAGACC
TTACGAGAATTTTCAGAATACAGAGGGAAAAGGCACTGCTTATTCCAGT
GCAGCCAGTCATGGTAATGCAGTGCACCAGCCCTCAGGGCTCACCAGCC
AACCTCAAGTACTGTATCAGAACAATGGATTATATAGCTCACATGGCTT
TGGAACAAGACCACTGGATCCAGGAACAGCAGGTCCCAGAGTTTGGTAC
AGGCCAATTCCAAGTCATATGCCTAGTCTGCATAATATCCCAGTGCCTG
AGACCAACTATCTAGGAAATACACCCACCATGCCATTCAGCTCCTTGCC
ACCAACAGATGAATCTATAAAATATACCATATACAATAGTACTGGCATT
CAGATTGGAGCCTACAATTATATGGAGATTGTGGGACGAGTTCATCAC
TACTAGACAGCACAAATACGAACTTCAAAGAAGAGCCAGCTGCTAAGTA
CCAAGCTATCTTTGATAATACCACTAGTCTGACGGATAAACACCTGGAC

CCAATCAGGGAAAATCTGGGAAAGCACTGGAAAAACTGTGCCCGTAAAC

TGGGCTTCACACAGTCTCAGATTGATGAAATTGACCATGACTATGAGCG

AGATGGACTGAAAGAAAAGGTTTACCAGATGCTCCAAAAGTGGGTGATG

AGGGAAGGCATAAAGGGAGCCACGGTGGGGAAGCTGGCCCAGGCGCTCC

ACCAGTGTTCCAGGATCGACCTTCTGAGCAGCTTGATTTACGTCAGCCA

GAACTAA.

Human TRAF6 CDS (SEQ ID NO: 36)
ATGAGTCTGCTAAACTGTGAAAACAGCTGTGGATCCAGCCAGTCTGAAA

GTGACTGCTGTGTGGCCATGGCCAGCTCCTGTAGCGCTGTAACAAAAGA

TGATAGTGTGGGTGGAACTGCCAGCACGGGGAACCTCTCCAGCTCATTT

ATGGAGGAGATCCAGGGATATGATGTAGAGTTTGACCCACCCCTGGAAA

GCAAGTATGAATGCCCCATCTGCTTGATGGCATTACGAGAAGCAGTGCA

AACGCCATGCGGCCATAGGTTCTGCAAAGCCTGCATCATAAAATCAATA

AGGGATGCAGGTCACAAATGTCCAGTTGACAATGAAATACTGCTGGAAA

ATCAACTATTTCCAGACAATTTTGCAAAACGTGAGATTCTTTCTCTGAT

GGTGAAATGTCCAAATGAAGGTTGTTTGCACAAGATGGAACTGAGACAT

CTTGAGGATCATCAAGCACATTGTGAGTTTGCTCTTATGGATTGTCCCC

AATGCCAGCGTCCCTTCCAAAAATTCCATATTAATATTCACATTCTGAA

GGATTGTCCAAGGAGACAGGTTTCTTGTGACAACTGTGCTGCATCAATG

GCATTTGAAGATAAAGAGATCCATGACCAGAACTGTCCTTTGGCAAATG

TCATCTGTGAATACTGCAATACTATACTCATCAGAGAACAGATGCCTAA

TCATTATGATCTAGACTGCCCTACAGCCCCAATTCCATGCACATTCAGT

ACTTTTGGTTGCCATGAAAAGATGCAGAGGAATCACTTGGCACGCCACC

TACAAGAGAACACCCAGTCACACATGAGAATGTTGGCCCAGGCTGTTCA

TAGTTTGAGCGTTATACCCGACTCTGGGTATATCTCAGAGGTCCGGAAT

TTCCAGGAAACTATTCACCAGTTAGAGGGTCGCCTTGTAAGACAAGACC

ATCAAATCCGGGAGCTGACTGCTAAAATGGAAACTCAGAGTATGTATGT

AAGTGAGCTCAAACGAACCATTCGAACCCTTGAGGACAAAGTTGCTGAA

ATCGAAGCACAGCAGTGCAATGGAATTTATATTTGGAAGATTGGCAACT

TTGGAATGCATTTGAAATGTCAAGAAGAGGAGAAACCTGTTGTGATTCA

TAGCCCTGGATTCTACACTGGCAAACCCGGGTACAAACTGTGCATGCGC

TTGCACCTTCAGTTACCGACTGCTCAGCGCTGTGCAAACTATATATCCC

TTTTTGTCCACACAATGCAAGGAGAATATGACAGCCACCTCCCTTGGCC

CTTCCAGGGTACAATACGCCTTACAATTCTTGATCAGTCTGAAGCACCT

GTAAGGCAAAACCACGAAGAGATAATGGATGCCAAACCAGAGCTGCTTG

CTTTCCAGCGACCCACAATCCCACGGAACCCAAAAGGTTTTGGCTATGT

AACTTTTATGCATCTGGAAGCCCTAAGACAAAGAACTTTCATTAAGGAT

GACACATTATTAGTGCGCTGTGAGGTCTCCACCCGCTTTGACATGGGTA

GCCTTCGGAGGGAGGGTTTTCAGCCACGAAGTACTGATGCAGGGGTATA

G.

Human TTP CDS (SEQ ID NO: 37)
ATGGCCAACCGTTACACCATGGATCTGACTGCCATCTACGAGAGCCTCC

TGTCGCTGAGCCCTGACGTGCCCGTGCCATCCGACCATGGAGGGACTGA

GTCCAGCCCAGGCTGGGGCTCCTCGGGACCCTGGAGCCTGAGCCCCTCC

GACTCCAGCCCGTCTGGGGTCACCTCCCGCCTGCCTGGCCGCTCCACCA

GCCTAGTGGAGGGCCGCAGCTGTGGCTGGGTGCCCCCACCCCCTGGCTT

CGCACCGCTGGCTCCCCGCCTGGGCCCTGAGCTGTCACCCTCACCCACT

TCGCCCACTGCAACCTCCACCACCCCCTCGCGCTACAAGACTGAGCTAT

GTCGGACCTTCTCAGAGAGTGGGCGCTGCCGCTACGGGGCCAAGTGCCA

GTTTGCCCATGGCCTGGGCGAGCTGCGCCAGGCCAATCGCCACCCCAAA

TACAAGACGGAACTCTGTCACAAGTTCTACCTCCAGGGCCGCTGCCCCT

ACGGCTCTCGCTGCCACTTCATCCACAACCCTAGCGAAGACCTGGCGGC

CCCGGGCCACCCTCCTGTGCTTCGCCAGAGCATCAGCTTCTCCGGCCTG

CCCTCTGGCCGCCGGACCTCACCACCACCACCAGGCCTGGCCGGCCCTT

CCCTGTCCTCCAGCTCCTTCTCGCCCTCCAGCTCCCCACCACCACCTGG

GGACCTTCCACTGTCACCCTCTGCCTTCTCTGCTGCCCCTGGCACCCCC

CTGGCTCGAAGAGACCCCACCCCAGTCTGTTGCCCCTCCTGCCGAAGGG

CCACTCCTATCAGCGTCTGGGGGCCCTTGGGTGGCCTGGTTCGGACCCC

CTCTGTACAGTCCCTGGGATCCGACCCTGATGAATATGCCAGCAGCGGC

AGCAGCCTGGGGGGCTCTGACTCTCCCGTCTTCGAGGCGGGAGTTTTTG

CACCACCCCAGCCCGTGGCAGCCCCCCGGCGACTCCCCATCTTCAATCG

CATCTCTGTTTCTGAGTGA.

An antisense nucleic acid molecule can be complementary to all or part of a non-coding region of the coding strand of a nucleotide sequence encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTPMEKK1protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein described herein. Antisense nucleic acids targeting a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTPMEKK1protein can be designed using the software available at the Integrated DNA Technologies website.

An antisense nucleic acid can be, for example, about 5, 10, 15, 18, 20, 22, 24, 25, 26, 28, 30, 32, 35, 36, 38, 40, 42, 44, 45, 46, 48, or 50 nucleotides or more in length. An antisense oligonucleotide can be constructed using enzymatic ligation reactions and chemical synthesis using procedures known in the art. For example, an antisense nucleic acid can be chemically synthesized using variously modified nucleotides or naturally occurring nucleotides designed to increase the physical stability of the duplex formed between the antisense and sense nucleic acids, e.g., phosphorothioate derivatives and acridine substituted nucleotides or to increase the biological stability of the molecules.

Examples of modified nucleotides which can be used to generate an antisense nucleic acid include 1-methylguanine, 1-methylinosine, 2,2-dimethylguanine, 2-methyladenine, 2-methylguanine, 3-methylcytosine, 2-methylthio-N6-isopentenyladenine, uracil-5-oxyacetic acid (v), wybutoxosine, pseudouracil, queosine, 2-thiocytosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a subject, e.g., a human subject. Alternatively, they can be generated in situ such that they hybridize with or bind to cellular mRNA and/or genomic DNA encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., an adenovirus vector, a lentivirus, or a retrovirus).

An antisense nucleic acid can be an α-anomeric nucleic acid molecule. An α-anomeric nucleic acid molecule forms specific double-stranded hybrids with complementary RNA in which, contrary to the usual, (3-units, the strands run parallel to each other (Gaultier et al., Nucleic Acids Res. 15:6625-6641, 1987). The antisense nucleic acid can also comprise a chimeric RNA-DNA analog (Inoue et al., FEBS Lett. 215:327-330, 1987) or a 2'-O-methylribonucleotide (Inoue et al., Nucleic Acids Res. 15:6131-6148, 1987).

Another example of an inhibitory nucleic acid is a ribozyme that has specificity for a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA, e.g., specificity for any one of SEQ ID NOs: 1-37). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haseloff and Gerlach, Nature 334:585-591, 1988)) can be used to catalytically cleave mRNA transcripts to thereby inhibit translation of the protein encoded by the mRNA. An AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be used to select a catalytic RNA having a specific ribonuclease activity from a pool of RNA molecules. See, e.g., Bartel et al., Science 261:1411-1418, 1993.

Alternatively, a ribozyme having specificity for an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be designed based upon the nucleotide sequence of any of the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA sequences disclosed herein. For example, a derivative of a Tetrahymena L-19 IVS RNA can be constructed in which the nucleotide sequence of the active site is complementary to the nucleotide sequence to be cleaved in an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (see, e.g., U.S. Pat. Nos. 4,987,071 and 5,116,742).

An inhibitory nucleic acid can also be a nucleic acid molecule that forms triple helical structures. For example, expression of an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide can be inhibited by targeting nucleotide sequences complementary to the regulatory region of the gene encoding the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Maher, Bioassays 14(12):807-15, 1992; Helene, Anticancer Drug Des. 6(6):569-84, 1991; and Helene, Ann. N.Y. Acad. Sci. 660:27-36, 1992.

In various embodiments, inhibitory nucleic acids can be modified at the sugar moiety, the base moiety, or phosphate backbone to improve, e.g., the solubility, stability, or hybridization, of the molecule. For example, the deoxyribose phosphate backbone of the nucleic acids can be modified to generate peptide nucleic acids (see, e.g., Hyrup et al., Bioorganic Medicinal Chem. 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to RNA and DNA under conditions of low ionic strength. PNA oligomers can be synthesized using standard solid phase peptide synthesis protocols (see, e.g., Perry-O'Keefe et al., Proc. Natl. Acad.

Sci. U.S.A. 93:14670-675, 1996). PNAs can be used as antisense or antigene agents for sequence-specific modulation of gene expression by, e.g., inducing transcription or translation arrest or inhibiting replication.

Small Molecules

In some embodiments, the anti-TNFα agent is a small molecule. In some embodiments, the small molecule is a tumor necrosis factor-converting enzyme (TACE) inhibitor (e.g., Moss et al., *Nature Clinical Practice Rheumatology* 4: 300-309, 2008). In some embodiments, the anti-TNFα agent is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the TACE inhibitor is TMI-005 and BMS-561392. Additional examples of small molecule inhibitors are described in, e.g., He et al., *Science* 310(5750):1022-1025, 2005.

In some examples, the anti-TNFα agent is a small molecule that inhibits the activity of one of AP-1, ASK1, IKK, JNK, MAPK, MEKK 1/4, MEKK4/7, MEKK 3/6, NIK, TRADD, RIP, NF-κB, and TRADD in a cell (e.g., in a cell obtained from a subject, a mammalian cell).

In some examples, the anti-TNFα agent is a small molecule that inhibits the activity of one of CD14, MyD88 (see, e.g., Olson et al., *Scientific Reports* 5:14246, 2015), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, 5B590885, ZM 336372, sorafenib, GW5074, TAK-632, CEP-32496, encorafenib (LGX818), CCT196969, LY3009120, R05126766 (CH5126766), PLX7904, and MLN2480).

In some examples, the anti-TNFα agent TNFα inhibitor is a small molecule that inhibits the activity of one of MK2 (PF 3644022 and PHA 767491), JNK (e.g., AEG 3482, BI 78D3, CEP 1347, c-JUN peptide, IQ 15, JIP-1 (153-163), SP600125, SU 3327, and TCS JNK6o), c-jun (e.g., AEG 3482, BI 78D3, CEP 1347, c-JUN peptide, IQ 15, JIP-1 (153-163), SP600125, SU 3327, and TCS JNK6o), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), MEK1/2 (e.g., Facciorusso et al., *Expert Review Gastroentrol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, IRAK (Chaudhary et al., *J. Med. Chem.* 58(1):96-110, 2015), LBP (see, e.g., U.S. Pat. No. 5,705,398), and TRAF6 (e.g., 3-[(2,5-Dimethylphenyl) amino]-1-phenyl-2-propen-1-one).

In some embodiments of any of the methods described herein, the inhibitory nucleic acid can be about 10 nucleotides to about 50 nucleotides (e.g., about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 28 nucleotides, about 10 nucleotides to about 26 nucleotides, about 10 nucleotides to about 25 nucleotides, about 10 nucleotides to about 24 nucleotides, about 10 nucleotides to about 22 nucleotides, about 10 nucleotides to about 20 nucleotides, about 10 nucleotides to about 18 nucleotides, about 10 nucleotides to about 16 nucleotides, about 10 nucleotides to about 14 nucleotides, about 10 nucleotides to about 12 nucleotides, about 12 nucleotides to about 50 nucleotides, about 12 nucleotides to about 45 nucleotides, about 12 nucleotides to about 40 nucleotides, about 12 nucleotides to about 35 nucleotides, about 12 nucleotides to about 30 nucleotides, about 12 nucleotides to about 28 nucleotides, about 12 nucleotides to about 26 nucleotides, about 12 nucleotides to about 25 nucleotides, about 12 nucleotides to about 24 nucleotides, about 12 nucleotides to about 22 nucleotides, about 12 nucleotides to about 20 nucleotides, about 12 nucleotides to about 18 nucleotides, about 12 nucleotides to about 16 nucleotides, about 12 nucleotides to about 14 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 28 nucleotides, about 15 nucleotides to about 26 nucleotides, about 15 nucleotides to about 25 nucleotides, about 15 nucleotides to about 24 nucleotides, about 15 nucleotides to about 22 nucleotides, about 15 nucleotides to about 20 nucleotides, about 15 nucleotides to about 18 nucleotides, about 15 nucleotides to about 16 nucleotides, about 16 nucleotides to about 50 nucleotides, about 16 nucleotides to about 45 nucleotides, about 16 nucleotides to about 40 nucleotides, about 16 nucleotides to about 35 nucleotides, about 16 nucleotides to about 30 nucleotides, about 16 nucleotides to about 28 nucleotides, about 16 nucleotides to about 26 nucleotides, about 16 nucleotides to about 25 nucleotides, about 16 nucleotides to about 24 nucleotides, about 16 nucleotides to about 22 nucleotides, about 16 nucleotides to about 20 nucleotides, about 16 nucleotides to about 18 nucleotides, about 18 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 28 nucleotides, about 20 nucleotides to about 26 nucleotides, about 20 nucleotides to about 25 nucleotides, about 20 nucleotides to about 24 nucleotides, about 20 nucleotides to about 22 nucleotides, about 24 nucleotides to about 50 nucleotides, about 24 nucleotides to about 45 nucleotides, about 24 nucleotides to about 40 nucleotides, about 24 nucleotides to about 35 nucleotides, about 24 nucleotides to about 30 nucleotides, about 24 nucleotides to about 28 nucleotides, about 24 nucleotides to about 26 nucleotides, about 24 nucleotides to about 25 nucleotides, about 26 nucleotides to about 50 nucleotides, about 26 nucleotides to about 45 nucleotides, about 26 nucleotides to about 40 nucleotides, about 26 nucleotides to about 35 nucleotides, about 26 nucleotides to about 30 nucleotides, about 26 nucleotides to about 28 nucleotides, about 28 nucleotides to about 50 nucleotides, about 28 nucleotides to about 45 nucleotides, about 28 nucleotides to about 40 nucleotides, about 28 nucleotides to about 35 nucleotides, about 28 nucleotides to about 30 nucleotides, about 30 nucleotides to about 50 nucleotides, about 30 nucleotides to about 45 nucleotides, about 30 nucleotides to about 40 nucleotides, about 30 nucleotides to about 38 nucleotides, about 30 nucleotides to about 36 nucleotides, about 30 nucleotides to about 34 nucleotides, about 30 nucleotides to about 32 nucleotides, about 32 nucleotides to about 50 nucleotides, about 32 nucleotides to about 45 nucleotides, about 32 nucleotides to about 40 nucleotides, about 32 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, about 42 nucleotides to about 50 nucleotides, about 42 nucleotides to about 45 nucleotides, or about 45 nucleotides to about 50 nucleotides) in length. One skilled in the art will appreciate that inhibitory nucleic acids may comprises at least one modified nucleic acid at either the 5' or 3' end of DNA or RNA.

In some embodiments, the inhibitory nucleic acid can be formulated in a liposome, a micelle (e.g., a mixed micelle), a nanoemulsion, or a microemulsion, a solid nanoparticle, or a nanoparticle (e.g., a nanoparticle including one or more synthetic polymers). Additional exemplary structural features of inhibitory nucleic acids and formulations of inhibitory nucleic acids are described in US 2016/0090598.

In some embodiments, the inhibitory nucleic acid (e.g., any of the inhibitory nucleic acid described herein) can include a sterile saline solution (e.g., phosphate-buffered saline (PBS)). In some embodiments, the inhibitory nucleic acid (e.g., any of the inhibitory nucleic acid described herein) can include a tissue-specific delivery molecule (e.g., a tissue-specific antibody).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

PREPARATIVE EXAMPLES

The following abbreviations have the indicated meanings:
ACN=acetonitrile
AcOH=acetic acid
AIBN=Azodiisobutyronitrile
9-BBN=9-borabicyclo[3.3.1]nonane
$Boc_2O$=Di-tert-butyl dicarbonate
$(Bpin)_2$=4,4,4',4',5,5,5',5'-octamethyl-2,2'-bi(1,3,2-dioxaborolane)
CAN=Diammonium cerium(IV) nitrate
$CCl_4$=Perchloromethane
$CHCl_3$=Chloroform
$ClSO_2OH$=Chlorosulfonic acid
Conc.=Concentrated
$Cs_2CO_3$=Cesium carbonate
DAST=diethylaminosulfur trifluoride
DBU=1,8-diazabicycloundec-7-ene
DCM=dichloromethane
DEA=diethylamine
DMF=N,N-dimethylformamide
DMSO=dimethyl sulfoxide
DIEA=N,N-diisopropylethylamine
EtOH=ethanol
FA=formic acid
HCHO=Formaldehyde
Hex=hexane
HPLC=high performance liquid chromatography
IPA=propan-2-ol
LC-MS=liquid chromatography-mass spectrometry
LDA=Lithium diisopropylamide
Me=methyl
MeOH=methanol
$NaBH_3CN$=Sodium cyanoborohydride
NaSH=Sodium hydrosulfide
NBS=N-bromosuccinimide
n-BuLi=n-Butyllithium
NMR=nuclear magnetic resonance
$PCl_5$=Phosphorus pentachloride
$Pd_2(dba)_3$=tris(dibenzylideneacetone)dipalladium
$Pd(dppf)Cl_2$=dichloro[1,1'-bis(diphenylphosphino)ferrocene]palladium
$Pd(PPh_3)_2Cl_2$=Bis(triphenylphosphine)palladium(II) chloride
Ph=phenyl
PMB=p-methoxybenzyl
$PPh_3Cl_2$=dichlorotriphenylphosphorane
Rt=Retention time
RT=room temperature
SFC=supercritical fluid chromatogram
Sat.=saturated
TBAF=tetra-n-butylammonium fluoride
TBS=tert-butyldimethylsilyl
TBDPSCl=tert-butyldiphenylsilyl chloride
TBSCl=tert-butyldimethylsilyl chloride
t-BuOK=Potassium t-butoxide
t-BuONO=tert-Butyl nitrite
TEA=triethylamine
TFA=trifluoroacetic acid
THF=tetrahydrofuran
TLC=thin layer chromatography
UV=ultraviolet
X-phos=2-(Dicyclohexylphosphino)-2',4',6'-triisopropylbiphenyl General The progress of reactions was often monitored by TLC or LC-MS. The identity of the products was often confirmed by LC-MS. The LC-MS was recorded using one of the following methods.

Method A: Shim-pack XR-ODS, C18, 3×50 mm, 2.5 um column, 1.0 uL injection, 1.5 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 um column, 1.0 uL injection, 1.5 mL/min flow rate, 90-900 amu scan range, 190-400 nm UV range, 10-95% (1.1 min), 95% (0.6 min) gradient with ACN and water (0.5% $NH_4HCO_3$), 2 minute total run time.

Method C: Shim-pack XR-ODS, C18, 3×50 mm, 2.5 um column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 mm, 2.2 um column, 1.0 uL injection, 1.5 mL/min flow rate, 90-900 amu scan range, 190-400 nm UV range, 10-95% (2.1 min), 95% (0.6 min) gradient with ACN and water (0.5% $NH_4HCO_3$), 3 minute total run time.

The final targets were purified by Prep-HPLC. The Prep-HPLC was carried out using the following method.

Method E: Pre-HPLC: Column, XBridge Shield RP18 OBD (19×250 mm, 10 um); mobile phase, Water (10 mmol/L NH₄HCO₃) and ACN, UV detection 254/210 nm.

NMR was recorded on BRUKER NMR 300.03 MHz, DUL-C-H, ULTRASHIELD™300, AVANCE II 300 B-ACS™120 or BRUKER NMR 400.13 MHz, BBFO, ULTRASHIELD™400, AVANCE III 400, B-ACS™120.

Racemic compounds of this invention can be resolved to give individual enantiomers using a variety of known methods. For example, chiral stationary phases can be used and the elution conditions can include normal phase or supercritical fluid with or without acidic or basic additives. Enantiomerically pure acids or bases can be used to form diatereomeric salts with the racemic compounds whereby pure enantiomers can be obtained by fractional crystallization. The racemates can also be derivatized with enantiomerically pure auxiliary reagents to form diastereomeric mixtures that can be separated. The auxiliary is then removed to give pure enantiomers.

Scheme of final targets: Schemes 1-6 illustrate several conditions used for coupling of acid 1 and sulfonimidoyl-amide 2 to afford acyl sulfonimidoylamide 3. As used in the schemes, rings "A" and "B" may be substituted as disclosed herein.

Scheme 1

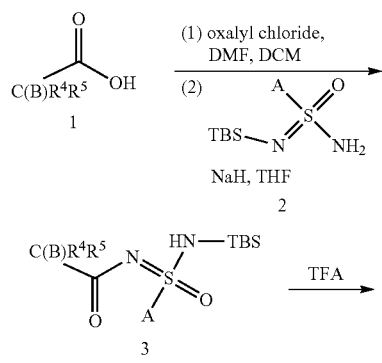

Scheme 1A

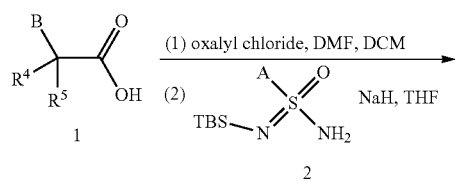

Scheme 1B

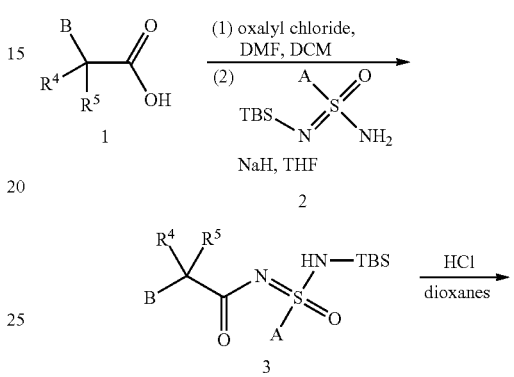

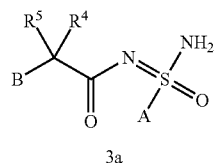

3a

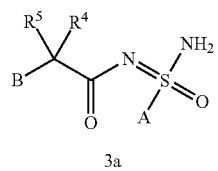

3a

Scheme 1C

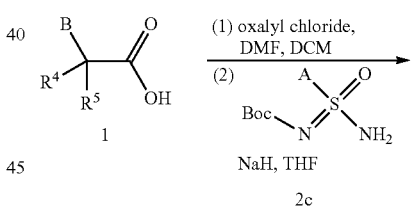

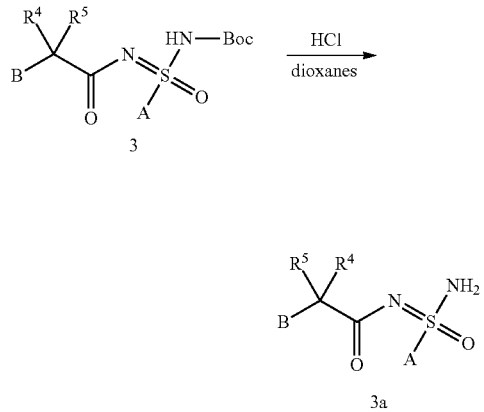

3a

Scheme 2
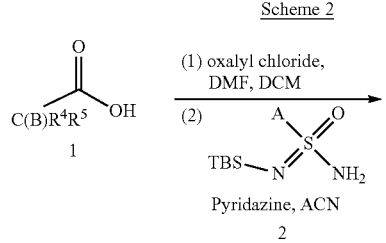
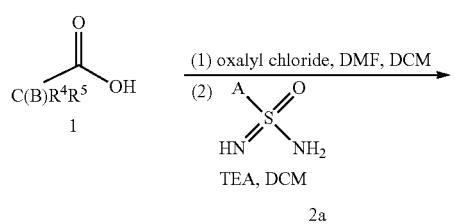
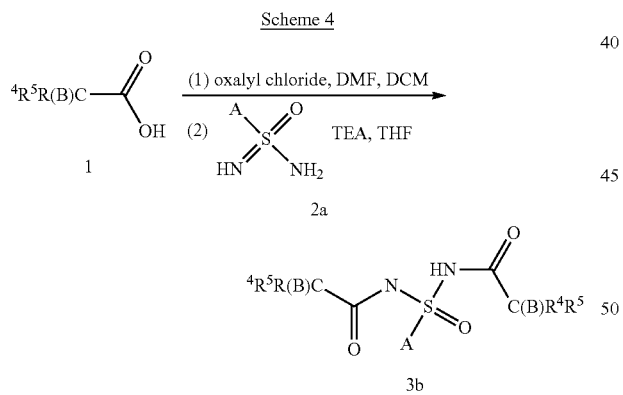
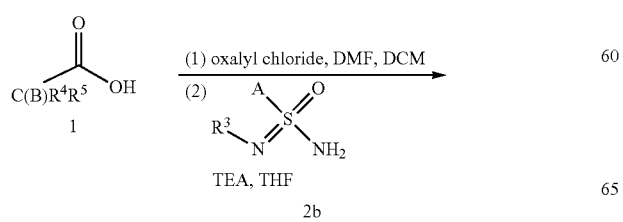
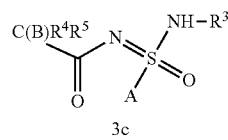
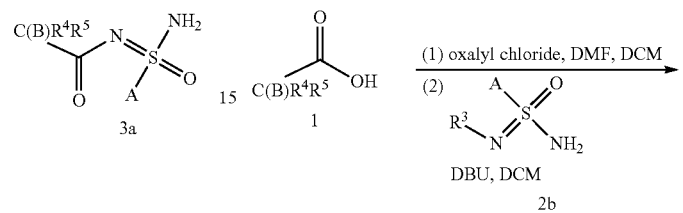
Schemes of Sulfonimidoylamide Intermediates: Schemes 7-12 illustrate the preparation of sulfonimidoylamide intermediates.
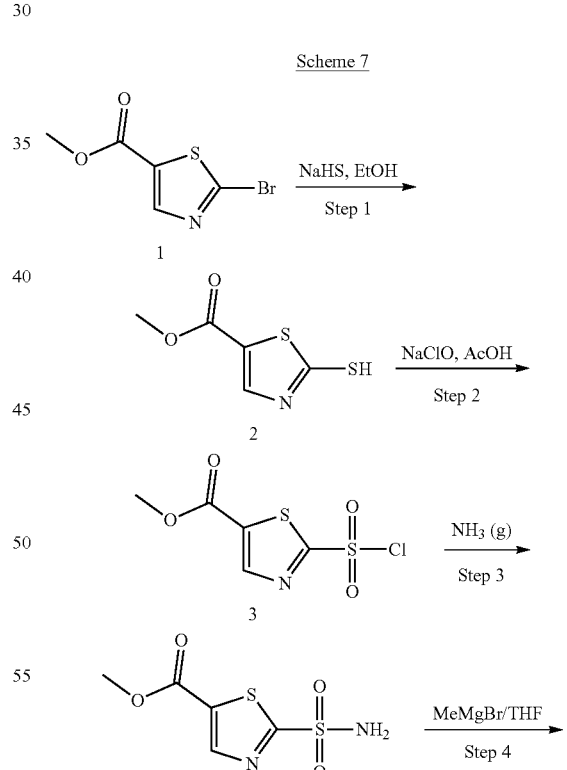

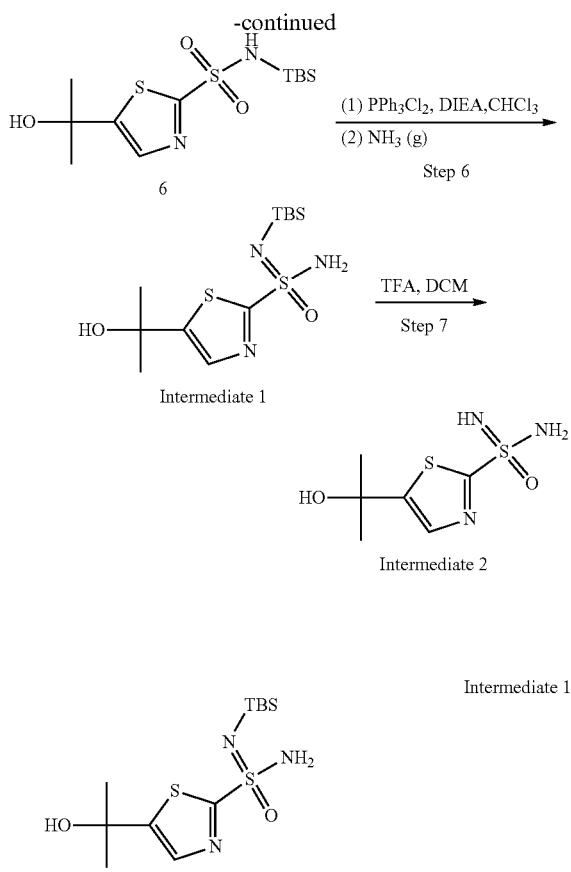

N'-(tert-butyl dimethylsilyl)-5-(2-hydroxypropan-2-yl)thiazole-2-sulfonimidamide Step 1: Methyl 2-mercaptothiazole-5-carboxylate Into a 2000-mL round-bottom flask was placed methyl 2-bromothiazole-5-carboxylate (100 g, 450 mmol), EtOH (1000 mL), and sodium hydrogensulfide (50 g, 890 mmol). The resulting solution was stirred for 2 h at 80° C. and then was cooled to 0° C. with a water/ice bath. The pH value of the solution was adjusted to 3 with hydrogen chloride (1 N). The solids were collected by filtration. This resulted in 63.2 g (80%) of the title compound as a light yellow solid. MS-ESI: 176.0 (M+1).

Step 2: Methyl 2-(chlorosulfonyl)thiazole-5-carboxylate

Into a 1000-mL round-bottom flask was placed methyl 2-mercaptothiazole-5-carboxylate (30 g, 170 mmol) and acetic acid (300 mL). This was followed by the addition of sodium hypochlorite (300 mL, 8%-10% wt.) in portions at 0° C. The resulting solution was stirred for 2 h at RT and then was diluted with 500 mL of water. The solution was extracted with 3×300 mL of DCM; and the combined organic layers were washed with 2×300 mL of brine, and dried over anhydrous $Na_2SO_4$. The crude product as a yellow solution in DCM was used in the next step.

Step 3: Methyl 2-sulfamoylthiazole-5-carboxylate

Into a 2000-mL round-bottom flask was placed methyl 2-(chlorosulfonyl)thiazole-5-carboxylate as a crude solution in DCM (900 mL). To the solution was introduced $NH_3$ (g) below 0° C. for 20 minutes. The resulting solution was stirred for 1 h at RT and was then concentrated under vacuum. The residue was applied onto a silica gel column and eluted with ethyl acetate/petroleum ether (1:5 to 1:3). This resulted in 23 g (75%, 2 steps) of the title compound as a white solid. MS-ESI: 223.0 (M+1).

Step 4: 5-(2-Hydroxypropan-2-yl)thiazole-2-sulfonamide

Into a 500-mL round-bottom flask purged with and maintained under nitrogen was placed a solution of methyl 2-sulfamoylthiazole-5-carboxylate (15 g, 67.5 mmol) in THF (150 mL). This was followed by the addition of MeMgBr/THF (3 M, 90 mL) dropwise with stirring at 0° C. The resulting solution was stirred for 14 h at RT and then was quenched by the addition of 100 mL of $NH_4Cl$ (sat.). The resulting solution was extracted with 3×150 mL of DCM; the organic layers were combined, dried over anhydrous $Na_2SO_4$, and concentrated under vacuum. The residue was applied onto a silica gel column and eluted with ethyl acetate/petroleum ether (1:5 to 1:3). This resulted in 11.5 g (78%) of the title compound as a white solid. MS-ESI: 223.0 (M+1), 221.0 (M-1) in positive and negative ion mode, respectively.

Step 5: N-(tert-butyldimethylsilyl)-5-(2-hydroxypropan-2-yl)thiazole-2-sulfonamide Into a 250-mL 3-necked round-bottom flask purged with and maintained under nitrogen was placed a solution of 5-(2-hydroxypropan-2-yl)thiazole-2-sulfonamide (5 g, 22.5 mmol) in THF (100 mL). Then to the above was added NaH (60% wt, 1.8 g, 45.0 mmol) in portions in an ice/water bath. After stirring for 20 minutes in an ice/water bath, this was followed by the addition of a solution of TBSCl (4.1 g, 27.2 mmol) in THF (10 mL) dropwise with stirring over 2 min at 0° C. The resulting solution was stirred for 4 h at RT. The reaction was quenched with sat. $NH_4Cl$ (100 mL) and extracted with 3×100 mL of ethyl acetate. The combined organic layers were dried over $Na_2SO_4$ and concentrated under vacuum. The crude solid was washed with ethyl acetate/hexane (1:5) (2×100 mL). This resulted in 6.81 g (90%) of the title compound as a yellow solid. MS-ESI: 337.1 (M+1), 335.1 (M-1) in positive and negative ion mode, respectively.

Step 6: N'-(tert-butyldimethylsilyl)-5-(2-hydroxypropan-2-yl)thiazole-2-sulfonimidamide Into a 100-mL 3-necked round-bottom flask purged with and maintained under nitrogen was placed a solution of $PPh_3Cl_2$ (3 g, 9.0 mmol) in $CHCl_3$ (100 mL). This was followed by the addition of DIEA (1.54 g, 11.9 mmol) dropwise with stirring at RT. The resulting solution was stirred for 10 min at RT. This was followed by the addition of a solution of N-(tert-butyldimethylsilyl)-5-(2-hydroxypropan-2-yl)thiazole-2-sulfonamide (2.0 g, 5.9 mmol) in $CHCl_3$ (30 mL) dropwise with stirring in an ice/water bath. The resulting solution was stirred for 30 min in an ice/water bath. To the above was introduced $NH_3$ (g) below 0° C. for 15 minutes. The resulting solution was stirred for 20 minutes at RT. The solids were filtered out and the filtrate was concentrated and the residue was dissolved in 300 mL of ethyl acetate. The solution was washed with brine (2×100 mL), dried over $Na_2SO_4$, and concentrated under vacuum.

The crude solid was washed with CHCl₃ (100 mL). Then the filtrate was concentrated under vacuum, and the residue was further purified by a silica gel column with ethyl acetate/petroleum ether (1:10 to 1:3). The original washed solid and solid from silica gel purification were combined. This resulted in 1.2 g (60%) of the title compound as a white solid. MS-ESI: 336.1 (M+1). ¹H-NMR (300 MHz, DMSO-d₆) δ7.66 (s, 1H), 7.12 (s, 2H), 5.78 (s, 1H), 1.51 (s, 6H), 0.86 (s, 9H), 0.02 (s, 3H), 0.01 (s, 3H).

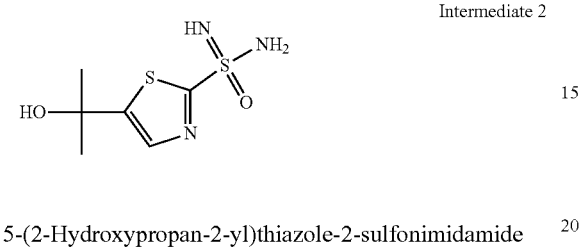

Intermediate 2

5-(2-Hydroxypropan-2-yl)thiazole-2-sulfonimidamide

Step 7:
5-(2-Hydroxypropan-2-yl)thiazole-2-sulfonimidamide

Into a 50-mL round-bottom flask was placed a solution of N'-(tert-butyldimethylsilyl)-5-(2-hydroxypropan-2-yl)thiazole-2-sulfonimidamide (200 mg, 0.60 mmol), DCM (3 mL), and TFA (0.3 mL). The resulting solution was stirred for 30 min at RT and then was concentrated under vacuum. The crude product was purified by Prep-HPLC using Method E with the following conditions: Column, C₁₈ silica gel, mobile phase, Water (10 mmol/L NH₄HCO₃) and ACN (10% to 50% in 20 min), Detector, UV detection 254/210 nm. This resulted in 100 mg (76%) of the title compound as a light yellow solid. MS-ESI: 222.0 (M+1).

Scheme 8

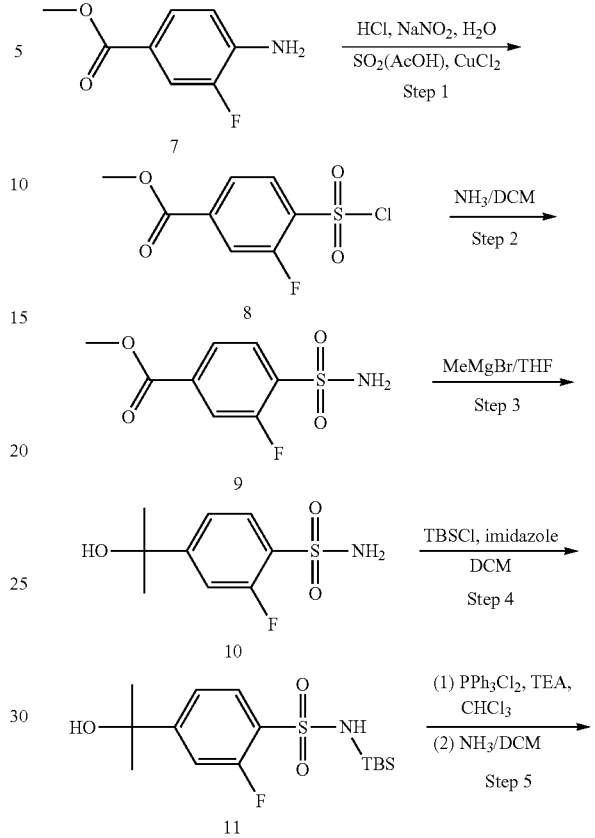

TABLE 2

The Intermediates in the following Table were prepared using similar procedures for converting compound 6 to Intermediate 2 shown in Scheme 7 by substituting ammonia with appropriated amine in Step 6.

| Intermediate # | Structure | IUPAC Name | Exact Mass [M + H]⁺ |
|---|---|---|---|
| Intermediate 3 | (structure) | 5-(2-hydroxypropan-2-yl)-N'-(4-methoxybenzyl)thiazole-2-sulfonimidamide | 342.1 |
| Intermediate 4 | (structure) | 5-(2-hydroxypropan-2-yl)-N'-methylthiazole-2-sulfonimidamide | 236.0 |

-continued

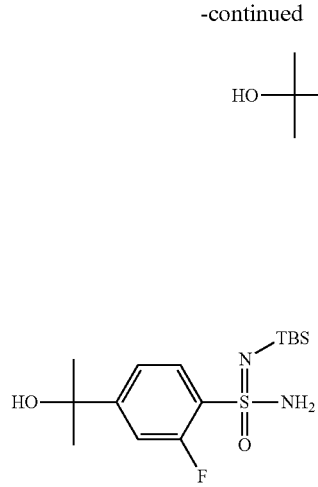

Intermediate 5

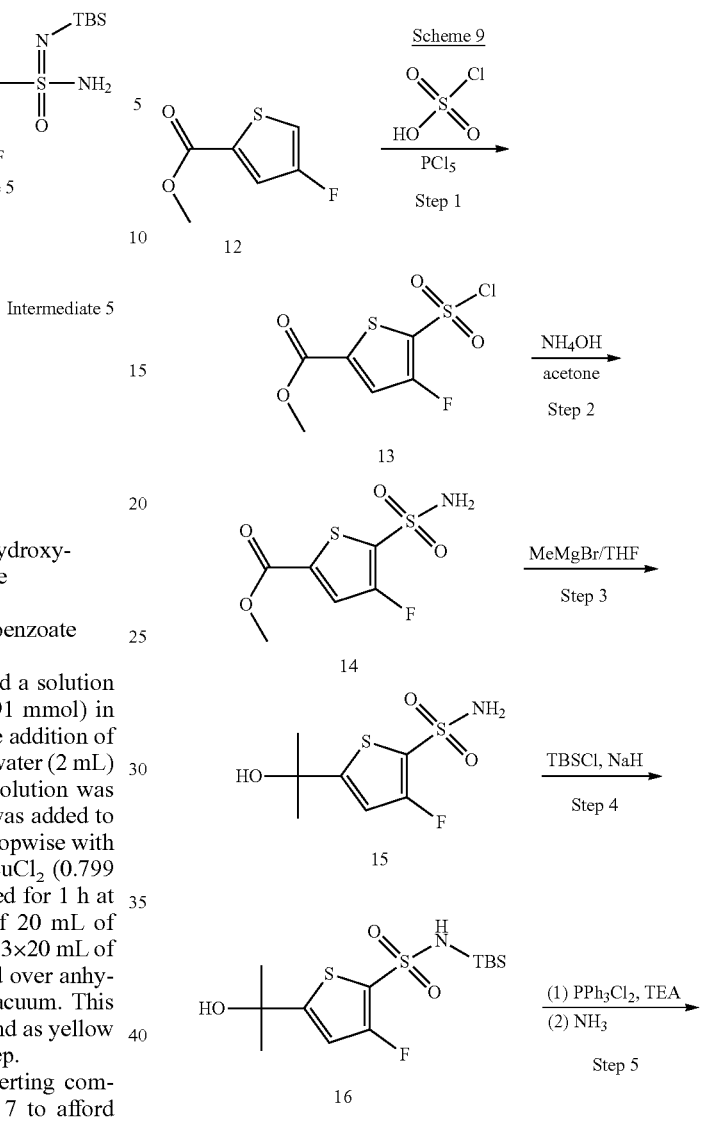

Intermediate 5

N'-(tert-butyldimethylsilyl)-2-fluoro-4-(2-hydroxy-propan-2-yl)benzenesulfonimidamide Step 1: Methyl 4-(chlorosulfonyl)-3-fluorobenzoate Into a 100-mL round-bottom flask was placed a solution of methyl 4-amino-3-fluorobenzoate (1.0 g, 5.91 mmol) in aq. HCl (6 N, 20 mL). This was followed by the addition of a solution of NaNO$_2$ (612.4 mg, 8.88 mmol) in water (2 mL) dropwise with stirring at 0° C. The resulting solution was stirred for 30 min at 0° C. The above mixture was added to a saturated solution of SO$_2$ in AcOH (20 mL) dropwise with stirring at 0° C. Then to the above was added CuCl$_2$ (0.799 g, 5.96 mmol). The resulting solution was stirred for 1 h at RT and then was quenched by the addition of 20 mL of water. The resulting solution was extracted with 3×20 mL of DCM. The organic layers were combined, dried over anhydrous Na$_2$SO$_4$, and then concentrated under vacuum. This resulted in 1 g (crude, 67%) of the title compound as yellow oil. The crude product was used in the next step.

Steps 2-5 used similar procedures for converting compound 3 to Intermediate 1 shown in Scheme 7 to afford Intermediate 5. MS-ESI: 347.2 (M+1).

TABLE 3

The Intermediates in the following Table were prepared using similar procedures for converting compound 7 to Intermediate 5 shown in Scheme 8 from appropriate starting materials.

| Intermediate # | Structure | IUPAC Name | Exact Mass [M + H]⁺ |
|---|---|---|---|
| Intermediate 6 | 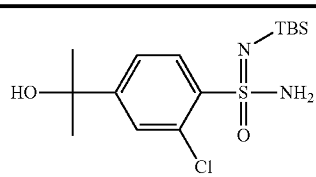 | N'-(tert-butyldimethylsilyl)-2-chloro-4-(2-hydroxypropan-2-yl)benzenesulfonimidamide | 363.1 |
| Intermediate 7 | 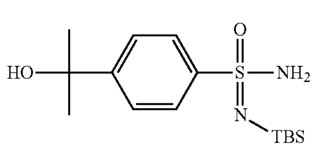 | N'-(tert-butyldimethylsilyl)-4-(2-hydroxypropan-2-yl)benzenesulfonimidamide | 329.1 |

383

-continued

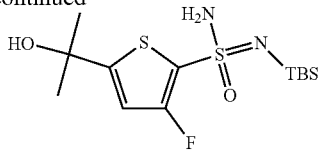

Intermediate 8

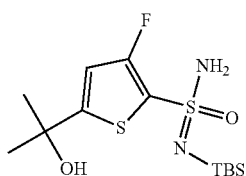

Intermediate 8

N'-(tert-butyl dimethyl silyl)-3-fluoro-5-(2-hydroxy-propan-2-yl)thiophene-2-sulfonimidamide Step 1: Methyl 5-(chlorosulfonyl)-4-fluorothiophene-2-carboxylate Into a 50-mL round-bottom flask was placed a solution of methyl 4-fluorothiophene-2-carboxylate (1.0 g, 6.24 mmol) in CHCl$_3$ (10 mL). Then to the above was added ClSO$_3$H (2.18 g, 18.7 mmol). The resulting solution was stirred for 12 h at RT. Then to the above was added PCl$_5$ (6.5 g, 31.2 mmol). The resulting solution was stirred for 2 h at 50° C. and then was quenched by the addition of 30 mL of water. The resulting solution was extracted with 3×30 mL of ethyl acetate; the organic layers were combined, dried over anhydrous Na$_2$O$_4$, and then concentrated under vacuum. This resulted in 1.2 g (crude, 74%) of the title compound as dark red oil. The crude product was used in the next step.

Step 2: Methyl 4-fluoro-5-sulfamoylthiophene-2-carboxylate

Into a 50-mL round-bottom flask was placed a solution of methyl 5-(chlorosulfonyl)-4-fluorothiophene-2-carboxylate (600 mg, 2.32 mmol) in acetone (6 mL). Then to the above was added aq. NH$_4$OH (25% wt., 2 mL). The mixture was stirred for 1 h at RT and then diluted with 10 mL of water. The resulting solution was extracted with 3×10 mL of ethyl acetate; the organic layers were combined, dried over anhydrous Na$_2$O$_4$, and then concentrated under vacuum. This resulted in 500 mg (crude, 90%) of the title compound as yellow oil. MS-ESI: 238.0 (M−1). Step 3-5 used similar procedures for converting compound 4 to Intermediate 1 shown in Scheme 7 to afford Intermediate 8. MS-ESI: 353.1 (M+1).

Scheme 10A

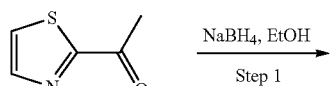

384

-continued

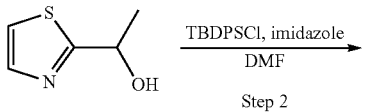

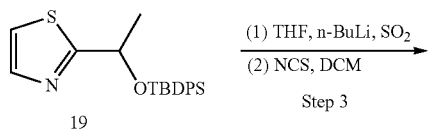

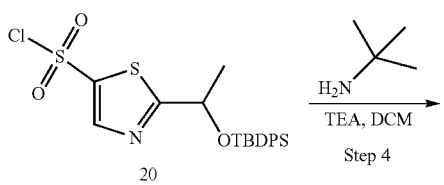

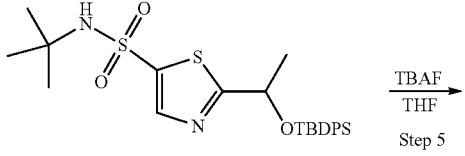

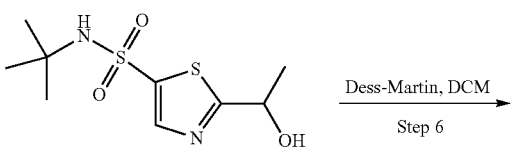

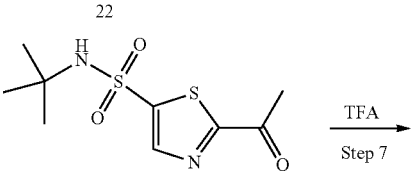

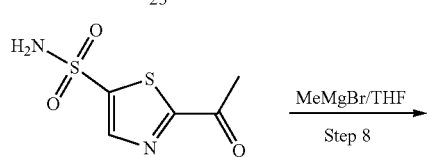

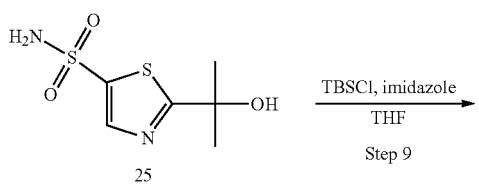

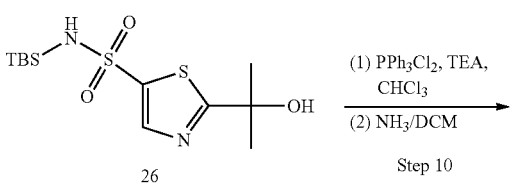

-continued

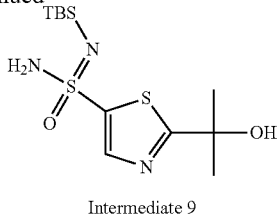

Intermediate 9

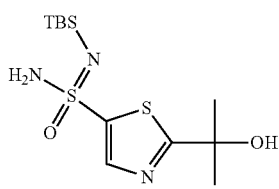

Intermediate 9

N'-(tert-butyldimethylsilyl)-2-(2-hydroxypropan-2-yl)thiazole-5-sulfonimidamide

Step 1: 1-(Thiazol-2-yl)ethanol

Into a 500-mL round-bottom flask was placed 1-(thiazol-2-yl)ethanone (20 g, 157 mmol) in EtOH (200 mL). This was followed by the addition of $NaBH_4$ (3 g, 81.3 mmol) in portions at 0° C. The resulting solution was stirred for 2 h at RT and was then quenched by the addition of 10 mL of $NH_4Cl$ (sat.). The resulting solution was diluted with 200 mL of water and extracted with 2×200 mL of DCM. The organic layers were combined, dried over anhydrous $Na_2O_4$, and then concentrated under vacuum. This resulted in 20 g (98%) of the title compound as light yellow oil. MS-ESI: 130.0 (M+1).

Step 2: 2-(1-(Tert-butyldiphenylsilyloxy)ethyl)thiazole

Into a 500-mL round-bottom flask was placed 1-(thiazol-2-yl)ethanol (20 g, 154.8 mmol), DMF (150 mL), and imidazole (20.5 g, 301 mmol). This was followed by the addition of TBDPSCl (46 g, 167 mmol) dropwise with stirring at 0° C. The mixture was stirred for 2 h at RT and then was diluted with 300 mL of water. The resulting solution was extracted with 3×200 mL of DCM. The organic layers were combined and concentrated under vacuum. The residue was applied onto a silica gel column and eluted with ethyl acetate/petroleum ether (1:100 to 1:80). This resulted in 55 g (97%) of the title compound as a colorless oil. MS-ESI: 368.1 (M+1).

Step 3: 2-(1-(Tert-butyldiphenylsilyloxy)ethyl)thiazole-5-sulfonyl chloride

Into a 500-mL 3-necked round-bottom flask purged with and maintained under nitrogen was placed 2-(1-(tert-butyldiphenylsilyloxy)ethyl)thiazole (30 g, 81.6 mmol) and THF (200 mL). This was followed by the addition of n-BuLi/THF (2.5 M, 35.2 mL) dropwise with stirring at −78° C. The resulting solution was stirred for 0.5 h at −78° C., and then $SO_2$ was introduced into the above reaction mixture. The reaction was slowly warmed to RT, and then NCS (12.8 g, 95.86 mmol) was added. The resulting solution was stirred for 1 h at RT. The solids were filtered out. The resulting filtrate was concentrated under vacuum. This resulted in 30 g (crude, 79%) of the title compound as brown oil. The crude product was used in the next step directly.

Step 4: N-tert-butyl-2-(1-(tert-butyldiphenylsilyloxy)ethyl)thiazole-5-sulfonamide Into a 500-mL round-bottom flask was placed 2-(1-(tert-butyldiphenylsilyloxy)ethyl)thiazole-5-sulfonyl chloride (crude, 30 g, 64.4 mmol), DCM (200 mL), and TEA (13 g, 128 mmol). This was followed by the addition of 2-methylpropan-2-amine (5.6 g, 76.6 mmol) dropwise with stirring at 0° C. The resulting solution was stirred for 2 h at RT and then was concentrated under vacuum. The residue was applied onto a silica gel column and eluted with ethyl acetate/petroleum ether (1:30 to 1:20). This resulted in 25 g (77%) of the title compound as brown oil. MS-ESI: 503.2 (M+1).

Step 5: N-tert-butyl-2-(1-hydroxyethyl)thiazole-5-sulfonamide

Into a 500-mL round-bottom flask was placed N-tert-butyl-2-(1-(tert-butyldiphenylsilyloxy)ethyl)thiazole-5-sulfonamide (25 g, 49.7 mmol), THF (200 mL), and TBAF (30 g, 99.67 mmol). The resulting solution was stirred for 2 h at RT and then was diluted with 200 mL of water. The resulting solution was extracted with 3×200 mL of DCM. The organic layers were combined and concentrated under vacuum. The residue was applied onto a silica gel column and eluted with ethyl acetate/petroleum ether (1:20 to 1:10). This resulted in 12 g (91%) of the title compound as light yellow oil. MS-ESI: 265.1 (M+1).

Step 6: 2-Acetyl-N-tert-butylthiazole-5-sulfonamide

Into a 500-mL round-bottom flask was placed a solution of N-tert-butyl-2-(1-hydroxyethyl)thiazole-5-sulfonamide (12 g, 45.4 mmol) in DCM (200 mL). To this solution was added Dess-Martin reagent (20 g, 47.2 mmol) in portions at RT. The resulting solution was stirred for 2 h at RT and then was concentrated under vacuum. The residue was applied onto a silica gel column and eluted with ethyl acetate/petroleum ether (1:20 to 1:10). This resulted in 9 g (76%) of the title compound as a light yellow solid. MS-ESI: 263.0 (M+1).

Step 7: 2-Acetylthiazole-5-sulfonamide

Into a 100-mL round-bottom flask was placed a solution of 2-acetyl-N-tert-butylthiazole-5-sulfonamide (7 g, 26.7 mmol) in DCM (20 mL). To the solution was added TFA (20 mL) at RT. The resulting solution was stirred for 14 h at 70° C. and then was concentrated under vacuum. The residue was applied onto a silica gel column and eluted with ethyl acetate/petroleum ether (1:5 to 1:3). This resulted in 5 g (91%) of the title compound as a yellow solid. MS-ESI: 207.0 (M+1).

Step 8: 2-(2-Hydroxypropan-2-yl)thiazole-5-sulfonamide

Into a 500-mL 3-necked round-bottom flask purged with and maintained under nitrogen was placed 2-acetylthiazole-5-sulfonamide (5 g, 4.85 mmol) in THF (100 mL). This was followed by the addition of MeMgBr (3 M in THF, 8.1 mL, 24.3 mmol) dropwise with stirring at 0° C. The resulting solution was stirred for 14 h at RT and then was quenched by the addition of 100 mL of NH₄Cl (sat.). The resulting solution was extracted with 2×150 mL of DCM. The organic layers were combined and concentrated under vacuum. The residue was applied onto a silica gel column and eluted with ethyl acetate/petroleum ether (1:5 to 1:3). This resulted in 2.9 g (54%) of the title compound as a light yellow solid. MS-ESI: 223.0 (M+1).

Step 9: N-(tert-butyldimethylsilyl)-2-(2-hydroxypropan-2-yl)thiazole-5-sulfonamide Into a 100-mL 3-necked round-bottom flask purged with and maintained under nitrogen was placed a solution of 2-(2-hydroxypropan-2-yl)thiazole-5-sulfonamide (1.5 g, 6.75 mmol) in THF (20 mL). Then to the above was added imidazole (0.92 g, 13.5 mmol). This was followed by the addition of a solution of TBSCl (5.1 g, 34 mmol) in THF (5 mL) dropwise with stirring over 2 min at 0° C. The resulting solution was stirred for 16 h at RT and then was concentrated under vacuum. The residue was applied onto a silica gel column and eluted with ethyl acetate/petroleum ether (1:3 to 1:2). This resulted in 1.13 g (50%) of the title compound as a yellow solid. MS-ESI: 337.1 (M+1).

Steps 10 used similar procedures employed for converting compound 6 to Intermediate 1 shown in Scheme 7 to afford Intermediate 9. MS-ESI: 336.1 (M+1).

Scheme 10B

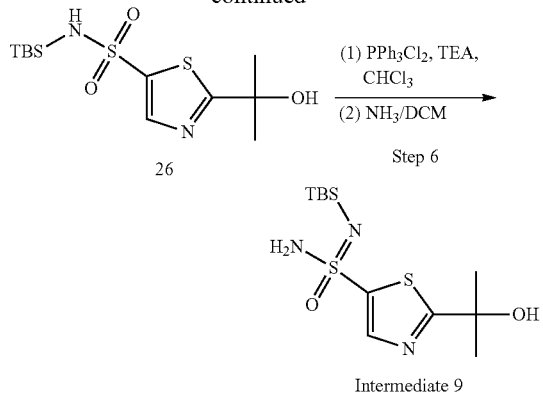

N'-(tert-butyldimethylsilyl)-2-(2-hydroxypropan-2-yl)thiazole-5-sulfonimidamide

Step 1: 2-(2-Methyl-1,3-dioxolan-2-yl)thiazole

Into a 500-mL round-bottom flask was placed a solution of 1-(thiazol-2-yl)ethanone (20 g, 157 mmol) in toluene (300 mL). To the solution was added TsOH (2.7 g, 15.7 mmol)) and ethane-1,2-diol (19.5 g, 314 mmol). The resulting solution was refluxed overnight, and water was separated from the solution during refluxing. The resulting solution was diluted with 200 mL of water and extracted with 2×100 mL of ethyl acetate. The organic layers were combined and dried over anhydrous Na₂O₄, then concentrated under vacuum. This resulted in 26.6 g (99%) of the title compound as light yellow oil. MS-ESI: 172.0 (M+1).

Step 2: 2-(2-Methyl-1,3-dioxolan-2-yl)thiazole-5-sulfonamide

Into a 500-mL 3-necked round-bottom flask purged with and maintained under nitrogen was placed a solution of 2-(2-methyl-1,3-dioxolan-2-yl)thiazole (14 g, 81.6 mmol) in THF (200 mL). This was followed by the addition of n-BuLi (2.5 M in THF, 35.2 mL) dropwise with stirring at −78° C. The resulting solution was stirred for 0.5 h at −78° C. and then SO₂ gas was introduced into the above reaction mixture. The reaction was slowly warmed to RT and then NCS (12.8 g, 95.86 mmol) was added. The resulting solution was stirred for 1 h at RT. The solids were filtered out. The resulting filtrate was concentrated under vacuum and was then diluted with DCM (160 mL). To the above was added a saturated solution of ammonia in DCM (300 mL). The resulting solution was stirred for 3 h at RT and then was concentrated under vacuum. The residue was applied onto a silica gel column and eluted with a gradient of ethyl acetate/ petroleum ether (1:20 to 1:5). This resulted in 12.5 g (61%) of the title compound as a yellow solid. MS-ESI: 251.0 (M+1).

Step 3: 2-Acetylthiazole-5-sulfonamide

Into a 250-mL round-bottom flask was placed a solution of 2-(2-methyl-1,3-dioxolan-2-yl)thiazole-5-sulfonamide (12.5 g, 50 mmol) in THF (125 mL). To the above was added aq. HCl (4 N, 50 mL). The resulting solution was stirred for 6 h at 70° C. The resulting solution was diluted with 100 mL of water and extracted with 2×200 mL of ethyl acetate. The organic layers were combined, dried over anhydrous $Na_2O_4$, and then concentrated under vacuum. The residue was applied onto a silica gel column and eluted with a gradient of ethyl acetate/petroleum ether (1:2 to 1:1). This resulted in 9.3 g (90%) of the title compound as a yellow solid. MS-ESI: 207.0 (M+1). Steps 4-6 used the same procedures for converting compound 24 to Intermediate 9 shown in Scheme 10A to afford Intermediate 9. MS-ESI: 336.1 (M+1).

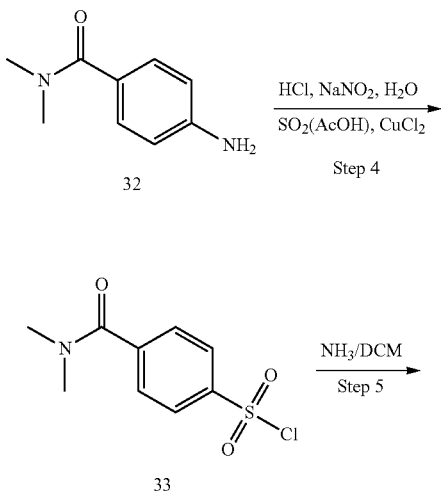

TABLE 4

The Intermediates in the following Table were prepared using the similar procedures for converting compound 17 to Intermediate 9 shown in Scheme 10B from appropriate starting materials.

| Intermediate # | Structure | IUPAC Name | Exact Mass [M + H]+ |
| --- | --- | --- | --- |
| Intermediate 10 | 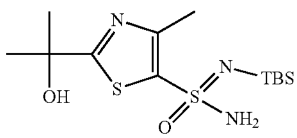 | N'-(tert-butyldimethylsilyl)-2-(2-hydroxypropan-2-yl)-4-methylthiazole-5-sulfonimidamide | 350.2 |

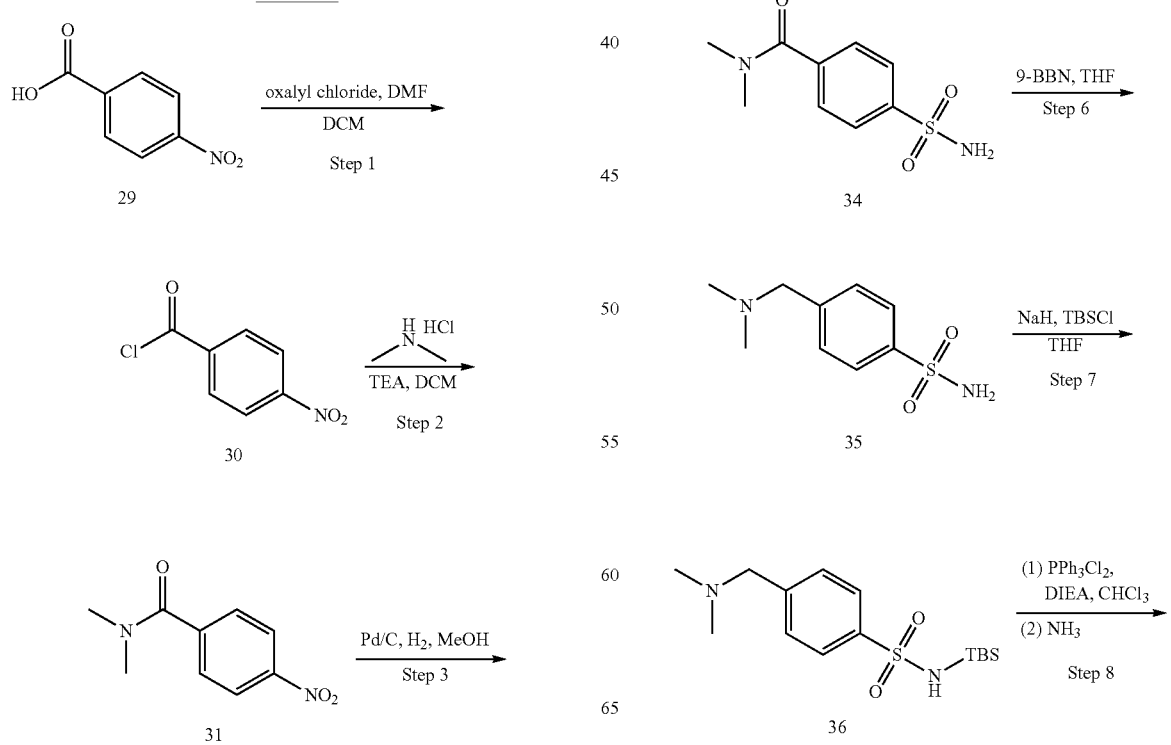

-continued

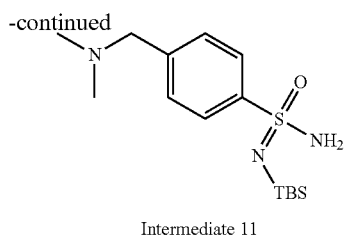

Intermediate 11

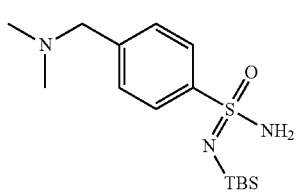

Intermediate 11

N'-(tert-butyldimethylsilyl)-4-((dimethylamino)
methyl)benzenesulfonimidamide

Step 1: 4-Nitrobenzoyl chloride

Into a 500-mL round-bottom flask was placed 4-nitrobenzoic acid (20 g, 120 mmol), DCM (200 mL), and DMF (0.2 mL). This was followed by the addition of oxalyl chloride (15 mL, 135 mmol) dropwise with stirring at 0° C. The resulting solution was stirred for 4 h at RT and then was concentrated under vacuum. This resulted in 22 g (crude) of the title compound as yellow oil. The crude product was used in the next step.

Step 2: N,N-dimethyl-4-nitrobenzamide

Into a 500-mL round-bottom flask was placed dimethylamine hydrochloride (9.8 g, 120 mmol), DCM (200 mL), and TEA (41.5 mL, 300 mmol). This was followed by the addition of 4-nitrobenzoyl chloride (22 g, crude) dropwise with stirring at 0° C. The resulting solution was stirred for 6 h at RT and then was concentrated under vacuum. The resulting mixture was washed with 2×50 mL of water. The solids were collected by filtration. This resulted in 16 g (69%, 2 steps) of the title compound as a white solid. MS-ESI: 195.1 (M+1).

Step 3: 4-Amino-N,N-dimethylbenzamide

Into a 250-mL round-bottom flask was placed N,N-dimethyl-4-nitrobenzamide (16 g, 82.4 mmol), MeOH (100 mL), and Pd/C (10% wt., 1 g). The flask was evacuated and flushed three times with hydrogen. The resulting solution was stirred for 12 h at RT under an atmosphere of hydrogen. The Pd/C catalysts were filtered out, and the filtrate was concentrated under vacuum. This resulted in 13 g (96%) of the title compound as a white solid. MS-ESI: 165.1 (M+1).

Step 4: 4-(Dimethylcarbamoyl)benzene-1-sulfonyl chloride

Into a 50-mL round-bottom flask was placed 4-amino-N,N-dimethylbenzamide (3 g, 18.3 mmol) and HCl (6 M, 12 mL). This was followed by the addition of a solution of NaNO$_2$ (1.5 g, 21.7 mmol) in water (3 mL) dropwise with stirring at 0° C. The resulting solution was stirred for 30 min at 0° C. The above mixture was added to a saturated solution of SO$_2$ in AcOH (100 mL) dropwise with stirring at 0° C. To the above was added CuCl$_2$ (4.8 g, 35.7 mmol). The resulting solution was stirred for 2 h at RT and then was quenched by the addition of 100 mL of water. The resulting solution was extracted with 2×100 mL of DCM. The organic layers were combined, dried over anhydrous Na$_2$O$_4$, and then concentrated under vacuum. This resulted in 5 g (crude) of the title compound as yellow oil. The crude product was used in the next step.

Step 5: N,N-dimethyl-4-sulfamoylbenzamide

Into a 250-mL round-bottom flask was placed 4-(dimethylcarbamoyl)benzene-1-sulfonyl chloride (5 g, 20.2 mmol) in DCM (20 mL). To the above was added a saturated solution of ammonia in DCM (80 mL). The resulting solution was stirred for 2 h at RT and then was concentrated under vacuum. The resulting mixture was washed with 3×100 mL of ethyl acetate. The solids were filtered out. The resulting filtrate was concentrated under vacuum. This resulted in 3.1 g (67%) of the title compound as a white solid. MS-ESI: 229.1 (M+1).

Step 6: 4-((Dimethylamino)methyl)benzenesulfonamide

Into a 100-mL round-bottom flask purged with and maintained under nitrogen was placed a solution of N,N-dimethyl-4-sulfamoylbenzamide (1.8 g, 7.9 mmol) in THF (50 mL). This was followed by the addition of 9-BBN (5.8 g, 47.5 mmol) in portions at 0° C. The resulting solution was stirred for 12 h at 70° C. and then was quenched by the addition of 20 mL of water/ice. The resulting solution was extracted with 3×100 mL of ethyl acetate and the organic layers were combined. The resulting mixture was washed with 200 mL of water and then the organic layer was concentrated under vacuum. The residue was applied onto a silica gel column and eluted with DCM/MeOH (20:1 to 15:1). This resulted in 1 g (59%) of the title compound as a white solid. MS-ESI: 215.1 (M+1).

Step 7: N-(tert-butyldimethylsilyl)-4-((dimethylamino)methyl)benzenesulfonamide Into a 250-mL round-bottom flask was placed a solution of 4-((dimethylamino)methyl)benzenesulfonamide (500 mg, 2.33 mmol) in THF (40 mL). This was followed by the addition NaH (60% wt., 170 mg) in portions at 0° C. Then TBSCl (1.75 g, 11.6 mmol) was added. The resulting solution was stirred for 2 h at RT and then was quenched by the addition of 30 mL of water. The resulting solution was extracted with 3×40 mL of ethyl acetate and the organic layers combined and concentrated under vacuum. The residue was applied onto a silica gel column and eluted with DCM/MeOH (30:1 to 20:1). This resulted in 540 mg (70%) of the title compound as a yellow solid. MS-ESI: 329.2 (M+1).

Step 8 used similar procedures for converting compound 6 to Intermediate 1 shown in Scheme 7 to afford Intermediate 11. MS-ESI: 328.2 (M+1).

TABLE 4

The Intermediates in the following Table were prepared using the similar procedures for converting compound 29 to Intermediate 11 shown in Scheme 11 from appropriate starting materials.

| Intermediate # | Structure | IUPAC Name | Exact Mass [M + H]+ |
| --- | --- | --- | --- |
| Intermediate 12 | 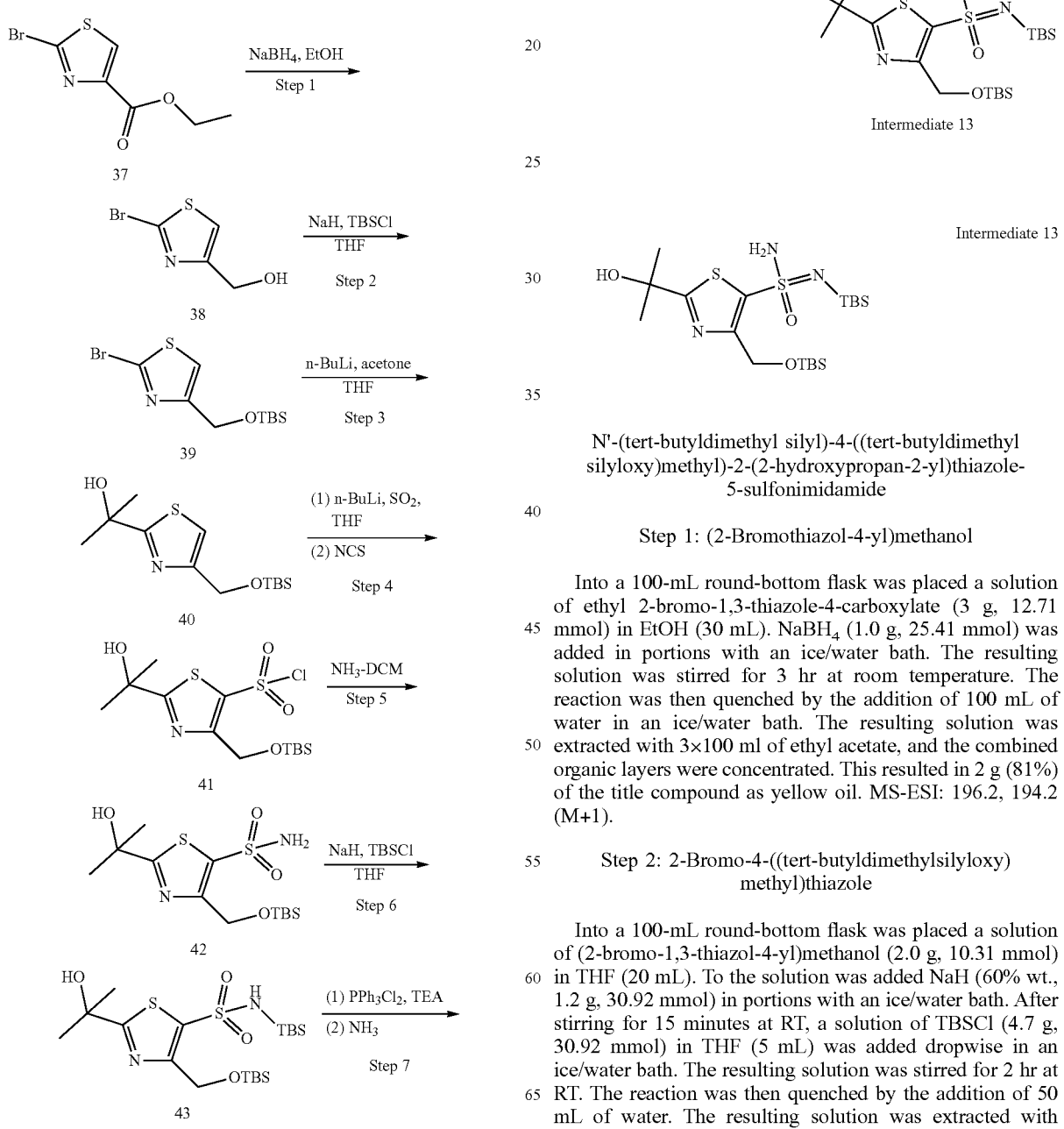 | N'-(tert-butyldimethylsilyl)-4-((dimethylamino)methyl)-2-fluorobenzenesulfonimidamide | 346.2 |

N'-(tert-butyldimethyl silyl)-4-((tert-butyldimethyl silyloxy)methyl)-2-(2-hydroxypropan-2-yl)thiazole-5-sulfonimidamide Step 1: (2-Bromothiazol-4-yl)methanol Into a 100-mL round-bottom flask was placed a solution of ethyl 2-bromo-1,3-thiazole-4-carboxylate (3 g, 12.71 mmol) in EtOH (30 mL). NaBH$_4$ (1.0 g, 25.41 mmol) was added in portions with an ice/water bath. The resulting solution was stirred for 3 hr at room temperature. The reaction was then quenched by the addition of 100 mL of water in an ice/water bath. The resulting solution was extracted with 3×100 ml of ethyl acetate, and the combined organic layers were concentrated. This resulted in 2 g (81%) of the title compound as yellow oil. MS-ESI: 196.2, 194.2 (M+1).

Step 2: 2-Bromo-4-((tert-butyldimethylsilyloxy) methyl)thiazole

Into a 100-mL round-bottom flask was placed a solution of (2-bromo-1,3-thiazol-4-yl)methanol (2.0 g, 10.31 mmol) in THF (20 mL). To the solution was added NaH (60% wt., 1.2 g, 30.92 mmol) in portions with an ice/water bath. After stirring for 15 minutes at RT, a solution of TBSCl (4.7 g, 30.92 mmol) in THF (5 mL) was added dropwise in an ice/water bath. The resulting solution was stirred for 2 hr at RT. The reaction was then quenched by the addition of 50 mL of water. The resulting solution was extracted with 3×100 ml of ethyl acetate, the organic layers were combined, dried over anhydrous Na₂SO₄ and concentrated under vacuum. The residue was applied onto a silica gel column and eluted with ethyl acetate/petroleum ether (1:30). This resulted in 2.5 g (79%) of the title compound as yellow oil. MS-ESI: 310.2, 308.2 (M+1).

Step 3: 2-(4-((Tert-butyldimethylsilyloxy)methyl) thiazol-2-yl)propan-2-ol

Into a 100-mL round-bottom flask purged and maintained with an inert atmosphere of nitrogen was placed a solution of 2-bromo-4-[[(tert-butyldimethylsilyl)oxy]methyl]-1,3-thiazole (2.5 g, 8.11 mmol) in THF (30 mL). To this solution was added n-BuLi (2.5 M in hexane, 4.86 mL, 12.16 mmol) dropwise at −78° C.; and the resulting mixture was stirred for 30 min at −78° C. To the above was added acetone (0.9 g, 16.22 mmol) dropwise at −78° C. The ensuing solution was then stirred for 1 hr at RT, after which the reaction was quenched by the addition of 100 mL of water. The resulting solution was extracted with 3×100 ml of ethyl acetate; the organic layers were combined, dried over anhydrous Na₂O₄, and concentrated under vacuum. The residue was applied onto a silica gel column and eluted with ethyl acetate/petroleum ether (1:10). This resulted in 2 g (86%) of the title compound as yellow oil. MS-ESI: 288.2 (M+1).

Step 4: 4-((Tert-butyldimethylsilyloxy)methyl)-2-(2-hydroxypropan-2-yl)thiazole-5-sulfonyl chloride Into a 250-mL round-bottom flask purged and maintained with an inert atmosphere of nitrogen was placed a solution of 2-(4-[[(tert-butyldimethylsilyl)oxy]methyl]-1,3-thiazol-2-yl)propan-2-ol (2 g, 6.96 mmol) in THF (20 mL). To this solution was added n-BuLi (2.5 M in hexane, 8.4 mL, 20.9 mmol) dropwise at −78° C.; the mixture was stirred for 30 min at −78° C. Then SO₂ was introduced in this solution for 10 minutes below −30° C. and stirred for 30 min at RT. The resulting solution was concentrated under vacuum. The crude solid was dissolved in DCM (30ml), followed by the addition of NCS (1.4 g, 10.4 mmol) in portions in an ice/water bath. The solution was stirred for 2 hr at RT. The resulting mixture was concentrated under vacuum. This resulted in 2.5 g (crude) of the title compound as a yellow solid.

Step 5: 4-((Tert-butyldimethylsilyloxy)methyl)-2-(2-hydroxypropan-2-yl)thiazole-5-sulfonamide Into a 100-mL round-bottom flask was placed a solution of 4-[[(tert-butyldimethylsilyl)oxy]methyl]-2-(2-hydroxypropan-2-yl)-1,3-thiazole-5-sulfonyl chloride (2.5 g, 6.48 mmol) in DCM (30 mL). To the above was added a saturated solution of ammonia in DCM (10 mL) in an ice/water bath. The resulting solution was stirred for 1 hr at room temperature. The resulting mixture was concentrated. The residue was applied onto a silica gel column and eluted with ethyl acetate/petroleum ether (1:5). This resulted in 1.2 g (51%) of the title compound as yellow oil. MS-ESI: 367.2 (M+1).

Step 6: N-(tert-butyldimethylsilyl)-4-((tert-butyldimethylsilyloxy)methyl)-2-(2-hydroxypropan-2-yl) thiazole-5-sulfonamide To a solution of 2-(2-hydroxypropan-2-yl)-1,3-thiazole-5-sulfonamide (1.2 g, 3.27 mmol) in THF (20 mL), NaH (60% wt., 0.4 g, 9.82 mmol) was added in portions with an ice/water bath. After stirring for 15 minutes at RT, a solution of TBSCl (1.5 g, 9.82 mmol) in THF (5 mL) was added dropwise in an ice/water bath. The resulting solution was stirred for 2 hr at RT. The reaction was quenched by the addition of 100 mL of water. The resulting solution was extracted with 3×100 ml of ethyl acetate, the organic layers were combined, dried over anhydrous Na₂SO₄ and concentrated under vacuum. This resulted in 1.3 g (83%) of the title compound as yellow oil. MS-ESI: 481.2 (M+¹).

Step 7: N'-(tert-butyldimethylsilyl)-4-((tert-butyldimethylsilyloxy)methyl)-2-(2-hydroxypropan-2-yl) thiazole-5-sulfonimidamide Into a 100-mL round-bottom flask purged and maintained with an inert atmosphere of nitrogen was placed a solution of PPh₃Cl₂ (1.4 g, 4.06 mmol) in CHCl₃ (10 mL), TEA (0.8 g, 8.11 mmol) was added dropwise in an ice/water bath. The solution was stirred at RT for 20 minutes. To this solution was added N-(tert-butyldimethylsilyl)-4-[[(tert-butyldimethylsilyl)oxy]methyl]-2-(2-hydroxypropan-2-yl)-1,3-thiazole-5-sulfonamide (1.3 g, 2.70 mmol) in CHCl₃ (10 mL) dropwise in ice/water bath, the solution was stirred for 0.5 hr at RT. A saturated solution of ammonia in DCM (20 mL) was poured into this solution at 0° C. The solution was stirred for 1 hr at RT. The resulting solution was concentrated under vacuum. The residue was applied onto a silica gel column and eluted with ethyl acetate/petroleum ether (1:5). This resulted in 600 mg (46%) of the title compound as a yellow solid. MS-ESI: 480.2 (M+1).

Schemes for phenylacetic acids Intermediates: Schemes 13-22 illustrate the preparation of phenylacetic acid intermediates.

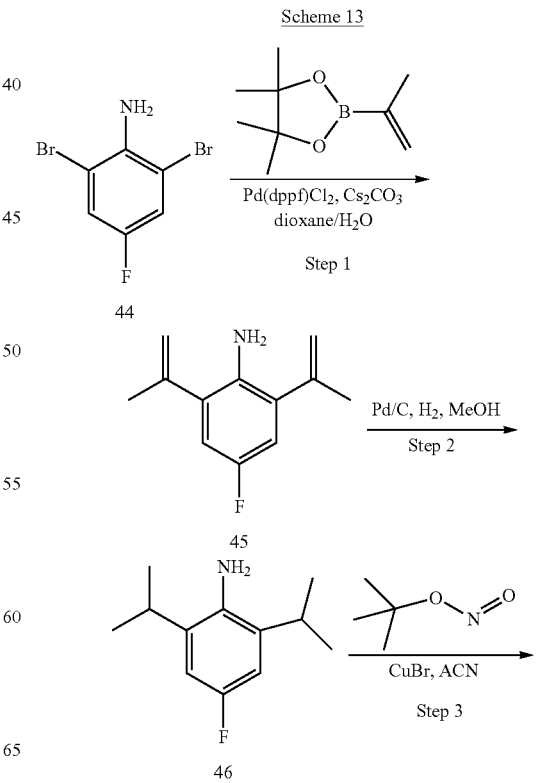

Scheme 13

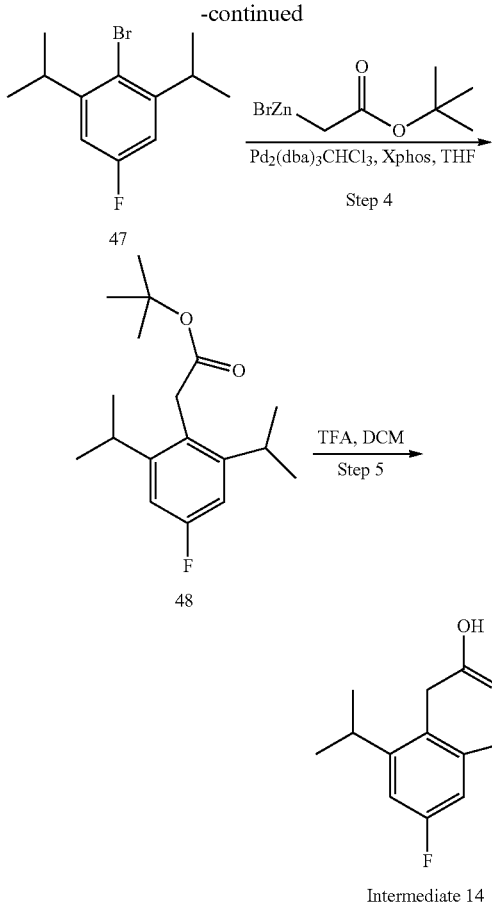

Step 4

47

Step 5

48

Intermediate 14

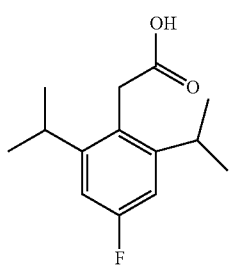

2-(4-Fluoro-2,6-diisopropylphenyl)acetic acid

Step 1: 4-Fluoro-2,6-di(prop-1-en-2-yl)aniline

Into a 500-mL round-bottom flask purged with and maintained under nitrogen was placed 2,6-dibromo-4-fluoroaniline (15 g, 55.8 mmol), dioxane (150 mL), water (15 mL), $Cs_2CO_3$ (55 g, 169 mmol), 4,4,5,5-tetramethyl-2-(prop-1-en-2-yl)-1,3,2-dioxaborolane (25 g, 149 mmol), and Pd(dppf)Cl$_2$ (4 g, 5.47 mmol). The resulting solution was stirred for 15 h at 100° C. and then was concentrated under vacuum. The mixture was diluted with 300 mL water, and extracted with ethyl acetate (3×300 mL). The organic layers were combined, dried over anhydrous $Na_2O_4$, and concentrated under vacuum. The residue was applied onto a silica gel column and eluted with ethyl acetate/petroleum ether (1:10 to 1:8). This resulted in 9.2 g (86%) of the title compound as brown oil. MS-ESI: 192.1 (M+1).

Step 2: 4-Fluoro-2,6-bis(propan-2-yl)aniline

Into a 500-mL round-bottom flask was placed 4-fluoro-2,6-bis(prop-1-en-2-yl)aniline (9.2 g, 48.1 mmol) in MeOH (200 mL). Then Pd/C (10% wt, 900 mg) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:10 to 1:8). This resulted in 7.2 g (77%) of the title compound as brown oil. MS-ESI: 196.1 (M+1).

Step 3: 2-Bromo-5-fluoro-1,3-bis(propan-2-yl)benzene

Into a 500-mL round-bottom flask purged with and maintained under nitrogen was placed 4-fluoro-2,6-bis(propan-2-yl)aniline (7 g, 35.9 mmol), ACN (300 mL), and CuBr (7.71 g, 53.9 mmol). This was followed by the addition of tert-butyl nitrite (5.55 g, 53.8 mmol) dropwise with stirring at 0° C. The resulting solution was stirred for 3 h at 60° C. and then was concentrated under vacuum. The residue was applied onto a silica gel column eluted with petroleum ether. This resulted in 3.0 g (32%) of the title compound as yellow oil. 41 NMR (400 MHz, DMSO-d$_6$): δ 7.09 (d, J=9.8 Hz, 2H), 3.40 (hept, J=6.9 Hz, 2H), 1.20 (d, J=6.8 Hz, 12H).

Step 4: Tert-butyl 2-[4-fluoro-2,6-bis(propan-2-yl)phenyl]acetate

Into a 250-mL 3-necked round-bottom flask purged with and maintained under nitrogen was placed 2-bromo-5-fluoro-1,3-bis(propan-2-yl)benzene (3.0 g, 11.6 mmol), THF (150 mL), X-phos (553 mg, 1.16 mmol), and Pd$_2$(dba)$_3$CHCl$_3$ (600 mg, 0.58 mmol). The resulting solution was stirred for 0.5 h at RT. Then, to the above, tert-butyl 2-(bromozincio)acetate (6.0 g, 23.04 mmol) was added. The resulting solution was stirred for 5 h at 70° C., after which it was quenched by the addition of 100 mL of NH$_4$Cl (sat.). The resulting solution was extracted with 3×100 mL of ethyl acetate, and the organic layers combined and concentrated under vacuum. The residue was applied onto a silica gel column and eluted with ethyl acetate/petroleum ether (1:100 to 3:97). This resulted in 3.14 g (92%) of the title compound as yellow oil. $^1$H NMR (400 MHz, DMSO-d$_6$) δ 6.93 (d, J=10.4 Hz, 2H), 3.67 (s, 2H), 3.19-3.07 (m, 2H), 1.39 (s, 9H), 1.15 (d, J=6.7 Hz, 12H).

Step 5: 2-(4-Fluoro-2,6-diisopropylphenyl)acetic acid

Into a 50-mL round-bottom flask was placed tert-butyl 2-[4-fluoro-2,6-bis(propan-2-yl)phenyl]acetate (1.56 g, 5.30 mmol), DCM (10 mL), and TFA (10 mL). The resulting solution was stirred for 3 h at RT and was then concentrated under vacuum. The crude product was dissolved in 100 mL of NaOH (4 N) and washed with 3×50 mL of DCM to remove impurities. The pH value of aqueous phase was adjusted to 2 with HCl (4 N); the aqueous phase was then extracted with 3×100 mL of DCM. The organic layers were combined, dried over anhydrous Na$_2$O$_4$, and concentrated under vacuum. This resulted in 1.09 g (86%) of the title compound as a light yellow solid. MS-ESI: 237.1 (M−1).

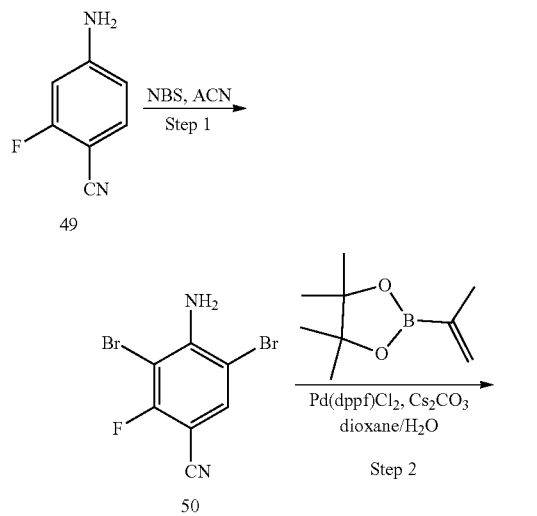

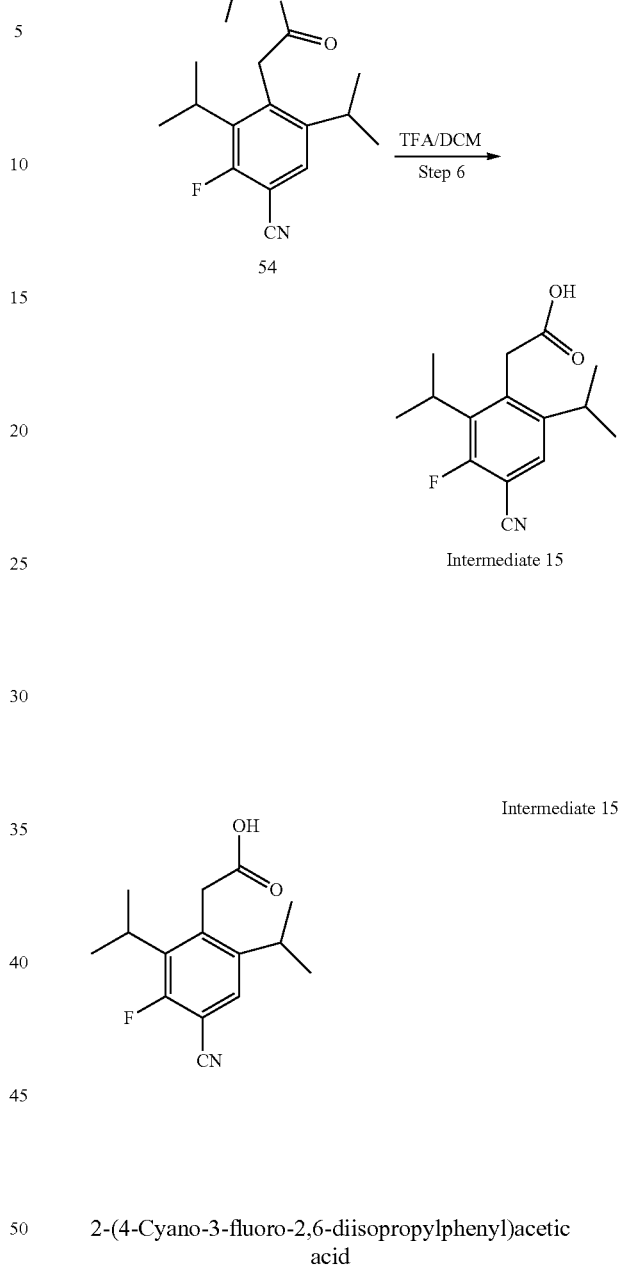

2-(4-Cyano-3-fluoro-2,6-diisopropylphenyl)acetic acid

Step 1: 4-amino-3,5-dibromo-2-fluorobenzonitrile

Into a 1000-mL round-bottom flask was placed 4-amino-2-fluorobenzonitrile (25 g, 184 mmol), ACN (500 mL), and NBS (81.7 g, 459 mmol). The resulting solution was stirred overnight at 75° C. and then was concentrated under vacuum. The residue was applied onto a silica gel column and eluted with ethyl acetate/petroleum ether (1:100 to 1:98). This resulted in 50 g (93%) of the title compound as brown oil. MS-ESI: 294.9/292.9/296.9 (M+1).

Steps 2-6 used similar procedures for converting compound 44 to Intermediate 14 shown in Scheme 13 to afford Intermediate 15. MS-ESI: 262.1 (M−1).

TABLE 5
The Intermediate in the following Table was prepared using the similar procedures for converting compound 49 to Intermediate 15 shown in Scheme 14 from appropriated starting materials.
| Intermediate # | Structure | IUPAC Name | Exact Mass [M − H]+ |
|---|---|---|---|
| Intermediate 16 | 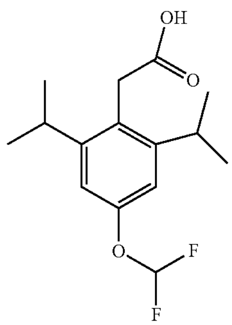 [SMILES: CC(C)c1cc(OC(F)F)cc(C(C)C)c1CC(=O)O] | 2-(4-(Difluoromethoxy)-2,6-diisopropylphenyl)acetic acid | 285.1 |
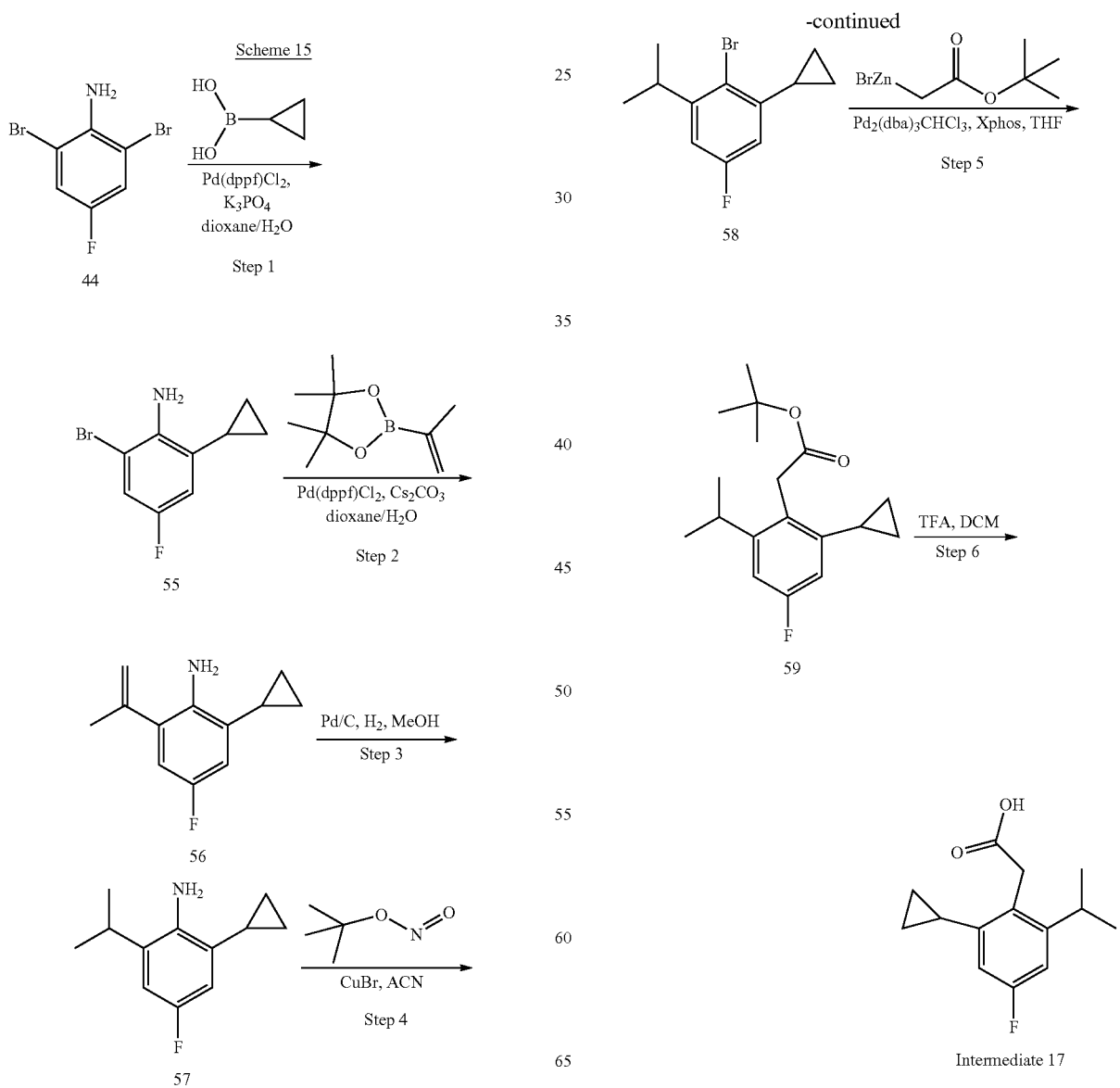

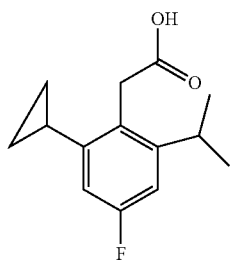

2-(2-Cyclopropyl-4-fluoro-6-isopropylphenyl)acetic acid

Intermediate 17

Step 1: 2-Bromo-6-cyclopropyl-4-fluorobenzenamine

Into a 500-mL round-bottom flask purged with and maintained under nitrogen was placed 2,6-dibromo-4-fluorobenzenamine (10 g, 37.2 mmol), 1,4-dioxane (200 mL), water (10 mL), $K_3PO_4$ (23.6 g, 111 mmol), cyclopropylboronic acid (9.59 g, 112 mmol), and Pd(dppf)Cl$_2$ (1.36 g, 1.86 mmol). The resulting solution was stirred overnight at 90° C. and then was concentrated under vacuum. The residue was applied onto a silica gel column and eluted with ethyl acetate/petroleum ether (1:40 to 1:20). This resulted in 3.4 g (40%) of the title compound as light yellow oil. MS-ESI: 230.0 (M+1).

Step 2: 2-Cyclopropyl-4-fluoro-6-(prop-1-en-2-yl)benzenamine

Into a 250-mL round-bottom flask purged with and maintained under nitrogen was placed 2-bromo-6-cyclopropyl-4-fluorobenzenamine (3.4 g, 14.8 mmol), dioxane (100 mL), water (10 mL), Cs$_2$CO$_3$ (14.5 g, 44.5 mmol), 4,4,5,5-tetramethyl-2-(prop-1-en-2-yl)-1,3,2-dioxaborolane (3.75 g, 22.3 mmol), and Pd(dppf)Cl$_2$ (1.1 g, 1.50 mmol). The resulting solution was stirred overnight at 110° C. and then concentrated under vacuum. The residue was applied onto a silica gel column and eluted with ethyl acetate/petroleum ether (1:40 to 1:20). This resulted in 1.7 g (60%) of the title compound as light yellow oil. MS-ESI: 192.1 (M+1).

Step 3: 2-Cyclopropyl-4-fluoro-6-isopropylbenzenamine

Into a 250-mL round-bottom flask was placed 2-cyclopropyl-4-fluoro-6-(prop-1-en-2-yl)benzenamine (1.7 g, 8.89 mmol), and MeOH (100 mL). Then Pd/C (10% wt, 100 mg) was added. The flask was evacuated and flushed three times with hydrogen. The resulting solution was stirred for 3 h at RT under an atmosphere of hydrogen. The solids were filtered out. The resulting mixture was concentrated under vacuum. This resulted in 1.53 g (89%) of the title compound as yellow oil. MS-ESI: 194.1 (M+1).

Steps 4-6 used similar procedures for converting compound 46 to Intermediate 14 shown in Scheme 13 to afford Intermediate 17. MS-ESI: 235.1 (M−1).

TABLE 7

The Intermediates in the following Table were prepared using the similar procedures for converting compound 44 to Intermediate 17 shown in Scheme 15 from appropriate starting materials.

| Intermediate # | Structure | IUPAC Name | Exact Mass [M − H]+ |
|---|---|---|---|
| Intermediate 18 | 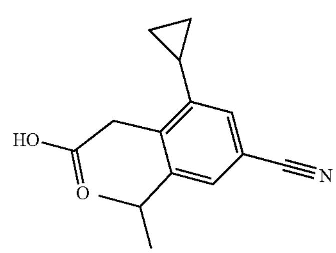 [SMILES: CC(C)c1cc(C#N)cc(C2CC2)c1CC(=O)O] | 2-(4-cyano-2-cyclopropyl-6-isopropylphenyl)acetic acid | 242.1 |
| Intermediate 19 | 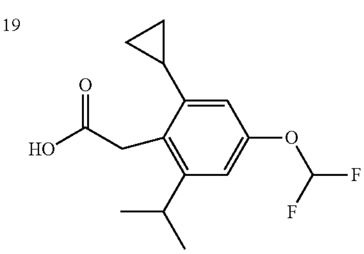 | 2-(2-cyclopropyl-4-(difluoromethoxy)-6-isopropylphenyl)acetic acid | 283.1 |

Scheme 16

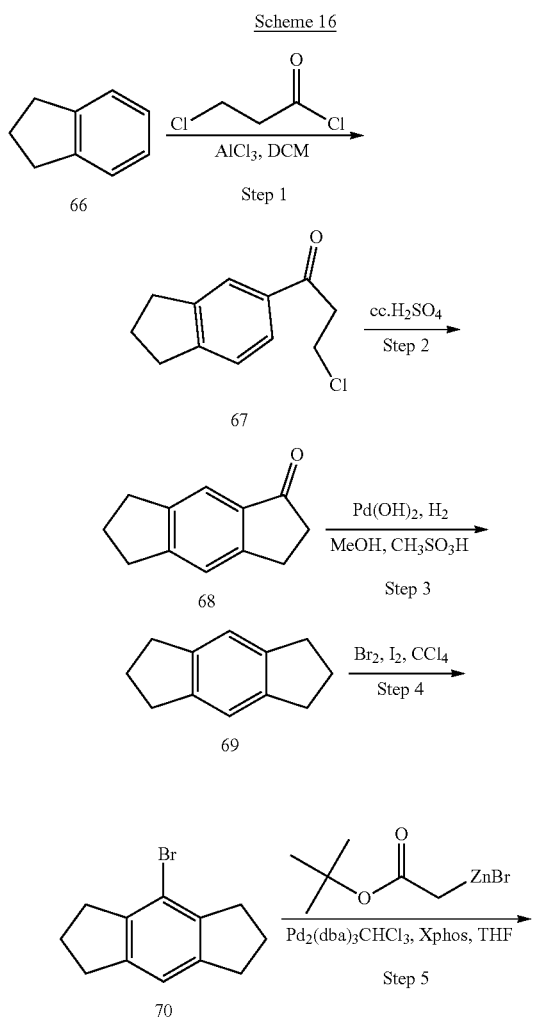

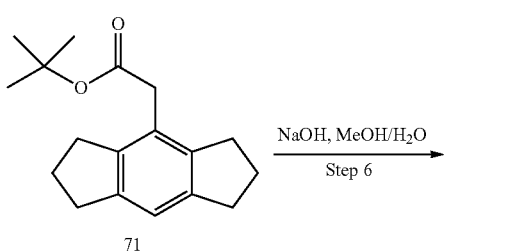

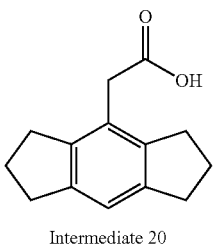

Intermediate 20

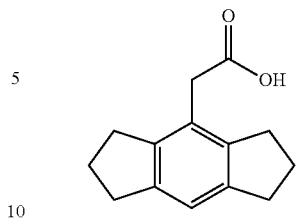

2-(1,2,3,5,6,7-Hexahydro-s-indacen-4-yl)acetic acid

Step 1: 3-Chloro-1-(2,3-dihydro-1H-inden-5-yl)propan-1-one

Into a 1000-mL round-bottom flask was placed a solution of AlCl$_3$ (37 g, 278 mmol) in DCM (400 mL). This was followed by the addition of a solution of 2,3-dihydro-1H-indene (30 g, 254 mmol) and 3-chloropropanoyl chloride (32.1 g, 253 mmol) in DCM (100 mL) dropwise with stirring at −10° C. in 30 min. The resulting solution was stirred for 16 h at RT. Then the reaction mixture was added dropwise to cold HCl (3 N, 400 mL) over 45 min at −10° C. The resulting solution was extracted with 3×200 mL of DCM; the organic layers combined, dried over anhydrous Na$_2$O$_4$, and concentrated under vacuum. This resulted in 53.5 g (crude) of the title compound as a yellow solid. The crude product was used in the next step.

Step 2: 1,2,3,5,6,7-Hexahydro-s-indacen-1-one

Into a 1000-mL round-bottom flask was placed a solution of 3-chloro-1-(2,3-dihydro-1H-inden-5-yl)propan-1-one (53.5 g, 253 mmol) in conc. H$_2$SO$_4$ (300 mL). The resulting solution was stirred for 16 h at 55° C. and was then quenched by adding the reaction mixture carefully to 1500 mL of water/ice. The solids were collected by filtration and then was dried over infrared lamp for 24 h. This resulted in 37.4 g (85%) of the title compound as a yellow solid.

Step 3: 1,2,3,5,6,7-Hexahydro-s-indacene

Into a 1000-mL round-bottom flask was placed a solution of 1,2,3,5,6,7-hexahydros-indacen-1-one (37.2 g, 216 mmol), MeOH (300 mL), and CH$_3$SO$_3$H (42 g, 437.5 mmol). Then Pd(OH)$_2$/C (20% wt., 8 g) was added. The flask was evacuated and flushed three times with hydrogen. The resulting solution was stirred for 16 h at RT under an atmosphere of hydrogen. The solids were filtered out. The resulting mixture was concentrated under vacuum. The residue was applied onto a silica gel column and eluted with ethyl acetate/petroleum ether (1:150 to 1:100). This resulted in 27.1 g (79%) of the title compound as a white solid.

Step 4: 4-Bromo-1,2,3,5,6,7-hexahydro-s-indacene

Into a 500-mL 3-necked round-bottom flask purged with and maintained under nitrogen was placed a solution of 1,2,3,5,6,7-hexahydro-s-indacene (15 g, 94.8 mmol) in CCl$_4$ (200 mL). Then I$_2$ (1.2 g, 4.72 mmol) was added. This was followed by the addition of a solution of Br$_2$ (16 g, 100 mmol) in CCl$_4$ (50 mL) dropwise with stirring at 0° C. in 10 min. The resulting solution was stirred for 2 h at 0° C. The reaction was then quenched by the addition of 150 mL of NH$_4$Cl (sat.). The resulting solution was extracted with 3×150 mL of DCM and the organic layers combined and dried over anhydrous $Na_2O_4$, then concentrated under vacuum. The crude product was applied onto a silica gel column and eluted with ethyl acetate/petroleum ether. This resulted in 18.0 g (80%) of the title compound as yellow oil. $^1$H NMR (300 MHz, DMSO-$d_6$) δ 7.02 (s, 1H), 2.95-2.75 (m, 8H), 2.03-2.01 (m, 4H).

Step 5: Tert-butyl 2-(1,2,3,5,6,7-hexahydro-s-indacen-4-yl)acetate

Into a 100-mL round-bottom flask purged with and maintained under nitrogen was placed a solution of 4-bromo-1,2,3,5,6,7-hexahydro-s-indacene (1 g, 4.2 mmol) in THF (20 mL). Then X-phos (200 mg, 0.42 mmol) and Pd$_2$(dba)$_3$CHCl$_3$ (220 mg, 0.21 mmol) were added. The resulting solution was stirred for 10 min at RT. This was followed by the addition of tert-butyl 2-(bromozincio)acetate (2.2 g, 8.45 mmol). The resulting solution was stirred for 4 h at 80° C. and was then quenched by the addition of 50 mL of NH$_4$Cl (sat.). The resulting solution was extracted with 3×100 mL of DCM. The organic layers were combined, dried over anhydrous Na$_2$O$_4$, and concentrated under vacuum. This resulted in 1.4 g (crude) of the title compound as brown oil. $^1$H NMR (400 MHz, DMSO-$d_6$) δ 6.96 (s, 1H), 3.47 (s, 2H), 2.80-2.78 (m, 8H), 2.01-1.99 (m, 4H), 1.39 (s, 9H).

Step 6: 2-(1,2,3,5,6,7-hexahydro-s-indacen-4-yl)acetic acid

Into a 40-mL sealed tube was placed a solution of tert-butyl 2-(1,2,3,5,6,7-hexahydro-s-indacen-4-yl)acetate (1.4 g, 5.14 mmol) in 6 M sodium hydroxide/MeOH (4/6 mL). The resulting solution was stirred for 16 h at 100° C. The reaction was then quenched by the addition of 20 mL of water. The resulting solution was extracted with 2×30 mL of DCM and the aqueous layers combined. The pH value of the solution was adjusted to 2 with hydrogen chloride (1 N). The resulting solution was extracted with 3×50 mL of ethyl acetate and the organic layers combined and dried over anhydrous Na$_2$O$_4$, then concentrated under vacuum. This resulted in 180 mg (19.8%, 2 steps) of the title compound as a yellow solid. MS-ESI: 215.1 (M−1).

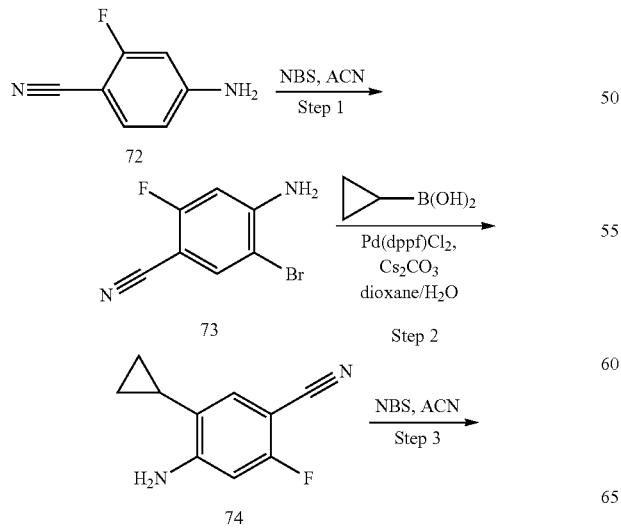

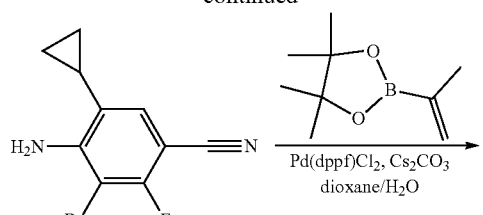

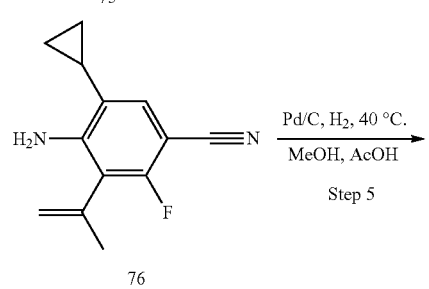

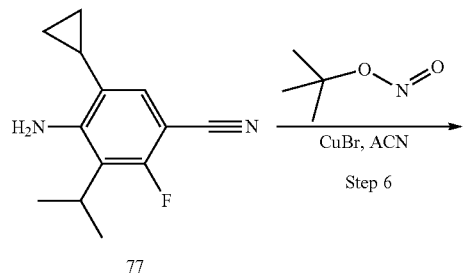

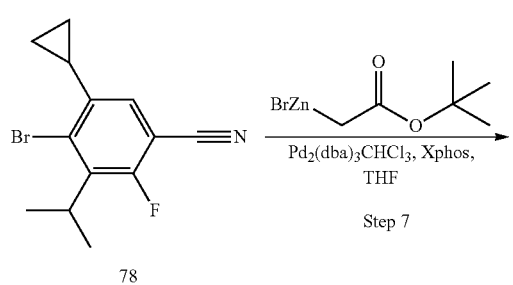

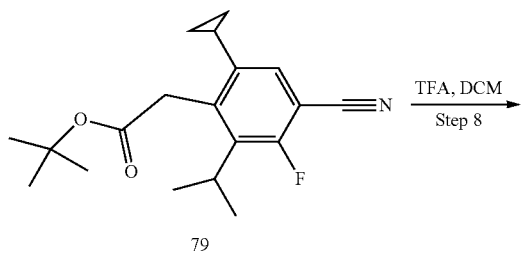

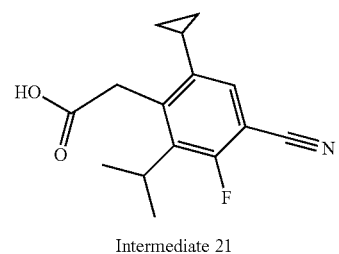 [SMILES: CC(C)c1c(F)c(C#N)cc(C2CC2)c1CC(=O)O]

Intermediate 21

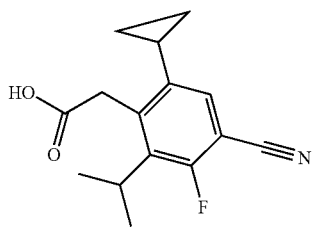

2-(4-Cyano-6-cyclopropyl-3-fluoro-2-isopropylphenyl)acetic acid

Step 1: 4-Amino-5-bromo-2-fluorobenzonitrile

Into a 250-mL round-bottom flask was placed a solution of 4-amino-2-fluorobenzonitrile (9 g, 66.1 mmol) in ACN (120 mL). Then NBS (12.4 g, 69.7 mmol) was added. The resulting solution was stirred overnight at 80° C. and then was concentrated under vacuum. The residue was applied onto a silica gel column and eluted with ethyl acetate/petroleum ether (1:20 to 1:10). This resulted in 10.9 g (77%) of the title compound as a yellow solid. MS-ESI: 215.0/217.0 (M+1). $^1$H NMR (300 MHz, DMSO-d$_6$) δ 7.89 (d, J=6.0 Hz, 1H), 6.69 (br s, 2H), 6.63 (d, J=12.0 Hz, 1H).

Step 2: 4-Amino-5-cyclopropyl-2-fluorobenzonitrile

Into a 250-mL round-bottom flask purged with and maintained under nitrogen was placed 4-amino-5-bromo-2-fluorobenzonitrile (6.37 g, 29.6 mmol), 1,4-dioxane (70 mL), water (10 mL), Cs$_2$CO$_3$ (9.7 g, 29.8 mmol), cyclopropylboronic acid (3.8 g, 44.2 mmol), and Pd(dppf)Cl$_2$ (1.08 g, 1.48 mmol). The resulting solution was stirred overnight at 90° C. and then was concentrated under vacuum. The residue was applied onto a silica gel column and eluted with ethyl acetate/petroleum ether (1:10 to 1:5). This resulted in 5.03 g (96%) of the title compound as a yellow solid. MS-ESI: 177.1 (M+1).

Step 3: 4-Amino-3-bromo-5-cyclopropyl-2-fluorobenzonitrile

Into a 250-mL round-bottom flask was placed 4-amino-5-cyclopropyl-2-fluorobenzonitrile (5.03 g, 28.7 mmol), ACN (50 mL), and NBS (5.6 g, 31.5 mmol). The resulting solution was stirred overnight at 80° C. and then was concentrated under vacuum. The residue was applied onto a silica gel column and eluted with ethyl acetate/petroleum ether (1:10 to 1:5). This resulted in 6.972 g (96%) of the title compound as a yellow solid. MS-ESI: 255.0/257.0 (M+1).

Step 4: 4-Amino-5-cyclopropyl-2-fluoro-3-(prop-1-en-2-yl)benzonitrile

Into a 250-mL round-bottom flask purged with and maintained under nitrogen was placed 4-amino-3-bromo-5-cyclopropyl-2-fluorobenzonitrile (6.972 g, 27.33 mmol), 1,4-dioxane (120 mL), water (20 mL), 4,4,5,5-tetramethyl-2-(prop-1-en-2-yl)-1,3,2-dioxaborolane (6.9 g, 41.0 mmol), Cs$_2$CO$_3$ (13.4 g, 41.0 mmol), and Pd(dppf)Cl$_2$ (0.4 g, 0.55 mmol). The resulting solution was stirred overnight at 80° C. and was then concentrated under vacuum. The residue was applied onto a silica gel column and eluted with ethyl acetate/petroleum ether (1:10 to 1:5). This resulted in 4.73 g (80%) of the title compound as a yellow solid. MS-ESI: 217.1 (M+1).

Step 5: 4-Amino-5-cyclopropyl-2-fluoro-3-isopropylbenzonitrile

Into a 250-mL round-bottom flask was placed 4-amino-5-cyclopropyl-2-fluoro-3-(prop-1-en-2-yl)benzonitrile (4.73 g, 21.97 mmol), MeOH (100 mL), and AcOH (0.5 mL). Then Pd/C (10% wt, 500 mg) was added. The flask was evacuated and flushed three times with hydrogen. The resulting solution was stirred for 4 h at 40° C. under an atmosphere of hydrogen. The solids were filtered out. The filtrate was concentrated under vacuum. This resulted in 4.71 g (99%) of the title compound as a light yellow solid. MS-ESI: 219.1 (M+1).

Steps 6-8 used similar procedures for converting compound 46 to Intermediate 14 shown in Scheme 13 to afford Intermediate 21. MS-ESI: 260.1 (M−1).

Scheme 18

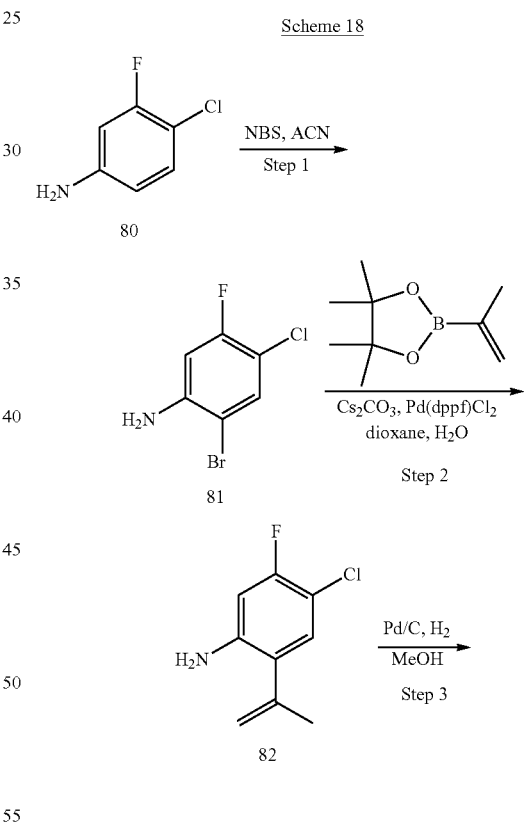

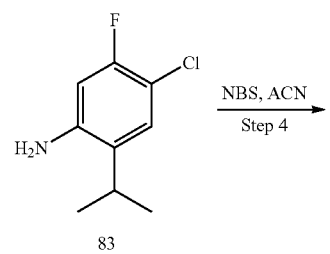

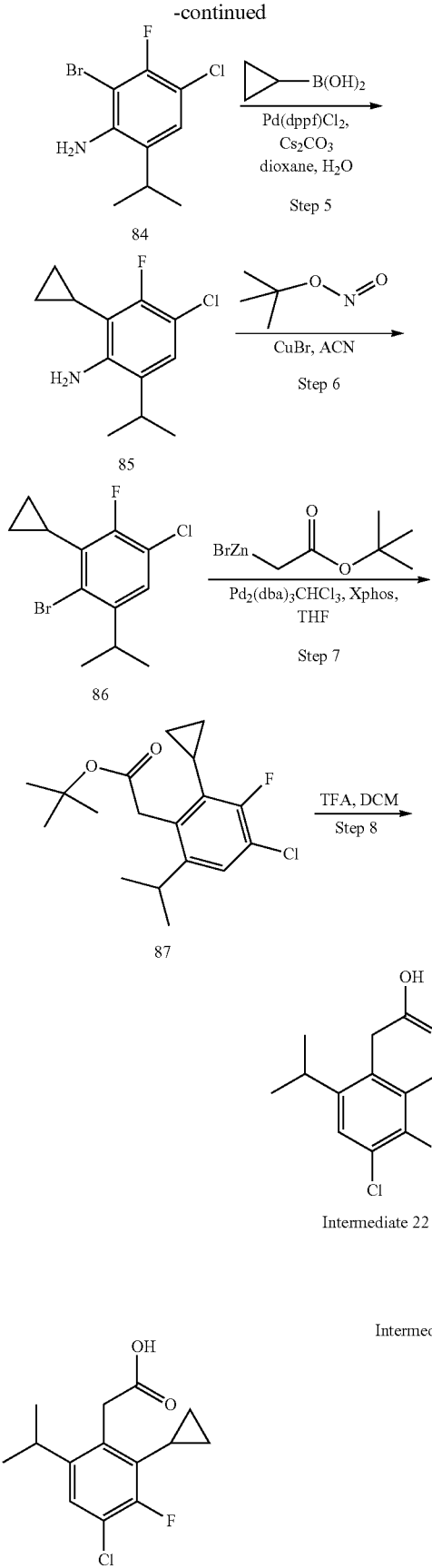

2-(4-Chloro-2-cyclopropyl-3-fluoro-6-isopropylphenyl)acetic acid

Step 1: 2-Bromo-4-chloro-5-fluorobenzenamine

Into a 1000-mL round-bottom flask was placed 4-chloro-3-fluorobenzenamine (20 g, 137 mmol, ACN (500 mL), and NBS (21.9 g, 123 mmol). The resulting solution was stirred overnight at RT and then was concentrated under vacuum. The residue was applied onto a silica gel column and eluted with ethyl acetate/petroleum ether (1:150 to 1:100). This resulted in 26.3 g (85%) of the title compound as a white solid. MS-ESI: 225.9/223.9/227.9 (M+1). $^1$H NMR (300 MHz, CDCl$_3$-d) δ 7.44 (d, J=8.0 Hz, 1H), 6.59 (d, J=8.8 Hz, 1H), 4.21 (s, 2H).

Step 2: 4-Chloro-5-fluoro-2-(prop-1-en-2-yl)benzenamine

Into a 1000-mL round-bottom flask purged with and maintained under nitrogen was placed 2-bromo-4-chloro-5-fluorobenzenamine (26.3 g, 117 mmol), 1,4-dioxane (500 mL), water (50 mL), 4,4,5,5-tetramethyl-2-(prop-1-en-2-yl)-1,3,2-dioxaborolane (23.7 g, 141 mmol), Cs$_2$CO$_3$ (76.6 g, 235 mmol), and Pd(dppf)Cl$_2$ (1.71 g, 2.34 mmol). The resulting solution was stirred overnight at 90° C. and was then concentrated under vacuum. The residue was applied onto a silica gel column and eluted with ethyl acetate/petroleum ether (1:150 to 1:100). This resulted in 12.6 g (58%) of the title compound as brown oil. MS-ESI: 186.0/188.0 (M+1).

Step 3: 4-Chloro-5-fluoro-2-isopropylbenzenamine

Into a 500-mL round-bottom flask was placed 4-chloro-5-fluoro-2-(prop-1-en-2-yl)benzenamine (12.6 g, 67.88 mmol) in MeOH (250 mL). Then Pd/C (10% wt, 1.2 g) was added. The flask was evacuated and flushed three times with hydrogen. The resulting solution was stirred for 3 h at RT under an atmosphere of hydrogen. The solids were filtered out. The filtrate was concentrated under vacuum. This resulted in 12.5 g (98%) of the title compound as light yellow oil. MS-ESI: 188.1/190.1 (M+1).

Step 4: 2-Bromo-4-chloro-3-fluoro-6-isopropylbenzenamine

Into a 500-mL round-bottom flask was placed 4-chloro-5-fluoro-2-isopropylbenzenamine (6 g, 32.0 mmol), ACN (200 mL), and NBS (6.25 g, 35.1 mmol). The resulting solution was stirred for 3 h at RT and then was concentrated under vacuum. The residue was applied onto a silica gel column and eluted with ethyl acetate/petroleum ether (1:150 to 1:100). This resulted in 8 g (94%) of the title compound as brown oil. MS-ESI: 268.0/266.0/270.0 (M+1).

Step 5: 4-Chloro-2-cyclopropyl-3-fluoro-6-isopropylbenzenamine

Into a 100-mL round-bottom flask purged with and maintained under nitrogen was placed 2-bromo-4-chloro-3-fluoro-6-isopropylbenzenamine (2.9 g, 10.9 mmol), 1,4-dioxane (40 mL), water (8 mL), cyclopropylboronic acid (1.12 g, 13.0 mmol), Cs$_2$CO$_3$ (7.08 g, 21.7 mmol), and Pd(dppf)Cl$_2$ (795 mg, 1.09 mmol). The resulting solution was stirred for 3 h at 90° C. and then was concentrated under vacuum. The residue was applied onto a silica gel column and eluted with ethyl acetate/petroleum ether (1:80 to 1:50). This resulted in 1.1 g (44%) of the title compound as light brown oil. MS-ESI: 228.1/230.1 (M+1).
Steps 6-8 used similar procedures for converting compound 46 to Intermediate 14 shown in Scheme 13 to afford Intermediate 22. MS-ESI: 271.1/273.1 (M−1).
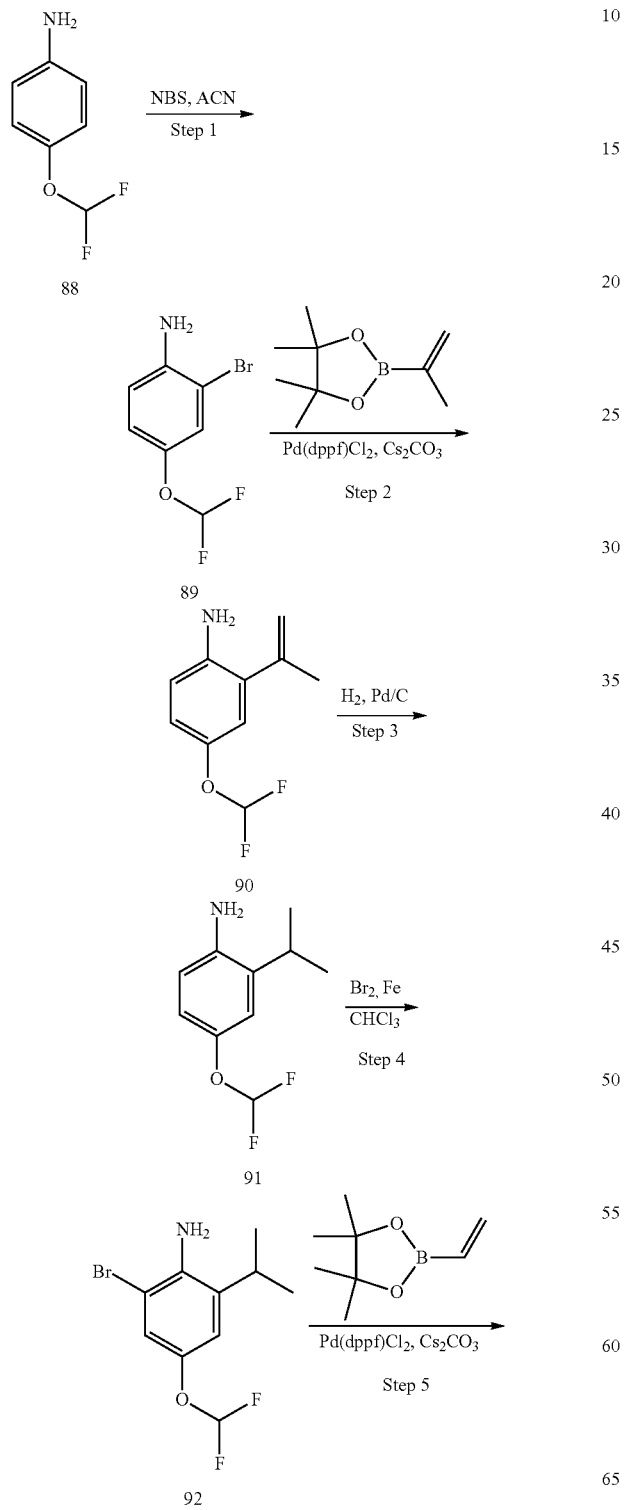
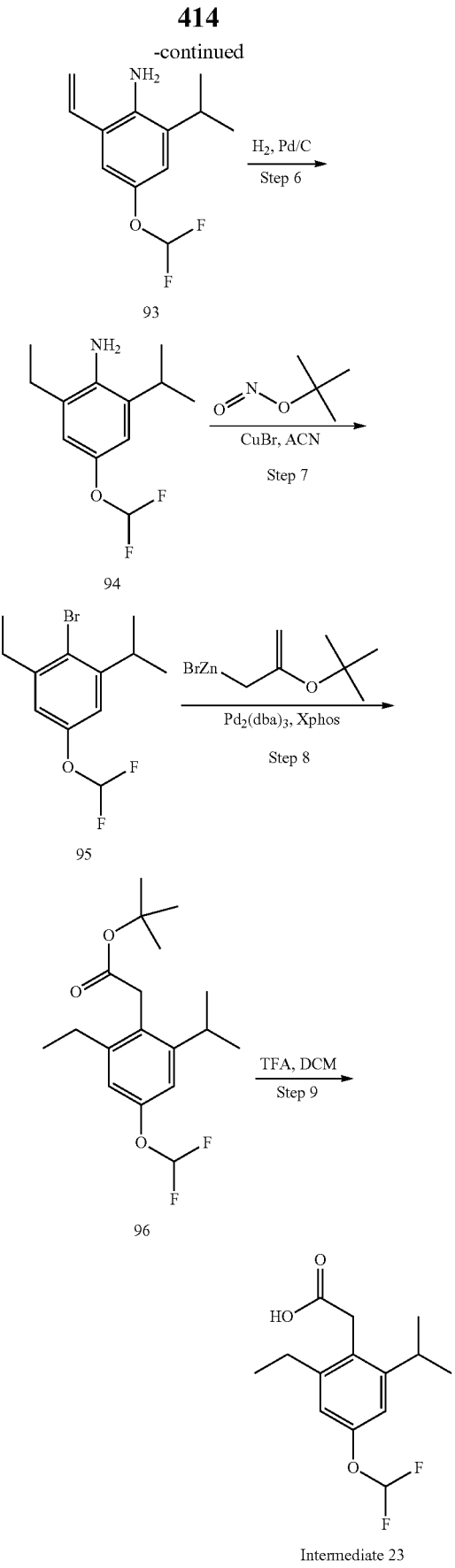

Intermediate 23

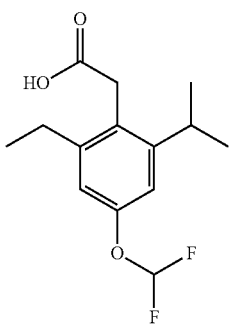

2-(4-(Difluoromethoxy)-2-ethyl-6-isopropylphenyl)acetic acid

Steps 1-3 used similar procedures for converting compound 80 to compound 83 shown in Scheme 18 to afford compound 91. MS-ESI: 202.1 (M+1).

Step 4:
2-Bromo-4-(difluoromethoxy)-6-isopropylbenzenamine

Into a 250-mL round-bottom flask was placed a mixture of 4-(difluoromethoxy)-2-isopropylbenzenamine (2.01 g, 10 mmol) and iron powder (1.12 g, 20 mmol) in CHCl₃ (50 mL). To this was added bromine (1.23 mL, 24 mmol). The resulting solution was stirred for 6 h at RT and diluted with water (200 mL). The mixture was extracted with 3×50 mL of ethyl acetate. The organic layers were combined, dried over Na₂O₄, and then concentrated under vacuum. The residue was applied onto a silica gel column and eluted with ethyl acetate/petroleum ether (1:100 to 1:10). This resulted in 2.24 g (80%) of the title compound as a yellow solid. MS-ESI: 280.0/282.0 (M+1).

Steps 5-9 used similar procedures for converting compound 44 to Intermediate 14 shown in Scheme 13 to afford Intermediate 23. MS-ESI: 271.1 (M−1).

Scheme 20

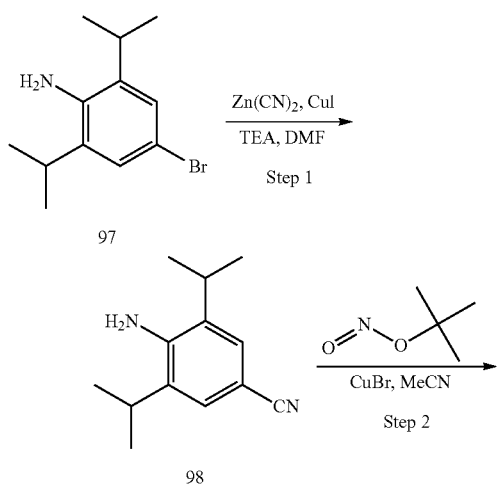

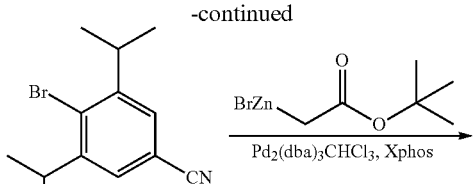

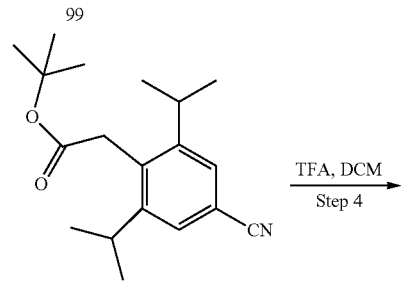

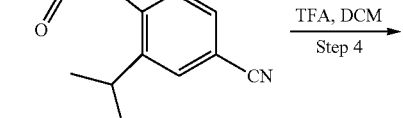

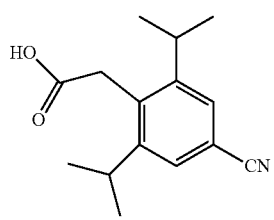

Intermediate 24

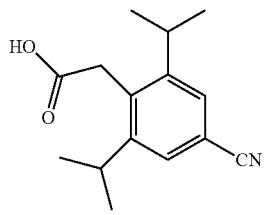

Intermediate 24

2-(4-Cyano-2,6-diisopropylphenyl)acetic acid

Step 1: 4-Amino-3,5-diisopropylbenzonitrile

Into a 100-mL round-bottom flask purged with and maintained under nitrogen was placed a solution of 4-bromo-2,6-diisopropylbenzenamine (commercially available, 5.1 g, 19.9 mmol) in DMF (30 mL). To the solution were added Zn(CN)₂ (2.80 g, 23.9 mmol), CuI (380 mg, 2.00 mmol), and TEA (3.0 g, 29.9 mmol). The resulting solution was stirred for 16 h at 120° C. and then was diluted with 30 mL of water. The solution was extracted with 3×30 mL of ethyl acetate and the combined organic layers were concentrated under vacuum. The residue was applied onto a silica gel column and eluted with ethyl acetate/petroleum ether (1:30 to 1:20). This resulted in 2.4 g (60%) of the title compound as a yellow solid. MS-ESI: 203.1 (M+1).

Steps 2-4 used similar procedures for converting compound 46 to Intermediate 14 shown in Scheme 13 to afford Intermediate 24. MS-ESI: 244.1 (M−1).

Scheme 21

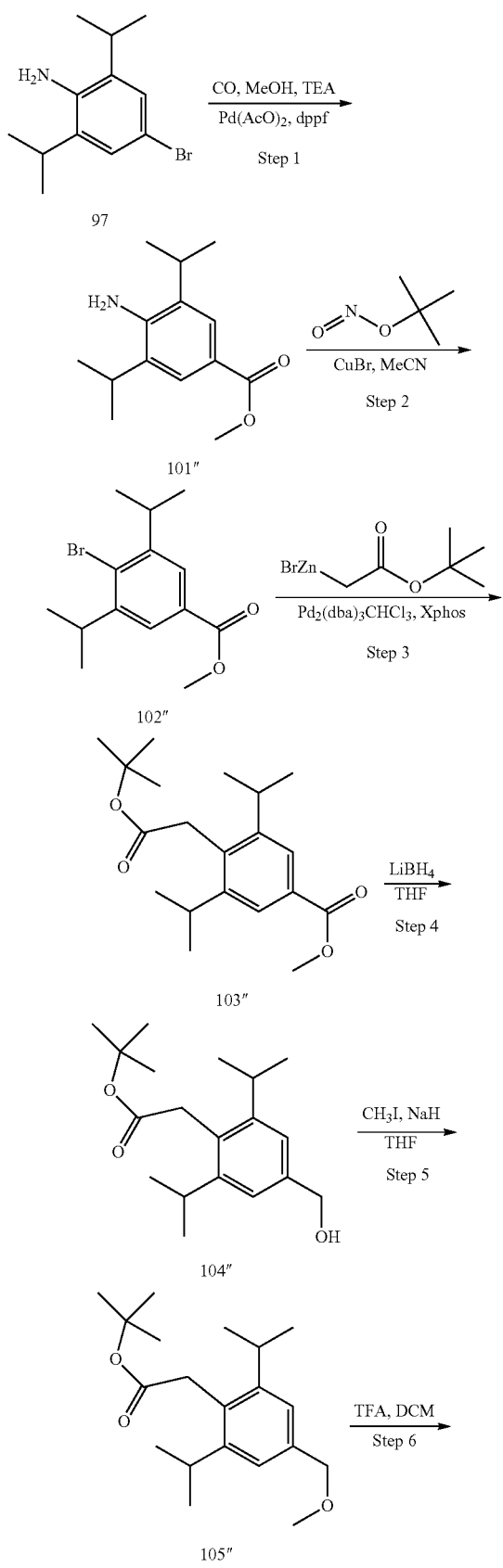

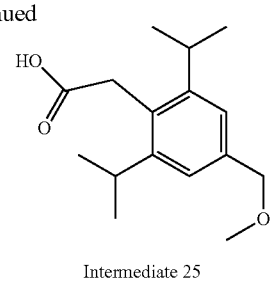

Intermediate 25

2-(2,6-diisopropyl-4-(methoxymethyl)phenyl)acetic acid

Step 1: Methyl 4-amino-3,5-diisopropylbenzoate

Into a 1-L autoclave was placed a solution of 4-bromo-2,6-diisopropylbenzenamine (10 g, 39 mmol) in MeOH (300 mL). To the solution were added Pd(OAc)$_2$ (1.75 g, 7.8 mmol), dppf (4.3 g, 7.8 mmol), and TEA (20 g, 195 mmol). After sealing the autoclave, the gas was exchanged with CO for 3 times. The reaction was stirred at 120° C. for overnight. After cooling the reaction mixture, the gas was exchanged with N$_2$, the reaction was concentrated and diluted with water (300 mL). The resulting solution was extracted with EtOAc (3×200 mL). The combined organic layers were dried over anhydrous Na$_2$SO$_4$ and concentrated. The residue was purified on SiO$_2$-gel column and eluted with ethyl acetate/petroleum ether (1:10 to 1:5). This resulted in 5.6 g (62%) of the title compound as a brown oil. MS-ESI: 236.2 (M+1)

Steps 2 and 3 used similar procedures for converting compound 46 to 48, shown in Scheme 13 to afford compound 103" as colorless oil. 335.2 (M+1)

Step 4: Tert-butyl 2-(4-(hydroxymethyl)-2,6-diisopropylphenyl)acetate

Into a 100 mL round bottom flask was placed a solution of methyl 4-(2-tert-butoxy-2-oxoethyl)-3,5-diisopropylbenzoate (2 g, 6.0 mmol) in THF (25 mL). LiBH$_4$ (264 mg, 12.0 mmol) was added to the mixture at 0° C. in portions, and the mixture was stirred at 0° C. for 1 h. The reaction was quenched with ice-water (20 mL). The solution was extracted with EtOAc (3×100 mL); the combined organic layers were dried over anhydrous Na$_2$SO$_4$ and concentrated under vacuum. The residue was purified with SiO$_2$-gel column and eluted with ethyl acetate/petroleum ether (1:5 to 1:2). This resulted in 1.1 g (60%) of the title compound as a white solid. MS-ESI: 307.2 (M+1).

Step 5: Tert-butyl 2-(2,6-diisopropyl-4-(methoxymethyl)phenyl)acetate

Into a 100 mL round bottom flask was placed a solution of tert-butyl 2-(4-(hydroxymethyl)-2,6-diisopropylphenyl)acetate (1.1 g, 3.6 mmol) in THF (20 mL). NaH (60% wt., 173 mg, 4.3 mmol) was added to the mixture at 0° C. in portions, and the mixture was stirred at 0° C. for 30 min. MeI (1.0 g, 7.2 mmol) was added to the mixture dropwise at 0° C.; the resulting mixture was stirred at RT for overnight. The reaction was quenched with ice-water (20 mL) and extracted with EtOAc (3×100 mL). The combined organic layer were dried over $Na_2SO_4$ and concentrated under vacuum. The residue was purified with $SiO_2$-gel column and eluted with ethyl acetate/petroleum ether (1:10-1:5). This resulted in 1.1 g (95%) of title compound as a colorless oil. MS-ESI: 321.2 (M+1).

Step 6: 2-(2,6-Diisopropyl-4-(methoxymethyl)phenyl)acetic acid

Into a 50-mL round-bottom flask was placed a solution of tert-butyl 2-[4-fluoro-2,6-bis(propan-2-yl)phenyl]acetate (1.1 g, 3.4 mmol) in DCM (10 mL) and TFA (10 mL). The resulting solution was stirred for 3 h at RT and then was concentrated under vacuum. This resulted in 1.0 g (crude) of the title compound as a light yellow solid. MS-ESI: 263.2 (M−1).

Scheme 22

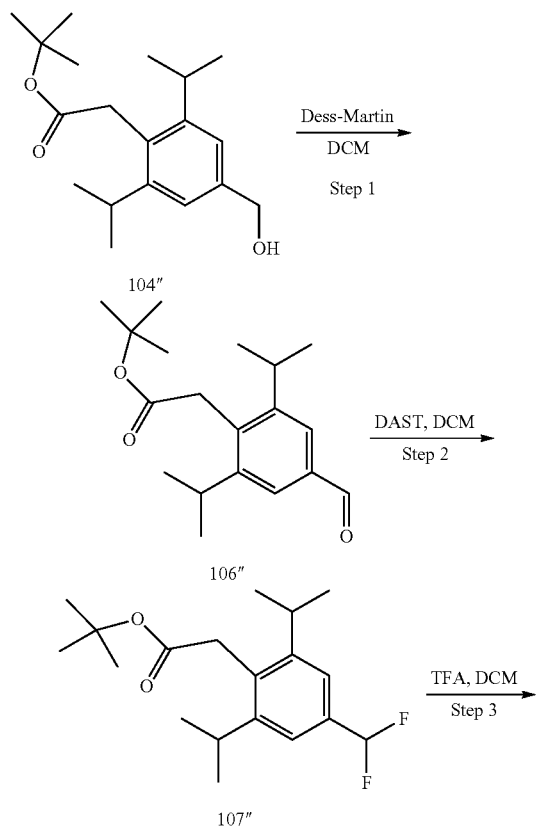

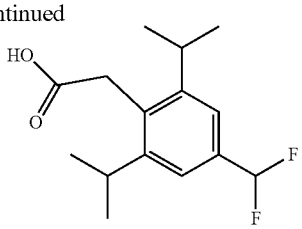

Intermediate 26

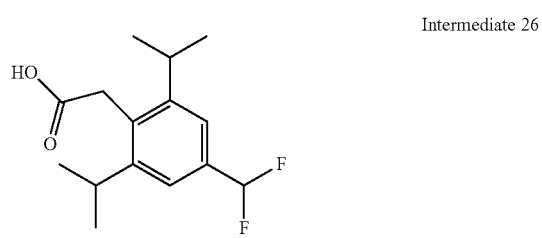 [SMILES: CC(C)c1cc(C(F)F)cc(C(C)C)c1CC(=O)O]

Intermediate 26

2-(4-(Difluoromethyl)-2,6-diisopropylphenyl)acetic acid

Step 1: Tert-butyl 2-(4-formyl-2,6-diisopropylphenyl)acetate

Into a 100 mL round bottom flask was placed a solution of tert-butyl 2-(4-(hydroxymethyl)-2,6-diisopropylphenyl)acetate (1.1 g, 3.6 mmol) in DCM (20 mL). Dess-Martin Periodinane (2.29 g, 5.4 mmol) was added to the mixture at 0° C. in portions. The mixture was stirred at RT overnight, after which the reaction was quenched with ice-water (20 mL) and extracted with DCM (3×50 mL). The combined organic layers were dried over anhydrous $Na_2SO_4$ and concentrated under vacuum. The residue was purified on a $SiO_2$-gel column and eluted with ethyl acetate/petroleum ether (1:20-1:10). This resulted in 0.98 g (90%) of title compound as a yellow solid. MS-ESI: 305.2 (M+1).

Step 2: Tert-butyl 2-(4-(difluoromethyl)-2,6-diisopropylphenyl)acetate

Into a 100 mL round bottom flask was placed a solution of tert-butyl 2-(4-formyl-2,6-diisopropylphenyl)acetate (912 mg, 3.0 mmol) in DCM (15 mL). DAST (2.41 g, 15 mmol) was added to the mixture at 0° C. in portions. The mixture was stirred at RT overnight, after which the reaction was quenched with water (10 mL) and extracted with DCM (3×30 mL). The combined organic layers were dried over $Na_2SO_4$ and concentrated under vacuum. The residue was purified with $SiO_2$-gel column and eluted with ethyl acetate/petroleum ether (1:20-1:15). This resulted in 586 mg (60%) of title compound as a yellow solid. MS-ESI: 327.2 (M+1).

Steps 3 used similar procedures for converting compound 105″ to Intermediate 25 shown in Scheme 21 to afford Intermediate 26. MS-ESI: 269.1 (M−1).

Schemes of Sulfonimidoylamide Intermediates: Schemes 23-30 illustrate the preparation of sulfonimidoylamide intermediates.

Scheme 23

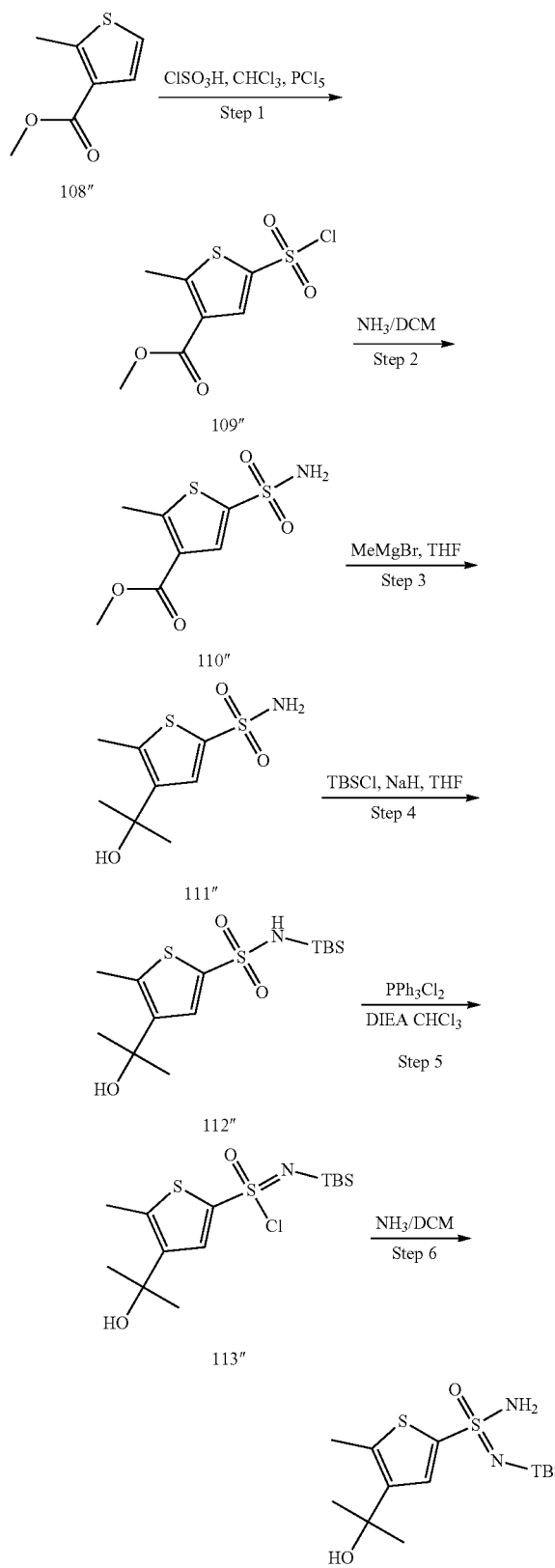

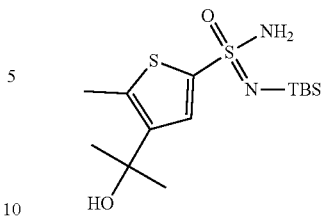

N'-(tert-butyl dim ethyl silyl)-4-(2-hydroxypropan-2-yl)-5-methylthiophene-2-sulfonimidamide

Step 1: Methyl 5-(chlorosulfonyl)-2-methylthiophene-3-carboxylate

Into a 250-mL round-bottom flask, was placed methyl 2-methylthiophene-3-carboxylate (5.0 g, 32.0 mmol), CHCl₃ (70 mL). This was followed by the addition of ClSO₂OH (5.6 g, 48.0 mmol) dropwise with stirring. To this was added PCl₅ (13.3 g, 64.0 mmol) with stirring. The resulting solution was stirred for 2 h at 60° C. in an oil bath. The reaction was then quenched by the addition of 150 mL of water/ice. The resulting solution was extracted with 3×80 ml of dichloromethane, dried over anhydrous sodium sulfate, and concentrated. This resulted in 5.2 g (63.8%) of the title compound as a yellow solid.

Step 2: Methyl 2-methyl-5-sulfamoylthiophene-3-carboxylate

Into a 250-mL round-bottom flask, was placed methyl 5-(chlorosulfonyl)-2-methylthiophene-3-carboxylate (5.2 g, 20.4 mmol) in DCM (50 mL), to this solution was added NH₃/DCM (50 mL, sat.) dropwise with stirring. The resulting solution was stirred for 2 h at 40° C. in an oil bath. The resulting mixture was concentrated. The residue was eluted from a silica gel with ethyl acetate/petroleum ether (2:3). This resulted in 4.6 g (95.8%) of the title compound as a yellow solid. MS-ESI: 236 [M+1].

Step 3: 4-(2-Hydroxypropan-2-yl)-5-methylthiophene-2-sulfonamide

Into a 250-mL 3-necked round-bottom flask purged and maintained with an inert atmosphere of nitrogen, was placed methyl 2-methyl-5-sulfamoylthiophene-3-carboxylate (4.6 g, 19.5 mmol) in THF (100 mL). This was followed by the addition of MeMgBr (29 mL, 87 mmol, 3M) dropwise with stirring at 0° C. in an ice bath. The resulting solution was stirred for 2 h at RT. The pH value of the solution was adjusted to 5 with HCl (2 M). The resulting solution was extracted with 3×100 ml of ethyl acetate, dried over anhydrous sodium sulfate, and concentrated. The residue was eluted from silica gel with ethyl acetate/petroleum ether (1:2). This resulted in 1.3 g (28.2%) of the title compound as a light yellow solid. MS-ESI: 236 [M+1].

Step 4: N-(tert-butyldimethylsilyl)-4-(2-hydroxypropan-2-yl)-5-methylthiophene-2-sulfonamide Into a 100-mL round-bottom flask, was placed 4-(2-hydroxypropan-2-yl)-5-methylthiophene-2-sulfonamide (1.3 g, 5.52 mmol) in THF (40 mL). To this was added NaH (60% wt. oil dispersion, 442 mg, 11.1 mmol) in portions with stirring at 0° C. This was followed by the addition of TBSCl (1.25 g, 8.29 mmol). The resulting solution was stirred for 1 h at RT. The reaction was then quenched by the addition of 50 mL of NH₄Cl solution. The resulting solution was extracted with 3×50 ml of ethyl acetate, dried over anhydrous sodium sulfate, and concentrated. The residue was eluted from silica gel with ethyl acetate/petroleum ether (1:2). This resulted in 1.2 g (62.1%) of the title compound as a white solid. MS-ESI:350[M+1].

Steps 5 and 6: N'-(tert-butyldimethylsilyl)-4-(2-hydroxypropan-2-yl)-5-methylthiophene-2-sulfonimidamide Into a 100-mL 3-necked round-bottom flask purged and maintained with an inert atmosphere of nitrogen, was placed a solution of PPh₃Cl₂ (3.51 g, 10.5 mmol) in CHCl₃ (40 mL). This was followed by the addition of DIEA (1.77 g, 13.7 mmol) dropwise with stirring at RT. The resulting solution was stirred for 10 min at RT and the reaction mixture was cooled to 0° C. To this was added a solution of N-(tert-butyldimethyl silyl)-4-(2-hydroxypropan-2-yl)-5-methylthiophene-2-sulfonamide (1.2 g, 3.43 mmol) in CHCl₃ (5 mL) dropwise with stirring at 0° C. The resulting solution was stirred for 30 min at 0° C. To the mixture was introduced NH₃ gas bubble for 15 min at 0° C. The resulting solution was stirred for 2 h at RT. The resulting solution was diluted with 50 mL of H₂O. The resulting solution was extracted with 3×100 ml of DCM and dried over anhydrous sodium sulfate and concentrated. The residue was eluted from silica gel with ethyl acetate/petroleum ether (1:1). This resulted in 930 mg (77.7%) of the title compound as a yellow solid. MS-ESI: 349 [M+1].

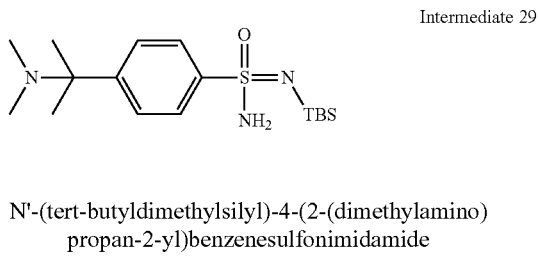

TABLE 12

The Intermediates in the following Table were prepared using similar procedure as shown in Scheme 23 above for converting compound 108" to Intermediate 27 starting from methyl thiophene-3-carboxylate.

| Intermediate # | Structure | IUPAC Name | Exact Mass [M + H]⁺ |
|---|---|---|---|
| Intermediate 28 | 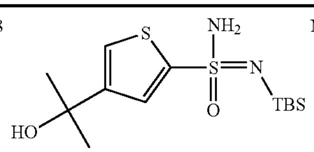 | N'-(tert-butyldimethylsilyl)-4-(2-hydroxypropan-2-yl)thiophene-2-sulfonimidamide | 335 |

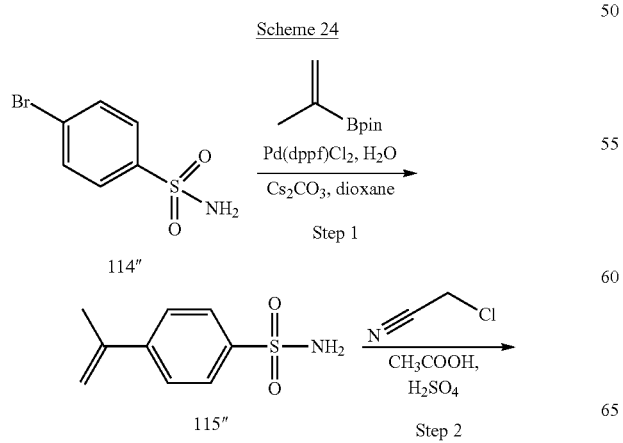

N'-(tert-butyldimethylsilyl)-4-(2-(dimethylamino)propan-2-yl)benzenesulfonimidamide Step 1: 4-(Prop-1-en-2-yl)benzenesulfonamide Into a 500-mL 3-necked round-bottom flask purged and maintained with an inert atmosphere of nitrogen, was placed a solution of 4-bromobenzene-1-sulfonamide (5.0 g, 21.2 mmol) in dioxane (75 mL) and H₂O (7.5 mL). To this solution was added 4,4,5,5-tetramethyl-2-(prop-1-en-2-yl)-

1,3,2-dioxaborolane (7.83 g, 46.59 mmol), Pd(dppf)Cl$_2$ (1.5 g, 2.12 mmol) and Cs$_2$CO$_3$ (27.6 g, 84.7 mmol). The resulting solution was stirred for 2 h at 85° C. The resulting solution was diluted with 400 mL of water. The resulting solution was extracted with 2×500 mL of ethyl acetate and dried over anhydrous sodium sulfate and concentrated. The residue was eluted from silica gel with ethyl acetate/petroleum ether (1:3). This resulted in 4.7 g (98.1%) of the title compound as a yellow solid. MS-ESI: 198.1 [M+1].

Step 2: 2-Chloro-N-(2-(4-sulfamoylphenyl)propan-2-yl)acetamide

Into a 1 L round-bottom flask, was placed a solution of 4-(prop-1-en-2-yl)benzene-1-sulfonamide (2.2 g, 11.2 mmol) in AcOH (280 mL). To the solution was added 2-chloroacetonitrile (16.8 g, 224 mmol). This was followed by the addition of H$_2$SO$_4$ (70 mL, 0.7 mmol) dropwise with stirring at 0° C. The resulting solution was stirred overnight at RT. The resulting solution was diluted with 500 mL of water/ice. The pH value of the solution was adjusted to 7 with a saturated solution of Na$_2$CO$_3$. The resulting solution was extracted with 3×1000 mL of DCM, dried over anhydrous sodium sulfate and concentrated. The residue was eluted from silica gel with ethyl acetate/petroleum ether (3:2). This resulted in 2.7 g (83.2%) of the crude title compound as a white solid. MS-ESI: 291.0 [M+1].

Step 3: 4-(2-Aminopropan-2-yl)benzenesulfonamide

Into a 100-mL round-bottom flask, was placed a solution of 2-chloro-N-[2-(4-sulfamoylphenyl)propan-2-yl] acetamide (1.0 g, 3.44 mmol) in ethanol (30 mL) and AcOH (6.0 mL, 99.93 mmol). To the solution was added thiourea (314.2 mg, 4.13 mmol). The resulting solution was stirred for overnight at 85° C. The resulting mixture was concentrated. The resulting mixture was washed with 50 mL of ethanol. The solids were collected by filtration. The solid was dried under infra-red for 16 h. This resulted in 520 mg (70.56%) of the crude title compound as a white solid. MS-ESI: 215.1 [M+1].

Step 4: 4-(2-(Dimethylamino)propan-2-yl)benzenesulfonamide

Into a 50-mL round-bottom flask, was placed a solution of 4-(2-aminopropan-2-yl)benzene-1-sulfonamide (500 mg, 2.33 mmol) in methanol (20 mL). This was followed by the addition of HCHO (140 mg, 4.67 mmol). The resulting solution was stirred for 30 min at RT. To this was added NaBH$_3$CN (439 mg, 7.0 mmol) in several batches at 0° C. The resulting solution was stirred for 1 h at RT. The reaction was then quenched by the addition of 50 mL of water. The resulting mixture was concentrated and washed with 20 mL of H$_2$O. The solids were collected by filtration and dried in an oven under reduced pressure at 50° C. This resulted in 300 mg (53.1%) of the crude title compound as a white solid. MS-ESI: 243.1[M+1].

Step 5: N-(tert-butyldimethylsilyl)-4-(2-(dimethylamino)propan-2-yl)benzenesulfonamide Into a 50-mL round-bottom flask, was placed a solution of 4-[2-(dimethylamino)propan-2-yl]benzene-1-sulfonamide (200 mg, 0.83 mmol) in THF (15 mL). This was followed by the addition of NaH (60% wt. oil dispersion, 66 mg, 1.65 mmol) at 0° C. The resulting solution was stirred for 10 min at RT. To this was added TBSCl (497 mg, 3.3 mmol). The resulting solution was stirred for 1 h at RT. The reaction was then quenched by the addition of 60 mL of water/ice. The resulting solution was extracted with 2×60 mL of ethyl acetate and dried over anhydrous sodium sulfate and concentrated. The residue was eluted from silica gel with ethyl acetate/petroleum ether (1:1). This resulted in 243 mg (82.5%) of the title compound as a white solid. MS-ESI: 357.2 [M+1].

Step 6: N'-(tert-butyldimethylsilyl)-4-(2-(dimethylamino)propan-2-yl)benzenesulfonimidamide Into a 250-mL 3-necked round-bottom flask purged and maintained with an inert atmosphere of nitrogen, was placed a solution of dichlorotriphenyl-λ5-phosphane (467 mg, 1.4 mmol) in CHCl$_3$ (30 mL). This was followed by the addition of DIEA (261 mg, 2.02 mmol) dropwise with stirring. The resulting solution was stirred for 15 min at RT, and the reaction system was cooled to 0° C. To this was added a solution of N-(tert-butyldimethylsilyl)-4-[2-(dimethylamino)propan-2-yl]benzene-1-sulfonamide (200 mg, 0.56 mmol) in CHCl$_3$ (10 mL) dropwise with stirring at 0° C. The resulting solution was stirred for 30 min at 0° C. To the mixture was added a solution of NH$_3$ in DCM (60 mL, sat.). The resulting solution was stirred for 2 h at RT. The resulting mixture was diluted with 80 mL of H$_2$O. The resulting solution was extracted with 2×100 mL of DCM and dried over anhydrous sodium sulfate and concentrated. The residue was eluted from silica gel with ethyl acetate/petroleum ether (1.4:1). This resulted in 140 mg (70.1%) of the title compound as a white solid. MS-ESI: 356.2 [M+1].

Scheme 25

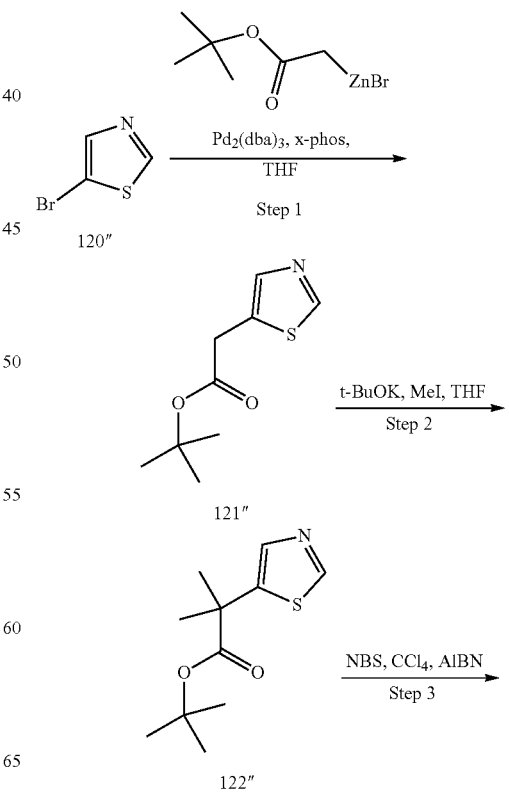

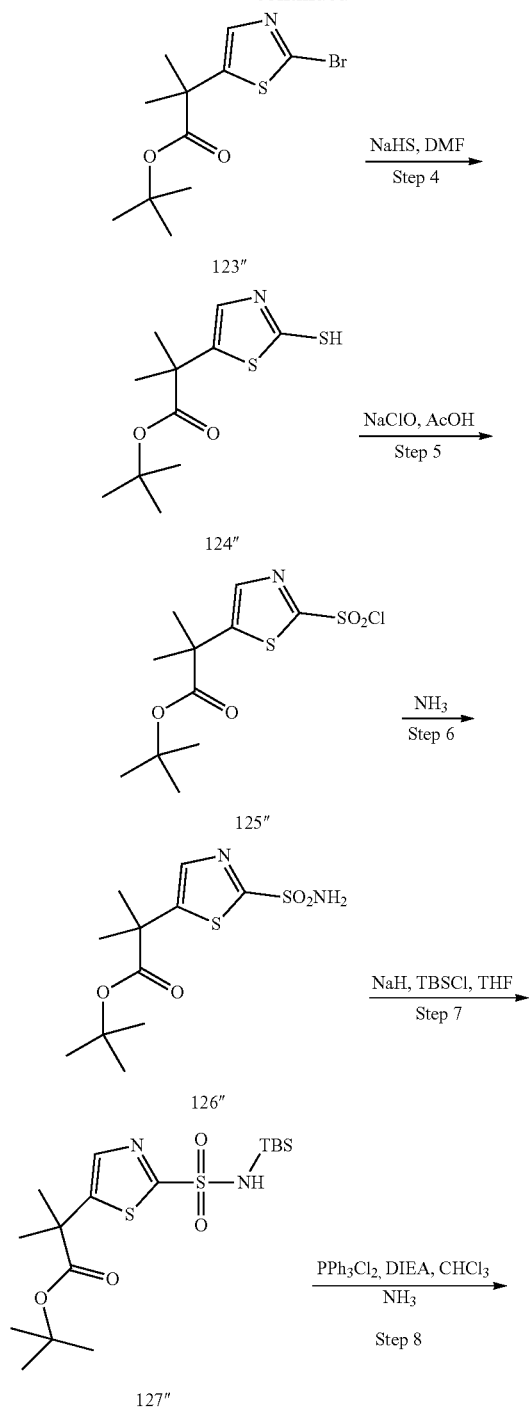

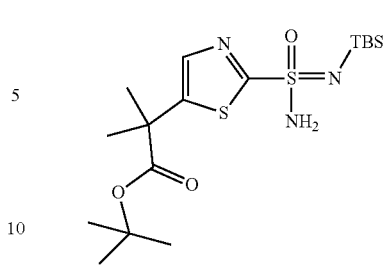

Intermediate 30

Tert-butyl 2-(2-(N'-(tert-butyldimethyl silyl)sulfamidimidoyl)thiazol-5-yl)-2-methylpropanoate Step 1: Tert-butyl 2-(thiazol-5-yl)acetate Into a 250-mL 3-necked round-bottom flask purged and maintained with an inert atmosphere of nitrogen, was placed a solution of 5-bromo-1,3-thiazole (3.0 g, 18.3 mmol) in THF (100 mL). This was followed by the addition of Pd$_2$(dba)$_3$ (947 mg, 0.91 mmol) and Xphos (1.05 g, 1.83 mmol). The resulting solution was stirred for 10 min at RT. To this was added tert-butyl 2-(bromozincio)acetate (9.5 g, 36.5 mmol). The resulting solution was stirred for 1.5 h at 60° C. The resulting mixture was diluted with 150 mL of H$_2$O. The resulting solution was extracted with 2×200 mL of ethyl acetate, dried over anhydrous sodium sulfate and concentrated. The residue was eluted from silica gel with ethyl acetate/petroleum ether (1:5). This resulted in 1.0 g (27.4%) of the title compound as a yellow liquid. MS-ESI: 200.1[M+1].

Step 2: Tert-butyl 2-methyl-2-(thiazol-5-yl)propanoate

Into a 250-mL round-bottom flask, was placed a solution of tert-butyl 2-(1,3-thiazol-5-yl)acetate (1.0 g, 5.02 mmol) in THF (50 mL). To the solution were added t-BuOK (2.30 g, 20.4 mmol) and MeI (2.91 g, 20.4 mmol). The resulting solution was stirred for 1 h at RT. The reaction was then quenched by the addition of 200 mL of water. The resulting solution was extracted with 3×200 mL of ethyl acetate dried over anhydrous sodium sulfate and concentrated. The residue was eluted from silica gel with ethyl acetate/petroleum ether (1:5). This resulted in 1.05 g (92.0%) of the title compound as brown yellow oil. MS-ESI: 228.1 [M+1].

Step 3: Tert-butyl 2-(2-bromothiazol-5-yl)-2-methylpropanoate

Into a 100-mL round-bottom flask purged and maintained with an inert atmosphere of nitrogen, was placed a solution of tert-butyl 2-methyl-2-(1,3-thiazol-5-yl)propanoate (500 mg, 2.2 mmol) in CCl$_4$ (30 mL). To the solution were added NBS (783 mg, 4.4 mmol) and AIBN (72.2 mg, 0.44 mmol). The resulting solution was stirred for 5 h at 70° C. The reaction was then quenched by the addition of 60 mL of water. The resulting solution was extracted with 2×100 mL of DCM, dried over anhydrous sodium sulfate, and concentrated. The residue was eluted from silica gel with ethyl acetate/petroleum ether (1:6). This resulted in 450 mg (66.9%) of the title compound as yellow oil. MS-ESI: 306.0 [M+1].

Step 4: Tert-butyl 2-(2-mercaptothiazol-5-yl)-2-methylpropanoate

Into a 50-mL round-bottom flask, was placed a solution of tert-butyl 2-(2-bromo-1,3-thiazol-5-yl)-2-methylpropanoate (450 mg, 1.5 mmol) in DMF (10 mL). To the solution was added NaSH (2.97 g, 30 mmol). The resulting solution was stirred overnight at 100° C. The pH value was adjusted to 6 with 1M HCl. The resulting solution was washed with 2×25 mL of H$_2$O and extracted with 2×50 mL of ethyl acetate. The organic layers were combined and dried over anhydrous sodium sulfate. The residue was eluted from silica gel with ethyl acetate/petroleum ether (1:1). This resulted in 350 mg (91.6%) of the title compound as yellow oil. MS-ESI: 260.1 [M+1].

Step 5: Tert-butyl 2-(2-(chlorosulfonyl)thiazol-5-yl)-2-methylpropanoate

Into a 25-mL round-bottom flask, was placed a solution of tert-butyl 2-methyl-2-(2-sulfanyl-1,3-thiazol-5-yl)propanoate (350 mg, 1.35 mmol) in AcOH (10 mL) at 0° C. To this was added NaClO (10% wt., 5.03 g, 67.4 mmol) dropwise with stirring at 0° C. The resulting solution was stirred for 90 min at RT. The resulting mixture was diluted with 2×100 mL of H$_2$O. The resulting solution was extracted with 150 mL of DCM, the combined organic layer was dried over anhydrous sodium sulfate and concentrated. This resulted in 100 mg (56.8%) of the title compound as yellow oil.

Step 6: Tert-butyl 2-methyl-2-(2-sulfamoylthiazol-5-yl)propanoate

Into a 50-mL round-bottom flask, was placed a solution of tert-butyl 2-[2-(chlorosulfonyl)-1,3-thiazol-5-yl]-2-methylpropanoate (100 mg, 0.31 mmol) in DCM (5 mL). To the above solution NH$_3$ (g) was introduced. The resulting solution was stirred for 20 min at RT. The resulting mixture was concentrated. The residue was eluted from silica gel with ethyl acetate/petroleum ether (3:4). This resulted in 90 mg (95.7%) of the title compound as a white solid. MS-ESI: 307.1 [M+1].

Step 7: Tert-butyl 2-(2-(N-(tert-butyldimethylsilyl)sulfamoyl)thiazol-5-yl)-2-methylpropanoate Into a 25-mL round-bottom flask, was placed a solution of tert-butyl 2-methyl-2-(2-sulfamoyl-1,3-thiazol-5-yl)propanoate (50 mg, 0.16 mmol) in THF (5 mL). This was followed by the addition of NaH (60% wt. oil dispersion, 9.6 mg, 0.24 mmol) at 0° C. To this was added TBSCl (49.2 mg, 0.33 mmol). The resulting solution was stirred for 40 min at RT. The reaction was then quenched by the addition of 30 mL of water/ice. The resulting solution was extracted with 2×50 mL of ethyl acetate, dried over anhydrous sodium sulfate and concentrated. The residue was eluted from silica gel with ethyl acetate/petroleum ether (1:3). This resulted in 120 mg (97.1%) of the title compound as a white solid. MS-ESI: 421.2 [M+1].

Step 8: Tert-butyl 2-(2-(N'-(tert-butyldimethylsilyl)sulfamidimidoyl)thiazol-5-yl)-2-methylpropanoate Into a 50-mL 3-necked round-bottom flask purged and maintained with an inert atmosphere of nitrogen, was placed a solution of PPh$_3$Cl$_2$ (236 mg, 0.71 mmol) in CHCl$_3$ (15 mL). This was followed by the addition of DIEA (147 mg, 1.14 mmol) dropwise with stirring at 0° C. The resulting solution was stirred for 15 min at RT. To this was added a solution of tert-butyl 2-[2-[(tert-butyldimethylsilyl)sulfamoyl]-1,3-thiazol-5-yl]-2-methylpropanoate (120 mg, 0.29 mmol) in CHCl$_3$ (4 mL) dropwise with stirring at 0° C. The resulting solution was stirred for 30 min at 0° C. To the above solution was introduced NH$_3$(g). The resulting solution was stirred for 1 h at RT. The resulting mixture was diluted with 50 mL of H$_2$O. The resulting solution was extracted with 2×75 mL of DCM, the combined organic layer was dried over anhydrous sodium sulfate and concentrated. The residue was eluted from silica gel with ethyl acetate/petroleum ether (1:6). This resulted in 80 mg (66.6%) of the title compound as a white solid. MS-ESI: 420.2 [M+1].

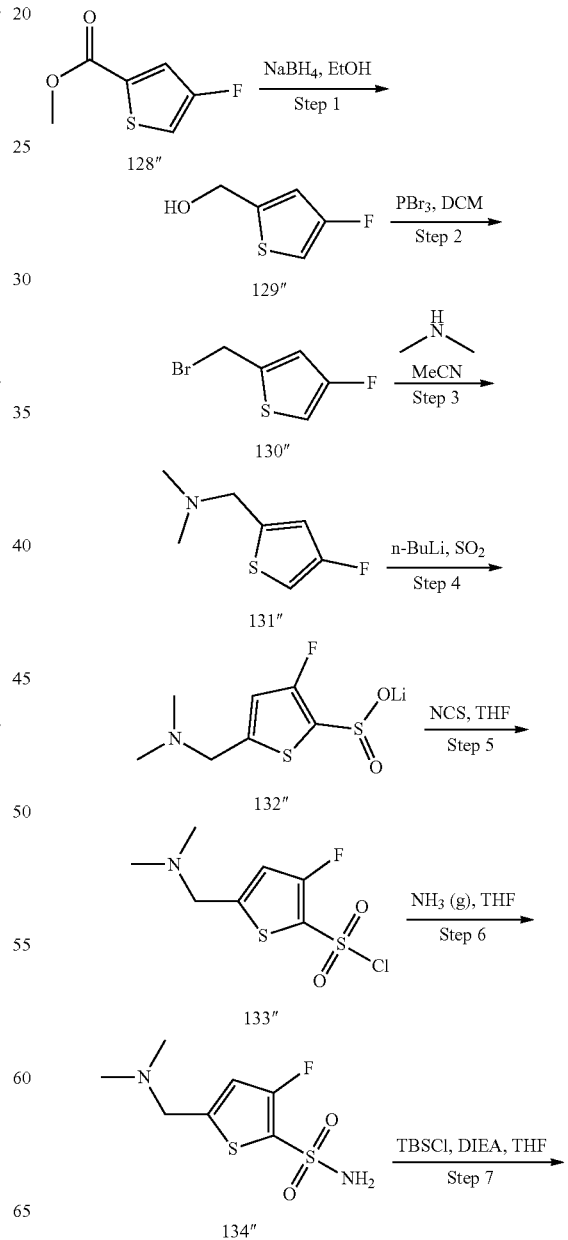

Scheme 26

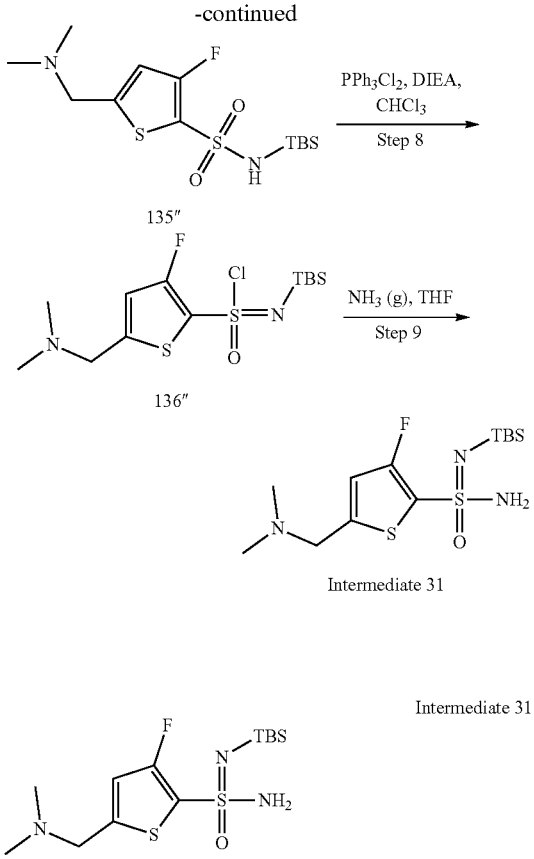

N'-(tert-butyldimethyl silyl)-5-((dimethyl amino) methyl)-3-fluorothiophene-2-sulfonimidamide

Step 1: (4-Fluorothiophen-2-yl)methanol

Into a 1000-mL 3-necked round-bottom flask purged and maintained with an inert atmosphere of nitrogen, was placed methyl 4-fluorothiophene-2-carboxylate (10 g, 62.4 mmol) in EtOH (300 mL). To the above solution was added NaBH$_4$ (4.74 g, 124.8 mmol) with stirring at 0° C. The resulting solution was stirred for 30 min at 0° C. The resulting solution was allowed to react for an additional 16 h at RT. The reaction was then quenched by the addition of 10 mL of water. The resulting mixture was extracted with 3×1000 mL of ethyl acetate. Evaporation of combined ethyl acetate solution resulted in 6.4 g (77.5%) of the title compound as white oil.

Step 2: 2-(Bromomethyl)-4-fluorothiophene

Into a 250-mL round-bottom flask, was placed (4-fluorothiophen-2-yl)methanol (8.5 g, 64.32 mmol) in DCM (70 mL). To the stirred solution was added PBr$_3$ (19.15 g, 70.75 mmol) at 0° C. The resulting solution was stirred for 30 min at 0° C., after which it was allowed to react for an additional 12 h at RT. The reaction was quenched with 20 mL of water and extracted with ethyl acetate 3×50 mL. The combined organic layer was dried over Na$_2$SO$_4$ and concentrated under vacuum. The residue was eluted from silica gel with ethyl acetate/petroleum ether (15/85). This resulted in 7.0 g (55.8%) of the title compound as yellow oil.

Step 3: 1-(4-Fluorothiophen-2-yl)-N,N-dimethylmethanamine

Into a 250-mL round-bottom flask, was placed 2-(bromomethyl)-4-fluorothiophene (7.4 g, 37.9 mmol). To the solution was added dimethylamine in THF (2M, 37.9 mmol). The resulting solution was stirred for 16 h at RT. The reaction mixture was concentrated under vacuum. The residue was eluted from silica gel with ethyl acetate/petroleum ether (17/83). This resulted in 5.62 g (92.6%) of the title compound as a solid. MS-ESI: 160 [M+1].

Step 4: Lithium 5-((dimethylamino)methyl)-3-fluorothiophene-2-sulfinate

Into a 250-mL 3-necked round-bottom flask purged and maintained with an inert atmosphere of nitrogen, was placed a solution of [(4-fluorothiophen-2-yl)methyl] dimethylamine (6.2 g, 38.9 mmol) in THF (60 mL), to the above solution was added n-BuLi (18.7 mL, 46.7 mmol, 2.5 M) dropwise at −78° C. in a liquid nitrogen/ethanol bath. The resulting solution was stirred for 30 min at −78° C. To the stirred solution, SO$_2$(g) (4.99 g, 78 mmol) was introduced in at −78° C. The resulting solution was allowed to react for an additional 120 min at RT. The resulting mixture was concentrated. This resulted in 10 g (crude) of the title compound as a yellow solid. MS-ESI: 228 [M−1].

Step 5: 5-((Dimethylamino)methyl)-3-fluorothiophene-2-sulfonyl chloride

Into a 500-mL round-bottom flask, was placed a solution of 5-[(dimethylamino)methyl]-3-fluorothiophene-2-sulfinic acid (10 g, 44.7 mmol) in THF (100 mL), to the above solution was added NCS (7.18 g, 54 mmol) at 0° C. The resulting solution was stirred for 30 min at 0° C. The resulting solution was allowed to react for an additional 100 min at RT. The reaction solution was used for next step without any purification.

Step 6: 5-((Dimethylamino)methyl)-3-fluorothiophene-2-sulfonamide

Into a 500-mL round-bottom flask, was placed a solution of 5-[(dimethylamino)methyl]-3-fluorothiophene-2-sulfonyl chloride (10 g, 38.8 mmol) in THF (100 mL). To the above NH$_3$ (g) was introduced for 15 min at 0° C. The resulting solution was allowed to react for an additional 100 min at RT. Then the reaction solution was concentrated. The residue was eluted from silica gel with ethyl acetate/petroleum ether (60/40). This resulted in 2.1 g (22.7%) of the title compound as yellow oil. MS-ESI: 239 [M+1].

Step 7: N-(tert-butyldimethylsilyl)-5-((dimethylamino)methyl)-3-fluorothiophene-2-sulfonamide Into a 100-mL round-bottom flask purged and maintained with an inert atmosphere of nitrogen, was placed a solution of 5-[(dimethylamino)methyl]-3-fluorothiophene-2-sulfonamide (1.8 g, 7.55 mmol) in THF (30 mL). To the above solution was added NaH (60% wt. oil dispersion, 600 mg, 15 mmol) with stirring at 0° C. The resulting solution was stirred for 30 min at 0° C. This was followed by the addition of TBSCl (1.37 g, 9.09 mmol) at 0° C. The resulting solution was allowed to react for an additional 15 h at RT. The reaction solution was concentrated. The residue was eluted from silica gel with ethyl acetate. This resulted in 2 g (75.1%) of the title compound as yellow oil. MS-ESI: 353 [M+1].

Step 8-1: N-(tert-butyldimethylsilyl)-5-((dimethyl-amino)methyl)-3-fluorothiophene-2-sulfonimidoyl chloride Into a 500-mL 3-necked round-bottom flask purged and maintained with an inert atmosphere of nitrogen, was placed a solution of PPh₃Cl₂ (59.2 g, 178 mmol) in CHCl₃ (100 mL). This was followed by the addition of DIEA (45.9 g, 355 mmol) dropwise with stirring at 0° C. The resulting solution was stirred for 15 min at RT. To this was added a solution of N-(tert-butyldimethylsilyl)-5-((dimethylamino)methyl)-3-fluorothiophene-2-sulfonamide (15.6 g, 44.4 mmol) in CHCl₃ (30 mL) dropwise with stirring at 0° C. The resulting solution was stirred for 30 min at 0° C. The reaction solution was used in the next step with no workup.

Step 8-2: N'-(tert-butyldimethylsilyl)-5-((dimethyl-amino)methyl)-3-fluorothiophene-2-sulfonimid-amide Into a 250-mL 3-necked round-bottom flask, was placed N-(tert-butyldimethylsilyl)-5-((dimethylamino)methyl)-3-fluorothiophene-2-sulfonimidoyl chloride (2.8 g, 0.27 mmol) in CHCl₃ (20 mL). To the above NH₃(g) was introduced for 15 min at 0° C. The resulting solution was stirred for 15 min at 0° C. The resulting solution was stirred for 1 h at RT. The resulting mixture was diluted with 50 mL of H₂O. The resulting solution was extracted with 2×75 mL of DCM, the combined organic layer was dried over anhydrous sodium sulfate and concentrated. The residue was eluted from silica gel with ethyl acetate/petroleum ether (1:6). This resulted in 250 mg (9.4%) of the title compound as a yellow solid. MS-ESI: 352 [M+1].

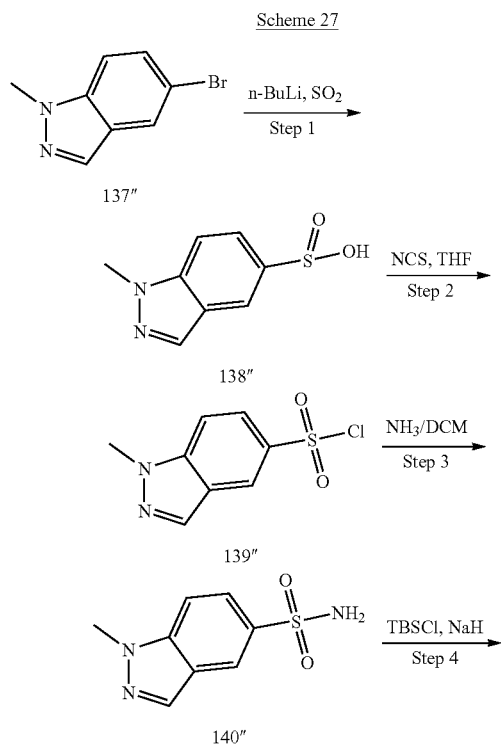

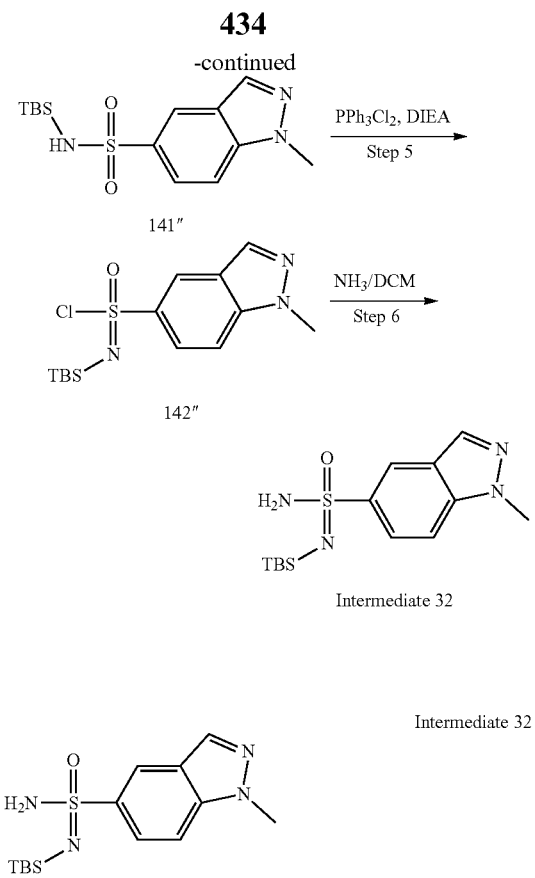

Step 1: 1-Methyl-1H-indazole-5-sulfinic acid

Into a 100-mL 3-necked round-bottom flask purged and maintained with an inert atmosphere of nitrogen, was placed 5-bromo-1-methyl-1H-indazole (700 mg, 3.32 mmol) in THF (5 mL). To the above solution was added n-BuLi (1.6 mL, 3.98 mmol, 2.5 M) dropwise at −78° C. in a liquid nitrogen/ethanol bath. Then the solution was stirred for 30 min at −78° C. To the stirred solution, SO₂ (g) was introduced at −78° C. for 15 min. The resulting solution was allowed to react for an additional 120 min at RT. The resulting mixture was concentrated. This resulted 500 mg (76.8%) of the title compound as a yellow solid.

Steps 2-6 used similar procedures for converting compound 132" to Intermediate 31 shown in Scheme 26 to afford Intermediate 32 from compound 138". MS-ESI: 325 (M+1).

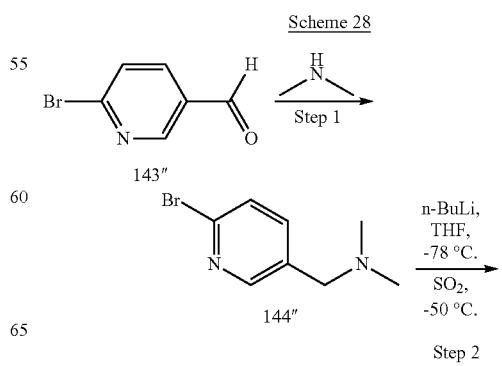

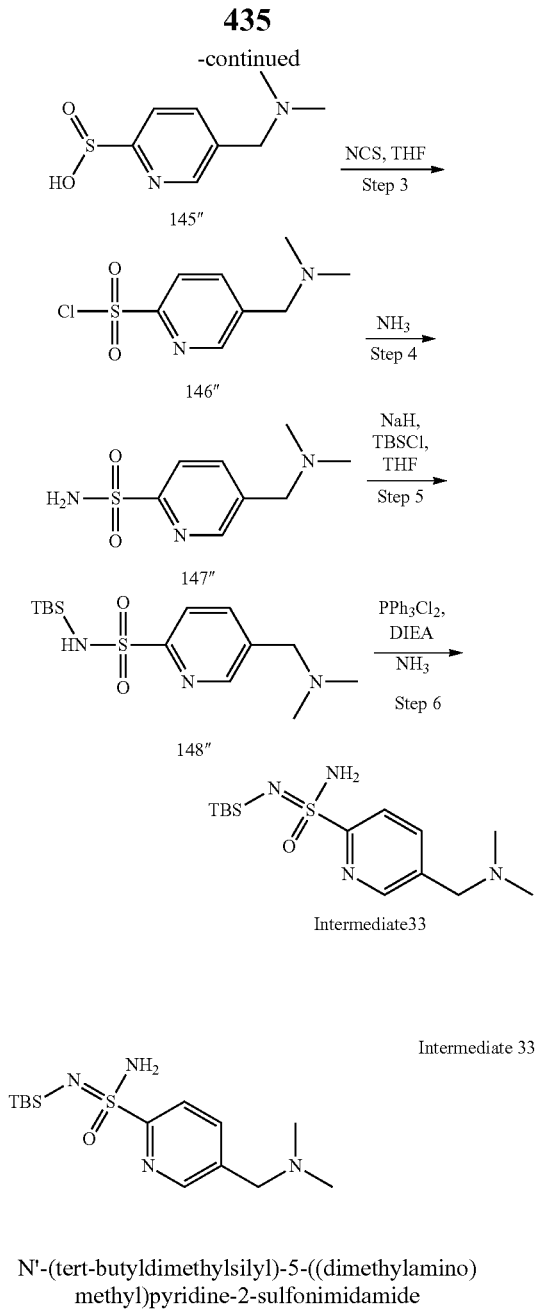

N'-(tert-butyldimethylsilyl)-5-((dimethylamino)methyl)pyridine-2-sulfonimidamide Step 1:
1-(6-Bromopyridin-3-yl)-N,N-dimethylmethanamine Into a 500 mL round-bottom flask, were added Ti(OEt)$_4$ (12.2 g, 53.7 mmol) and dimethylamine (4.85 g, 107 mmol) in methanol (50 mL) at RT. To this stirred solution was added 6-bromopyridine-3-carbaldehyde (5 g, 26.9 mmol) in methanol (30 mL) dropwise at 0° C. After stirring at RT for 3 h, NaBH$_4$ (1.02 g, 26.9 mmol) was added and the resulting mixture was stirred overnight. The reaction was quenched by the addition of water/ice (30 mL) at 0° C. The resulting mixture was extracted with ethyl acetate (3×50 mL). The combined organic layers were dried over anhydrous Na$_2$SO$_4$. After filtration, the filtrate was concentrated under reduced pressure. The residue was purified by silica gel chromatography, eluted with ethyl acetate/petroleum ether (5:1) to afford the title compound (3.5 g, 60.5%) as yellow oil. MS-ESI: 215 (M+1).

Step 2:
5-((Dimethylamino)methyl)pyridine-2-sulfinic acid

Into a 250-mL 3-necked round-bottom flask purged and maintained with an inert atmosphere of nitrogen, was placed [(6-bromopyridin-3-yl)methyl]dimethylamine (3.5 g, 16.27 mmol) in THF (30 mL). This was followed by the addition of n-BuLi (7.2 mL, 17.9 mmol, 2.5 M) dropwise with stirring at −78° C. in 30 min. To this was bubbled SO$_2$ at −78° C. for 15 min. The resulting solution was stirred for 1 h at −78° C. The resulting mixture was concentrated under vacuum. The crude product the title compound (4.0 g) was used in the next step directly without further purification.

Step 3:
5-((Dimethylamino)methyl)pyridine-2-sulfonyl chloride

Into a 250 mL round-bottom flask, was placed 5-[(dimethylamino)methyl]pyridine-2-sulfinic acid (4.0 g crude) and THF (25 mL) at RT. To a stirred solution was added NCS (4 g, 0.03 mmol) in portions at 0° C. The resulting solution was stirred for 1.5 h at RT. The resulting mixture was used in the next step with no workup.

Step 4:
5-((Dimethylamino)methyl)pyridine-2-sulfonamide

Into a 250 mL round-bottom flask, were added 5-[(dimethylamino)methyl]pyridine-2-sulfonyl chloride (crude from previous step) at RT. To this was bubbled NH$_3$ (g) for 10 min at 0° C. The resulting mixture was stirred for 1 h at 0° C. The residue was purified by reverse-phase flash chromatography with the following conditions (column, C$_{18}$ silica gel; mobile phase, MeCN in water, 10% to 50% gradient in 10 min; detector, UV 254 nm.) to afford the title compound (1.2 g, 32.7%) as a yellow solid. MS-ESI: 216 [M+1]

Step 5: N-(tert-butyldimethylsilyl)-5-((dimethylamino)methyl)pyridine-2-sulfonamide Into a 100 mL round-bottom flask, were added 5-[(dimethylamino)methyl]pyridine-2-sulfonamide (700 mg, 3.25 mmol) in THF (15 mL) at 0° C. To this stirred solution was added NaH (60% wt. oil dispersion, 260 mg, 6.5 mmol) in portions at 0° C. under nitrogen atmosphere. The resulting mixture was stirred for 15 min at 0° C. under nitrogen atmosphere. Then TBSCl (980 mg, 6.5 mmol) was added to the above reaction mixture. After the addition was complete, the resulting mixture was stirred for 2 h at RT. The reaction was quenched by the addition of water/ice (10 mL) at 0° C. The resulting mixture was extracted with ethyl acetate (3×20 mL). The combined organic layers were dried over anhydrous Na$_2$SO$_4$. After filtration, the filtrate was concentrated under reduced pressure. The crude title compound (1.15 g) was used in the next step directly without further purification. MS-ESI: 330 [M+1].

Step 6: N'-(tert-butyldimethylsilyl)-5-((dimethylamino)methyl)pyridine-2-sulfonimidamide Into a 250 mL 3-necked round-bottom flask, was added PPh$_3$Cl$_2$ (5.89 g, 13.9 mmol) in CHCl$_3$ (18 mL). To this stirred solution was added DIEA (3.61 g, 27.9 mmol) dropwise at 0° C. under nitrogen atmosphere. The resulting mixture was stirred for 15 min at 0° C. under nitrogen atmosphere. Then N-(tert-butyldimethylsilyl)-5-[(dimethylamino)methyl]pyridine-2-sulfonamide (1.15 g, 3.49 mmol) in CHCl₃ (3 mL) was added to the above resulting mixture dropwise at 0° C. under nitrogen atmosphere. After the addition was complete the resulting mixture was stirred for 30 min. Then NH₃ (g) in DCM (40 mL) was added to the resulting mixture. The resulting mixture was stirred overnight. The resulting mixture was filtered, the filter cake was washed with ethyl acetate (3×20 mL). The filtrate was concentrated under reduced pressure. The residue was purified by Prep-TLC (ethyl acetate/methanol 100:1) to afford the title compound (600 mg, 52.3%) as a yellow solid. MS-ESI: 329 (M+1).

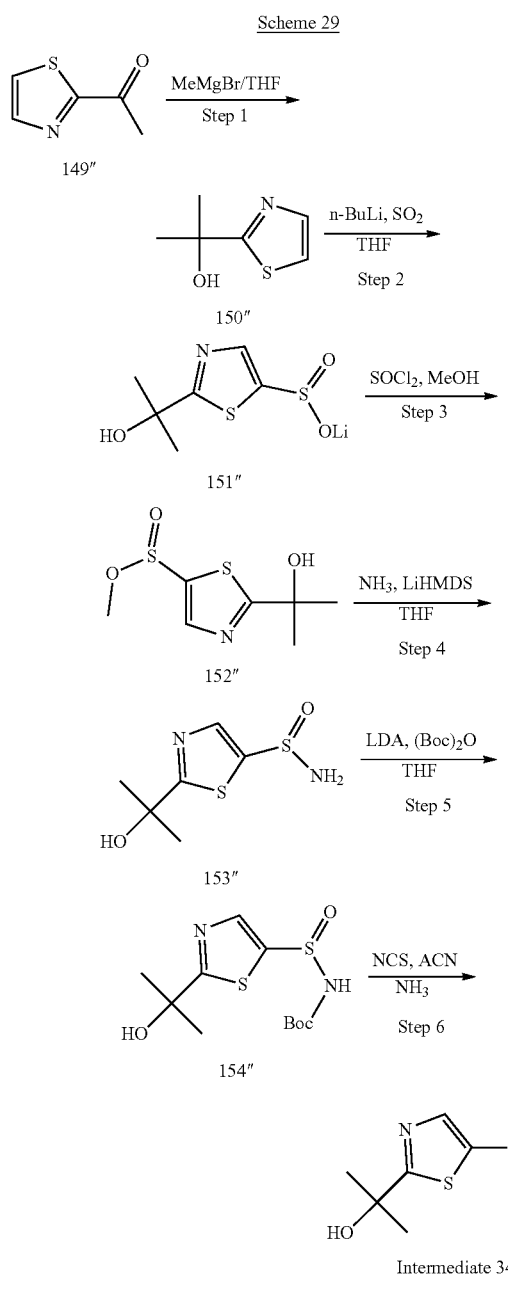

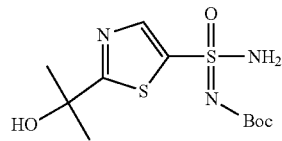

Intermediate 34

N'-(tert-butoxycarbonyl)-2-(2-hydroxypropan-2-yl)thiazole-5-sulfonimidamide

Step 1: 2-(Thiazol-2-yl)propan-2-ol

Into a 10-L 4-necked round-bottom flask purged with and maintained under nitrogen was placed a solution of 1-(thiazol-2-yl)ethanone (200 g, 1.6 mol) in THF (4 L). This was followed by the addition of MeMgBr (3 M in THF, 942 mL) dropwise with stirring at 0° C. The mixture was stirred at 0° C. for 2 h. After warmed the mixture to RT, the solution was stirred for an additional 16 h. Then the reaction was quenched by the addition of 3 L of NH₄Cl (sat.). The resulting solution was extracted with 3×1 L of ethyl acetate. The organic layers were combined and dried over anhydrous Na₂O₄, then concentrated under vacuum. The residue was applied onto a silica gel column and eluted with a gradient of ethyl acetate/petroleum ether (1:3 to 1:1). This resulted in 210 g (93%) of the title compound as brown oil. MS-ESI: 144.0 (M+1). ¹H NMR (400 MHz, DMSO-d₆) δ 7.68 (d, J=3.2 Hz, 1H), 7.54 (d, J=3.2 Hz, 1H), 5.94 (s, 1H), 1.51 (s, 6H).

Step 2: Lithium 2-(2-hydroxypropan-2-yl)thiazole-5-sulfinate

Into a 10-L 4-necked round-bottom flask purged with and maintained under nitrogen, was placed a solution of 2-(thiazol-2-yl)propan-2-ol (50 g, 349 mmol) in THF (1.5 L). This was followed by the addition of n-BuLi (2.5 M in hexane, 350 mL) dropwise with stirring at −78° C. The mixture was stirred at −78° C. for 1 h. Then SO₂ was bubbled into the mixture for 15 min below −30° C. The mixture was stirred for an additional 1 h at RT and then was concentrated under vacuum. This resulted in 87 g (crude) of the title compound as a light yellow solid. The crude product was used directly in the next step.

Step 3: Methyl 2-(2-hydroxypropan-2-yl)thiazole-5-sulfinate

Into a 2-L 3-necked round-bottom flask, lithium 2-(2-hydroxypropan-2-yl)thiazole-5-sulfinate (87 g, crude) was dissolved in anhydrous MeOH (500 mL). Then SOCl₂ (43 g, 360 mmol) was added to the mixture dropwise with stirring at 0° C. The mixture was stirred overnight at RT and then was concentrated under vacuum. The residue was diluted with 500 mL of ethyl acetate. The resulting solution was washed with 2×200 mL of water and 2×200 mL of brine. The organic phase was dried over anhydrous Na₂O₄, then concentrated under vacuum. This resulted in 72 g (crude) title compound as light yellow oil. The crude product was used directly in the next step. MS-ESI: 222[M+1]. ¹H NMR (400 MHz, DMSO-d₆) δ 8.15 (s, 1H), 6.32 (s, 1H), 3.65 (s, 3H), 1.53 (d, J=2.0 Hz, 6H).

Step 4: 2-(2-Hydroxypropan-2-yl)thiazole-5-sulfinamide

Into a 10-L 4-necked round-bottom flask purged with and maintained under nitrogen, was placed a solution of methyl 2-(2-hydroxypropan-2-yl)thiazole-5-sulfinate (72 g, 326 mmol) in THF (500 mL). Then to the above NH$_3$ (0.5 M in THF, 2.0 L) was added. After cooling to −78° C., LiHMDS (1 M in THF, 2.0 L) was added to the mixture dropwise with stirring. Then the mixture was stirred at −78° C. for 2 h. The reaction was quenched by the addition of 500 mL of NH$_4$Cl (sat.). The resulting solution was extracted with 3×300 mL of ethyl acetate. The organic layers were combined, dried over anhydrous Na$_2$O$_4$, then concentrated under vacuum. This resulted in 32 g (crude) title compound as brown oil. The crude product was used directly in the next step. MS-ESI: 207 [M+1]. $^1$H NMR (400 MHz, DMSO-d$_6$) δ 7.77 (s, 1H), 6.73 (s, 2H), 6.17 (s, 1H), 1.51 (d, J=1.4 Hz, 6H).

Step 5: Tert-butyl 2-(2-hydroxypropan-2-yl)thiazol-5-ylsulfinylcarbamate

Into a 1-L 3-necked round-bottom flask purged with and maintained under nitrogen, was placed a solution of 2-(2-hydroxypropan-2-yl)thiazole-5-sulfinamide (32 g, crude) in THF (300 mL). This was followed by the addition of LDA (2 M in THF, 116 mL) dropwise with string at 0° C. The mixture was stirred at 0° C. for 1 h, then (Boc)$_2$O (33.8 g, 155 mmol) was added in portions at 0° C. The mixture was warmed to RT and stirred for an additional 2 h. The reaction was quenched with 200 mL of ice-water (200 mL), and the pH value of the solution was adjusted to 6 with HCOOH. The resulting solution was extracted with 3×200 mL of ethyl acetate. The organic layers were combined, dried over anhydrous Na$_2$O$_4$, and then concentrated under vacuum. The residue was eluted from silica gel with a gradient of ethyl acetate/petroleum ether (1:2 to 1:1). This resulted in 19 g (18%, 4 steps) title compound as a white solid. MS-ESI: 307 [M+1].

Step 6: N-(tert-butyldimethylsilyl)-2-(2-hydroxypropan-2-yl)thiazole-5-sulfonimidamide Into a 1-L 3-necked round-bottom flask purged with and maintained under nitrogen, tert-butyl 2-(2-hydroxypropan-2-yl)thiazol-5-ylsulfinylcarbamate (19 g, 62 mmol) was dissolved in freshly distilled ACN (200 mL). Then to the above solution was added NCS (9.8 g, 74 mmol) in portions. The mixture was stirred for 1 h at RT and then NH$_3$ was bubbled in the mixture for 15 min. The mixture was stirred at RT for 2 h and then was concentrated under vacuum. The residue was applied onto a silica gel column and eluted with a gradient of ethyl acetate/petroleum ether (1:2 to 1:1). This resulted in 13 g (65%) of the title compound as a white solid. MS-ESI: 322 [M+1]. $^1$H NMR (300 MHz, DMSO-d$_6$) δ 7.99 (s, 1H), 7.72 (s, 2H), 6.29 (s, 1H), 1.49 (d, J=2.0 Hz, 6H), 1.27 (s, 9H).

Scheme 30

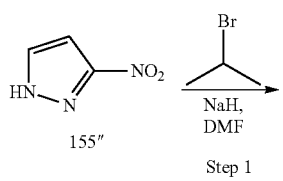

Step 1

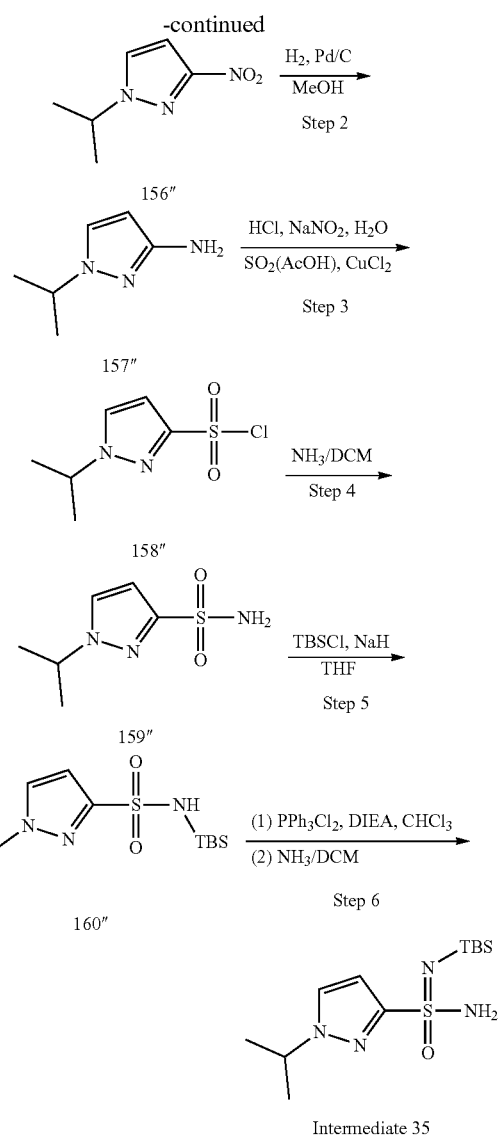

N'-(tert-butyldimethyl silyl)-1-isopropyl-1H-pyrazole-3-sulfonimidamide

Step 1: 1-Isopropyl-3-nitro-1H-pyrazole

Into a 250-mL round-bottom flask, was placed a solution of 3-nitro-1H-pyrazole (10 g, 88.4 mmol) in DMF (100 mL). This was followed by the addition of NaH (60% wt. oil dispersion, 3.9 g, 97.5 mmol) in portions at 0° C. The resulting solution was stirred for 0.5 h at 0° C. This was followed by the addition of 2-bromopropane (14.1 g, 114.6 mmol) dropwise with stirring at 0° C. in 10 min. The resulting solution was stirred for 16 h at RT and then was quenched by the addition of 100 mL of water. The resulting solution was extracted with 3×100 mL of ethyl acetate. The organic layers were combined and dried over anhydrous Na$_2$O$_4$, and then concentrated under vacuum. The residue was eluted from silica gel and eluted with a gradient of ethyl acetate/petroleum ether (1:5 to 1:3). This resulted in 11.8 g (86%) of the title compound as yellow oil. MS-ESI: 156.1 (M+1).

Step 2: 3-Amino-1-(propan-2-yl)-1H-pyrazole

Into a 250-mL round-bottom flask, was placed a solution of 1-isopropyl-3-nitro-1H-pyrazole (10.8 g, 69.6 mmol) in MeOH (100 mL). Then Pd/C (10% wt., 1.5 g) was added. The flask was evacuated and flushed three times with hydrogen. The mixture was stirred for 24 h at RT under an atmosphere of hydrogen. The solids were filtered out. The resulting filtrate was concentrated under vacuum. This resulted in 7.27 g (83%) of the title compound as yellow oil. MS-ESI: 126.1 (M+1).

Step 3: 1-isopropyl-1H-pyrazole-3-sulfonyl chloride

Into a 1 L round-bottom flask, was placed a solution of 3-amino-1-(propan-2-yl)-1H-pyrazole (10 g, 80 mmol) in aq. HCl (6 N, 200 mL). This was followed by the addition of a solution of NaNO$_2$ (8.28 g, 120 mmol) in water (20 mL) dropwise with stirring at 0° C. The resulting solution was stirred for 30 min at 0° C. The above mixture was added to a saturated solution of SO$_2$ in AcOH (200 mL) dropwise with stirring at 0° C. Then to the above was added CuCl$_2$ (10.8 g, 80.7 mmol). The resulting solution was stirred for 1 h at RT and was then quenched by the addition of 200 mL of water. The resulting solution was extracted with 3×200 mL of DCM. The organic layers were combined, dried over anhydrous Na$_2$SO$_4$ and concentrated under vacuum. This resulted in 10 g (59.8%) of the title compound as yellow oil. The product was used in the next step without further purification.

Step 4: 1-isopropyl-1H-pyrazole-3-sulfonamide

Into a 1000 mL round bottom flask, was placed a solution of 1-isopropyl-1H-pyrazole-3-sulfonyl chloride (10 g, 47.8 mmol) in DCM (50 mL). This was followed by the addition of a saturated solution of ammonia in DCM (500 mL) in portions with stirring at 0° C. The resulting solution was stirred for 1 h at 0° C. The resulting solution was concentrated and the residue was purified with SiO$_2$-gel column and eluted with ethyl acetate/petroleum ether (1:2 to 1:1). This resulted in 8.13 g (90%) of the title compound as yellow solid. MS-ESI: 190 [M+1].

Steps 5-6 used similar procedures for converting compound 147" to Intermediate 33 shown in Scheme 28 to afford compound intermediate 35 from compound 159". MS-ESI: 303 (M+1).

Schemes for phenylacetic acids Intermediates: Schemes 31-47 illustrate the preparation of phenylacetic acid intermediates.

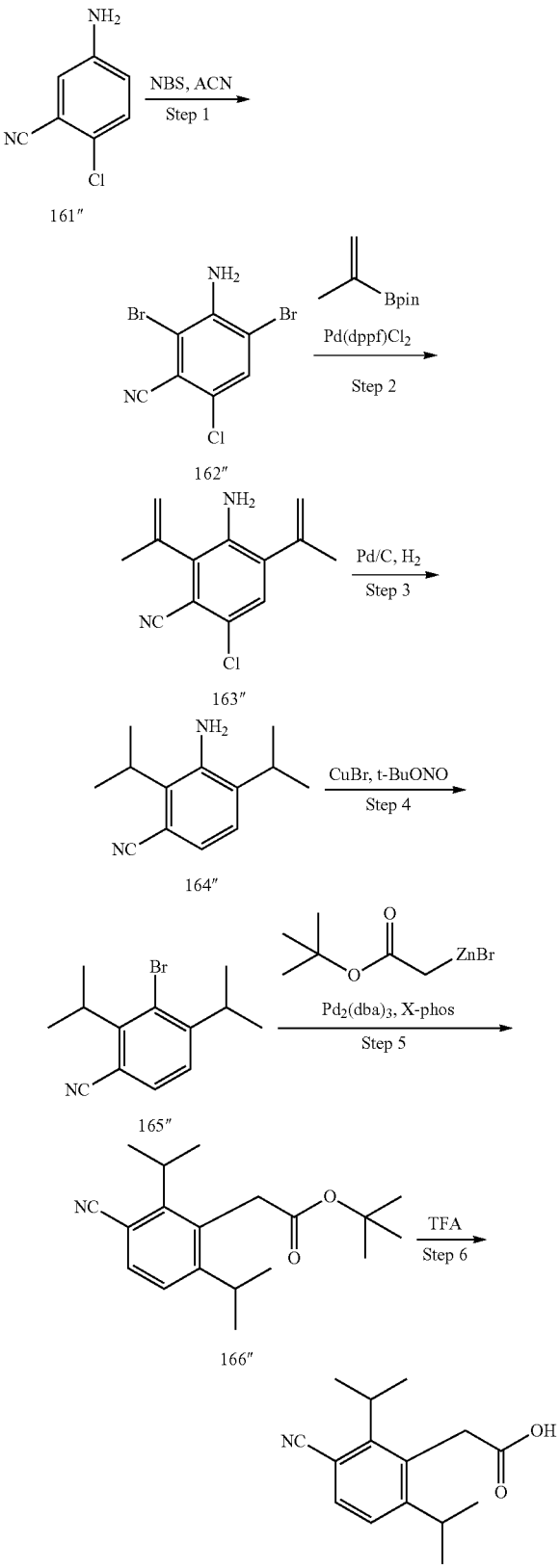

Scheme 31

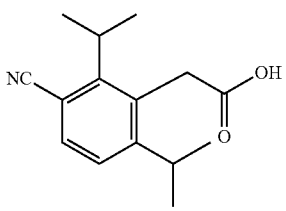

Intermediate 36

2-(3-Cyano-2,6-diisopropylphenyl)acetic acid

Step 1: 3-Amino-2,4-dibromo-6-chlorobenzonitrile

Into a 500-mL round-bottom flask, was placed 5-amino-2-chlorobenzonitrile (10 g, 65.7 mmol) in ACN (200 mL). To the stirred solution was added NBS (29 g, 162 mmol) in portions. The resulting solution was stirred for 14 h at RT. The resulting mixture was concentrated. The residue was eluted from silica gel with ethyl acetate/petroleum ether (1:15 to 1:5). This resulted in 18 g of the title compound as a yellow solid. MS-ESI: 308/310 (M+1).

Step 2: 3-Amino-6-chloro-2,4-di(prop-1-en-2-yl)benzonitrile

Into a 500-mL round-bottom flask purged and maintained with an inert atmosphere of nitrogen, was placed 3-amino-2,4-dibromo-6-chlorobenzonitrile (15 g, 48.0 mmol) in dioxane (200 mL) and $H_2O$ (20 mL), 2-(tetramethyl-1,3,2-dioxaborolan-2-yl)prop-2-en-1-ylium (18.5 g, 111 mmol), $Cs_2CO_3$ (47 g, 144 mmol) and Pd(dppf)$Cl_2$ (1.5 g). The resulting solution was stirred for 14 h at 100° C. in an oil bath. The resulting mixture was concentrated. The residue was eluted from silica gel with ethyl acetate/petroleum ether (1:0 to 1:25). This resulted in 10 g of the title compound as brown oil. MS-ESI: 233 (M+1).

Step 3: 3-Amino-2,4-diisopropylbenzonitrile

Into a 500-mL round-bottom flask purged and maintained with an inert atmosphere of nitrogen, was placed 3-amino-6-chloro-2,4-bis(prop-1-en-2-yl)benzonitrile (10 g, 43 mmol) in methanol (50 mL), to the stirred solution was added Pd/C (10% wt., 2 g). The flask was evacuated and filled three times with hydrogen. The resulting solution was stirred overnight at RT. The solids were filtered out. The resulting mixture was concentrated under vacuum. This resulted in 8 g of the title compound as brown oil. MS-ESI: 203 (M+1).

Step 4: 3-Bromo-2,4-diisopropylbenzonitrile

Into a 250-mL round-bottom flask, was placed 3-amino-2,4-bis(propan-2-yl)benzonitrile (8 g, 39.5 mmol) in ACN (150 mL), to the stirred solution was added CuBr (11.3 g, 79.1 mmol) and tert-butyl nitrite (8.2 g, 79.1 mmol). The resulting solution was stirred for 3 h at 60° C. in an oil bath. The resulting mixture was concentrated. The residue was eluted from silica gel with ethyl acetate/petroleum ether (1:50). This resulted in 4.2 g (39.90%) of the title compound as purple oil. MS-ESI: 266/268[M+1]

Step 5: Tert-butyl 2-(3-cyano-2,6-diisopropylphenyl)acetate

Into a 250-mL round-bottom flask purged and maintained with an inert atmosphere of nitrogen, was placed 3-bromo-2,4-bis(propan-2-yl)benzonitrile (3.1 g, 11.6 mmol) in THF (100 mL), to the stirred solution was added Xphos (555.2 mg, 1.16 mmol), Pd$_2$(dba)$_3$ (533.2 mg, 0.58 mmol) and tert-butyl 2-(bromozincio)acetate (7.6 g, 29.12 mmol). The resulting solution was stirred for 3 h at 65° C. in an oil bath. The resulting mixture was concentrated. The residue was eluted from silica gel with ethyl acetate/petroleum ether (1:50). This resulted in 3.0 g (85.5%) of the title compound as purple oil. MS-ESI: 302 [M+1].

Step 6: 2-(3-Cyano-2,6-diisopropylphenyl)acetic acid

Into a 100-mL round-bottom flask, was placed tert-butyl 2-[3-cyano-2,6-bis(propan-2-yl)phenyl]acetate (3.4 g, 11.28 mmol) in DCM (15 mL), to the stirred solution was added TFA (15 mL). The resulting solution was stirred for 3 h at RT. The resulting mixture was concentrated. The residue was eluted from silica gel with ethyl acetate/petroleum ether (1:3). This resulted in 2.6 g (93.9%) of the title compound as a light yellow solid. MS-ESI: 246 [M+1].

TABLE 13

The Intermediates in the following Table were prepared using the similar procedures for converting compound 161" to Intermediate 36 shown in Scheme 31 from appropriated starting materials.

| Intermediate # | Structure | IUPAC Name | Exact Mass [M − H]⁻ |
|---|---|---|---|
| Intermediate 37 | 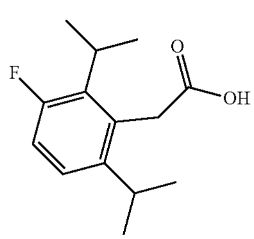 [SMILES: CC(C)c1ccc(F)c(C(C)C)c1CC(=O)O] | 2-(3-fluoro-2,6-diisopropylphenyl)acetic acid | 237 |

TABLE 13-continued
The Intermediates in the following Table were prepared using the similar procedures for converting compound 161" to Intermediate 36 shown in Scheme 31 from appropriated starting materials.
| Intermediate # | Structure | IUPAC Name | Exact Mass [M − H]⁻ |
|---|---|---|---|
| Intermediate 38 | 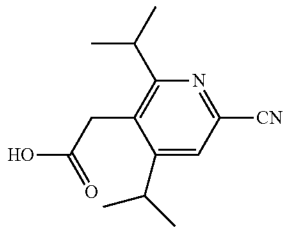 [SMILES: CC(C)c1cc(C#N)nc(C(C)C)c1CC(=O)O] | 2-(6-cyano-2,4-diisopropylpyridin-3-yl)acetic acid | 247 |
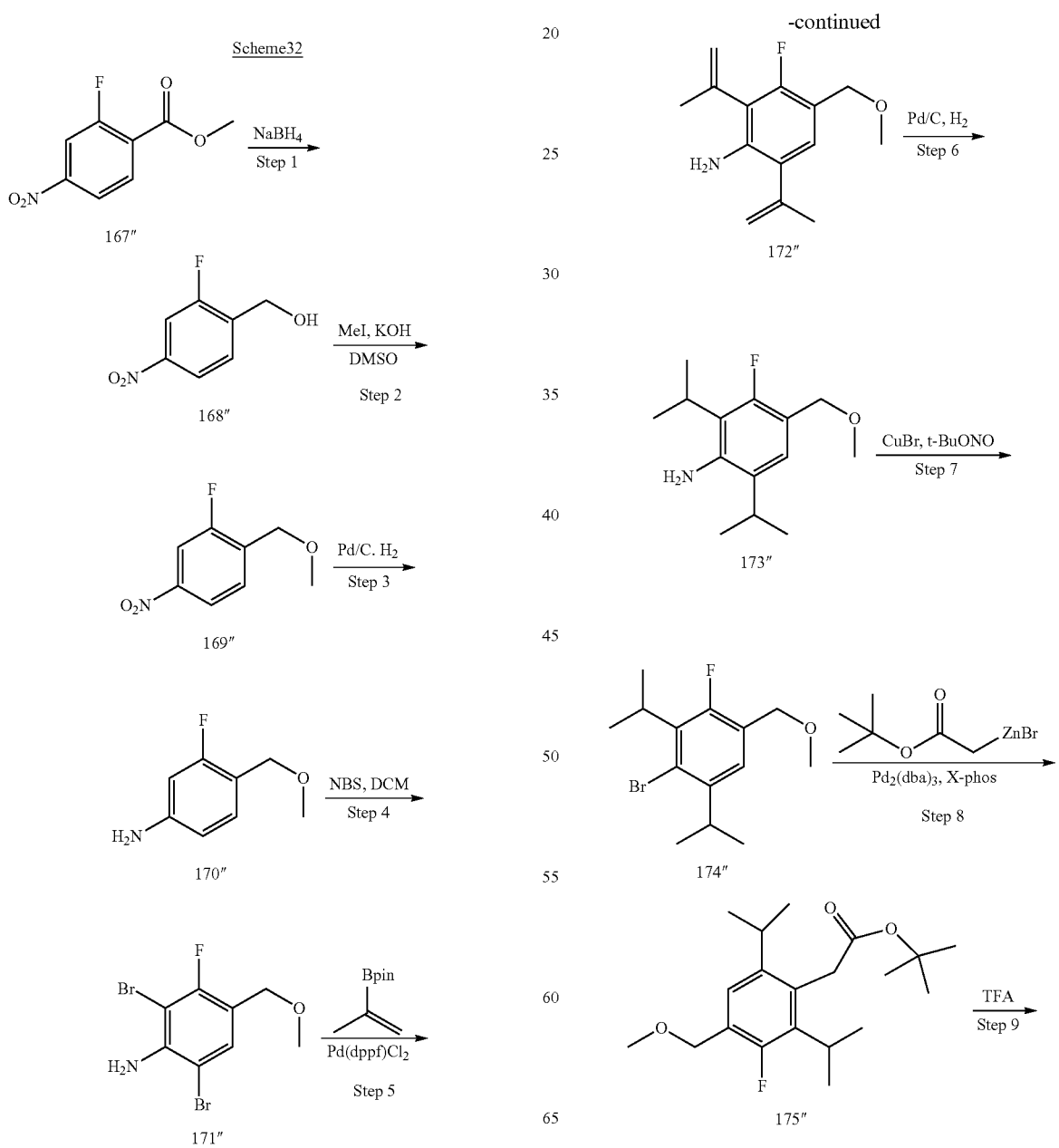

-continued

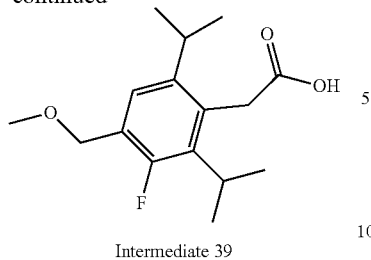

Intermediate 39

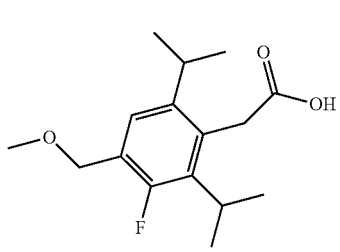

Intermediate 39

2-(3-Fluoro-2,6-diisopropyl-4-(methoxymethyl)phenyl)acetic acid

Step 1: (2-Fluoro-4-nitrophenyl)methanol

Into a 500-mL round-bottom flask, was placed methyl 2-fluoro-4-nitrobenzoate (10 g, 50.2 mmol) in methanol (100 mL). This was followed by the addition of NaBH$_4$ (9.5 g, 251 mmol) in portions over 30 min. The resulting solution was stirred for 4 h at RT. The resulting solution was diluted with 400 mL of ethyl acetate. The resulting mixture was washed with 200 mL of water and 200 mL of brine. The organic layer was dried over anhydrous sodium sulfate and then concentrated. This resulted in 3.6 g of the title compound as an off white solid. MS-ESI: 172 (M+1).

Step 2: 2-Fluoro-1-(methoxymethyl)-4-nitrobenzene

Into a 50-mL round-bottom flask, was placed (2-fluoro-4-nitrophenyl)methanol (3.6 g, 21.0 mmol) in DMSO (10 mL). To the stirred solution was added KOH (4.72 g, 84.2 mmol) in portions and MeI (11.9 g, 84.1 mmol) dropwise at RT. The resulting solution was stirred for overnight at RT. The reaction was then quenched by the addition of water. The resulting solution was extracted with 200 mL of dichloromethane. The organic layers were combined and washed with 200 mL of brine. Then the organic layer was dried over anhydrous sodium sulfate and concentrated. The residue was eluted from silica gel with ethyl acetate/petroleum ether (1:1) to give the title compound as 2.1 g yellow solid. MS-ESI: 186 (M+1).

Step 3: 3-Fluoro-4-(methoxymethyl)aniline

Into a 250-mL round-bottom flask purged and maintained with an inert atmosphere of nitrogen, was placed 2-fluoro-1-(methoxymethyl)-4-nitrobenzene (2.4 g, 12.9 mmol) in methanol (50 mL), to the stirred solution was added Pd/C (10% wt. oil dispersion, 240 mg). The flask was evacuated and filled three times with hydrogen. The resulting solution was stirred overnight at RT. The solids were filtered out. The resulting mixture was concentrated under vacuum. The resulting mixture was concentrated to give the title compound as 2.4 g yellow solid. MS-ESI: 156 (M+1).

Step 4: 2,6-Dibromo-3-fluoro-4-(methoxymethyl)aniline

Into a 100-mL round-bottom flask, was placed 3-fluoro-4-(methoxymethyl)aniline (1.7 g, 10.96 mmol) in DCM (50 mL). This was followed by the addition of NBS (4.3 g, 12.1 mmol) in portions. The resulting solution was stirred for 1 h at RT. The reaction was then quenched by the addition of water/ice. The resulting solution was extracted with 200 mL of ethyl acetate. The resulting mixture was washed with 200 mL of water and 200 mL of brine. The organic layer was dried over anhydrous sodium sulfate and concentrated. The residue was eluted from silica gel with ethyl acetate/petroleum ether (1:3) to give 4 g title compound as a yellow solid. MS-ESI: 311/313 (M+1).

Step 5: 3-Fluoro-4-(methoxymethyl)-2,6-di(prop-1-en-2-yl)aniline

Into a 500-mL round-bottom flask purged and maintained with an inert atmosphere of nitrogen, was placed 2,6-dibromo-3-fluoro-4-(methoxymethyl)aniline (14 g, 44.7 mmol) in dioxane (200 mL) and H$_2$O (20 mL). To the stirred solution was added 4,4,5,5-tetramethyl-2-(prop-1-en-2-yl)-1,3,2-dioxaborolane (18.8 g, 111 mmol), Pd(dppf)Cl$_2$ (3.27 g, 4.47 mmol) and Cs$_2$CO$_3$ (29.2 g, 89.5 mmol). The resulting solution was stirred for 5 h at 65° C. in an oil bath. The reaction was then quenched by the addition of 10 mL of water. The resulting solution was extracted with 3×20 ml of ethyl acetate and dried over anhydrous sodium sulfate and concentrated. The residue was eluted from silica gel with ethyl acetate/petroleum ether (1:5). This resulted in 2.0 g (19.0%) of the title compound as yellow oil. MS-ESI: 236 (M+1).

Step 6: 3-Fluoro-2,6-diisopropyl-4-(methoxymethyl)aniline

Into a 100-mL round-bottom flask, was placed 3-fluoro-4-(methoxymethyl)-2,6-bis(prop-1-en-2-yl) aniline (2.0 g, 8.50 mmol) in methanol (20 mL). To the stirred solution was added Pd/C (10% wt., 200 mg). The flask was evacuated and filled three times with hydrogen. The resulting solution was stirred 5 h at RT. The solids were filtered out. The resulting filtrate was concentrated under vacuum. This resulted in 1.8 g (88.5%) of the title compound as yellow oil. MS-ESI: 240 (M+1).

Step 7: 2-Bromo-4-fluoro-1,3-diisopropyl-5-(methoxymethyl)benzene

Into a 100-mL round-bottom flask purged and maintained with an inert atmosphere of nitrogen, was placed 3-fluoro-4-(methoxymethyl)-2,6-bis(propan-2-yl)aniline (1.0 g, 4.18 mmol) in CH$_3$CN (30 mL). To the above solution was added CuBr (2.4 g, 16.7 mmol) and t-BuONO (–1.72 g, 16.7 mmol) with stirring. The resulting solution was stirred for 3 h at 65° C. in an oil bath. The reaction was then quenched by the addition of 20 mL of water. The resulting solution was extracted with 3×20 ml of ethyl acetate and dried over anhydrous sodium sulfate and concentrated. The residue was eluted from silica gel with petroleum ether. This resulted in 500 mg (39.4%) of the title compound as a yellow solid. MS-ESI: 303/305 [M+1].

Step 8: Tert-butyl 2-(3-fluoro-2,6-diisopropyl-4-(methoxymethyl)phenyl)acetate

Into a 100-mL round-bottom flask purged and maintained with an inert atmosphere of argon, was placed 2-bromo-4-fluoro-5-(methoxymethyl)-1,3-bis(propan-2-yl)benzene (1.0 g, 3.30 mmol) in THF (40 mL). To the stirred solution was added tert-butyl 2-(bromozincio)acetate (2.58 g, 9.89 mmol), $Pd_2(dba)_3CHCl_3$ (170 mg, 0.16 mmol), and Xphos (157 mg, 0.33 mmol). The resulting solution was stirred for 3 h at 65° C. in an oil bath. The reaction was then quenched by the addition of 20 mL of water. The resulting solution was extracted with 3×30 ml of DCM and dried over anhydrous sodium sulfate and concentrated. The residue was eluted from silica gel with ethyl acetate/petroleum ether (1:20). This resulted in 200 mg (17.9%) of the title compound as yellow oil. MS-ESI: 339 [M+1].

Step 9: 2-(3-Fluoro-2,6-diisopropyl-4-(methoxymethyl)phenyl)acetic acid

Into a 50-mL round-bottom flask, was placed tert-butyl 3-fluoro-4-(methoxymethyl)-2,6-bis(propan-2-yl)benzoate (300 mg, 0.92 mmol) in DCM (6 mL), to the stirred solution was added TFA (2 mL). The resulting solution was stirred for 2 h at RT. The resulting mixture was concentrated. The residue was eluted from silica gel with DCM/methanol (1:20). This resulted in 170 mg of the title compound as yellow oil. MS-ESI: 281 (M−1).

TABLE 14

The Intermediates in the following Table were prepared using the similar procedures for converting compound 167″ to Intermediate 39 shown in Scheme 32 from appropriated starting materials.

| Intermediate # | Structure | IUPAC Name | Exact Mass [M − H]⁻ |
| --- | --- | --- | --- |
| Intermediate 40 | 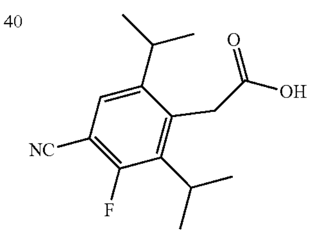 | 2-(4-cyano-3-fluoro-2,6-diisopropylphenyl)acetic acid | 262 |
| Intermediate 41 | 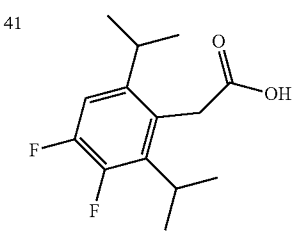 | 2-(3,4-difluoro-2,6-diisopropylphenyl)acetic acid | 255 |
| Intermediate 42 | 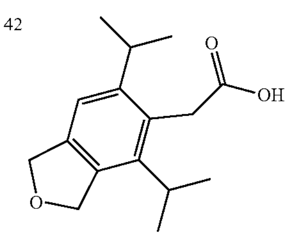 | 2-(4,6-diisopropyl-1,3-dihydroisobenzofuran-5-yl)acetic acid | 261 |
| Intermediate 43 | 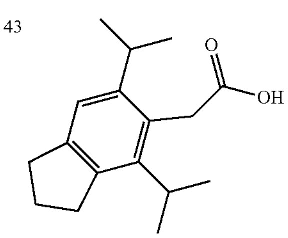 | 2-(4,6-diisopropyl-2,3-dihydro-1H-inden-5-yl)acetic acid | 259 |

Scheme 33

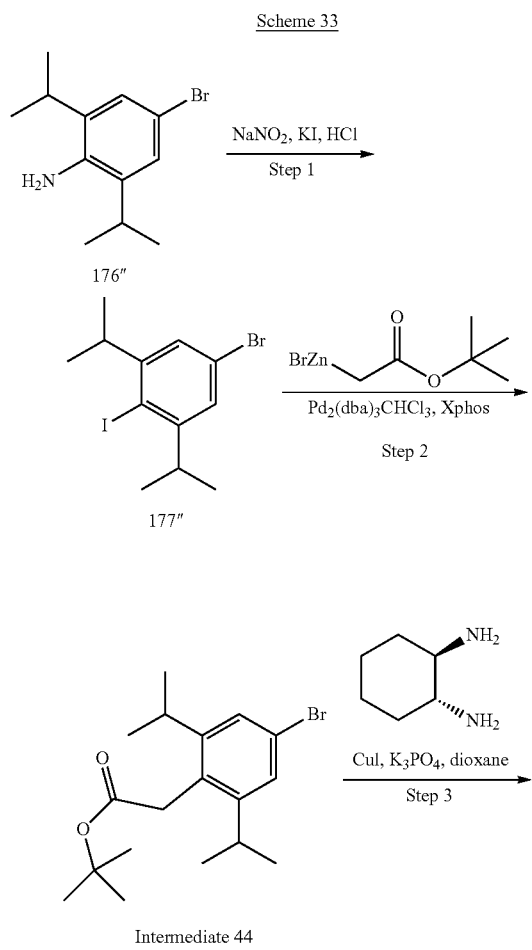

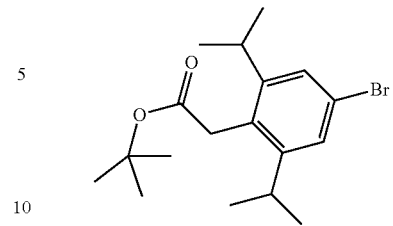

Intermediate 44

Tert-butyl 2-(4-bromo-2,6-diisopropylphenyl)acetate

Step 1: 5-Bromo-2-iodo-1,3-diisopropylbenzene

Into a 500-mL round-bottom flask purged and maintained with an inert atmosphere of nitrogen, was placed 4-bromo-2,6-bis(propan-2-yl)aniline (5 g, 19.6 mmol) in HCl (6 M, 60 mL). This was followed by the addition of a solution of NaNO$_2$ (2.5 g, 36.3 mmol) in water (5 mL) dropwise with stirring at −10° C. The resulting solution was stirred for 30 min at −10° C. Then to the above was added KI (11 g, 66.3 mmol). The resulting solution was stirred for 1 h at RT. The reaction was then quenched by the addition of 100 mL of water. The resulting solution was extracted with 2×200 mL of ethyl acetate and the organic layers combined. The residue was eluted from silica gel with ethyl acetate/petroleum ether (0/1). This resulted in 5.95 g (83.0%) of the title compound as a brown liquid. MS-ESI: 366/368 (M+1).

Step 2: Tert-butyl 2-(4-bromo-2,6-diisopropylphenyl)acetate

Into a 100-mL round-bottom flask purged and maintained with an inert atmosphere of nitrogen, was placed 5-bromo-2-iodo-1,3-bis(propan-2-yl)benzene (2.0 g, 5.45 mmol) in THF (50 mL). To the stirred solution was added Pd$_2$(dba)$_3$ (504 mg, 0.55 mmol), Xphos (262 mg, 0.55 mmol) and tert-butyl 2-(bromozincio)acetate (2.13 g, 8.66 mmol). The resulting solution was stirred for 30 min at RT. The resulting solution was allowed to react with stirring for an additional 3 h at 60° C. The resulting mixture was concentrated. The residue was eluted from silica gel with petroleum ether. This resulted in 360 mg (18.6%) of the title compound as a solid. MS-ESI: 355/357 (M+1).

Intermediate 45

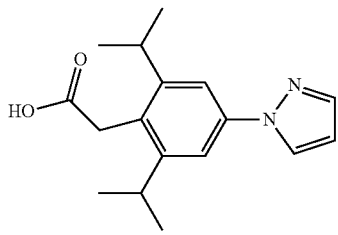

2-(2,6-diisopropyl-4-(1H-pyrazol-1-yl)phenyl)acetic acid

Step 3: Tert-butyl 2-(2,6-diisopropyl-4-(1H-pyrazol-1-yl)phenyl)acetate

Into a 50-mL round-bottom flask purged and maintained with an inert atmosphere of nitrogen, was placed a mixture

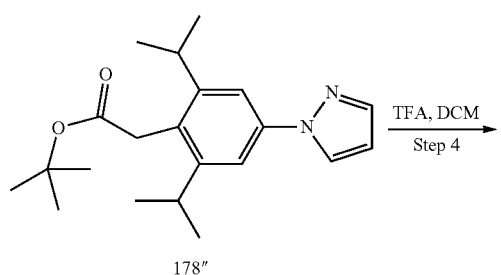

Intermediate 45 of tert-butyl 2-(4-bromo-2,6-diisopropylphenyl)acetate (360 mg, 1.01 mmol) in dioxane (10 mL). To the stirred solution was added 1H-pyrazole (275 mg, 4.04 mmol), copper(I) iodide (76 mg, 0.40 mmol) and potassium phosphate (642 mg, 3.03 mmol). To the above (1R,2R)-cyclohexane-1,2-diamine (0.05 mL, 0.40 mmol) was added dropwise. The resulting solution was refluxed overnight. The reaction was then concentrated and the residue was eluted from silica gel with ethyl acetate/petroleum ether (1:20). This resulted in 120 mg (35%) of the title compound as a yellow oil. MS-ESI: 342.2 (M+1).

Step 4: 2-(2,6-Diisopropyl-4-(1H-pyrazol-1-yl)phenyl)acetic acid

Into a 50-mL sealed tube purged and maintained with an inert atmosphere of nitrogen, was placed a solution of tert-butyl 2-(2,6-diisopropyl-4-(1H-pyrazol-1-yl)phenyl)acetate (120 mg, 0.35 mmol) in TFA (10 mL). The resulting solution was stirred overnight at RT. The reaction was then concentrated and used in the next step without purification. MS-ESI: 286.2 (M+1).

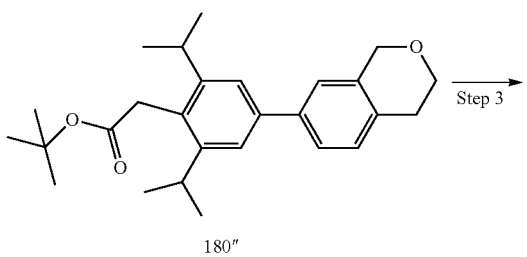

180''

TABLE 15

The Intermediates in the following Table were prepared using the similar procedures for converting compound 176'' to Intermediate 44 shown in Scheme 33 from appropriated starting materials.

| Intermediate # | Structure | IUPAC Name | Exact Mass [M + H]+ |
|---|---|---|---|
| Intermediate 46 | 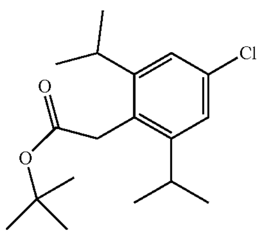 [SMILES: CC(C)c1cc(Cl)cc(C(C)C)c1CC(=O)OC(C)(C)C] | tert-butyl 2-(4-chloro-2,6-diisopropylphenyl)acetate | 311 |

Scheme 34

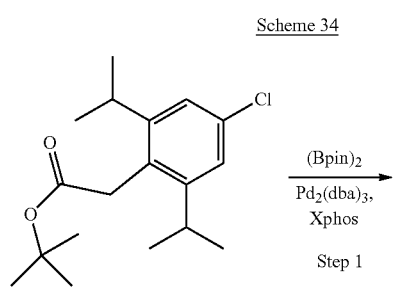

Intermediate 46

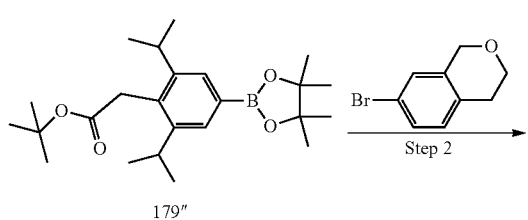

179''

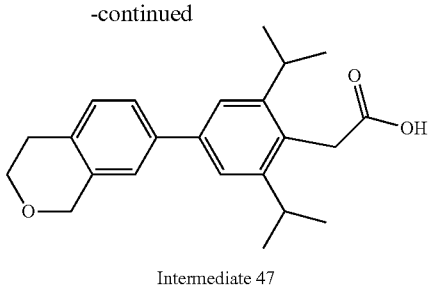

Intermediate 47

Intermediate 47

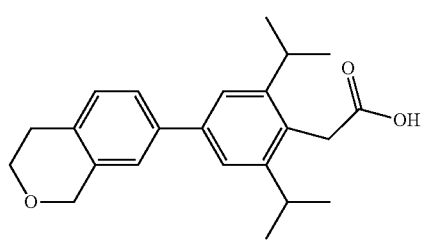

2-(4-(Isochroman-7-yl)-2,6-diisopropylphenyl)acetic acid

Step 1: Tert-butyl 2-(2,6-diisopropyl-4-(4,4,5,5-tetramethyl-1,3,2-dioxaborolan-2-yl)phenyl)acetate Into a 50-mL round-bottom flask purged and maintained with an inert atmosphere of nitrogen, was placed tert-butyl 2-[4-chloro-2,6-bis(propan-2-yl)phenyl]acetate (310 mg, 1.00 mmol) in dioxane (10 mL). To the stirred solution was added 4,4,4',4',5,5,5',5'-octamethyl-2,2'-bi(1,3,2-dioxaborolane) (508 mg, 2.0 mmol). KOAc (195 mg, 1.99 mmol), Xphos (95.1 mg, 0.20 mmol) Pd$_2$(dba)$_3$ (91.3 mg, 0.10 mmol). The resulting solution was stirred for 16 h at 90° C. in an oil bath under nitrogen. Then the mixture was concentrated and the residue was eluted from silica gel with ethyl acetate/petroleum ether (1:20). This resulted in 400 mg (99.7%) of the title compound as a crude solid. MS-ESI:403 (M+1).

Step 2: Tert-butyl 2-(4-(isochroman-7-yl)-2,6-diisopropylphenyl)acetate

Into a 50-mL round-bottom flask purged and maintained with an inert atmosphere of nitrogen, was placed tert-butyl 2-(2,6-diisopropyl-4-(4,4,5,5-tetramethyl-1,3,2-dioxaborolan-2-yl)phenyl)acetate (402 mg, 1.00 mmol) in dioxane (10 mL) and H$_2$O (2.5 mL). To the stirred solution was added Cs$_2$CO$_3$ (652.0 mg, 2.00 mmol), 7-bromo-3,4-dihydro-1H-2-benzopyran (212.9 mg, 1.00 mmol) and Pd(dppf)Cl$_2$ (73.1 mg, 0.10 mmol). The resulting solution was stirred for 4 h at 80° C. in an oil bath. The resulting solution was diluted with 20 mL of ethyl acetate. The resulting mixture was washed with 2×20 mL of H$_2$O and 2×20 mL of brine. The residue was eluted from silica gel with ethyl acetate/petroleum ether (1:10). This resulted in 300 mg (73.4%) of the title compound as a light brown solid. MS-ESI: 409 (M+1).

Step 3: 2-(4-(Isochroman-7-yl)-2,6-diisopropylphenyl)acetic acid

Into a 25-mL round-bottom flask purged and maintained with an inert atmosphere of nitrogen, was placed tert-butyl 2-[4-(3,4-dihydro-1H-2-benzopyran-7-yl)-2,6-bis(propan-2-yl)phenyl]acetate (300 mg, 0.73 mmol) in DCM (4 mL) and TFA (1 mL). The resulting solution was stirred for 16 h at RT. The resulting mixture was concentrated. The residue was eluted from silica gel with ethyl acetate/petroleum ether (1:2). This resulted in 80 mg (30.9%) of the title compound as a light brown solid. MS-ESI: 351(M−1).

Scheme 35

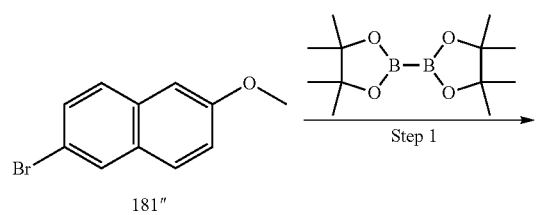

181''

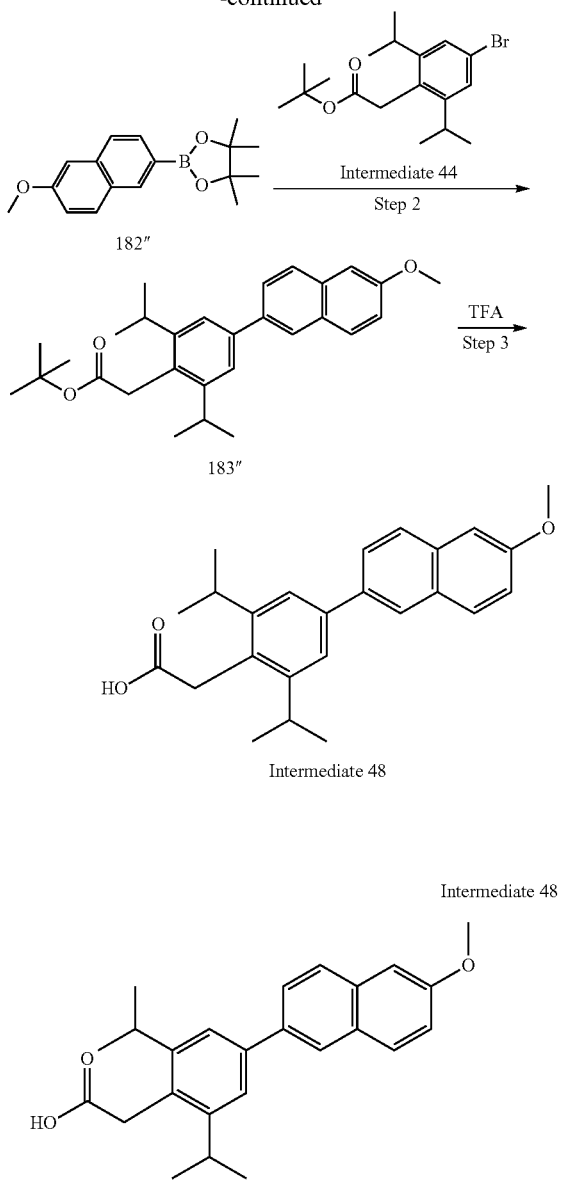

Intermediate 48

2-(2,6-Diisopropyl-4-(6-methoxynaphthalen-2-yl)phenyl)acetic acid

Step 1: 2-(6-Methoxynaphthalen-2-yl)-4,4,5,5-tetramethyl-1,3,2-dioxaborolane Into a 50-mL round-bottom flask, was placed 2-bromo-6-methoxynaphthalene (115 mg, 0.49 mmol) in dioxane (5 mL), to the stirred solution was added potassium acetate (175 mg, 1.27 mmol), 4,4,5,5-tetramethyl-2-(4,4,5,5-tetramethyl-1,3,2-dioxaborolan-2-yl)-1,3,2-dioxaborolane (113 mg, 0.45 mmol) and Pd(PPh$_3$)$_2$Cl$_2$ (9 mg). The resulting solution was stirred for 10 h at 110° C. The resulting solution was extracted with 3×20 mL of ethyl acetate and dried over anhydrous sodium sulfate. The solids were filtered out. The resulting mixture was concentrated under vacuum. This resulted in 120 mg of the title compound as an off-white solid. MS-ESI: 285 (M+1).

Step 2: 2-(2,6-Diisopropyl-4-(6-methoxynaphthalen-2-yl)phenyl)acetic acid

Into a 50-mL round-bottom flask, was placed 2-(6-methoxynaphthalen-2-yl)-4,4,5,5-tetramethyl-1,3,2-dioxaborolane (100 mg) in dioxane (15 mL) and H₂O (1.5 mL), to the stirred solution was added Cs₂CO₃ (344 mg), Pd(dppf)Cl₂ (27.5 mg), 2-[4-bromo-2,6-bis(propan-2-yl)phenyl]acetic acid (125 mg). The resulting solution was stirred for 15 h at 80° C. The resulting mixture was concentrated under vacuum. The residue was eluted from silica gel with ethyl acetate/petroleum ether (1:3). This resulted in 90 mg (58.9%) of the title compound as a yellow solid. MS-ESI: 433 (M+1).

Step 3: 2-(2,6-Diisopropyl-4-(6-methoxynaphthalen-2-yl)phenyl)acetic acid

Into a 50-mL round-bottom flask, was placed tert-butyl 2-[4-(6-methoxynaphthalen-2-yl)-2,6-bis(propan-2-yl)phenyl]acetate (80 mg, 0.18 mmol) in DCM (5 mL) and TFA (2.0 mL). The resulting solution was stirred for 1 h at RT. The resulting mixture was concentrated. This resulted in 80 mg (crude) of the title compound as a light yellow solid. MS-ESI: 377 [M+1]

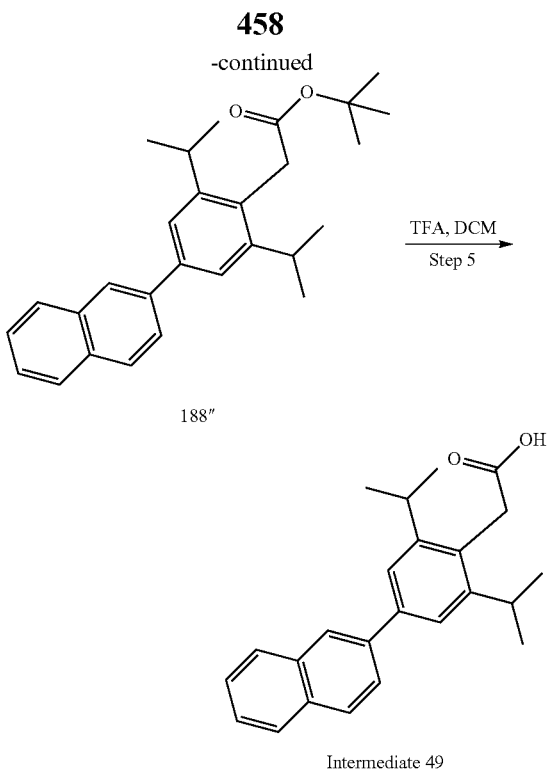

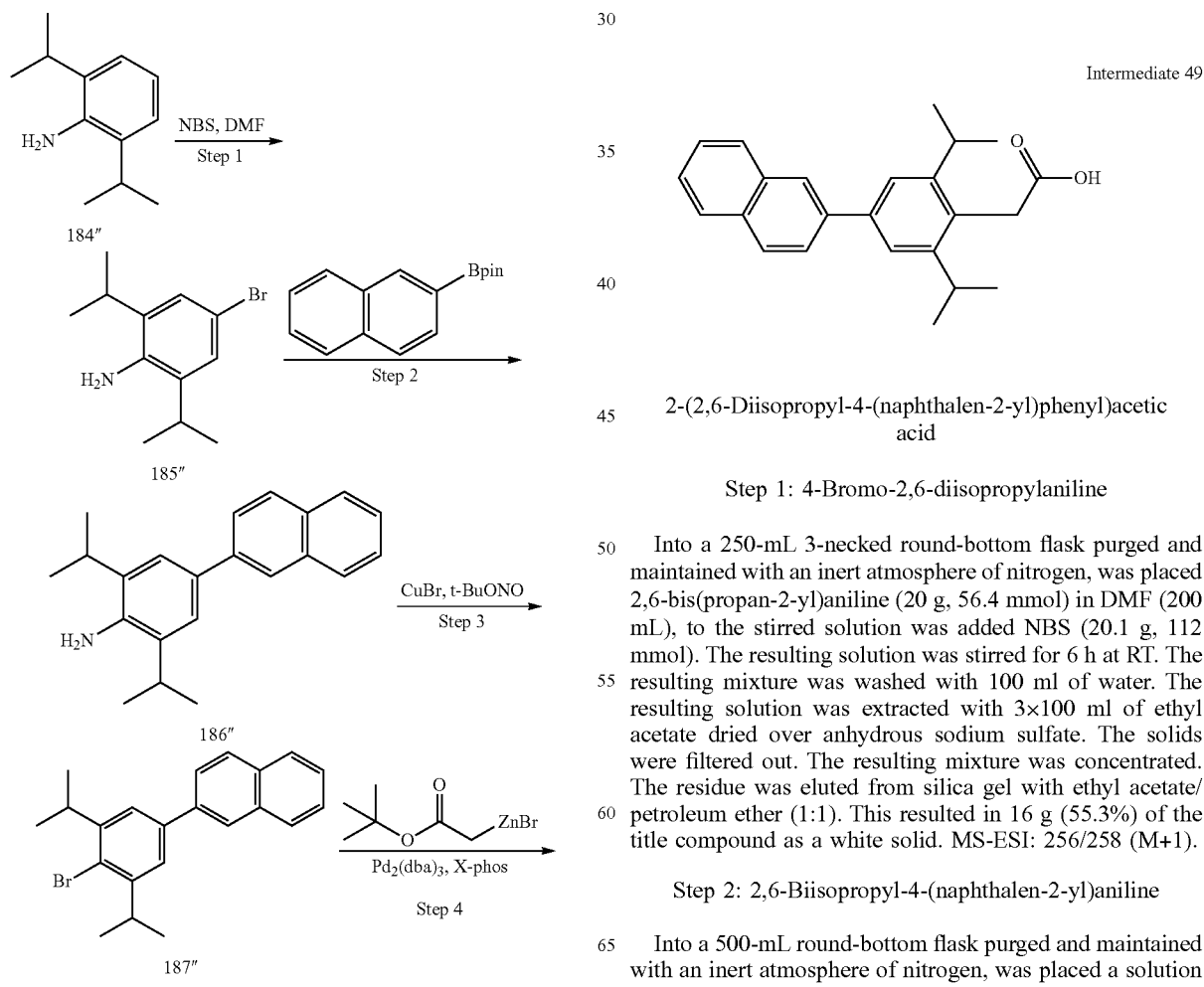

Scheme 36

2-(2,6-Diisopropyl-4-(naphthalen-2-yl)phenyl)acetic acid

Step 1: 4-Bromo-2,6-diisopropylaniline

Into a 250-mL 3-necked round-bottom flask purged and maintained with an inert atmosphere of nitrogen, was placed 2,6-bis(propan-2-yl)aniline (20 g, 56.4 mmol) in DMF (200 mL), to the stirred solution was added NBS (20.1 g, 112 mmol). The resulting solution was stirred for 6 h at RT. The resulting mixture was washed with 100 ml of water. The resulting solution was extracted with 3×100 ml of ethyl acetate dried over anhydrous sodium sulfate. The solids were filtered out. The resulting mixture was concentrated. The residue was eluted from silica gel with ethyl acetate/petroleum ether (1:1). This resulted in 16 g (55.3%) of the title compound as a white solid. MS-ESI: 256/258 (M+1).

Step 2: 2,6-Biisopropyl-4-(naphthalen-2-yl)aniline

Into a 500-mL round-bottom flask purged and maintained with an inert atmosphere of nitrogen, was placed a solution of 4-bromo-2,6-bis(propan-2-yl)aniline (10 g, 39.0 mmol) in dioxane (250 mL) and H₂O (25 mL). To the stirred solution was added 4,4,5,5-tetramethyl-2-(naphthalen-2-yl)-1,3,2-dioxaborolane (11.9 g, 46.8 mmol), Pd(dppf)Cl₂ (7.81 g, 7.8 mmol) and Cs₂CO₃ (25.4 g, 78.1 mmol). The resulting solution was stirred for 10 min at RT. The resulting solution was then allowed to react for an additional 19 h at 80° C. The resulting mixture was concentrated. The residue was eluted from silica gel with ethyl acetate/petroleum ether (1:1). This resulted in 6.5 g (54.9%) of the title compound as a red solid. MS-ESI: 304 (M+1).

Step 3: 2-(4-Bromo-3,5-diisopropylphenyl)naphthalene

Into a 250-mL round-bottom flask purged and maintained with an inert atmosphere of nitrogen, was placed a solution of 4-(naphthalen-2-yl)-2,6-bis(propan-2-yl)aniline (6.0 g, 19.8 mmol) in ACN (100 mL). To the stirred solution was added tert-butyl nitrite (4.08 g, 39.5 mmol) and CuBr (5.67 g, 39.5 mmol). The resulting solution was stirred for 30 min at RT. The resulting solution was allowed to react with stirring for an additional 180 min at 60° C. The mixture was concentrated and the residue was eluted from silica gel with PE. This resulted in 105 mg (17.3%) of the title compound as a red solid. MS-ESI: 367/369 (M+1).

Step 4: Tert-butyl 2-(2,6-diisopropyl-4-(naphthalen-2-yl)phenyl)acetate

Into a 100-mL round-bottom flask purged and maintained with an inert atmosphere of nitrogen, was placed a solution of 2-[4-bromo-3,5-bis(propan-2-yl)phenyl]naphthalene (2 g, 5.44 mmol) in THF (50 mL), to the above solution was added XPhos (0.3 g, 0.54 mmol), and Pd₂(dba)₃CH₂Cl₂ (0.2 g, 0.27 mmol). The resulted solution was stirred for 15 min at RT. Then to the mixture was added tert-butyl 2-(bromozincio)acetate (2.8 g, 10.9 mmol) with stirring. The resulting solution was allowed to react for an additional 180 min at 65° C. The residue was eluted from silica gel with PE. This resulted in 1.0 g (45.6%) of the title compound as a yellow solid. MS-ESI: 403 (M+1).

Step 5: 2-(2,6-Diisopropyl-4-(naphthalen-2-yl)phenyl)acetic acid

Into a 250-mL round-bottom flask, was placed tert-butyl 2-[4-(naphthalen-2-yl)-2,6-bis(propan-2-yl)phenyl]acetate (2.48 g, 6.16 mmol) in TFA (20 mL) and DCM (20 mL). The resulting solution was stirred for 5 h at RT. Then the mixture was concentrated. The residue was eluted from silica gel with ethyl acetate/petroleum ether (13/100). This resulted in 1.68 g (78.5%) of the title compound as a yellow solid. MS-ESI: 347 (M+1).

TABLE 16

The Intermediates in the following Table were prepared using the similar procedures for converting compound 184" to Intermediate 49 shown in Scheme 36 from appropriated starting materials.

| Intermediate # | Structure | IUPAC Name | Exact Mass [M − H]⁻ |
|---|---|---|---|
| Intermediate 50 | 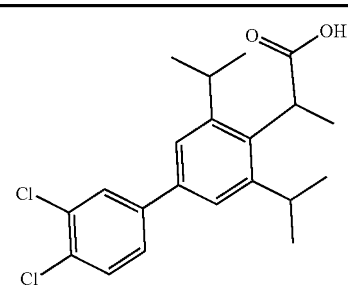 | 2-(3',4'-dichloro-3,5-diisopropyl-[1,1'-biphenyl]-4-yl)acetic acid | 363 |
| Intermediate 51 | 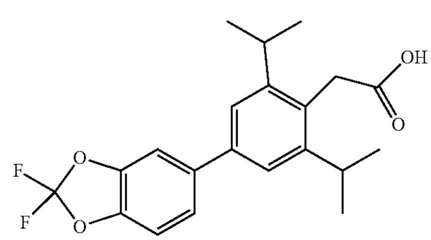 [SMILES: CC(C)c1cc(-c2ccc3c(c2)OC(F)(F)O3)cc(C(C)C)c1CC(=O)O] | 2-(4-(2,2-difluorobenzo[d][1,3]dioxol-5-yl)-2,6-diisopropylphenyl)acetic acid | 375 |
| Intermediate 52 | 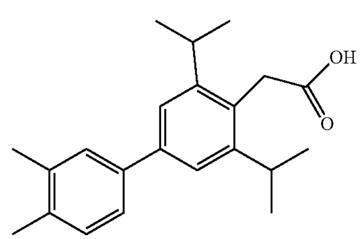 [SMILES: Cc1ccc(-c2cc(C(C)C)c(CC(=O)O)c(C(C)C)c2)cc1C] | 2-(3,5-diisopropyl-3',4'-dimethyl-[1,1'-biphenyl]-4-yl)acetic acid | 323 |

TABLE 16-continued

The Intermediates in the following Table were prepared using the similar procedures for converting compound 184″ to Intermediate 49 shown in Scheme 36 from appropriated starting materials.

| Intermediate # | Structure | IUPAC Name | Exact Mass [M − H]⁻ |
|---|---|---|---|
| Intermediate 53 | 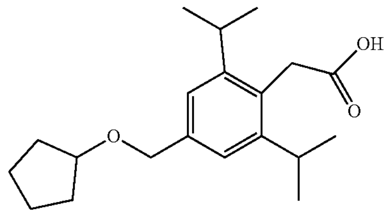 [SMILES: CC(C)c1cc(COC2CCCC2)cc(C(C)C)c1CC(=O)O] | 2-(4-((cyclopentyloxy)methyl)-2,6-diisopropylphenyl)acetic acid | 317 |

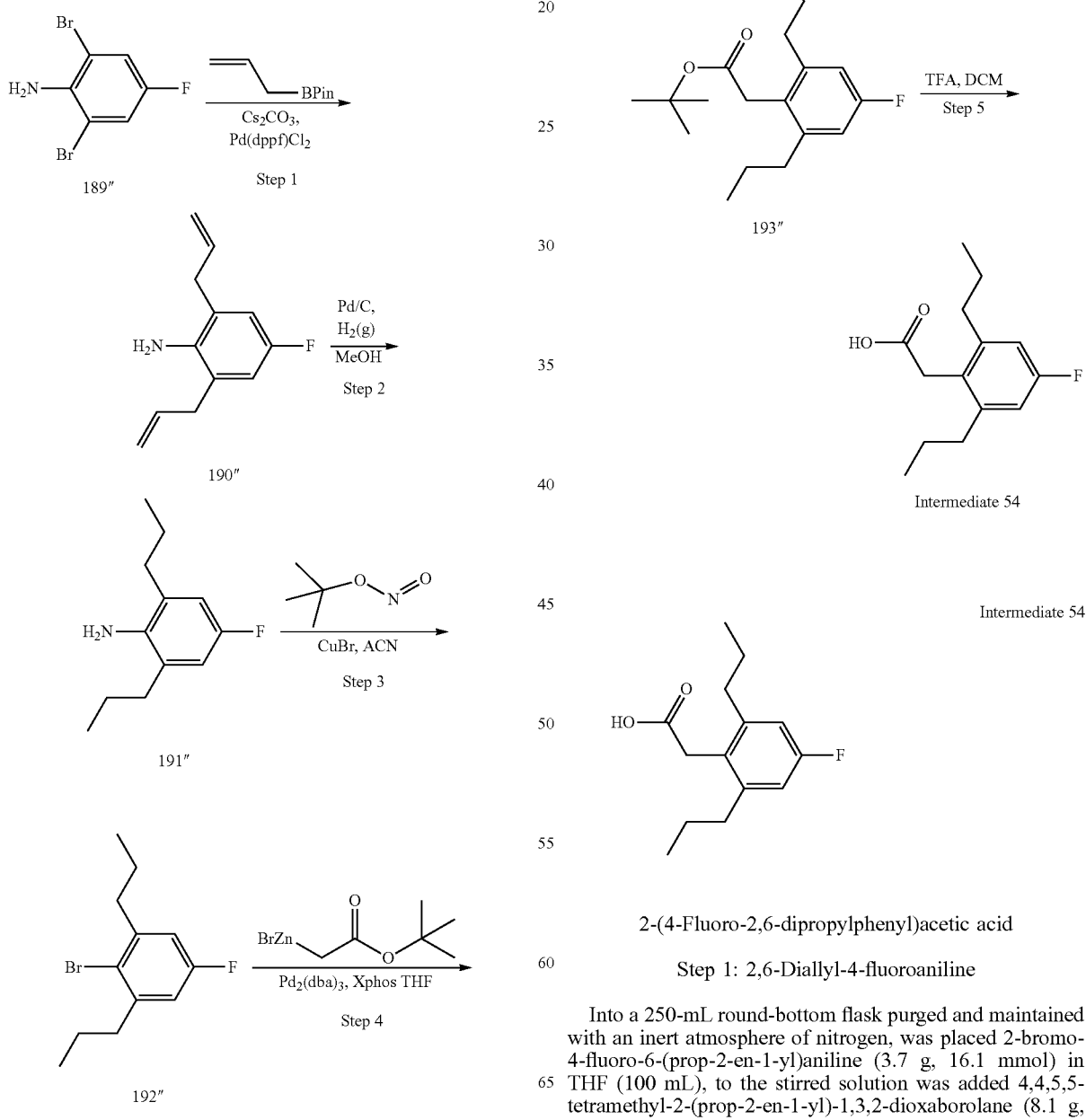

2-(4-Fluoro-2,6-dipropylphenyl)acetic acid

Step 1: 2,6-Diallyl-4-fluoroaniline

Into a 250-mL round-bottom flask purged and maintained with an inert atmosphere of nitrogen, was placed 2-bromo-4-fluoro-6-(prop-2-en-1-yl)aniline (3.7 g, 16.1 mmol) in THF (100 mL), to the stirred solution was added 4,4,5,5-tetramethyl-2-(prop-2-en-1-yl)-1,3,2-dioxaborolane (8.1 g, 48.2 mmol), $Cs_2CO_3$ (15.7 g, 48.2 mmol) and $Pd(dppf)Cl_2$ (588 mg, 0.80 mmol). The resulting solution was stirred overnight at 70° C. in an oil bath. The resulting mixture was concentrated under vacuum. The residue was eluted from silica gel with ethyl acetate/petroleum ether (1:10). This resulted in 2.6 g (84.5%) of the title compound as yellow oil. MS-ESI: 192 [M+1].

Step 2: 4-Fluoro-2,6-dipropylaniline

Into a 100-mL round-bottom flask, was placed 4-fluoro-2,6-bis(prop-2-en-1-yl)aniline (2.6 g, 13.59 mmol) in methanol (50 mL). To the stirred solution was added Pd/C (10% wt., 300 mg). The flask was evacuated and filled three times with hydrogen. The resulting solution was stirred 5 h at RT under hydrogen. The solids were filtered out. The resulting mixture was concentrated under vacuum. This resulted in 2.5 g (94.1%) of the title compound as light yellow oil. MS-ESI: 196 [M+1]

Step 3: 2-Bromo-5-fluoro-1,3-dipropylbenzene

Into a 100-mL round-bottom flask purged and maintained with an inert atmosphere of nitrogen, was placed 4-fluoro-2,6-dipropylaniline (840 mg, 4.30 mmol) in ACN (20 mL). To the stirred solution was added CuBr (1.2 g, 8.60 mmol) and tert-butyl nitrite (888 mg, 8.61 mmol). The resulting solution was stirred for 3 h at 60° C. in an oil bath. The resulting mixture was concentrated under vacuum. The residue was eluted from silica gel with petroleum ether. This resulted in 640 mg (57.4%) of the title compound as light yellow oil. MS-ESI: [M+1].

Step 4: Tert-butyl 2-(4-fluoro-2,6-dipropylphenyl)acetate

Into a 100-mL round-bottom flask purged and maintained with an inert atmosphere of nitrogen, was placed 2-bromo-5-fluoro-1,3-dipropylbenzene (460 mg, 1.77 mmol) in THF (10 mL). To the mixture was added Xphos (85 mg, 0.18 mmol) and Pd$_2$(dba)$_3$ (82 mg, 0.09 mmol). The resulting solution was stirred for 30 min at RT. Then to the above was added tert-butyl 2-(bromozincio)acetate (1.4 g, 5.32 mmol). The resulting solution was stirred for 3 h at 65° C. in an oil bath. The reaction was then quenched by the addition of 10 mL of NH$_4$Cl (sat.). The resulting solution was extracted with 3×10 mL of DCM. The organic layers were combined, dried over anhydrous sodium sulfate, and concentrated under vacuum. This resulted in 300 mg (57.4%) of the title compound as light yellow oil. MS-ESI: 295 [M+1].

Step 5: 2-(4-Fluoro-2,6-dipropylphenyl)acetic acid

Into a 50-mL round-bottom flask, was placed tert-butyl 2-(4-fluoro-2,6-dipropylphenyl)acetate (300 mg) in DCM (4 mL) and TFA (2 mL). The resulting solution was stirred for 2 h at RT. The resulting mixture was concentrated under vacuum. The crude product was purified by Prep-TLC with ethyl acetate/petroleum ether (1:3). This resulted in 165 mg (67.9%) of the title compound as a light yellow solid. MS-ESI: 239 [M+1]

TABLE 17

The Intermediates in the following Table were prepared using the similar procedures for converting compound 189" to Intermediate 54 shown in Scheme 37 from appropriated starting materials.

| Intermediate # | Structure | IUPAC Name | Exact Mass [M + H]$^+$ |
|---|---|---|---|
| Intermediate 55 | 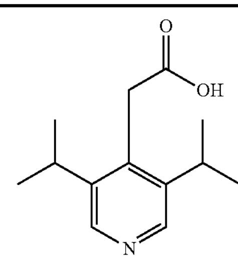 | 2-(3,5-diisopropylpyridin-4-yl)acetic acid | 222 |
| Intermediate 56 | 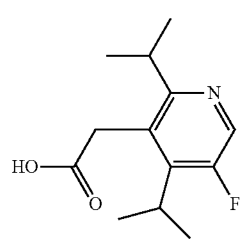 [SMILES: CC(C)c1ncc(F)c(C(C)C)c1CC(=O)O] | 2-(5-fluoro-2,4-diisopropylpyridin-3-yl)acetic acid | 240 |
| Intermediate 57 | 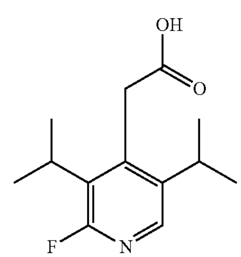 [SMILES: CC(C)c1cnc(F)c(C(C)C)c1CC(=O)O] | 2-(2-fluoro-3,5-diisopropylpyridin-4-yl)acetic acid | 240 |

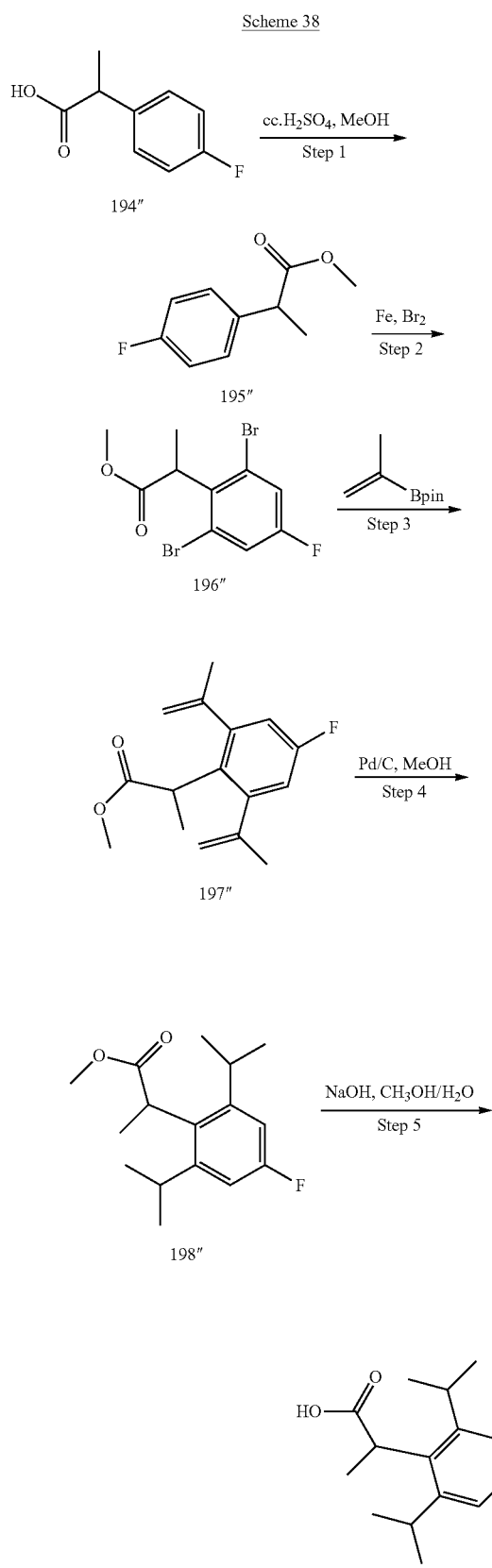

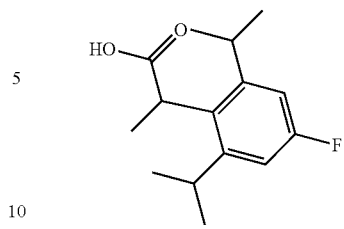

Intermediate 58

2-(4-Fluoro-2,6-diisopropylphenyl)propanoic acid

Step 1: Methyl 2-(4-fluorophenyl)propanoate

Into a 100-mL round-bottom flask, was placed a solution of 2-(4-fluorophenyl)propanoic acid (2 g, 11.89 mmol) in methanol (20 mL). To the mixture conc. $H_2SO_4$ (0.05 mL) was added. The resulting solution was stirred for 16 h at 85° C. The reaction was then quenched by the addition of 100 mL of water. The resulting solution was extracted with 3×50 mL of dichloromethane and the organic layers combined. The solids were filtered out. The mixture was dried over anhydrous sodium sulfate and concentrated under vacuum. This resulted in 2.1 g (97%) of the title compound as yellow oil. MS-ESI: 183 [M+1].

Step 2: Methyl 2-(2,6-dibromo-4-fluorophenyl)propanoate

Into a 100-mL round-bottom flask purged and maintained with an inert atmosphere of nitrogen, was placed a solution of methyl 2-(4-fluorophenyl)propanoate (1.7 g, 9.33 mmol) in $CHCl_3$ (20 mL). To the stirred solution was added Fe powder (0.21 g) and $Br_2$ (1.92 mL). The resulting solution was stirred for 16 h at 50° C. The reaction was then quenched by the addition of 50 mL of saturated $Na_2S_2O_3$ solution. The resulting solution was extracted with 3×50 mL of DCM and the organic layers were combined, dried over anhydrous sodium sulfate and concentrated under vacuum. This resulted in 1.03 g (32%) of the title compound as yellow crude oil. MS-ESI: 339/341 [M+1].

Step 3: Methyl 2-(4-fluoro-2,6-di(prop-1-en-2-yl)phenyl)propanoate

Into a 40-mL sealed tube purged and maintained with an inert atmosphere of nitrogen, was placed a solution of methyl 2-(2,6-dibromo-4-fluorophenyl)propanoate (1.03 g, 3.03 mmol) in dioxane (10 mL) and $H_2O$ (1 mL). To the stirred solution was added $Cs_2CO_3$ (2 g, 6.14 mmol), Pd(dppf)$Cl_2$ (230 mg, 0.31 mmol) and 4,4,5,5-tetramethyl-2-(prop-1-en-2-yl)-1,3,2-dioxaborolane (1.07 g, 6.37 mmol). The resulting solution was stirred for 6 h at 110° C. The resulting mixture was concentrated under vacuum. The residue was eluted from silica gel with ethyl acetate/petroleum ether (1:6). This resulted in 754 mg (95%) of the title compound as yellow oil. MS-ESI: 263 [M+1].

Step 4: Methyl 2-(4-fluoro-2,6-diisopropylphenyl)propanoate

Into a 50-mL round-bottom flask purged and maintained with an inert atmosphere of $H_2$, was placed a solution of methyl 2-[4-fluoro-2,6-bis(prop-1-en-2-yl)phenyl]propanoate (820 mg, 3.13 mmol) in methanol (20 mL). To the stirred solution was added Pd/C (10% wt., 0.2 g). The resulting solution was stirred for 4 h at RT. The solids were filtered out. The resulting mixture was concentrated under vacuum. This resulted in 700 mg (84%) of the title compound as yellow crude oil. MS-ESI: 267 [M+1].

Step 5:
2-(4-Fluoro-2,6-diisopropylphenyl)propanoic acid

Into a 40-mL sealed tube, was placed a solution of methyl 2-[4-fluoro-2,6-bis(propan-2-yl)phenyl]propanoate (300 mg, 1.13 mmol) in 6 M sodium hydroxide (3 mL) and MeOH (3 mL). The resulting solution was stirred for 3 h at 90° C. The reaction was then quenched by the addition of 50 mL of water. The pH value of the solution was adjusted to 2 with hydrogen chloride (1 M). The resulting solution was extracted with 2×50 mL of ethyl acetate and the organic layers combined. The solids were filtered out. The mixture was dried over anhydrous sodium sulfate and concentrated under vacuum. This resulted in 150 mg (53%) of the title compound as yellow oil. MS-ESI: 253 [M+1].

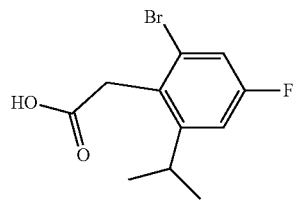

intermediate 59

Steps 1-4 used similar procedures for converting compound 189" to compound 193" shown in Scheme 37 to afford compound 203" from compound 199". MS-ESI: 253 (M+1).

Step 5:
2-(2-bromo-4-fluoro-6-isopropylphenyl)acetic acid

Into a 100-mL 3-necked round-bottom flask purged and maintained with an inert atmosphere of nitrogen, was placed tert-butyl 2-[4-fluoro-2-(propan-2-yl)phenyl]acetate (1.0 g, 3.96 mmol) in CHCl₃ (25 mL). To the solution was added AcOH (0.01 mL), Fe powder (22.1 mg, 0.40 mmol) and Br₂ (3.17 g, 19.8 mmol). The resulting solution was stirred for 16 h at 50° C. in an oil bath. The reaction was then quenched by the addition of 20 mL of Na₂S₂O₃. The resulting solution was extracted with 2×20 ml of ethyl acetate concentrated. The residue was eluted from silica gel with ethyl acetate/petroleum ether (1:2). This resulted in 700 mg (64.2%) of the title compound as a white solid. MS-ESI: 275 [M+1].

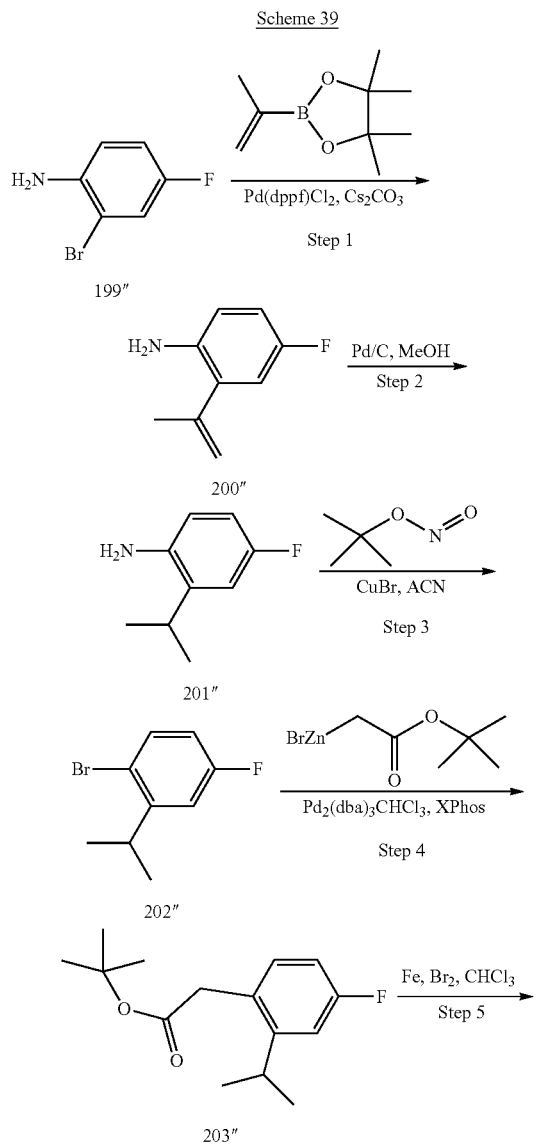

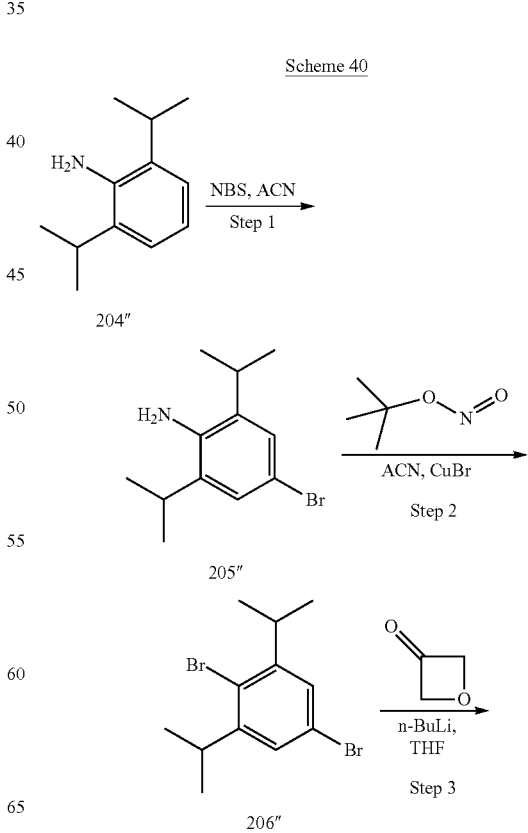

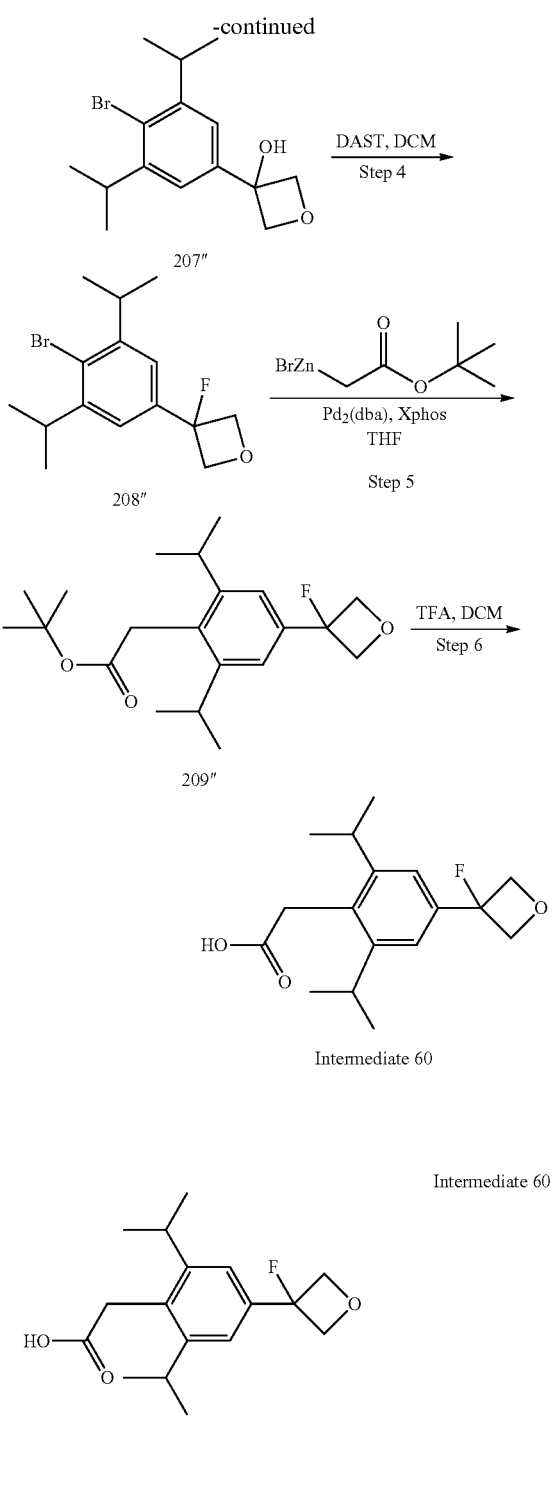

2-(4-(3-Fluorooxetan-3-yl)-2,6-diisopropylphenyl)acetic acid

Step 1: 4-Bromo-2,6-diisopropylaniline

Into a 500-mL round-bottom flask, was placed 2,6-bis(propan-2-yl)aniline (10 g, 56.4 mmol) in ACN (200 mL), to the stirred solution was added NBS (11.0 g, 62.0 mmol). The resulting solution was stirred overnight at RT. The resulting mixture was concentrated under vacuum. The residue was eluted from silica gel with petroleum ether. This resulted in 9.5 g (65.7%) of the title compound as brown oil. MS-ESI: 256/258 [M+1].

Step 2: 2,5-Dibromo-1,3-diisopropylbenzene

Into a 500-mL round-bottom flask purged and maintained with an inert atmosphere of nitrogen, was placed 4-bromo-2,6-bis(propan-2-yl)aniline (6.4 g, 24.9 mmol) in ACN (200 mL). To the stirred solution was added CuBr (7.2 g, 50.2 mmol) and tert-butyl nitrite (5.2 g, 50.5 mmol). The resulting solution was stirred for 3 h at 65° C. in an oil bath. The resulting mixture was concentrated under vacuum. The residue was eluted from silica gel with petroleum ether. This resulted in 5 g (62.5%) of the title compound as light yellow oil. MS-ESI: 319/321/323 [M+1].

Step 3: 3-(4-Bromo-3,5-diisopropylphenyl)oxetan-3-ol

Into a 100-mL 3-necked round-bottom flask purged and maintained with an inert atmosphere of nitrogen, was placed 2,5-dibromo-1,3-bis(propan-2-yl)benzene (5 g, 15.6 mmol) in THF (50 mL). This was followed by the addition of n-BuLi (2.5 M, 6.25 mL, 15.6 mmol) dropwise with stirring at −78° C. The resulting solution was stirred for 30 min at −78° C. To the above was added a solution of oxetan-3-one (1.13 g, 15.6 mmol) in THF (2 mL) dropwise with stirring at −78° C. The resulting solution was slowly warmed to RT and stirred for 2 h at RT. The reaction was then quenched by the addition of 100 mL of NH$_4$Cl (sat.). The resulting solution was extracted with 3×100 mL of ethyl acetate and the organic layers combined and dried over anhydrous sodium sulfate and concentrated under vacuum. The residue was eluted from silica gel with ethyl acetate/petroleum ether (1:3). The crude product was purified by Flash-Prep-HPLC with the following conditions: Column, C$_{18}$ silica gel; mobile phase, H$_2$O (0.1% FA) and ACN (40% to 70% ACN gradient in 30 min), Detector, UV 254/210 nm. This resulted in 1.25 g (25.5%) of the title compound as a white solid. MS-ESI: 313/315[M+1].

Step 4: 3-(4-Bromo-3,5-diisopropylphenyl)-3-fluorooxetane

Into a 50-mL 3-necked round-bottom flask purged and maintained with an inert atmosphere of nitrogen, was placed 3-[4-bromo-3,5-bis(propan-2-yl)phenyl]oxetan-3-ol (600 mg, 1.92 mmol) in DCM (10 mL). This was followed by the addition of DAST (618 mg, 3.83 mmol) dropwise with stirring at 0° C. The resulting solution was stirred overnight at RT. The reaction was then quenched by the addition of 5 mL of methanol. The resulting mixture was concentrated under vacuum. The residue was eluted from silica gel with ethyl acetate/petroleum ether (1:10). This resulted in 430 mg (71.2%) of the title compound as a white solid. MS-ESI: 315/317[M+1].

Step 5: Tert-butyl 2-(4-(3-fluorooxetan-3-yl)-2,6-diisopropylphenyl)acetate

Into a 100-mL round-bottom flask, was placed 3-[4-bromo-3,5-bis(propan-2-yl)phenyl]-3-fluorooxetane (420 mg, 1.33 mmol) in THF (20 mL), to the mixture was added Xphos (60 mg, 0.13 mmol) and Pd$_2$(dba)$_3$ (61 mg, 0.07 mmol). The resulting solution was stirred for 30 min at RT. Then to the above was added tert-butyl 2-(bromozincio)

acetate (694.0 mg, 2.66 mmol). The resulting solution was stirred for 3 h at 60° C. in an oil bath. The resulting mixture was concentrated under vacuum. The residue was eluted from silica gel with ethyl acetate/petroleum ether (1:10). resulted in 450 mg (96.3%) of the title compound as a light yellow solid. MS-ESI: 351 [M+1].

Step 6: 2-(4-(3-Fluorooxetan-3-yl)-2,6-diisopropylphenyl)acetic acid

Into a 50-mL round-bottom flask, was placed tert-butyl 2-[4-(3-fluorooxetan-3-yl)-2,6-bis(propan-2-yl) phenyl]acetate (450 mg, 1.28 mmol) in DCM (4 mL) and TFA (2 mL). The resulting solution was stirred overnight at RT. The resulting mixture was concentrated under vacuum. The residue was eluted from silica gel with ethyl acetate/petroleum ether (1:3). This resulted in 300 mg (79.3%) of the title compound as a light yellow solid. MS-ESI: 295[M+1].

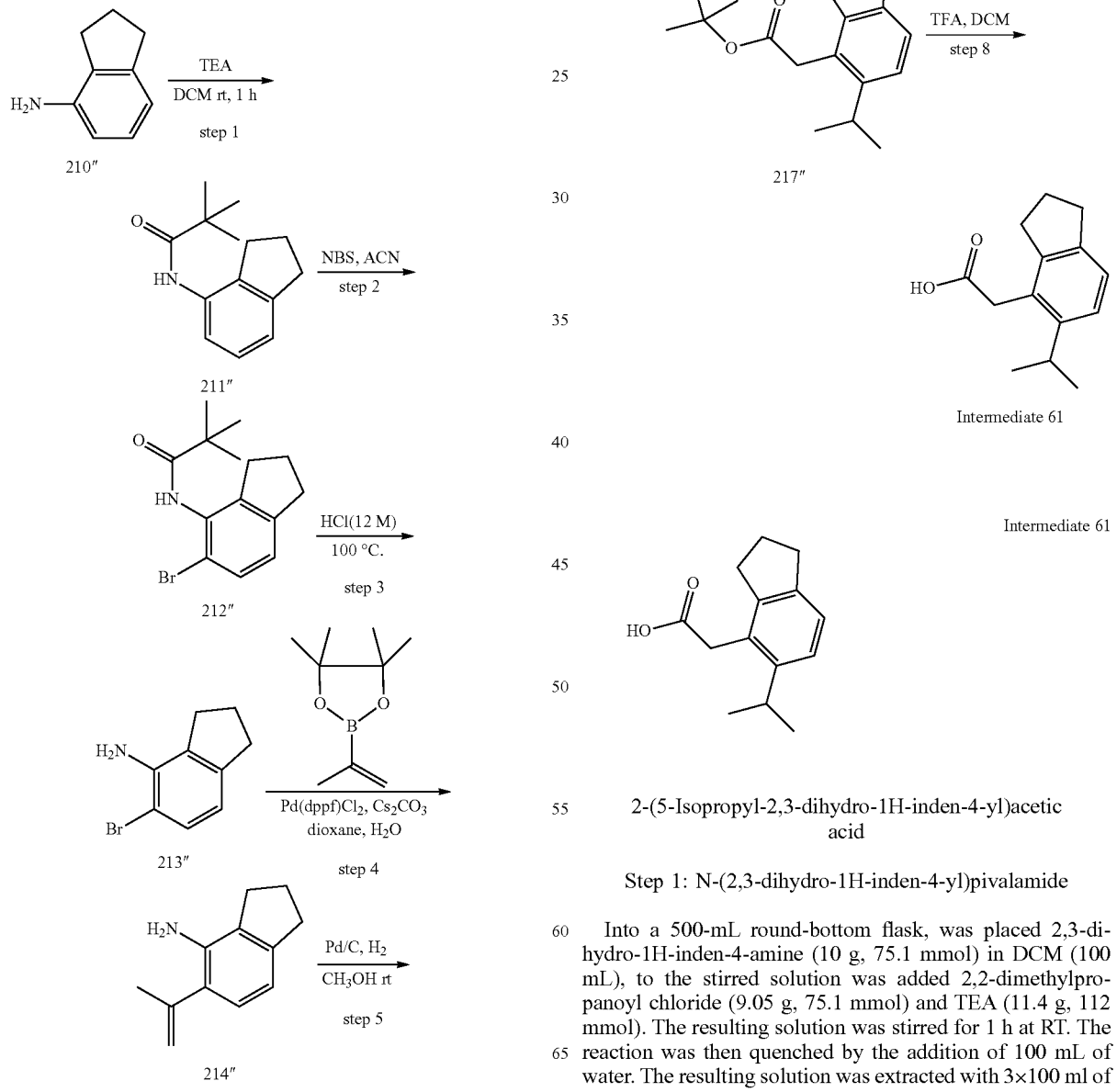

2-(5-Isopropyl-2,3-dihydro-1H-inden-4-yl)acetic acid

Step 1: N-(2,3-dihydro-1H-inden-4-yl)pivalamide

Into a 500-mL round-bottom flask, was placed 2,3-dihydro-1H-inden-4-amine (10 g, 75.1 mmol) in DCM (100 mL), to the stirred solution was added 2,2-dimethylpropanoyl chloride (9.05 g, 75.1 mmol) and TEA (11.4 g, 112 mmol). The resulting solution was stirred for 1 h at RT. The reaction was then quenched by the addition of 100 mL of water. The resulting solution was extracted with 3×100 ml of DCM and dried over anhydrous sodium sulfate and concentrated. This resulted in 15 g (91.9%) of the title compound as an off-white solid. MS-ESI: 218 [M+1].

Step 2: N-(5-bromo-2,3-dihydro-1H-inden-4-yl)pivalamide

Into a 500-mL round-bottom flask purged and maintained with an inert atmosphere of nitrogen, was placed a solution of N-(2,3-dihydro-1H-inden-4-yl)-2,2-dimethylpropanamide (9 g, 41.5 mmol) in ACN (200 mL). To above solution was added NBS (8.86 g, 49.8 mmol). The resulting solution was stirred for 15 h at RT, after which it was extracted with 3×200 ml of DCM. The organic layers were combined, washed with 3×200 ml of aq. Na$_2$CO$_3$, dried over anhydrous sodium sulfate, and concentrated. This resulted in 12 g of the title compound as a brown solid. MS-ESI: 296/298 [M+1]

Step 3: 5-Bromo-2,3-dihydro-1H-inden-4-amine

Into a 500-mL round-bottom flask, was placed a solution of N-(5-bromo-2,3-dihydro-1H-inden-4-yl)-2,2-dimethylpropanamide (10 g, 33.8 mmol) in HCl (200 mL). The resulting solution was stirred for 15 h at 100° C. The reaction was then quenched by the addition of water. The resulting solution was extracted with 3×500 mL of ethyl acetate dried over anhydrous sodium sulfate and concentrated under vacuum. The residue was eluted from silica gel with ethyl acetate/petroleum ether (1:10). This resulted in 7 g (97.7%) of the title compound as a brown solid. MS-ESI: 212/214 [M+1].

Step 4: 5-(Prop-1-en-2-yl)-2,3-dihydro-1H-inden-4-amine

Into a 500-mL round-bottom flask purged and maintained with an inert atmosphere of nitrogen, was placed a solution of 5-bromo-2,3-dihydro-1H-inden-4-amine (7 g, 33 mmol) in dioxane (250 mL) and H$_2$O (25 mL). To the above was added 4,4,5,5-tetramethyl-2-(prop-1-en-2-yl)-1,3,2-dioxaborolane (8.32 g, 49.5 mmol), Cs$_2$CO$_3$ (32.2 g, 99.0 mmol) and Pd(dppf)Cl$_2$ (2.41 g, 3.3 mmol). The resulting solution was stirred for 15 h at 95° C. The reaction was then quenched by the addition of water. The resulting solution was extracted with 3×200 mL of DCM and concentrated. The residue was eluted from silica gel with ethyl acetate/petroleum ether (1:10). This resulted in 4 g (69.9%) of the title compound as a brown solid. MS-ESI: 174 [M+1].

Step 5: 5-Isopropyl-2,3-dihydro-1H-inden-4-amine

Into a 250-mL round-bottom flask, was placed a solution of 5-(prop-1-en-2-yl)-2,3-dihydro-1H-inden-4-amine (4 g, 23.09 mmol) in methanol (100 mL), to the stirred solution was added Pd/C (10% wt., 400 mg). The flask was evacuated and flushed three times with hydrogen. The resulting solution was stirred overnight at RT under hydrogen. The solids were filtered out. The resulting mixture was concentrated under vacuum. This resulted in 4 g (98.8%) of the title compound as a brown solid. MS-ESI: 176 [M+1].

Steps 6-8 used similar procedures for converting compound 191" to intermediate 54 shown in Scheme 37 to afford intermediate 61 from compound 215". MS-ESI: 219 (M+1).

Scheme 42

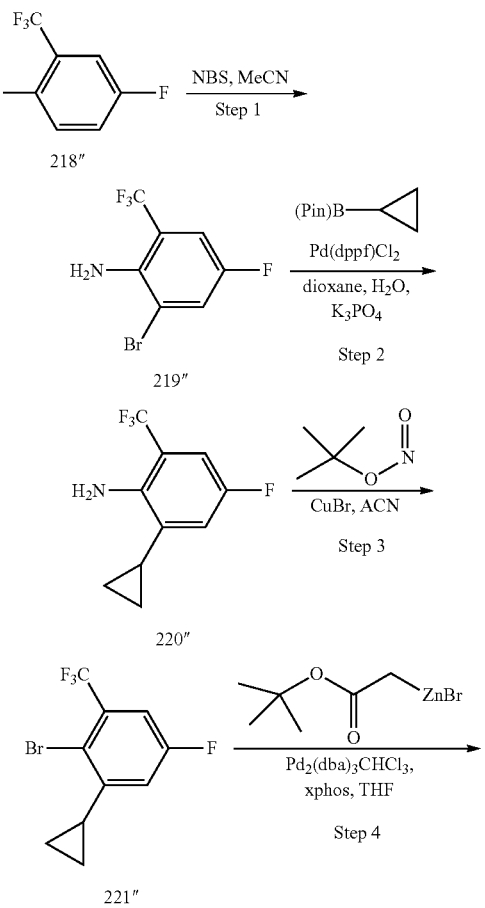

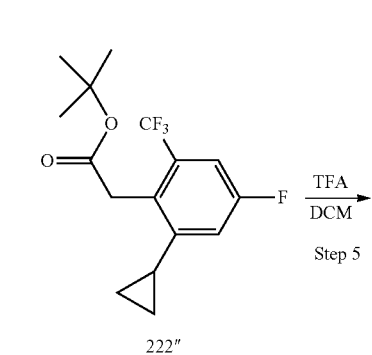

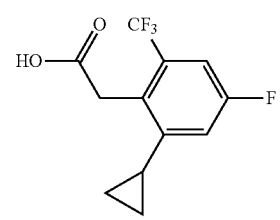

Intermediate 62

Intermediate 62

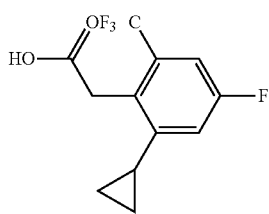

2-(2-Cyclopropyl-4-fluoro-6-(trifluoromethyl)phenyl)acetic acid

Step 1: 2-Bromo-4-fluoro-6-(trifluoromethyl)aniline

Into a 250-mL round-bottom flask, was placed 4-fluoro-2-(trifluoromethyl)aniline (11.6 g, 64.7 mmol) in ACN (100 mL). This was followed by the addition of NBS (12.6 mg, 71.2 mmol) in portions with stirring at 0° C. The resulting solution was stirred for 2 h at RT. The reaction was then quenched by the addition of water. The resulting solution was extracted with 3×100 mL of ethyl acetate. The residue was eluted from silica gel with ethyl acetate/petroleum ether (1:20). This resulted in 13 g (77.8%) of the title compound as a red solid. MS-ESI: 258/260 (M+1).

Step 2: 2-Cyclopropyl-4-fluoro-6-(trifluoromethyl)aniline

Into a 500-mL round-bottom flask purged and maintained with an inert atmosphere of nitrogen, was placed 2-bromo-4-fluoro-6-(trifluoromethyl)aniline (10 g, 38.7 mmol) in dioxane (200 mL) and H$_2$O (10 mL). To the stirred solution was added K$_3$PO$_4$ (24.6 g, 116.2 mmol), Pd(dppf)Cl$_2$ (2.84 g, 3.88 mmol) and cyclopropylboronic acid or ester (4.99 g, 58.1 mmol). The resulting solution was stirred for overnight at 90° C. in an oil bath. The solids were filtered out. The resulting mixture was concentrated. The residue was eluted from silica gel with ethyl acetate/petroleum ether (1:20). This resulted in 7.5 g (88.2%) of the title compound as a yellow oil. MS-ESI: 220 (M+1).

Step 3: 2-Bromo-1-cyclopropyl-5-fluoro-3-(trifluoromethyl)benzene

Into a 100-mL round-bottom flask, was placed 2-cyclopropyl-4-fluoro-6-(trifluoromethyl)aniline (1.5 g, 6.85 mmol) in ACN (30 mL). To the above solution was added tert-butyl nitrite (1.41 g, 13.7 mmol) and CuBr (1.96 g, 13.7 mmol). The resulting solution was stirred for 3 h at 60° C. The resulting mixture was concentrated. The residue was eluted from silica gel with ethyl acetate/petroleum ether (1:20). This resulted in 1 g (51.6%) of the title compound as a yellow liquid. MS-ESI:283/285 (M+1).

Step 4: Tert-butyl 2-[2-cyclopropyl-4-fluoro-6-(trifluoromethyl)phenyl]acetate

Into a 100-mL round-bottom flask purged and maintained with an inert atmosphere of nitrogen, was placed 2-bromo-1-cyclopropyl-5-fluoro-3-(trifluoromethyl)benzene (360 mg, 1.27 mmol) in THF (10 mL), Xphos (121.26 mg, 0.25 mmol), Pd$_2$(dba)$_3$.CHCl$_3$ (131.6 mg, 0.13 mmol), and tert-butyl 2-(bromozincio)acetate (662.4 mg, 2.54 mmol). The resulting solution was stirred for 2 h at 65° C. The resulting mixture was concentrated. The residue was eluted from silica gel with ethyl acetate/petroleum ether (1:20). This resulted in 300 mg (74.1%) of the title compound as yellow oil. MS-ESI: 319 (M+1).

Step 5: 2-[2-Cyclopropyl-4-fluoro-6-(trifluoromethyl)phenyl]acetic acid

Into a 50-mL round-bottom flask, was placed tert-butyl 2-[2-cyclopropyl-4-fluoro-6-(trifluoromethyl) phenyl]acetate (300 mg, 0.94 mmol) in TFA (2 mL) and DCM (2 mL). The resulting solution was stirred for 2 h at RT. The resulting mixture was concentrated. The residue was eluted from silica gel with ethyl acetate/petroleum ether (1:5). This resulted in 230 mg (93.0%) of the title compound as a yellow solid. MS-ESI: 263 (M+1).

Scheme 43

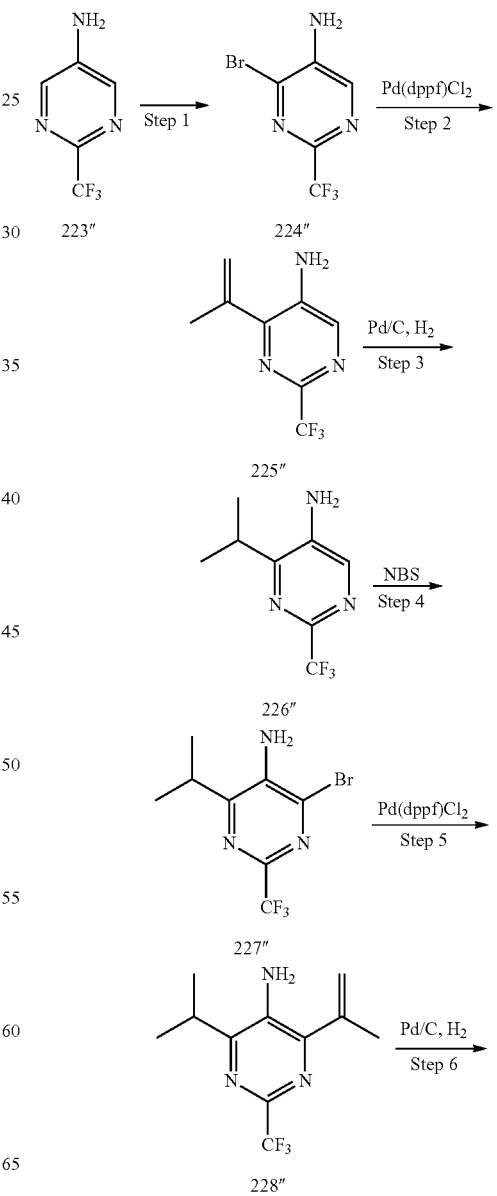

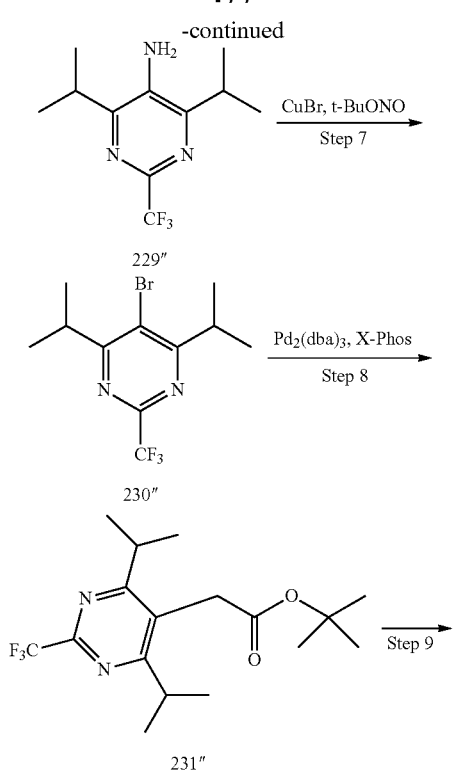

Intermediate 63

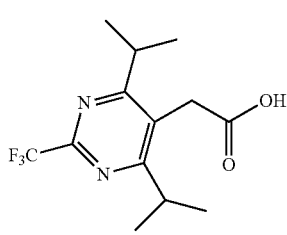

2-(4,6-Diisopropyl-2-(trifluoromethyl)pyrimidin-5-yl)acetic acid

Step 1: 4-Bromo-2-(trifluoromethyl)pyrimidin-5-amine

Into a 100-mL round-bottom flask purged and maintained with an inert atmosphere of nitrogen, was placed 2-(trifluoromethyl)pyrimidin-5-amine (2 g, 12.3 mmol) in acetonitrile (20 mL), to this stirred solution was added NB S (2.62 g, 14.7 mmol). The resulting solution was stirred for 12 h at RT. The resulting solution was diluted with 40 mL of water. The resulting solution was extracted with 2×30 mL of dichloromethane and concentrated. The residue was eluted from silica gel with ethyl acetate/petroleum ether (1:50 to 1:20). This resulted in 1.6 g (53.9%) of the title compound as a brown solid. MS-ESI: 242/244 [M+1]

Step 2: 4-(Prop-1-en-2-yl)-2-(trifluoromethyl)pyrimidin-5-amine

Into a 100-mL round-bottom flask purged and maintained with an inert atmosphere of nitrogen, was placed 4-bromo-2-(trifluoromethyl)pyrimidin-5-amine (1.6 g, 6.61 mmol) in dioxane (20 mL). This was followed by the addition of 4,4,5,5-tetramethyl-2-(prop-1-en-2-yl)-1,3,2-dioxaborolane (1.44 g, 8.57 mmol), Pd(dppf)Cl$_2$ (241 mg, 0.33 mmol), and Cs$_2$CO$_3$ (3.23 g, 9.92 mmol). The resulting solution was stirred for 14 h at 100° C. in an oil bath. The resulting solution was diluted with 40 mL of water. The resulting solution was extracted with 3×30 mL of DCM and concentrated. The residue was eluted from silica gel with ethyl acetate/petroleum ether (1:5). This resulted in 1.1 g (81.8%) of the title compound as a brown solid. MS-ESI: 204 [M+1].

Step 3: 4-Isopropyl-2-(trifluoromethyl)pyrimidin-5-amine

Into a 100-mL round-bottom flask purged and maintained with an inert atmosphere of nitrogen, was placed 4-(prop-1-en-2-yl)-2-(trifluoromethyl)pyrimidin-5-amine (1.2 g, 5.91 mmol) in methanol (20 mL), to the stirred solution was added Pd/C (10% wt., 200 mg). The flask was evacuated and filled three times with hydrogen. The resulting solution was stirred 16 h at RT under hydrogen. The solids were filtered out. The resulting mixture was concentrated under vacuum. This resulted in 1.1 g (90.8%) of the title compound as a brown solid. MS-ESI: 206 [M+1].

Step 4: 4-Bromo-6-isopropyl-2-(trifluoromethyl)pyrimidin-5-amine

Into a 50-mL round-bottom flask purged and maintained with an inert atmosphere of nitrogen, was placed 4-(propan-2-yl)-2-(trifluoromethyl)pyrimidin-5-amine (1.1 g, 5.36 mmol) in acetonitrile (20 mL), to this solution was added NBS (1.15 g, 6.46 mmol) in portions with stirring. The resulting solution was stirred for 12 h at RT. The resulting solution was diluted with 40 mL of water. The resulting solution was extracted with 2×30 mL of DCM concentrated. The residue was eluted from silica gel with ethyl acetate/petroleum ether (1:40 to 1:30). This resulted in 1.0 g (65.6%) of the title compound as a brown solid. MS-ESI: 284/286 [M+1].

Steps 5-9 used similar procedures for converting compound 189" to intermediate 54 shown in Scheme 37 to afford intermediate 63 from compound 227". MS-ESI: 291 (M+1).

Scheme 44

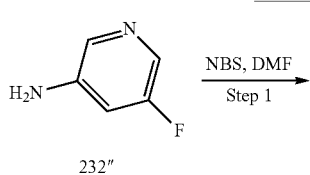

232"

-continued

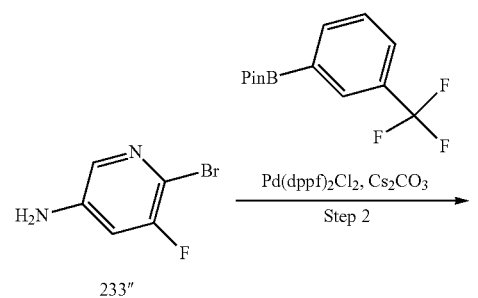

233″

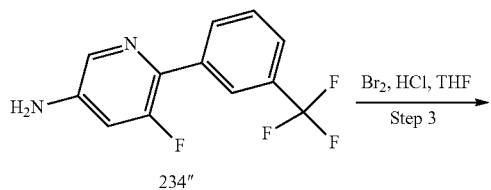

234″

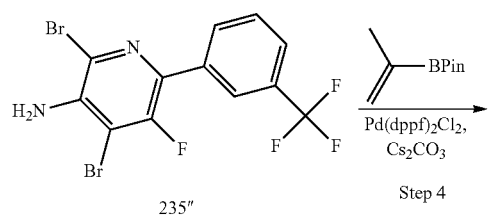

235″

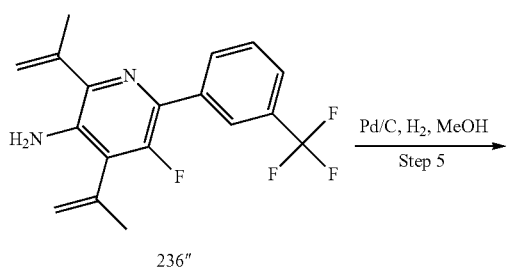

236″

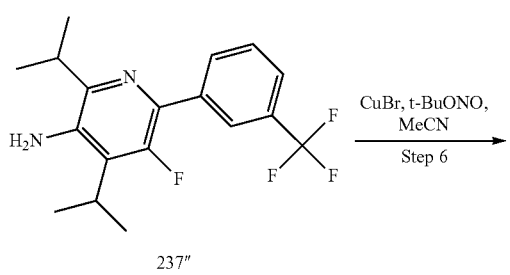

237″

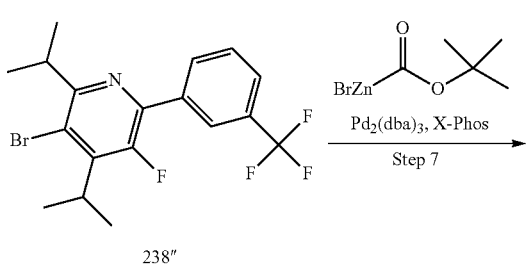

238″

-continued

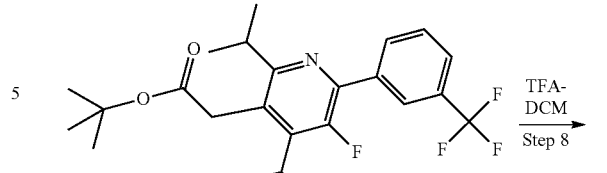

239″

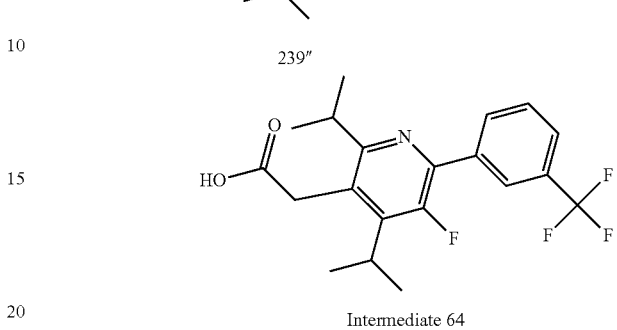

Intermediate 64

Intermediate 64

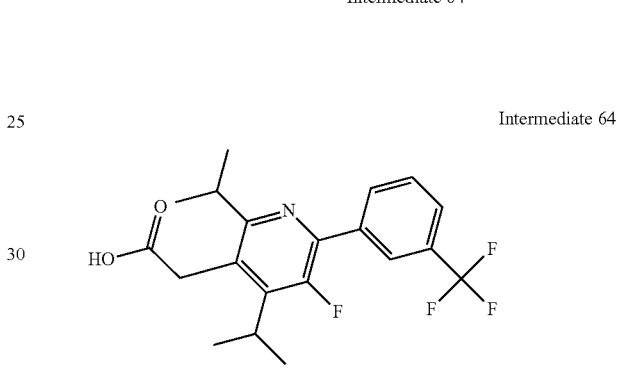

2-(5-Fluoro-2,4-diisopropyl-6-(3-(trifluoromethyl) phenyl)pyri din-3-yl)acetic acid Step 1: 6-Bromo-5-fluoropyridin-3-amine Into a 100 mL round-bottom flask, was added 5-fluoro-pyridin-3-amine (2 g, 17.9 mmol) in DMF (15 mL) at RT. To the stirred solution was added NB S (3.19 g, 17.9 mmol) in DMF (5 mL) dropwise at RT. The resulting solution was stirred for 1 h at RT and diluted with water (75 mL). The resulting mixture was extracted with ethyl acetate (3×20 mL). The combined organic layers were dried over anhydrous $Na_2SO_4$. After filtration, the filtrate was concentrated under reduced pressure. The residue was purified by silica gel chromatography, eluted with EtOAc/petroleum ether (8:1) to afford the title compound (3 g, 79%) as a dark yellow solid. ME-ESI: 191/193 [M+1].

Step 2: s5-Fluoro-6-(3-(trifluoromethyl)phenyl)pyridin-3-amine

Into a 500-mL round-bottom flask purged and maintained with an inert atmosphere of nitrogen, was added 6-bromo-5-fluoropyridin-3-amine (3 g, 15.7 mmol) in dioxane (200 mL) and $H_2O$ (20 mL) at RT. To the stirred solution were added $Pd(dppf)Cl_2$ (1.15 g, 1.57 mmol) and $Cs_2CO_3$ (10.2 g, 31.4 mmol) at RT under nitrogen atmosphere. Then 4,4,5,5-tetramethyl-2-[3-(trifluoromethyl)phenyl]-1,3,2-dioxa-borolane (17.1 g, 62.8 mmol) was added to the above mixture. After the addition was complete and the resulting mixture was stirred at 80° C. in an oil bath overnight. The mixture was concentrated and applied into silica gel and eluted with ethyl acetate/petroleum ether (12:1) to afford the title compound (4.1 g, 94.7%) as a yellow oil. MS-ESI: 257 [M+1].

Step 3: 2,4-Dibromo-5-fluoro-6-(3-(trifluoromethyl) phenyl)pyridin-3-amine

Into a 250 mL round-bottom flask, were added 5-fluoro-6-[3-(trifluoromethyl)phenyl]pyridin-3-amine (4.1 g, 16.0 mmol) in THF (25 mL) at RT. To the stirred solution was added HCl (2 M, 13.5 mL) in one portion at RT. To this mixture was added Br₂ (2.4 mL) dropwise. After the addition was complete, the resulting mixture was stirred for 4 h at RT. The resulting mixture was extracted with ethyl acetate (3×90 mL). The combined organic layers were dried over anhydrous Na₂SO₄. After filtration, the filtrate was concentrated under reduced pressure. The residue was purified by silica gel chromatography, eluted with EtOAc/petroleum ether (20:1) to afford the title compound (2.25 g, 33.9%) as a yellow solid. ME-ESI: 413/415/417 [M+1].

Steps 4-8 used procedures for converting compound 189" to intermediate 54 shown in Scheme 37 to afford intermediate 64 from compound 235". MS-ESI: 384 (M+1).

Scheme 45

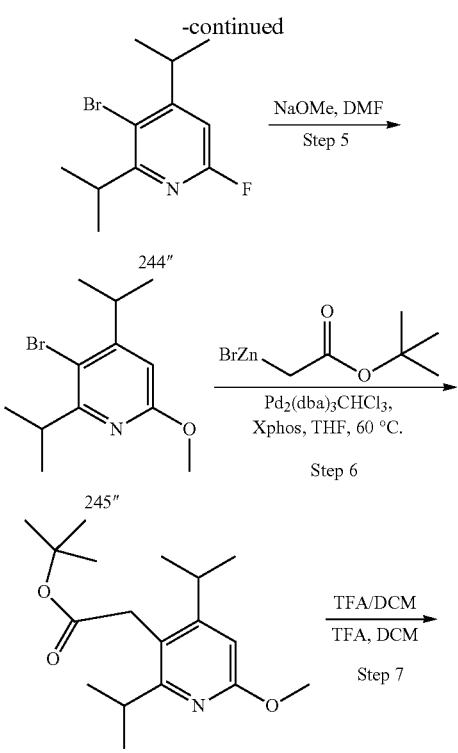

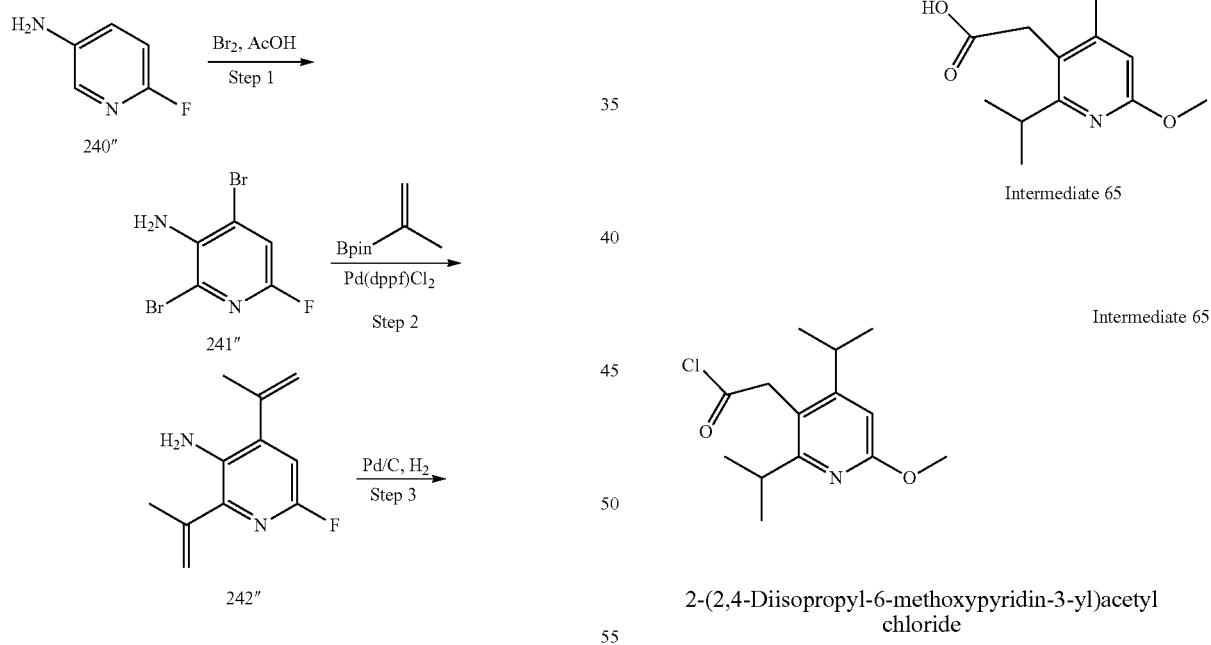

2-(2,4-Diisopropyl-6-methoxypyridin-3-yl)acetyl chloride

Step 1: 2,4-Dibromo-6-fluoropyridin-3-amine

Into a 1-L round-bottom flask, was placed a solution of 6-fluoropyridin-3-amine (4.05 g, 36.1 mmol) in AcOH (40 mL). This was followed by the addition of a solution of Br₂ (4.1 mL, 79.9 mmol) in AcOH (50 mL) dropwise with stirring at 0° C. The resulting solution was stirred for 16 h at RT. The resulting mixture was washed with 150 ml of saturated solution of NaHCO₃, extracted with 3×200 ml of dichloromethane, and dried over anhydrous sodium sulfate. This resulted in 5 g (51.2%) of the title compound as a yellow solid. MS-ESI: 269/271/273[M+1].

483

Steps 2-4 used similar procedures for converting compound 189 to compound 192 shown in Scheme 37 to afford compound 244 from compound 241. MS-ESI: 260/262 (M+1).

Step 5: 3-Bromo-2,4-diisopropyl-6-methoxypyridine

Into a 25-mL round-bottom flask, was placed a solution of 3-bromo-6-fluoro-2,4-bis(propan-2-yl)pyridine (130 mg, 0.50 mmol) in DMF (5 mL). To the solution was added CH₃ONa (108 mg, 2.0 mmol). The resulting solution was stirred overnight at RT. The resulting mixture was washed with 20 ml of H$_2$O. The resulting solution was extracted with 2×25 ml of ethyl acetate dried over anhydrous sodium sulfate and concentrated. The residue was eluted from silica gel with petroleum ether. This resulted in 100 mg (73.5%) of the title compound as yellow oil. MS-ESI: 272/274 [M+1].

Steps 6-7 used similar procedures for converting compound 192" to intermediate 54 shown in Scheme 37 to afford intermediate 65 from compound 245". MS-ESI: 252 (M+1).

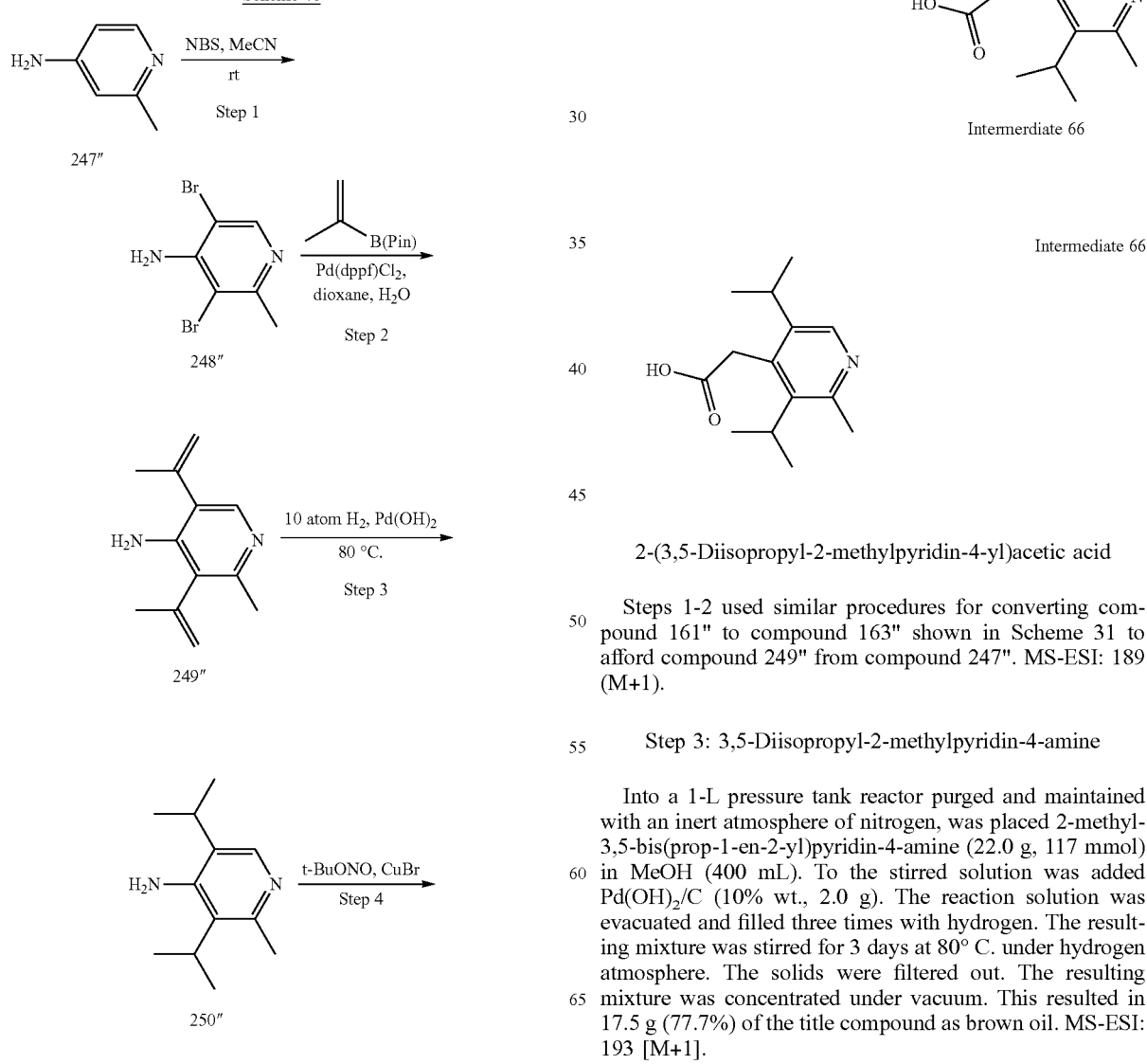

484

2-(3,5-Diisopropyl-2-methylpyridin-4-yl)acetic acid

Steps 1-2 used similar procedures for converting compound 161" to compound 163" shown in Scheme 31 to afford compound 249" from compound 247". MS-ESI: 189 (M+1).

Step 3: 3,5-Diisopropyl-2-methylpyridin-4-amine

Into a 1-L pressure tank reactor purged and maintained with an inert atmosphere of nitrogen, was placed 2-methyl-3,5-bis(prop-1-en-2-yl)pyridin-4-amine (22.0 g, 117 mmol) in MeOH (400 mL). To the stirred solution was added Pd(OH)$_2$/C (10% wt., 2.0 g). The reaction solution was evacuated and filled three times with hydrogen. The resulting mixture was stirred for 3 days at 80° C. under hydrogen atmosphere. The solids were filtered out. The resulting mixture was concentrated under vacuum. This resulted in 17.5 g (77.7%) of the title compound as brown oil. MS-ESI: 193 [M+1].

Steps 4-6 used similar procedures for converting compound 164″ to Intermediate 36 shown in Scheme 31 to afford intermediate 66 from compound 250″. MS-ESI: 235 (M+1).

Scheme 47

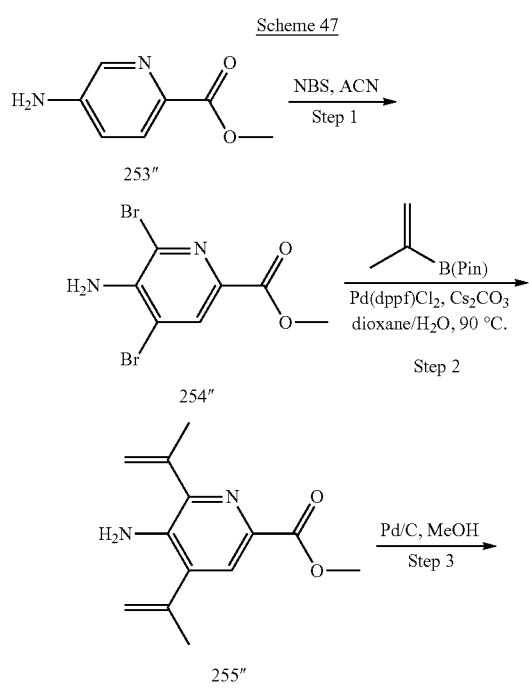

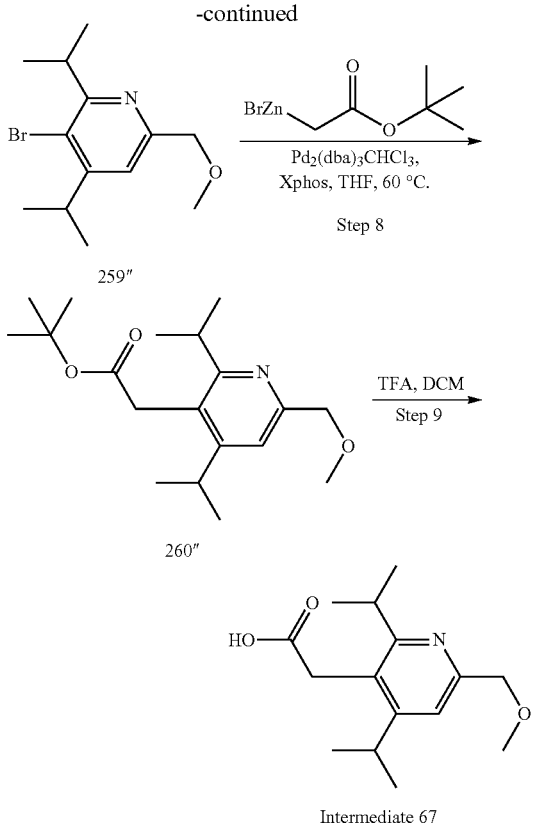

2-(2,4-Diisopropyl-6-(methoxymethyl)pyridin-3-yl)acetic acid

Steps 1-4 used similar procedures for converting compound 161″ to compound 165″ shown in Scheme 31 to afford compound 257″ from compound 253″. MS-ESI: 300/302 (M+1).

Step 5:
(5-Bromo-4,6-diisopropylpyridin-2-yl)methanol

Into a 50-mL round-bottom flask, was placed methyl 5-bromo-4,6-bis(propan-2-yl)pyridine-2-carboxylate (1.4 g, 4.66 mmol) in methanol (10 mL). This was followed by the addition of NaBH₄ (532 mg, 13.9 mmol) in several batches at 0° C. The resulting solution was stirred for 1 h at RT. The reaction was then quenched by the addition of 20 mL of water. The resulting solution was extracted with 3×30 mL of ethyl acetate concentrated. This resulted in 1.2 g (94.5%) of the title compound as an off-white solid. MS-ESI: 272/274 [M+1].

Step 6: 3-Bromo-2,4-diisopropyl-6-(methoxymethyl)pyridine

Into a 100-mL round-bottom flask purged and maintained with an inert atmosphere of nitrogen, was placed [5-bromo-4,6-bis(propan-2-yl)pyridin-2-yl]methanol (800 mg, 2.94 mmol) in THF (10 mL). This was followed by the addition of NaH (60% wt. oil dispersion, 353 mg, 8.82 mmol) in several batches at 0° C. The resulting solution was stirred for 20 min at RT. To this was added CH$_3$I (1.25 g, 8.82 mmol) dropwise with stirring at 0° C. The resulting solution was allowed to react, with stirring, overnight at RT. The reaction was then quenched by the addition of 20 mL of water. The resulting solution was extracted with 3×30 mL of dichloromethane and concentrated. The residue was eluted from silica gel with ethyl acetate/petroleum ether (1:10). This resulted in 820 mg (97.4%) of the title compound as light yellow oil.

Steps 8-9 used similar procedures for converting compound 165″ to intermediate 36 shown in Scheme 31 to afford intermediate 67 from compound 259″. MS-ESI: 286/287 (M+1).

Example 1 (131)

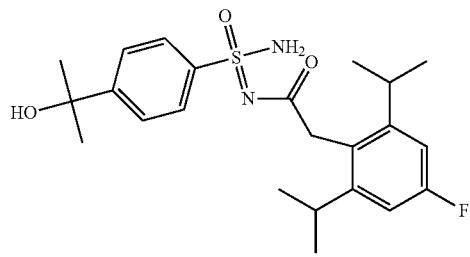 [SMILES: CC(C)c1cc(F)cc(C(C)C)c1CC(=O)N=S(N)(=O)c1ccc(C(C)(C)O)cc1]

2-(4-Fluoro-2,6-diisopropylphenyl)-N-(4-(2-hydroxypropan-2-yl)phenylsulfonimidoyl)acetamide (Scheme 1)

Examples 2 (131b) and 3 (131a)

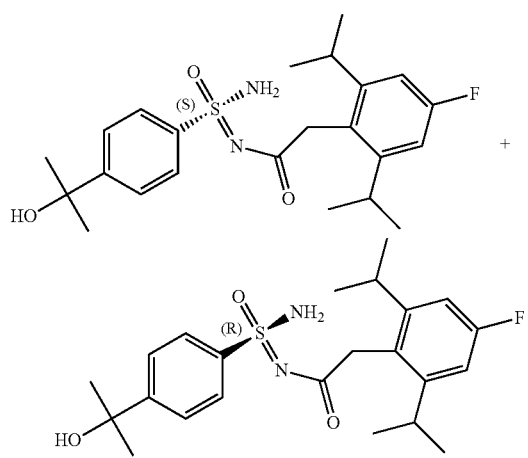

(S)- and (R)-2-(4-Fluoro-2,6-diisopropylphenyl)-N-(4-(2-hydroxypropan-2-yl)phenylsulfonimidoyl)acetamide

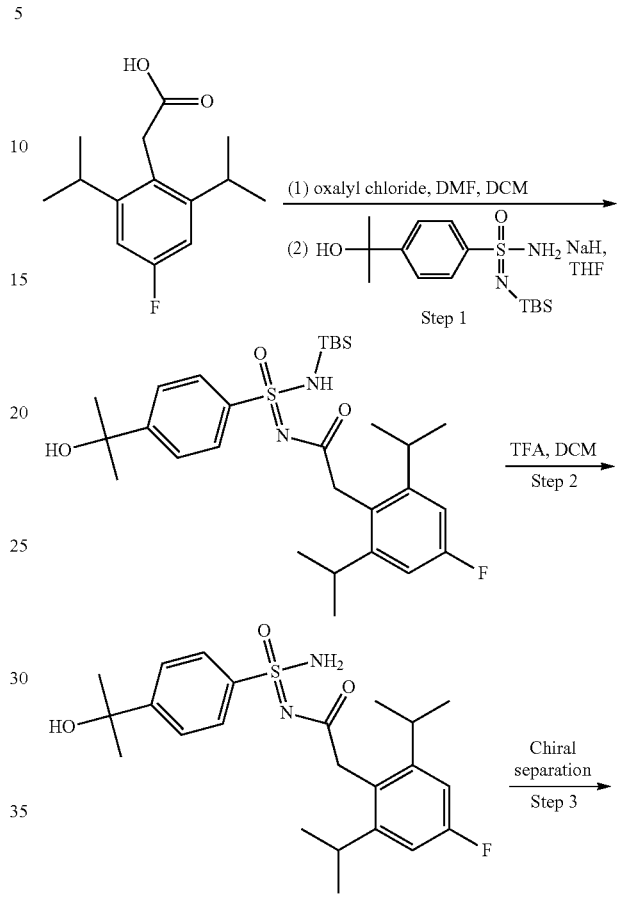

Example 1

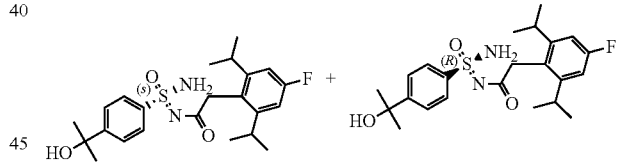

Examples 2 and 3 (stereochemistry not assigned)

Step 1: N-(tert-butyldimethylsilylamino-4-(2-hydroxypropan-2-yl)phenylhydrosulfonimidoyl)-2-(4-fluoro-2,6-diisopropylphenyl)acetamide Into a 50-mL round-bottom flask was placed 2-(4-fluoro-2,6-diisopropylphenyl)acetic acid (73 mg, 0.31 mmol), DCM (2 mL), and DMF (0.05 mL). This was followed by the addition of oxalyl chloride (0.5 mL) dropwise with stirring at RT. The solution was stirred for 30 min at RT and then was concentrated under vacuum. Into a 50-mL round-bottom flask was placed a solution of N'-(tert-butyldimethylsilyl)-4-(2-hydroxypropan-2-yl)benzenesulfonimidamide (100 mg, 0.30 mmol) in THF (3 mL). This was followed by the addition of NaH (60% wt., 42 mg, 1.04 mmol) in portions at 0° C. The solution was stirred for 5 min at RT. Then to the above was added the solution of 2-(4-fluoro-2,6-diisopropylphenyl)acetyl chloride in THF (1 mL) prepared as shown above. The resulting solution was stirred for 1 h at RT, after which it was quenched by the addition of 5 mL of water and extracted with 2×5 mL of ethyl acetate. The combined organic layers were dried over anhydrous $Na_2O_4$, and concentrated under vacuum. This resulted in 159 mg (96%) of the title compound as yellow crude oil. MS-ESI: 547.3 (M−1).

Step 2: 2-(4-Fluoro-2,6-diisopropylphenyl)-N-(4-(2-hydroxypropan-2-yl)phenylsulfonimidoyl)acetamide Into a 50-mL round-bottom flask was placed a solution of N-(tert-butyldimethylsilylamino-4-(2-hydroxylpropan-2-yl)phenylhydrosulfonimidoyl)-2-(4-fluoro-2,6-diisopropylphenyl)acetamide (159 mg, 0.29 mmol) in DCM (10 mL). Then TFA (0.2 mL) was added. The resulting solution was stirred for 1 h at RT and was concentrated under vacuum after that. The crude product was purified by Prep-HPLC using method E eluted with a gradient of 2650% ACN. This resulted in 13.0 mg (10%) of Example 1 as a white solid. MS-ESI: 435.3 (M+1). $^1$H NMR (300 MHz, DMSO-$d_6$) δ 7.75 (d, J=8.7 Hz, 2H), 7.61 (d, J=8.7 Hz, 2H), 7.57 (s, 2H), 6.82 (d, J=10.5 Hz, 2H), 5.21 (s, 1H), 3.62-3.54 (m, 2H) 3.07-2.98 (m, 2H), 1.41 (s, 6H), 1.13 (d, J=6.9 Hz, 6H), 1.08 (d, J=6.9 Hz, 6H).

Step 3: Chiral Separation

The product obtained as described in the previous step (90 mg) was resolved by Chiral-Prep-HPLC using the following conditions: Column, ChiralPak ID, 2*25 cm, 5 um; mobile phase, Hex and IPA (hold 40% IPA over 16 min); Flow rate, 20 mL/min; Detector, UV 254/220 nm. This resulted in 16.0 mg (front peak, enantiomer 1, 99% ee) of Example 2 as a white solid and 44.8 mg (second peak, enantiomer 2, 99% ee) of Example 3 as a light yellow solid. Absolute stereochemistry of these two isomers has not been assigned.

Example 2: MS-ESI: 435.1 (M+1). $^1$H NMR (300 MHz, DMSO-$d_6$) δ 7.75 (d, J=8.4 Hz, 2H), 7.61 (d, J=9.0 Hz, 4H), 6.82 (d, J=10.5 Hz, 2H), 5.18 (s, 1H), 3.62-3.58 (m, 2H), 3.07-2.98 (m, 2H), 1.41 (s, 6H), 1.08 (d, J=6.9 Hz, 6H), 1.00 (d, J=6.6 Hz, 6H).

Example 3: MS-ESI: 435.1 (M+1). $^1$H NMR (300 MHz, DMSO-$d_6$) δ 7.74 (d, J=8.7 Hz, 2H), 7.57 (d, J=8.4 Hz, 4H), 6.81 (d, J=10.5 Hz, 2H), 5.21 (s, 1H), 3.58-3.57 (m, 2H), 3.09-3.02 (m, 2H), 1.41 (s, 6H), 1.07 (d, J=6.6 Hz, 6H), 1.01 (d, J=6.6 Hz, 6H).

Example 4 (129)

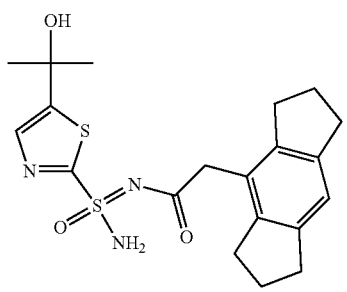 [SMILES: CC(C)(O)c1cnc(S(N)(=O)=NC(=O)Cc2c3c(cc4c2CCC4)CCC3)s1]

2-(1,2,3,5,6,7-Hexahydro-s-indacen-4-yl)-N-(5-(2-hydroxypropan-2-yl)thiazol-2-ylsulfonimidoyl)acetamide (Scheme 2)

Examples 5 (129b) and 6 (129a)

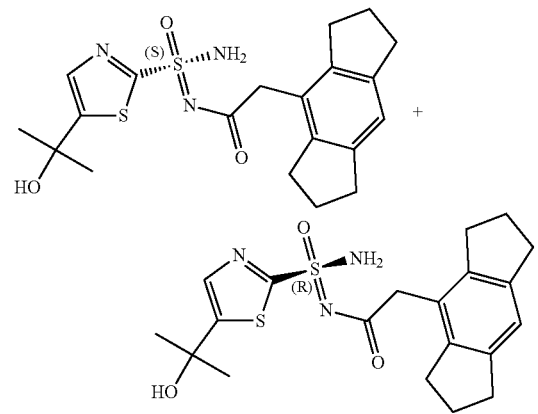

(S)- and (R)-2-(1,2,3,5,6,7-Hexahydro-s-indacen-4-yl)-N-(5-(2-hydroxypropan-2-yl)thiazol-2-ylsulfonimidoyl)acetamide

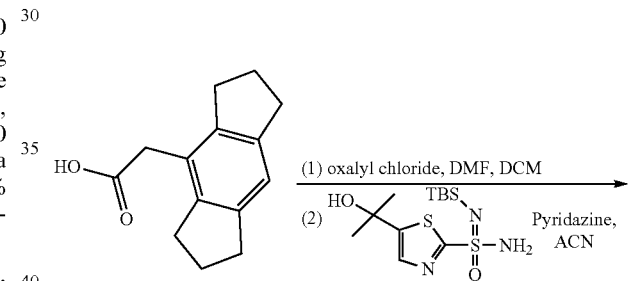

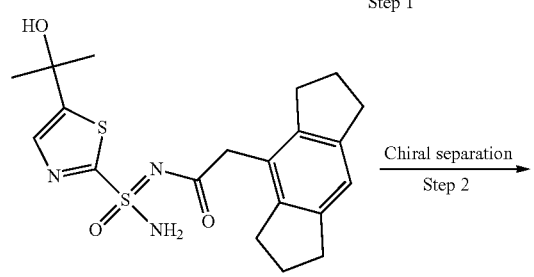

Example 4

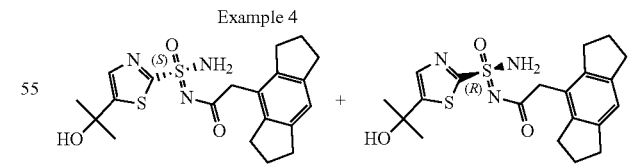

Examples 5 and 6 (stereochemistry not assigned)

Step 1: 2-(1,2,3,5,6,7-Hexahydro-s-indacen-4-yl)-N-(5-(2-hydroxypropan-2-yl)thiazol-2-ylsulfonimidoyl) acetamide Into a 50-mL round-bottom flask was placed 2-(1,2,3,5,6,7-hexahydro-s-indacen-4-yl)acetic acid (100 mg, 0.46 mmol), DCM (2 mL), and DMF (0.05 mL). This was followed by the addition of oxalyl chloride (0.5 mL) dropwise with stirring at RT. The solution was stirred for 30 min at RT and then was concentrated under vacuum. The above mixture was diluted in ACN (3 mL). This was followed by the addition of a solution of pyridazine (37 mg, 0.46 mmol) in ACN (1 mL). The solution was stirred for 1 min at RT and then a solution of N'-(tert-butyldimethylsilyl)-5-(2-hydroxypropan-2-yl)thiazole-2-sulfonimidamide (154 mg, 0.46 mmol) in ACN (2 mL) was added. The resulting solution was stirred for 2 h at RT, after which it was concentrated under vacuum. The resulting residue was applied onto a silica gel column and eluted with ethyl acetate/petroleum ether (1:2 to 1:1). The crude product was purified by Prep-HPLC using method E eluted with a gradient of 26 50% ACN. This resulted in 10 mg (5%) of Example 4 as a white solid. MS-ESI: 420.2 (M+1). $^1$H NMR (300 MHz, DMSO-$d_6$) δ 7.84 (br s, 2H), 7.72 (s, 1H), 6.89 (s, 1H), 5.85 (s, 1H), 3.48-3.37 (m, 2H), 2.80-2.70 (m, 8H), 1.99-1.90 (m, 4H), 1.52-1.51 (m, 6H).

Step 2: Chiral Separation

The product obtained as described in the previous step (40 mg) was resolved by Chiral-Prep-HPLC using the following conditions: ChiralPak IG, 2*25 cm, 5 um; mobile phase, Hex (0.1% TFA) and EtOH (hold 30% EtOH over 13.5 min); Flow rate, 20 mL/min; Detector, UV 254/220 nm. This resulted in 15.3 mg (front peak, enantiomer 1, 100% ee) of Example 5 as a white solid and 14.4 mg (second peak, enantiomer 2, 100% ee) of Example 6 as a white solid. Absolute stereochemistry of these two isomers has not been assigned.

Example 5: MS-ESI: 420.2 (M+1). $^1$H NMR (300 MHz, DMSO-$d_6$) δ 8.12 (s, 2H), 7.80 (s, 1H), 6.90 (s, 1H), 5.93 (s, 1H), 3.48-3.40 (m, 2H), 2.80-2.50 (m, 8H), 2.08-1.89 (m, 4H), 1.54-1.52 (m, 6H).

Example 6: MS-ESI: 420.2 (M+1). $^1$H NMR (300 MHz, DMSO-$d_6$) δ 8.12 (s, 2H), 7.80 (s, 1H), 6.91 (s, 1H), 5.93 (s, 1H), 3.48-3.40 (m, 2H), 2.80-2.69 (m, 8H), 1.99-1.90 (m, 4H), 1.54-1.52 (m, 6H).

Example 7 (132)

2-(4-Fluoro-2,6-diisopropylphenyl)-N-(5-(2-hydroxypropan-2-yl)thiazole-2-sulfonimidoyl)acetamide (Scheme 3)

Examples 8 (132b) and 9 (132a)

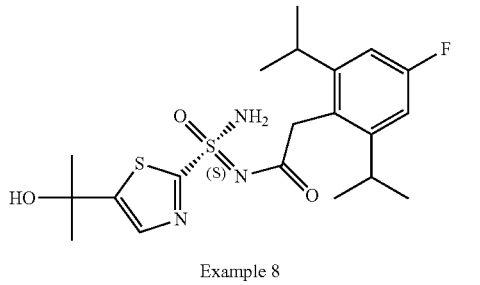

Example 8

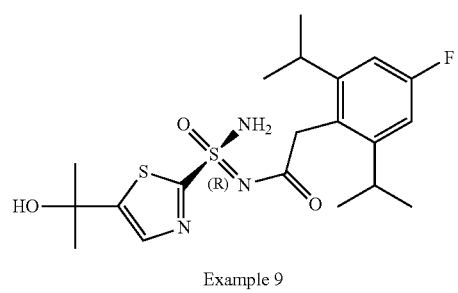

Example 9

(S)- and (R)-2-(4-fluoro-2,6-diisopropyl phenyl)-N-(5-(2-hydroxypropan-2-yl)thiazole-2-sulfonimidoyl) acetamide

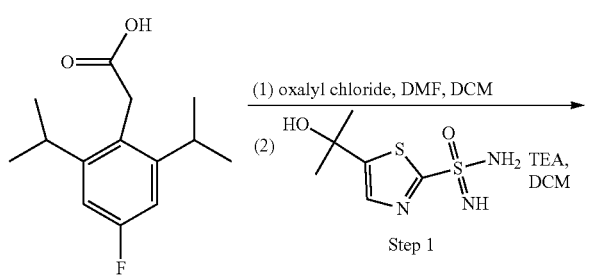

Step 1

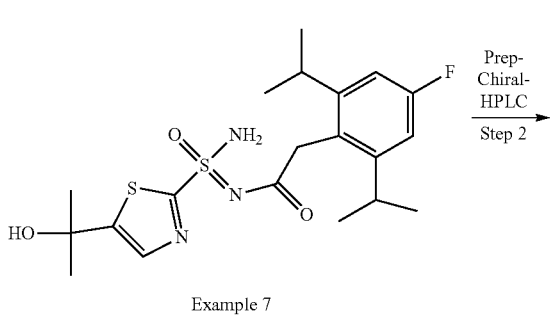

Example 7

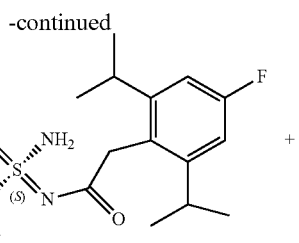

Examples 8

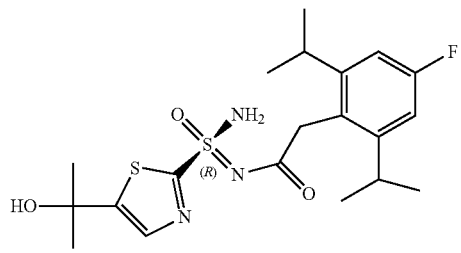

Examples 9

Step 1: 2-(4-Fluoro-2,6-diisopropylphenyl)-N-(5-(2-hydroxypropan-2-yl)thiazole-2-sulfonimidoyl)acetamide Into a 50-mL round-bottom flask was placed 2-(4-fluoro-2,6-diisopropylphenyl)acetic acid (108 mg, 0.45 mmol), DCM (3 mL), and DMF (0.05 mL). This was followed by the addition of oxalyl chloride (0.5 mL) dropwise with stirring at RT. The solution was stirred for 30 min at RT and then was concentrated under vacuum. To the above mixture, diluted in DCM (1 mL), was added to a solution of 5-(2-hydroxypropan-2-yl)thiazole-2-sulfonimidamide (60 mg, 0.27 mmol) and TEA (150 mg, 1.48 mmol) in DCM (3 mL) dropwise with stirring at RT. The resulting solution was stirred for 1 h at RT and was then concentrated under vacuum. The crude product was purified by Prep-HPLC using method E eluted with a gradient of 2244% ACN. This resulted in 2.1 mg (1%) of Example 7 as a white solid. MS-ESI: 442.3 (M+1). $^1$H NMR (300 MHz, CD$_3$OD-d$_4$) δ 7.67 (s, 1H), 6.75 (d, J=10.5 Hz, 2H), 3.74 (s, 2H), 3.17-3.03 (m, 2H), 1.58 (s, 6H), 1.12 (d, J=6.8 Hz, 6H), 1.10 (d, J=6.8 Hz, 6H).

Step 2: Chiral Separation

The product obtained in the previous step (10 mg) was resolved by Chiral-Prep-HPLC using following conditions: Column, ChiralPak ID, 2*25 cm, 5 um; mobile phase, Hex (0.1% FA) and EtOH (hold 20% EtOH in over 10 min); Flow rate, 20 mL/min; Detector, UV 254/220 nm. This resulted in 3.6 mg (front peak, enantiomer 1, 99% ee) of Example 8 as a yellow solid and 3.1 mg (second peak, enantiomer 2, 99% ee) of Example 9 as a yellow solid. Single crystal X-ray crystallographic analysis was performed on compound 132b. Table N below shows fractional atomic coordinates of compound 132b, and FIG. 1 shows ball and stick models of the asymmetrical unit containing two crystallographically independent molecules of compound 132b, with hydrogen atoms omitted for clarity. Based on these results, the absolute stereochemistry of compound 132b was assigned as (S) by single crystal X-ray structure determination. Therefore, compound 132a was assigned as the (R) isomer.

Example 8: MS-ESI: 442.2 (M+1). $^1$H NMR (300 MHz, DMSO-d$_6$) δ 8.21 (br s, 2H), 7.75 (s, 1H), 6.84 (d, J=10.5 Hz, 2H), 5.88 (s, 1H), 3.65-3.63 (m, 2H), 3.10-2.97 (m, 2H), 1.51 (s, 6H), 1.09 (d, J=6.9 Hz, 6H), 1.04 (d, J=6.9 Hz, 6H).

Example 9: MS-ESI: 442.2 (M+1). $^1$H NMR (300 MHz, DMSO-d$_6$) δ 7.73 (s, 1H), 6.83 (d, J=10.5 Hz, 2H), 5.87 (s, 1H), 3.63-3.59 (m, 2H), 3.10-3.03 (m, 2H), 1.51 (s, 6H), 1.09 (d, J=6.9 Hz, 6H), 1.04 (d, J=6.6 Hz, 6H).

TABLE N

Fractional Atomic Coordinates (×10$^4$) and Equivalent Isotropic Displacement Parameters (Å$^2$ × 10$^3$) for Example 8. U$_{eq}$ is defined as ⅓ of the trace of the orthogonalised U$_{IJ}$ tensor.

| Atom | x | y | z | U(eq) |
|---|---|---|---|---|
| S3 | 6096 (2) | 1631.9 (12) | 6214.0 (7) | 43.8 (3) |
| S1 | 4186 (3) | 6312.8 (13) | 3775.3 (8) | 49.4 (4) |
| S4 | 7832 (3) | 4132.7 (15) | 5650.5 (8) | 53.7 (4) |
| S2 | 4909 (3) | 9172.1 (15) | 3606.7 (9) | 64.2 (5) |
| O4 | 7737 (8) | 1198 (4) | 5669 (2) | 56.1 (11) |
| O5 | 9907 (8) | 1617 (5) | 7085 (2) | 62.4 (12) |
| O1 | 2799 (9) | 5566 (4) | 4214 (2) | 64.9 (13) |
| F2 | 14863 (9) | 1324 (5) | 9826 (3) | 88.3 (14) |
| N4 | 6228 (9) | 1015 (5) | 6933 (2) | 47.7 (11) |
| O2 | 102 (9) | 7078 (6) | 2977 (2) | 70.3 (14) |
| F1 | −4874 (11) | 7107 (6) | 161 (3) | 100.7 (17) |
| N5 | 3489 (10) | 1470 (6) | 6026 (3) | 54.6 (13) |
| O3 | 2378 (9) | 12418 (4) | 4594 (2) | 60.3 (12) |
| N3 | 1905 (9) | 8406 (5) | 4478 (2) | 46.5 (11) |
| N1 | 4115 (10) | 6318 (5) | 3000 (3) | 55.1 (13) |
| N2 | 6903 (11) | 5865 (6) | 3894 (3) | 60.1 (15) |
| N6 | 5327 (10) | 4040 (5) | 6756 (3) | 58.1 (14) |
| O6 | 8678 (13) | 6628 (6) | 5147 (3) | 86.0 (18) |
| C3 | 3284 (10) | 10337 (6) | 4107 (3) | 45.2 (13) |
| C27 | 8106 (11) | 1236 (5) | 7308 (3) | 46.2 (14) |
| C29 | 9664 (12) | 1054 (6) | 8500 (3) | 50.9 (15) |
| C32 | 13181 (13) | 1229 (7) | 9385 (3) | 59.3 (17) |
| C24 | 7970 (11) | 6826 (6) | 5836 (3) | 50.5 (14) |
| C6 | 6192 (12) | 11937 (7) | 4004 (4) | 63.5 (18) |
| C30 | 10056 (13) | 2297 (6) | 8708 (3) | 55.4 (16) |
| C22 | 5791 (13) | 5307 (6) | 6651 (3) | 59.0 (17) |
| C28 | 7637 (12) | 955 (6) | 8054 (3) | 51.2 (15) |
| C23 | 7090 (11) | 5560 (6) | 6085 (3) | 46.0 (14) |
| C1 | 3454 (11) | 7995 (6) | 4013 (3) | 46.6 (13) |
| C2 | 1819 (11) | 9753 (6) | 4535 (3) | 48.0 (13) |
| C34 | 11159 (13) | −85 (6) | 8717 (3) | 55.8 (16) |
| C9 | 415 (13) | 7159 (7) | 1501 (3) | 57.2 (17) |
| C31 | 11805 (14) | 2368 (7) | 9156 (4) | 63.5 (18) |
| C10 | −915 (15) | 8349 (7) | 1276 (4) | 65.2 (19) |
| C33 | 12915 (14) | 27 (7) | 9168 (3) | 60.3 (17) |
| C4 | 3585 (11) | 11787 (6) | 4018 (3) | 46.4 (14) |
| C7 | 2090 (13) | 6835 (7) | 2692 (3) | 55.1 (16) |
| C8 | 2514 (14) | 7140 (8) | 1955 (3) | 64.7 (19) |
| C13 | −1943 (16) | 5980 (8) | 843 (4) | 71 (2) |
| C12 | −3143 (15) | 7121 (8) | 616 (4) | 70 (2) |
| C14 | −148 (15) | 5971 (7) | 1295 (4) | 67 (2) |
| C38 | 8604 (16) | 3579 (7) | 8461 (4) | 73 (2) |
| C5 | 2485 (14) | 12376 (7) | 3372 (4) | 64.0 (18) |
| C35 | 10957 (16) | −1446 (7) | 8477 (4) | 72 (2) |
| C11 | −2668 (16) | 8307 (8) | 821 (4) | 76 (2) |
| C21 | 6299 (10) | 3342 (6) | 6257 (3) | 45.8 (14) |
| C39 | 10220 (20) | 4381 (9) | 8022 (5) | 99 (3) |
| C40 | 7385 (19) | 4354 (9) | 9037 (6) | 101 (3) |
| C15 | 1040 (20) | 4634 (9) | 1552 (6) | 95 (3) |
| C26 | 9960 (20) | 7080 (12) | 6237 (6) | 120 (5) |
| C18 | −480 (20) | 9672 (9) | 1490 (5) | 98 (3) |
| C37 | 10310 (40) | −2330 (12) | 9044 (6) | 153 (6) |
| C25 | 5915 (17) | 7965 (8) | 5857 (6) | 92 (3) |
| C17 | −680 (30) | 3869 (11) | 1918 (6) | 132 (5) |
| C16 | 2410 (20) | 3878 (10) | 979 (8) | 124 (5) |
| C19 | 80 (40) | 10550 (14) | 950 (8) | 198 (10) |
| C36 | 13120 (30) | −2025 (15) | 8091 (10) | 199 (10) |
| C20 | −2400 (50) | 10316 (15) | 1931 (10) | 292 (18) |

Example 10 (134)

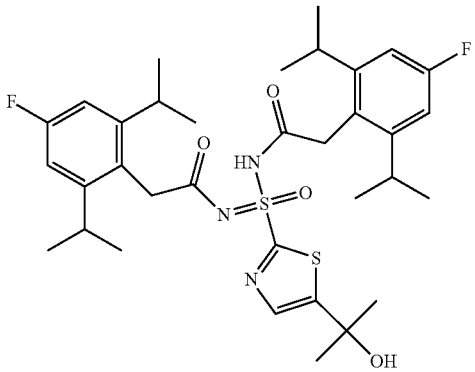 [SMILES: CC(C)c1cc(F)cc(C(C)C)c1CC(=O)N=S(=O)(NC(=O)Cc1c(C(C)C)cc(F)cc1C(C)C)c1ncc(C(C)(C)O)s1]

N,N-(5-(2-hydroxypropan-2-yl)thiazol-2-ylsulfinyl)
bis(2-(4-fluoro-2,6-diisopropylphenyl)acetamide)
(Scheme 4)

Into a 50-mL round-bottom flask was placed 2-(4-fluoro-2,6-diisopropylphenyl)acetic acid (242 mg, 1.02 mmol), DCM (3 mL), and DMF (0.05 mL). This was followed by the addition of oxalyl chloride (0.5 mL) dropwise with stirring at RT. The solution was stirred for 30 min at RT and then was concentrated under vacuum. To the above mixture, diluted in DCM (2 mL), was added to a solution of 5-(2-hydroxypropan-2-yl)thiazole-2-sulfonimidamide (220 mg, 0.99 mmol) and TEA (400 mg, 3.95 mmol) in DCM (3 mL) dropwise with stirring at RT. The resulting solution was stirred for 1 h at RT and was then concentrated under vacuum. The crude product was purified by Prep-HPLC using method E eluted with a gradient of 63 65% ACN. This resulted in 51.6 mg (8%) of Example 10 as a white solid. MS-ESI: 660.5 (M−1). $^1$H NMR (300 MHz, CD$_3$OD-d$_4$) δ 7.59 (s, 1H), 5.75 (d, J=10.2 Hz, 4H), 3.82 (s, 4H), 3.16-3.06 (m, 4H), 1.59 (s, 6H), 1.32-1.13 (m, 24H).

Example 11 (137)

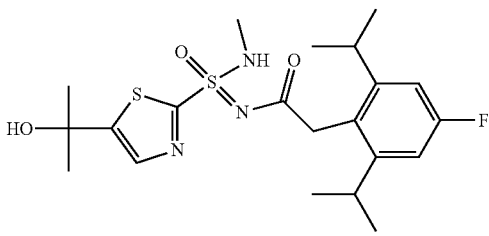 [SMILES: CNS(=O)(=NC(=O)Cc1c(C(C)C)cc(F)cc1C(C)C)c1ncc(C(C)(C)O)s1]

2-(4-Fluoro-2,6-diisopropylphenyl)-N-(5-(2-hydroxypropan-2-yl)-N-methylthiazole-2-sulfonimidoyl)acetamide (Scheme 5)

Into a 50-mL round-bottom flask was placed 2-(4-fluoro-2,6-diisopropylphenyl)acetic acid (233 mg, 0.98 mmol), DCM (3 mL), and DMF (0.05 mL). This was followed by the addition of oxalyl chloride (0.5 mL) dropwise with stirring at RT. The solution was stirred for 30 min at RT and then was concentrated under vacuum. To the above mixture, diluted in DCM (2 mL), was added to a solution of 5-(2-hydroxypropan-2-yl)-N'-methylthiazole-2-sulfonimidamide (230 mg, 0.98 mmol) and TEA (400 mg, 3.95 mmol) in DCM (3 mL) dropwise with stirring at RT. The resulting solution was stirred for 1 h at RT and then was concentrated under vacuum. The crude product was purified by Prep-HPLC using method E eluted with a gradient of 20 80% ACN. This resulted in 17.7 mg (4%) of Example 11 as a light yellow solid. MS-ESI: 456.2 (M+1). $^1$H NMR (300 MHz, DMSO-d$_6$) major tautomer β 8.34 (s, 1H), 7.85 (s, 1H), 6.86 (d, J=10.5 Hz, 2H), 5.94 (s, 1H), 3.71 (d, J=3.6 Hz, 2H), 3.14-3.02 (m, 2H), 2.55 (s, 3H), 1.52 (s, 6H), 1.13 (d, J=4.5 Hz, 6H), 1.09 (d, J=4.5 Hz, 6H).

Example 12 (136)

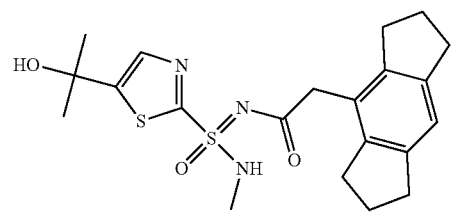 [SMILES: CNS(=O)(=NC(=O)Cc1c2c(cc3c1CCC3)CCC2)c1ncc(C(C)(C)O)s1]

2-(1,2,3,5,6,7-Hexahydro-s-indacen-4-yl)-N-(5-(2-hydroxypropan-2-yl)-N-methylthiazole-2-sulfonimidoyl)acetamide (Scheme 6)

Into a 50-mL round-bottom flask was placed 2-(1,2,3,5,6,7-hexahydro-s-indacen-4-yl)acetic acid (156 mg, 0.72 mmol), DCM (3 mL), and DMF (0.05 mL). This was followed by the addition of oxalyl chloride (0.5 mL) dropwise with stirring at RT. The solution was stirred for 30 min at RT and then was concentrated under vacuum. To the above mixture, diluted in DCM (2 mL), was added to a solution of 5-(2-hydroxypropan-2-yl)-N'-methylthiazole-2-sulfonimidamide (170 mg, 0.72 mmol) and DBU (370 mg, 2.43 mmol) in DCM (3 mL) dropwise with stirring at RT. The resulting solution was stirred for 2 h at RT and then was quenched by the addition of 10 mL of water. The resulting solution was extracted with 3×10 mL of ethyl acetate, dried over anhydrous Na$_2$O$_4$, and then concentrated under vacuum. The crude product was purified by Prep-HPLC using method E eluted with a gradient of 5~15% ACN. This resulted in 11.3 mg (4%) of the title compound as a light yellow solid. MS-ESI: 434.3 (M+1). $^1$H NMR (300 MHz, CD$_3$OD-d$_4$) major tautomer δ 7.75 (s, 1H), 6.89 (s, 1H), 3.56 (s, 2H), 2.83-2.73 (m, 8H), 2.61 (s, 3H), 2.06-1.95 (m, 4H), 1.59 (s, 6H).

TABLE 8

Example in the following table was prepared using similar conditions as described in Example 1 and Scheme 1 from appropriate starting materials.

| Example # | Compound Number | Structure | IUPAC Name | LC-MS [M + H]+ |
|---|---|---|---|---|
| 13 | 133 | 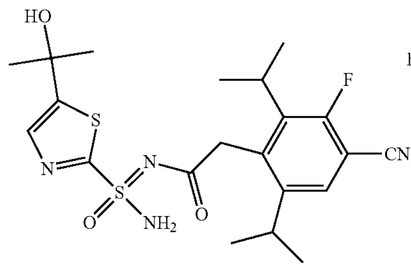 [SMILES: CC(C)c1cc(C#N)c(F)c(C(C)C)c1CC(=O)N=S(N)(=O)c1ncc(C(C)(C)O)s1] | 2-(4-cyano-3-fluoro-2,6-diisopropylphenyl)-N-(5-(2-hydroxypropan-2-yl)thiazol-2-ylsulfonimidoyl)acetamide | 467.2 |

TABLE 9

Examples in the following table were prepared using similar conditions as described in Example 4 and Scheme 2 from appropriate starting materials.

| Example # | Compound Number | Structure | IUPAC Name | LC-MS [M + H]+ |
|---|---|---|---|---|
| 14 | 141 | 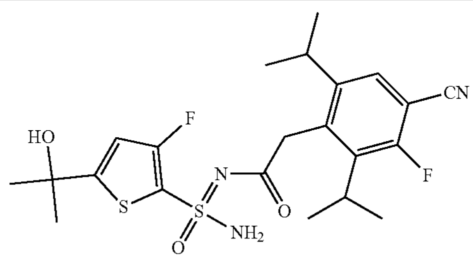 [SMILES: CC(C)c1cc(C#N)c(F)c(C(C)C)c1CC(=O)N=S(N)(=O)c1sc(C(C)(C)O)cc1F] | 2-(4-cyano-3-fluoro-2,6-diisopropylphenyl)-N-(3-fluoro-5-(2-hydroxypropan-2-yl)thiophen-2-ylsulfonimidoyl)acetamide | 484.2 |
| 15 | 139 | 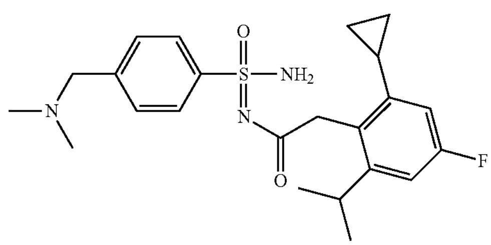 [SMILES: CC(C)c1cc(F)cc(C2CC2)c1CC(=O)N=S(N)(=O)c1ccc(CN(C)C)cc1] | 2-(2-cyclopropyl-4-fluoro-6-isopropylphenyl)-N-(4-((dimethylamino)methyl)phenylsulfonimidoyl)acetamide | 432.2 |
| 16 | 138 | 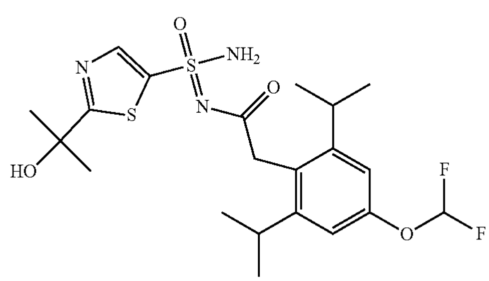 [SMILES: CC(C)c1cc(OC(F)F)cc(C(C)C)c1CC(=O)N=S(N)(=O)c1cnc(C(C)(C)O)s1] | 2-(4-(difluoromethoxy)-2,6-diisopropylphenyl)-N-(2-(2-hydroxypropan-2-yl)thiazol-5-ylsulfonimidoyl)acetamide | 490.3 |
| 17 | 140 | 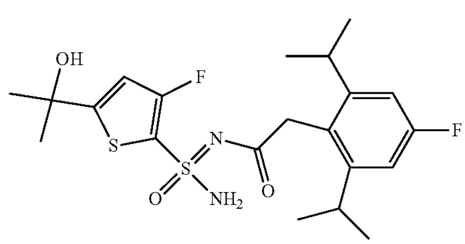 [SMILES: CC(C)c1cc(F)cc(C(C)C)c1CC(=O)N=S(N)(=O)c1sc(C(C)(C)O)cc1F] | 2-(4-fluoro-2,6-diisopropylphenyl)-N-(3-fluoro-5-(2-hydroxypropan-2-yl)thiophen-2-ylsulfonimidoyl)acetamide | 459.2 |

TABLE 9-continued

Examples in the following table were prepared using similar conditions as described in Example 4 and Scheme 2 from appropriate starting materials.

| Example # | Compound Number | Structure | IUPAC Name | LC-MS [M + H]+ |
|---|---|---|---|---|
| 18 | 142 | 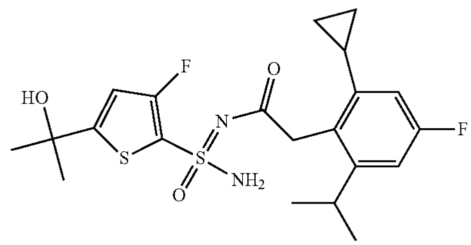 [SMILES: CC(C)c1cc(F)cc(C2CC2)c1CC(=O)N=S(N)(=O)c1sc(C(C)(C)O)cc1F] | 2-(2-cyclopropyl-4-fluoro-6-isopropylphenyl)-N-(3-fluoro-5-(2-hydroxypropan-2-yl)thiophen-2-ylsulfonimidoyl)acetamide | 457.2 |
| 19 | 143 | 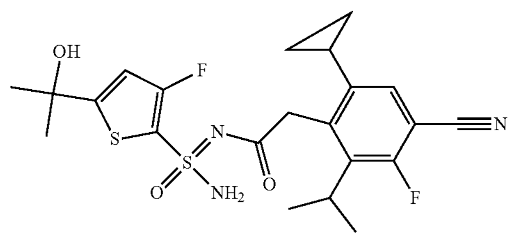 [SMILES: CC(C)c1c(F)c(C#N)cc(C2CC2)c1CC(=O)N=S(N)(=O)c1sc(C(C)(C)O)cc1F] | 2-(4-cyano-6-cyclopropyl-3-fluoro-2-isopropylphenyl)-N-(3-fluoro-5-(2-hydroxypropan-2-yl)thiophen-2-ylsulfonimidoyl)acetamide | 482.2 |
| 20 | 197 | 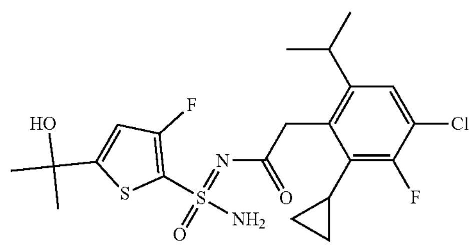 [SMILES: CC(C)c1cc(Cl)c(F)c(C2CC2)c1CC(=O)N=S(N)(=O)c1sc(C(C)(C)O)cc1F] | 2-(4-chloro-2-cyclopropyl-3-fluoro-6-isopropylphenyl)-N-(3-fluoro-5-(2-hydroxypropan-2-yl)thiophen-2-ylsulfonimidoyl)acetamide | 491.2 |
| 21 | 101 | 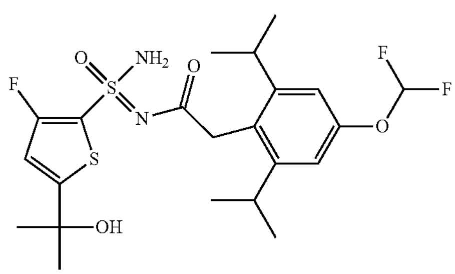 [SMILES: CC(C)c1cc(OC(F)F)cc(C(C)C)c1CC(=O)N=S(N)(=O)c1sc(C(C)(C)O)cc1F] | 2-(4-(difluoromethoxy)-2,6-diisopropylphenyl)-N-(3-fluoro-5-(2-hydroxypropan-2-yl)thiophen-2-ylsulfonimidoyl)acetamide | 507.2 |
| 22 | 152 | 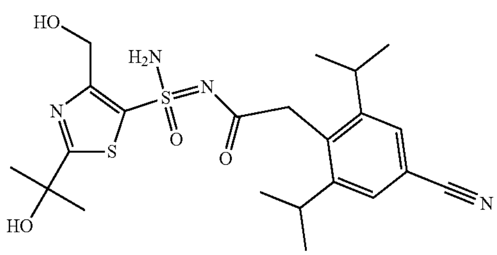 [SMILES: CC(C)c1cc(C#N)cc(C(C)C)c1CC(=O)N=S(N)(=O)c1sc(C(C)(C)O)nc1CO] | 2-(4-cyano-2,6-diisopropylphenyl)-N-(4-(hydroxymethyl)-2-(2-hydroxypropan-2-yl)thiazol-5-ylsulfonimidoyl)acetamide | 479.2 |
| 23 | 150 | 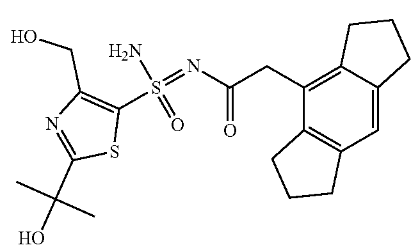 [SMILES: CC(C)(O)c1nc(CO)c(S(N)(=O)=NC(=O)Cc2c3c(cc4c2CCC4)CCC3)s1] | 2-(1,2,3,5,6,7-hexahydros-indacen-4-yl)-N-(4-(hydroxymethyl)-2-(2-hydroxypropan-2-yl)thiazol-5-ylsulfonimidoyl)acetamide | 450.2 |

TABLE 9-continued

Examples in the following table were prepared using similar conditions as described in Example 4 and Scheme 2 from appropriate starting materials.

| Example # | Compound Number | Structure | IUPAC Name | LC-MS [M + H]+ |
|---|---|---|---|---|
| 24 | 148 | 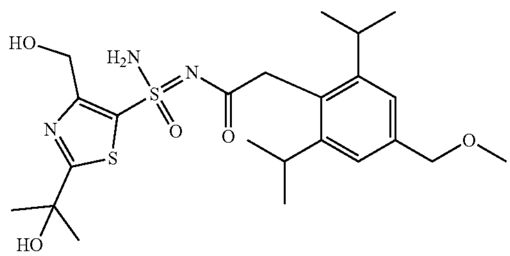 [SMILES: COCc1cc(C(C)C)c(CC(=O)N=S(N)(=O)c2sc(C(C)(C)O)nc2CO)c(C(C)C)c1] | 2-(2,6-diisopropyl-4-(methoxymethyl)phenyl)-N-(4-(hydroxymethyl)-2-(2-hydroxypropan-2-yl)thiazole-5-sulfonimidoyl)acetamide | 498.2 |
| 25 | 147 | 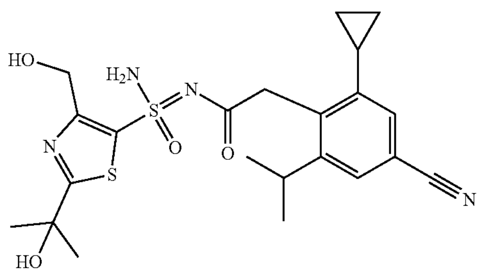 [SMILES: CC(C)c1cc(C#N)cc(C2CC2)c1CC(=O)N=S(N)(=O)c1sc(C(C)(C)O)nc1CO] | 2-(4-cyano-2-cyclopropyl-6-isopropylphenyl)-N-(4-(hydroxymethyl)-2-(2-hydroxypropan-2-yl)thiazole-5-sulfonimidoyl)acetamide | 477.2 |
| 26 | 113 | 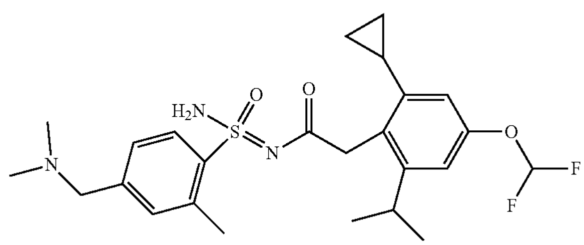 [SMILES: Cc1cc(CN(C)C)ccc1S(N)(=O)=NC(=O)Cc1c(C(C)C)cc(OC(F)F)cc1C1CC1] | 2-(2-cyclopropyl-4-(difluoromethoxy)-6-isopropylphenyl)-N-(4-((dimethylamino)methyl)-2-methylphenylsulfonimidoyl)acetamide | 494.2 |
| 27 | 151 | 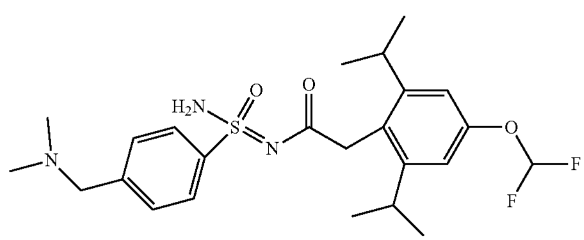 [SMILES: CC(C)c1cc(OC(F)F)cc(C(C)C)c1CC(=O)N=S(N)(=O)c1ccc(CN(C)C)cc1] | 2-(4-(difluoromethoxy)-2,6-diisopropylphenyl)-N-(4-((dimethylamino)methyl)phenyl-sulfonimidoyl)acetamide | 482.2 |
| 28 | 114 | 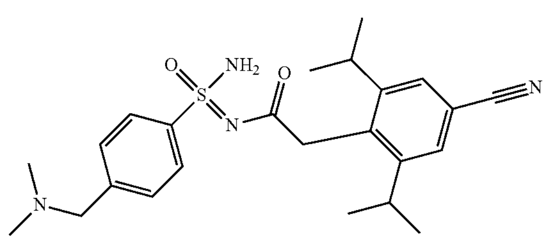 [SMILES: CC(C)c1cc(C#N)cc(C(C)C)c1CC(=O)N=S(N)(=O)c1ccc(CN(C)C)cc1] | 2-(4-cyano-2,6-diisopropylphenyl)-N-(4-((dimethylamino)methyl)phenyl-sulfonimidoyl)acetamide | 441.2 |
| 29 | 112 | 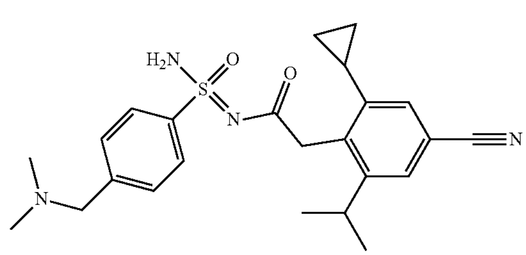 [SMILES: CC(C)c1cc(C#N)cc(C2CC2)c1CC(=O)N=S(N)(=O)c1ccc(CN(C)C)cc1] | 2-(4-cyano-2-cyclopropyl-6-isopropylphenyl)-N-(4-((dimethylamino)methyl)phenyl-sulfonimidoyl)acetamide | 439.2 |

TABLE 9-continued

Examples in the following table were prepared using similar conditions as described in Example 4 and Scheme 2 from appropriate starting materials.

| Example # | Compound Number | Structure | IUPAC Name | LC-MS [M + H]⁺ |
|---|---|---|---|---|
| 30 | 116 | 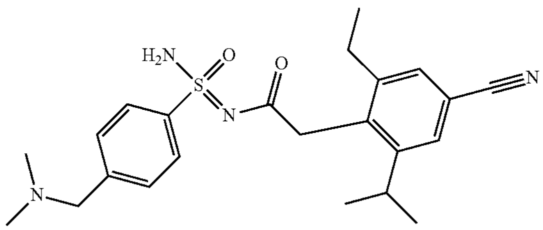 [SMILES: CCc1cc(C#N)cc(C(C)C)c1CC(=O)N=S(N)(=O)c1ccc(CN(C)C)cc1] | 2-(4-cyano-2-ethyl-6-isopropylphenyl)-N-(4-((dimethylamino)methyl)phenylsulfonimidoyl)acetamide | 427.2 |
| 31 | 105 | 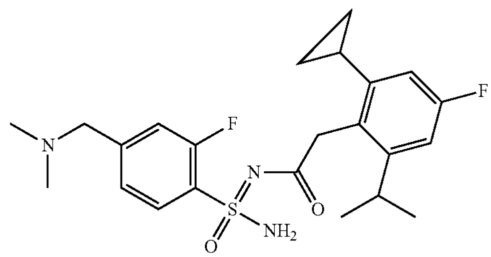 [SMILES: CC(C)c1cc(F)cc(C2CC2)c1CC(=O)N=S(N)(=O)c1ccc(CN(C)C)cc1F] | 2-(2-cyclopropyl-4-fluoro-6-isopropylphenyl)-N-(4-((dimethylamino)methyl)-2-fluorophenylsulfonimidoyl)acetamide | 450.2 |
| 32 | 117 | 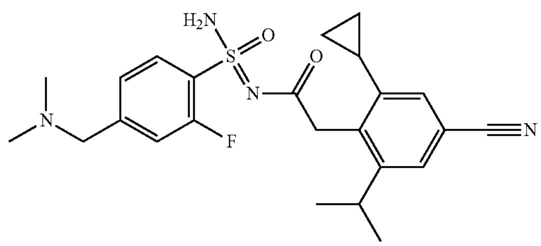 [SMILES: CC(C)c1cc(C#N)cc(C2CC2)c1CC(=O)N=S(N)(=O)c1ccc(CN(C)C)cc1F] | 2-(4-cyano-2-cyclopropyl-6-isopropylphenyl)-N-(4-((dimethylamino)methyl)-2-fluorophenylsulfonimidoyl)acetamide | 457.2 |
| 33 | 109 | 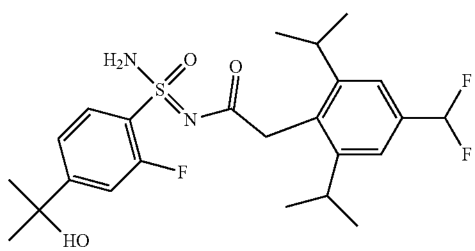 [SMILES: CC(C)c1cc(C(F)F)cc(C(C)C)c1CC(=O)N=S(N)(=O)c1ccc(C(C)(C)O)cc1F] | 2-(4-(difluoromethyl)-2,6-diisopropylphenyl)-N-(2-fluoro-4-(2-hydroxypropan-2-yl)phenylsulfonimidoyl)acetamide | 485.2 |
| 34 | 146 | 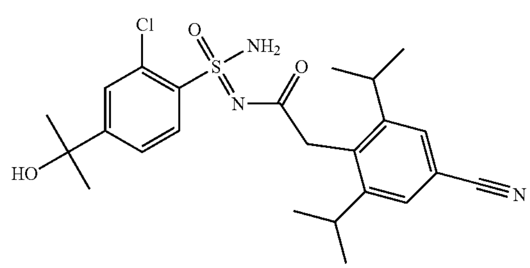 [SMILES: CC(C)c1cc(C#N)cc(C(C)C)c1CC(=O)N=S(N)(=O)c1ccc(C(C)(C)O)cc1Cl] | N-(2-chloro-4-(2-hydroxypropan-2-yl)phenylsulfonimidoyl)-2-(4-cyano-2,6-diisopropylphenyl)acetamide | 476.2 |
| 35 | 110 | 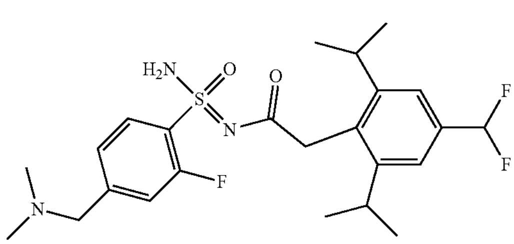 [SMILES: CC(C)c1cc(C(F)F)cc(C(C)C)c1CC(=O)N=S(N)(=O)c1ccc(CN(C)C)cc1F] | 2-(4-(difluoromethyl)-2,6-diisopropylphenyl)-N-(4-((dimethylamino)methyl)-2-fluorophenylsulfonimidoyl)acetamide | 484.2 |

TABLE 9-continued

*Examples in the following table were prepared using similar conditions as described in Example 4 and Scheme 2 from appropriate starting materials.*

| Example # | Compound Number | Structure | IUPAC Name | LC-MS [M + H]+ |
|---|---|---|---|---|
| 36 | 126 | 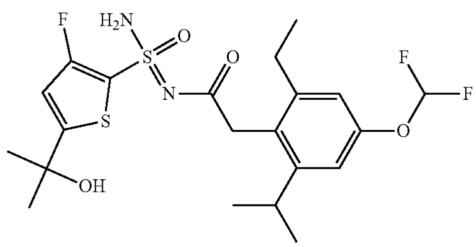 [SMILES: CCc1cc(OC(F)F)cc(C(C)C)c1CC(=O)N=S(N)(=O)c1sc(C(C)(C)O)cc1F] | 2-(4-(difluoromethoxy)-2-ethyl-6-isopropylphenyl)-N-(3-fluoro-5-(2-hydroxypropan-2-yl)thiophene-2-sulfonimidoyl)acetamide | 493.1 |
| 37 | 104 | 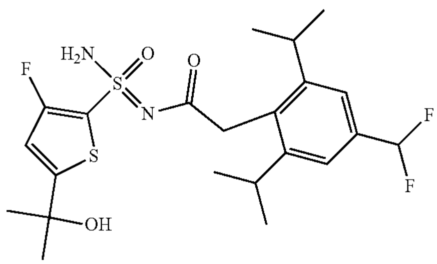 [SMILES: CC(C)c1cc(C(F)F)cc(C(C)C)c1CC(=O)N=S(N)(=O)c1sc(C(C)(C)O)cc1F] | 2-(4-(difluoromethyl)-2,6-diisopropylphenyl)-N-(3-fluoro-5-(2-hydroxypropan-2-yl)thiophene-2-sulfonimidoyl)acetamide | 491.2 |
| 38 | 130 | 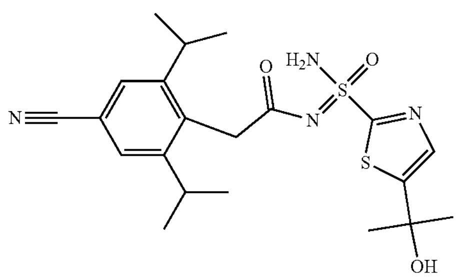 [SMILES: CC(C)c1cc(C#N)cc(C(C)C)c1CC(=O)N=S(N)(=O)c1ncc(C(C)(C)O)s1] | 2-(4-cyano-2,6-diisopropylphenyl)-N-(5-(2-hydroxypropan-2-yl)thiazole-2-sulfonimidoyl)acetamide | 449.2 |
| 39 | 107 | 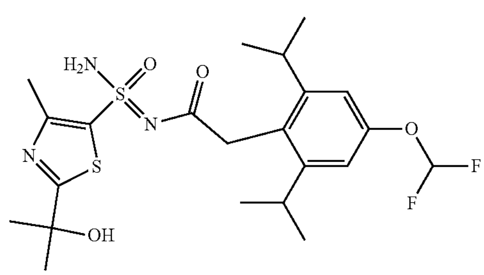 [SMILES: Cc1nc(C(C)(C)O)sc1S(N)(=O)=NC(=O)Cc1c(C(C)C)cc(OC(F)F)cc1C(C)C] | 2-(4-(difluoromethoxy)-2,6-diisopropylphenyl)-N-(2-(2-hydroxypropan-2-yl)-4-methylthiazole-5-sulfonimidoyl)acetamide | 504.2 |
| 40 | 106 | 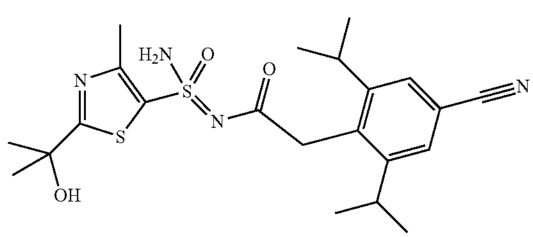 [SMILES: Cc1nc(C(C)(C)O)sc1S(N)(=O)=NC(=O)Cc1c(C(C)C)cc(C#N)cc1C(C)C] | 2-(4-cyano-2,6-diisopropylphenyl)-N-(2-(2-hydroxypropan-2-yl)-4-methylthiazole-5-sulfonimidoyl)acetamide | 463.2 |

TABLE 10

Example in the following table was prepared using similar conditions as described in Example 11 and Scheme 5 from appropriate starting materials.

| Example # | Compound Number | Structure | IUPAC Name | LC-MS [M + H]+ |
|---|---|---|---|---|
| 41 | 135 | 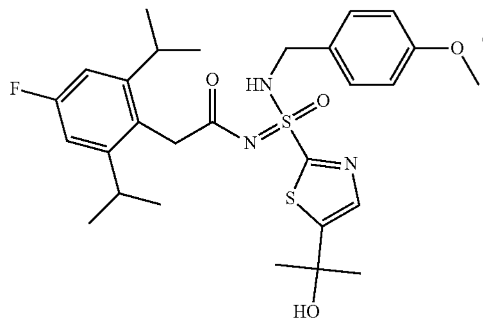 [SMILES: COc1ccc(CNS(=O)(=NC(=O)Cc2c(C(C)C)cc(F)cc2C(C)C)c2ncc(C(C)(C)O)s2)cc1] | 2-(4-fluoro-2,6-diisopropylphenyl)-N-(5-(2-hydroxypropan-2-yl)-N-(4-methoxybenzyl)thiazole-2-sulfonimidoyl)acetamide | 562.5 |

TABLE 11

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 42 | 133b or 133a | 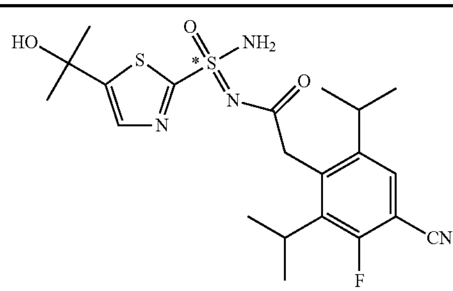 | (S)-or (R)-2-(4-cyano-3-fluoro-2,6-diisopropylphenyl)-N-(5-(2-hydroxypropan-2-yl)thiazol-2-ylsulfonimidoyl)acetamide | ChiralPak IC, 2*25 cm, 5 um | 50% IPA in CO₂ | 467.2 |
| 43 | 133a or 133b | 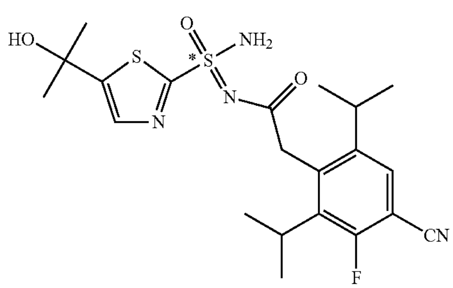 [SMILES: CC(C)c1cc(C#N)c(F)c(C(C)C)c1CC(=O)N=S(N)(=O)c1ncc(C(C)(C)O)s1] | (R)- or (S)-2-(4-cyano-3-fluoro-2,6-diisopropylphenyl)-N-(5-(2-hydroxypropan-2-yl)thiazol-2-ylsulfonimidoyl)acetamide | ChiralPak IC, 2*25 cm, 5 um | 50% IPA in CO₂ | 467.2 |
| 44 | 141b or 141a | 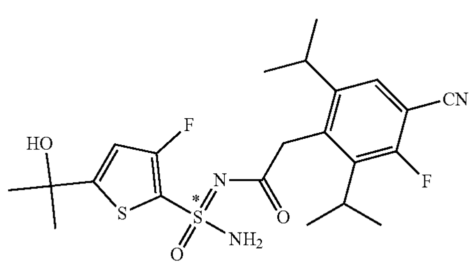 [SMILES: CC(C)c1cc(C#N)c(F)c(C(C)C)c1CC(=O)N=S(N)(=O)c1sc(C(C)(C)O)cc1F] | (S)- or (R)-2-(4-cyano-3-fluoro-2,6-diisopropylphenyl)-N-(3-fluoro-5-(2-hydroxypropan-2-yl)thiophen-2-ylsulfonimidoyl)acetamide | ChiralPak ID, 2*25 cm, 5 um | 30% EtOH in Hex (1% TFA) | 484.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 45 | 141a or 141b | 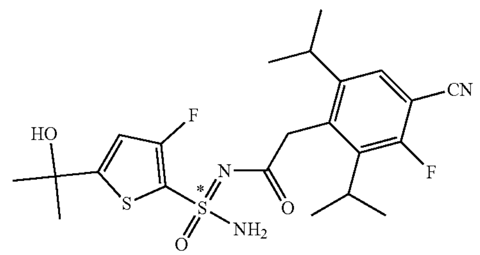 [SMILES: CC(C)c1cc(C#N)c(F)c(C(C)C)c1CC(=O)N=S(N)(=O)c1sc(C(C)(C)O)cc1F] | (R)- or (S)-2-(4-cyano-3-fluoro-2,6-diisopropylphenyl)-N-(3-fluoro-5-(2-hydroxypropan-2-yl)thiophen-2-ylsulfonimidoyl)acetamide | ChiralPak ID, 2*25 cm, 5 um | 30% EtOH in Hex (1% TFA) | 484.2 |
| 46 | 139b or 139a | 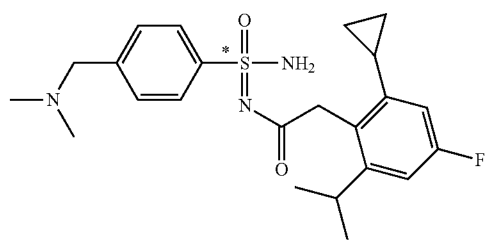 [SMILES: CC(C)c1cc(F)cc(C2CC2)c1CC(=O)N=S(N)(=O)c1ccc(CN(C)C)cc1] | (S)- or (R)-2-(2-cyclopropyl-4-fluoro-6-isopropylphenyl)-N-(4-((dimethylamino)methyl)phenyl-sulfonimidoyl)acetamide | ChiralPak IC, 2*25 cm, 5 um | 15% EtOH in Hex | 432.1 |
| 47 | 139a or 139b | 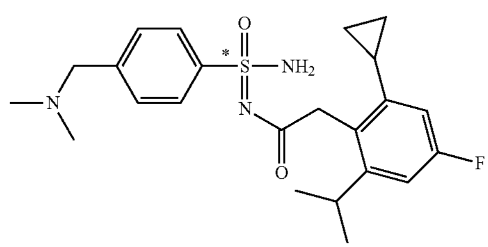 [SMILES: CC(C)c1cc(F)cc(C2CC2)c1CC(=O)N=S(N)(=O)c1ccc(CN(C)C)cc1] | (R)- or (S)-2-(2-cyclopropyl-4-fluoro-6-isopropylphenyl)-N-(4-((dimethylamino)methyl)phenyl-sulfonimidoyl)acetamide | ChiralPak IC, 2*25 cm, 5 um | 15% EtOH in Hex | 432.1 |
| 48 | 138b or 138a | 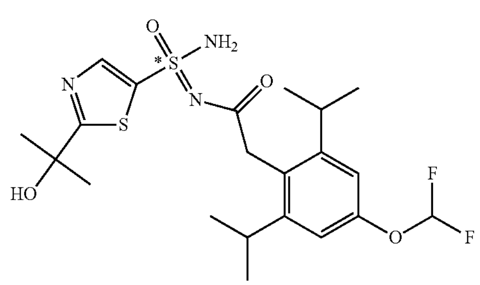 [SMILES: CC(C)c1cc(OC(F)F)cc(C(C)C)c1CC(=O)N=S(N)(=O)c1cnc(C(C)(C)O)s1] | (S)- or (R)-2-(4-(difluoromethoxy)-2,6-diisopropylphenyl)-N-(2-(2-hydroxypropan-2-yl)thiazol-5-ylsulfonimidoyl)acetamide | ChiralPak IG, 2*25 cm, 5 um | 8% IPA in Hex (1% TFA) | 490.1 |
| 49 | 138a or 138b | 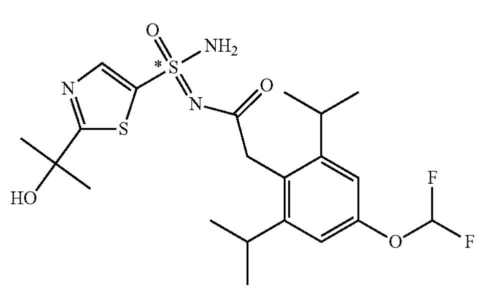 [SMILES: CC(C)c1cc(OC(F)F)cc(C(C)C)c1CC(=O)N=S(N)(=O)c1cnc(C(C)(C)O)s1] | (R)- or (S)-2-(4-(difluoromethoxy)-2,6-diisopropylphenyl)-N-(2-(2-hydroxypropan-2-yl)thiazol-5-ylsulfonimidoyl)acetamide | ChiralPak IG, 2*25 cm, 5 um | 8% IPA in Hex (1% TFA) | 490.1 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 50 | 140b or 140a | 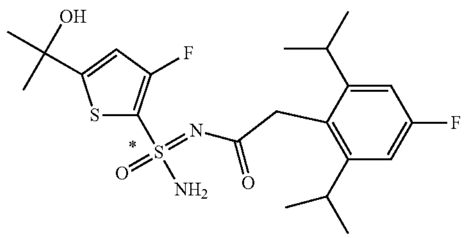 [SMILES: CC(C)c1cc(F)cc(C(C)C)c1CC(=O)N=S(N)(=O)c1sc(C(C)(C)O)cc1F] | (S)- or (R)-2-(4-fluoro-2,6-diisopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% DEA) | 459.2 |
| 51 | 140a or 140b | 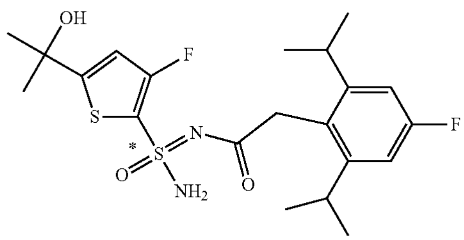 [SMILES: CC(C)c1cc(F)cc(C(C)C)c1CC(=O)N=S(N)(=O)c1sc(C(C)(C)O)cc1F] | (R)- or (S)-2-(4-fluoro-2,6-diisopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% DEA) | 459.2 |
| 52 | 144b or 144a | 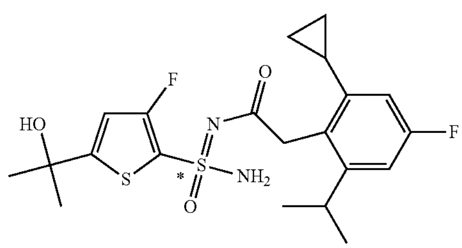 [SMILES: CC(C)c1cc(F)cc(C2CC2)c1CC(=O)N=S(N)(=O)c1sc(C(C)(C)O)cc1F] | (S)- or (R)-2-(2-cyclopropyl-4-fluoro-6-isopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex | 457.2 |
| 53 | 144a or 144b | 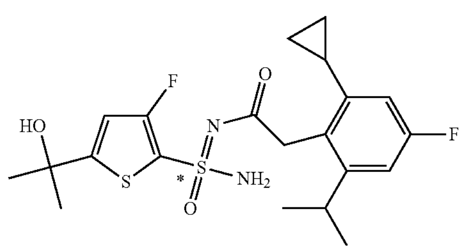 [SMILES: CC(C)c1cc(F)cc(C2CC2)c1CC(=O)N=S(N)(=O)c1sc(C(C)(C)O)cc1F] | (R)- or (S)-2-(2-cyclopropyl-4-fluoro-6-isopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex | 457.2 |
| 54 | 145b or 145a | 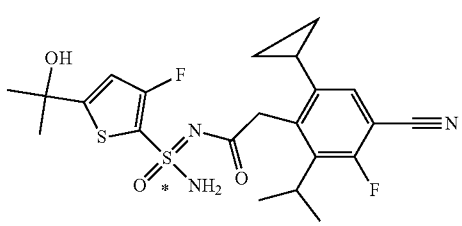 [SMILES: CC(C)c1c(F)c(C#N)cc(C2CC2)c1CC(=O)N=S(N)(=O)c1sc(C(C)(C)O)cc1F] | (S)- or (R)-2-(4-cyano-6-cyclopropyl-3-fluoro-2-isopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% FA) | 482.2 |
| 55 | 145a or 145b | 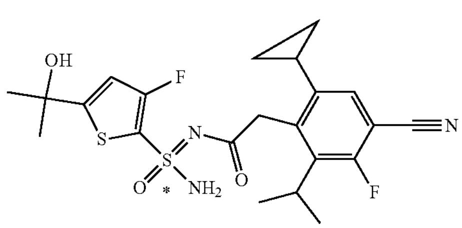 [SMILES: CC(C)c1c(F)c(C#N)cc(C2CC2)c1CC(=O)N=S(N)(=O)c1sc(C(C)(C)O)cc1F] | (R)- or (S)-2-(4-cyano-6-cyclopropyl-3-fluoro-2-isopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% FA) | 482.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]$^+$ |
|---|---|---|---|---|---|---|
| 56 | 197b or 197a | 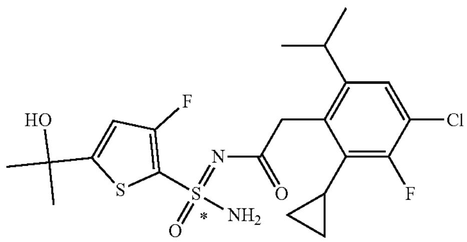 [SMILES: CC(C)c1cc(Cl)c(F)c(C2CC2)c1CC(=O)N=S(N)(=O)c1sc(C(C)(C)O)cc1F] | (S)- or (R)-2-(4-chloro-2-cyclopropyl-3-fluoro-6-isopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% DEA) | 491.2 |
| 57 | 197a or 197b | 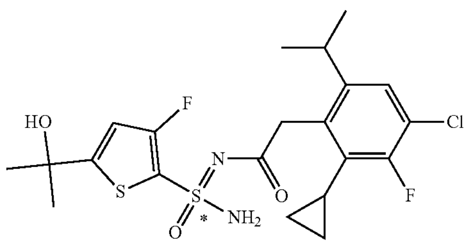 [SMILES: CC(C)c1cc(Cl)c(F)c(C2CC2)c1CC(=O)N=S(N)(=O)c1sc(C(C)(C)O)cc1F] | (R)- or (S)-2-(4-chloro-2-cyclopropyl-3-fluoro-6-isopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% DEA) | 491.2 |
| 58 | 116 | 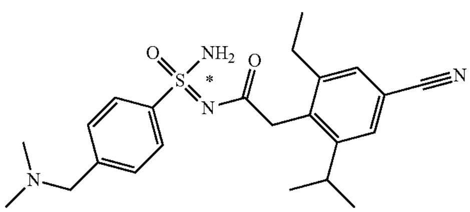 [SMILES: CCc1cc(C#N)cc(C(C)C)c1CC(=O)N=S(N)(=O)c1ccc(CN(C)C)cc1] | (S)- or (R)-2-(4-cyano-2-ethyl-6-isopropylphenyl)-N-(4-((dimethylamino)methyl)phenyl-sulfonimidoyl)acetamide | ChiralPak ADH, 2*25 cm, 5 um | 30% EtOH in Hex (0.1% DEA) | 427.2 |
| 59 | 116a or 116b | 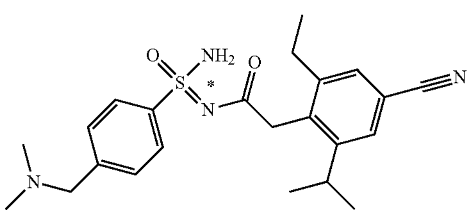 [SMILES: CCc1cc(C#N)cc(C(C)C)c1CC(=O)N=S(N)(=O)c1ccc(CN(C)C)cc1] | (R)- or (S)-2-(4-cyano-2-ethyl-6-isopropylphenyl)-N-(4-((dimethylamino)methyl)phenyl-sulfonimidoyl)acetamide | ChiralPak ADH, 2*25 cm, 5 um | 30% EtOH in Hex (0.1% DEA) | 427.2 |
| 60 | 106 | 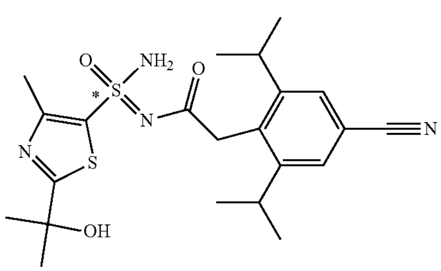 [SMILES: Cc1nc(C(C)(C)O)sc1S(N)(=O)=NC(=O)Cc1c(C(C)C)cc(C#N)cc1C(C)C] | (S)- or (R)-2-(4-cyano-2,6-diisopropylphenyl)-N-(2-(2-hydroxypropan-2-yl)-4-methylthiazole-5-sulfonimidoyl)acetamide | ChiralPak IC, 2*25 cm, 5 um | 30% IPA in Hex (0.1% DEA) | 463.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 61 | 106a or 106b | 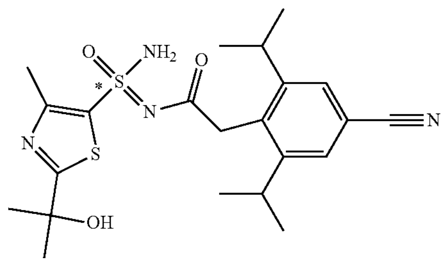 [SMILES: Cc1nc(C(C)(C)O)sc1S(N)(=O)=NC(=O)Cc1c(C(C)C)cc(C#N)cc1C(C)C] | (R)- or (S)- 2-(4-cyano-2,6-diisopropylphenyl)-N-(2-(2-hydroxypropan-2-yl)-4-methylthiazole-5-sulfonimidoyl)acetamide | ChiralPak IC, 2*25 cm, 5 um | 30% IPA in Hex (0.1% DEA) | 463.2 |
| 62 | 117a or 117b | 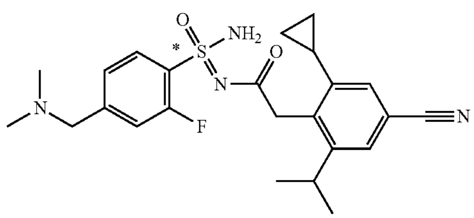 [SMILES: CC(C)c1cc(C#N)cc(C2CC2)c1CC(=O)N=S(N)(=O)c1ccc(CN(C)C)cc1F] | (S)- or (R)- 2-(4-cyano-2-cyclopropyl-6-isopropylphenyl)-N-(4-((dimethylamino)methyl)-2-fluorophenylsulfonimidoyl)acetamide | ChiralCEL OD, 2*25 cm, 5 um | 30% EtOH in Hex (0.1% FA) | 457.2 |
| 63 | 117b or 117a | 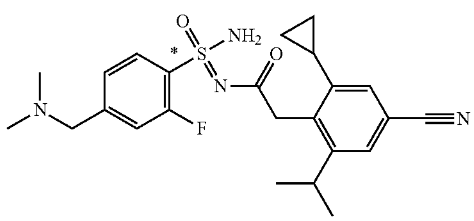 [SMILES: CC(C)c1cc(C#N)cc(C2CC2)c1CC(=O)N=S(N)(=O)c1ccc(CN(C)C)cc1F] | (R)- or (S)- 2-(4-cyano-2-cyclopropyl-6-isopropylphenyl)-N-(4-((dimethylamino)methyl)-2-fluorophenylsulfonimidoyl)acetamide | ChiralCEL OD, 2*25 cm, 5 um | 30% EtOH in Hex (0.1% FA) | 457.2 |
| 64 | 152b or 152a | 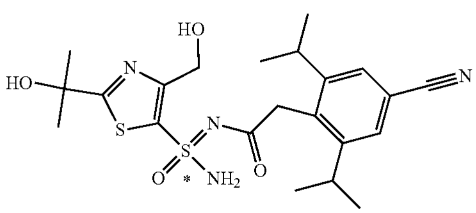 [SMILES: CC(C)c1cc(C#N)cc(C(C)C)c1CC(=O)N=S(N)(=O)c1sc(C(C)(C)O)nc1CO] | (S)- or (R)- 2-(4-cyano-2,6-diisopropylphenyl)-N-(4-(hydroxymethyl)-2-(2-hydroxypropan-2-yl)thiazol-5-ylsulfonimidoyl)acetamide | ChiralPak ID, 2*25 cm, 5 um | 80% EtOH in Hex (0.1% FA) | 480.2 |
| 65 | 152a or 152b | 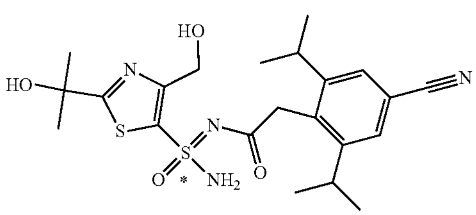 [SMILES: CC(C)c1cc(C#N)cc(C(C)C)c1CC(=O)N=S(N)(=O)c1sc(C(C)(C)O)nc1CO] | (R)- or (S)- 2-(4-cyano-2,6-diisopropylphenyl)-N-(4-(hydroxymethyl)-2-(2-hydroxypropan-2-yl)thiazol-5-ylsulfonimidoyl)acetamide | ChiralPak ID, 2*25 cm, 5 um | 80% EtOH in Hex (0.1% FA) | 480.2 |
| 66 | 150b or 150a | 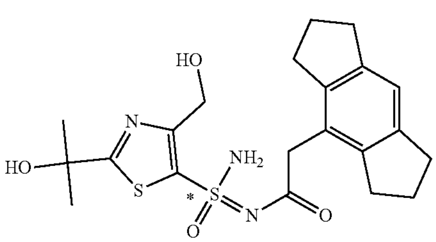 [SMILES: CC(C)(O)c1nc(CO)c(S(N)(=O)=NC(=O)Cc2c3c(cc4c2CCC4)CCC3)s1] | (S)- or (R)- 2-(1,2,3,5,6,7-hexahydros-indacen-4-yl)-N-(4-(hydroxymethyl)-2-(2-hydroxypropan-2-yl)thiazol-5-ylsulfonimidoyl)acetamide | ChiralPak ID, 2*25 cm, 5 um | 88% IPA in Hex (0.1% FA) | 450.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 67 | 150a or 150b | 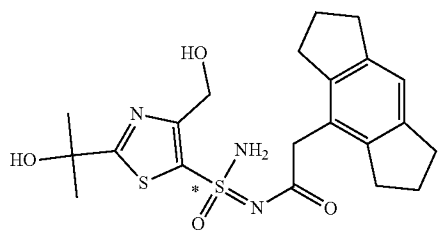 [SMILES: CC(C)(O)c1nc(CO)c(S(N)(=O)=NC(=O)Cc2c3c(cc4c2CCC4)CCC3)s1] | (R)- or (S)-2-(1,2,3,5,6,7-hexahydros-indacen-4-yl)-N-(4-(hydroxymethyl)-2-(2-hydroxypropan-2-yl)thiazol-5-ylsulfonimidoyl)acetamide | ChiralPak ID, 2*25 cm, 5 um | 88% IPA in Hex (0.1% FA) | 450.2 |
| 68 | 148b or 148a | 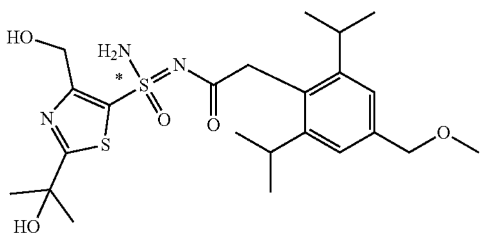 [SMILES: COCc1cc(C(C)C)c(CC(=O)N=S(N)(=O)c2sc(C(C)(C)O)nc2CO)c(C(C)C)c1] | (S)- or (R)-2-(2,6-diisopropyl-4-(methoxymethyl)phenyl)-N-(4-(hydroxymethyl)-2-(2-hydroxypropan-2-yl)thiazol-5-ylsulfonimidoyl)acetamide | ChiralPak ID, 2*25 cm, 5 um | 75% IPA in Hex (0.1% FA) | 498.2 |
| 69 | 148a or 148b | 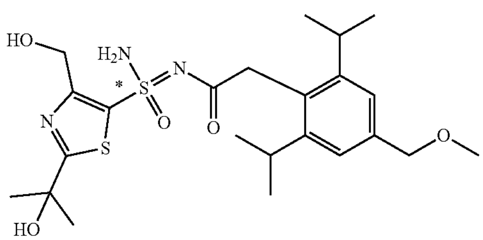 [SMILES: COCc1cc(C(C)C)c(CC(=O)N=S(N)(=O)c2sc(C(C)(C)O)nc2CO)c(C(C)C)c1] | (R)- or (S)-2-(2,6-diisopropyl-4-(methoxymethyl)phenyl)-N-(4-(hydroxymethyl)-2-(2-hydroxypropan-2-yl)thiazol-5-ylsulfonimidoyl)acetamide | ChiralPak ID, 2*25 cm, 5 um | 75% IPA in Hex (0.1% FA) | 498.2 |
| 70 | 147b or 147a | 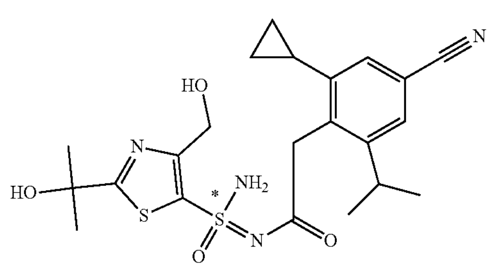 [SMILES: CC(C)c1cc(C#N)cc(C2CC2)c1CC(=O)N=S(N)(=O)c1sc(C(C)(C)O)nc1CO] | (S)- or (R)-2-(4-cyano-2-cyclopropyl-6-isopropylphenyl)-N-(4-(hydroxymethyl)-2-(2-hydroxypropan-2-yl)thiazol-5-ylsulfonimidoyl)acetamide | ChiralPak IC, 2*25 cm, 5 um | 15% EtOH in Hex | 477.2 |
| 71 | 147a or 147b | 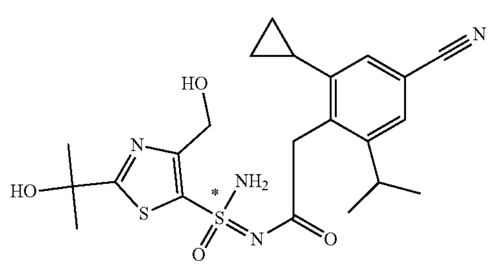 [SMILES: CC(C)c1cc(C#N)cc(C2CC2)c1CC(=O)N=S(N)(=O)c1sc(C(C)(C)O)nc1CO] | (R)- or (S)-2-(4-cyano-2-cyclopropyl-6-isopropylphenyl)-N-(4-(hydroxymethyl)-2-(2-hydroxypropan-2-yl)thiazol-5-ylsulfonimidoyl)acetamide | ChiralPak IC, 2*25 cm, 5 um | 15% EtOH in Hex | 477.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 72 | 114b or 114a | 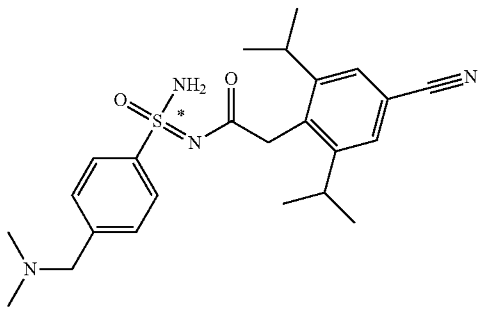 [SMILES: CC(C)c1cc(C#N)cc(C(C)C)c1CC(=O)N=S(N)(=O)c1ccc(CN(C)C)cc1] | (S)- or (R)-2-(4-cyano-2,6-diisopropylphenyl)-N-(4-((dimethylamino)methyl)phenyl-sulfonimidoyl)acetamide | ChiralPak ID, 2*25 cm, 5 um | 50% IPA in Hex (0.1% DEA) | 441.2 |
| 73 | 114a or 114b | 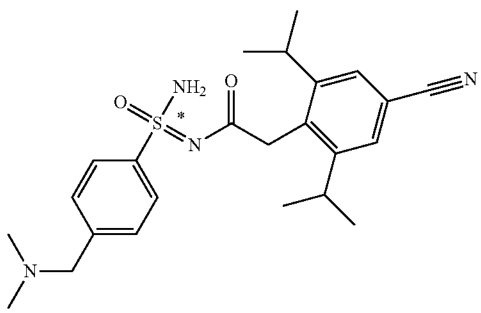 [SMILES: CC(C)c1cc(C#N)cc(C(C)C)c1CC(=O)N=S(N)(=O)c1ccc(CN(C)C)cc1] | (R)- or (S)-2-(4-cyano-2,6-diisopropylphenyl)-N-(4-((dimethylamino)methyl)phenyl-sulfonimidoyl)acetamide | ChiralPak ID, 2*25 cm, 5 um | 50% IPA in Hex (0.1% DEA) | 441.2 |
| 74 | 112b or 112a | 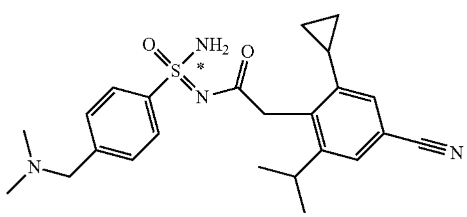 [SMILES: CC(C)c1cc(C#N)cc(C2CC2)c1CC(=O)N=S(N)(=O)c1ccc(CN(C)C)cc1] | (S)- or (R)-2-(4-cyano-2-cyclopropyl-6-isopropylphenyl)-N-(4-((dimethylamino)methyl)phenyl-sulfonimidoyl)acetamide | ChiralPak IG, 2*25 cm, 5 um | 25% IPA in Hex (0.1% DEA) | 439.2 |
| 75 | 112a or 112b | 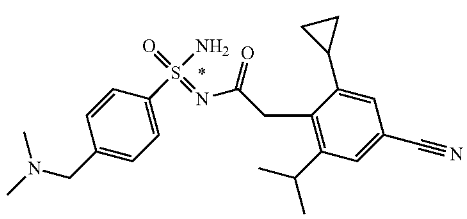 [SMILES: CC(C)c1cc(C#N)cc(C2CC2)c1CC(=O)N=S(N)(=O)c1ccc(CN(C)C)cc1] | (R)- or (S)-2-(4-cyano-2-cyclopropyl-6-isopropylphenyl)-N-(4-((dimethylamino)methyl)phenyl-sulfonimidoyl)acetamide | ChiralPak IG, 2*25 cm, 5 um | 25% EtOH in Hex (0.1% DEA) | 439.2 |
| 76 | 101b or 101a | 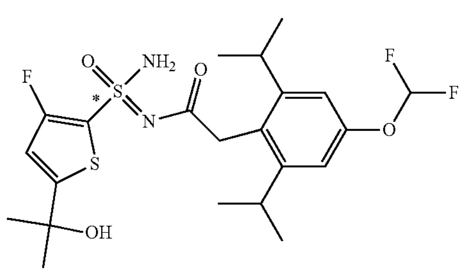 [SMILES: CC(C)c1cc(OC(F)F)cc(C(C)C)c1CC(=O)N=S(N)(=O)c1sc(C(C)(C)O)cc1F] | (S)- or (R)-2-(4-(difluoromethoxy)-2,6-diisopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% DEA) | 507.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]$^+$ |
|---|---|---|---|---|---|---|
| 77 | 101a or 101b | 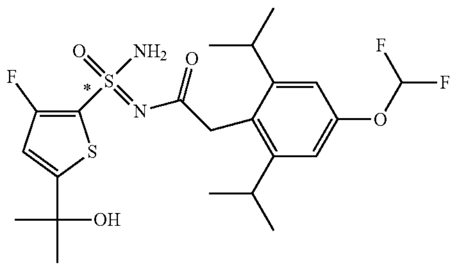 [SMILES: CC(C)c1cc(OC(F)F)cc(C(C)C)c1CC(=O)N=S(N)(=O)c1sc(C(C)(C)O)cc1F] | (R)- or (S)-2-(4-(difluoromethoxy)-2,6-diisopropylphenyl)-N-(3-fluoro-5-(2-hydroxypropan-2-yl)thiophen-2-ylsulfonimidoyl)acetamide | ChiralPak ID, 2*25 cm, 5 um | 30% IPA in Hex (0.1% DEA) | 507.2 |
| 78 | 126b or 126a | 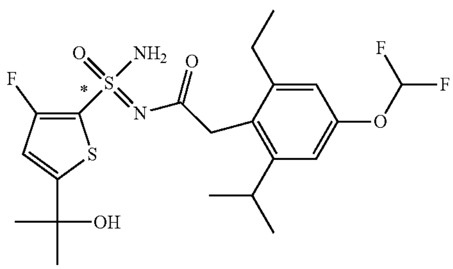 [SMILES: CCc1cc(OC(F)F)cc(C(C)C)c1CC(=O)N=S(N)(=O)c1sc(C(C)(C)O)cc1F] | (S)- or (R)-2-(4-(difluoromethoxy)-2-ethyl-6-isopropylphenyl)-N-(3-fluoro-5-(2-hydroxypropan-2-yl)thiophen-2-ylsulfonimidoyl)acetamide | ChiralPak ID, 2*25 cm, 5 um | 25% IPA in Hex (0.1% DEA) | 493.2 |
| 79 | 126a or 126b | 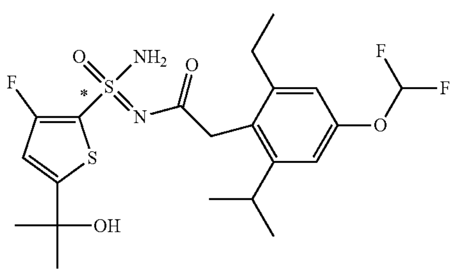 [SMILES: CCc1cc(OC(F)F)cc(C(C)C)c1CC(=O)N=S(N)(=O)c1sc(C(C)(C)O)cc1F] | (R)- or (S)-2-(4-(difluoromethoxy)-2-ethyl-6-isopropylphenyl)-N-(3-fluoro-5-(2-hydroxypropan-2-yl)thiophen-2-ylsulfonimidoyl)acetamide | ChiralPak ID, 2*25 cm, 5 um | 25% IPA in Hex (0.1% DEA) | 493.2 |
| 80 | 104b or 104a | 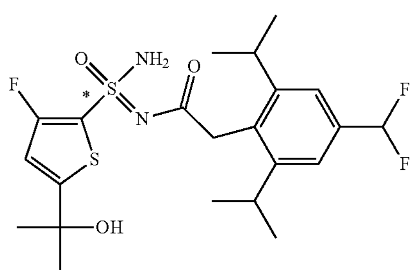 [SMILES: CC(C)c1cc(C(F)F)cc(C(C)C)c1CC(=O)N=S(N)(=O)c1sc(C(C)(C)O)cc1F] | (S)- or (R)-2-(4-(difluoromethyl)-2,6-diisopropylphenyl)-N-(3-fluoro-5-(2-hydroxypropan-2-yl)thiophen-2-ylsulfonimidoyl)acetamide | ChiralPak IC, 2*25 cm, 5 um | 15% IPA in Hex (0.1% FA) | 491.2 |
| 81 | 104a or 104b | 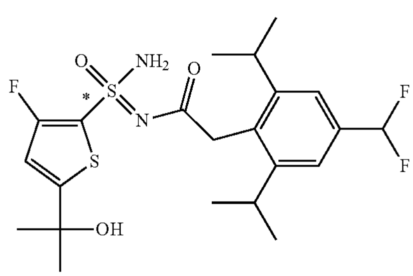 [SMILES: CC(C)c1cc(C(F)F)cc(C(C)C)c1CC(=O)N=S(N)(=O)c1sc(C(C)(C)O)cc1F] | (R)- or (S)-2-(4-(difluoromethyl)-2,6-diisopropylphenyl)-N-(3-fluoro-5-(2-hydroxypropan-2-yl)thiophen-2-ylsulfonimidoyl)acetamide | ChiralPak IC, 2*25 cm, 5 um | 15% IPA in Hex (0.1% FA) | 491.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 82 | 130b or 130a | 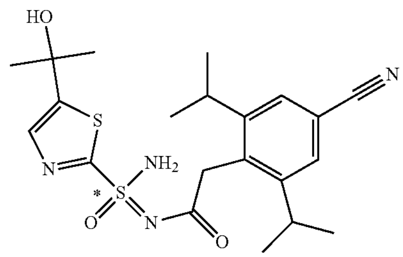 [SMILES: CC(C)c1cc(C#N)cc(C(C)C)c1CC(=O)N=S(N)(=O)c1ncc(C(C)(C)O)s1] | (R)- or (S)-2-(4-cyano-2,6-diisopropylphenyl)-N-(5-(2-hydroxypropan-2-yl)thiazol-2-ylsulfonimidoyl)acetamide | ChiralPak IG, 2*25 cm, 5 um | 15% IPA in Hex (0.1% FA) | 449.2 |
| 83 | 130a or 130b | 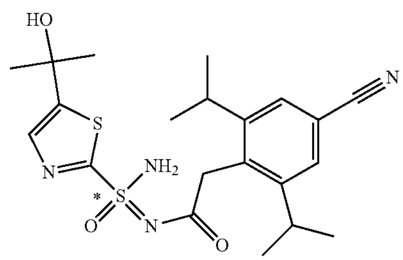 [SMILES: CC(C)c1cc(C#N)cc(C(C)C)c1CC(=O)N=S(N)(=O)c1ncc(C(C)(C)O)s1] | (S)- or (R)-2-(4-cyano-2,6-diisopropylphenyl)-N-(5-(2-hydroxypropan-2-yl)thiazol-2-ylsulfonimidoyl)acetamide | ChiralPak IG, 2*25 cm, 5 um | 15% IPA in Hex (0.1% FA) | 449.2 |
| 84 | 107b or 107a | 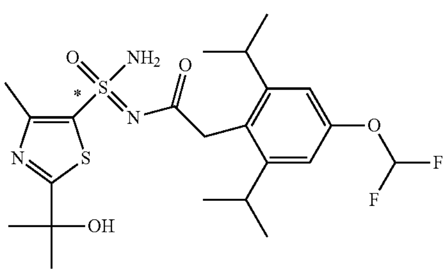 [SMILES: Cc1nc(C(C)(C)O)sc1S(N)(=O)=NC(=O)Cc1c(C(C)C)cc(OC(F)F)cc1C(C)C] | (S)- or (R)-2-(4-(difluoromethoxy)-2,6-diisopropylphenyl)-N-(2-(2-hydroxypropan-2-yl)-4-methylthiazol-5-ylsulfonimidoyl)acetamide | ChiralPak IC, 2*25 cm, 5 um | 10% IPA in Hex (0.1% FA) | 504.2 |
| 85 | 107a or 107b | 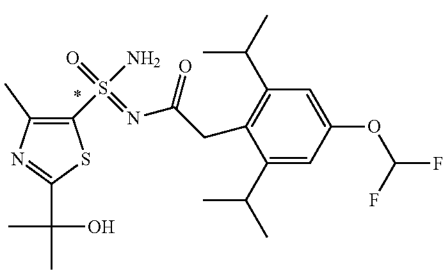 [SMILES: Cc1nc(C(C)(C)O)sc1S(N)(=O)=NC(=O)Cc1c(C(C)C)cc(OC(F)F)cc1C(C)C] | (R)- or (S)-2-(4-(difluoromethoxy)-2,6-diisopropylphenyl)-N-(2-(2-hydroxypropan-2-yl)-4-methylthiazol-5-ylsulfonimidoyl)acetamide | ChiralPak IC, 2*25 cm, 5 um | 10% IPA in Hex (0.1% FA) | 504.2 |
| 86 | 109a or 109b | 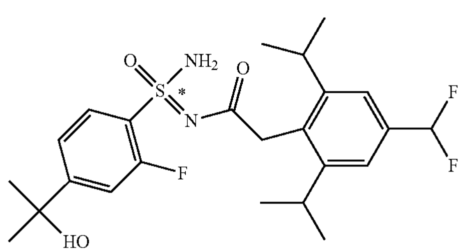 [SMILES: CC(C)c1cc(C(F)F)cc(C(C)C)c1CC(=O)N=S(N)(=O)c1ccc(C(C)(C)O)cc1F] | (S)- or (R)-2-(4-(difluoromethyl)-2,6-diisopropylphenyl)-N-(2-fluoro-4-(2-hydroxypropan-2-yl)phenylsulfonimidoyl)acetamide | ChiralPak IF, 2*25 cm, 5 um | 15% EtOH in Hex (0.1% DEA) | 485.2 |

TABLE 11-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Compound Number | Structure | IUPAC Name | Column | Eluents | LC-MS [M + H]+ |
|---|---|---|---|---|---|---|
| 87 | 109b or 109a | 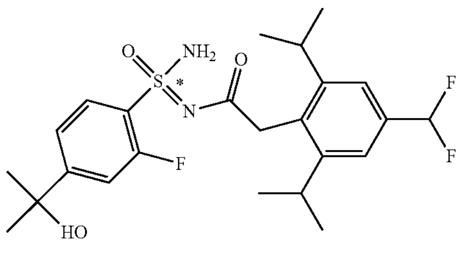 [SMILES: CC(C)c1cc(C(F)F)cc(C(C)C)c1CC(=O)N=S(N)(=O)c1ccc(C(C)(C)O)cc1F] | (R)- or (S)-2-(4-(difluoromethyl)-2,6-diisopropylphenyl)-N-(2-fluoro-4-(2-hydroxypropan-2-yl)phenylsulfonimidoyl)acetamide | ChiralPak IF, 2*25 cm, 5 um | 15% EtOH in Hex (0.1% DEA) | 485.2 |
| 88 | 201b | 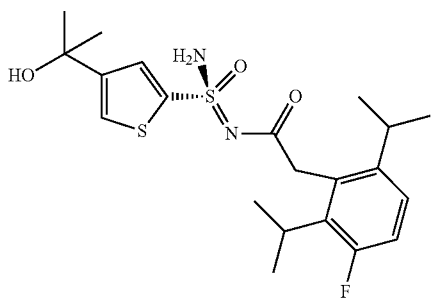 [SMILES: CC(C)c1ccc(F)c(C(C)C)c1CC(=O)N=[S@@](N)(=O)c1cc(C(C)(C)O)cs1] | (R)-N-(amino(4-(2-hydroxypropan-2-yl)thiophen-2-yl)oxo)-λ6-sulfanylidene)-2-(3-fluoro-2,6-diisopropylphenyl)acetamide | ChiralPak IF, 2*25 cm, 5 um | 15% EtOH in Hex (0.1% DEA) | 440.59 |
| 89 | 301 | 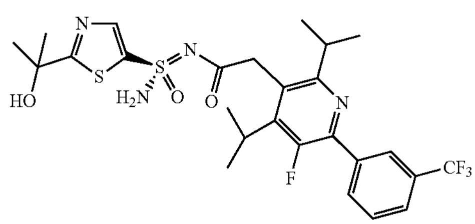 [SMILES: CC(C)c1nc(-c2cccc(C(F)(F)F)c2)c(F)c(C(C)C)c1CC(=O)N=[S@@](N)(=O)c1cnc(C(C)(C)O)s1] | (R)-N-(amino(2-(2-hydroxypropan-2-yl)thiazol-5-yl)oxo)-λ6-sulfanylidene)-2-(5-fluoro-2,4-diisopropyl-6-(3-(trifluoromethyl)phenyl)pyridin-3-yl)acetamide | ChiralPak IF, 2*25 cm, 5 um | 15% EtOH in Hex (0.1% DEA) | 586.66 |

Example 88 (Compound 241)

N-(amino(4-(2-(dimethylamino)propan-2-yl)phenyl)(oxo)-λ$^6$-sulfaneylidene)-2-(4-fluoro-2,6-diisopropylphenyl)acetamide (Scheme 1A)

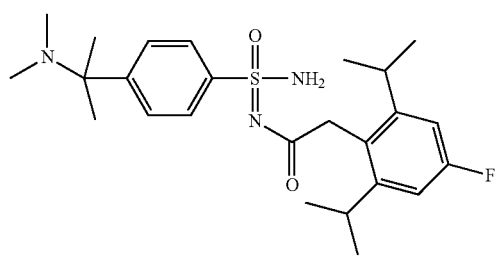 [SMILES: CC(C)c1cc(F)cc(C(C)C)c1CC(=O)N=S(N)(=O)c1ccc(C(C)(C)N(C)C)cc1]

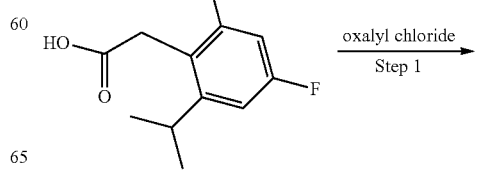

oxalyl chloride
Step 1

527

-continued

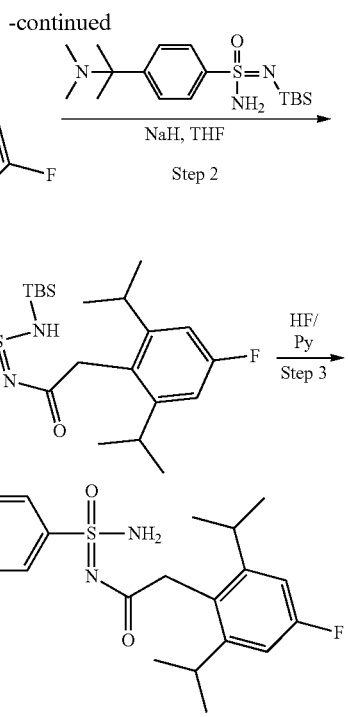

Example 88

Step 1: 2-(4-Fluoro-2,6-diisopropylphenyl)acetyl chloride

Into a 25-mL round-bottom flask, was placed a solution of 2-[4-fluoro-2,6-bis(propan-2-yl)phenyl] acetic acid (20 mg, 0.08 mmol) in DCM (2 mL). This was followed by the addition of DMF (0.005 mL) with stirring. To this was added oxalic dichloride (0.5 mL) dropwise with stirring at 0° C. The resulting solution was stirred for 1 h at RT. The resulting mixture was concentrated. This resulted in 21 mg (97.4%) of the title compound as a yellow solid. This crude product was used in the next step.

528

Step 2: N-(((tert-butyldimethylsilyl)amino)(4-(2-(dimethylamino)propan-2-yl)phenyl)(oxo)-$\lambda^6$-sulfaneylidene)-2-(4-fluoro-2,6-diisopropylphenyl)acetamide Into a 25-mL round-bottom flask, was placed a solution of N-(tert-butyldimethylsilyl)-4-[2-(dimethylamino) propan-2-yl]benzene-1-sulfonoimidamide (20 mg, 0.06 mmol) in THF (3 mL). To this was added NaH (60% wt. oil dispersion, 12 mg, 0.3 mmol) at 0° C. To the mixture was added a solution of 2-[4-fluoro-2,6-bis(propan-2-yl) phenyl]acetyl chloride (14.4 mg, 0.06 mmol) in DCM (1 mL) dropwise with stirring at 0° C. The resulting solution was stirred for 1 h at RT. The reaction was then quenched by the addition of 20 mL of water. The resulting solution was extracted with 2×25 mL of ethyl acetate, dried over anhydrous sodium sulfate, and concentrated. The residue was eluted from silica gel with ethyl acetate/petroleum ether (1:1). This resulted in 20 mg (61.7%) of the title compound as a white solid. MS-ESI: 576 (M+1).

Step 3: N-(amino(4-(2-(dimethylamino)propan-2-yl)phenyl)(oxo)-$\lambda^6$-sulfaneylidene)-2-(4-fluoro-2,6-diisopropylphenyl)acetamide Into a 25-mL round-bottom flask, was placed a solution of N-[[(tert-butyldimethylsilyl)amino] ([4-[2-(dimethylamino)propan-2-yl]phenyl])oxo-$\lambda^6$-sulfanylidene]-2-[4-fluoro-2,6-bis(propan-2-yl)phenyl]acetamide (20 mg, 0.03 mmol) in DCM (2 mL). This was followed by the addition of HF-Pyridine (70% wt., 1 mL) dropwise with stirring. The resulting solution was stirred for 30 min at RT. The resulting mixture was washed with 20 mL of H$_2$O. The resulting solution was extracted with 2×25 mL of ethyl acetate dried over anhydrous sodium sulfate. The resulting mixture was concentrated. The crude product was purified by Prep-HPLC with the following conditions: Column, XBridge Shield RP18 OBD, 19*250 mm, 10 um; mobile phase, water (10 mM NH$_4$HCO$_3$) and ACN (30% to 50% ACN gradient in 10 min); Detector, UV220/254 nm. This resulted in 5.2 mg (32.4%) of Example 88 as a white solid. MS-ESI: 462.3 (M+1).$^1$H-NMR (400 MHz, CD$_3$OD-d$_4$) δ 7.87 (d, J=8.4 Hz, 2H), 7.69 (d, J=8.4 Hz, 2H), 6.76 (d, J=10.4 Hz, 2H), 3.74 (s, 2H), 3.12-3.08 (m, 2H), 2.16 (s, 6H), 1.39 (s, 6H), 1.11 (dd, J=15.2, 6.8 Hz, 12H).

TABLE 18

Examples in the following table were prepared using similar conditions as described in Example 88 and Scheme 1A from appropriate starting materials.

| Example # | Compound # | Structure | IUPAC Name | Exact Mass [M + H]$^+$ |
|---|---|---|---|---|
| 89 | 219 | ![structure] | N-(amino(5-((dimethylamino)methyl)-3-fluorothiophen-2-yl)(oxo)-$\lambda^6$-sulfaneylidene)-2-(3-fluoro-2,6-diisopropylphenyl)acetamide | 458 |

TABLE 18-continued

Examples in the following table were prepared using similar conditions as described in Example 88 and Scheme 1A from appropriate starting materials.

| Example # | Compound # | Structure | IUPAC Name | Exact Mass [M + H]⁺ |
|---|---|---|---|---|
| 90 | 218 | 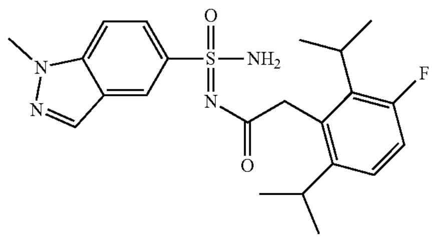 [SMILES: CC(C)c1ccc(F)c(C(C)C)c1CC(=O)N=S(N)(=O)c1ccc2c(cnn2C)c1] | N-(amino(1-methyl-1H-indazol-5-yl)(oxo)-λ⁶-sulfaneylidene)-2-(3-fluoro-2,6-diisopropylphenyl)acetamide | 431 |
| 91 | 217 | 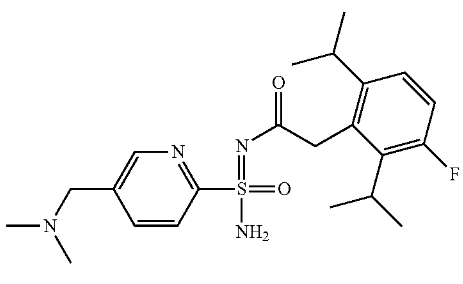 [SMILES: CC(C)c1ccc(F)c(C(C)C)c1CC(=O)N=S(N)(=O)c1ccc(CN(C)C)cn1] | N-(amino(5-((dimethylamino)methyl)pyridin-2-yl)(oxo)-λ⁶-sulfaneylidene)-2-(3-fluoro-2,6-diisopropylphenyl)acetamide | 435 |
| 92 | 214 | 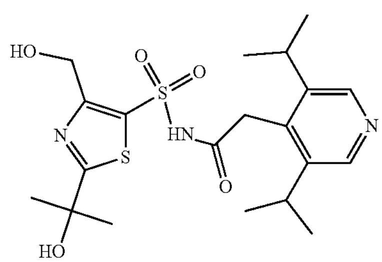 [SMILES: CC(C)c1cncc(C(C)C)c1CC(=O)NS(=O)(=O)c1sc(C(C)(C)O)nc1CO] | 2-(3,5-diisopropylpyridin-4-yl)-N-((4-(hydroxymethyl)-2-(2-hydroxypropan-2-yl)thiazol-5-yl)sulfonyl)acetamide | 456 |

Example 93 (Compound 235)

N-(amino(5-(2-hydroxypropan-2-yl)thiazol-2-yl)(oxo)-λ⁶-sulfaneylidene)-2-(4-(3-hydroxyoxetan-3-yl)-2,6-diisopropylphenyl)acetamide (Scheme 1B)

Example 94 (Compound 230)

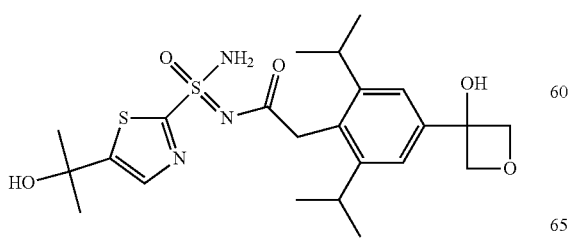

531

N-(amino(5-(2-hydroxypropan-2-yl)thiazol-2-yl)(oxo)-λ⁶-sulfaneylidene)-2-(4-(3-fluorooxetan-3-yl)-2,6-diisopropylphenyl)acetamide (Scheme 1B)

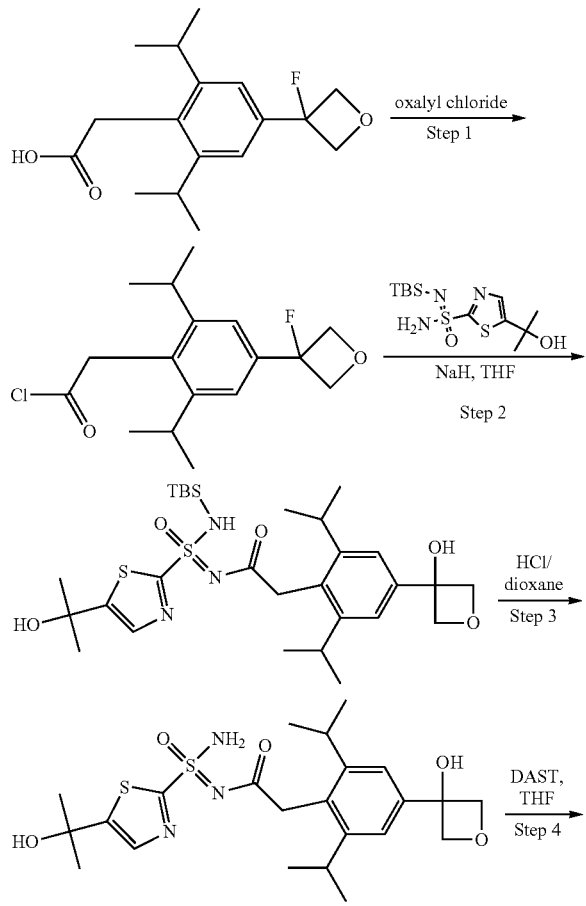

Example 93

Example 94

Step 1: 2-(4-(3-fluorooxetan-3-yl)-2,6-diisopropylphenyl)acetyl chloride

Into a 50-mL round-bottom flask, was placed 2-[4-(3-fluorooxetan-3-yl)-2,6-bis(propan-2-yl)phenyl] acetic acid (150 mg, 0.51 mmol) in DCM (3 mL) and DMF (0.05 mL). This was followed by the addition of oxalic dichloride (0.5 mL) dropwise with stirring at RT. The resulting solution was stirred for 30 min at RT. The resulting mixture was concentrated under vacuum. This resulted in 159 mg (99.7%) of the title compound as a light yellow solid.

532

Step 2: N-(((tert-butyldimethylsilyl)amino)(5-(2-hydroxypropan-2-yl)thiazol-2-yl)(oxo)-λ⁶-sulfaneylidene)-2-(4-(3-hydroxyoxetan-3-yl)-2,6-diisopropylphenyl)acetamide Into a 50-mL round-bottom flask, was placed N-(tert-butyldimethylsilyl)-5-(2-hydroxypropan-2-yl)-1,3-thiazole-2-sulfonoimidamide (173 mg, 0.52 mmol) in THF (5 mL). This was followed by the addition of NaH (60% wt. oil dispersion, 62.4 mg, 1.56 mmol) in portions at 0° C. The resulting solution was stirred for 10 min at RT. Then to the above was added a solution of 2-[4-(3-fluorooxetan-3-yl)-2,6-bis(propan-2-yl)phenyl]acetyl chloride (159 mg, 0.51 mmol) in THF (2 mL) dropwise with stirring at 0° C. The resulting solution was stirred for 2 h at RT. The reaction was then quenched by the addition of 5 mL of water. The resulting solution was extracted with 3×5 mL of ethyl acetate. The organic layers were combined, dried over anhydrous sodium sulfate, and concentrated under vacuum. This resulted in 200 mg (64.5%) of the title compound as an off-white solid. MS-ESI: 610 (M+1).

Step 3: N-(amino(5-(2-hydroxypropan-2-yl)thiazol-2-yl)(oxo)-λ⁶-sulfaneylidene)-2-(4-(3-hydroxyoxetan-3-yl)-2,6-diisopropylphenyl)acetamide Into a 50-mL round-bottom flask, was placed N-[[(tert-butyldimethylsilyl)amino][5-(2-hydroxypropan-2-yl)-1,3-thiazol-2-yl]oxo-λ⁶-sulfanylidene]-2-[4-(3-hydroxyoxetan-3-yl)-2,6-bis(propan-2-yl)phenyl]acetamide (200 mg, 0.33 mmol) in THF (2 mL), to the stirred solution was added HCl/dioxane (4 M, 5 mL). The resulting solution was stirred overnight at RT. The resulting mixture was concentrated under vacuum. The crude product was purified by Prep-HPLC with the following conditions: Column, XBridge Prep $C_{18}$ OBD, 5 um, 19*150 mm; mobile phase, water (10 mM $NH_4HCO_3$) and ACN (5% to 40% ACN gradient over 8 min); Detector, UV 254/210 nm. This resulted in 14.0 mg (8.61%) of Example 93 as a white solid. MS-ESI: 496.3 (M+1). 41-NMR: (DMSO-$d_6$, 400 MHz): δ 7.40 (s, 1H), 7.23 (s, 2H), 6.14 (s, 1H), 5.54 (s, 1H), 4.73-4.66 (m, 4H), 3.92 (s, 1H), 3.49-3.46 (m, 2H), 3.31-3.22 (m, 2H), 1.47 (s, 6H), 1.12 (d, J=8.4 Hz, 6H), 1.10 (d, J=8.4 Hz, 6H).

Step 4: N-(amino(5-(2-hydroxypropan-2-yl)thiazol-2-yl)(oxo)-λ⁶-sulfaneylidene)-2-(4-(3-fluorooxetan-3-yl)-2,6-diisopropylphenyl)acetamide Into a 50-mL 3-necked round-bottom flask purged and maintained with an inert atmosphere of nitrogen, was placed N-[amino[5-(2-hydroxypropan-2-yl)-1,3-thiazol-2-yl]oxo-λ⁶-sulfanylidene]-2-[4-(3-hydroxyoxetan-3-yl)-2,6-bis(propan-2-yl)phenyl]acetamide (83 mg, 0.17 mmol) in THF (5 mL). This was followed by the addition of a solution of DAST (54.0 mg, 0.33 mmol) in DCM (1 mL) dropwise with stirring at 0° C. The resulting solution was stirred overnight at RT. The resulting mixture was concentrated under vacuum. The crude product was purified by Prep-HPLC with the following conditions: Column, XBridge BEH130 Prep $C_{18}$ OBD, 19×150 mm, 5 um 13 nm; mobile phase, water (10 mM $NH_4HCO_3$) and ACN (30% to 60% ACN gradient in 7 min); Detector, UV 254/210 nm. This resulted in 15.1 mg (17.9%) of Example 94 as a white solid. MS-ESI: 498.2 (M+1). ¹H NMR (DMSO-$d_6$, 400 MHz): δ 7.96 (s, 2H), 7.76 (s, 1H), 7.18 (s, 2H), 5.87 (s, 1H), 4.98-4.87 (m, 4H), 3.77-3.65 (m, 2H), 3.13-3.05 (m, 2H), 1.51 (s, 6H), 1.13 (d, J=8.4 Hz, 6H), 1.11 (d, J=8.4 Hz, 6H).

TABLE 19

Examples in the following table were prepared using similar conditions as described in Example 94 and Scheme 1B from appropriate materials

| Example # | Compound # | Structure | IUPAC Name | Exact Mass [M + H]+ |
|---|---|---|---|---|
| 95 | 245 | 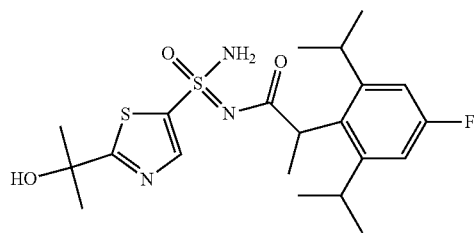 [SMILES: CC(C)c1cc(F)cc(C(C)C)c1C(C)C(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(4-fluoro-2,6-dipropylphenyl)acetamide | 442 |

Example 96 (Compound 244)

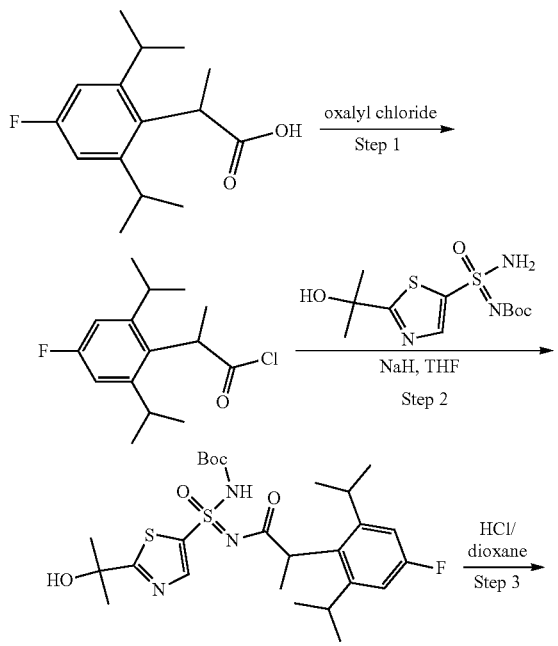

N-(amino(2-(2-hydroxypropan-2-yl)thiazol-5-yl)(oxo)-$\lambda^6$-sulfaneylidene)-2-(4-fluoro-2,6-diisopropylphenyl)propanamide (Scheme 1C)

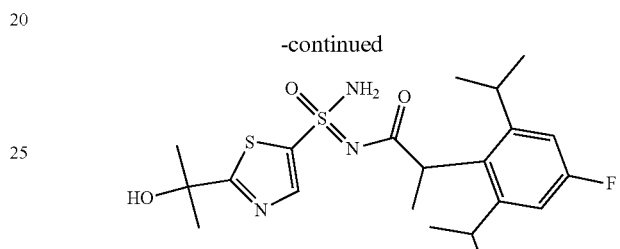

Example 96

Step 1: 2-(4-Fluoro-2,6-diisopropylphenyl)propanoyl chloride

Into a 50-mL round-bottom flask, was placed 2-[4-fluoro-2,6-bis(propan-2-yl)phenyl]propanoic acid (200 mg, 0.79 mmol) in DCM (20 mL), this was followed by the addition of oxalic dichloride (2 mL). The resulting solution was stirred for 15 min at RT. The resulting mixture was concentrated. This resulted in 200 mg (93.1%) of the title compound as off-white oil.

Step 2: Tert-butyl(N-(2-(4-fluoro-2,6-diisopropylphenyl)propanoyl)-2-(2-hydroxypropan-2-yl) thiazole-5-sulfonimidoyl)carbamate Into a 50-mL round-bottom flask, was placed tert-butyl N-[amino[2-(2-hydroxypropan-2-yl)-1,3-thiazol-5-yl] methylidene-$\lambda^6$-sulfanylidene]carbamate (235.9 mg, 0.74 mmol) in THF (20 mL). To the mixture was added 2-[4-fluoro-2,6-bis(propan-2-yl)phenyl]propanoyl chloride (200 mg, 0.74 mmol) and NaH (60% wt. oil dispersion, 59.2 mg, 1.48 mmol). The resulting solution was stirred for 16 h at RT. The reaction was then quenched by the addition of 20 mL of water. The resulting solution was extracted with 3×20 ml of ethyl acetate, dried over anhydrous sodium sulfate, and concentrated. The resulting mixture was concentrated. The residue was eluted from silica gel with ethyl acetate/petroleum ether (1:1). This resulted in 200 mg (48.9%) of the title compound as an off-white solid. MS-ESI: 556 (M+1).

Step 3: N-(amino(2-(2-hydroxypropan-2-yl)thiazol-5-yl)(oxo)-λ⁶-sulfaneylidene)-2-(4-fluoro-2,6-diisopropylphenyl)propanamide Into a 50-mL round-bottom flask, was placed tert-butyl N-[([2-[4-fluoro-2,6-bis(propan-2-yl)phenyl]propanoyl]imino)[2-(2-hydroxypropan-2-yl)-1,3-thiazol-5-yl]methylidene-λ⁶-sulfanyl]carbamate (100 mg, 0.18 mmol) in THF (5 mL). To the stirred solution was added HCl/dioxane (10 mL, 4 M) dropwise. The resulting solution was stirred for 16 h at RT. The resulting mixture was concentrated. The crude product was purified by Prep-HPLC with the following conditions: Column: XBridge Shield RP18 OBD Column 19*250 mm, 10 um; Mobile Phase A: water (10 mM $NH_4HCO_3$), Mobile Phase B: ACN; Flow rate: 25 mL/min; Gradient: 27% B to 45% B in 9 min; 254/210 nm; Rt: 7.77 min. This resulted in 20 mg (24.4%) of Example 96 as a white solid. MS-ESI: 456.2 (M+1). ¹H-NMR (400 MHz, DMSO-$d_6$, ppm) δ: 8.00-7.92 (m, 3H), 7.05-6.91 (m, 2H), 6.25 (s, 1H), 3.87-3.81 (m, 1H), 3.16-2.98 (m, 2H), 1.49 (s, 6H), 1.27-1.24 (m, 3H), 1.19-1.13 (m, 12H).

TABLE 20

Examples in the following table were prepared using similar conditions as described in Example 96 and Scheme 1C from appropriate starting materials.

| Example # | Compound # | Structure | IUPAC Name | Exact Mass [M + H]⁺ |
|---|---|---|---|---|
| 97 | 221 | 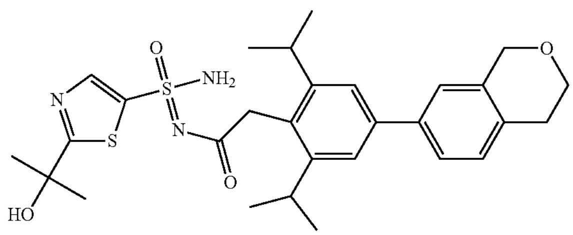 [SMILES: CC(C)c1cc(-c2ccc3c(c2)COCC3)cc(C(C)C)c1CC(=O)N=S(N)(=O)c1cnc(C(C)(C)O)s1] | N-(amino(2-(2-hydroxypropan-2-yl)thiazol-5-yl)(oxo)-λ⁶-sulfaneylidene)-2-(4-(isochroman-7-yl)-2,6-diisopropylphenyl)acetamide | 556 |
| 98 | 220 | 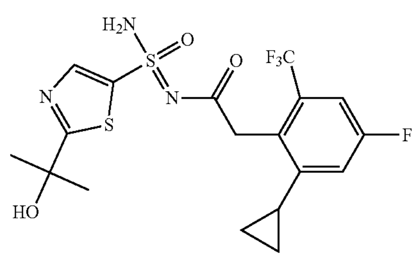 [SMILES: CC(C)(O)c1ncc(S(N)(=O)=NC(=O)Cc2c(C3CC3)cc(F)cc2C(F)(F)F)s1] | N-(amino(2-(2-hydroxypropan-2-yl)thiazol-5-yl(oxo)-λ⁶-sulfaneylidene)-2-(2-cyclopropyl-4-fluoro-6-(trifluoromethyl)phenyl)acetamide | 466 |
| 99 | 304 | 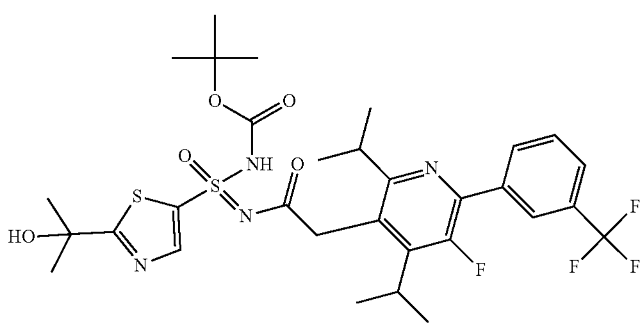 [SMILES: CC(C)c1nc(-c2cccc(C(F)(F)F)c2)c(F)c(C(C)C)c1CC(=O)N=S(=O)(NC(=O)OC(C)(C)C)c1cnc(C(C)(C)O)s1] | tert-butyl (N-(2-(5-fluoro-2,4-diisopropyl-6-(3-(trifluoromethyl)phenyl)pyridin-3-yl)acetyl)-2-(2-hydroxypropan-2-yl)thiazole-5-sulfonimidoyl)carbamate | 687 |
| 100 | 301 | 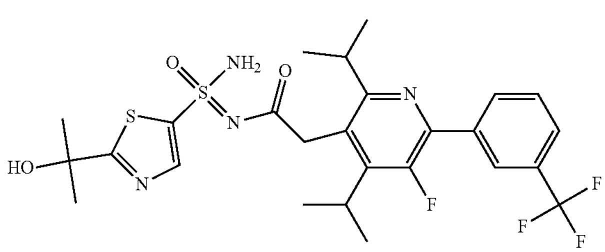 [SMILES: CC(C)c1nc(-c2cccc(C(F)(F)F)c2)c(F)c(C(C)C)c1CC(=O)N=S(N)(=O)c1cnc(C(C)(C)O)s1] | N-(amino(2-(2-hydroxypropan-2-yl)thiazol-5-yl)(oxo)-λ⁶-sulfaneylidene)-2-(5-fluoro-2,4-diisopropyl-6-(3-(trifluoromethyl)phenyl)pyridin-3-yl)acetamide | 587 |

TABLE 20-continued

Examples in the following table were prepared using similar conditions as described in Example 96 and Scheme 1C from appropriate starting materials.

| Example # | Compound # | Structure | IUPAC Name | Exact Mass [M + H]+ |
|---|---|---|---|---|
| 101 | 212 | 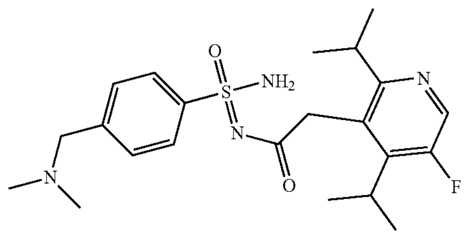 [SMILES: CC(C)c1ncc(F)c(C(C)C)c1CC(=O)N=S(N)(=O)c1ccc(CN(C)C)cc1] | N-(amino(4-((dimethylamino)methyl)phenyl)(oxo)-λ⁶-sulfaneylidene)-2-(5-fluoro-2,4-diisopropylpyridin-3-yl)acetamide | 435 |

Example 102 (Compound 240)

N-(amino(2-(2-hydroxypropan-2-yl)thiazol-5-yl)(oxo)-λ⁶-sulfaneylidene)-2-(4-fluoro-2-isopropyl-6-(tetrahydrofuran-3-yl)phenyl)acetamide (Scheme 1C)

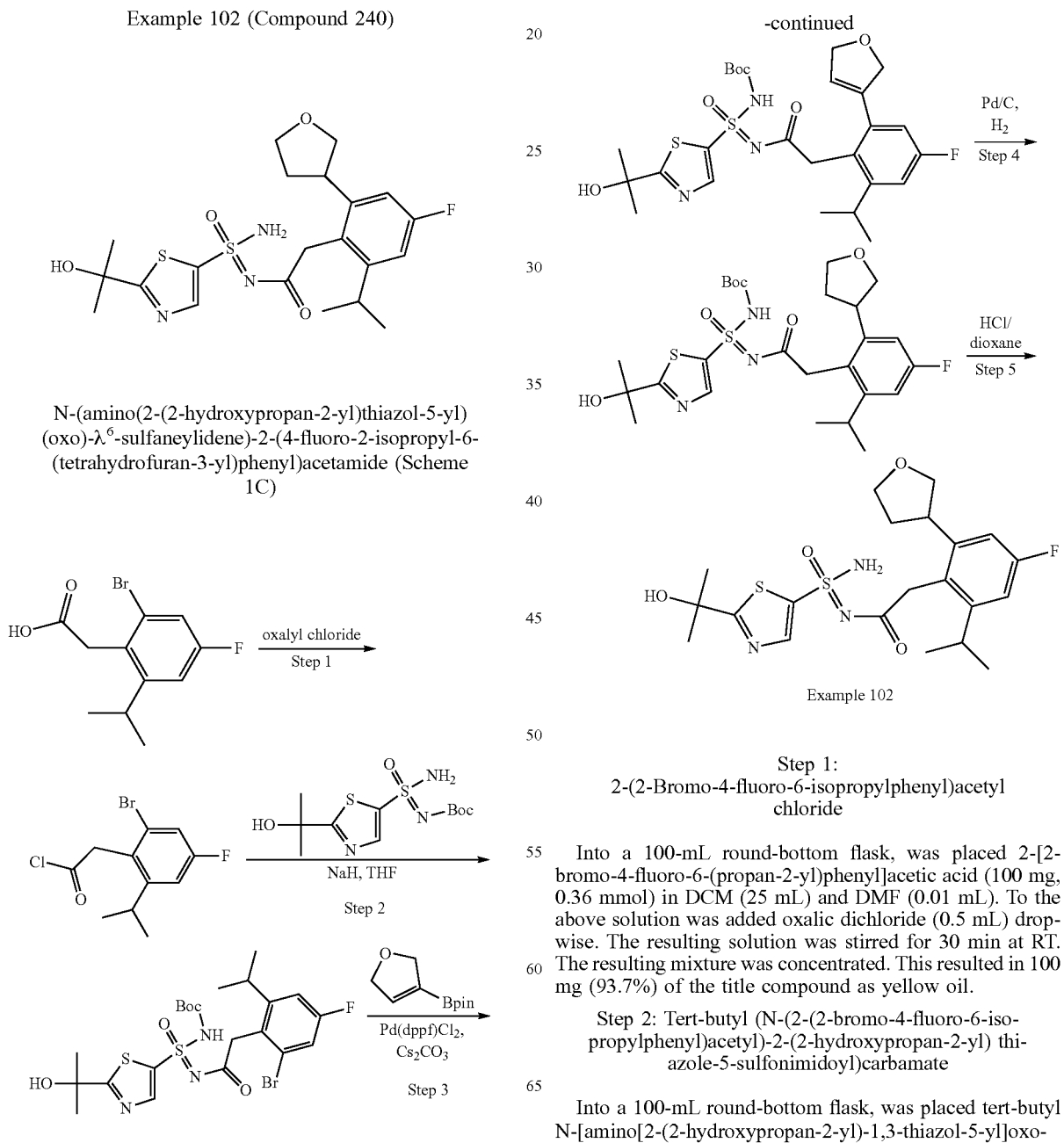

Example 102

Step 1: 2-(2-Bromo-4-fluoro-6-isopropylphenyl)acetyl chloride

Into a 100-mL round-bottom flask, was placed 2-[2-bromo-4-fluoro-6-(propan-2-yl)phenyl]acetic acid (100 mg, 0.36 mmol) in DCM (25 mL) and DMF (0.01 mL). To the above solution was added oxalic dichloride (0.5 mL) dropwise. The resulting solution was stirred for 30 min at RT. The resulting mixture was concentrated. This resulted in 100 mg (93.7%) of the title compound as yellow oil.

Step 2: Tert-butyl (N-(2-(2-bromo-4-fluoro-6-isopropylphenyl)acetyl)-2-(2-hydroxypropan-2-yl) thiazole-5-sulfonimidoyl)carbamate Into a 100-mL round-bottom flask, was placed tert-butyl N-[amino[2-(2-hydroxypropan-2-yl)-1,3-thiazol-5-yl]oxo- λ⁶-sulfanylidene]carbamate (116.7 mg, 0.36 mmol) in THF (25 mL). To the mixture was added NaH (60% wt. oil dispersion, 29.2 mg, 0.73 mmol) in portions with stirring. The resulting solution was stirred for 30 min at RT. 2-[2-bromo-4-fluoro-6-(propan-2-yl)phenyl]acetyl chloride (100 mg, 0.34 mmol) was added to the solution. The resulting solution was stirred for an additional 1 h at RT. The reaction was then quenched by the addition of 5 mL of water. The resulting solution was extracted with 2×10 ml of ethyl acetate and concentrated. This resulted in 219 mg (crude) title compound as a white solid. MS-ESI: 578 (M+1).

Step 3: Tert-butyl (N-(2-(2-(2,5-dihydrofuran-3-yl)-4-fluoro-6-isopropylphenyl)acetyl)-2-(2-hydroxypropan-2-yl)thiazole-5-sulfonimidoyl)carbamate Into a 100-mL round-bottom flask purged and maintained with an inert atmosphere of nitrogen, was placed tert-butyl (N-(2-(2-bromo-4-fluoro-6-isopropylphenyl)acetyl)-2-(2-hydroxypropan-2-yl) thiazole-5-sulfonimidoyl)carbamate (395 mg, 0.68 mmol) in dioxane (60 mL) and H₂O (12 mL). This was followed by the addition of Cs₂CO₃ (667.4 mg, 2.05 mmol), 2-(2,5-dihydrofuran-3-yl)-4,4,5,5-tetramethyl-1,3,2-dioxaborolane (201 mg, 1.02 mmol) and Pd(dppf)Cl₂ (50 mg, 0.07 mmol). The resulting solution was stirred for 16 h at 95°C in an oil bath. The resulting solution was diluted with H₂O (50 mL), extracted with 2×15 ml of ethyl acetate and concentrated. The residue was eluted from silica gel with ethyl acetate/petroleum ether (1:1). This resulted in 187 mg (50.9%) of the title compound as a dark orange solid. MS-ESI: 568 (M+1).

Step 4: Tert-butyl (N-(2-(4-fluoro-2-isopropyl-6-(tetrahydrofuran-3-yl)phenyl)acetyl)-2-(2-hydroxypropan-2-yl)thiazole-5-sulfonimidoyl)carbamate Into a 100-mL round-bottom flask, was placed tert-butyl N-([2-[2-(2,5-dihydrofuran-3-yl)-4-fluoro-6-(propan-2-yl) phenyl]acetamido][2-(2-hydroxypropan-2-yl)-1,3-oxazol-5-yl]oxo-λ⁶-sulfanylidene)carbamate (237 mg, 0.43 mmol) in methanol (25 mL). To the above solution was added Pd/C (10% wt., 30 mg) with stirring. The solution was evacuated and filled three times with hydrogen. The resulting solution was stirred for 16 h at RT. The solids were filtered out. The resulting mixture was concentrated. The residue was eluted from silica gel with DCM/methanol (10:1). This resulted in 234 mg (98.3%) of the title compound as a white solid. MS-ESI: 570 (M+1).

Step 5: N-(amino(2-(2-hydroxypropan-2-yl)thiazol-5-yl)(oxo)-λ⁶-sulfaneylidene)-2-(4-fluoro-2-isopropyl-6-(tetrahydrofuran-3-yl)phenyl)acetamide Into a 50-mL round-bottom flask, was placed tert-butyl N-[([2-[4-fluoro-2-(oxolan-3-yl)-6-(propan-2-yl)phenyl] acetyl]imino)[2-(2-hydroxypropan-2-yl)-1,3-thiazol-5-yl] oxo-λ⁶-sulfanyl]carbamate (200 mg, 0.35 mmol) in HCl/dioxane (4M, 10 mL). The resulting solution was stirred for 1 h at RT. The resulting mixture was concentrated. The crude product was purified by Prep-HPLC with the following conditions: Column, XBridge Prep C₁₈ OBD, 5 um, 19*150 mm; mobile phase, water (10 mM NH₄HCO₃) and ACN (7% to 45% ACN gradient in 7 min); Detector, UV 254/210 nm. This resulted in 20 mg (12.13%) of Example 102 as a white solid. MS-ESI: 470 (M+1).

¹H-NMR (400 MHz, DMSO-d₆, ppm) δ: 8.06 (br s, 2H), 7.03 (d, J=8.0 Hz, 1H), 7.03 (d, J=12.4 Hz, 1H), 6.28 (s, 1H), 4.01-3.97 (m, 1H), 3.91-3.89 (m, 1H), 3.79-3.77 (m, 1H), 3.55 (s, 2 H), 3.55-3.45 (m, 3H), 2.91-2.86 (m, 1H), 2.25-2.23 (m, 1H), 1.48 (s, 6H), 1.06 (d, J=6.8 Hz, 3H), 1.01 (d, J=6.8 Hz, 3H).

TABLE 21

Examples in the following table were prepared using similar conditions as described in Example 4 and Scheme 2 from appropriate starting materials.

| Example # | Compound # | Structure | IUPAC Name | Exact Mass [M + H]⁺ |
|---|---|---|---|---|
| 103 | 258 | 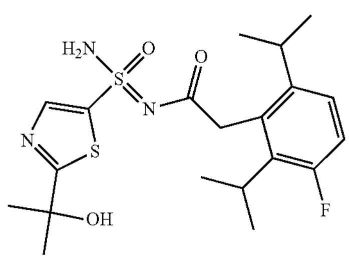 [SMILES: CC(C)c1ccc(F)c(C(C)C)c1CC(=O)N=S(N)(=O)c1cnc(C(C)(C)O)s1] | N-(amino(2-(2-hydroxypropan-2-yl)thiazol-5-yl)(oxo)-λ⁶-sulfaneylidene)-2-(3-fluoro-2,6-diisopropylphenyl)acetamide | 442 |
| 104 | 257 | 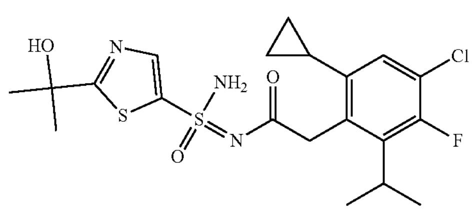 [SMILES: CC(C)c1c(F)c(Cl)cc(C2CC2)c1CC(=O)N=S(N)(=O)c1cnc(C(C)(C)O)s1] | N-(amino(2-(2-hydroxypropan-2-yl)thiazol-5-yl)(oxo)-λ⁶-sulfaneylidene)-2-(4-chloro-6-cyclopropyl-3-fluoro-2-isopropylphenyl)acetamide | 474 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 105 | 256 | 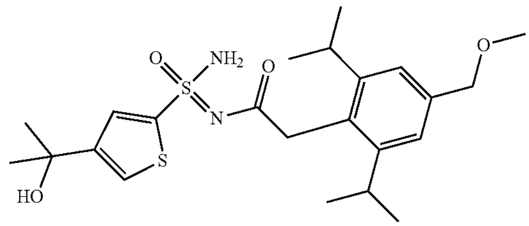 [SMILES: COCc1cc(C(C)C)c(CC(=O)N=S(N)(=O)c2cc(C(C)(C)O)cs2)c(C(C)C)c1] | N-(amino(4-(2-hydroxypropan-2-yl)thiophen-2-yl)(oxo)-$\lambda^6$-sulfaneylidene)-2-(2,6-diisopropyl-4-(methoxymethyl)phenyl)acetamide | 467 |
| 106 | 201 | 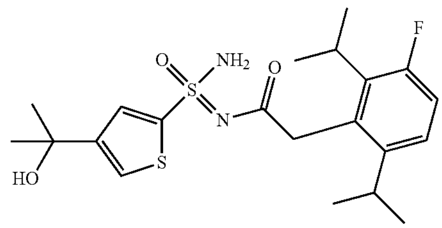 [SMILES: CC(C)c1ccc(F)c(C(C)C)c1CC(=O)N=S(N)(=O)c1cc(C(C)(C)O)cs1] | N-(amino(4-(2-hydroxypropan-2-yl)thiophen-2-yl)(oxo)-$\lambda^6$-sulfaneylidene)-2-(3-fluoro-2,6-diisopropylphenyl)acetamide | 441 |
| 107 | 255 | 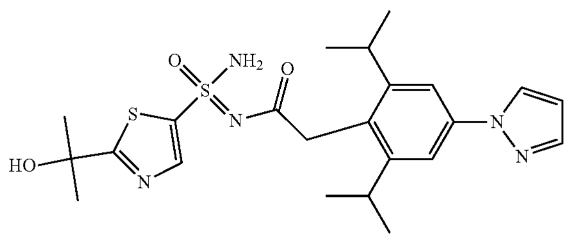 [SMILES: CC(C)c1cc(-n2cccn2)cc(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(2,6-diisopropyl-4-(1H-pyrazol-1-yl)phenyl)acetamide | 490 |
| 108 | 254 | 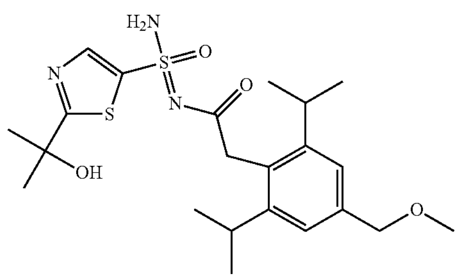 [SMILES: COCc1cc(C(C)C)c(CC(=O)N=S(N)(=O)c2cnc(C(C)(C)O)s2)c(C(C)C)c1] | N-(amino(2-(2-hydroxypropan-2-yl)thiazol-5-yl)(oxo)-$\lambda^6$-sulfaneylidene)-2-(2,6-diisopropyl-4-(methoxymethyl)phenyl)acetamide | 468 |
| 109 | 253 | 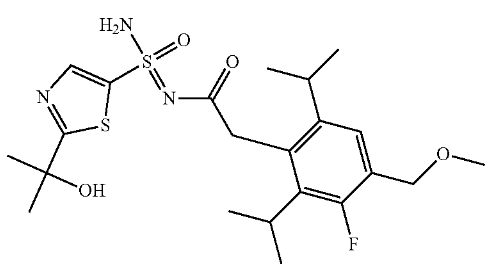 [SMILES: COCc1cc(C(C)C)c(CC(=O)N=S(N)(=O)c2cnc(C(C)(C)O)s2)c(C(C)C)c1F] | N-(amino(2-(2-hydroxypropan-2-yl)thiazol-5-yl)(oxo)-$\lambda^6$-sulfaneylidene)-2-(3-fluoro-2,6-diisopropyl-4-(methoxymethyl)phenyl)acetamide | 486 |
| 110 | 252 | 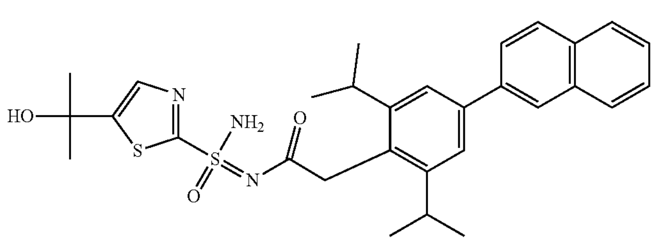 [SMILES: CC(C)c1cc(-c2ccc3ccccc3c2)cc(C(C)C)c1CC(=O)N=S(N)(=O)c1ncc(C(C)(C)O)s1] | N-(amino(5-(2-hydroxypropan-2-yl)thiazol-2-yl)(oxo)-$\lambda^6$-sulfaneylidene)-2-(2,6-diisopropyl-4-(naphthalen-2-yl)phenyl)acetamide | 550 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 111 | 251 | 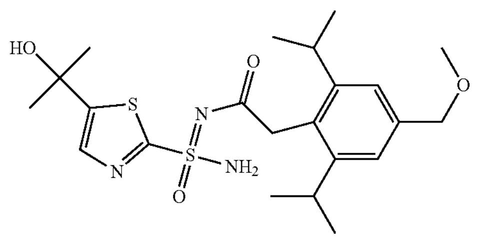 [SMILES: COCc1cc(C(C)C)c(CC(=O)N=S(N)(=O)c2ncc(C(C)(C)O)s2)c(C(C)C)c1] | N-(amino(5-(2-hydroxypropan-2-yl)thiazol-2-yl)(oxo)-$\lambda^6$-sulfaneylidene)-2-(2,6-diisopropyl-4-(methoxymethyl)phenyl)acetamide | 468 |
| 112 | 250 | 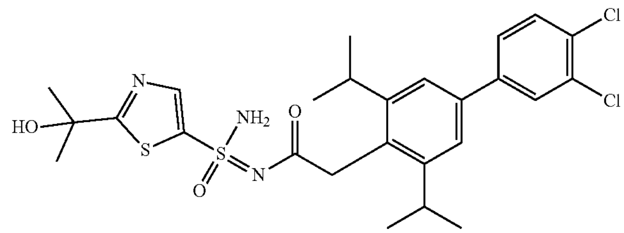 [SMILES: CC(C)c1cc(-c2ccc(Cl)c(Cl)c2)cc(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(3',4'-dichloro-3,5-diisopropyl-[1,1'-biphenyl]-4-yl)acetamide | 568 |
| 113 | 249 | 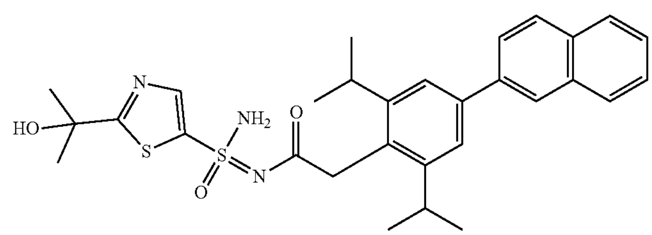 [SMILES: CC(C)c1cc(-c2ccc3ccccc3c2)cc(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(2,6-diisopropyl-4-(naphthalen-2-yl)phenyl)acetamide | 550 |
| 114 | 248 | 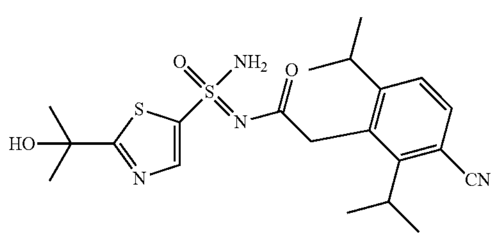 [SMILES: CC(C)c1ccc(C#N)c(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(3-cyano-2,6-diisopropylphenyl)acetamide | 449 |
| 115 | 247 | 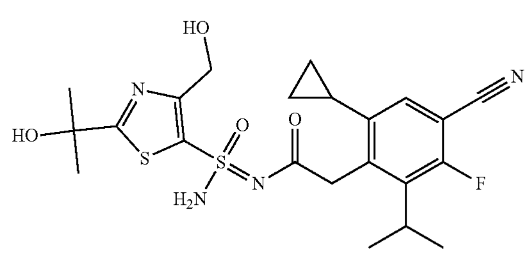 [SMILES: CC(C)c1c(F)c(C#N)cc(C2CC2)c1CC(=O)N=S(N)(=O)c1sc(C(C)(C)O)nc1CO] | N-(amino(4-(hydroxymethyl)-2-(2-hydroxypropan-2-yl)thiazol-5-yl)(oxo)-$\lambda^6$-sulfaneylidene)-2-(4-cyano-6-cyclopropyl-3-fluoro-2-isopropylphenyl)acetamide | 495 |
| 116 | 246 | 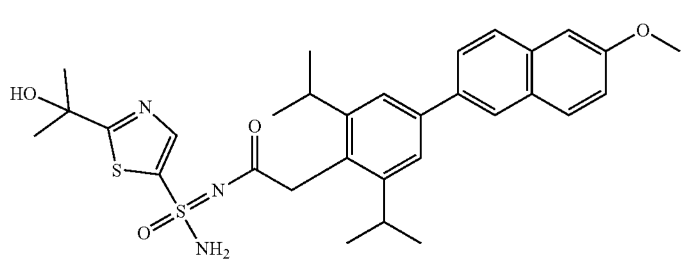 [SMILES: COc1ccc2cc(-c3cc(C(C)C)c(CC(=O)N=S(N)(=O)c4cnc(C(C)(C)O)s4)c(C(C)C)c3)ccc2c1] | N-(amino(2-(2-hydroxypropan-2-yl)thiazol-5-yl)(oxo)-$\lambda^6$-sulfaneylidene)-2-(2,6-diisopropyl-4-(6-methoxynaphthalen-2-yl)phenyl)acetamide | 580 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 117 | 309 | 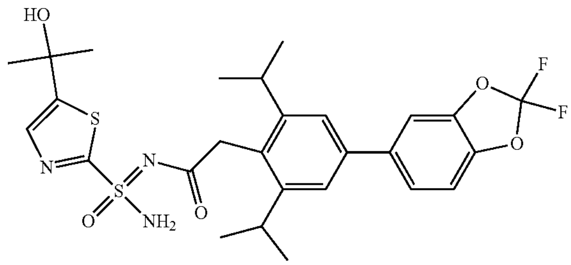 [SMILES: CC(C)c1cc(-c2ccc3c(c2)OC(F)(F)O3)cc(C(C)C)c1CC(=O)N=S(N)(=O)c1ncc(C(C)(C)O)s1] | N-(amino(5-(2-hydroxypropan-2-yl)thiazol-2-yl)(oxo)-λ6-sulfaneylidene)-2-(4-(2,2-difluorobenzo[d][1,3]dioxol-5-yl)-2,6-diisopropylphenyl)acetamide | 580 |
| 118 | 310 | 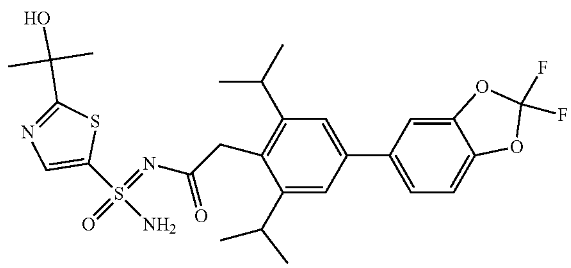 [SMILES: CC(C)c1cc(-c2ccc3c(c2)OC(F)(F)O3)cc(C(C)C)c1CC(=O)N=S(N)(=O)c1cnc(C(C)(C)O)s1] | N-(amino(2-(2-hydroxypropan-2-yl)thiazol-5-yl)(oxo)-λ6-sulfaneylidene)-2-(4-(2,2-difluorobenzo[d][1,3]dioxol-5-yl)-2,6-diisopropylphenyl)acetamide | 580 |
| 119 | 243 | 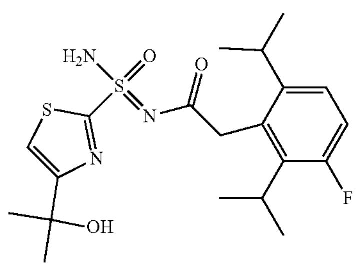 [SMILES: CC(C)c1ccc(F)c(C(C)C)c1CC(=O)N=S(N)(=O)c1nc(C(C)(C)O)cs1] | N-(amino(4-(2-hydroxypropan-2-yl)thiazol-2-yl)(oxo)-λ6-sulfaneylidene)-2-(3-fluoro-2,6-diisopropylphenyl)acetamide | 442 |
| 120 | 242 | 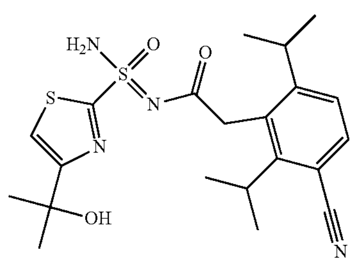 [SMILES: CC(C)c1ccc(C#N)c(C(C)C)c1CC(=O)N=S(N)(=O)c1nc(C(C)(C)O)cs1] | N-(amino(4-(2-hydroxypropan-2-yl)thiazol-2-yl)(oxo)-λ6-sulfaneylidene)-2-(3-cyano-2,6-diisopropylphenyl)acetamide | 449 |
| 121 | 239 | 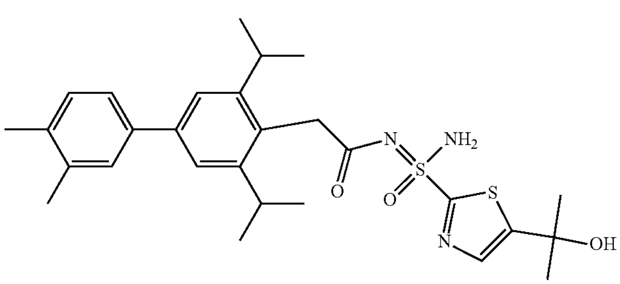 [SMILES: Cc1ccc(-c2cc(C(C)C)c(CC(=O)N=S(N)(=O)c3ncc(C(C)(C)O)s3)c(C(C)C)c2)cc1C] | N-(amino(5-(2-hydroxypropan-2-yl)thiazol-2-yl)(oxo)-λ6-sulfaneylidene)-2-(3,5-diisopropyl-3',4'-dimethyl-[1,1'-biphenyl]-4-yl)acetamide | 528 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 122 | 238 | 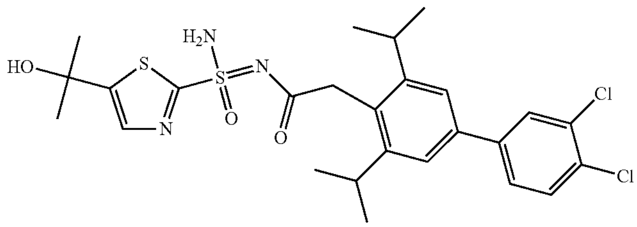 [SMILES: CC(C)c1cc(-c2ccc(Cl)c(Cl)c2)cc(C(C)C)c1CC(=O)N=S(N)(=O)c1ncc(C(C)(C)O)s1] | N-(amino(5-(2-hydroxypropan-2-yl)thiazol-2-yl)(oxo)-λ6-sulfaneylidene)-2-(3',4'-dichloro-3,5-diisopropyl-[1,1'-biphenyl]-4-yl)acetamide | 568 |
| 123 | 237 | 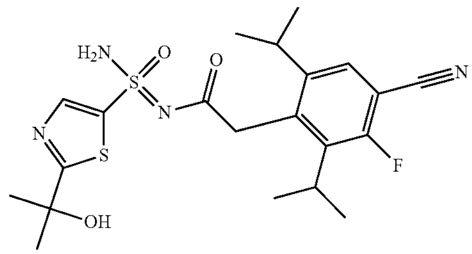 [SMILES: CC(C)c1cc(C#N)c(F)c(C(C)C)c1CC(=O)N=S(N)(=O)c1cnc(C(C)(C)O)s1] | N-(amino(2-(2-hydroxypropan-2-yl)thiazol-5-yl)(oxo)-λ6-sulfaneylidene)-2-(4-cyano-3-fluoro-2,6-diisopropylphenyl)acetamide | 467 |
| 124 | 236 | 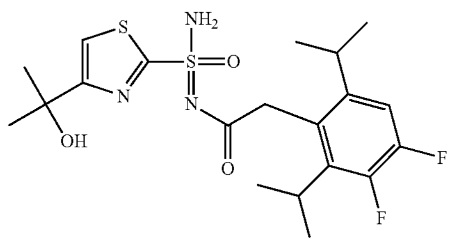 [SMILES: CC(C)c1cc(F)c(F)c(C(C)C)c1CC(=O)N=S(N)(=O)c1nc(C(C)(C)O)cs1] | N-(amino(4-(2-hydroxypropan-2-yl)thiazol-2-yl)(oxo)-λ6-sulfaneylidene)-2-(3,4-difluoro-2,6-diisopropylphenyl)acetamide | 460 |
| 125 | 234 | 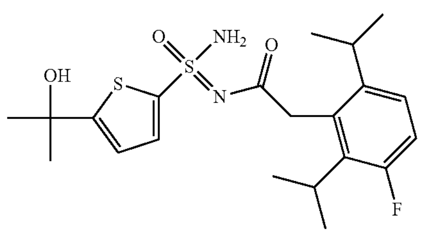 [SMILES: CC(C)c1ccc(F)c(C(C)C)c1CC(=O)N=S(N)(=O)c1ccc(C(C)(C)O)s1] | N-(amino(5-(2-hydroxypropan-2-yl)thiophen-2-yl)(oxo)-λ6-sulfaneylidene)-2-(3-fluoro-2,6-diisopropylphenyl)acetamide | 441 |
| 126 | 233 | 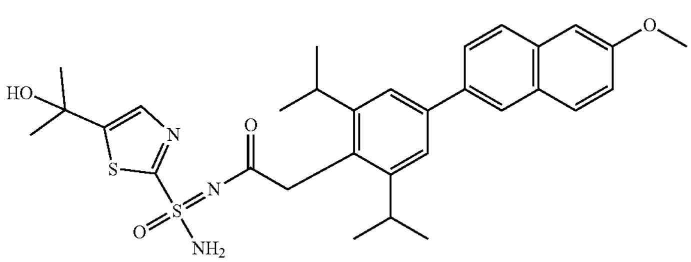 [SMILES: COc1ccc2cc(-c3cc(C(C)C)c(CC(=O)N=S(N)(=O)c4ncc(C(C)(C)O)s4)c(C(C)C)c3)ccc2c1] | N-(amino(5-(2-hydroxypropan-2-yl)thiazol-2-yl)(oxo)-λ6-sulfaneylidene)-2-(2,6-diisopropyl-4-(6-methoxynaphthalen-2-yl)phenyl)acetamide | 580 |
| 127 | 232 | 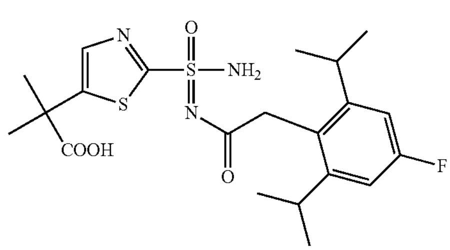 [SMILES: CC(C)c1cc(F)cc(C(C)C)c1CC(=O)N=S(N)(=O)c1ncc(C(C)(C)C(=O)O)s1] | 2-(2-(N'-(2-(4-fluoro-2,6-diisopropylphenyl)acetyl)sulfamidimidoyl)thiazol-5-yl)-2-methylpropanoic acid | 470 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 128 | 120 | 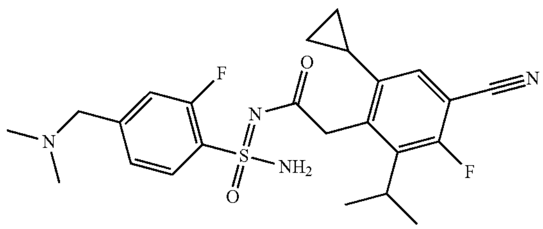 [SMILES: CC(C)c1c(F)c(C#N)cc(C2CC2)c1CC(=O)N=S(N)(=O)c1ccc(CN(C)C)cc1F] | N-(amino(4-((dimethylamino)methyl)-2-fluorophenyl)(oxo)-$\lambda^6$-sulfaneylidene)-2-(4-cyano-6-cyclopropyl-3-fluoro-2-isopropylphenyl)acetamide | 475 |
| 129 | 229 | 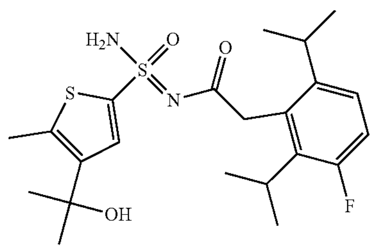 [SMILES: Cc1sc(S(N)(=O)=NC(=O)Cc2c(C(C)C)ccc(F)c2C(C)C)cc1C(C)(C)O] | N-(amino(4-(2-hydroxypropan-2-yl)-5-methylthiophen-2-yl)(oxo)-$\lambda^6$-sulfaneylidene)-2-(3-fluoro-2,6-diisopropylphenyl)acetamide | 455 |
| 130 | 228 | 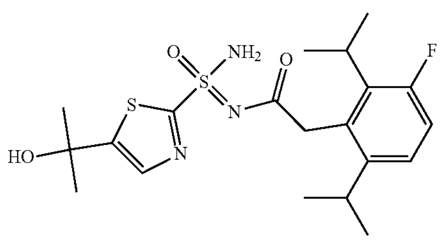 [SMILES: CC(C)c1ccc(F)c(C(C)C)c1CC(=O)N=S(N)(=O)c1ncc(C(C)(C)O)s1] | N-(amino(5-(2-hydroxypropan-2-yl)thiazol-2-yl)(oxo)-$\lambda^6$-sulfaneylidene)-2-(3-fluoro-2,6-diisopropylphenyl)acetamide | 442 |
| 132 | 227 | 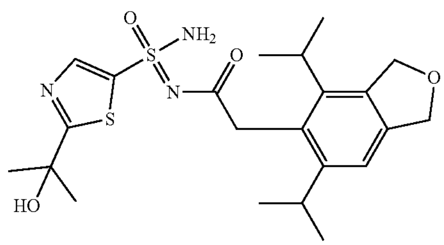 [SMILES: CC(C)c1cc2c(c(C(C)C)c1CC(=O)N=S(N)(=O)c1cnc(C(C)(C)O)s1)COC2] | N-(amino(2-(2-hydroxypropan-2-yl)thiazol-5-yl)(oxo)-$\lambda^6$-sulfaneylidene)-2-(4,6-diisopropyl-1,3-dihydroisobenzofuran-5-yl)acetamide | 466 |
| 133 | 226 | 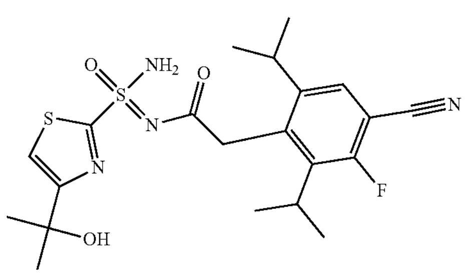 [SMILES: CC(C)c1cc(C#N)c(F)c(C(C)C)c1CC(=O)N=S(N)(=O)c1nc(C(C)(C)O)cs1] | N-(amino(4-(2-hydroxypropan-2-yl)thiazol-2-yl)(oxo)-$\lambda^6$-sulfaneylidene)-2-(4-cyano-3-fluoro-2,6-diisopropylphenyl)acetamide | 467 |
| 134 | 225 | 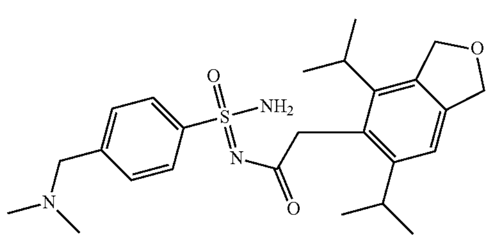 [SMILES: CC(C)c1cc2c(c(C(C)C)c1CC(=O)N=S(N)(=O)c1ccc(CN(C)C)cc1)COC2] | N-(amino(4-((dimethylamino)methyl)phenyl(oxo)-$\lambda^6$-sulfaneylidene)-2-(4,6-diisopropyl-1,3-dihydroisobenzofuran-5-yl)acetamide | 458 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]$^+$ |
|---|---|---|---|---|
| 135 | 224 | 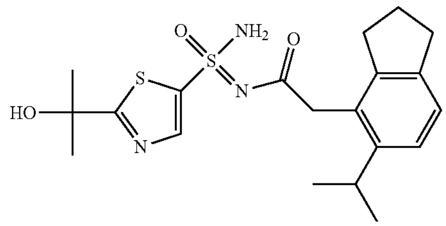 [SMILES: CC(C)c1ccc2c(c1CC(=O)N=S(N)(=O)c1cnc(C(C)(C)O)s1)CCC2] | N-(amino(2-(2-hydroxypropan-2-yl)thiazol-5-yl)(oxo)-λ$^6$-sulfaneylidene)-2-(5-isopropyl-2,3-dihydro-1H-inden-4-yl)acetamide | 422 |
| 136 | 191 | 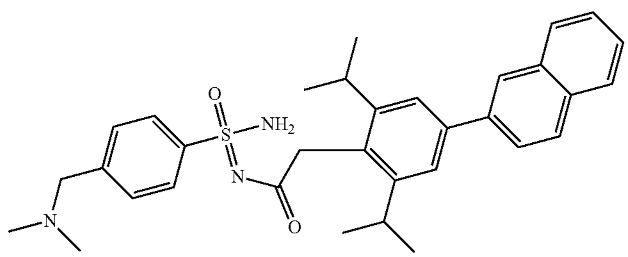 [SMILES: CC(C)c1cc(-c2ccc3ccccc3c2)cc(C(C)C)c1CC(=O)N=S(N)(=O)c1ccc(CN(C)C)cc1] | N-(amino(4-((dimethylamino)methyl)phenyl)(oxo)-λ$^6$-sulfaneylidene)-2-(2,6-diisopropyl-4-(naphthalen-2-yl)phenyl)acetamide | 542 |
| 137 | 222 | 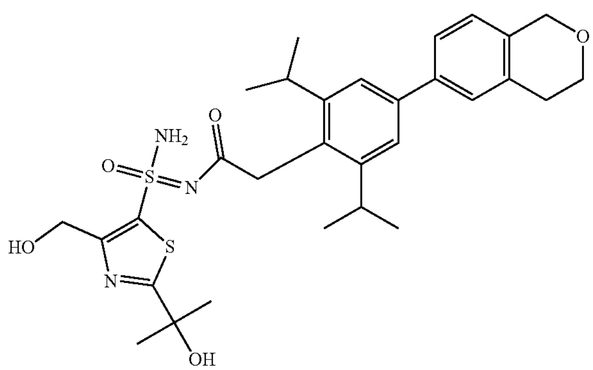 [SMILES: CC(C)c1cc(-c2ccc3c(c2)CCOC3)cc(C(C)C)c1CC(=O)N=S(N)(=O)c1sc(C(C)(C)O)nc1CO] | N-(amino(4-(hydroxymethyl)-2-(2-hydroxypropan-2-yl)thiazol-5-yl)(oxo)-λ$^6$-sulfaneylidene)-2-(4-(isochroman-6-yl)-2,6-diisopropylphenyl)acetamide | 586 |
| 138 | 307 | 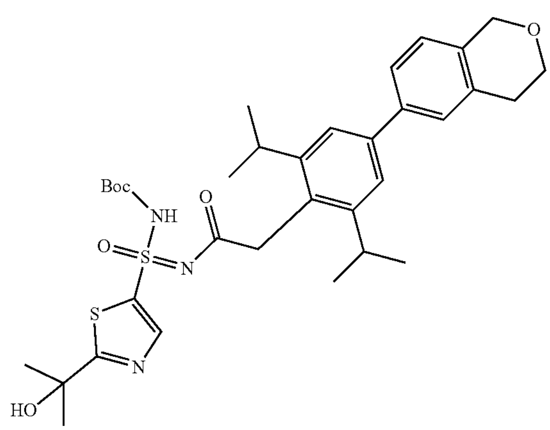 [SMILES: CC(C)c1cc(-c2ccc3c(c2)CCOC3)cc(C(C)C)c1CC(=O)N=S(=O)(NC(=O)OC(C)(C)C)c1cnc(C(C)(C)O)s1] | tert-butyl (2-(2-hydroxypropan-2-yl)-N-(2-(4-(isochroman-6-yl)-2,6-diisopropylphenyl)acetyl)thiazole-5-sulfonimidoyl)carbamate | 656 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 139 | 231 | 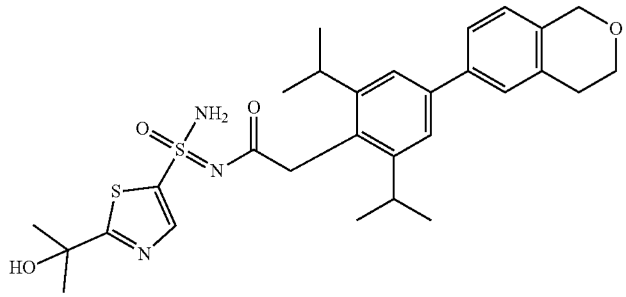 [SMILES: CC(C)c1cc(-c2ccc3c(c2)CCOC3)cc(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(4-(isochroman-6-yl)-2,6-diisopropylphenyl)acetamide | 556 |
| 140 | 306 | 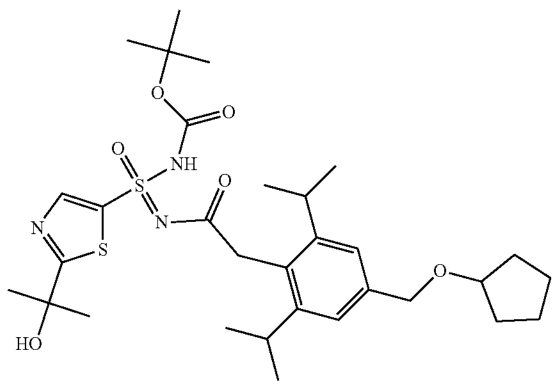 [SMILES: CC(C)c1cc(COC2CCCC2)cc(C(C)C)c1CC(=O)N=S(=O)(NC(=O)OC(C)(C)C)c1cnc(C(C)(C)O)s1] | tert-butyl (N-(2-(4-((cyclopentyloxy)methyl)-2,6-diisopropylphenyl)acetyl)-2-(2-hydroxypropan-2-yl)thiazole-5-sulfonimidoyl)carbamate | 622 |
| 141 | 305 | 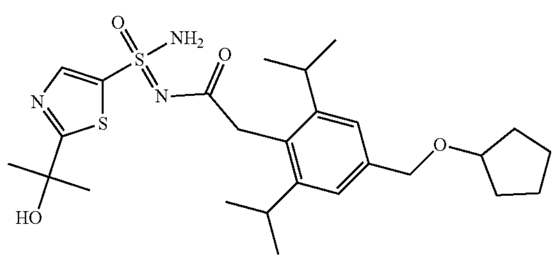 [SMILES: CC(C)c1cc(COC2CCCC2)cc(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(4-((cyclopentyloxy)methyl)-2,6-diisopropylphenyl)acetamide | 522 |
| 142 | 216 | 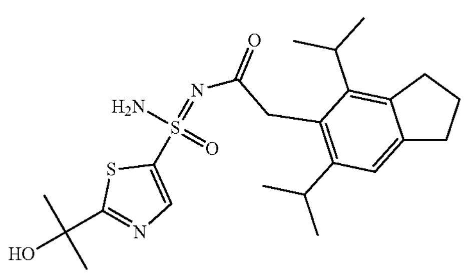 [SMILES: CC(C)c1cc2c(c(C(C)C)c1CC(=O)N=S(N)(=O)c1cnc(C(C)(C)O)s1)CCC2] | N-(amino(2-(2-hydroxypropan-2-yl)thiazol-5-yl)(oxo)-$\lambda^6$-sulfaneylidene)-2-(4,6-diisopropyl-2,3-dihydro-1H-inden-5-yl)acetamide | 464 |
| 143 | 215 | 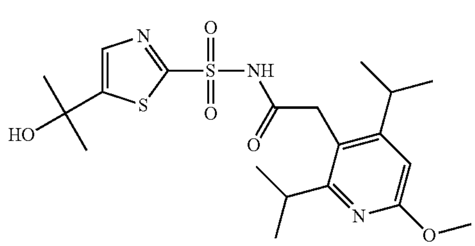 [SMILES: COc1cc(C(C)C)c(CC(=O)NS(=O)(=O)c2ncc(C(C)(C)O)s2)c(C(C)C)n1] | 2-(2,4-diisopropyl-6-methoxypyridin-3-yl)-N-((5-(2-hydroxypropan-2-yl)thiazol-2-yl)sulfonyl)acetamide | 456 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 144 | 203 | 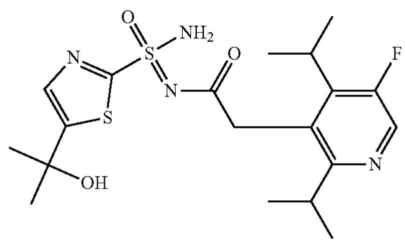 [SMILES: CC(C)c1ncc(F)c(C(C)C)c1CC(=O)N=S(N)(=O)c1ncc(C(C)(C)O)s1] | N-(amino(5-(2-hydroxypropan-2-yl)thiazol-2-yl)(oxo)-$\lambda^6$-sulfaneylidene)-2-(5-fluoro-2,4-diisopropylpyridin-3-yl)acetamide | 443 |
| 145 | 213 | 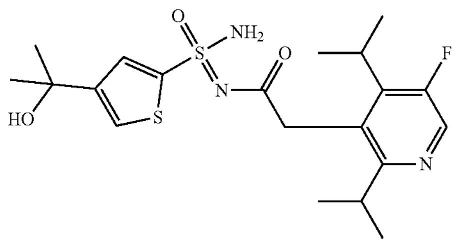 [SMILES: CC(C)c1ncc(F)c(C(C)C)c1CC(=O)N=S(N)(=O)c1cc(C(C)(C)O)cs1] | N-(amino(4-(2-hydroxypropan-2-yl)thiophen-2-yl)(oxo)-$\lambda^6$-sulfaneylidene)-2-(5-fluoro-2,4-diisopropylpyridin-3-yl)acetamide | 442 |
| 146 | 204 | 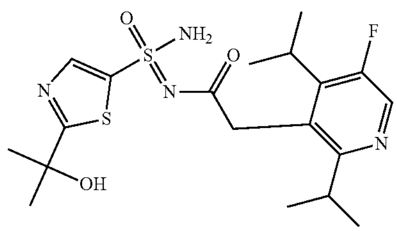 [SMILES: CC(C)c1ncc(F)c(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(5-fluoro-2,4-diisopropylpyridin-3-yl)acetamide | 443 |
| 147 | 202 | 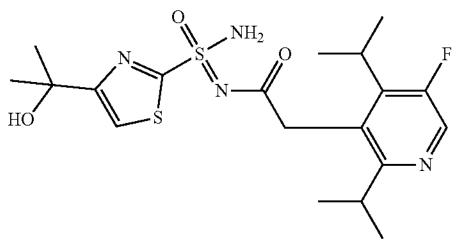 [SMILES: CC(C)c1ncc(F)c(C(C)C)c1CC(=O)N=S(N)(=O)c1nc(C(C)(C)O)cs1] | N-(amino(4-(2-hydroxypropan-2-yl)thiazol-2-yl)(oxo)-$\lambda^6$-sulfaneylidene)-2-(5-fluoro-2,4-diisopropylpyridin-3-yl)acetamide | 443 |
| 148 | 211 | 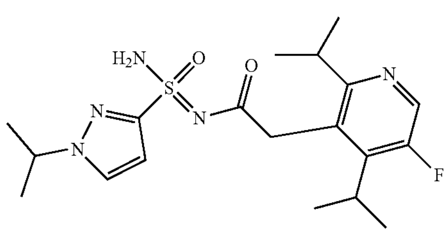 [SMILES: CC(C)c1ncc(F)c(C(C)C)c1CC(=O)N=S(N)(=O)c1ccn(C(C)C)n1] | N-(amino(1-isopropyl-1H-pyrazol-3-yl)(oxo)-$\lambda^6$-sulfaneylidene)-2-(5-fluoro-2,4-diisopropylpyridin-3-yl)acetamide | 410 |
| 149 | 210 | 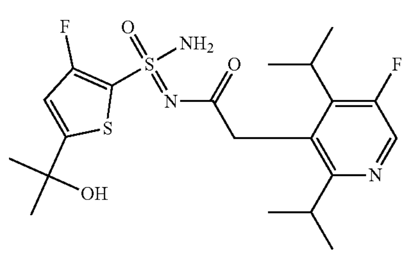 [SMILES: CC(C)c1ncc(F)c(C(C)C)c1CC(=O)N=S(N)(=O)c1sc(C(C)(C)O)cc1F] | N-(amino(3-fluoro-5-(2-hydroxypropan-2-yl)thiophen-2-yl)(oxo)-$\lambda^6$-sulfaneylidene)-2-(5-fluoro-2,4-diisopropylpyridin-3-yl)acetamide | 460 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 150 | 209 | 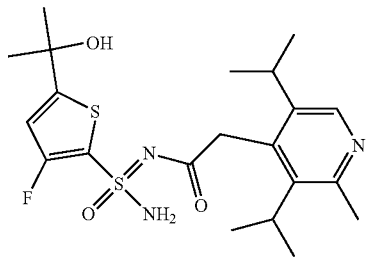 [SMILES: Cc1ncc(C(C)C)c(CC(=O)N=S(N)(=O)c2sc(C(C)(C)O)cc2F)c1C(C)C] | N-(amino(3-fluoro-5-(2-hydroxypropan-2-yl)thiophen-2-yl)(oxo)-$\lambda^6$-sulfaneylidene)-2-(3,5-diisopropyl-2-methylpyridin-4-yl)acetamide | 456 |
| 151 | 208 | 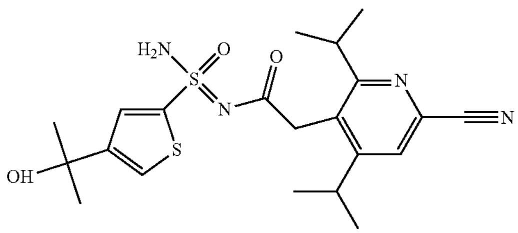 [SMILES: CC(C)c1cc(C#N)nc(C(C)C)c1CC(=O)N=S(N)(=O)c1cc(C(C)(C)O)cs1] | N-(amino(4-(2-hydroxypropan-2-yl)thiophen-2-yl)(oxo)-$\lambda^6$-sulfaneylidene)-2-(6-cyano-2,4-diisopropylpyridin-3-yl)acetamide | 449 |
| 152 | 207 | 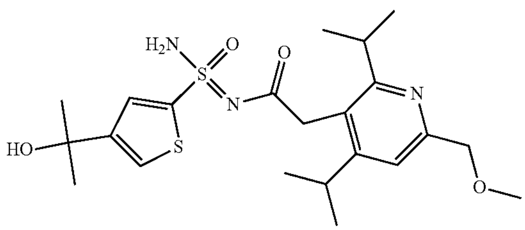 [SMILES: COCc1cc(C(C)C)c(CC(=O)N=S(N)(=O)c2cc(C(C)(C)O)cs2)c(C(C)C)n1] | N-(amino(4-(2-hydroxypropan-2-yl)thiophen-2-yl)(oxo)-$\lambda^6$-sulfaneylidene)-2-(2,4-diisopropyl-6-(methoxymethyl)pyridin-3-yl)acetamide | 468 |
| 153 | 206 | 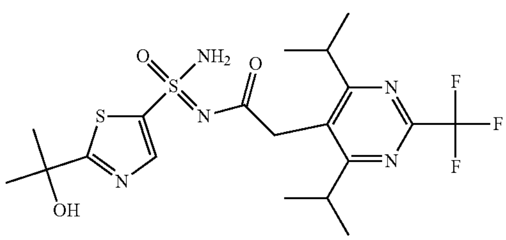 [SMILES: CC(C)c1nc(C(F)(F)F)nc(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(4,6-diisopropyl-2-(trifluoromethyl)pyrimidin-5-yl)acetamide | 494 |
| 154 | 205 | 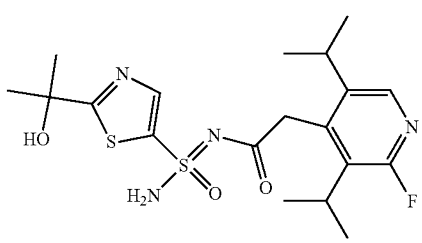 [SMILES: CC(C)c1cnc(F)c(C(C)C)c1CC(=O)N=S(N)(=O)c1cnc(C(C)(C)O)s1] | N-(amino(2-(2-hydroxypropan-2-yl)thiazol-5-yl)(oxo)-$\lambda^6$-sulfaneylidene)-2-(2-fluoro-3,5-diisopropylpyridin-4-yl)acetamide | 443 |
| 220 | 263 | 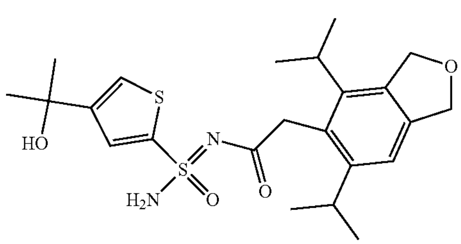 [SMILES: CC(C)c1cc2c(c(C(C)C)c1CC(=O)N=S(N)(=O)c1cc(C(C)(C)O)cs1)COC2] | N-(amino(4-(2-hydroxypropan-2-yl)thiophen-2-yl)(oxo)-$\lambda^6$-sulfaneylidene)-2-(4,6-diisopropyl-1,3-dihydroisobenzofuran-5-yl)acetamide | 465 |

TABLE 21-continued

Examples in the following table were prepared using similar conditions as described in Example 4 and Scheme 2 from appropriate starting materials.

| Example # | Compound # | Structure | IUPAC Name | Exact Mass [M + H]+ |
|---|---|---|---|---|
| 221 | 264 | 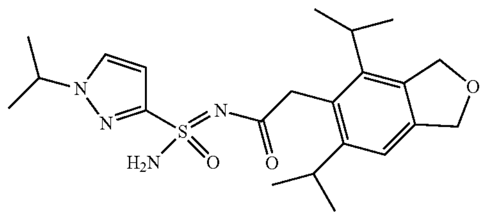 [SMILES: CC(C)c1cc2c(c(C(C)C)c1CC(=O)N=S(N)(=O)c1ccn(C(C)C)n1)COC2] | N-(amino(1-isopropyl-1H-pyrazol-3-yl)(oxo)-$\lambda^6$-sulfaneylidene)-2-(4,6-diisopropyl-1,3-dihydroisobenzofuran-5-yl)acetamide | 433 |

TABLE 22

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 155 | 261b | 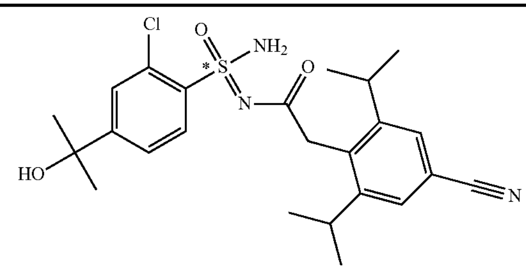 | (R) or (S)-N-(amino(2-chloro-4-(2-hydroxypropan-2-yl)phenyl)(oxo)-λ⁶-sulfaneylidene)-2-(4-cyano-2,6-diisopropylphenyl)acetamide | CHIRALPAK ID, 2*25 cm (5 um) | IPA in Hex (0.1% FA) | 476 |
| 156 | 261a | 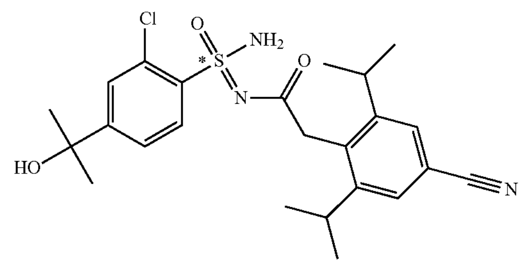 [SMILES: CC(C)c1cc(C#N)cc(C(C)C)c1CC(=O)N=S(N)(=O)c1ccc(C(C)(C)O)cc1Cl] | (S) or (R)-N-(amino(2-chloro-4-(2-hydroxypropan-2-yl)phenyl)(oxo)-λ⁶-sulfaneylidene)-2-(4-cyano-2,6-diisopropylphenyl)acetamide | CHIRALPAK ID, 2*25 cm (5 um) | IPA in Hex (0.1% FA) | 476 |
| 157 | 256a | 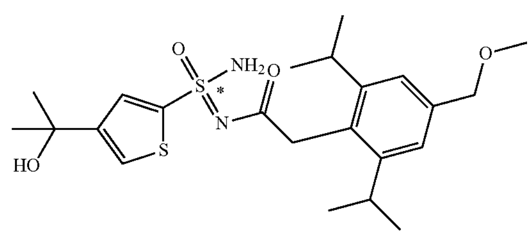 [SMILES: COCc1cc(C(C)C)c(CC(=O)N=S(N)(=O)c2cc(C(C)(C)O)cs2)c(C(C)C)c1] | (R) or (S)-N-(amino(4-(2-hydroxypropan-2-yl)thiophen-2-yl)(oxo)-λ⁶-sulfaneylidene)-2-(2,6-diisopropyl-4-(methoxymethyl)phenyl)acetamide | CHIRALPAK ID, 2*25 cm (5 um) | IPA in Hex:DC M = 5:1 | 465 (M − 1) |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]$^+$ |
|---|---|---|---|---|---|---|
| 158 | 256b | 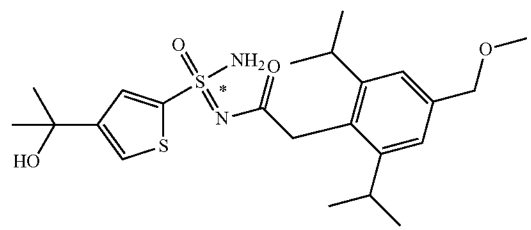 [SMILES: COCc1cc(C(C)C)c(CC(=O)N=S(N)(=O)c2cc(C(C)(C)O)cs2)c(C(C)C)c1] | (S) or (R)-N-(amino(4-(2-hydroxypropan-2-yl)thiophen-2-yl)(oxo)-λ$^6$-sulfaneylidene)-2-(2,6-diisopropyl-4-(methoxymethyl)phenyl)acetamide | CHIRALPAK ID, 2*25 cm (5 um) | IPA in Hex:DCM = 5:1 | 465 (M − 1) |
| 159 | 201b | 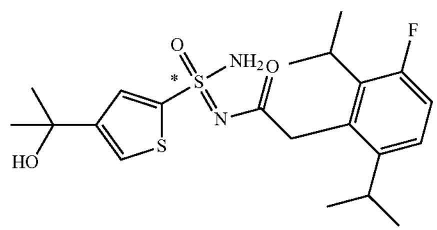 [SMILES: CC(C)c1ccc(F)c(C(C)C)c1CC(=O)N=S(N)(=O)c1cc(C(C)(C)O)cs1] | (R) or (S)-N-(amino(4-(2-hydroxypropan-2-yl)thiophen-2-yl)(oxo)-λ$^6$-sulfaneylidene)-2-(3-fluoro-2,6-diisopropylphenyl)acetamide | CHIRALPAK ID, 2*25 cm (5 um) | IPA in Hex:DCM = 5:1 | 441 |
| 160 | 201a | 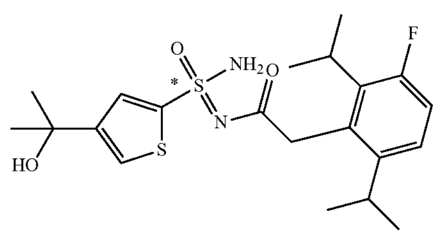 [SMILES: CC(C)c1ccc(F)c(C(C)C)c1CC(=O)N=S(N)(=O)c1cc(C(C)(C)O)cs1] | (S) or (R)-N-(amino(4-(2-hydroxypropan-2-yl)thiophen-2-yl)(oxo)-λ$^6$-sulfaneylidene)-2-(3-fluoro-2,6-diisopropylphenyl)acetamide | CHIRALPAK ID, 2*25 cm (5 um) | IPA in Hex:DCM = 5:1 | 441 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]$^+$ |
|---|---|---|---|---|---|---|
| 161 | 258a | 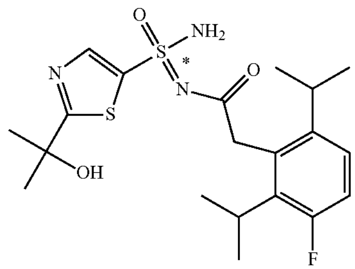 [SMILES: CC(C)c1ccc(F)c(C(C)C)c1CC(=O)N=S(N)(=O)c1cnc(C(C)(C)O)s1] | (R) or (S)-N-(amino(2-(2-hydroxypropan-2-yl)thiazol-5-yl)(oxo)-λ$^6$-sulfaneylidene)-2-(3-fluoro-2,6-diisopropylphenyl)acetamide | Chiralpak ID, 2*25 cm, 5 um | IPA in Hex (0.1% FA) | 440 (M − 1) |
| 162 | 258b | 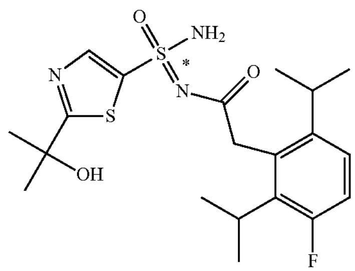 [SMILES: CC(C)c1ccc(F)c(C(C)C)c1CC(=O)N=S(N)(=O)c1cnc(C(C)(C)O)s1] | (S) or (R)-N-(amino(2-(2-hydroxypropan-2-yl)thiazol-5-yl)(oxo)-λ$^6$-sulfaneylidene)-2-(3-fluoro-2,6-diisopropylphenyl)acetamide | Chiralpak ID, 2*25 cm, 5 um | IPA in Hex (0.1% FA) | 440 (M − 1) |
| 163 | 249a | 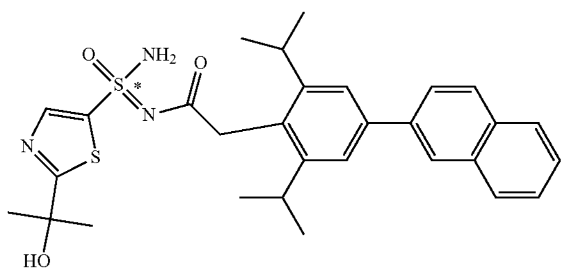 [SMILES: CC(C)c1cc(-c2ccc3ccccc3c2)cc(C(C)C)c1CC(=O)N=S(N)(=O)c1cnc(C(C)(C)O)s1] | (R) or (S)-N-(amino(2-(2-hydroxypropan-2-yl)thiazol-5-yl)(oxo)-λ$^6$-sulfaneylidene)-2-(2,6-diisopropyl-4-(naphthalen-2-yl)phenyl)acetamide | Chiralpak ID, 2*25 cm, 5 um | IPA in Hex (0.1% FA) | 550 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 164 | 249b | 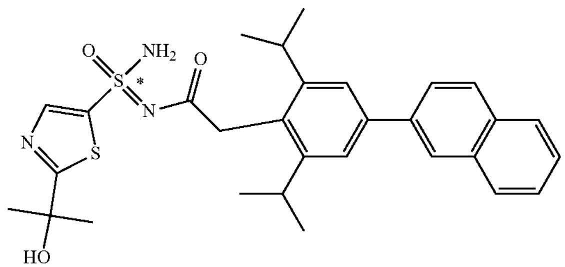 [SMILES: CC(C)c1cc(-c2ccc3ccccc3c2)cc(C(C)C)c1CC(=O)N=S(N)(=O)c1cnc(C(C)(C)O)s1] | (S) or (R)-N-(amino(2-(2-hydroxypropan-2-yl)thiazol-5-yl)(oxo)-λ$^6$-sulfaneylidene)-2-(2,6-diisopropyl-4-(naphthalen-2-yl)phenyl)acetamide | Chiralpak ID, 2*25 cm, 5 um | IPA in Hex (0.1% FA) | 550 |
| 165 | 309b | 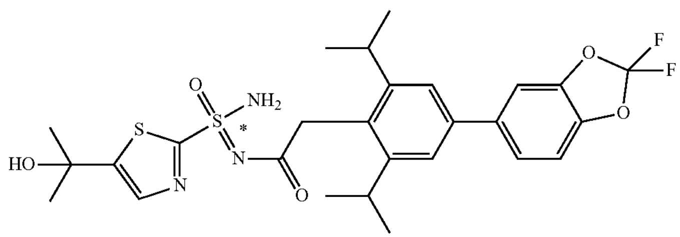 [SMILES: CC(C)c1cc(-c2ccc3c(c2)OC(F)(F)O3)cc(C(C)C)c1CC(=O)N=S(N)(=O)c1ncc(C(C)(C)O)s1] | (S) or (R)-N-(amino(5-(2-hydroxypropan-2-yl)thiazol-2-yl)(oxo)-λ$^6$-sulfaneylidene)-2-(4-(2,2-difluorobenzo[d][1,3]dioxol-5-yl)-2,6-diisopropylphenyl)acetamide | CHIRALPAK IF, 2*25 cm, 5 um | EtOH in Hex (0.1% FA) | 580 |
| 166 | 309a | 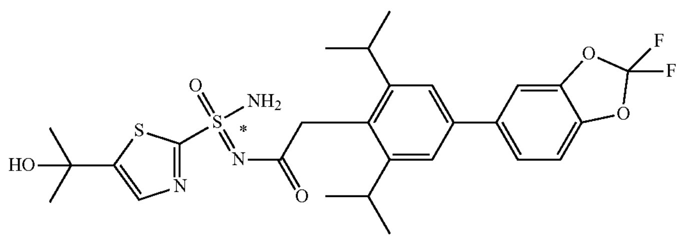 [SMILES: CC(C)c1cc(-c2ccc3c(c2)OC(F)(F)O3)cc(C(C)C)c1CC(=O)N=S(N)(=O)c1ncc(C(C)(C)O)s1] | (R) or (S)-N-(amino(5-(2-hydroxypropan-2-yl)thiazol-2-yl)(oxo)-λ$^6$-sulfaneylidene)-2-(4-(2,2-difluorobenzo[d][1,3]dioxol-5-yl)-2,6-diisopropylphenyl)acetamide | CHIRALPAK IF, 2*25 cm, 5 um | EtOH in Hex (0.1% FA) | 580 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 167 | 239a | 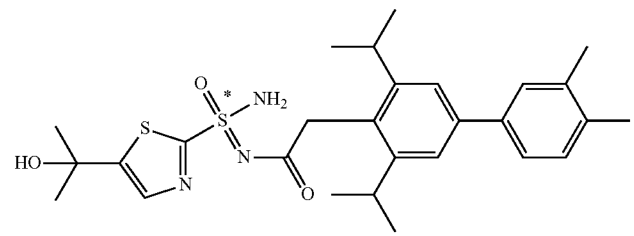 [SMILES: Cc1ccc(-c2cc(C(C)C)c(CC(=O)N=S(N)(=O)c3ncc(C(C)(C)O)s3)c(C(C)C)c2)cc1C] | (S) or (R)-N-(amino(5-(2-hydroxypropan-2-yl)thiazol-2-yl)(oxo)-λ6-sulfaneylidene)-2-(3,5-diisopropyl-3',4'-dimethyl-[1,1'-biphenyl]-4-yl)acetamide | CHIRALPAK IF, 2*25 cm, 5 um | EtOH in Hex (0.1% FA) | 528 |
| 168 | 239b | 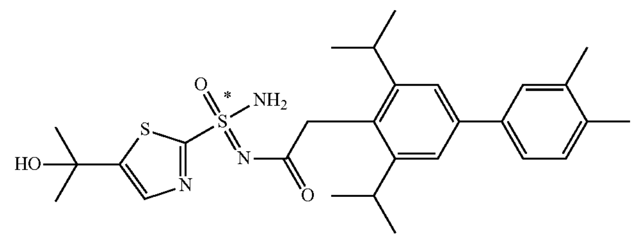 [SMILES: Cc1ccc(-c2cc(C(C)C)c(CC(=O)N=S(N)(=O)c3ncc(C(C)(C)O)s3)c(C(C)C)c2)cc1C] | (R) or (S)-N-(amino(5-(2-hydroxypropan-2-yl)thiazol-2-yl)(oxo)-λ6-sulfaneylidene)-2-(3,5-diisopropyl-3',4'-dimethyl-[1,1'-biphenyl]-4-yl)acetamide | CHIRALPAK IF, 2*25 cm, 5 um | EtOH in Hex (0.1% FA) | 528 |
| 169 | 238a | 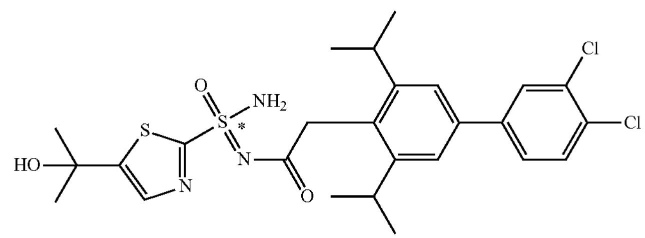 | (S) or (R)-N-(amino(5-(2-hydroxypropan-2-yl)thiazol-2-yl)(oxo)-λ6-sulfaneylidene)-2-(3',4'-dichloro-3,5-diisopropyl-[1,1'-biphenyl]-4-yl)acetamide | CHIRALPAK IF, 2*25 cm, 5 um | IPA in Hex (0.1% FA) | 568 |
| 170 | 238b | 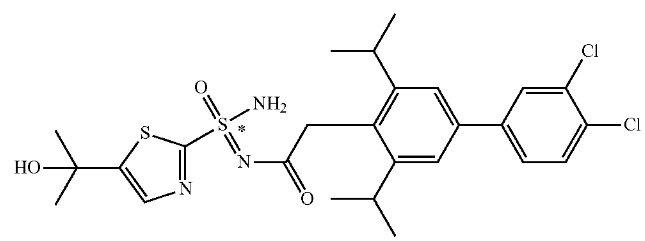 [SMILES: CC(C)c1cc(-c2ccc(Cl)c(Cl)c2)cc(C(C)C)c1CC(=O)N=S(N)(=O)c1ncc(C(C)(C)O)s1] | (R) or (S)-N-(amino(5-(2-hydroxypropan-2-yl)thiazol-2-yl)(oxo)-λ6-sulfaneylidene)-2-(3',4'-dichloro-3,5-diisopropyl-[1,1'-biphenyl]-4-yl)acetamide | CHIRALPAK IF, 2*25 cm, 5 um | IPA in Hex (0.1% FA) | 568 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 171 | 221a | 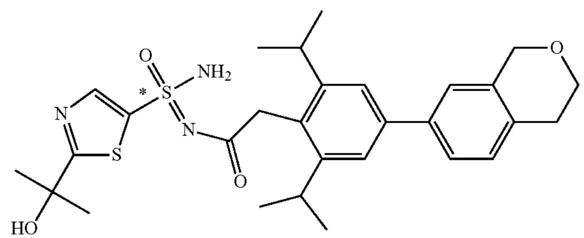 [SMILES: CC(C)c1cc(-c2ccc3c(c2)COCC3)cc(C(C)C)c1CC(=O)N=S(N)(=O)c1cnc(C(C)(C)O)s1] | (R) or (S)-N-(amino(2-(2-hydroxypropan-2-yl)thiazol-5-yl)(oxo)-λ⁶-sulfaneylidene)-2-(4-(isochroman-7-yl)-2,6-diisopropylphenyl)acetamide | CHIRALPAK IF, 2*25 cm, 5 um | EtOH in Hex (0.1% FA) | 556 |
| 172 | 221b | 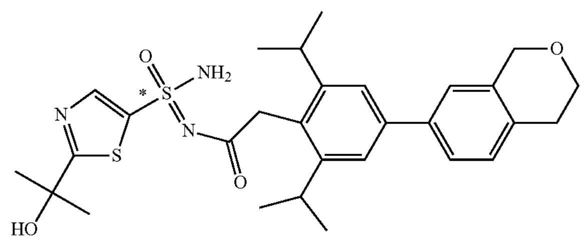 [SMILES: CC(C)c1cc(-c2ccc3c(c2)COCC3)cc(C(C)C)c1CC(=O)N=S(N)(=O)c1cnc(C(C)(C)O)s1] | (S) or (R)-N-(amino(2-(2-hydroxypropan-2-yl)thiazol-5-yl)(oxo)-λ⁶-sulfaneylidene)-2-(4-(isochroman-7-yl)-2,6-diisopropylphenyl)acetamide | CHIRALPAK IF, 2*25 cm, 5 um | EtOH in Hex (0.1% FA) | 556 |
| 173 | 229a | 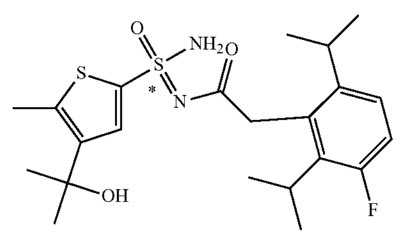 [SMILES: Cc1sc(S(N)(=O)=NC(=O)Cc2c(C(C)C)ccc(F)c2C(C)C)cc1C(C)(C)O] | (R) or (S)-N-(amino(4-(2-hydroxypropan-2-yl)-5-methylthiophen-2-yl)(oxo)-λ⁶-sulfaneylidene)-2-(3-fluoro-2,6-diisopropylphenyl)acetamide | CHIRALPAK IC, 2*25 cm, 5 um | IPA in Hex (0.1% FA) | 455 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 174 | 229b | 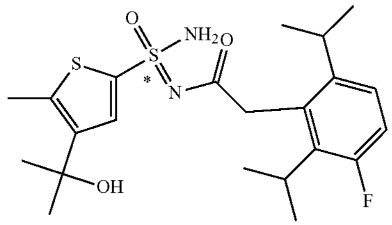 [SMILES: Cc1sc(S(N)(=O)=NC(=O)Cc2c(C(C)C)ccc(F)c2C(C)C)cc1C(C)(C)O] | (S) or (R)-N-(amino(4-(2-hydroxypropan-2-yl)-5-methylthiophen-2-yl)(oxo)-λ6-sulfaneylidene)-2-(3-fluoro-2,6-diisopropylphenyl)acetamide | CHIRALPAK IC, 2*25 cm, 5 um | IPA in Hex (0.1% FA) | 455 |
| 175 | 234b | 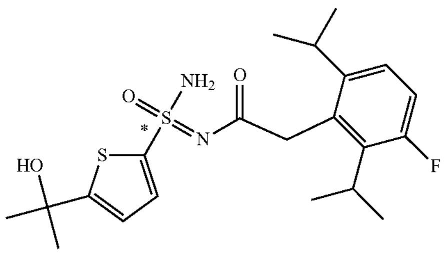 [SMILES: CC(C)c1ccc(F)c(C(C)C)c1CC(=O)N=S(N)(=O)c1ccc(C(C)(C)O)s1] | (S) or (R)-N-(amino(5-(2-hydroxypropan-2-yl)thiophen-2-yl)(oxo)-λ6-sulfaneylidene)-2-(3-fluoro-2,6-diisopropylphenyl)acetamide | Chiralpak ID, 2*25 cm, 5 um | IPA in Hex (0.1% FA) | 441 |
| 176 | 234a | 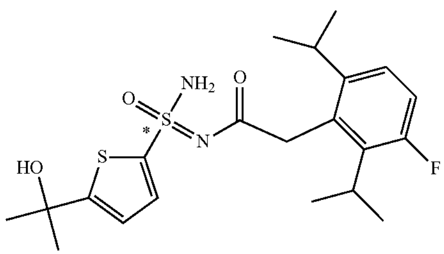 [SMILES: CC(C)c1ccc(F)c(C(C)C)c1CC(=O)N=S(N)(=O)c1ccc(C(C)(C)O)s1] | (R) or (S)-N-(amino(5-(2-hydroxypropan-2-yl)thiophen-2-yl)(oxo)-λ6-sulfaneylidene)-2-(3-fluoro-2,6-diisopropylphenyl)acetamide | Chiralpak ID, 2*25 cm, 5 um | IPA in Hex (0.1% FA) | 441 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 177 | 236a | 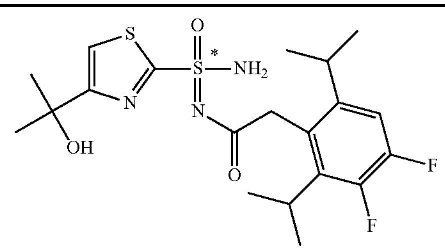 | (R) or (S)-N-(amino(4-(2-hydroxypropan-2-yl)thiazol-2-yl)(oxo)-λ⁶-sulfaneylidene)-2-(3,4-difluoro-2,6-diisopropylphenyl)acetamide | Chiralpak ID, 2*25 cm, 5 um | IPA in Hex (0.1% FA) | 460 |
| 178 | 236b | 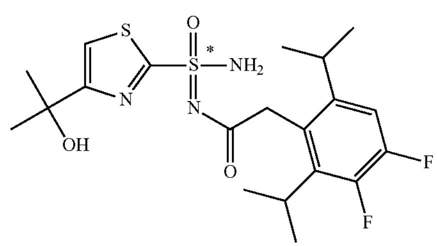 [SMILES: CC(C)c1cc(F)c(F)c(C(C)C)c1CC(=O)N=S(N)(=O)c1nc(C(C)(C)O)cs1] | (S) or (R)-N-(amino(4-(2-hydroxypropan-2-yl)thiazol-2-yl)(oxo)-λ⁶-sulfaneylidene)-2-(3,4-difluoro-2,6-diisopropylphenyl)acetamide | Chiralpak ID, 2*25 cm, 5 um | IPA in Hex (0.1% FA) | 460 |
| 179 | 242a | 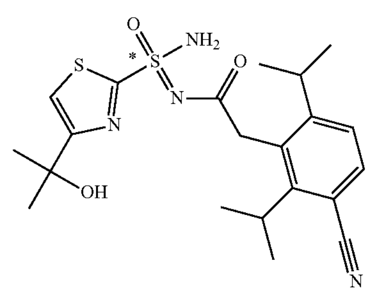 [SMILES: CC(C)c1ccc(C#N)c(C(C)C)c1CC(=O)N=S(N)(=O)c1nc(C(C)(C)O)cs1] | (R) or (S)-N-(amino(4-(2-hydroxypropan-2-yl)thiazol-2-yl)(oxo)-λ⁶-sulfaneylidene)-2-(3-cyano-2,6-diisopropylphenyl)acetamide | Chiralpak ID, 2*25 cm, 5 um | IPA in Hex (0.1% FA) | 449 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 180 | 242b | 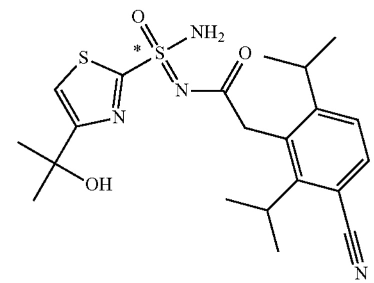 [SMILES: CC(C)c1ccc(C#N)c(C(C)C)c1CC(=O)N=S(N)(=O)c1nc(C(C)(C)O)cs1] | (S) or (R)-N-(amino(4-(2-hydroxypropan-2-yl)thiazol-2-yl)(oxo)-λ6-sulfaneylidene)-2-(3-cyano-2,6-diisopropylphenyl)acetamide | Chiralpak ID, 2*25 cm, 5 um | IPA in Hex (0.1% FA) | 449 |
| 181 | 243a | 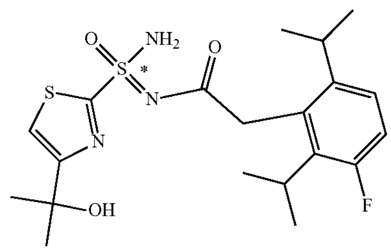 [SMILES: CC(C)c1ccc(F)c(C(C)C)c1CC(=O)N=S(N)(=O)c1nc(C(C)(C)O)cs1] | (R) or (S)-N-(amino(4-(2-hydroxypropan-2-yl)thiazol-2-yl)(oxo)-λ6-sulfaneylidene)-2-(3-fluoro-2,6-diisopropylphenyl)acetamide | Chiralpak ID, 2*25 cm, 5 um | IPA in Hex (0.1% FA) | 442 |
| 182 | 243b | 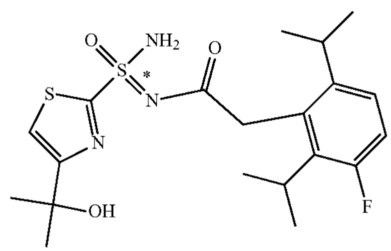 [SMILES: CC(C)c1ccc(F)c(C(C)C)c1CC(=O)N=S(N)(=O)c1nc(C(C)(C)O)cs1] | (S) or (R)-N-(amino(4-(2-hydroxypropan-2-yl)thiazol-2-yl)(oxo)-λ6-sulfaneylidene)-2-(3-fluoro-2,6-diisopropylphenyl)acetamide | Chiralpak ID, 2*25 cm, 5 um | IPA in Hex (0.1% FA) | 442 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 183 | 227a | 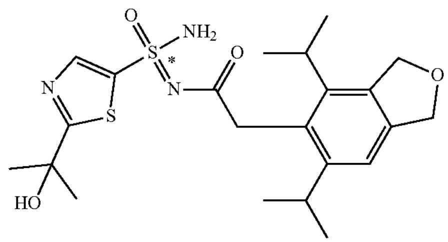 [SMILES: CC(C)c1cc2c(c(C(C)C)c1CC(=O)N=S(N)(=O)c1cnc(C(C)(C)O)s1)COC2] | (R) or (S)-N-(amino(2-(2-hydroxypropan-2-yl)thiazol-5-yl)(oxo)-λ⁶-sulfaneylidene)-2-(4,6-diisopropyl-1,3-dihydroisobenzofuran-5-yl)acetamide | Chiralpak IA, 2*25 cm, 5 um | EtOH in Hex (0.1% FA) | 466 |
| 184 | 227b | 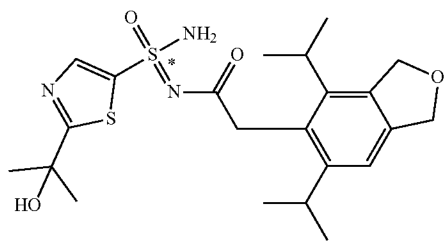 [SMILES: CC(C)c1cc2c(c(C(C)C)c1CC(=O)N=S(N)(=O)c1cnc(C(C)(C)O)s1)COC2] | (S) or (R)-N-(amino(2-(2-hydroxypropan-2-yl)thiazol-5-yl)(oxo)-λ⁶-sulfaneylidene)-2-(4,6-diisopropyl-1,3-dihydroisobenzofuran-5-yl)acetamide | Chiralpak IA, 2*25 cm, 5 um | EtOH in Hex (0.1% FA) | 466 |
| 185 | 251b | 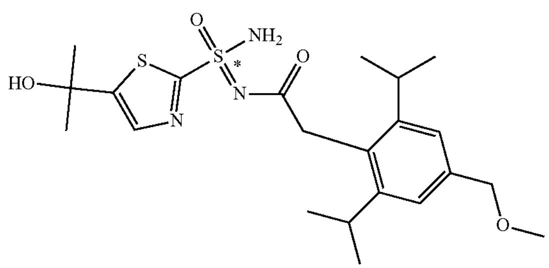 [SMILES: COCc1cc(C(C)C)c(CC(=O)N=S(N)(=O)c2ncc(C(C)(C)O)s2)c(C(C)C)c1] | (R) or (S)-N-(amino(5-(2-hydroxypropan-2-yl)thiazol-2-yl)(oxo)-λ⁶-sulfaneylidene)-2-(2,6-diisopropyl-4-(methoxymethyl)phenyl)acetamide | Chiralpak ID, 2*25 cm, 5 um | IPA in Hex (0.1% FA) | 468 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 186 | 251a | 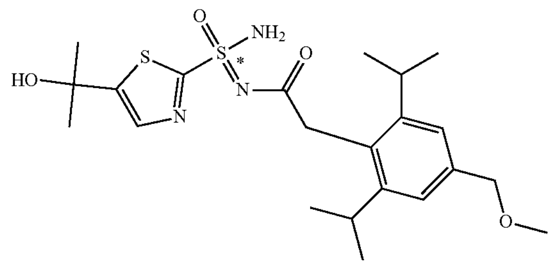 [SMILES: COCc1cc(C(C)C)c(CC(=O)N=S(N)(=O)c2ncc(C(C)(C)O)s2)c(C(C)C)c1] | (S) or (R)-N-(amino(5-(2-hydroxypropan-2-yl)thiazol-2-yl)(oxo)-λ6-sulfaneylidene)-2-(2,6-diisopropyl-4-(methoxymethyl)phenyl)acetamide | Chiralpak ID, 2*25 cm, 5 um | IPA in Hex (0.1% FA) | 468 |
| 187 | 228a | 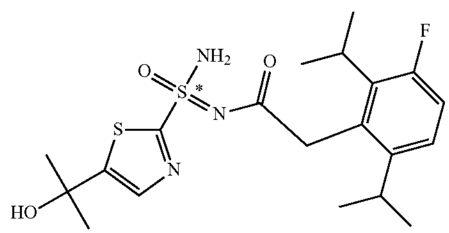 [SMILES: CC(C)c1ccc(F)c(C(C)C)c1CC(=O)N=S(N)(=O)c1ncc(C(C)(C)O)s1] | (S) or (R)-N-(amino(5-(2-hydroxypropan-2-yl)thiazol-2-yl)(oxo)-λ6-sulfaneylidene)-2-(3-fluoro-2,6-diisopropylphenyl)acetamide | Chiralpak ID, 2*25 cm, 5 um | IPA in Hex (0.1% FA) | 442 |
| 188 | 228b | 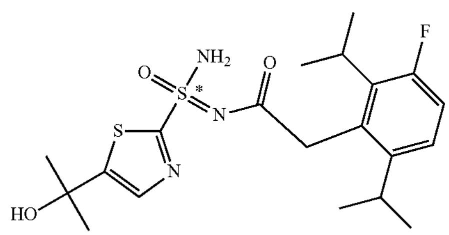 [SMILES: CC(C)c1ccc(F)c(C(C)C)c1CC(=O)N=S(N)(=O)c1ncc(C(C)(C)O)s1] | (R) or (S)-N-(amino(5-(2-hydroxypropan-2-yl)thiazol-2-yl)(oxo)-λ6-sulfaneylidene)-2-(3-fluoro-2,6-diisopropylphenyl)acetamide | Chiralpak ID, 2*25 cm, 5 um | IPA in Hex (0.1% FA) | 442 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]$^+$ |
|---|---|---|---|---|---|---|
| 189 | 226a | 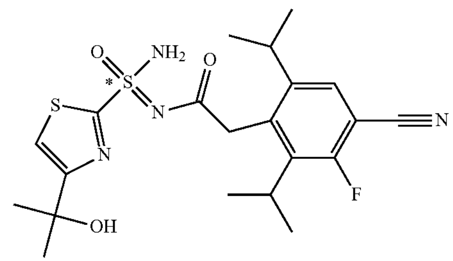 [SMILES: CC(C)c1cc(C#N)c(F)c(C(C)C)c1CC(=O)N=S(N)(=O)c1nc(C(C)(C)O)cs1] | (S) or (R)-N-(amino(4-(2-hydroxypropan-2-yl)thiazol-2-yl)(oxo)-$\lambda^6$-sulfaneylidene)-2-(4-cyano-3-fluoro-2,6-diisopropylphenyl)acetamide | CHIRALPAK IG, 20*250 mm, 5 um | IPA in Hex (0.1% FA) | 467 |
| 190 | 226b | 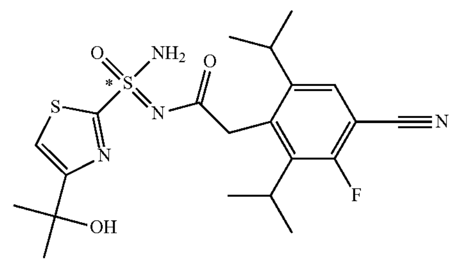 [SMILES: CC(C)c1cc(C#N)c(F)c(C(C)C)c1CC(=O)N=S(N)(=O)c1nc(C(C)(C)O)cs1] | (R) or (S)-N-(amino(4-(2-hydroxypropan-2-yl)thiazol-2-yl)(oxo)-$\lambda^6$-sulfaneylidene)-2-(4-cyano-3-fluoro-2,6-diisopropylphenyl)acetamide | CHIRALPAK IG, 20*250 mm, 5 um | IPA in Hex (0.1% FA) | 467 |
| 191 | 225a | 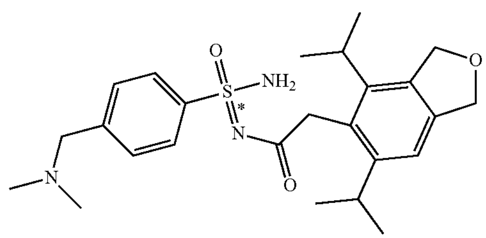 [SMILES: CC(C)c1cc2c(c(C(C)C)c1CC(=O)N=S(N)(=O)c1ccc(CN(C)C)cc1)COC2] | (R) or (S)-N-(amino(4-((dimethylamino)methyl)phenyl)(oxo)-$\lambda^6$-sulfaneylidene)-2-(4,6-diisopropyl-1,3-dihydroisobenzofuran-5-yl)acetamide | Chiralpak ID, 2*25 cm, 5 um | EtOH in Hex (8 mM NH$_3$·MeOH) | 458 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 192 | 225b | 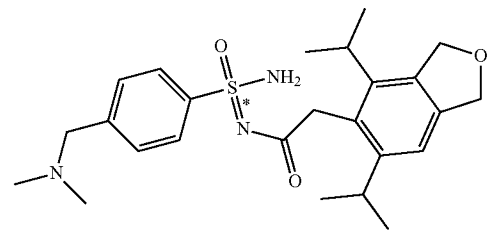 [SMILES: CC(C)c1cc2c(c(C(C)C)c1CC(=O)N=S(N)(=O)c1ccc(CN(C)C)cc1)COC2] | (S) or (R)-N-(amino(4-((dimethylamino)methyl)phenyl)(oxo)-λ6-sulfaneylidene)-2-(4,6-diisopropyl-1,3-dihydroisobenzofuran-5-yl)acetamide | Chiralpak ID, 2*25 cm, 5 um | EtOH in Hex (8 mM NH3•MeOH) | 458 |
| 193 | 224b | 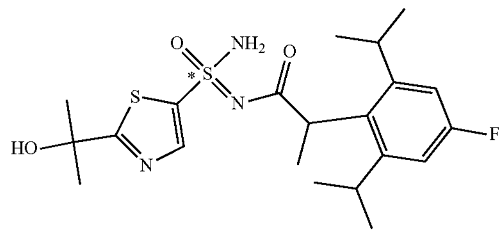 [SMILES: CC(C)c1cc(F)cc(C(C)C)c1C(C)C(=O)N=S(N)(=O)c1cnc(C(C)(C)O)s1] | (S, S) and (S, R)-N-(amino(2-(2-hydroxypropan-2-yl)thiazol-5-yl(oxo)-λ6-sulfaneylidene)-2-(4-fluoro-2,6-diisopropylphenyl)propanamide | Chiralpak IA, 2*25 cm, 5 um | IPA in Hex (0.1% FA) | 456 |
| 194 | 244ba | 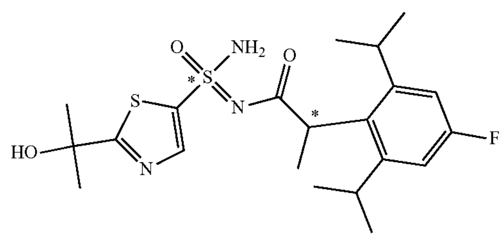 [SMILES: CC(C)c1cc(F)cc(C(C)C)c1C(C)C(=O)N=S(N)(=O)c1cnc(C(C)(C)O)s1] | (R, S) or (R, R)-N-(amino(2-(2-hydroxypropan-2-yl)thiazol-5-yl)(oxo)-λ6-sulfaneylidene)-2-(4-fluoro-2,6-diisopropylphenyl)propanamide | Chiralpak IA, 2*25 cm, 5 um | IPA in Hex (0.1% FA) | 456 |
| 195 | 244aa | 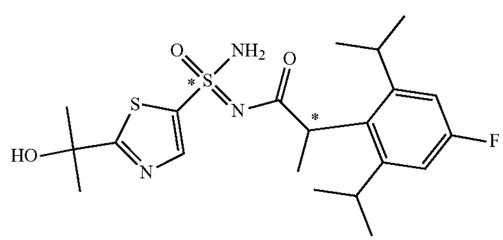 [SMILES: CC(C)c1cc(F)cc(C(C)C)c1C(C)C(=O)N=S(N)(=O)c1cnc(C(C)(C)O)s1] | (R, R) or (R, S)-N-(amino(2-(2-hydroxypropan-2-yl)thiazol-5-yl)(oxo)-λ6-sulfaneylidene)-2-(4-fluoro-2,6-diisopropylphenyl)propanamide | Chiralpak IA, 2*25 cm, 5 um | IPA in Hex (0.1% FA) | 456 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 196 | 220a | 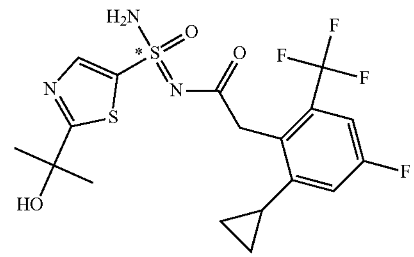 [SMILES: CC(C)(O)c1ncc(S(N)(=O)=NC(=O)Cc2c(C3CC3)cc(F)cc2C(F)(F)F)s1] | (R) or (S)-N-(amino(2-(2-hydroxypropan-2-yl)thiazol-5-yl)(oxo)-λ6-sulfaneylidene)-2-(2-cyclopropyl-4-fluoro-6-(trifluoromethyl)phenyl)acetamide | Chiralpak IC, 2*25 cm, 5 um | EtOH in Hex (0.1% FA) | 466 |
| 197 | 220b | 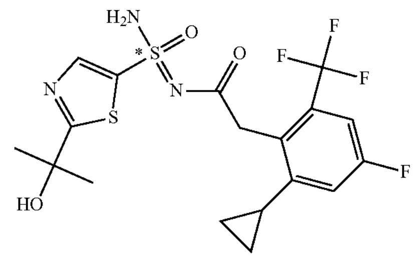 [SMILES: CC(C)(O)c1ncc(S(N)(=O)=NC(=O)Cc2c(C3CC3)cc(F)cc2C(F)(F)F)s1] | (S) or (R)-N-(amino(2-(2-hydroxypropan-2-yl)thiazol-5-yl)(oxo)-λ6-sulfaneylidene)-2-(2-cyclopropyl-4-fluoro-6-(trifluoromethyl)phenyl)acetamide | Chiralpak IC, 2*25 cm, 5 um | EtOH in Hex (0.1% FA) | 466 |
| 198 | 218a | 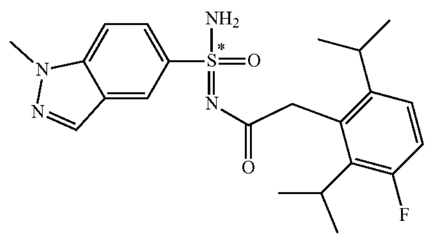 [SMILES: CC(C)c1ccc(F)c(C(C)C)c1CC(=O)N=S(N)(=O)c1ccc2c(cnn2C)c1] | (R) or (S)-N-(amino(1-methyl-1H-indazol-5-yl)(oxo)-λ6-sulfaneylidene)-2-(3-fluoro-2,6-diisopropylphenyl)acetamide | CHIRALPAK IG, 2*25 cm, (5 um) | EtOH in Hex (8 mM NH3•MeOH) | 431 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]$^+$ |
|---|---|---|---|---|---|---|
| 199 | 218b | 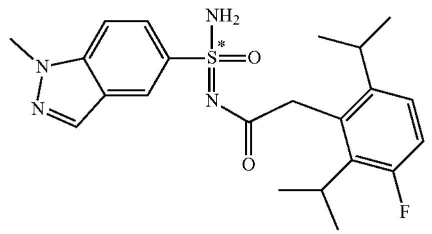 [SMILES: CC(C)c1ccc(F)c(C(C)C)c1CC(=O)N=S(N)(=O)c1ccc2c(cnn2C)c1] | (S) or (R)-N-(amino(1-methyl-1H-indazol-5-yl)(oxo)-$\lambda^6$-sulfaneylidene)-2-(3-fluoro-2,6-diisopropylphenyl)acetamide | CHIRALPAK IG, 2*25 cm, (5 um) | EtOH in Hex (8 mM NH$_3$•MeOH) | 431 |
| 200 | 217a | 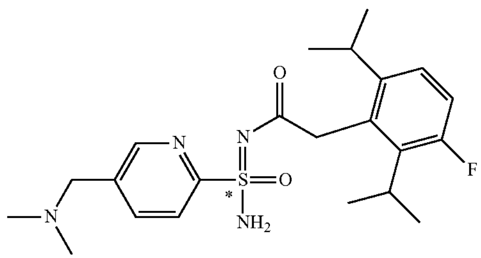 [SMILES: CC(C)c1ccc(F)c(C(C)C)c1CC(=O)N=S(N)(=O)c1ccc(CN(C)C)cn1] | (R) or (S)-N-(amino(5-((dimethylamino)methyl)pyridin-2-yl)(oxo)-$\lambda^6$-sulfaneylidene)-2-(3-fluoro-2,6-diisopropylphenyl)acetamide | CHIRALPAK ID, 2*25 cm, (5 um) | IPA in Hex (8 mM NH$_3$•MeOH) | 435 |
| 201 | 217b | 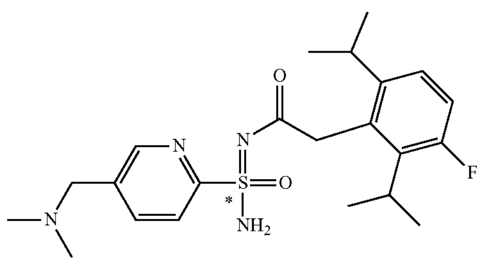 [SMILES: CC(C)c1ccc(F)c(C(C)C)c1CC(=O)N=S(N)(=O)c1ccc(CN(C)C)cn1] | (S) or (R)-N-(amino(5-((dimethylamino)methyl)pyridin-2-yl)(oxo)-$\lambda^6$-sulfaneylidene)-2-(3-fluoro-2,6-diisopropylphenyl)acetamide | CHIRALPAK ID, 2*25 cm, (5 um) | IPA in Hex (8 mM NH$_3$•MeOH) | 435 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 202 | 303 | 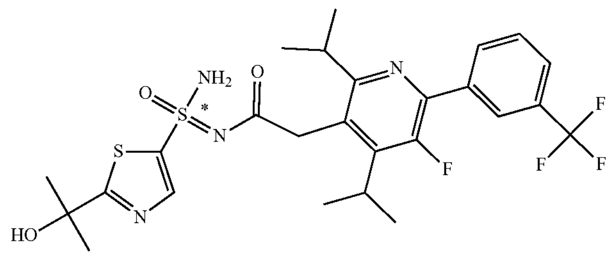 [SMILES: CC(C)c1nc(-c2cccc(C(F)(F)F)c2)c(F)c(C(C)C)c1CC(=O)N=S(N)(=O)c1cnc(C(C)(C)O)s1] | N-(amino(2-(2-hydroxypropan-2-yl)thiazol-5-yl)(oxo)-λ$^6$-sulfaneylidene)-2-(5-fluoro-2,4-diisopropyl-6-(3-(trifluoromethyl)phenyl)pyridin-3-yl)acetamide | Chiralpak ID, 2*25 cm, 5 um | IPA in Hex (0.1% FA) | 587 |
| 203 | 302 | 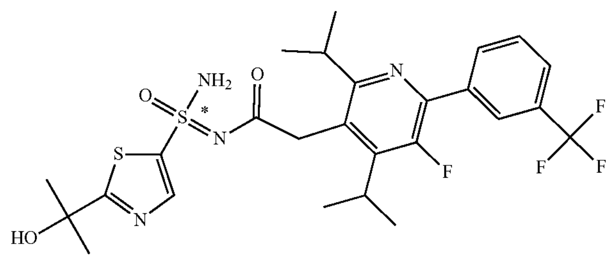 [SMILES: CC(C)c1nc(-c2cccc(C(F)(F)F)c2)c(F)c(C(C)C)c1CC(=O)N=S(N)(=O)c1cnc(C(C)(C)O)s1] | (S) or (R)-N-(amino(2-(2-hydroxypropan-2-yl)thiazol-5-yl)(oxo)-λ$^6$-sulfaneylidene)-2-(5-fluoro-2,4-diisopropyl-6-(3-(trifluoromethyl)phenyl)pyridin-3-yl)acetamide | Chiralpak ID, 2*25 cm, 5 um | IPA in Hex (0.1% FA) | 587 |
| 204 | 203b | 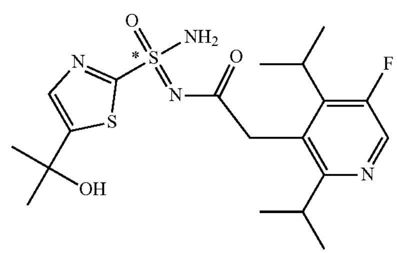 [SMILES: CC(C)c1ncc(F)c(C(C)C)c1CC(=O)N=S(N)(=O)c1ncc(C(C)(C)O)s1] | N-(amino(5-(2-hydroxypropan-2-yl)thiazol-2-yl)(oxo)-λ$^6$-sulfaneylidene)-2-(5-fluoro-2,4-diisopropylpyridin-3-yl)acetamide | CHIRALPAK IF, 2*25 cm, 5 um | EtOH in Hex (0.1% FA) | 443 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 205 | 203a | 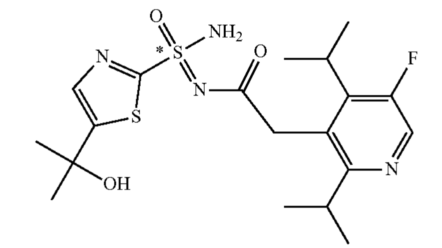 [SMILES: CC(C)c1ncc(F)c(C(C)C)c1CC(=O)N=S(N)(=O)c1ncc(C(C)(C)O)s1] | (S) or (R)-N-(amino(5-(2-hydroxypropan-2-yl)thiazol-2-yl)(oxo)-λ$^6$-sulfaneylidene)-2-(5-fluoro-2,4-diisopropylpyridin-3-yl)acetamide | CHIRALPAK IF, 2*25 cm, 5 um | EtOH in Hex (0.1% FA) | 443 |
| 206 | 202a | 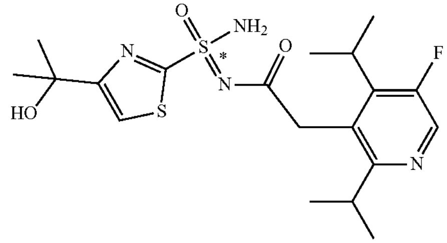 [SMILES: CC(C)c1ncc(F)c(C(C)C)c1CC(=O)N=S(N)(=O)c1nc(C(C)(C)O)cs1] | N-(amino(4-(2-hydroxypropan-2-yl)thiazol-2-yl)(oxo)-λ$^6$-sulfaneylidene)-2-(5-fluoro-2,4-diisopropylpyridin-3-yl)acetamide | Chiralpak ID, 2*25 cm, 5 um | IPA in Hex (0.1% FA) | 443 |
| 207 | 202b | 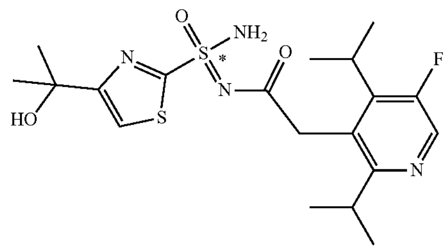 [SMILES: CC(C)c1ncc(F)c(C(C)C)c1CC(=O)N=S(N)(=O)c1nc(C(C)(C)O)cs1] | (S) or (R)-N-(amino(4-(2-hydroxypropan-2-yl)thiazol-2-yl)(oxo)-λ$^6$-sulfaneylidene)-2-(5-fluoro-2,4-diisopropylpyridin-3-yl)acetamide | Chiralpak ID, 2*25 cm, 5 um | IPA in Hex (0.1% FA) | 443 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]⁺ |
|---|---|---|---|---|---|---|
| 208 | 213a | 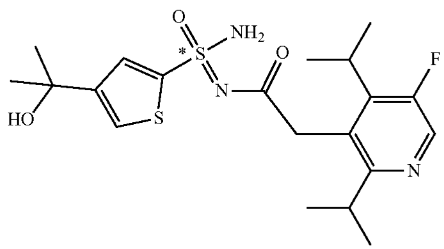 [SMILES: CC(C)c1ncc(F)c(C(C)C)c1CC(=O)N=S(N)(=O)c1cc(C(C)(C)O)cs1] | N-(amino(4-(2-hydroxypropan-2-yl)thiophen-2-yl)(oxo)-λ⁶-sulfaneylidene)-2-(5-fluoro-2,4-diisopropylpyridin-3-yl)acetamide | Chiralpak ID, 2*25 cm, 5 um | IPA in Hex (0.1% FA) | 442 |
| 209 | 213b | 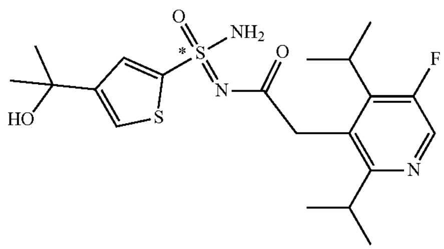 [SMILES: CC(C)c1ncc(F)c(C(C)C)c1CC(=O)N=S(N)(=O)c1cc(C(C)(C)O)cs1] | (S) or (R)-N-(amino(4-(2-hydroxypropan-2-yl)thiophen-2-yl)(oxo)-λ⁶-sulfaneylidene)-2-(5-fluoro-2,4-diisopropylpyridin-3-yl)acetamide | Chiralpak ID, 2*25 cm, 5 um | IPA in Hex (0.1% FA) | 442 |
| 210 | 210a | 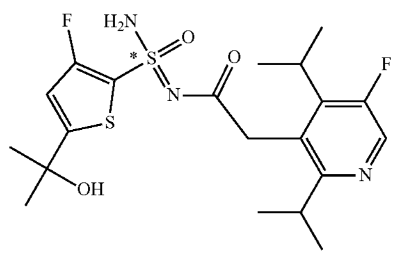 [SMILES: CC(C)c1ncc(F)c(C(C)C)c1CC(=O)N=S(N)(=O)c1sc(C(C)(C)O)cc1F] | (S) or (R)-N-(amino(3-fluoro-5-(2-hydroxypropan-2-yl)thiophen-2-yl)(oxo)-λ⁶-sulfaneylidene)-2-(5-fluoro-2,4-diisopropylpyridin-3-yl)acetamide | CHIRALPAK IG, 20*250 mm, 5 um | IPA in Hex (0.1% FA) | 460 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]$^+$ |
|---|---|---|---|---|---|---|
| 211 | 210b | 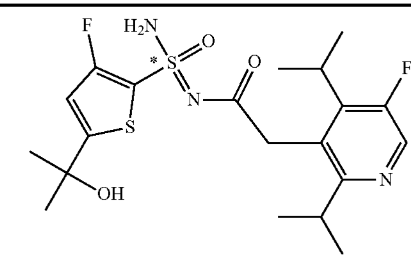 | N-(amino(3-fluoro-5-(2-hydroxypropan-2-yl)thiophen-2-yl)(oxo)-λ$^6$-sulfaneylidene)-2-(5-fluoro-2,4-diisopropylpyridin-3-yl)acetamide | CHIRALPAK IG, 20*250 mm, 5 um | IPA in Hex (0.1% FA) | 460 |
| 212 | 216a | 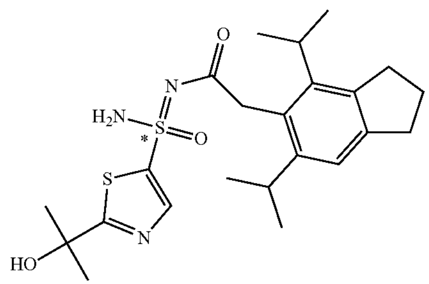 [SMILES: CC(C)c1cc2c(c(C(C)C)c1CC(=O)N=S(N)(=O)c1cnc(C(C)(C)O)s1)CCC2] | (R) or (S)-N-(amino(2-(2-hydroxypropan-2-yl)thiazol-5-yl)(oxo)-λ$^6$-sulfaneylidene)-2-(4,6-diisopropyl-2,3-dihydro-1H-inden-5-yl)acetamide | Chiralpak ID, 2*25 cm, 5 um | EtOH in MTBE (0.1% FA) | 464 |
| 213 | 216b | 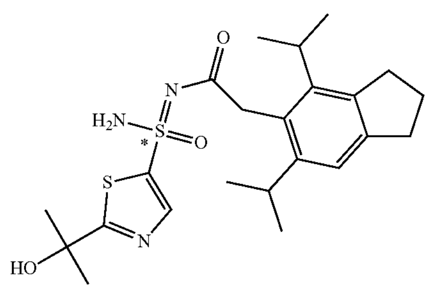 [SMILES: CC(C)c1cc2c(c(C(C)C)c1CC(=O)N=S(N)(=O)c1cnc(C(C)(C)O)s1)CCC2] | (S) or (R)-N-(amino(2-(2-hydroxypropan-2-yl)thiazol-5-yl)(oxo)-λ$^6$-sulfaneylidene)-2-(4,6-diisopropyl-2,3-dihydro-1H-inden-5-yl)acetamide | Chiralpak ID, 2*25 cm, 5 um | EtOH in MTBE (0.1% FA) | 464 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]$^+$ |
|---|---|---|---|---|---|---|
| 214 | 110a' | 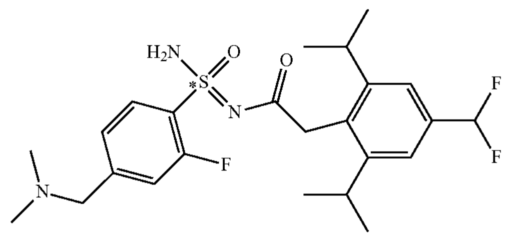 [SMILES: CC(C)c1cc(C(F)F)cc(C(C)C)c1CC(=O)N=S(N)(=O)c1ccc(CN(C)C)cc1F] | (R) or (S)-N-(amino(4-((dimethylamino)methyl)-2-fluorophenyl)(oxo)-$\lambda^6$-sulfaneylidene)-2-(4-(difluoromethyl)-2,6-diisopropylphenyl)acetamide | CHIRALPAK IG, 2*25 cm, (5 um) | EtOH in Hex (8 mM NH$_3$•MeOH) | 484 |
| 215 | 110b' | 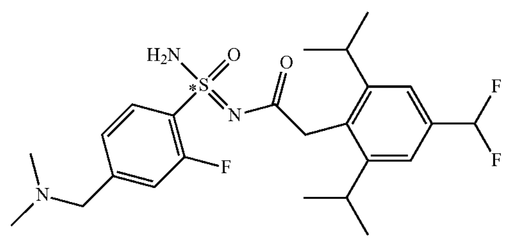 [SMILES: CC(C)c1cc(C(F)F)cc(C(C)C)c1CC(=O)N=S(N)(=O)c1ccc(CN(C)C)cc1F] | (S) or (R)-N-(amino(4-((dimethylamino)methyl)-2-fluorophenyl)(oxo)-$\lambda^6$-sulfaneylidene)-2-(4-(difluoromethyl)-2,6-diisopropylphenyl)acetamide | CHIRALPAK IG, 2*25 cm, (5 um) | EtOH in Hex (8 mM NH$_3$•MeOH) | 484 |
| 216 | 263a | 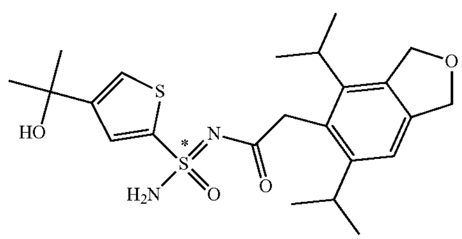 [SMILES: CC(C)c1cc2c(c(C(C)C)c1CC(=O)N=S(N)(=O)c1cc(C(C)(C)O)cs1)COC2] | (R) or (S)-N-(amino(4-(2-hydroxypropan-2-yl)thiophen-2-yl)(oxo)-$\lambda^6$-sulfaneylidene)-2-(4,6-diisopropyl-1,3-dihydroisobenzofuran-5-yl)acetamide | CHIRALPAK IG, 2*25 cm, (5 um) | EtOH in Hex (8 mM NH$_3$•MeOH) | 465 |
| 217 | 263b | 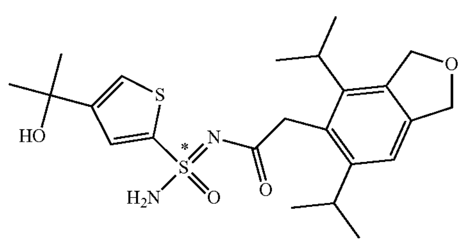 [SMILES: CC(C)c1cc2c(c(C(C)C)c1CC(=O)N=S(N)(=O)c1cc(C(C)(C)O)cs1)COC2] | (S) or (R)-N-(amino(4-(2-hydroxypropan-2-yl)thiophen-2-yl)(oxo)-$\lambda^6$-sulfaneylidene)-2-(4,6-diisopropyl-1,3-dihydroisobenzofuran-5-yl)acetamide | CHIRALPAK IG, 2*25 cm, (5 um) | EtOH in Hex (8 mM NH$_3$•MeOH) | 465 |

TABLE 22-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. Assigned stereochemistry in compound names are tentative.

| Example # | Compound # | Structure | IUPAC Name | Column | Eluents | LC-MS [M + H]+ |
|---|---|---|---|---|---|---|
| 218 | 264a | 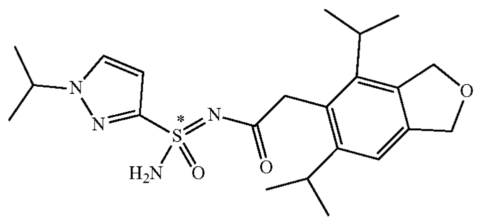 [SMILES: CC(C)c1cc2c(c(C(C)C)c1CC(=O)N=S(N)(=O)c1ccn(C(C)C)n1)COC2] | (R) or (S)-N-(amino(1-isopropyl-1H-pyrazol-3-yl)(oxo)-λ6-sulfaneylidene)-2-(4,6-diisopropyl-1,3-dihydroisobenzofuran-5-yl)acetamide | Chiralpak ID, 2*25 cm, 5 um | EtOH in Hex (0.1% FA) | 433 |
| 219 | 264b | 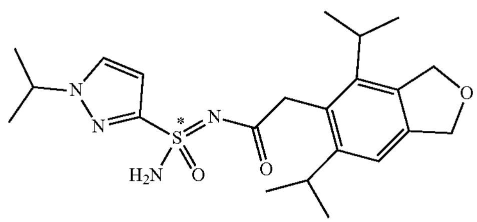 [SMILES: CC(C)c1cc2c(c(C(C)C)c1CC(=O)N=S(N)(=O)c1ccn(C(C)C)n1)COC2] | (S) or (R)-N-(amino(1-isopropyl-1H-pyrazol-3-yl)(oxo)-λ6-sulfaneylidene)-2-(4,6-diisopropyl-1,3-dihydroisobenzofuran-5-yl)acetamide | Chiralpak ID, 2*25 cm, 5 um | EtOH in Hex (0.1% FA) | 433 |

Example 159: $^1$H NMR (400 MHz, DMSO-d$_6$) δ 7.92 (s, 2H), 7.62 (s, 1H), 7.60 (s, 1H), 7.08 (dd, J=8.7, 5.5 Hz, 1H), 6.91 (dd, J=11.9, 8.6 Hz, 1H), 5.19 (s, 1H), 3.68 (d, J=2.5 Hz, 2H), 3.20-2.90 (m, 2H), 1.39 (s, 6H), 1.25-1.04 (m, 12H).

Example 183: $^1$H NMR (400 MHz, DMSO-d$_6$) δ 8.07 (br s, 3H), 7.04 (s, 1H), 6.29 (s, 1H), 5.05 (s, 2H), 4.88 (s, 2H), 3.77-3.62 (m, 2H), 3.25-2.90 (m, 2H), 1.48 (s, 6H), 1.15-0.99 (m, 12H).

Example 216: $^1$H NMR (300 MHz, DMSO-d$_6$) δ 7.82 (br s, 2H), 7.59 (s, 1H), 7.58 (s, 1H), 7.03 (s, 1H), 5.19 (s, 1H), 5.04 (s, 2H), 4.87 (s, 2H), 3.67 (s, 2H), 3.25-3.00 (m, 2H), 1.38 (s, 6H), 1.20-0.80 (m, 12H).

The following protocol is suitable for testing the activity of the compounds disclosed herein.

Procedure 1: IL-1β Production in PMA-Differentiated THP-1 Cells Stimulated with Gramicidin THP-1 cells were purchased from the American Type Culture Collection and sub-cultured according to instructions from the supplier. Cells were cultured in complete RPMI 1640 (containing 10% heat inactivated FBS, penicillin (100 units/ml) and streptomycin (100 μg/ml)), and maintained in log phase prior to experimental setup. Prior to the experiment, compounds were dissolved in dimethyl sulfoxide (DMSO) to generate a 30 mM stock. The compound stock was first pre-diluted in DMSO to 3, 0.34, 0.042 and 0.0083 mM intermediate concentrations and subsequently spotted using Echo550 liquid handler into an empty 384-well assay plate to achieve desired final concentration (e.g. 100, 33, 11, 3.7, 1.2, 0.41, 0.14, 0.046, 0.015, 0.0051, 0.0017 μM). DMSO was backfilled in the plate to achieve a final DMSO assay concentration of 0.37%. The plate was then sealed and stored at room temperature until required.

THP-1 cells were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, and resuspended in RPMI 1640 (containing 2% heat inactivated FBS, penicillin (100 units/ml) and streptomycin (100 μg/ml). The cells were plated in the 384-well assay plate containing the spotted compounds at a density of 50,000 cells/well (final assay volume 50 μl). Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). The plates were incubated for 18 h at 4° C. and read using the preset HTRF program (donor emission at 620 nm, acceptor emission at 668 nm) of the SpectraMax i3x spectrophotometer (Molecular Devices, software SoftMax 6). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1β production in PMA-differentiated THP-1 cells.

Procedure 2: IL-1β Production in PMA-Differentiated THP-1 Cells Stimulated with Gramicidin THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. Compounds were dissolved in dimethyl sulfoxide (DMSO) to generate a 30 mM stock. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were first dissolved in assay medium to obtain a 5× top concentration of 500 μM. 10 step dilutions (1:3) were then undertaken in assay medium containing 1.67% DMSO. 5× compound solutions were added to the culture medium to achieve desired final concentration (e.g. 100, 33, 11, 3.7, 1.2, 0.41, 0.14, 0.046, 0.015, 0.0051, 0.0017 μM). Final DMSO concentration was at 0.37%. Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1β production in PMA-differentiated THP-1 cells.

Procedure 3

1. Experimental procedure
   1.1 Cell Culture
   1) Culture THP-1 cells in the complete RPMI-1640 medium with 10% FBS at 37° C., 5% CO$_2$.
   2) Passage the cells every 3 days by inoculating 3×10$^5$ cells per ml.
   1.2 Compound Preparation
   Prepare the 3-fold serial dilution of the compounds with DMSO in a 384-well LDV Microplate using TECAN EVO system to generate the compound source plate with 10 concentrations. Top concentration is 30 mM.
   1.3 Cell preparation
   1) Centrifuge THP-1 cells at 350 g for 5 min.
   2) Re-suspend cells with complete RMPI-1640 medium, and count cells.
   3) Seed cells in T225 flask, about 2.5×10$^7$ per flask, treat cells with 20 ng/ml PMA (final DMSO concentration<1%).
   4) Incubate overnight.
   1.4 THP-1 Stimulation
   1) Wash adherent THP-1 cells with PBS, and detach cells with 4 ml trypsin for T225 flask.
   2) Centrifuge cells at 350 g for 5 min, re-suspend cells with RPMI-1640 containing 2% FBS and count cells with trypan blue.
   3) Transfer 50 nl/well the serial dilution of test compound to 384-well plate by Echo; For the high control and first point of CRID3 (MCC950), transfer 165 nl, then backfill to make the DMSO concentration is consistent in all wells, the plate layout is as below.

4) Seed 50k cells in 40 µl RPMI-1640 with 2% FBS per well in 384-well plate.
5) Incubate for 1 h at 37° C., 5% $CO_2$.
6) Prepare 5× gramicidin, add 10 µl per well, the final concentration is 5 µM, incubate for 2 hrs at 37° C., 5% $CO_2$.
7) Centrifuge at 350 g for 1 min.
8) Pipet 16 µl supernatant by apricot, and transfer into white 384 proxiplate. FIG. 3 depicts the layout of the plates: HC: 100 µM CRID3 (MCC950)+5 µM gramicidin LC: 5 µM Gramicidin.

1.5 IL-1β detection
1) Homogenize the 5× diluent #5 with a vortex and add 1 volume of stock solution in 4 volumes of distilled water.
2) Thaw 20× stock solution of anti-IL1β-Cryptate-antibody and anti-IL1β XL-antibody. Dilute these two antibodies to 1× with detection buffer #3.
3) Pre-mix the two ready-to-use antibody solutions just prior to use.
4) Dispense 4 ul of pre-mixed Anti-IL1β antibodies working solution into all wells.
5) Seal the plate and incubate overnight at 4° C.
6) Read the cell plate using EnVison and plot Readout vs. the test compound concentration to calculate the $IC_{50}$.

2. Data Analysis:
1. $IC_{50}$ of compounds can be calculated using the following formulas
Formula for $IC_{50}$ % inhibition=100−100×[$HC_{ave}$−Readout/($HC_{ave}$−$LC_{ave}$)]

2. Fit the normalized data in a dose-response manner using XLfit, and calculate the compound concentration.

Table 12 shows the biological activity of compounds in hTHP-1 assay containing 2% fetal bovine serum: <0.008 µM="++++++"; ≥0.008 and <0.04 µM="+++++"; ≥0.04 and <0.2 µM="++++"; ≥0.2 and <1 µM="+++"; ≥1 and <5 µM="++"; ≥5 and <30 µM="+".

TABLE 12

Average $IC_{50}$ of compounds in hTHP-1 assay

| Example # | Compound Number | hTHP-1 $IC_{50}$ |
|---|---|---|
| 1 | 131 | ++ |
| 2 | 131b or 131a | ++ |
| 3 | 131a or 131b | >30 µM |
| 4 | 129 | + |
| 5 | 129b or 129a | >30 µM |
| 6 | 129a or 129b | ++ |
| 7 | 132 | +++ |
| 8 | 132b | ++ |
| 9 | 132a | +++ |
| 10 | 134 | + |
| 11 | 137 | + |
| 12 | 136 | >30 µM |
| 13 | 133 | +++ |
| 14 | 141 | +++++ |
| 15 | 139 | ++ |
| 16 | 138 | +++ |
| 17 | 140 | +++++ |
| 18 | 142 | ++++ |
| 19 | 143 | +++++ |
| 20 | 197 | +++ |
| 21 | 101 | ++++ |
| 22 | 152 | +++ |
| 23 | 150 | ++ |
| 24 | 148 | +++ |
| 25 | 147 | ++ |
| 26 | 113 | ++ |
| 27 | 151 | ++ |
| 28 | 114 | ++ |
| 29 | 112 | + |
| 30 | 116 | + |
| 31 | 105 | ++ |
| 32 | 117 | + |
| 33 | 109 | +++ |
| 34 | 146 | ++ |
| 35 | 110 | +++ |
| 36 | 126 | +++ |
| 37 | 104 | ++++ |
| 38 | 130 | +++ |
| 39 | 107 | +++ |
| 40 | 106 | +++ |
| 41 | 135 | + |
| 42 | 133b or 133a | ++++ |
| 43 | 133a or 133b | ++ |
| 44 | 141b or 141a | ++++ |
| 45 | 141a or 141b | ++ |
| 46 | 139b or 139a | >30 µM |
| 47 | 139a or 139b | +++ |
| 48 | 138b or 138a | ++++ |
| 49 | 138a or 138b | + |
| 50 | 140b or 140a | +++++ |
| 51 | 140a or 140b | +++ |
| 52 | 144b or 144a | +++++ |
| 53 | 144a or 144b | ++ |
| 54 | 145b or 145a | +++++ |
| 55 | 145a or 145b | ++ |
| 56 | 197b or 197a | +++ |
| 57 | 197a or 197b | ++ |
| 58 | 116b or 116a | >30 µM |
| 59 | 116a or 116b | + |
| 60 | 106b or 106a | ++++ |
| 61 | 106a or 106b | + |
| 62 | 117b or 117a | ++ |
| 63 | 117a or 117b | >30 µM |
| 64 | 152b or 152a | +++ |
| 65 | 152a or 152b | + |
| 66 | 150b or 150a | +++ |
| 67 | 150a or 150b | >30 µM |
| 68 | 148b or 148a | +++ |
| 69 | 148a or 148b | + |
| 70 | 147b or 147a | +++ |
| 71 | 147a or 147b | + |
| 72 | 114b or 114a | ++ |
| 73 | 114a or 114b | >30 µM |
| 74 | 112b or 112a | >30 µM |
| 75 | 112a or 112b | ++ |
| 76 | 101b or 101a | ++++ |
| 77 | 101a or 101b | ++ |
| 78 | 126b or 126a | +++ |
| 79 | 126a or 126b | + |
| 80 | 104b or 104a | +++++ |
| 81 | 104a or 104b | +++ |
| 82 | 130b or 130a | + |
| 83 | 130a or 130b | ++++ |
| 84 | 107b or 107a | ++++ |
| 85 | 107a or 107b | + |
| 86 | 110b or 110a | ++ |
| 87 | 110a or 110b | ++++ |
| 88 | 241 | +++ |
| 89 | 219 | +++ |
| 90 | 218 | + |
| 91 | 217 | + |
| 92 | 214 | >30 µM |
| 93 | 235 | >30 µM |
| 94 | 230 | ++ |
| 95 | 245 | +++ |
| 96 | 244 | >30 µM |
| 97 | 221 | +++ |
| 98 | 220 | + |
| 99 | 304 | ++ |
| 100 | 301 | +++ |

TABLE 12-continued

Average $IC_{50}$ of compounds in hTHP-1 assay

| Example # | Compound Number | hTHP-1 $IC_{50}$ |
|---|---|---|
| 101 | 212 | + |
| 102 | 240 | + |
| 103 | 258 | +++ |
| 104 | 257 | +++ |
| 105 | 256 | ++++ |
| 106 | 201 | ++++ |
| 107 | 255 | + |
| 108 | 254 | ++++ |
| 109 | 253 | ++++ |
| 110 | 252 | +++ |
| 111 | 251 | ++++ |
| 112 | 250 | +++ |
| 113 | 249 | +++++ |
| 114 | 248 | ++ |
| 115 | 247 | +++ |
| 116 | 246 | + |
| 117 | 309 | ++++ |
| 118 | 310 | +++ |
| 119 | 243 | +++ |
| 120 | 242 | +++ |
| 121 | 239 | +++ |
| 122 | 238 | +++ |
| 123 | 237 | +++ |
| 124 | 236 | +++ |
| 125 | 234 | +++ |
| 126 | 233 | +++ |
| 127 | 232 | + |
| 128 | 120 | +++ |
| 129 | 229 | ++++ |
| 130 | 228 | ++ |
| 131 | 308 | + |
| 132 | 227 | ++ |
| 133 | 226 | +++ |
| 134 | 225 | ++ |
| 135 | 224 | ++ |
| 136 | 191 | +++ |
| 137 | 222 | +++ |
| 138 | 307 | ++ |
| 139 | 231 | +++ |
| 140 | 306 | +++ |
| 141 | 305 | ++++ |
| 142 | 216 | ++ |
| 143 | 215 | ++ |
| 144 | 203 | + |
| 145 | 213 | +++ |
| 146 | 204 | + |
| 147 | 202 | ++ |
| 148 | 211 | + |
| 149 | 210 | +++ |
| 150 | 209 | + |
| 151 | 208 | +++ |
| 152 | 207 | +++ |
| 153 | 206 | ++ |
| 154 | 205 | + |
| 155 | 261b | +++ |
| 156 | 261a | +++ |
| 157 | 256a | +++++ |
| 158 | 256b | ++ |
| 159 | 201a | ++++ |
| 160 | 201b | +++ |
| 161 | 258a | ++++ |
| 162 | 258b | + |
| 163 | 249a | ++++ |
| 164 | 249b | ++ |
| 165 | 309b | ++ |
| 166 | 309a | ++++ |
| 167 | 239a | ++ |
| 168 | 239b | +++ |
| 169 | 238a | ++ |
| 170 | 238b | +++ |
| 171 | 221a | +++ |
| 172 | 221b | + |
| 173 | 229a | +++ |
| 174 | 229b | + |
| 175 | 234b | ++ |
| 176 | 234a | +++ |
| 177 | 236a | ++++ |
| 178 | 236b | ++ |
| 179 | 242a | +++ |
| 180 | 242b | + |
| 181 | 243a | ++++ |
| 182 | 243b | + |
| 183 | 227a | +++ |
| 184 | 227b | + |
| 185 | 251b | ++++ |
| 186 | 251a | + |
| 187 | 228a | + |
| 188 | 228b | +++ |
| 189 | 226a | ++ |
| 190 | 226b | ++++ |
| 191 | 225a | ++ |
| 192 | 225b | >30 µM |
| 193 | 244b | >30 µM |
| 194 | 244ab | + |
| 195 | 244aa | >30 µM |
| 196 | 220a | + |
| 197 | 220b | >30 µM |
| 198 | 218a | + |
| 199 | 218b | >30 µM |
| 200 | 217a | ++ |
| 201 | 217b | >30 µM |
| 202 | 303 | +++ |
| 203 | 302 | + |
| 204 | 203b | ++ |
| 205 | 203a | >30 µM |
| 206 | 202a | +++ |
| 207 | 202b | >30 µM |
| 208 | 213a | ++++ |
| 209 | 213b | ++ |
| 210 | 210a | + |
| 211 | 210b | +++ |
| 212 | 216a | >30 µM |
| 213 | 216b | ++ |
| 214 | 110a' | ++++ |
| 215 | 110b' | ++ |
| 216 | 263a | +++ |
| 217 | 263b | + |
| 218 | 264a | + |
| 219 | 264b | >30 µM |
| 220 | 263 | ++++ |
| 221 | 264 | + |
|  | 259 | >17 µM |
|  | 259a | + |
|  | 259b | >30 µM |
|  | 262a | >30 µM |
|  | 262b | + |

A number of embodiments of the invention have been described. Nevertheless, it will be understood that various modifications may be made without departing from the spirit and scope of the invention. Accordingly, other embodiments are within the scope of the following claims.

We claim:

1. A compound of Formula AA

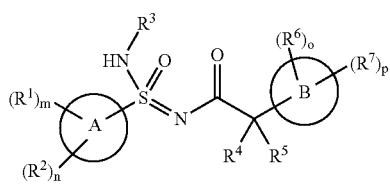

Formula AA wherein
m=0, 1, or 2;
n=0, 1, or 2;
o=1 or 2;
p=0, 1, 2, or 3;
wherein
A is:
thiophenyl optionally substituted with 1 or 2 $R^1$ and optionally substituted with 1 or 2 $R^2$;
phenyl optionally substituted with 1 or 2 $R^1$ and optionally substituted with 1 or 2 $R^2$;
thiazolyl optionally substituted with 1 or 2 $R^1$ and optionally substituted with 1 or 2 $R^2$;
oxazolyl optionally substituted with 1 or 2 $R^1$ and optionally substituted with 1 or 2 $R^2$;
pyridyl optionally substituted with 1 or 2 $R^1$ and optionally substituted with 1 or 2 $R^2$;
pyrazolyl optionally substituted with 1 or 2 $R^1$ and optionally substituted with 1 or 2 $R^2$;
B is phenyl, pyridyl, or pyrimidinyl;

wherein
at least one $R^6$ is ortho to the bond connecting the B ring to the $C(R^4R^5)$ group of Formula AA;
$R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, $S(O)C_1$-$C_6$ alkyl, 5- to 10-membered heteroaryl, and 3- to 7-membered heterocycloalkyl,
wherein the $C_1$-$C_6$ alkyl and 3- to 7-membered heterocycloalkyl is optionally substituted with one or more substituents each independently selected from hydroxy and oxo;
$R^6$ and $R^7$ are each independently selected from $C_1$-$C_6$ alkyl, $C_1$-$C_6$ alkoxy, halo, CN, $NO_2$ $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_5$-$C_8$ carbocyclic ring, wherein the carbocyclic ring is optionally independently substituted with one or more hydroxy or oxo;
each of $R^4$ and $R^5$ is independently selected from hydrogen and $C_1$-$C_6$ alkyl;
$R^{10}$ is $C_1$-$C_6$ alkyl;
each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;
$R^{13}$ is $C_1$-$C_6$ alkyl, $C_6$-$C_{10}$ aryl, or 5- to 10-membered heteroaryl;
each of $R^{11}$ and $R^{12}$ at each occurrence is independently selected from hydrogen and $C_1$-$C_6$ alkyl;
$R^3$ is hydrogen,
or a pharmaceutically acceptable salt thereof.

2. The compound of claim 1, wherein A is any one of:
thiophenyl optionally substituted with 1 or 2 $R^1$ and optionally substituted with 1 or 2 $R^2$;
oxazolyl optionally substituted with 1 or 2 $R^1$ and optionally substituted with 1 or $2R^2$;
thiazolyl optionally substituted with 1 or 2 $R^1$ and optionally substituted with 1 or $2R^2$; or
phenyl optionally substituted with 1 or 2 $R^1$ and optionally substituted with 1 or $2R^2$.

3. The compound of claim 1, wherein m=1 and n=0; optionally wherein the substituted ring A is any one of:

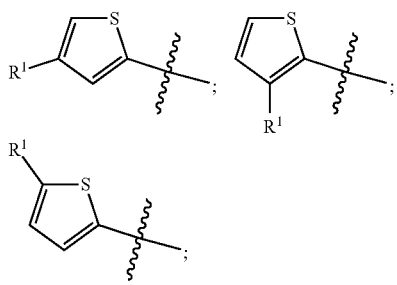

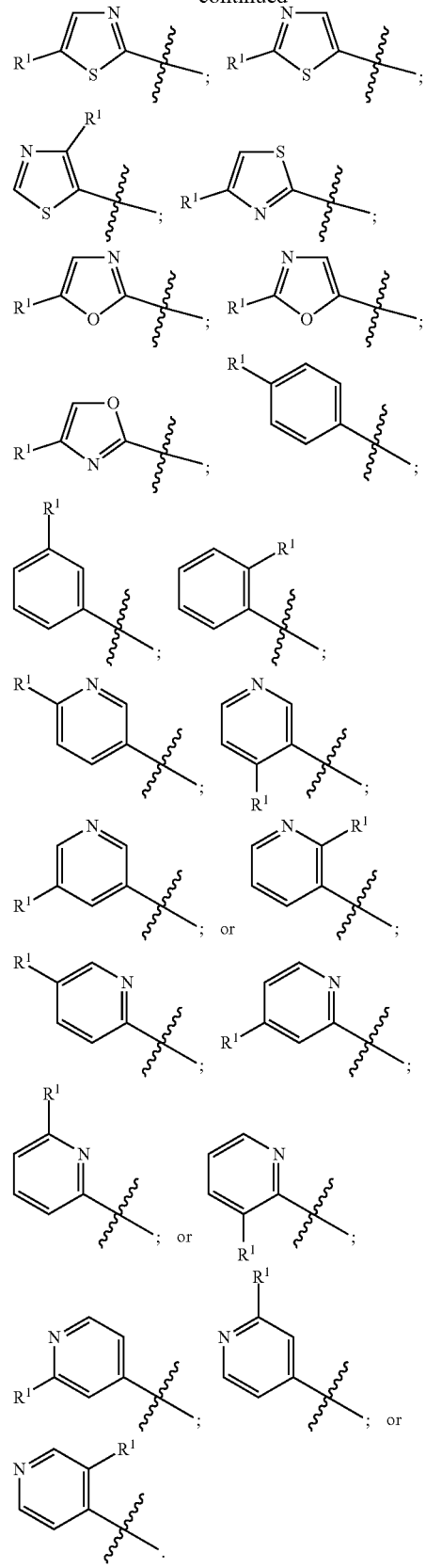

4. The compound of claim 1, wherein m=1 and n=1; optionally wherein the substituted ring A is any one of:

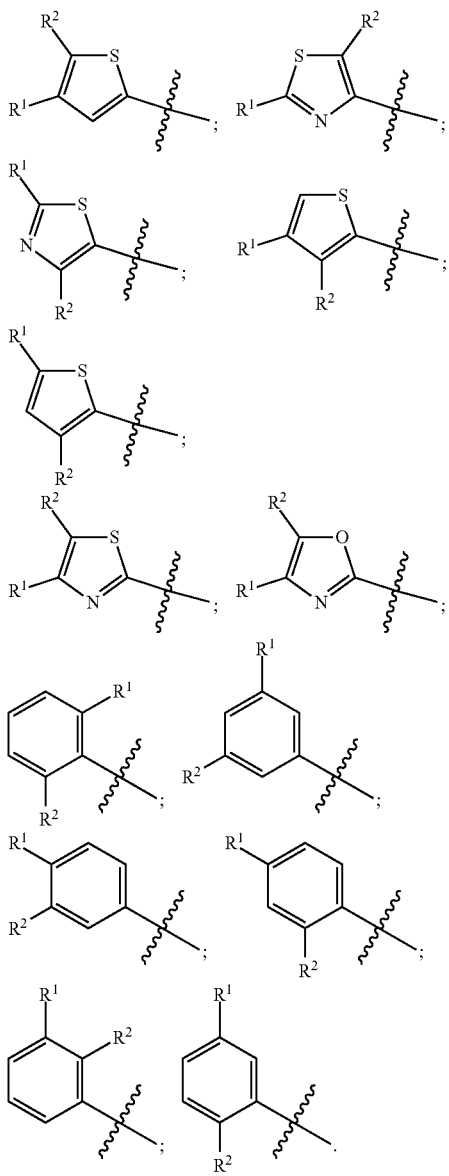

5. The compound of claim 1, wherein m=2 and n=1; optionally wherein the substituted ring A is any one of:

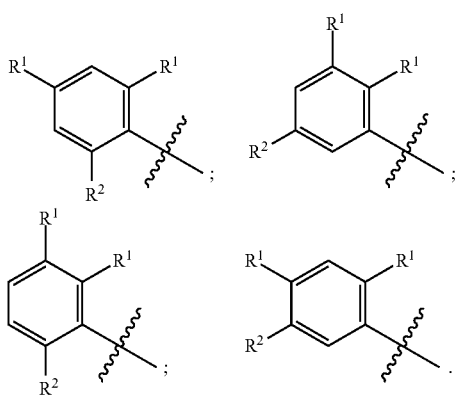

6. The compound of claim 1, wherein $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; $S(O_2)CH_3$; and $S(O_2)NR^{11}R^{12}$.

7. The compound of claim 1, wherein $R^2$ is selected from the group consisting of fluoro; chloro; cyano; methyl; methoxy; ethoxy; isopropyl; 1-hydroxy-2-methylpropan-2-yl; 2-hydroxy-2-propyl; hydroxymethyl; 1-hydroxyethyl; 2-hydroxyethyl; 1-hydroxy-2-propyl; 1-hydroxy-1-cyclopropyl; $COCH_3$; COPh; 2-methoxy-2-propyl; (dimethylamino)methyl; $S(O_2)CH_3$; and $S(O_2)NR^{11}R^{12}$.

8. The compound of claim 1, wherein B is phenyl substituted with 1 or 2 $R^6$ and optionally substituted with 1, 2, or 3 $R^7$; optionally wherein the substituted ring B is any one of

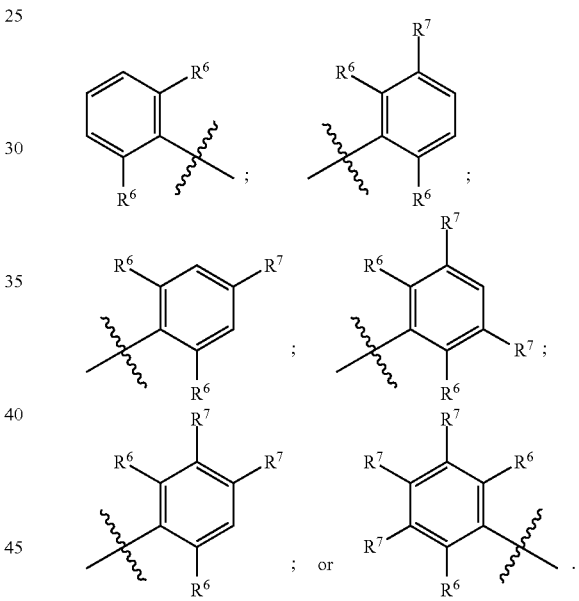

9. The compound of claim 1, wherein B is pyridyl; o=1 or 2; and p=0, 1, or 2; optionally wherein the substituted ring B is

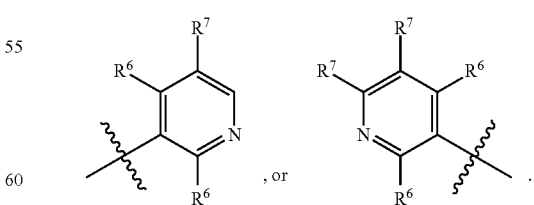

10. The compound of claim 1, wherein each of $R^4$ and $R^5$ is hydrogen.

11. The compound, selected from the group consisting of the compounds below:

| Compound | Structure |
|---|---|
| 101 | 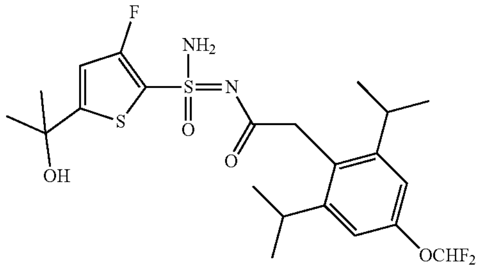 |
| 101a | (R) |
| 101b | (S) |
| 102 | 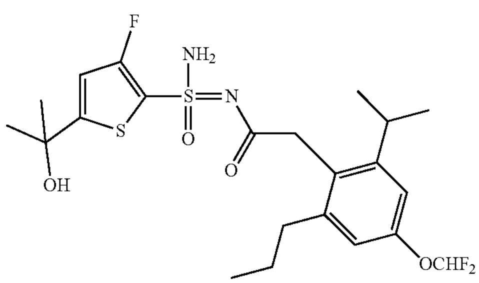 [SMILES: CCCc1cc(OC(F)F)cc(C(C)C)c1CC(=O)N=S(N)(=O)c1sc(C(C)(C)O)cc1F] |
| 103 | 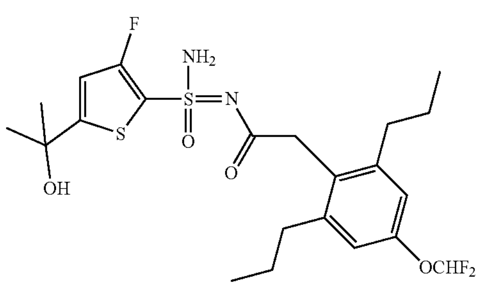 [SMILES: CCCc1cc(OC(F)F)cc(CCC)c1CC(=O)N=S(N)(=O)c1sc(C(C)(C)O)cc1F] |

-continued

| Compound | Structure |
|---|---|
| 104 | 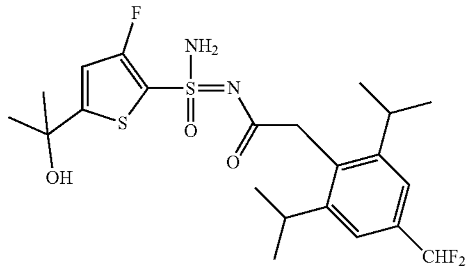 [SMILES: CC(C)c1cc(C(F)F)cc(C(C)C)c1CC(=O)N=S(N)(=O)c1sc(C(C)(C)O)cc1F] |
| 104a | 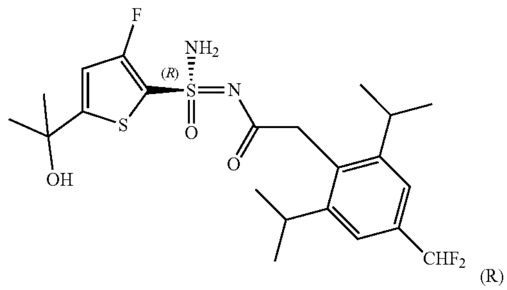 |
| 104b | 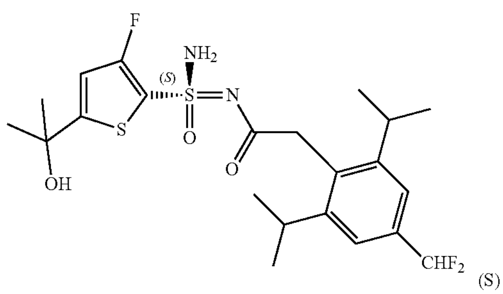 |
| 105 | 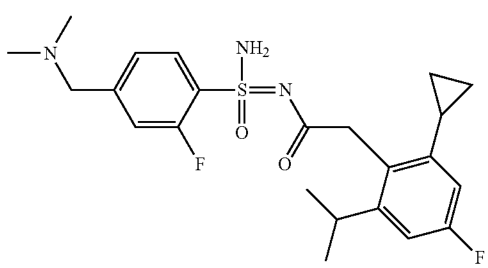 [SMILES: CC(C)c1cc(F)cc(C2CC2)c1CC(=O)N=S(N)(=O)c1ccc(CN(C)C)cc1F] |
| 106 | 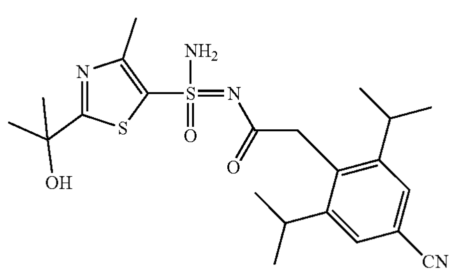 [SMILES: Cc1nc(C(C)(C)O)sc1S(N)(=O)=NC(=O)Cc1c(C(C)C)cc(C#N)cc1C(C)C] |

| Compound | Structure |
|---|---|
| 106a | (R)-isomer structure with thiazole, S(=O)(NH₂)=N, amide linked to 2,6-diisopropyl-4-cyanophenyl |
| 106b | (S)-isomer structure with thiazole, S(=O)(NH₂)=N, amide linked to 2,6-diisopropyl-4-cyanophenyl |
| 107 | thiazole, S(=O)(NH₂)=N, amide linked to 2,6-diisopropyl-4-(OCHF₂)phenyl |
| 107a | (R)-isomer of 107 |
| 107b | (S)-isomer of 107 |

-continued
| Compound | Structure |
|---|---|
| 108 | 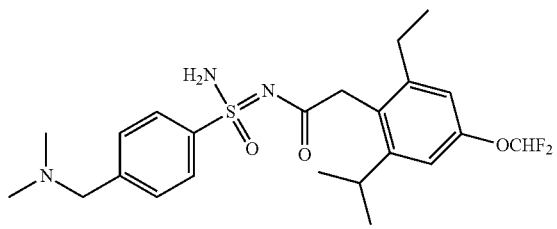 [SMILES: CCc1cc(OC(F)F)cc(C(C)C)c1CC(=O)N=S(N)(=O)c1ccc(CN(C)C)cc1] |
| 109 | 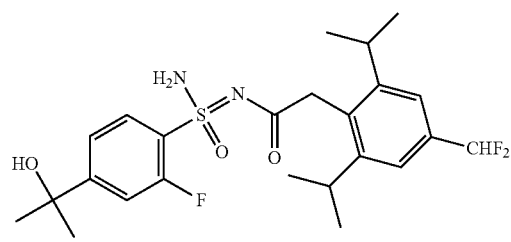 [SMILES: CC(C)c1cc(C(F)F)cc(C(C)C)c1CC(=O)N=S(N)(=O)c1ccc(C(C)(C)O)cc1F] |
| 110 | 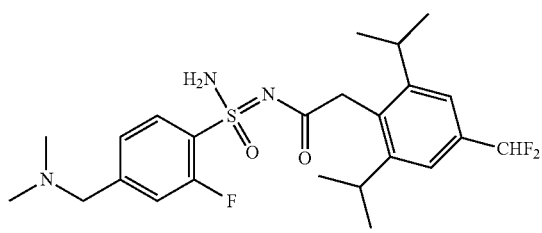 [SMILES: CC(C)c1cc(C(F)F)cc(C(C)C)c1CC(=O)N=S(N)(=O)c1ccc(CN(C)C)cc1F] |
| 110a | 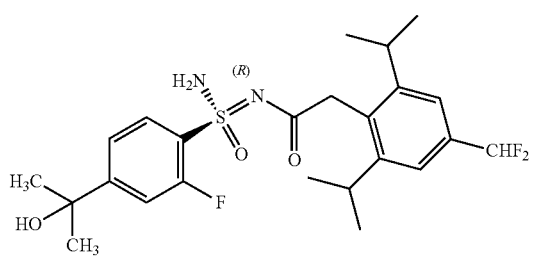(R) |
| 110b | 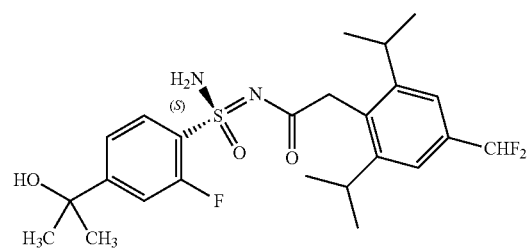(S) |
| 111 | 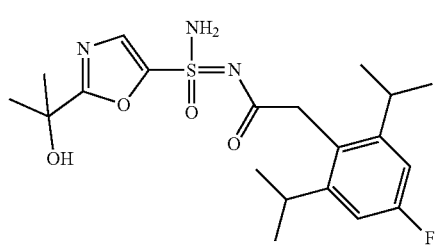 [SMILES: CC(C)c1cc(F)cc(C(C)C)c1CC(=O)N=S(N)(=O)c1cnc(C(C)(C)O)o1] |

-continued

| Compound | Structure |
|---|---|
| 112 | 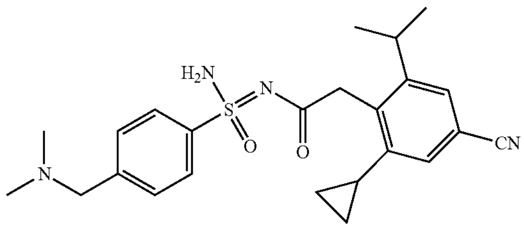 [SMILES: CC(C)c1cc(C#N)cc(C2CC2)c1CC(=O)N=S(N)(=O)c1ccc(CN(C)C)cc1] |
| 112a | (R) |
| 112b | (S) |
| 113 | 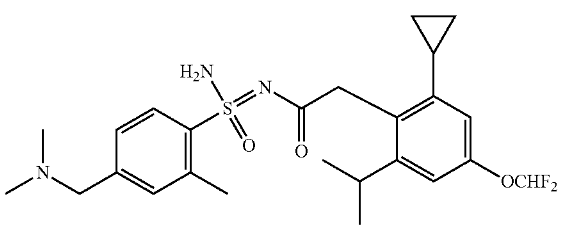 [SMILES: Cc1cc(CN(C)C)ccc1S(N)(=O)=NC(=O)Cc1c(C(C)C)cc(OC(F)F)cc1C1CC1] |
| 114 | 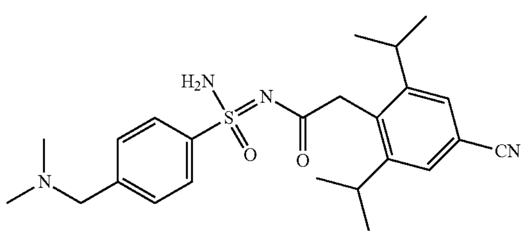 [SMILES: CC(C)c1cc(C#N)cc(C(C)C)c1CC(=O)N=S(N)(=O)c1ccc(CN(C)C)cc1] |
| 114a | (R) |

-continued
| Compound | Structure |
|---|---|
| 114b | 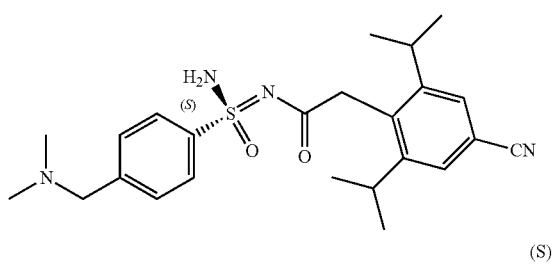 (S) |
| 115 | 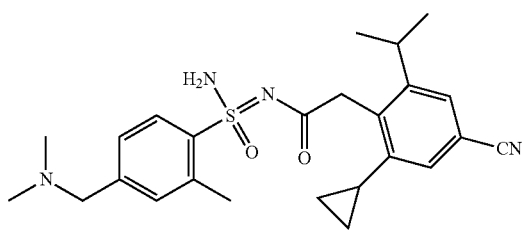 |
| 116 | 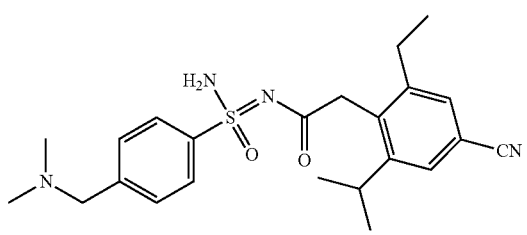 |
| 116a | 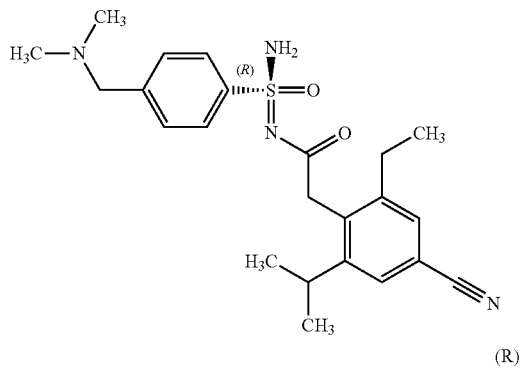 (R) |
| 116b | 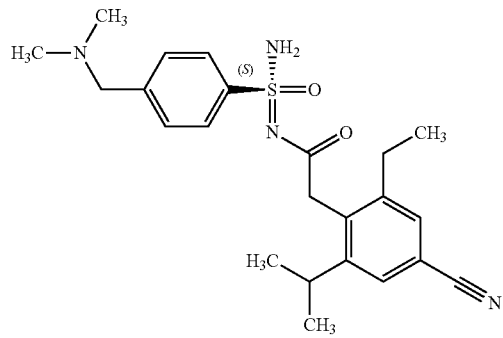 (S) |

-continued
| Compound | Structure |
|---|---|
| 117 | 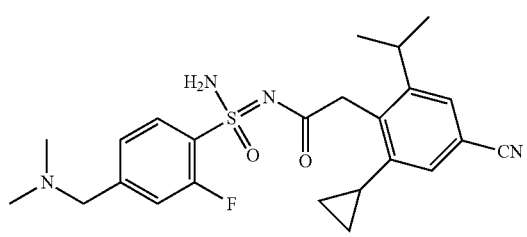 [SMILES: CC(C)c1cc(C#N)cc(C2CC2)c1CC(=O)N=S(N)(=O)c1ccc(CN(C)C)cc1F] |
| 117a | 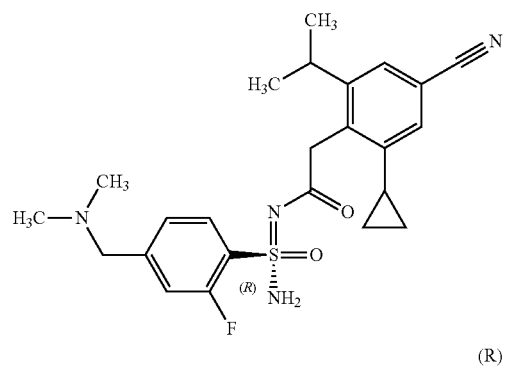 (R) |
| 117b | 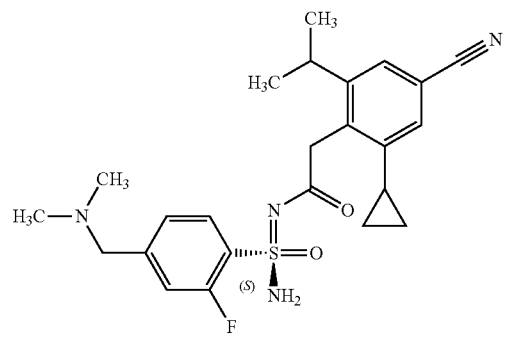 (S) |
| 118 | 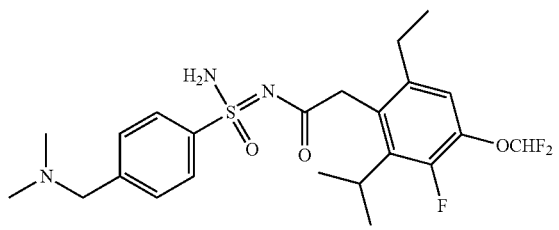 |
| 119 | 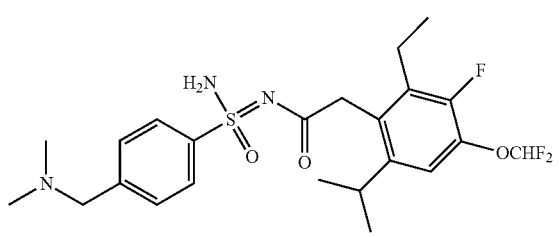 [SMILES: CCc1c(F)c(OC(F)F)cc(C(C)C)c1CC(=O)N=S(N)(=O)c1ccc(CN(C)C)cc1] |

-continued
| Compound | Structure |
|---|---|
| 120 | 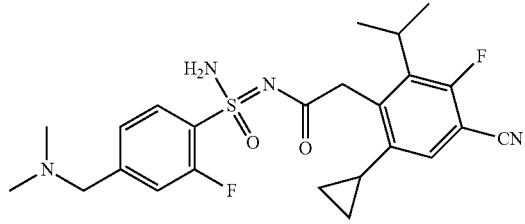 [SMILES: CC(C)c1c(F)c(C#N)cc(C2CC2)c1CC(=O)N=S(N)(=O)c1ccc(CN(C)C)cc1F] |
| 121 | 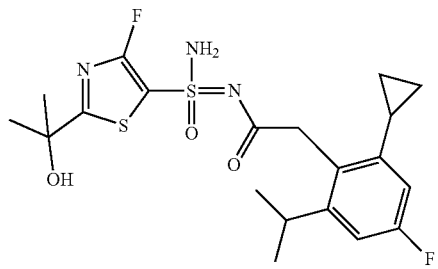 [SMILES: CC(C)c1cc(F)cc(C2CC2)c1CC(=O)N=S(N)(=O)c1sc(C(C)(C)O)nc1F] |
| 122 | 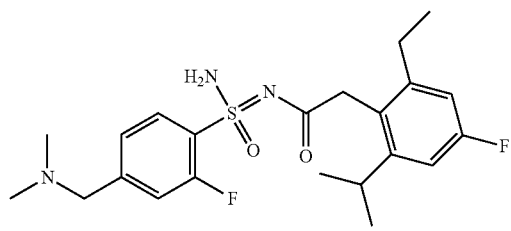 [SMILES: CCc1cc(F)cc(C(C)C)c1CC(=O)N=S(N)(=O)c1ccc(CN(C)C)cc1F] |
| 123 | 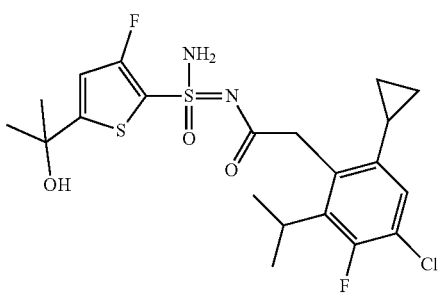 [SMILES: CC(C)c1c(F)c(Cl)cc(C2CC2)c1CC(=O)N=S(N)(=O)c1sc(C(C)(C)O)cc1F] |
| 123a | 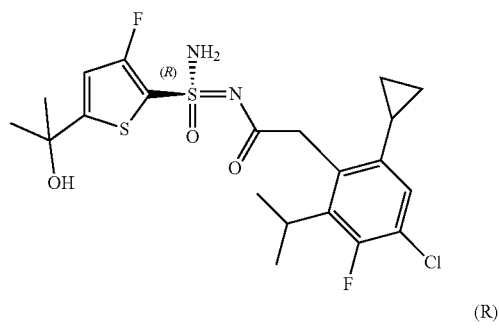 |

-continued
| Compound | Structure |
|---|---|
| 123b | 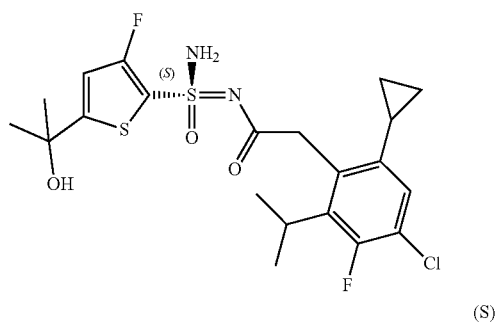 (S) |
| 124 | 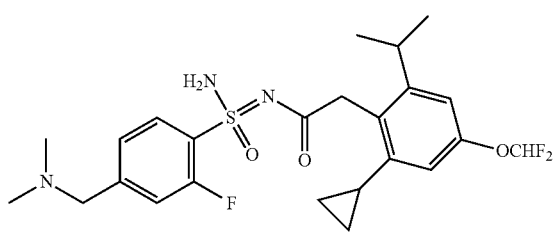 |
| 125 | 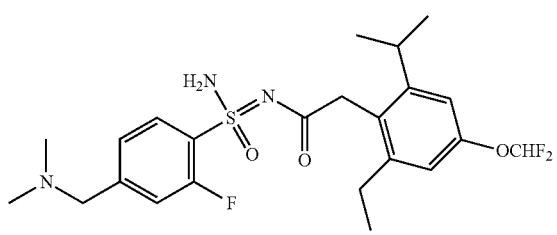 |
| 126 | 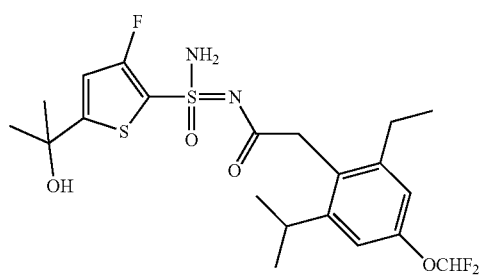 |
| 126a | 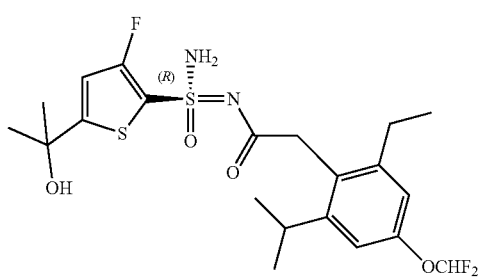 (R) |

-continued
| Compound | Structure |
|---|---|
| 126b | 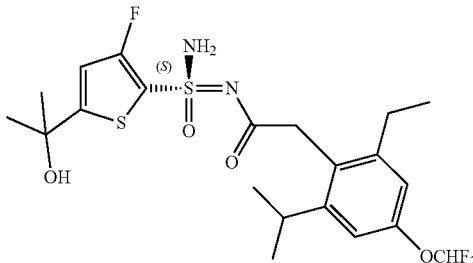 |
| 127 | 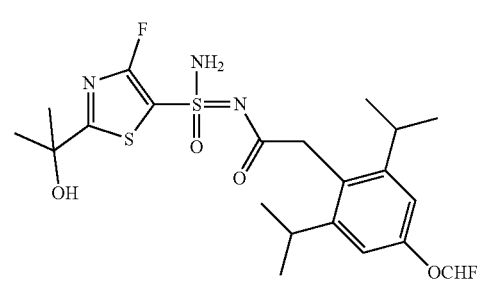 |
| 128 | 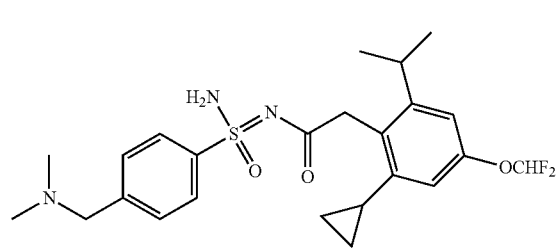 [SMILES: CC(C)c1cc(OC(F)F)cc(C2CC2)c1CC(=O)N=S(N)(=O)c1ccc(CN(C)C)cc1] |
| 129 | 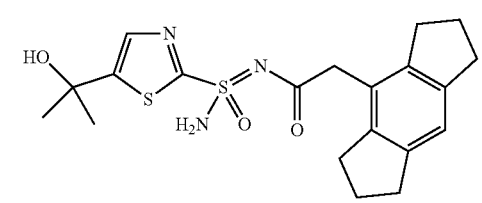 [SMILES: CC(C)(O)c1cnc(S(N)(=O)=NC(=O)Cc2c3c(cc4c2CCC4)CCC3)s1] |
| 129a | 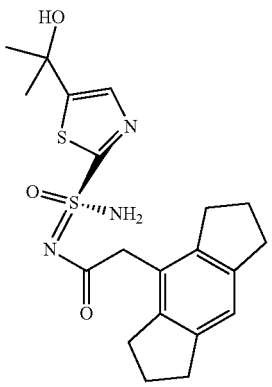 [SMILES: CC(C)(O)c1cnc([S@](N)(=O)=NC(=O)Cc2c3c(cc4c2CCC4)CCC3)s1] |

-continued
| Compound | Structure |
|---|---|
| 129b | 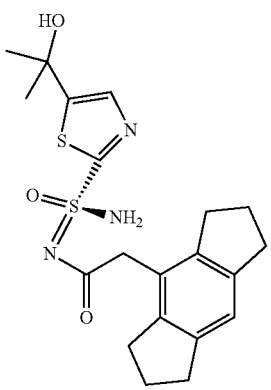 [SMILES: CC(C)(O)c1cnc([S@@](N)(=O)=NC(=O)Cc2c3c(cc4c2CCC4)CCC3)s1] |
| 130 | 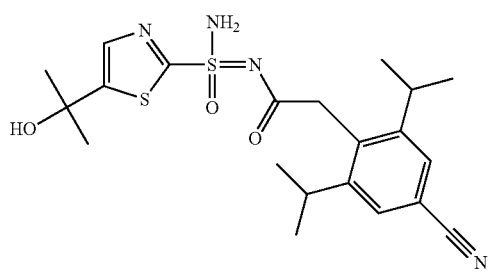 [SMILES: CC(C)c1cc(C#N)cc(C(C)C)c1CC(=O)N=S(N)(=O)c1ncc(C(C)(C)O)s1] |
| 130a | 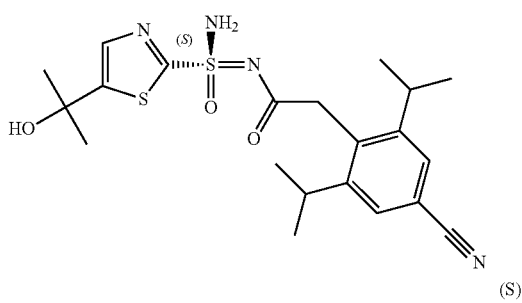 |
| 130b | 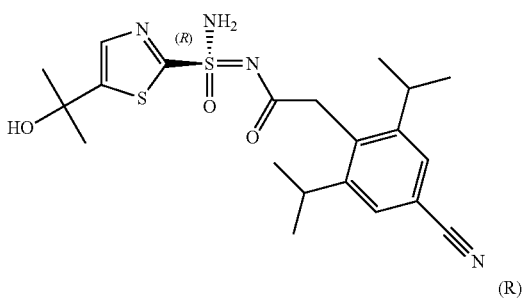 |
| 131 | 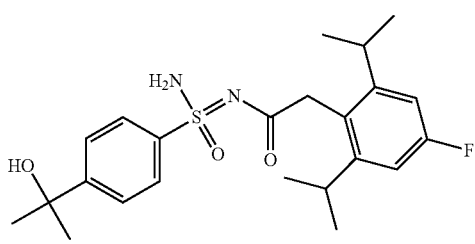 [SMILES: CC(C)c1cc(F)cc(C(C)C)c1CC(=O)N=S(N)(=O)c1ccc(C(C)(C)O)cc1] |

-continued
| Compound | Structure |
|---|---|
| 131a | 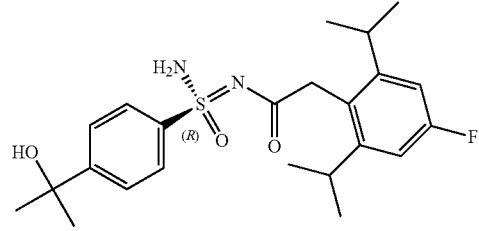 |
| 131b | 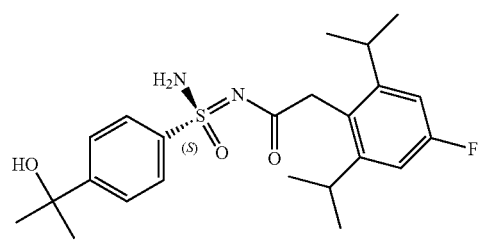 |
| 132 | 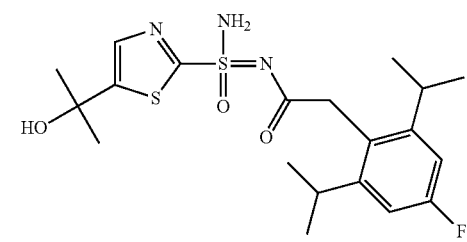 [SMILES: CC(C)c1cc(F)cc(C(C)C)c1CC(=O)N=S(N)(=O)c1ncc(C(C)(C)O)s1] |
| 132a | 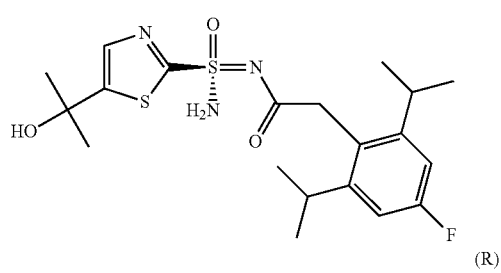 |
| 132b | 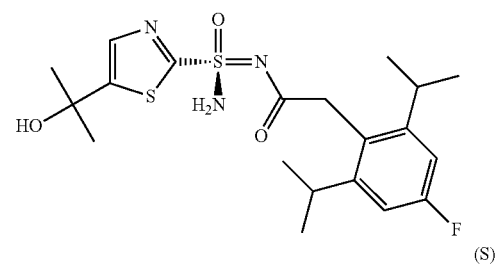 |
| 133 | 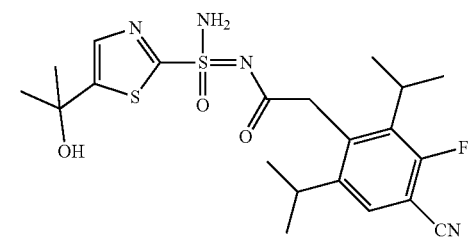 [SMILES: CC(C)c1cc(C#N)c(F)c(C(C)C)c1CC(=O)N=S(N)(=O)c1ncc(C(C)(C)O)s1] |

-continued

| Compound | Structure |
|---|---|
| 133a | 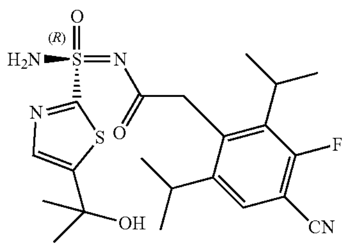 |
| 133b | 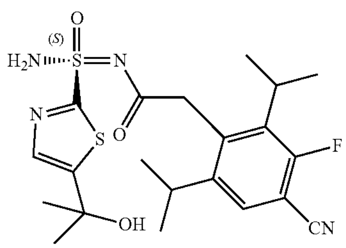 |
| 134 | 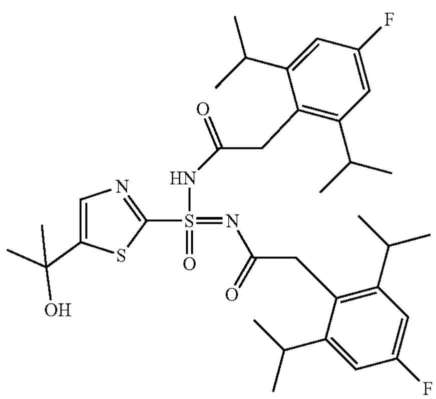 [SMILES: CC(C)c1cc(F)cc(C(C)C)c1CC(=O)N=S(=O)(NC(=O)Cc1c(C(C)C)cc(F)cc1C(C)C)c1ncc(C(C)(C)O)s1] |
| 135 | 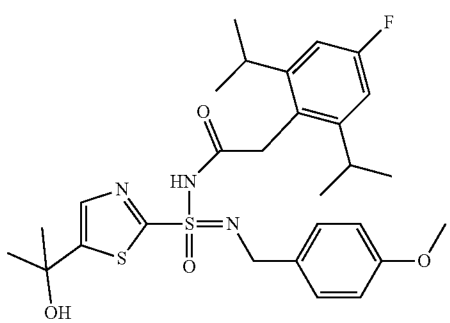 [SMILES: COc1ccc(CN=S(=O)(NC(=O)Cc2c(C(C)C)cc(F)cc2C(C)C)c2ncc(C(C)(C)O)s2)cc1] |
| 136 | 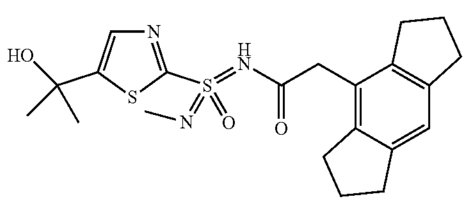 |

-continued
| Compound | Structure |
|---|---|
| 137 | 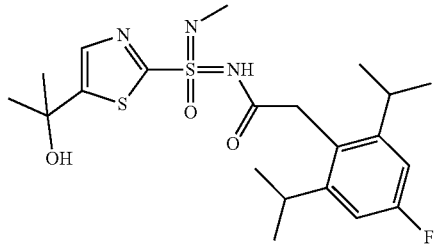 |
| 138 | 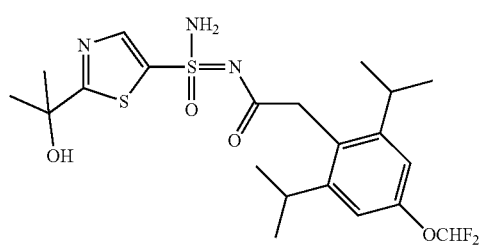 [SMILES: CC(C)c1cc(OC(F)F)cc(C(C)C)c1CC(=O)N=S(N)(=O)c1cnc(C(C)(C)O)s1] |
| 138a | 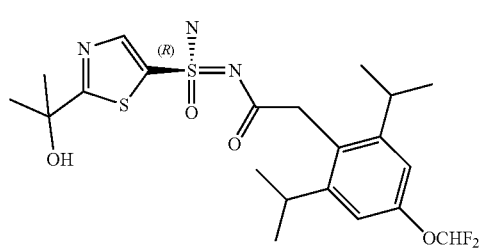 |
| 138b | 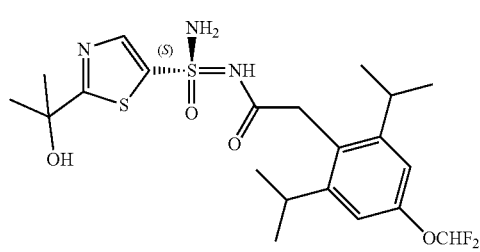 |
| 139 | 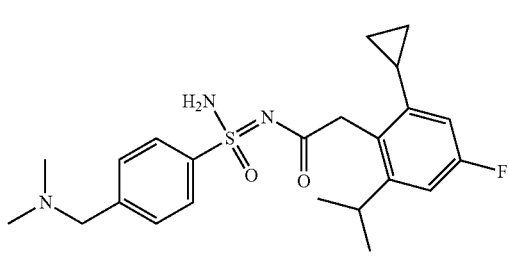 [SMILES: CC(C)c1cc(F)cc(C2CC2)c1CC(=O)N=S(N)(=O)c1ccc(CN(C)C)cc1] |
| 139a | 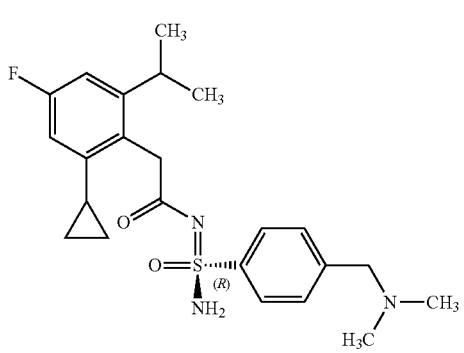 |

-continued
| Compound | Structure |
|---|---|
| 139b | 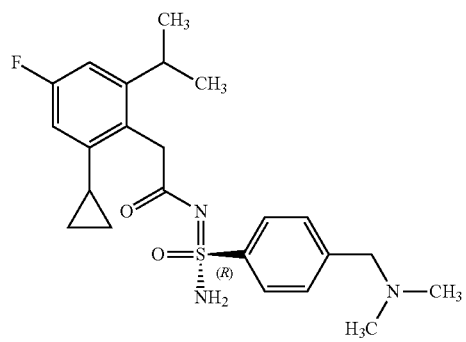 |
| 140 | 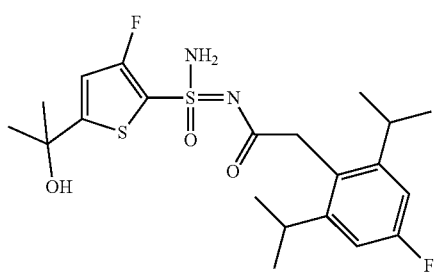 [SMILES: CC(C)c1cc(F)cc(C(C)C)c1CC(=O)N=S(N)(=O)c1sc(C(C)(C)O)cc1F] |
| 140a | 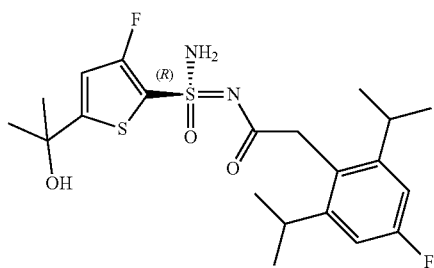 |
| 140b | 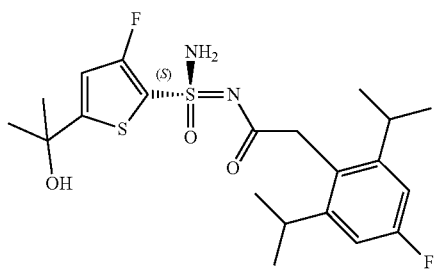 |
| 141 | 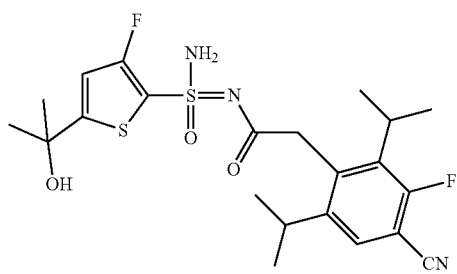 [SMILES: CC(C)c1cc(C#N)c(F)c(C(C)C)c1CC(=O)N=S(N)(=O)c1sc(C(C)(C)O)cc1F] |

-continued
| Compound | Structure |
|---|---|
| 141a | 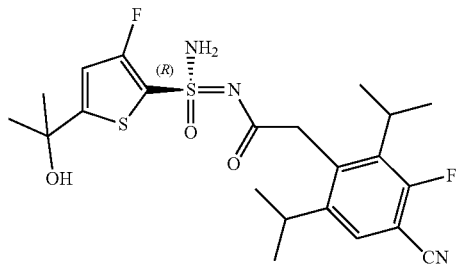 |
| 141b | 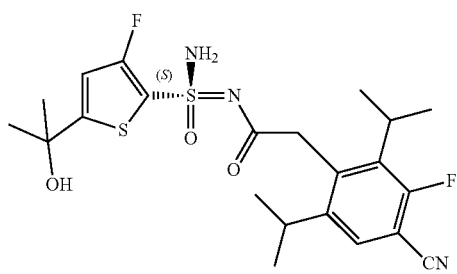 |
| 142 | 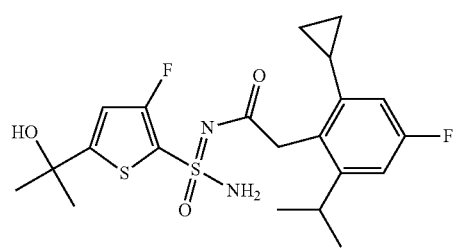 [SMILES: CC(C)c1cc(F)cc(C2CC2)c1CC(=O)N=S(N)(=O)c1sc(C(C)(C)O)cc1F] |
| 143 | 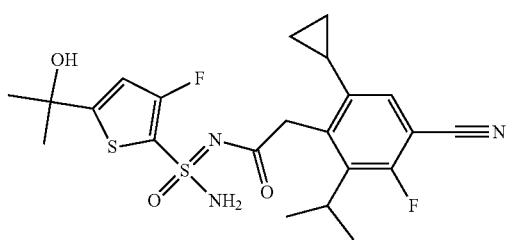 [SMILES: CC(C)c1c(F)c(C#N)cc(C2CC2)c1CC(=O)N=S(N)(=O)c1sc(C(C)(C)O)cc1F] |
| 144 | 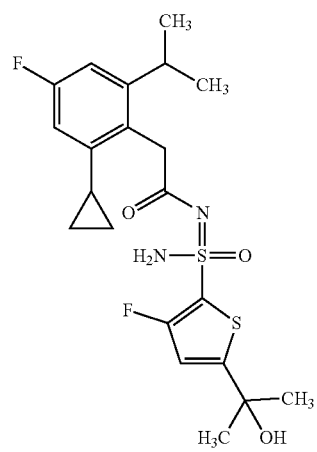 [SMILES: CC(C)c1cc(F)cc(C2CC2)c1CC(=O)N=S(N)(=O)c1sc(C(C)(C)O)cc1F] |

-continued
| Compound | Structure |
|---|---|
| 144a | 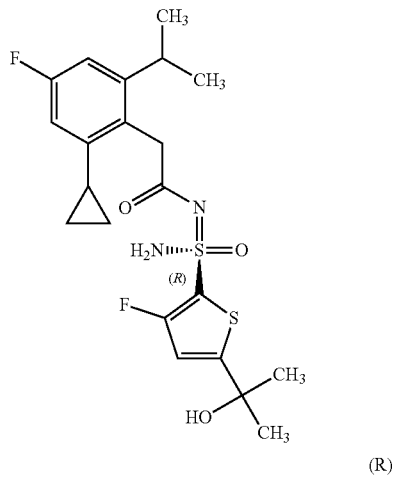 (R) |
| 144b | 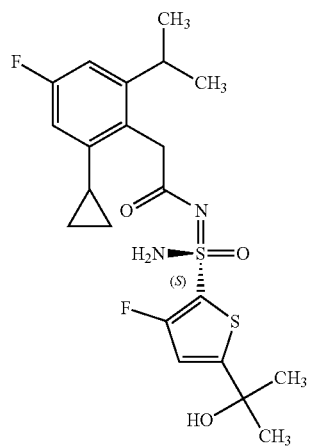 (S) |
| 145 | 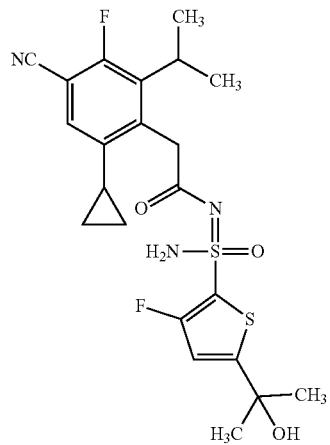 |

| Compound | Structure |
|---|---|
| 145a | 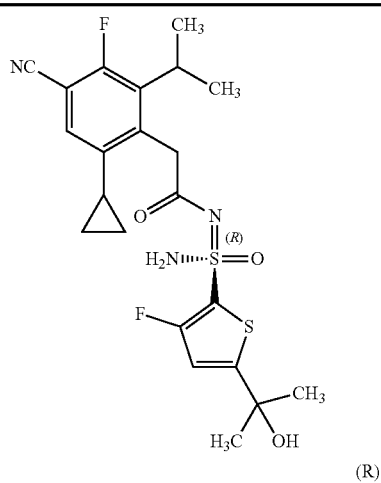 (R) |
| 145b | 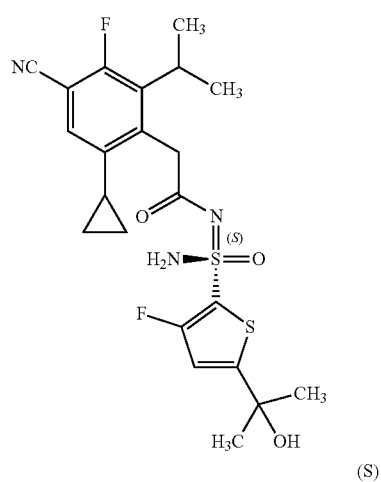 (S) |
| 146 | 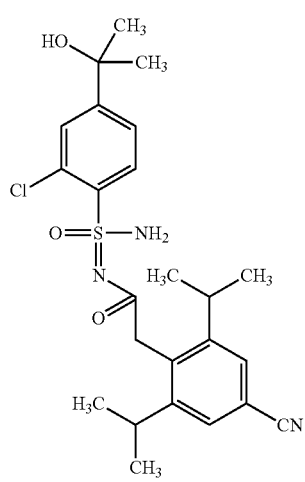 |

-continued

| Compound | Structure |
|---|---|
| 147 | 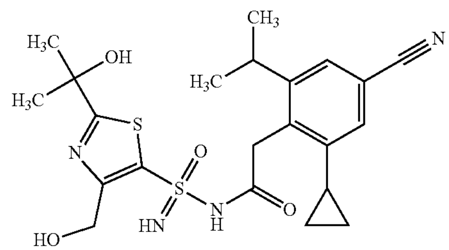 [SMILES: CC(C)c1cc(C#N)cc(C2CC2)c1CC(=O)NS(=N)(=O)c1sc(C(C)(C)O)nc1CO] |
| 147a | 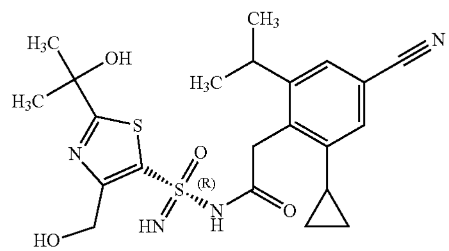 |
| 147b | 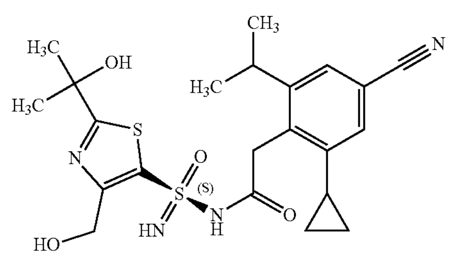 |
| 148 | 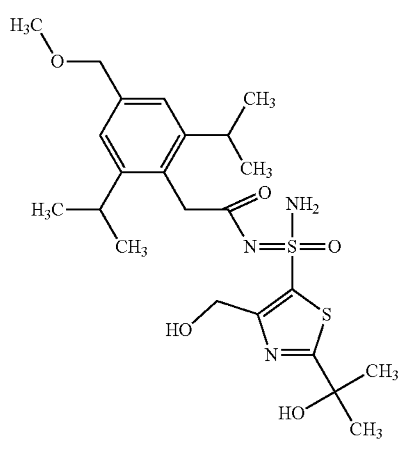 [SMILES: COCc1cc(C(C)C)c(CC(=O)N=S(N)(=O)c2sc(C(C)(C)O)nc2CO)c(C(C)C)c1] |

-continued
| Compound | Structure |
|---|---|
| 148a | 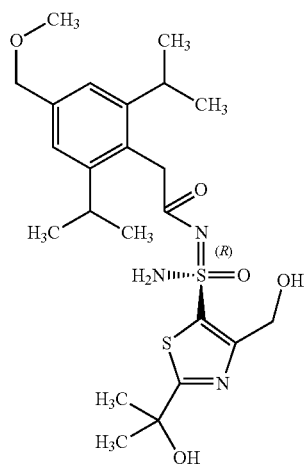 |
| 148b | 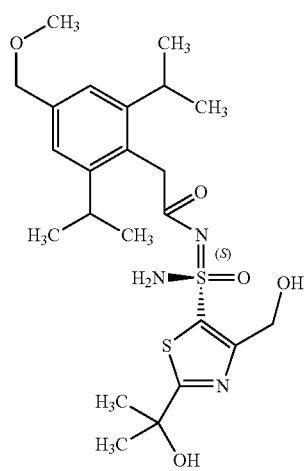 |
| 149a | 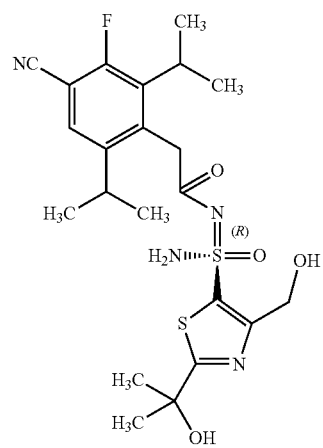 |

-continued
| Compound | Structure |
|---|---|
| 149b | 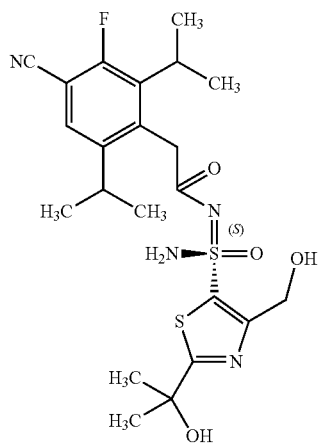 |
| 150 | 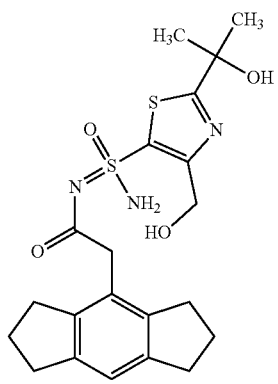 [SMILES: CC(C)(O)c1nc(CO)c(S(N)(=O)=NC(=O)Cc2c3c(cc4c2CCC4)CCC3)s1] |
| 150a | 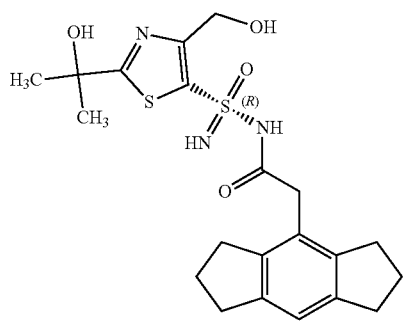 |
| 150b | 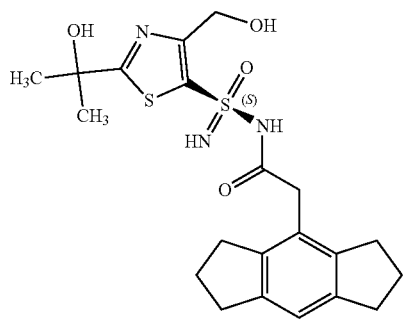 |

-continued

| Compound | Structure |
|---|---|
| 151 | 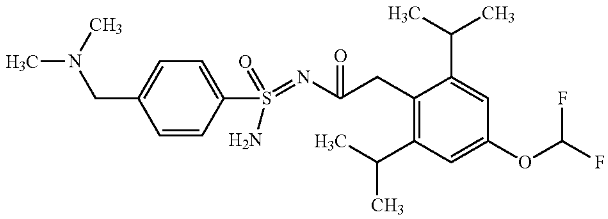 [SMILES: CC(C)c1cc(OC(F)F)cc(C(C)C)c1CC(=O)N=S(N)(=O)c1ccc(CN(C)C)cc1] |
| 152 | 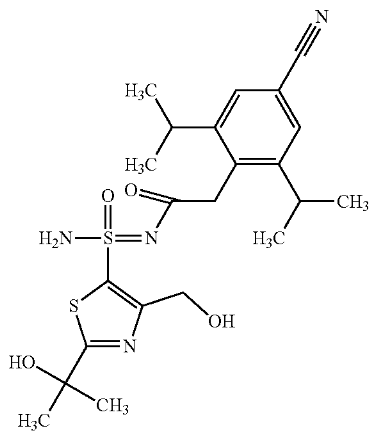 [SMILES: CC(C)c1cc(C#N)cc(C(C)C)c1CC(=O)N=S(N)(=O)c1sc(C(C)(C)O)nc1CO] |
| 152a | 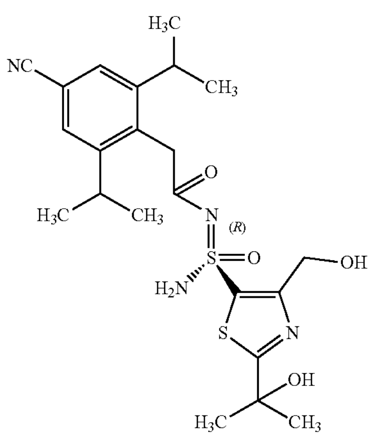 |
| 152b | 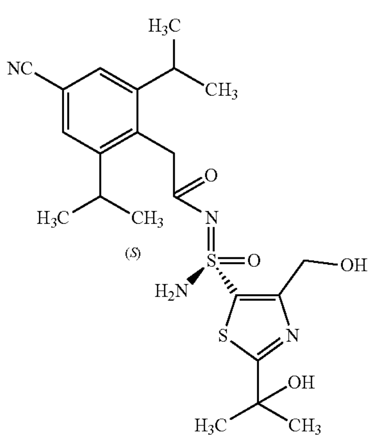 |

-continued
| Compound | Structure |
|---|---|
| 153 | 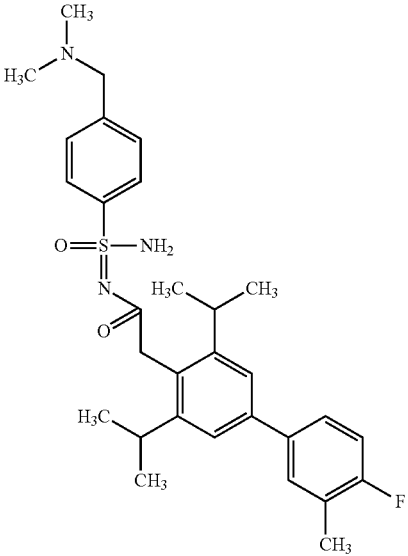 [SMILES: Cc1cc(-c2cc(C(C)C)c(CC(=O)N=S(N)(=O)c3ccc(CN(C)C)cc3)c(C(C)C)c2)ccc1F] |
| 154 | 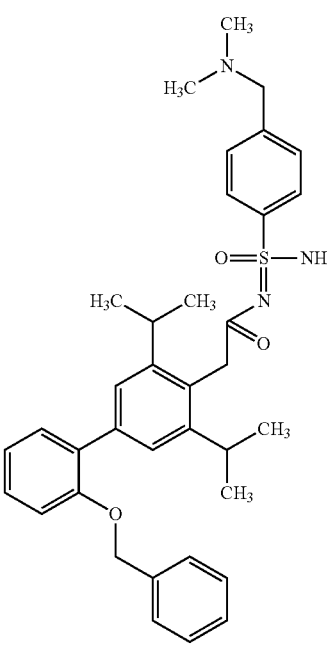 |

-continued

| Compound | Structure |
|---|---|
| 155 | 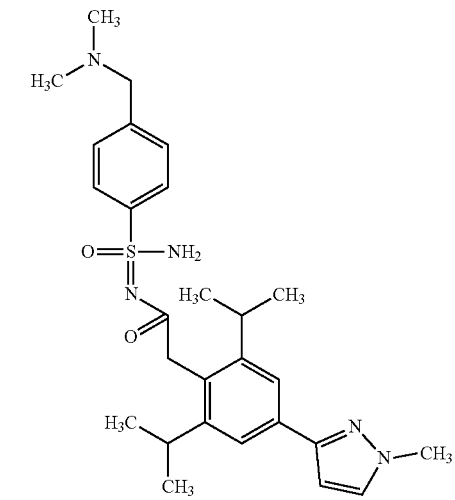 |
| 158 | 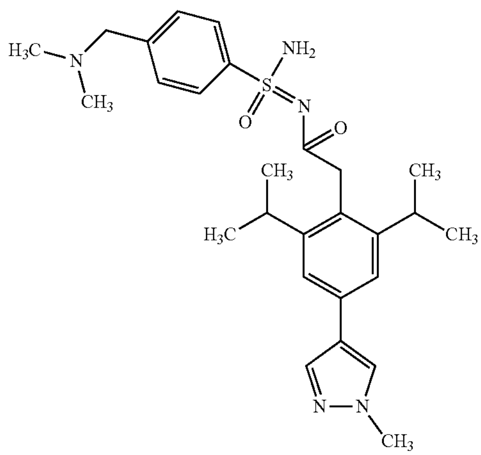 [SMILES: CC(C)c1cc(-c2cnn(C)c2)cc(C(C)C)c1CC(=O)N=S(N)(=O)c1ccc(CN(C)C)cc1] |
| 159 | 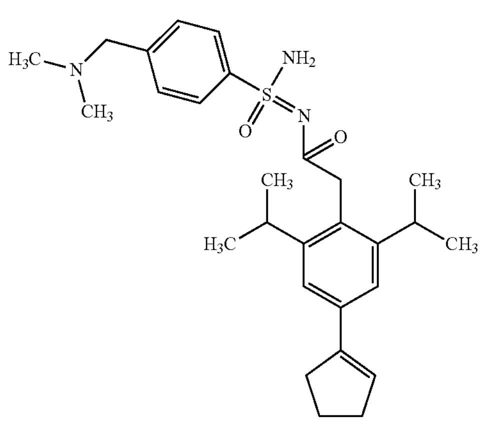 [SMILES: CC(C)c1cc(C2=CCCC2)cc(C(C)C)c1CC(=O)N=S(N)(=O)c1ccc(CN(C)C)cc1] |

-continued
| Compound | Structure |
|---|---|
| 160 | 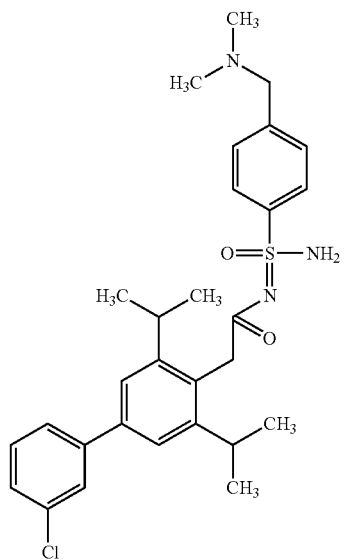 [SMILES: CC(C)c1cc(-c2cccc(Cl)c2)cc(C(C)C)c1CC(=O)N=S(N)(=O)c1ccc(CN(C)C)cc1] |
| 161 | 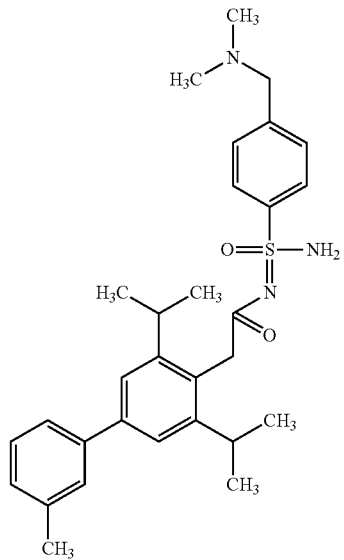 [SMILES: Cc1cccc(-c2cc(C(C)C)c(CC(=O)N=S(N)(=O)c3ccc(CN(C)C)cc3)c(C(C)C)c2)c1] |

| Compound | Structure |
|---|---|
| 162 | 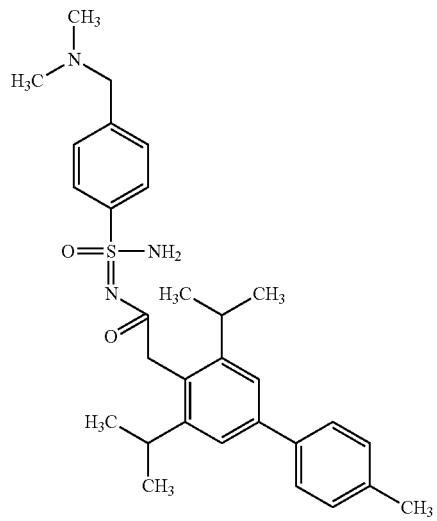 |
| 163 | 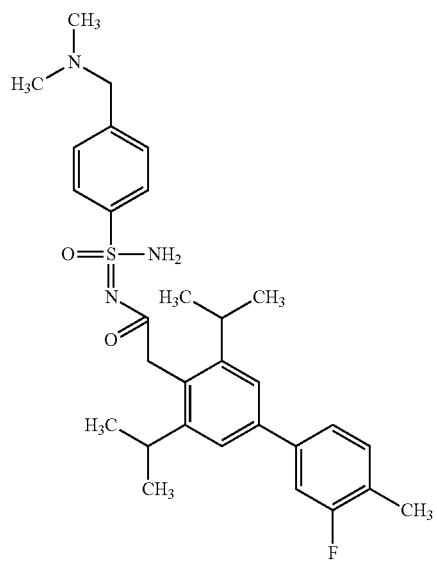 |

-continued
| Compound | Structure |
|---|---|
| 164 | 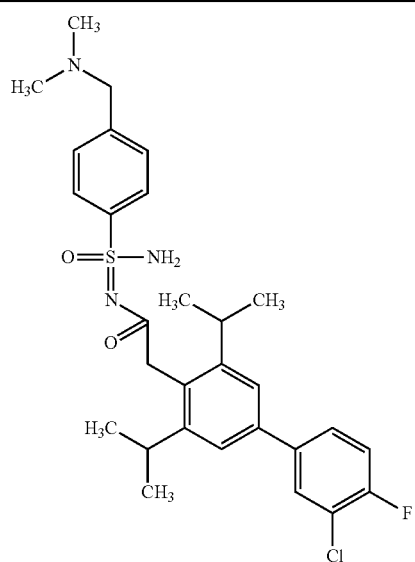 |
| 165 | 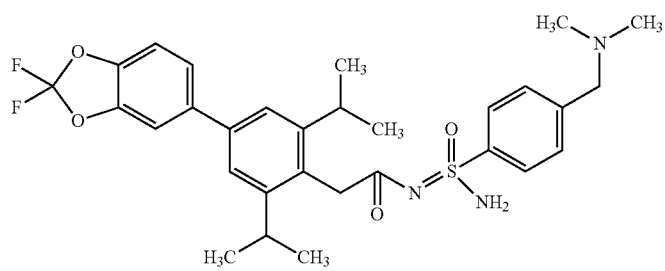 [SMILES: CC(C)c1cc(-c2ccc3c(c2)OC(F)(F)O3)cc(C(C)C)c1CC(=O)N=S(N)(=O)c1ccc(CN(C)C)cc1] |
| 168 | 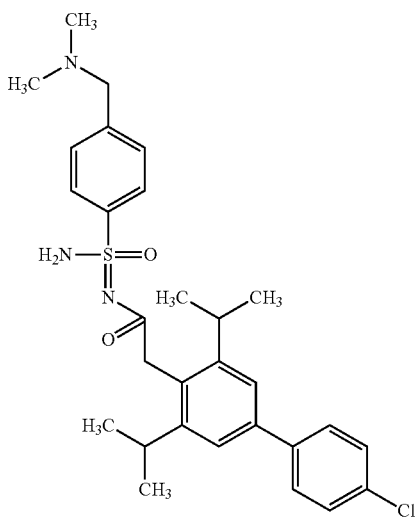 [SMILES: CC(C)c1cc(-c2ccc(Cl)cc2)cc(C(C)C)c1CC(=O)N=S(N)(=O)c1ccc(CN(C)C)cc1] |

-continued
| Compound | Structure |
|---|---|
| 169 | 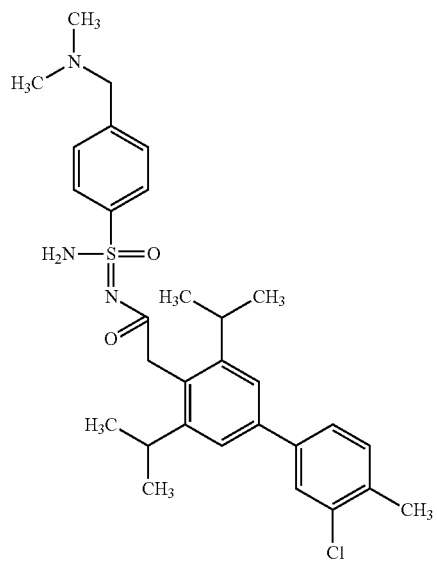 |
| 170 | 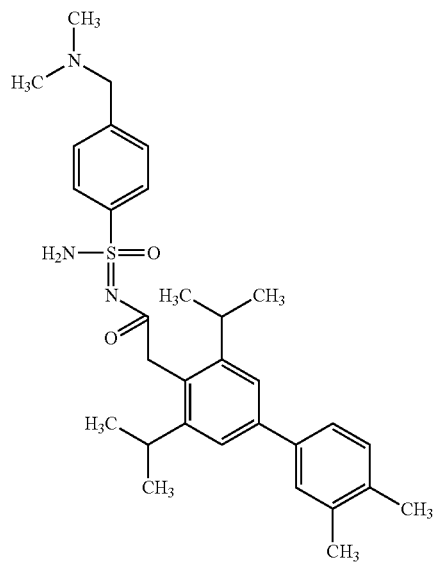 |

| Compound | Structure |
|---|---|
| 171 | 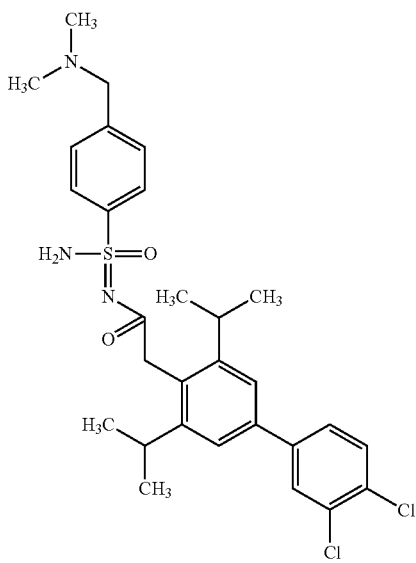 [SMILES: CC(C)c1cc(-c2ccc(Cl)c(Cl)c2)cc(C(C)C)c1CC(=O)N=S(N)(=O)c1ccc(CN(C)C)cc1] |
| 172 | 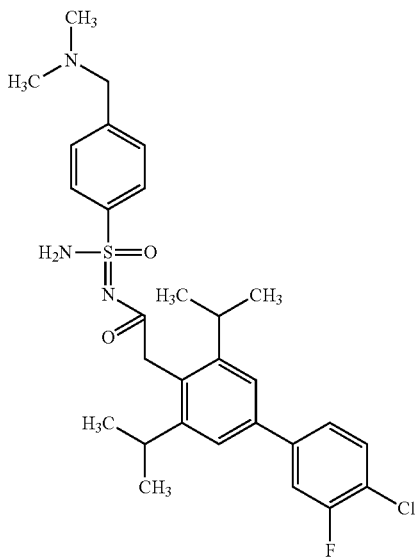 [SMILES: CC(C)c1cc(-c2ccc(Cl)c(F)c2)cc(C(C)C)c1CC(=O)N=S(N)(=O)c1ccc(CN(C)C)cc1] |

-continued
| Compound | Structure |
|---|---|
| 173 | 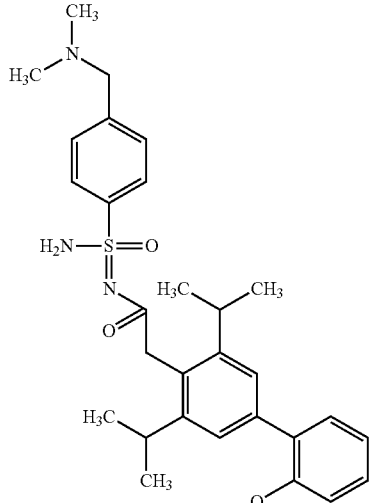 |
| 176 | 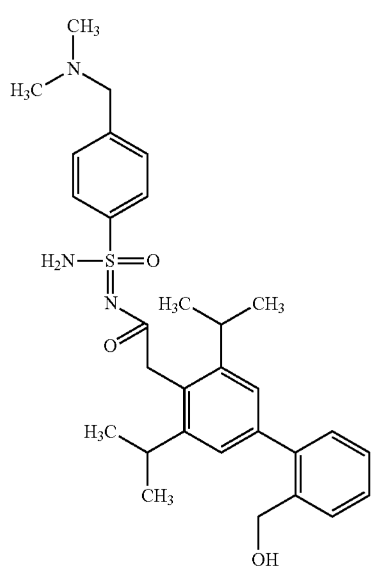 [SMILES: CC(C)c1cc(-c2ccccc2CO)cc(C(C)C)c1CC(=O)N=S(N)(=O)c1ccc(CN(C)C)cc1] |

-continued
| Compound | Structure |
|---|---|
| 177 | 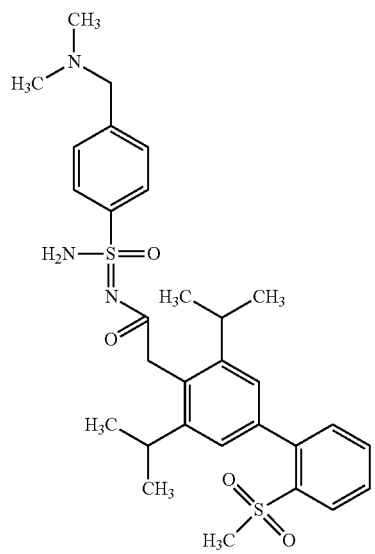 [SMILES: CC(C)c1cc(-c2ccccc2S(C)(=O)=O)cc(C(C)C)c1CC(=O)N=S(N)(=O)c1ccc(CN(C)C)cc1] |
| 178 | 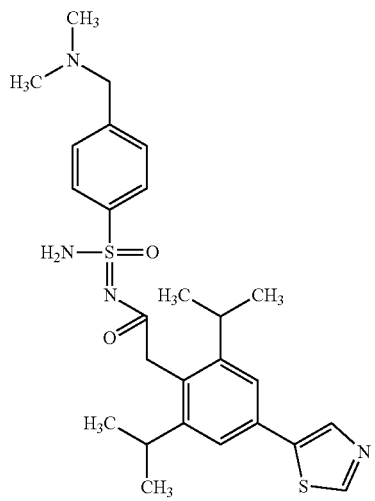 [SMILES: CC(C)c1cc(-c2cncs2)cc(C(C)C)c1CC(=O)N=S(N)(=O)c1ccc(CN(C)C)cc1] |

-continued
| Compound | Structure |
|---|---|
| 180 | 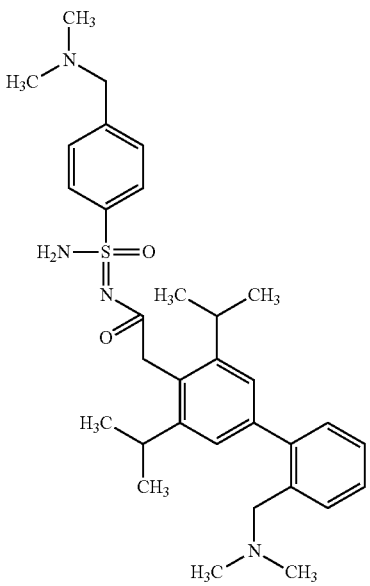 [SMILES: CC(C)c1cc(-c2ccccc2CN(C)C)cc(C(C)C)c1CC(=O)N=S(N)(=O)c1ccc(CN(C)C)cc1] |
| 181 | 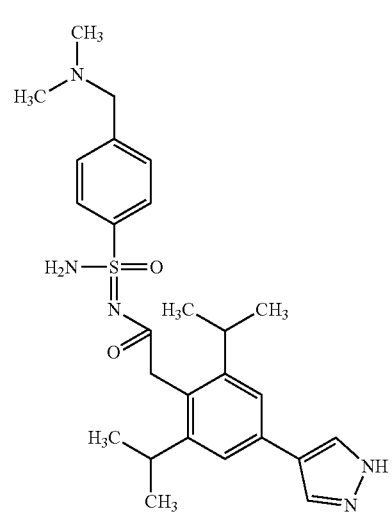 [SMILES: CC(C)c1cc(-c2cn[nH]c2)cc(C(C)C)c1CC(=O)N=S(N)(=O)c1ccc(CN(C)C)cc1] |
| 182 | 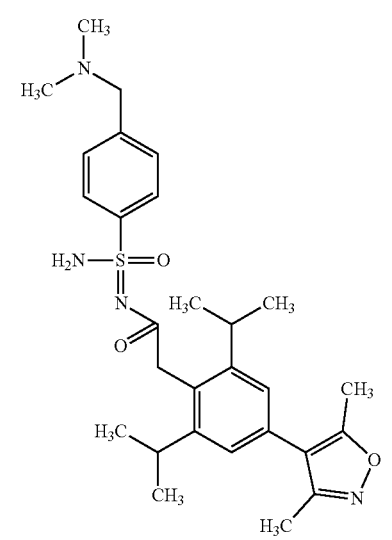 [SMILES: Cc1noc(C)c1-c1cc(C(C)C)c(CC(=O)N=S(N)(=O)c2ccc(CN(C)C)cc2)c(C(C)C)c1] |

-continued
| Compound | Structure |
|---|---|
| 183 | 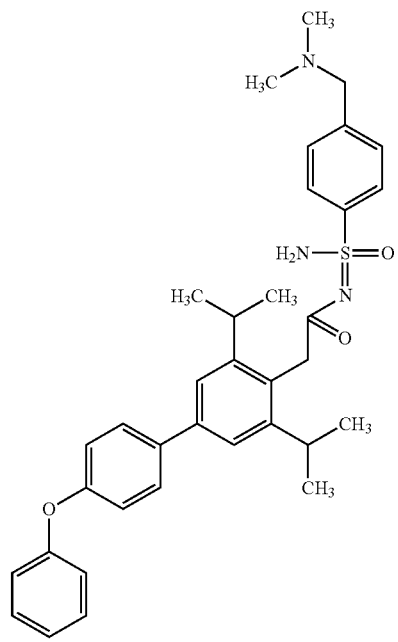 [SMILES: CC(C)c1cc(-c2ccc(Oc3ccccc3)cc2)cc(C(C)C)c1CC(=O)N=S(N)(=O)c1ccc(CN(C)C)cc1] |
| 184 | 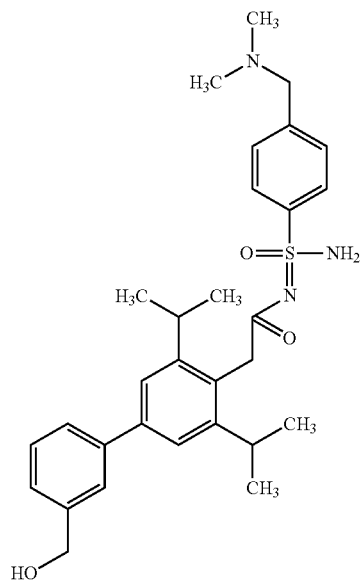 [SMILES: CC(C)c1cc(-c2cccc(CO)c2)cc(C(C)C)c1CC(=O)N=S(N)(=O)c1ccc(CN(C)C)cc1] |

-continued
| Compound | Structure |
|---|---|
| 185 | 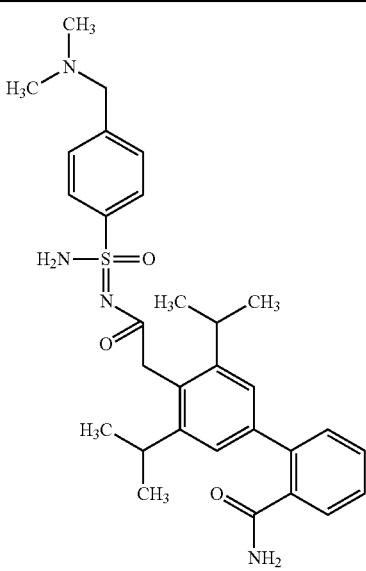 |
| 186 | 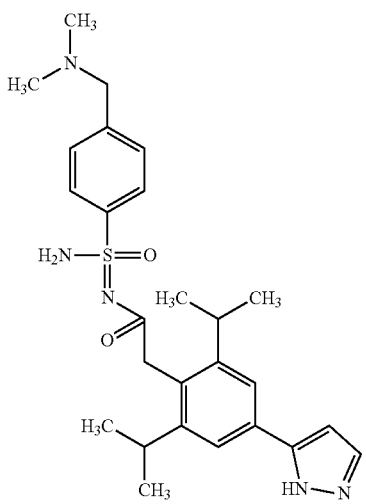 |
| 189 | 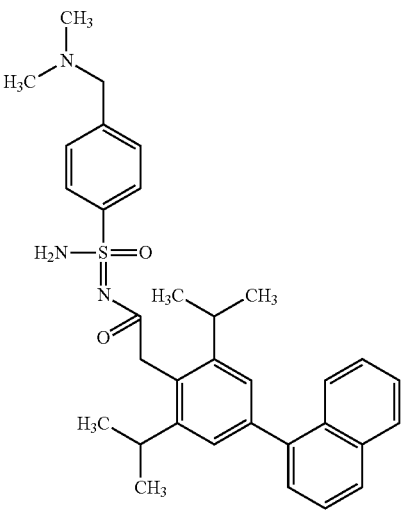 [SMILES: CC(C)c1cc(-c2cccc3ccccc23)cc(C(C)C)c1CC(=O)N=S(N)(=O)c1ccc(CN(C)C)cc1] |

| Compound | Structure |
|---|---|
| 190 | 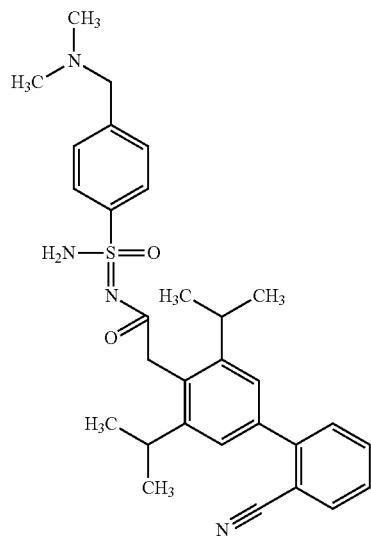 [SMILES: CC(C)c1cc(-c2ccccc2C#N)cc(C(C)C)c1CC(=O)N=S(N)(=O)c1ccc(CN(C)C)cc1] |
| 191 | 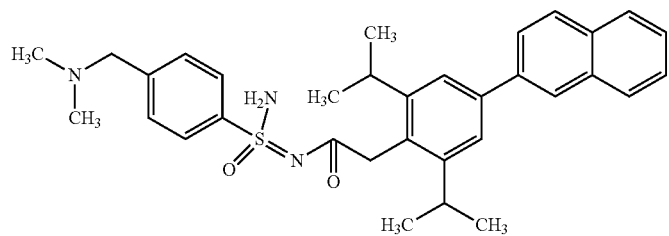 [SMILES: CC(C)c1cc(-c2ccc3ccccc3c2)cc(C(C)C)c1CC(=O)N=S(N)(=O)c1ccc(CN(C)C)cc1] |
| 192 | 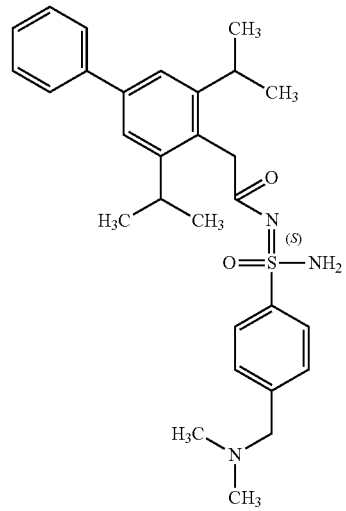 |

| Compound | Structure |
|---|---|
| 194 | 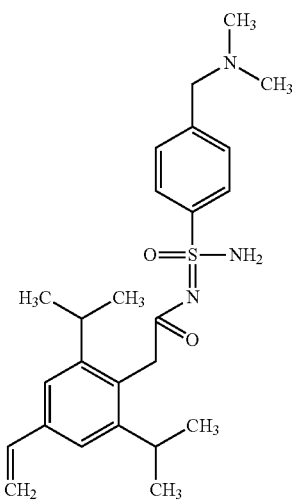 [SMILES: C=Cc1cc(C(C)C)c(CC(=O)N=S(N)(=O)c2ccc(CN(C)C)cc2)c(C(C)C)c1] |
| 195 | 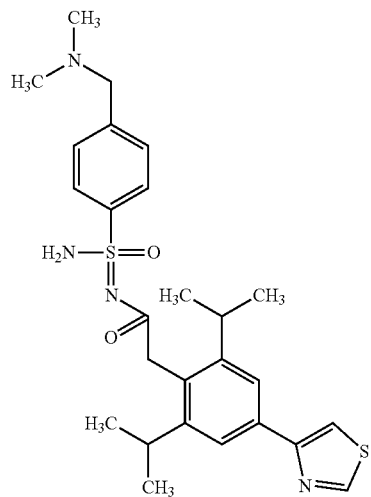 [SMILES: CC(C)c1cc(-c2cscn2)cc(C(C)C)c1CC(=O)N=S(N)(=O)c1ccc(CN(C)C)cc1] |
| 196 | 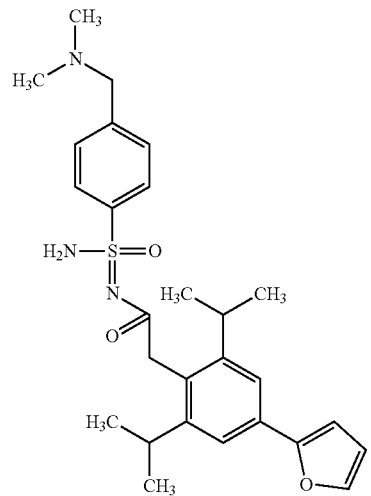 |

-continued

| Compound | Structure |
|---|---|
| 197 | 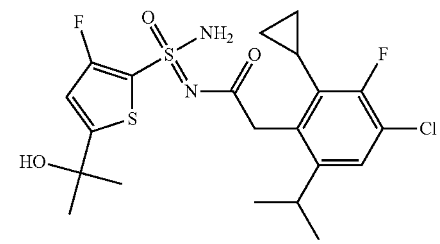 [SMILES: CC(C)c1cc(Cl)c(F)c(C2CC2)c1CC(=O)N=S(N)(=O)c1sc(C(C)(C)O)cc1F] |
| 197a | (R) |
| 197b | (S) |
| 198 | 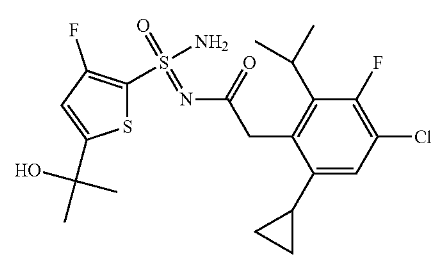 [SMILES: CC(C)c1c(F)c(Cl)cc(C2CC2)c1CC(=O)N=S(N)(=O)c1sc(C(C)(C)O)cc1F] |
| 198a | (R) |

| Compound | Structure |
|---|---|
| 198b | 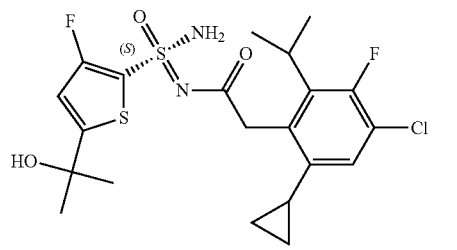 (S) |
| Compound | Structure |
|---|---|
| 104a | 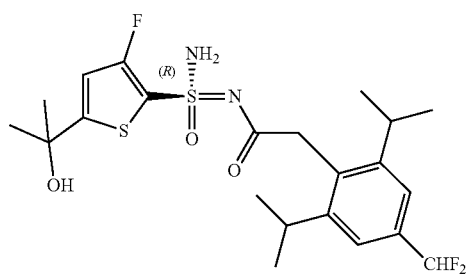 |
| 104b | 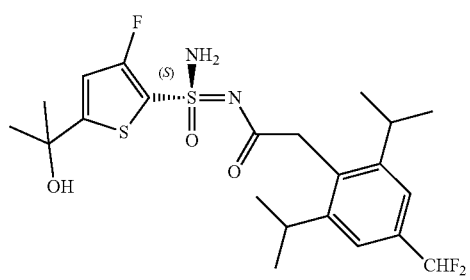 |
| 106a | 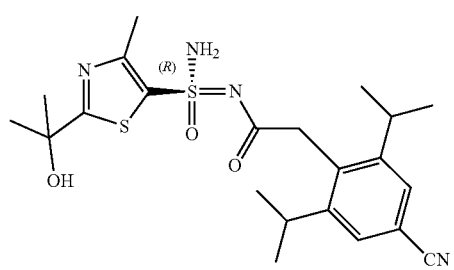 |
| 106b | 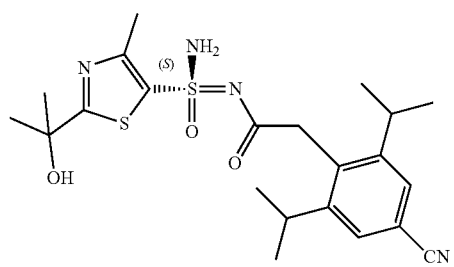 |

-continued
| Compound | Structure |
|---|---|
| 107a | 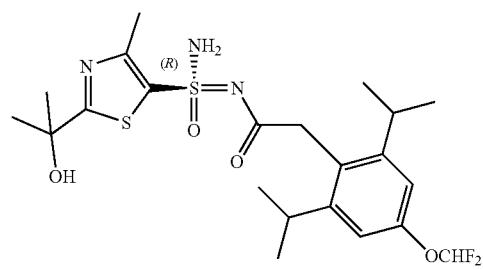 |
| 107b | 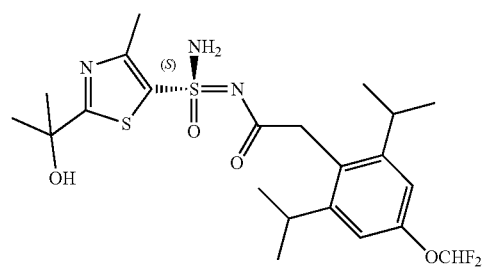 |
| 110a | 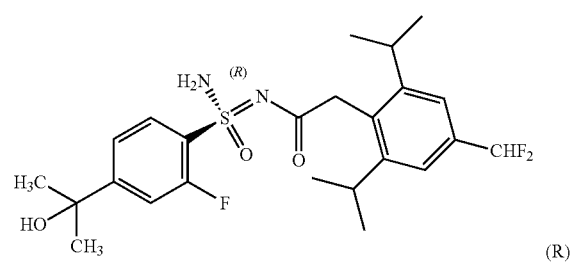 |
| 110b | 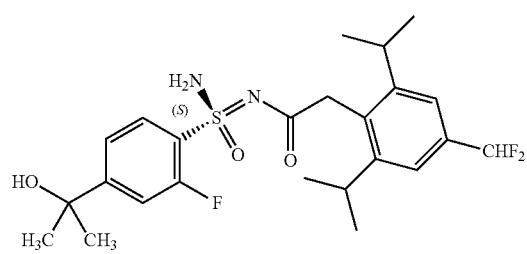 |
| 126a | 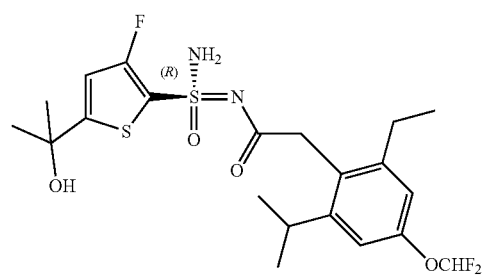 |

-continued
| Compound | Structure |
|---|---|
| 126b | 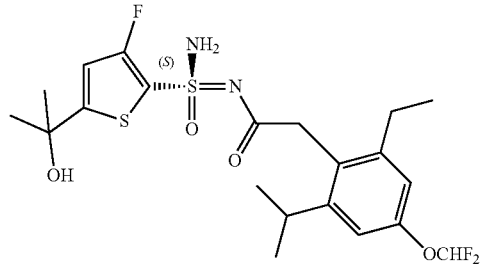 |
| 130a | 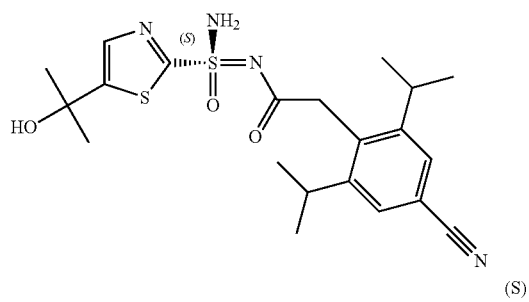 |
| 130b | 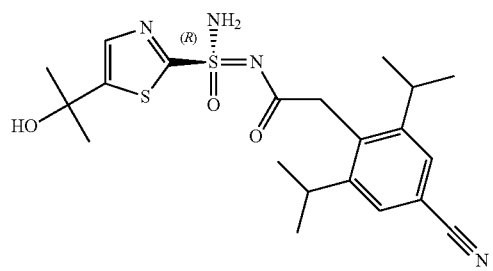 |
| 146 | 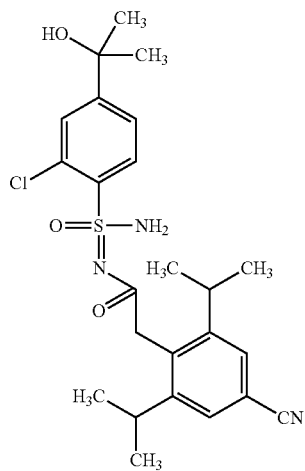 [SMILES: CC(C)c1cc(C#N)cc(C(C)C)c1CC(=O)N=S(N)(=O)c1ccc(C(C)(C)O)cc1Cl] |
| 147 | 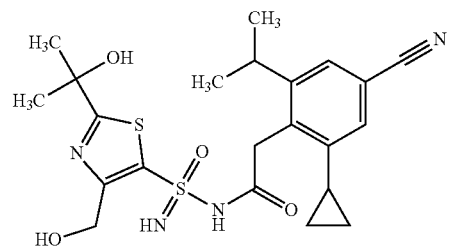 [SMILES: CC(C)c1cc(C#N)cc(C2CC2)c1CC(=O)NS(=N)(=O)c1sc(C(C)(C)O)nc1CO] |

-continued
| Compound | Structure |
|---|---|
| 148 | 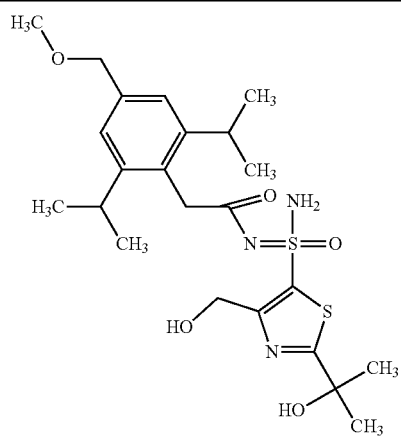 |
| 149a | 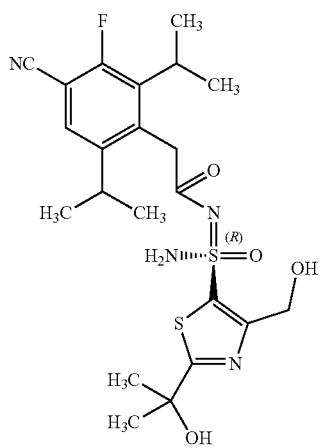 |
| 149b | 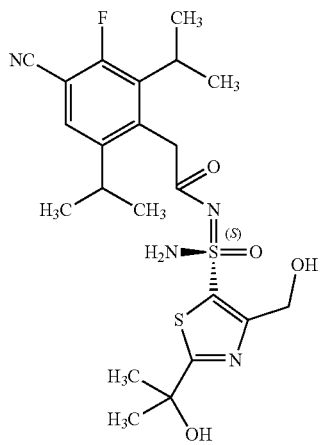 |

-continued
| Compound | Structure |
|---|---|
| 150 | 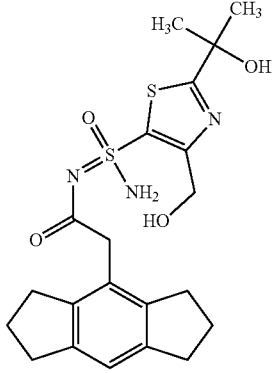 [SMILES: CC(C)(O)c1nc(CO)c(S(N)(=O)=NC(=O)Cc2c3c(cc4c2CCC4)CCC3)s1] |
| 151 | 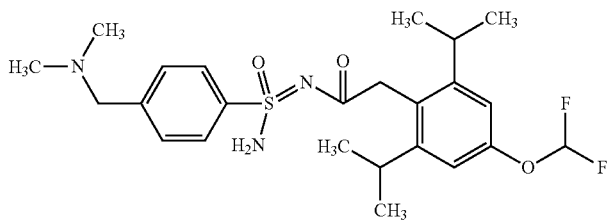 [SMILES: CC(C)c1cc(OC(F)F)cc(C(C)C)c1CC(=O)N=S(N)(=O)c1ccc(CN(C)C)cc1] |
| 152 | 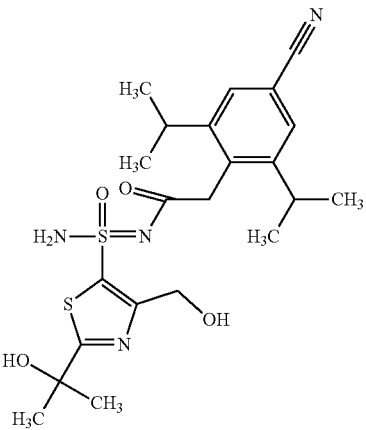 [SMILES: CC(C)c1cc(C#N)cc(C(C)C)c1CC(=O)N=S(N)(=O)c1sc(C(C)(C)O)nc1CO] |
| 152a | 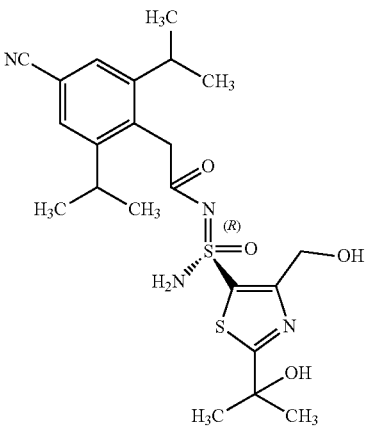 |

-continued

| Compound | Structure |
|---|---|
| 152b | 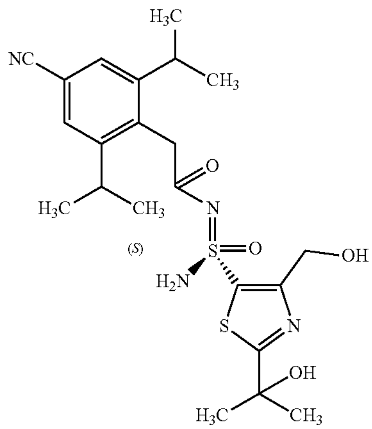 |
| 110a' | 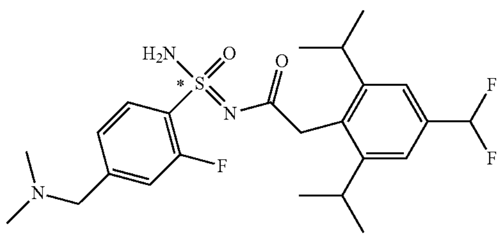 [SMILES: CC(C)c1cc(C(F)F)cc(C(C)C)c1CC(=O)N=S(N)(=O)c1ccc(CN(C)C)cc1F] |
| 110b' | 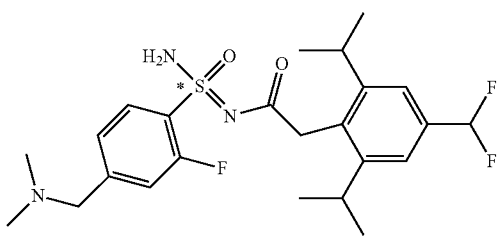 [SMILES: CC(C)c1cc(C(F)F)cc(C(C)C)c1CC(=O)N=S(N)(=O)c1ccc(CN(C)C)cc1F] |
| 201 | 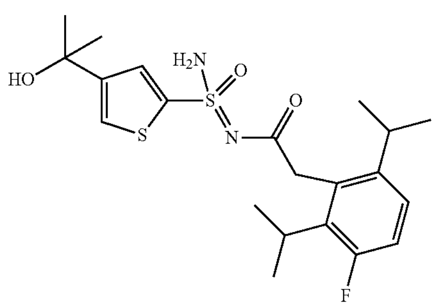 [SMILES: CC(C)c1ccc(F)c(C(C)C)c1CC(=O)N=S(N)(=O)c1cc(C(C)(C)O)cs1] |
| 201b | 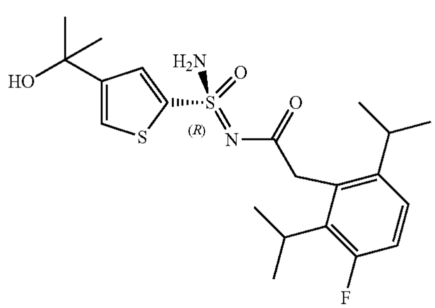 |

| Compound | Structure |
|---|---|
| 201a | 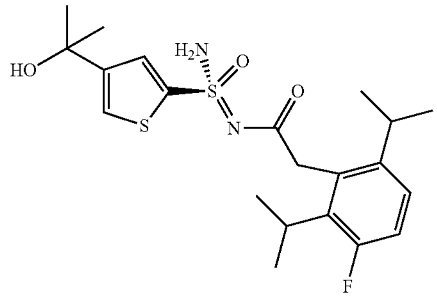 [SMILES: CC(C)c1ccc(F)c(C(C)C)c1CC(=O)N=[S@](N)(=O)c1cc(C(C)(C)O)cs1] |
| 202 | 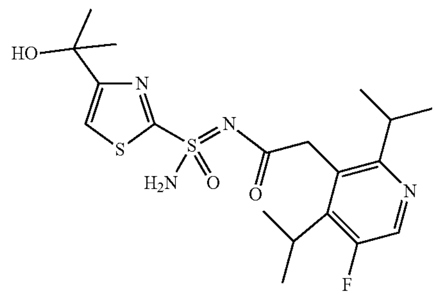 [SMILES: CC(C)c1ncc(F)c(C(C)C)c1CC(=O)N=S(N)(=O)c1nc(C(C)(C)O)cs1] |
| 202a | 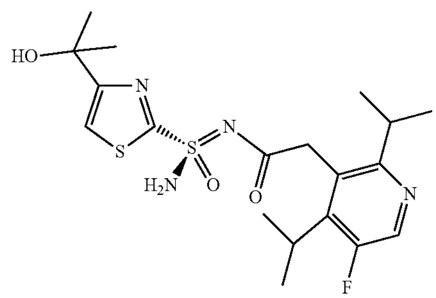 [SMILES: CC(C)c1ncc(F)c(C(C)C)c1CC(=O)N=[S@](N)(=O)c1nc(C(C)(C)O)cs1] |
| 203 | 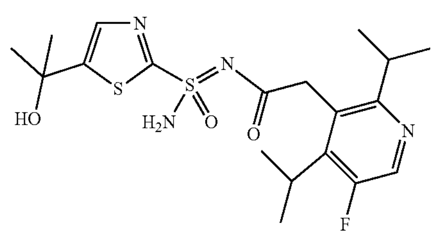 [SMILES: CC(C)c1ncc(F)c(C(C)C)c1CC(=O)N=S(N)(=O)c1ncc(C(C)(C)O)s1] |
| 203b | 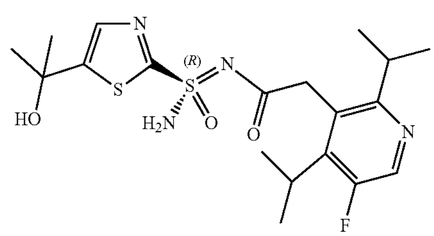 |
| 204 | 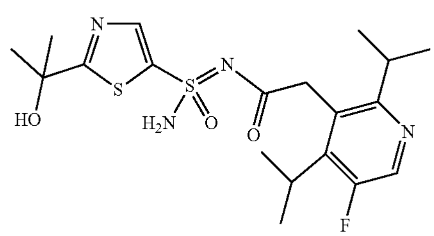 [SMILES: CC(C)c1ncc(F)c(C(C)C)c1CC(=O)N=S(N)(=O)c1cnc(C(C)(C)O)s1] |

-continued
| Compound | Structure |
|---|---|
| 204b | 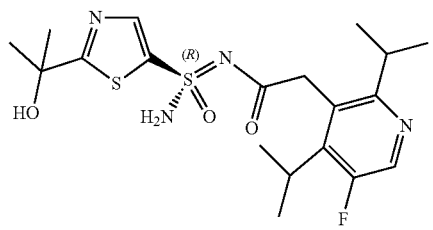 |
| 204a | 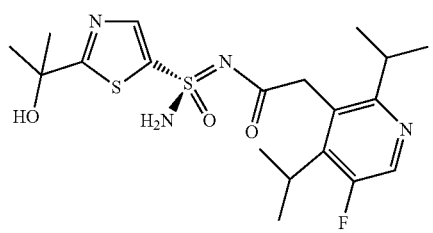 [SMILES: CC(C)c1ncc(F)c(C(C)C)c1CC(=O)N=[S@](N)(=O)c1cnc(C(C)(C)O)s1] |
| 205 | 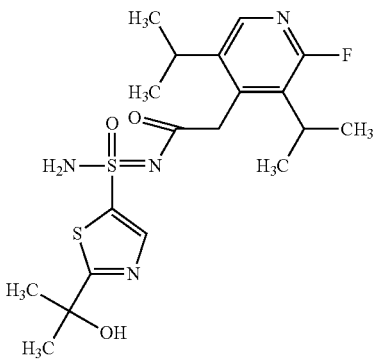 [SMILES: CC(C)c1cnc(F)c(C(C)C)c1CC(=O)N=S(N)(=O)c1cnc(C(C)(C)O)s1] |
| 206 | 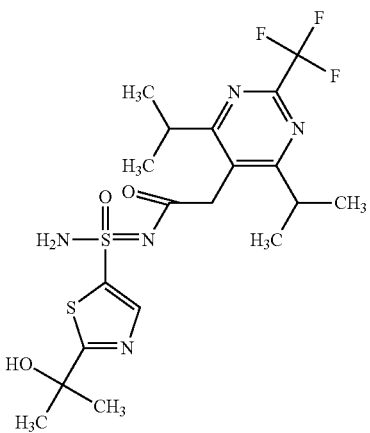 [SMILES: CC(C)c1nc(C(F)(F)F)nc(C(C)C)c1CC(=O)N=S(N)(=O)c1cnc(C(C)(C)O)s1] |

-continued
| Compound | Structure |
|---|---|
| 207 | 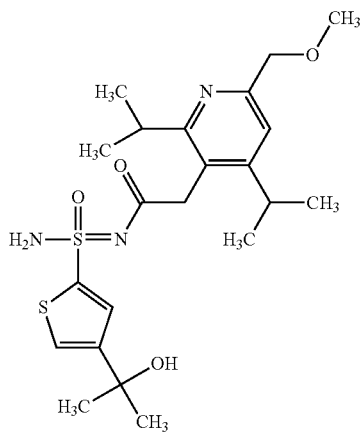 [SMILES: COCc1cc(C(C)C)c(CC(=O)N=S(N)(=O)c2cc(C(C)(C)O)cs2)c(C(C)C)n1] |
| 208 | 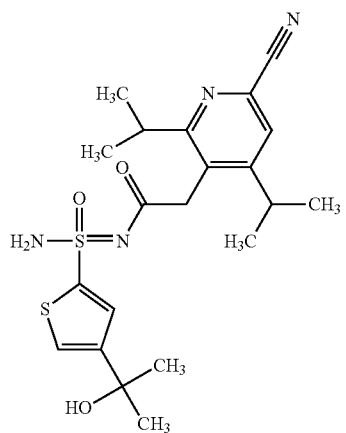 [SMILES: CC(C)c1cc(C#N)nc(C(C)C)c1CC(=O)N=S(N)(=O)c1cc(C(C)(C)O)cs1] |
| 209 | 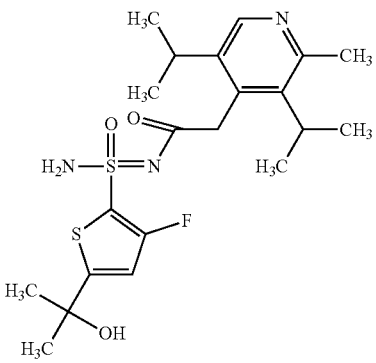 [SMILES: Cc1ncc(C(C)C)c(CC(=O)N=S(N)(=O)c2sc(C(C)(C)O)cc2F)c1C(C)C] |
| 210 | 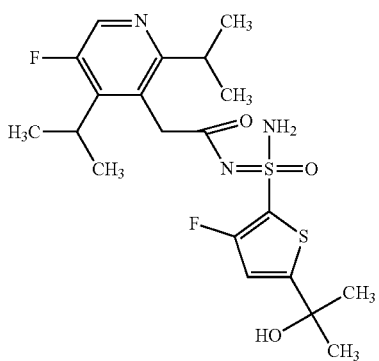 [SMILES: CC(C)c1ncc(F)c(C(C)C)c1CC(=O)N=S(N)(=O)c1sc(C(C)(C)O)cc1F] |

| Compound | Structure |
|---|---|
| 210b | 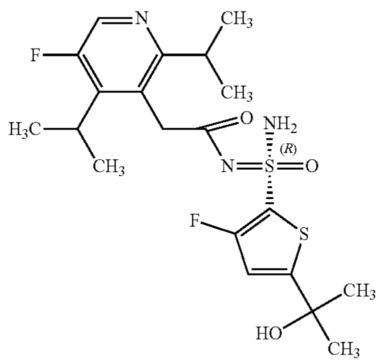 |
| 211 | 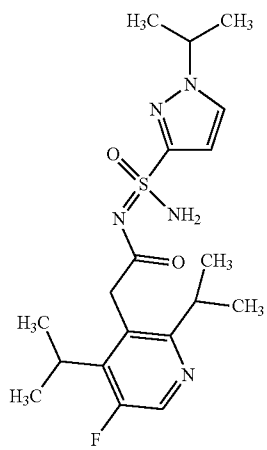 [SMILES: CC(C)c1ncc(F)c(C(C)C)c1CC(=O)N=S(N)(=O)c1ccn(C(C)C)n1] |
| 213 | 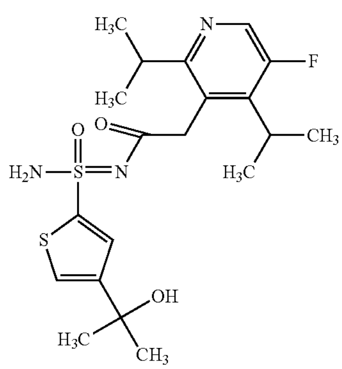 [SMILES: CC(C)c1ncc(F)c(C(C)C)c1CC(=O)N=S(N)(=O)c1cc(C(C)(C)O)cs1] |
| 213a | 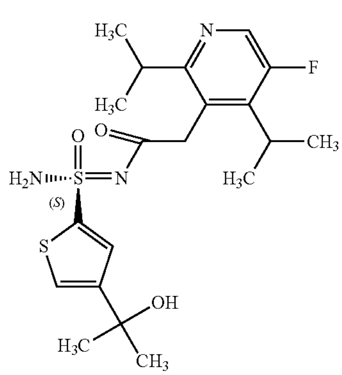 |

| Compound | Structure |
|---|---|
| 213b | 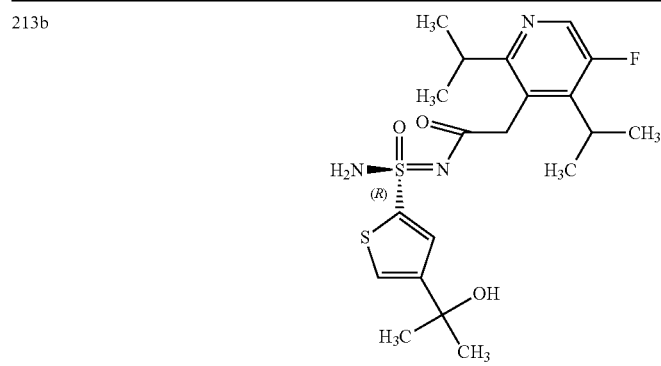 |
| 215 | 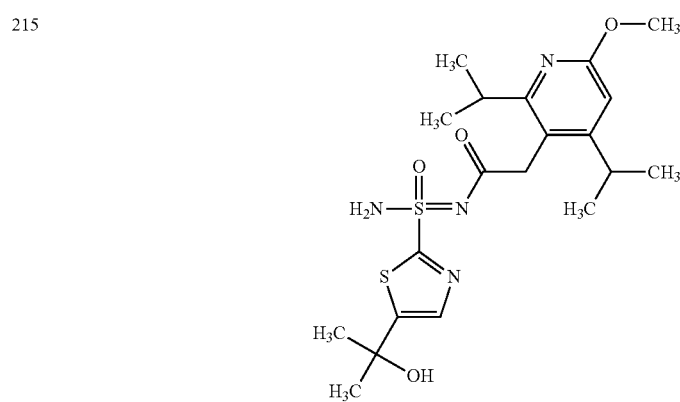 |
| 216 | 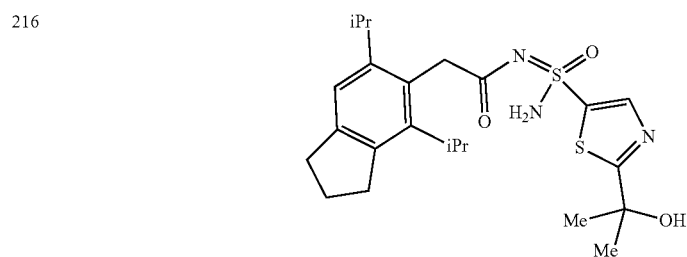 |
| 216a | 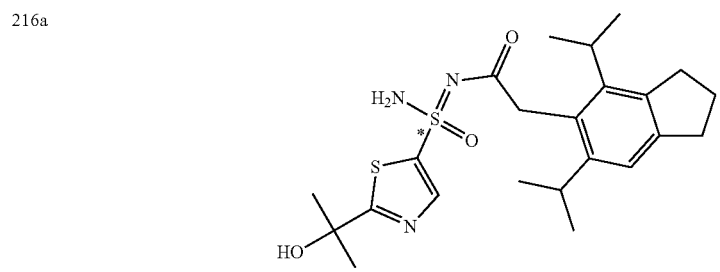 |
| 216b | 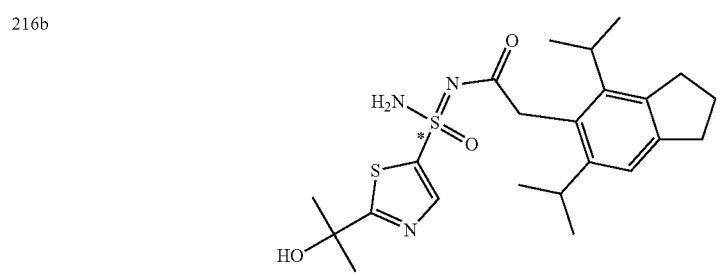 |

| Compound | Structure |
|---|---|
| 217 | 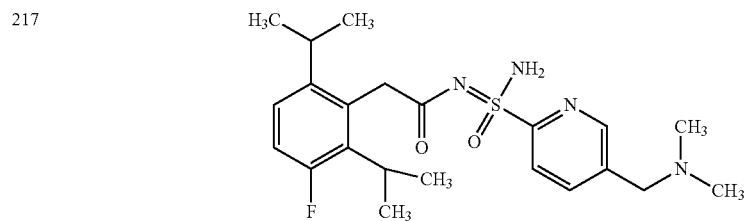 |
| 217a | 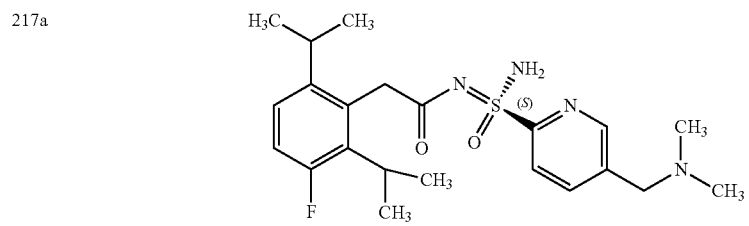 |
| 218 | 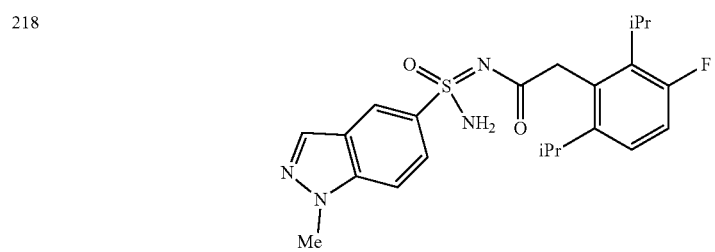 |
| 218a | 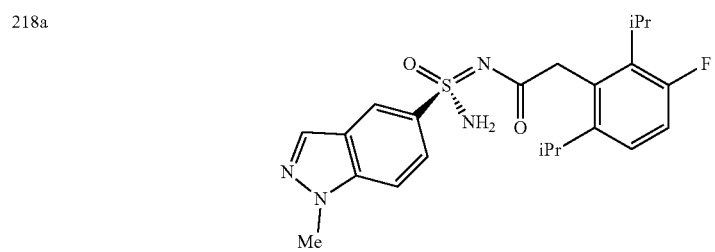 |
| 219 | 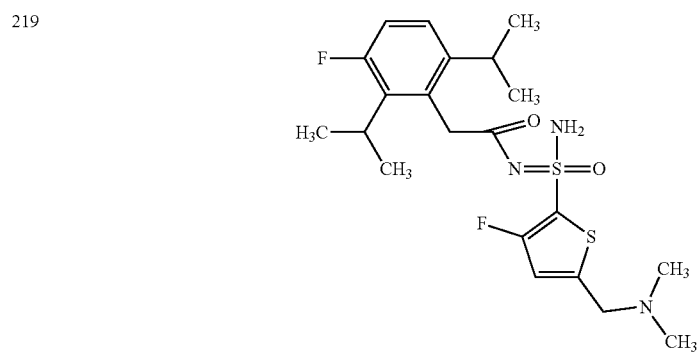 |

-continued
| Compound | Structure |
|---|---|
| 220 | 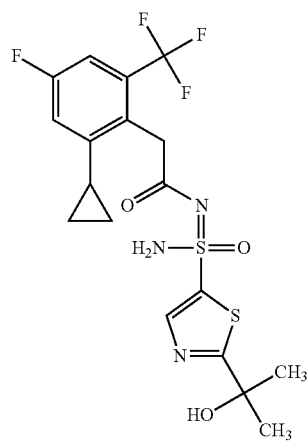 [SMILES: CC(C)(O)c1ncc(S(N)(=O)=NC(=O)Cc2c(C3CC3)cc(F)cc2C(F)(F)F)s1] |
| 220a | 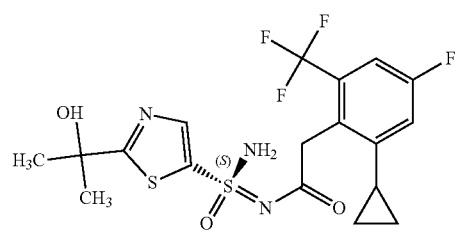 |
| 221 | 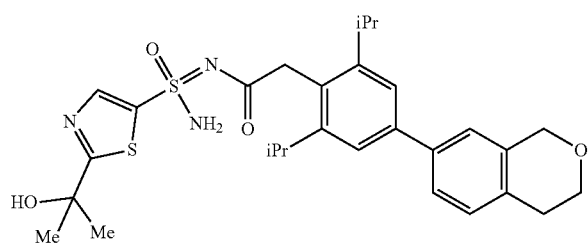 |
| 221a | 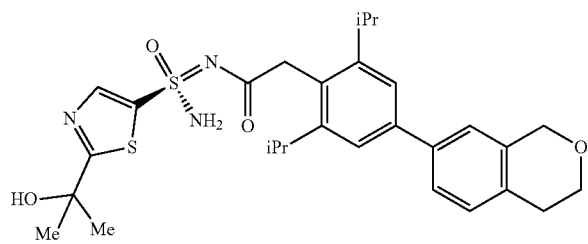 [SMILES: CC(C)c1cc(-c2ccc3c(c2)COCC3)cc(C(C)C)c1CC(=O)N=[S@](N)(=O)c1cnc(C(C)(C)O)s1] |
| 221b | 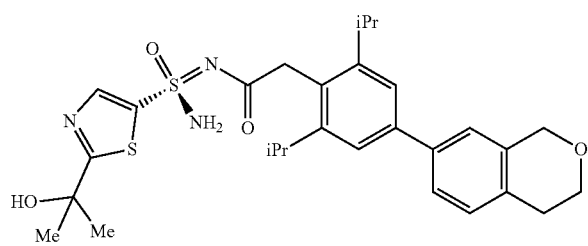 [SMILES: CC(C)c1cc(-c2ccc3c(c2)COCC3)cc(C(C)C)c1CC(=O)N=[S@@](N)(=O)c1cnc(C(C)(C)O)s1] |

-continued
| Compound | Structure |
|---|---|
| 222 | 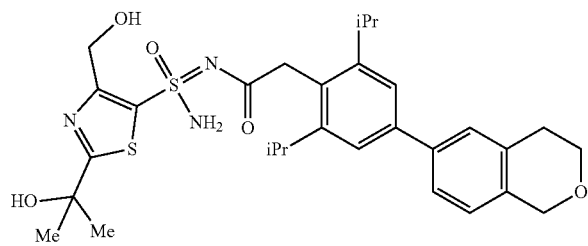 [SMILES: CC(C)c1cc(-c2ccc3c(c2)CCOC3)cc(C(C)C)c1CC(=O)N=S(N)(=O)c1sc(C(C)(C)O)nc1CO] |
| 224 | 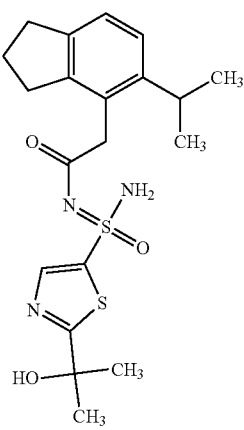 [SMILES: CC(C)c1ccc2c(c1CC(=O)N=S(N)(=O)c1cnc(C(C)(C)O)s1)CCC2] |
| 225 | 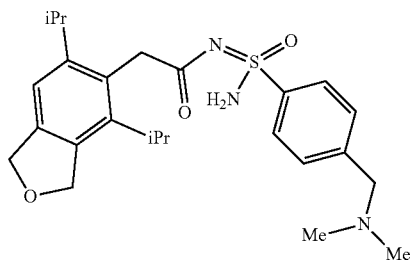 [SMILES: CC(C)c1cc2c(c(C(C)C)c1CC(=O)N=S(N)(=O)c1ccc(CN(C)C)cc1)COC2] |
| 225a | 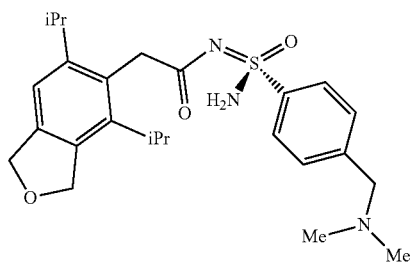 [SMILES: CC(C)c1cc2c(c(C(C)C)c1CC(=O)N=[S@](N)(=O)c1ccc(CN(C)C)cc1)COC2] |

-continued
| Compound | Structure |
|---|---|
| 226 | 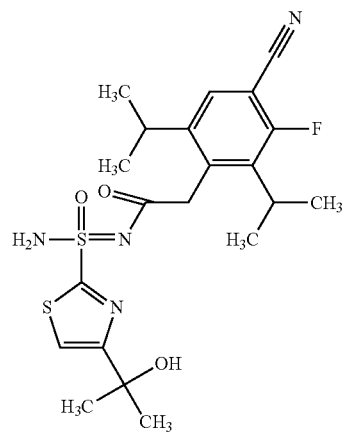 [SMILES: CC(C)c1cc(C#N)c(F)c(C(C)C)c1CC(=O)N=S(N)(=O)c1nc(C(C)(C)O)cs1] |
| 226a | 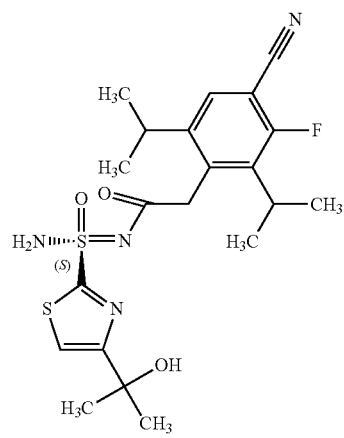 |
| 226b | 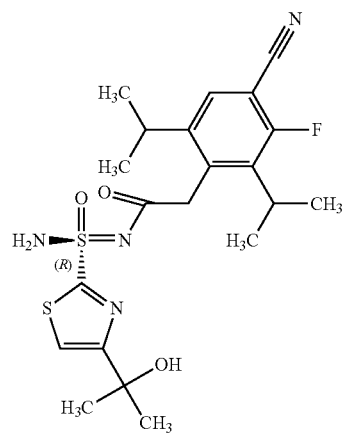 |
| 227 | 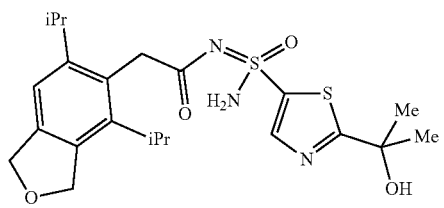 [SMILES: CC(C)c1cc2c(c(C(C)C)c1CC(=O)N=S(N)(=O)c1cnc(C(C)(C)O)s1)COC2] |

| Compound | Structure |
|---|---|
| 227a | 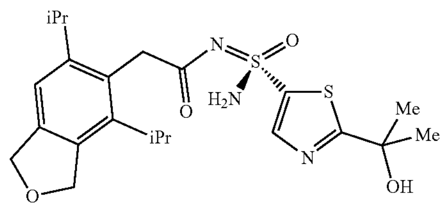 [SMILES: CC(C)c1cc2c(c(C(C)C)c1CC(=O)N=[S@](N)(=O)c1cnc(C(C)(C)O)s1)COC2] |
| 227b | 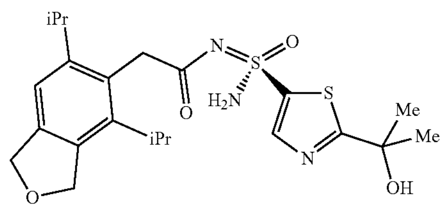 [SMILES: CC(C)c1cc2c(c(C(C)C)c1CC(=O)N=[S@@](N)(=O)c1cnc(C(C)(C)O)s1)COC2] |
| 228 | 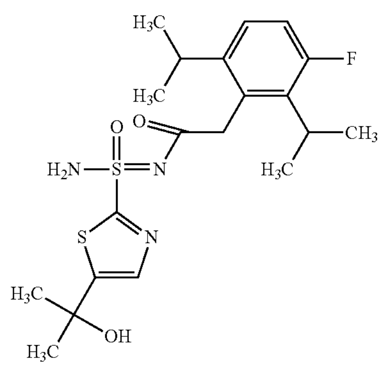 [SMILES: CC(C)c1ccc(F)c(C(C)C)c1CC(=O)N=S(N)(=O)c1ncc(C(C)(C)O)s1] |
| 228a | 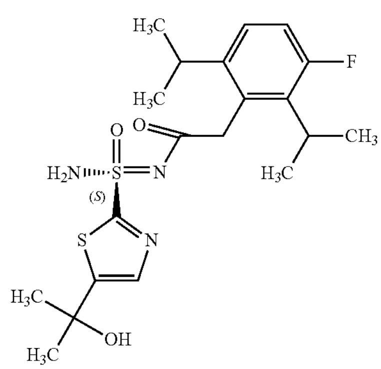 |
| 228b | 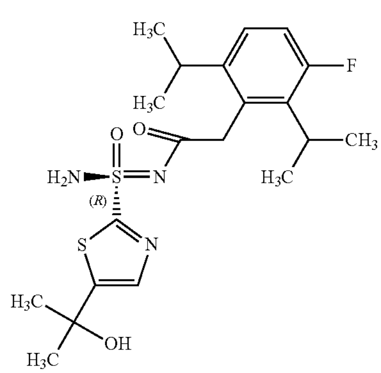 |

| Compound | Structure |
|---|---|
| 229 | 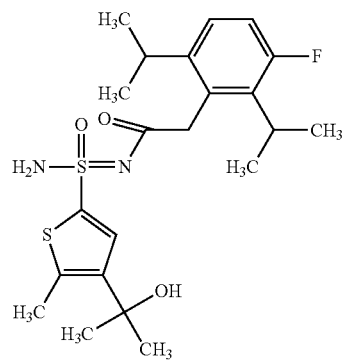 [SMILES: Cc1sc(S(N)(=O)=NC(=O)Cc2c(C(C)C)ccc(F)c2C(C)C)cc1C(C)(C)O] |
| 229a | 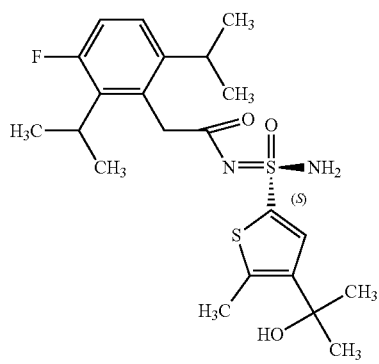 |
| 229b | 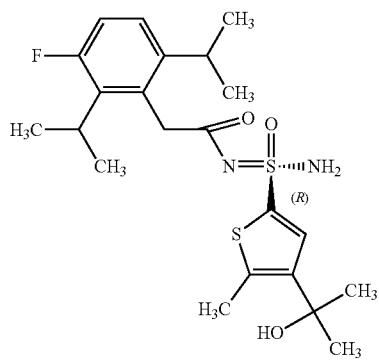 |
| 230 | 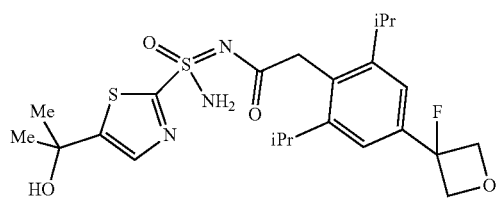 [SMILES: CC(C)c1cc(C2(F)COC2)cc(C(C)C)c1CC(=O)N=S(N)(=O)c1ncc(C(C)(C)O)s1] |
| 231 | 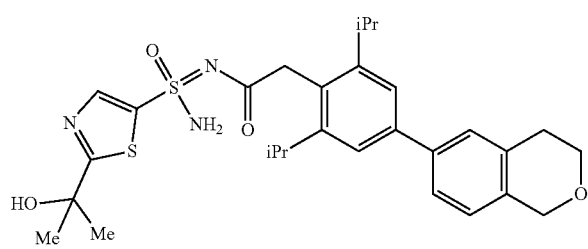 |

-continued
| Compound | Structure |
|---|---|
| 232 | 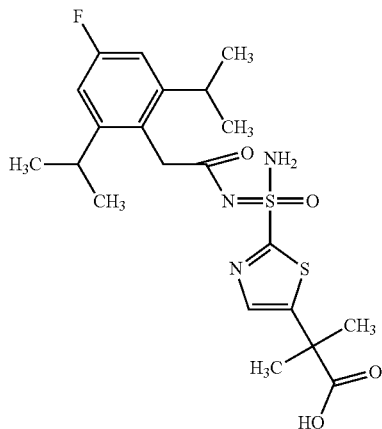 [SMILES: CC(C)c1cc(F)cc(C(C)C)c1CC(=O)N=S(N)(=O)c1ncc(C(C)(C)C(=O)O)s1] |
| 233 | 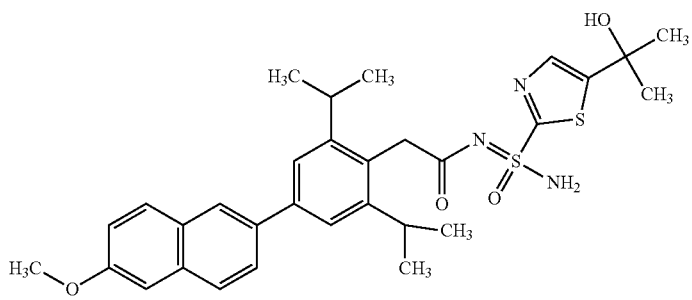 [SMILES: COc1ccc2cc(-c3cc(C(C)C)c(CC(=O)N=S(N)(=O)c4ncc(C(C)(C)O)s4)c(C(C)C)c3)ccc2c1] |
| 234 | 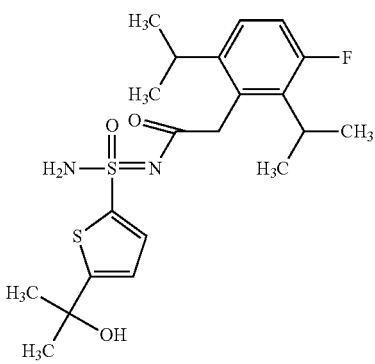 [SMILES: CC(C)c1ccc(F)c(C(C)C)c1CC(=O)N=S(N)(=O)c1ccc(C(C)(C)O)s1] |
| 234a | 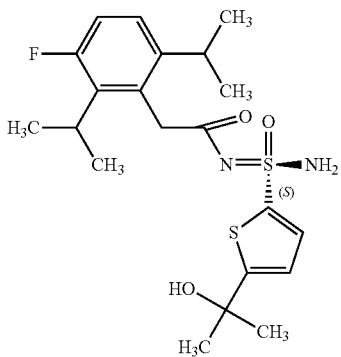 |

| Compound | Structure |
|---|---|
| 234b | 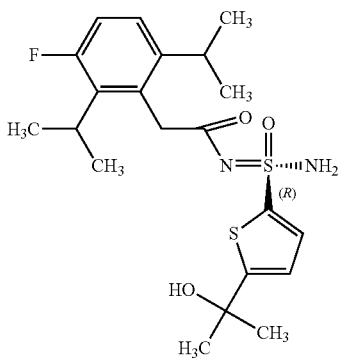 |
| 236 | 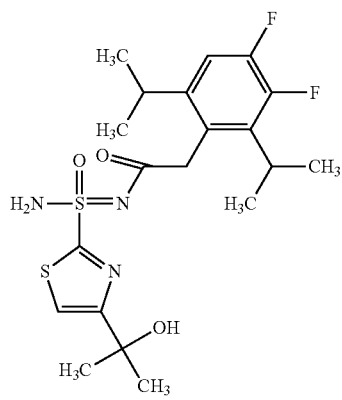 [SMILES: CC(C)c1cc(F)c(F)c(C(C)C)c1CC(=O)N=S(N)(=O)c1nc(C(C)(C)O)cs1] |
| 236a | 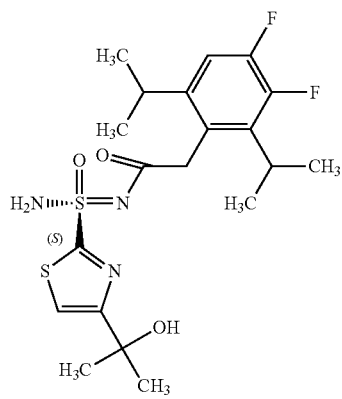 |
| 236b | 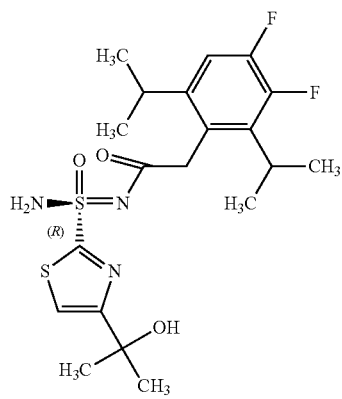 |

| Compound | Structure |
|---|---|
| 237 | 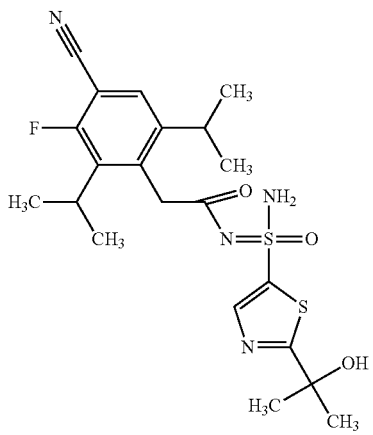 [SMILES: CC(C)c1cc(C#N)c(F)c(C(C)C)c1CC(=O)N=S(N)(=O)c1cnc(C(C)(C)O)s1] |
| 238 | 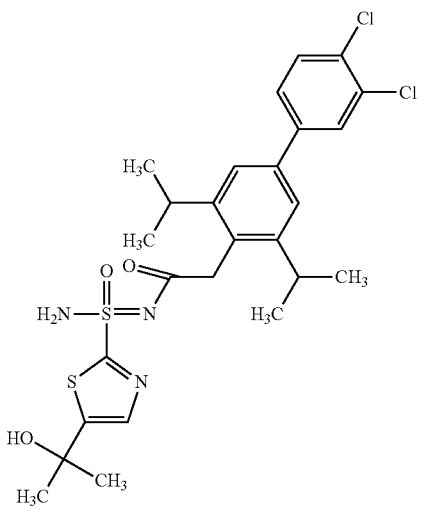 [SMILES: CC(C)c1cc(-c2ccc(Cl)c(Cl)c2)cc(C(C)C)c1CC(=O)N=S(N)(=O)c1ncc(C(C)(C)O)s1] |
| 238a | 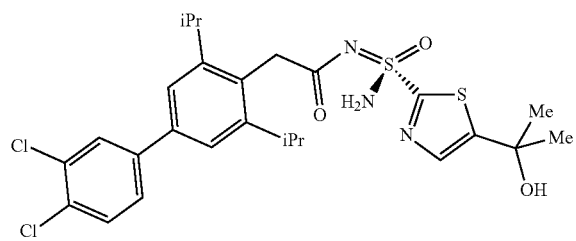 [SMILES: CC(C)c1cc(-c2ccc(Cl)c(Cl)c2)cc(C(C)C)c1CC(=O)N=[S@](N)(=O)c1ncc(C(C)(C)O)s1] |
| 238b | 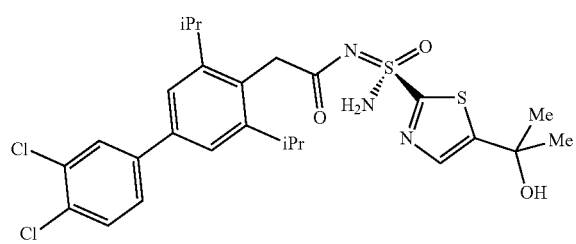 [SMILES: CC(C)c1cc(-c2ccc(Cl)c(Cl)c2)cc(C(C)C)c1CC(=O)N=[S@@](N)(=O)c1ncc(C(C)(C)O)s1] |

| Compound | Structure |
|---|---|
| 239 | 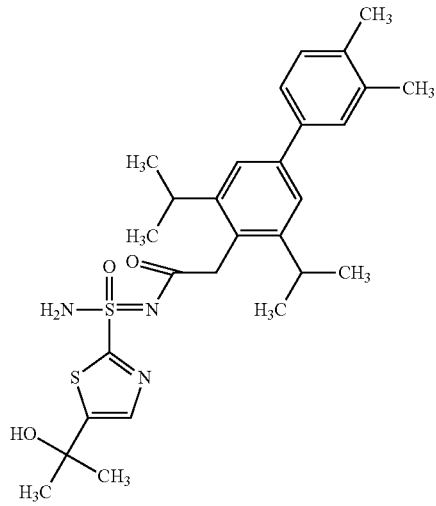 [SMILES: Cc1ccc(-c2cc(C(C)C)c(CC(=O)N=S(N)(=O)c3ncc(C(C)(C)O)s3)c(C(C)C)c2)cc1C] |
| 239a | 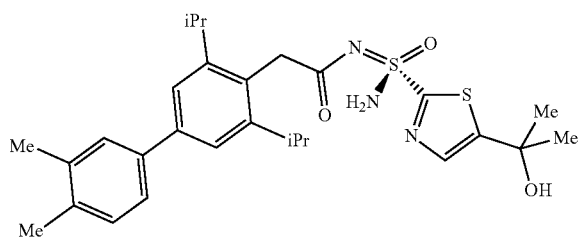 [SMILES: Cc1ccc(-c2cc(C(C)C)c(CC(=O)N=[S@](N)(=O)c3ncc(C(C)(C)O)s3)c(C(C)C)c2)cc1C] |
| 239b | 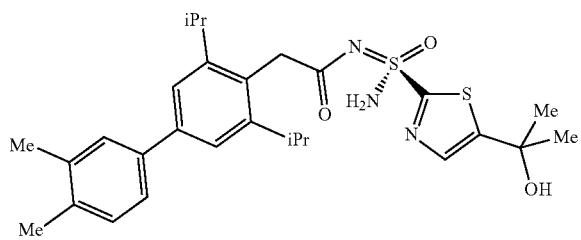 [SMILES: Cc1ccc(-c2cc(C(C)C)c(CC(=O)N=[S@@](N)(=O)c3ncc(C(C)(C)O)s3)c(C(C)C)c2)cc1C] |
| 241 | 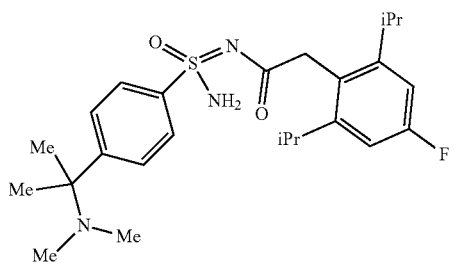 [SMILES: CC(C)c1cc(F)cc(C(C)C)c1CC(=O)N=S(N)(=O)c1ccc(C(C)(C)N(C)C)cc1] |

-continued

| Compound | Structure |
|---|---|
| 242 | 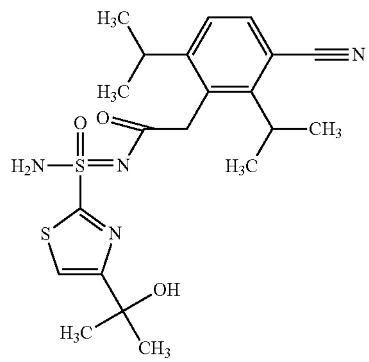 [SMILES: CC(C)c1ccc(C#N)c(C(C)C)c1CC(=O)N=S(N)(=O)c1nc(C(C)(C)O)cs1] |
| 242a | 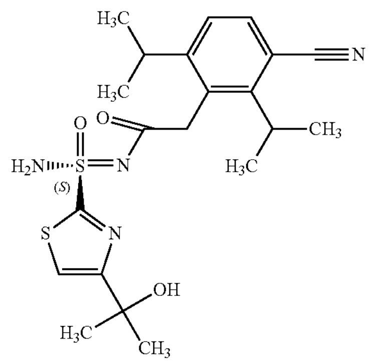 |
| 242b | 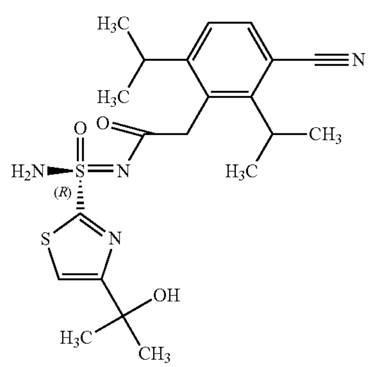 |
| 243 | 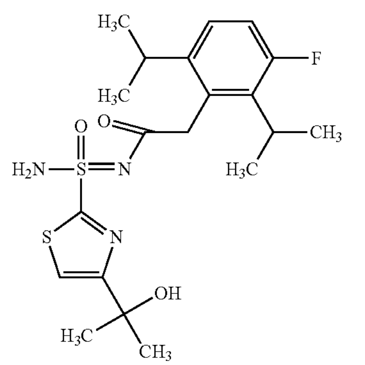 [SMILES: CC(C)c1ccc(F)c(C(C)C)c1CC(=O)N=S(N)(=O)c1nc(C(C)(C)O)cs1] |

| Compound | Structure |
|---|---|
| 243a | (structure) |
| 243b | (structure) |
| 244ba | (structure) |
| 245 | (structure) |

US 11,370,763 B2
795                                                                    796
-continued
| Compound | Structure |
|---|---|
| 247 | 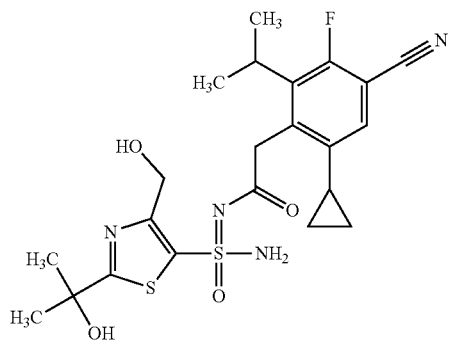 [SMILES: CC(C)c1c(F)c(C#N)cc(C2CC2)c1CC(=O)N=S(N)(=O)c1sc(C(C)(C)O)nc1CO] |
| 248 | 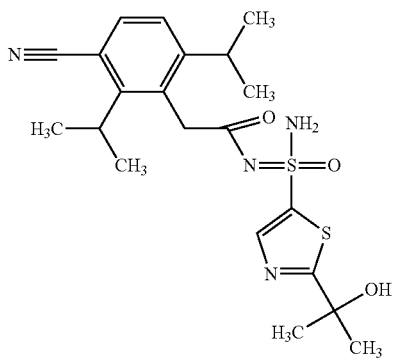 [SMILES: CC(C)c1ccc(C#N)c(C(C)C)c1CC(=O)N=S(N)(=O)c1cnc(C(C)(C)O)s1] |
| 249 | 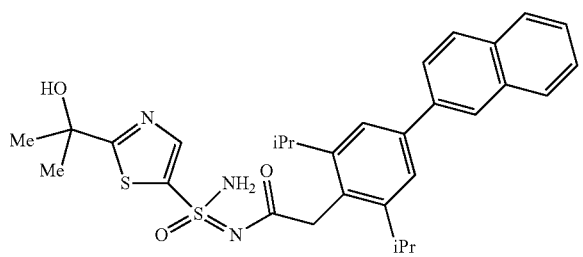 [SMILES: CC(C)c1cc(-c2ccc3ccccc3c2)cc(C(C)C)c1CC(=O)N=S(N)(=O)c1cnc(C(C)(C)O)s1] |
| 249a | 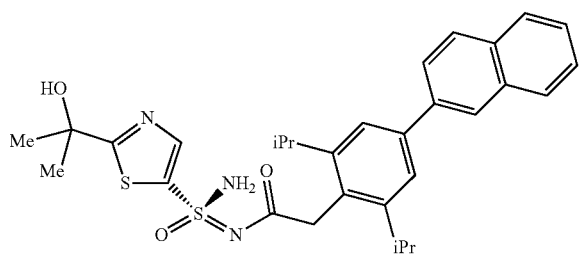 [SMILES: CC(C)c1cc(-c2ccc3ccccc3c2)cc(C(C)C)c1CC(=O)N=[S@](N)(=O)c1cnc(C(C)(C)O)s1] |
| 249b | 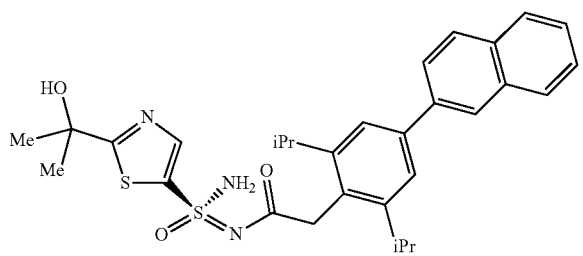 [SMILES: CC(C)c1cc(-c2ccc3ccccc3c2)cc(C(C)C)c1CC(=O)N=[S@@](N)(=O)c1cnc(C(C)(C)O)s1] |

-continued
| Compound | Structure |
|---|---|
| 250 | 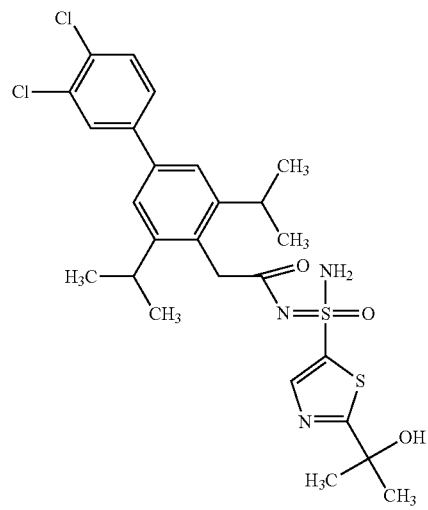 [SMILES: CC(C)c1cc(-c2ccc(Cl)c(Cl)c2)cc(C(C)C)c1CC(=O)N=S(N)(=O)c1cnc(C(C)(C)O)s1] |
| 251 | 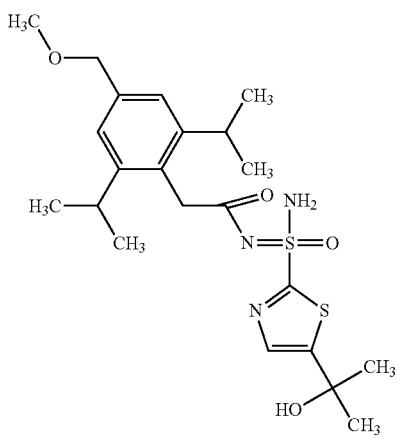 [SMILES: COCc1cc(C(C)C)c(CC(=O)N=S(N)(=O)c2ncc(C(C)(C)O)s2)c(C(C)C)c1] |
| 251a | 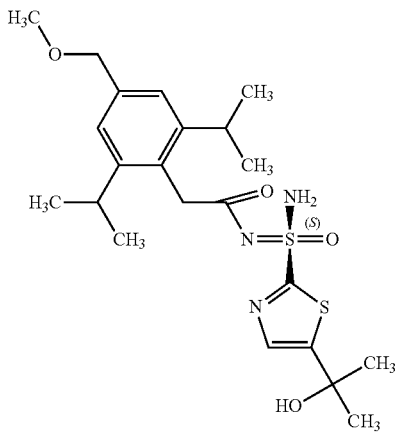 |

| Compound | Structure |
|---|---|
| 251b | (structure) |
| 252 | (structure) |
| 253 | (structure) |
| 254 | (structure) |

| Compound | Structure |
|---|---|
| 255 | (structure) |
| 256 | (structure) |
| 256a | (structure) |

| Compound | Structure |
|---|---|
| 256b | (structure shown) |
| 257 | (structure shown) |
| 258 | (structure shown) |
| 258a | (structure shown) |

-continued
| Compound | Structure |
|---|---|
| 258b | 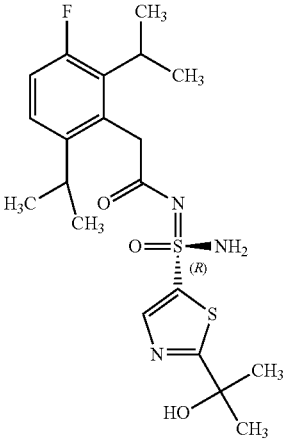 |
| 261a | 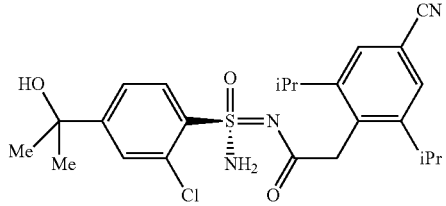 [SMILES: CC(C)c1cc(C#N)cc(C(C)C)c1CC(=O)N=[S@](N)(=O)c1ccc(C(C)(C)O)cc1Cl] |
| 261b | 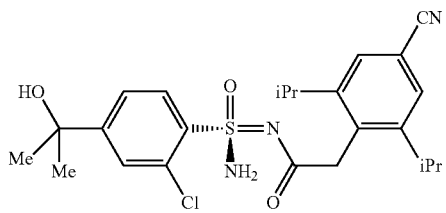 [SMILES: CC(C)c1cc(C#N)cc(C(C)C)c1CC(=O)N=[S@@](N)(=O)c1ccc(C(C)(C)O)cc1Cl] |
| 262b | 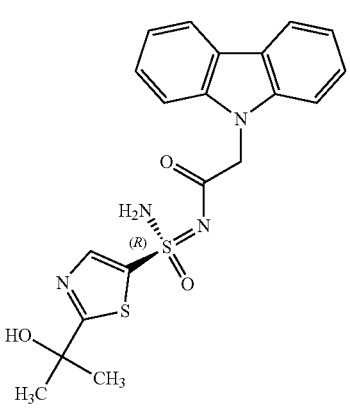 |
| 263 | 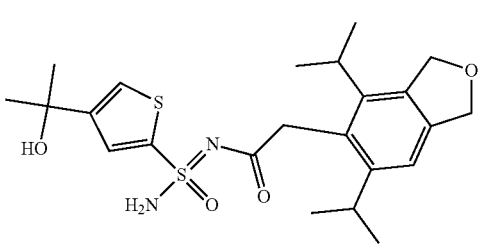 [SMILES: CC(C)c1cc2c(c(C(C)C)c1CC(=O)N=S(N)(=O)c1cc(C(C)(C)O)cs1)COC2] |

| Compound | Structure |
|---|---|
| 263a | (structure) |
| 263b | (structure) |
| 264 | (structure) |
| 264a | (structure) | and a pharmaceutically acceptable salt thereof.

12. The compound of claim 1, wherein the sulfur in the moiety S(=O)(NHR³)=N— has (S) stereochemistry, or (R) stereochemistry.

13. A pharmaceutical composition comprising a compound or salt as claimed in claim 1 and one or more pharmaceutically acceptable excipients.

* * * * *

SEQUENCE LISTING

<160> NUMBER OF SEQ ID NOS: 37

<210> SEQ ID NO 1
<211> LENGTH: 702
<212> TYPE: DNA
<213> ORGANISM: Homo sapiens

<400> SEQUENCE: 1

| | | | | | | |
|---|---|---|---|---|---|---|
| atgagcactg | aaagcatgat | ccgggacgtg | gagctggccg | aggaggcgct | ccccaagaag | 60 |
| acagggggc | cccagggctc | caggcggtgc | ttgttcctca | gcctcttctc | cttcctgatc | 120 |
| gtggcaggcg | ccaccacgct | cttctgcctg | ctgcactttg | gagtgatcgg | ccccagagg | 180 |
| gaagagttcc | ccagggacct | ctctctaatc | agccctctgg | cccaggcagt | cagatcatct | 240 |
| tctcgaaccc | cgagtgacaa | gcctgtagcc | catgttgtag | caaaccctca | agctgagggg | 300 |
| cagctccagt | ggctgaaccg | ccgggccaat | gccctcctgg | ccaatggcgt | ggagctgaga | 360 |
| gataaccagc | tggtggtgcc | atcagagggc | ctgtacctca | tctactccca | ggtcctcttc | 420 |
| aagggccaag | gctgcccctc | cacccatgtg | ctcctcaccc | acaccatcag | ccgcatcgcc | 480 |
| gtctcctacc | agaccaaggt | caacctcctc | tctgccatca | gagcccctg | ccagagggag | 540 |
| accccagagg | gggctgaggc | caagccctgg | tatgagccca | tctatctggg | aggggtcttc | 600 |
| cagctggaga | agggtgaccg | actcagcgct | gagatcaatc | ggcccgacta | tctcgacttt | 660 |
| gccgagtctg | ggcaggtcta | ctttgggatc | attgccctgt | ga | | 702 |

<210> SEQ ID NO 2
<211> LENGTH: 1368
<212> TYPE: DNA
<213> ORGANISM: Homo sapiens

<400> SEQUENCE: 2

| | | | | | | |
|---|---|---|---|---|---|---|
| atgggcctct | ccaccgtgcc | tgacctgctg | ctgccactgg | tgctcctgga | gctgttggtg | 60 |
| ggaatatacc | cctcaggggt | tattggactg | gtccctcacc | taggggacag | ggagaagaga | 120 |
| gatagtgtgt | gtccccaagg | aaaatatatc | caccctcaaa | ataattcgat | ttgctgtacc | 180 |
| aagtgccaca | aaggaaccta | cttgtacaat | gactgtccag | gccgggggca | ggatacggac | 240 |
| tgcagggagt | gtgagagcgg | ctccttcacc | gcttcagaaa | accacctcag | acactgcctc | 300 |
| agctgctcca | aatgccgaaa | ggaaatgggt | caggtggaga | tctcttcttg | cacagtggac | 360 |
| cgggacaccg | tgtgtggctg | caggaagaac | cagtaccggc | attattggag | tgaaaacctt | 420 |
| ttccagtgct | tcaattgcag | cctctgcctc | aatgggaccg | tgcacctctc | ctgccaggag | 480 |
| aaacagaaca | ccgtgtgcac | ctgccatgca | ggtttctttc | taagagaaaa | cgagtgtgtc | 540 |
| tcctgtagta | actgtaagaa | aagcctggag | tgcacgaagt | tgtgcctacc | ccagattgag | 600 |
| aatgttaagg | gcactgagga | ctcaggcacc | acagtgctgt | tgcccctggt | catttctttt | 660 |
| ggtcttttgcc | ttttatccct | cctcttcatt | ggtttaatgt | atcgctacca | acggtggaag | 720 |
| tccaagctct | actccattgt | ttgtgggaaa | tcgacacctg | aaaaagaggg | ggagcttgaa | 780 |
| ggaactacta | ctaagcccct | ggccccaaac | ccaagcttca | gtcccactcc | aggcttcacc | 840 |
| cccaccctgg | gcttcagtcc | cgtgcccagt | tccaccttca | cctccagctc | cacctatacc | 900 |
| cccggtgact | gtcccaactt | gcggctcccc | gcagagagg | tggcaccacc | ctatcagggg | 960 |
| gctgacccca | tccttgcgac | agccctcgcc | tccgacccca | tcccaacccc | ccttcagaag | 1020 |
| tgggaggaca | gcgcccacaa | gccacagagc | ctagacactg | atgacccgc | gacgctgtac | 1080 |
| gccgtggtgg | agaacgtgcc | cccgttgcgc | tggaaggaat | tcgtgcggcg | cctagggctg | 1140 |

-continued

```
agcgaccacg agatcgatcg gctggagctg cagaacgggc gctgcctgcg cgaggcgcaa    1200
tacagcatgc tggcgacctg gaggcggcgc acgccgcggc gcgaggccac gctggagctg    1260
ctgggacgcg tgctccgcga catggacctg ctgggctgcc tggaggacat cgaggaggcg    1320 cttttgcggcc ccgccgccct cccgcccgcg cccagtcttc tcagatga                1368
```

<210> SEQ ID NO 3
<211> LENGTH: 281
<212> TYPE: DNA
<213> ORGANISM: Homo sapiens

<400> SEQUENCE: 3

```
attcttcccc tggtggccat gggacccagg tcaatgtcac ctgcatcgtg aacgtctgta      60
gcagctctga ccacagctca cagtgctcct cccaagccag ctccacaatg ggagacacag     120
attccagccc ctcggagtcc ccgaaggacg agcaggtccc cttctccaag gaggaatgtg     180
cctttcggtc acagctggag acgccagaga ccctgctggg gagcaccgaa gagaagcccc     240
tgccccttgg agtgcctgat gctgggatga agcccagtta a                        281
```

<210> SEQ ID NO 4
<211> LENGTH: 939
<212> TYPE: DNA
<213> ORGANISM: Homo sapiens

<400> SEQUENCE: 4

```
atggcagctg ggcaaaatgg gcacgaagag tgggtgggca gcgcatacct gtttgtggag      60
tcctcgctgg acaaggtggt cctgtcggat gcctacgcgc accccagca gaaggtggca     120 gtgtacaggg ctctgcaggc tgccttggca gagagcggcg ggagcccgga cgtgctgcag     180
atgctgaaga tccaccgcag cgacccgcag ctgatcgtgc agctgcgatt ctgcgggcgg     240
cagccctgtg gccgcttcct ccgcgcctac cgcgagggg cgctgcgcgc cgcgctgcag     300
aggagcctgg cggccgcgct cgcccagcac tcggtgccgc tgcaactgga gctgcgcgcc     360
ggcgccgagc ggctggacgc tttgctggcg gacgaggagc gctgtttgag ttgcatccta     420
gcccagcagc ccgaccggct ccgggatgaa gaactggctg agctggagga tgcgctgcga     480
aatctgaagt gcggctcggg ggccggggt ggcgacgggg aggtcgcttc ggccccttg      540 cagccccgg tgccctctct gtcggaggtg aagccgccgc cgccgccgcc acctgcccag     600
acttttctgt ccagggtca gcctgtagtg aatcggccgc tgagcctgaa ggaccaacag     660
acgttcgcgc gctctgtggg tctcaaatgg cgcaaggtgg ggcgctcact gcagcgaggc     720
tgccgggcgc tgcgggaccc ggcgctggac tcgctggcct acgagtacga gcgcgaggga     780
ctgtacgagc aggccttcca gctgctgcgg cgcttcgtgc aggccgaggg ccgccgcgcc     840
acgctgcagc gcctggtgga ggcactcgag gagaacgagc tcaccagcct ggcagaggac     900
ttgctgggcc tgaccgatcc caatggcggc ctggcctag                           939
```

<210> SEQ ID NO 5
<211> LENGTH: 1506
<212> TYPE: DNA
<213> ORGANISM: Homo sapiens

<400> SEQUENCE: 5

```
atggctgcag ctagcgtgac ccccctggc tccctggagt tgctacagcc cggcttctcc       60
aagaccctcc tggggaccaa gctggaagcc aagtacctgt gctccgcctg cagaaacgtc     120
```

```
ctccgcaggc ccttccaggc gcagtgtggc caccggtact gctccttctg cctggccagc      180
atcctcagct ctgggcctca gaactgtgct gcctgtgttc acgagggcat atatgaagaa      240
ggcatttcta ttttagaaag cagttcggcc ttcccagata atgctgcccg cagggaggtg      300
gagagcctgc cggccgtctg tcccagtgat ggatgcacct ggaaggggac cctgaaagaa      360
tacgagagct gccacgaagg ccgctgcccg ctcatgctga ccgaatgtcc cgcgtgcaaa      420
ggcctggtcc gccttggtga aaaggagcgc cacctggagc acgagtgccc ggagagaagc      480
ctgagctgcc ggcattgccg ggcaccctgc tgcggagcag acgtgaaggc gcaccacgag      540
gtctgcccca gttccccctt aacttgtgac ggctgcggca agaagaagat cccccgggag      600
aagtttcagg accacgtcaa gacttgtggc aagtgtcgag tcccttgcag attccacgcc      660
atcggctgcc tcgagacggt agagggtgag aaacagcagg agcacgaggt gcagtggctg      720
cgggagcacc tggccatgct actgagctcg gtgctggagg caaagcccct cttgggagac      780
cagagccacg cggggtcaga gctcctgcag aggtgcgaga gcctggagaa gaagacggcc      840
acttttgaga acattgtctg cgtcctgaac cgggaggtgg agagggtggc catgactgcc      900
gaggcctgca gccggcagca ccggctggac caagacaaga ttgaagccct gagtagcaag      960
gtgcagcagc tggagaggag cattggcctc aaggacctgg cgatggctga cttggagcag     1020
aaggtcttgg agatggaggc atccacctac gatgggtct tcatctggaa gatctcagac     1080
ttcgccagga agcgccagga agctgtggct ggccgcatac ccgccatctt ctccccagcc     1140
ttctacacca gcaggtacgg ctacaagatg tgtctgcgta tctacctgaa cggcgacggc     1200
accgggcgag gaacacacct gtccctcttc tttgtggtga tgaagggccc gaatgacgcc     1260
ctgctgcggt ggcccttcaa ccagaaggtg accttaatgc tgctcgacca gaataaccgg     1320
gagcacgtga ttgacgcctt caggcccgac gtgacttcat cctcttttca gaggccagtc     1380
aacgacatga acatcgcaag cggctgcccc ctcttctgcc ccgtctccaa gatggaggca     1440
aagaattcct acgtgcggga cgatgccatc ttcatcaagg ccattgtgga cctgacaggg     1500
ctctaa                                                                 1506

<210> SEQ ID NO 6
<211> LENGTH: 1044
<212> TYPE: DNA
<213> ORGANISM: Homo sapiens

<400> SEQUENCE: 6
atggaaacac ccttctacgg cgatgaggcg ctgagcggcc tgggcggcgg cgccagtggc       60
agcggcggca gcttcgcgtc cccgggccgc ttgttccccg gggcgccccc gacggccgcg      120
gccggcagca tgatgaagaa ggacgcgctg acgctgagcc tgagtgagca ggtggcggca      180
gcgctcaagc ctgcggccgc gccgcctcct accccctgc gcgccgacgg cgcccccagc       240
gcggcacccc ccgacggcct gctcgcctct cccgacctgg gctgctgaa gctggcctcc       300
cccgagctcg agcgcctcat catccagtcc aacgggctgg tcaccaccac gccgacgagc      360
tcacagttcc tctacccccaa ggtggcggcc agcgaggagc aggagttcgc cgagggcttc      420
gtcaaggccc tggaggattt acacaagcag aaccagctcg cgcgcggcgc ggccgctgcc      480
gccgccgccg ccgccgccgg ggggccctcg ggcacggcca cgggctccgc gccccccggc      540
gagctggccc cggcgcggc cgcgcccgaa gcgcctgtct acgcgaacct gagcagctac      600
gcgggcggcg ccggggcgc ggggggcgcc gcgacggtcg ccttcgctgc cgaacctgtg      660
cccttcccgc cgccgccacc cccaggcgcg ttggggccgc cgcgcctggc tgcgctcaag      720
```

-continued

| | |
|---|---|
| gacgagccac agacggtgcc cgacgtgccg agcttcggcg agagcccgcc gttgtcgccc | 780 |
| atcgacatgg acacgcagga gcgcatcaag gcggagcgca agcggctgcg caaccgcatc | 840 |
| gccgcctcca agtgccgcaa gcgcaagctg gagcgcatct cgcgcctgga agagaaagtg | 900 |
| aagaccctca agagtcagaa cacggagctg gcgtccacgg cgagcctgct gcgcgagcag | 960 |
| gtggcgcagc tcaagcagaa agtcctcagc cacgtcaaca gcggctgcca gctgctgccc | 1020 |
| cagcaccagg tgcccgcgta ctga | 1044 |

<210> SEQ ID NO 7
<211> LENGTH: 4124
<212> TYPE: DNA
<213> ORGANISM: Homo sapiens

<400> SEQUENCE: 7

| | |
|---|---|
| atgagcacgg aggcggacga gggcatcact ttctctgtgc caccttcgc cccctcgggc | 60 |
| ttctgcacca tccccgaggg cggcatctgc aggaggggag gagcggcggc ggtgggcgag | 120 |
| ggcgaggagc accagctgcc accgccgccg ccgggcagtt tctggaacgt ggagagcgcc | 180 |
| gctgccctg catcggttg tccggcggcc acctcctcga gcagtgccac ccgaggccgg | 240 |
| ggcagctctg ttggcggggg cagccgacgg accacggtgg catatgtgat caacgaagcg | 300 |
| agccaagggc aactggtggt ggccgagagc gaggccctgc agagcttgcg ggaggcgtgc | 360 |
| gagacagtgg gcgccaccct ggaaccctgc attttgggaa actcgacttt ggagaaacca | 420 |
| ccgtgctgga ccgcttttac aatgcagata ttgcggtggt ggagatgagc gatgccttcc | 480 |
| ggcagccgtc cttgttttac caccttgggg tgagagaaag tttcagcatg ccaacaaca | 540 |
| tcatcctcta ctgcgatact aactcggact ctctgcagtc actgaaggaa atcatttgcc | 600 |
| agaagaatac tatgtgcact gggaactaca cctttgttcc ttacatgata actccacata | 660 |
| acaaagtcta ctgctgtgac agcagcttca tgaaggggtt gacagagctc atgcaaccga | 720 |
| acttcgagct gcttcttgga cccatctgct tacctcttgt ggatcgtttt attcaacttt | 780 |
| tgaaggtggc acaagcaagt tctagccagt acttccggga atctatactc aatgacatca | 840 |
| ggaaagctcg taatttatac actggtaaag aattggcagc tgagttggca agaattcggc | 900 |
| agcgagtaga taatatcgaa gtcttgacag cagatattgt cataaatctg ttactttcct | 960 |
| acagagatat ccaggactat gattctattg tgaagctggt agagacttta gaaaaactgc | 1020 |
| caacctttga tttggcctcc catcaccatg tgaagtttca ttatgcattt gcactgaata | 1080 |
| ggagaaatct ccctggtgac agagcaaaag ctcttgatat tatgattccc atggtgcaaa | 1140 |
| gcgaaggaca agttgcttca gatatgtatt gcctagttgg tcgaatctac aaagatatgt | 1200 |
| ttttggactc taatttcacg gacactgaaa gcagagacca tggagcttct tggttcaaaa | 1260 |
| aggcatttga atctgagcca acactacagt caggaattaa ttatgcggtc ctcctcctgg | 1320 |
| cagctggaca ccagtttgaa tcttcctttg agctccggaa agttggggtg aagctaagta | 1380 |
| gtcttcttgg taaaaaggga aacttggaaa aactccagag ctactgggaa gttggatttt | 1440 |
| ttctgggggc cagcgtccta gccaatgacc acatgagagt cattcaagca tctgaaaagc | 1500 |
| tttttaaact gaagacacca gcatggtacc tcaagtctat tgtagagaca attttgatat | 1560 |
| ataagcattt tgtgaaactg accacagaac agcctgtggc caagcaagaa cttgtggact | 1620 |
| tttggatgga tttcctggtc gaggccacaa agacagatgt tactgtggtt aggttttccag | 1680 |
| tattaatatt agaaccaacc aaaatctatc aaccttctta tttgtctatc aacaatgaag | 1740 |

```
ttgaggaaaa gacaatctct atttggcacg tgcttcctga tgacaagaaa ggtatacatg    1800
agtggaattt tagtgcctct tctgtcaggg gagtgagtat ttctaaattt gaagaaagat    1860
gctgctttct ttatgtgctt cacaattctg atgatttcca aatctatttc tgtacagaac    1920
ttcattgtaa aaagtttttt gagatggtga acaccattac cgaagagaag gggagaagca    1980
cagaggaagg agactgtgaa agtgacttgc tggagtatga ctatgaatat gatgaaaatg    2040
gtgacagagt cgttttagga aaaggcactt atgggatagt ctacgcaggt cgggacttga    2100
gcaaccaagt cagaattgct attaaggaaa tcccagagag agacagcaga tactctcagc    2160
ccctgcatga agaaatagca ttgcataaac acctgaagca caaaaatatt gtccagtatc    2220
tgggctcttt cagtgagaat ggtttcatta aaatcttcat ggagcaggtc cctggaggaa    2280
gtctttctgc tctccttcgt tccaaatggg gtccattaaa agacaatgag caaacaattg    2340
gcttttatac aaagcaaata ctggaaggat taaaatatct ccatgacaat cagatagttc    2400
accgggacat aaagggtgac aatgtgttga ttaatacctg cagtggtgtt ctcaagatct    2460
ctgacttcgg aacatcaaag aggcttgctg gcataaaccc ctgtactgaa acttttactg    2520
gtaccctcca gtatatggca ccagaaataa tagataaagg accaagaggc tacgaaaaag    2580
cagcagacat ctggtctctg ggctgtacaa tcattgaaat ggccacagga aaaccccat    2640 tttatgaact gggagaacca caagcagcta tgttcaaggt gggaatgttt aaagtccacc    2700
ctgagatccc agagtccatg tctgcagagg ccaaggcatt catactgaaa tgttttgaac    2760
cagatcctga caagagagcc tgtgctaacg acttgcttgt tgatgagttt ttaaaagttt    2820
caagcaaaaa gaaaaagaca caacctaagc tttcagctct ttcagctgga tcaaatgaat    2880
atctcaggag tatatccttg ccggtacctg tgctggtgga ggacaccagc agcagcagtg    2940 agtacgctc agtttcaccc gacacggagt tgaaagtgga ccccttctct ttcaaaacaa    3000
gagccaagtc ctgcggagaa agagatgtca agggaattcg acactctttt tgggcattc    3060 cagatgagaa ttttgaagat cacagtgctc ctccttcccc tgaagaaaaa gattctggat    3120
tcttcatgct gaggaaggac agtgagaggc gagctaccct tcacaggatc ctgacggaag    3180
accaagacaa aattgtgaga aacctaatgg aatctttagc tcaggggct gaagaaccga    3240 aactaaaatg ggaacacatc acaaccctca ttgcaagcct cagagaattt gtgagatcca    3300
ctgaccgaaa aatcatagcc accacactgt caaagctgaa actggagctg acttcgaca    3360 gccatggcat tagccaagtc caggtggtac tctttggttt tcaagatgct gtcaataaag    3420
ttcttcggaa tcataacatc aagccgcact ggatgtttgc cttagacagt atcattcgga    3480
aggcggtaca gacagccatt accatcctgg ttccagaact aaggccacat ttcagccttg    3540
catctgagag tgatactgct gatcaagaag acttggatgt agaagatgac catgaggaac    3600
agccttcaaa tcaaactgtc cgaagacctc aggctgtcat tgaagatgct gtggctacct    3660
caggcgtgag cacgctcagt tctactgtgt ctcatgattc ccagagtgct caccggtcac    3720
tgaatgtaca gcttggaagg atgaaaatag aaaccaatag attactggaa gaattggttc    3780
ggaaagagaa agaattacaa gcactccttc atcgagctat tgaagaaaaa gaccaagaaa    3840
ttaaacacct gaagcttaag tcccaaccca tagaaattcc tgaattgcct gtatttcatc    3900
taaattcttc tggcacaaat actgaagatt ctgaacttac cgactggctg agagtgaatg    3960
gagctgatga agacactata agccggtttt tggctgaaga ttatacacta ttggatgttc    4020
tctactatgt tacacgtgat gacttaaaat gcttgagact aaggggaggg atgctgtgca    4080
cactgtggaa ggctatcatt gactttcgaa acaaacagac ttga                    4124
```

<210> SEQ ID NO 8
<211> LENGTH: 1128
<212> TYPE: DNA
<213> ORGANISM: Homo sapiens

<400> SEQUENCE: 8

```
atggagcgcg cgtcctgctt gttgctgctg ctgctgccgc tggtgcacgt ctctgcgacc      60
acgccagaac cttgtgagct ggacgatgaa gatttccgct gcgtctgcaa cttctccgaa     120
cctcagcccg actggtccga agccttccag tgtgtgtctg cagtagaggt ggagatccat     180
gccggcggtc tcaacctaga gccgtttcta aagcgcgtcg atgcggacgc cgacccgcgg     240
cagtatgctg acacggtcaa ggctctccgc gtgcggcggc tcacagtggg agccgcacag     300
gttcctgctc agctactggt aggcgccctg cgtgtgctag cgtactcccg cctcaaggaa     360
ctgacgctcg aggacctaaa gataaccggc accatgcctc cgctgcctct ggaagccaca     420
ggacttgcac tttccagctt gcgcctacgc aacgtgtcgt gggcgacagg gcgttcttgg     480
ctcgccgagc tgcagcagtg gctcaagcca ggcctcaagg tactgagcat tgcccaagca     540
cactcgcctg cctttcctg cgaacaggtt cgcgccttcc cggcccttac cagcctagac     600
ctgtctgaca atcctggact gggcgaacgc ggactgatgg cggctctctg tcccacaag     660
ttcccggcca tccagaatct agcgctgcgc aacacaggaa tggagacgcc cacaggcgtg     720
tgcgccgcac tggcggcggc aggtgtgcag ccccacagcc tagacctcag ccacaactcg     780
ctgcgcgcca ccgtaaaccc tagcgctccg agatgcatgt ggtccagcgc cctgaactcc     840
ctcaatctgt cgttcgctgg gctggaacag gtgcctaaag gactgccagc caagctcaga     900
gtgctcgatc tcagctgcaa cagactgaac agggcgccgc agcctgacga gctgcccgag     960
gtggataacc tgacactgga cgggaatccc ttcctggtcc ctggaactgc cctcccccac    1020
gagggctcaa tgaactccgg cgtggtccca gcctgtgcac gttcgaccct gtcggtgggg    1080
gtgtcgggaa ccctggtgct gctccaaggg gcccggggct tgcctaa                  1128
```

<210> SEQ ID NO 9
<211> LENGTH: 1140
<212> TYPE: DNA
<213> ORGANISM: Homo sapiens

<400> SEQUENCE: 9

```
atggcggcgg cggcggctca ggggggcggg ggcggggagc ccgtagaac cgaggggggtc       60
ggcccggggg tcccggggga ggtggagatg gtgaaggggc agccgttcga cgtgggcccg     120
cgctacacgc agttgcagta catcggcgag ggcgcgtacg gcatggtcag ctcggcctat     180
gaccacgtgc gcaagactcg cgtggccatc aagaagatca gccccttcga acatcagacc     240
tactgccagc gcacgctccg ggagatccag atcctgctgc gcttccgcca tgagaatgtc     300
atcggcatcc gagacattct gcgggcgtcc acctggaag ccatgagaga tgtctacatt     360
gtgcaggacc tgatggagac tgacctgtac aagttgctga aaagccagca gctgagcaat     420
gaccatatct gctacttcct ctaccagatc ctgcggggcc tcaagtacat ccactccgcc     480
aacgtgctcc accgagatct aaagccctcc aacctgctca tcaacaccac ctgcgacctt     540
aagatttgtg atttcggcct ggccggatt gccgatcctg agcatgacca caccggcttc     600
ctgacggagt atgtggctac gcgctggtac cgggccccag agatcatgct gaactccaag     660
ggctatacca agtccatcga catctggtct gtgggctgca ttctggctga gatgctctct     720
```

| | |
|---|---|
| aaccggccca tcttccctgg caagcactac ctggatcagc tcaaccacat tctgggcatc | 780 |
| ctgggctccc catcccagga ggacctgaat tgtatcatca acatgaaggc ccgaaactac | 840 |
| ctacagtctc tgccctccaa gaccaaggtg gcttgggcca agcttttccc caagtcagac | 900 |
| tccaaagccc ttgacctgct ggaccggatg ttaaccttta accccaataa acggatcaca | 960 |
| gtggaggaag cgctggctca ccctacctg gagcagtact atgacccgac ggatgagcca | 1020 |
| gtggccgagg agcccttcac cttcgccatg gagctggatg acctacctaa ggagcggctg | 1080 |
| aaggagctca tcttccagga gacagcacgc ttccagcccg gagtgctgga ggcccctag | 1140 |

<210> SEQ ID NO 10
<211> LENGTH: 1083
<212> TYPE: DNA
<213> ORGANISM: Homo sapiens

<400> SEQUENCE: 10

| | |
|---|---|
| atggcggcgg cggcggcggc gggcgcgggc ccggagatgg tccgcgggca ggtgttcgac | 60 |
| gtggggccgc gctacaccaa cctctcgtac atcggcgagg gcgcctacgg catggtgtgc | 120 |
| tctgcttatg ataatgtcaa caaagttcga gtagctatca gaaaaatcag cccctttgag | 180 |
| caccagacct actgccagag aaccctgagg gagataaaaa tcttactgcg cttcagacat | 240 |
| gagaacatca ttggaatcaa tgacattatt cgagcaccaa ccatcgagca atgaaaagat | 300 |
| gtatatatag tacaggacct catggaaaca gatctttaca agctcttgaa gacacaaacac | 360 |
| ctcagcaatg accatatctg ctattttctc taccagatcc tcagagggtt aaaatatatc | 420 |
| cattcagcta acgttctgca ccgtgacctc aagccttcca acctgctgct caacaccacc | 480 |
| tgtgatctca agatctgtga ctttggcctg gcccgtgttg cagatccaga ccatgatcac | 540 |
| acagggttcc tgacagaata tgtggccaca cgttggtaca gggctccaga aattatgttg | 600 |
| aattccaagg gctacaccaa gtccattgat atttggtctg taggctgcat tctggcagaa | 660 |
| atgctttcta caggcccat ctttccaggg aagcattatc ttgaccagct gaaccacatt | 720 |
| ttgggtattc ttggatcccc atcacaagaa gacctgaatt gtataataaa tttaaaagct | 780 |
| aggaactatt tgctttctct tccacacaaa aataaggtgc catggaacag ctgttccca | 840 |
| aatgctgact ccaaagctct ggacttattg acaaaatgt tgacattcaa cccacacaag | 900 |
| aggattgaag tagaacaggc tctgccccac ccatatctgg agcagtatta cgacccgagt | 960 |
| gacgagccca tcgccgaagc accattcaag ttcgacatgg aattggatga cttgcctaag | 1020 |
| gaaaagctca agaactaat ttttgaagag actgctagat ccagccagg atacagatct | 1080 |
| taa | 1083 |

<210> SEQ ID NO 11
<211> LENGTH: 2265
<212> TYPE: DNA
<213> ORGANISM: Homo sapiens

<400> SEQUENCE: 11

| | |
|---|---|
| atgttttcag gggggtgtca tagccccggg tttggccgcc ccagccccgc cttccccgcc | 60 |
| ccggggagcc cgcccctgc cccgcgtccc tgccgacagg aaacaggtga gcagattgcc | 120 |
| atcaagcagt gccggcagga gctcagcccc cggaaccgag agcggtggtg cctggagatc | 180 |
| cagatcatga gaaggctgac ccacccccaat gtggtggctg cccgagatgt ccctgagggg | 240 |
| atgcagaact ggcgcccaa tgacctgccc ctgctggcca tggagtactg ccaaggagga | 300 |
| gatctccgga gtacctgaa ccagtttgag aactgctgtg gtctgcggga aggtgccatc | 360 |

```
ctcaccttgc tgagtgacat tgcctctgcg cttagatacc ttcatgaaaa cagaatcatc    420
catcgggatc taaagccaga aaacatcgtc ctgcagcaag gagaacagag gttaatacac    480
aaaattattg acctaggata tgccaaggag ctggatcagg gcagtctttg cacatcattc    540
gtggggaccc tgcagtacct ggccccagag ctactggagc agcagaagta cacagtgacc    600
gtcgactact ggagcttcgg caccctggcc tttgagtgca tcacgggctt ccggcccttc    660
ctccccaact ggcagcccgt gcagtggcat tcaaaagtgc ggcagaagag tgaggtggac    720
attgttgtta gcgaagactt gaatggaacg gtgaagtttt caagctcttt accctacccc    780
aataatctta acagtgtcct ggctgagcga ctggagaagt ggctgcaact gatgctgatg    840
tggcaccccc gacagagggg cacggatccc acgtatgggc caatggctg cttcaaggcc     900 ctggatgaca tcttaaactt aaagctggtt catatcttga acatggtcac gggcaccatc    960
cacacctacc ctgtgacaga ggatgagagt ctgcagagct gaaggccag aatccaacag    1020 gacacgggca tcccagagga ggaccaggag ctgctgcagg aagcgggcct ggcgttgatc   1080
cccgataagc ctgccactca gtgtatttca gacggcaagt taaatgaggg ccacacattg   1140
gacatggatc ttgttttct ctttgacaac agtaaaatca cctatgagac tcagatctcc    1200
ccacggcccc aacctgaaag tgtcagctgt atccttcaag agcccaagag gaatctcgcc   1260
ttcttccagc tgaggaaggt gtggggccag gtctggcaca gcatccagac cctgaaggaa   1320
gattgcaacc ggctgcagca gggacagcga ccgccatga tgaatctcct ccgaaacaac    1380
agctgcctct ccaaaatgaa gaattccatg gcttccatgt ctcagcagct caaggccaag   1440
ttggatttct tcaaaaccag catccagatt gacctggaga agtacagcga gcaaaccgag   1500
tttgggatca catcagataa actgctgctg gcctggaggg aaatggagca ggctgtggag   1560
ctctgtgggc gggagaacga agtgaaactc ctggtagaac ggatgatggc tctgcagacc   1620
gacattgtgg acttacagag gagccccatg ggccggaagc agggggggaac gctgacgac   1680 ctagaggagc aagcaaggga gctgtacagg agactaaggg aaaaacctcg agaccagcga   1740
actgagggtg acagtcagga aatggtacgg ctgctgcttc aggcaattca gagcttcgag   1800
aagaaagtgc gagtgatcta tacgcagctc agtaaaactg tggtttgcaa gcagaaggcg   1860
ctggaactgt tgcccaaggt ggaagaggtg gtgagcttaa tgaatgagga tgagaagact   1920
gttgtccggc tgcaggagaa gcggcagaag gagctctgga atctcctgaa gattgcttgt   1980
agcaaggtcc gtggtcctgt cagtggaagc ccggatagca tgaatgcctc tcgacttagc   2040
cagcctgggc agctgatgtc tcagccctcc acggcctcca acagcttacc tgagccagcc   2100
aagaagagtg aagaactggt ggctgaagca cataacctct gcaccctgct agaaaatgcc   2160
atacaggaca ctgtgaggga acaagaccag agtttcacgg ccctagactg gagctggtta   2220
cagacggaag aagaagagca cagctgcctg gagcaggcct catga                   2265
```

<210> SEQ ID NO 12
<211> LENGTH: 954
<212> TYPE: DNA
<213> ORGANISM: Homo sapiens

<400> SEQUENCE: 12

```
atgttccagg cggccgagcg ccccccaggag tgggccatgg agggccccccg cgacgggctg    60 aagaaggagc ggctactgga cgaccgccac gacagcggcc tggactccat gaaagacgag   120
gagtacgagc agatggtcaa ggagctgcag gagatccgcc tcgagccgca ggaggtgccg   180
```

| | |
|---|---|
| cgcggctcgg agccctggaa gcagcagctc accgaggacg gggactcgtt cctgcacttg | 240 |
| gccatcatcc atgaagaaaa ggcactgacc atggaagtga tccgccaggt gaagggagac | 300 |
| ctggccttcc tcaacttcca gaacaacctg cagcagactc cactccactt ggctgtgatc | 360 |
| accaaccagc cagaaattgc tgaggcactt ctgggagctg gctgtgatcc tgagctccga | 420 |
| gactttcgag gaaatacccc cctacacctt gcctgtgagc agggctgcct ggccagcgtg | 480 |
| ggagtcctga ctcagtcctg caccaccccg cacctccact ccatcctgaa ggctaccaac | 540 |
| tacaatggcc acacgtgtct acacttagcc tctatccatg ctacctggga tcgtggag | 600 |
| cttttggtgt ccttgggtgc tgatgtcaat gctcaggagc cctgtaatgg ccggactgcc | 660 |
| cttcacctcg cagtggacct gcaaaatcct gacctggtgt cactcctgtt gaagtgtggg | 720 |
| gctgatgtca acagagttac ctaccagggc tattctccct accagctcac ctggggccgc | 780 |
| ccaagcaccc ggatacagca gcagctgggc cagctgacac tagaaaacct tcagatgctg | 840 |
| ccagagagtg aggatgagga gagctatgac acagagtcag agttcacgga gttcacagag | 900 |
| gacgagctgc cctatgatga ctgtgtgttt ggaggccagc gtctgacgtt atga | 954 |

<210> SEQ ID NO 13
<211> LENGTH: 2139
<212> TYPE: DNA
<213> ORGANISM: Homo sapiens

<400> SEQUENCE: 13

| | |
|---|---|
| atggccgggg ggccgggccc gggggagccc gcagccccg gcgcccagca cttcttgtac | 60 |
| gaggtgccgc cctgggtcat gtgccgcttc tacaaagtga tggacgccct ggagcccgcc | 120 |
| gactggtgcc agttcgccgc cctgatcgtg cgcgaccaga ccgagctgcg gctgtgcgag | 180 |
| cgctccggga agcgcacggc cagcgtcctg tggccctgga tcaaccgcaa cgcccgtgtg | 240 |
| gccgacctcg tgcacatcct cacgcacctg cagctgctcc gtgcgcggga catcatcaca | 300 |
| gcctggcacc ctcccgcccc gcttccgtcc ccaggcacca ctgccccgag gcccagcagc | 360 |
| atccctgcac ccgccgaggc cgaggcctgg agccccggga agttgccatc ctcagcctcc | 420 |
| accttcctct cccagctttt ccaggctcc cagacccatt cagggcctga gctcggcctg | 480 |
| gtcccaagcc ctgcttccct gtggcctcca ccgccatctc cagccccttc ttctaccaag | 540 |
| ccaggcccag agagctcagt gtccctcctg caggagccc gcccctttcc gttttgctgg | 600 |
| cccctctgtg agatttcccg gggcacccac aacttctcgg aggagctcaa gatcggggag | 660 |
| ggtggctttg ggtgcgtgta ccgggcggtg atgaggaaca cggtgtatgc tgtgaagagg | 720 |
| ctgaaggaga acgctgacct ggagtggact gcagtgaagc agagcttcct gaccgaggtg | 780 |
| gagcagctgt ccaggtttcg tcacccaaac attgtggact tgctggcta ctgtgctcag | 840 |
| aacggcttct actgcctggt gtacggcttc ctgcccaacg gctccctgga ggaccgtctc | 900 |
| cactgccaga cccaggcctg cccacctctc tcctggcctc agcgactgga catccttctg | 960 |
| ggtacagccc gggcaattca gtttctacat caggacagcc ccagcctcat ccatggagac | 1020 |
| atcaagagtt ccaacgtcct tctggatgag aggctgacac ccaagctggg agactttggc | 1080 |
| ctggcccggt tcagccgctt tgccgggtcc agccccagcc agagcagcat ggtggcccgg | 1140 |
| acacagacag tgcggggcac cctggcctac ctgcccgagg agtacatcaa gacgggaagg | 1200 |
| ctggctgtgg acacgacac cttcagcttt gggtggtag tgctagagac cttggctggt | 1260 |
| cagagggctg tgaagacgca cggtgccagg accaagtatc tgaaagacct ggtggaagag | 1320 |
| gaggctgagg aggctggagt ggctttgaga agcacccaga gcacactgca agcaggtctg | 1380 |

```
gctgcagatg cctgggctgc tcccatcgcc atgcagatct acaagaagca cctggacccc   1440
aggcccgggc cctgcccacc tgagctgggc ctgggcctgg ccagctggc ctgctgctgc   1500 ctgcaccgcc gggccaaaag gaggcctcct atgacccagg tgtacgagag ctagagaag   1560 ctgcaggcag tggtggcggg ggtgcccggg cattcggagg ccgccagctg catcccccct   1620
tccccgcagg agaactccta cgtgtccagc actggcagag cccacagtgg ggctgctcca   1680
tggcagcccc tggcagcgcc atcaggagcc agtgcccagg cagcagagca gctgcagaga   1740
ggccccaacc agcccgtgga gagtgacgag agcctaggcg gcctctctgc tgccctgcgc   1800
tcctggcact tgactccaag ctgccctctg gacccagcac cctcaggga ggccggctgt   1860 cctcaggggg acacggcagg agaatcgagc tgggggagtg gcccaggatc ccggcccaca   1920
gccgtggaag gactggccct tggcagctct gcatcatcgt cgtcagagcc accgcagatt   1980
atcatcaacc ctgcccgaca aagatggtc cagaagctgg ccctgtacga ggatggggcc   2040
ctggacagcc tgcagctgct gtcgtccagc tccctcccag gcttgggcct ggaacaggac   2100
aggcaggggc ccgaagaaag tgatgaattt cagagctga                         2139

<210> SEQ ID NO 14
<211> LENGTH: 1284
<212> TYPE: DNA
<213> ORGANISM: Homo sapiens

<400> SEQUENCE: 14
atgagcagaa gcaagcgtga caacaatttt tatagtgtag agattggaga ttctacattc     60
acagtcctga aacgatatca gaatttaaaa cctataggct caggagctca aggaatagta   120
tgcgcagctt atgatgccat tcttgaaaga aatgttgcaa tcaagaagct aagccgacca   180
tttcagaatc agactcatgc caagcgggcc tacagagagc tagttcttat gaaatgtgtt   240
aatcacaaaa atataattgg ccttttgaat gttttcacac cacagaaatc cctagaagaa   300
tttcaagatg tttacatagt catggagctc atggatgcaa atctttgcca agtgattcag   360
atggagctag atcatgaaag aatgtcctac cttctctatc agatgctgtg tggaatcaag   420
caccttcatt ctgctggaat tattcatcgg gacttaaagc ccagtaatat agtagtaaaa   480
tctgattgca cttttgaagat tcttgacttc ggtctggcca ggactgcagg aacgagtttt   540
atgatgacgc cttatgtagt gactcgctac tacagagcac ccgaggtcat ccttggcatg   600
ggctacaagg aaaacgttga catttggtca gttgggtgca tcatgggaga atgatcaaa   660 ggtggtgttt tgttcccagg tacagatcat attgatcagt ggaataaagt tattgaacag   720
cttggaacac catgtcctga attcatgaag aaactgcaac caacagtaag gacttacgtt   780
gaaaacagac ctaaatatgc tggatatagc tttgagaaac tcttccctga tgtcctttc    840 ccagctgact cagaacacaa caaacttaaa gccagtcagg caagggattt gttatccaaa   900
atgctggtaa tagatgcatc taaaaggatc tctgtagatg aagctctcca acacccgtac   960
atcaatgtct ggtatgatcc ttctgaagca gaagctccac caccaaagat ccctgacaag  1020
cagttagatg aaagggaaca cacaatagaa gagtggaaag aattgatata taggaagtt  1080 atggacttgg aggagagaac caagaatgga gttatacggg gcagccctc tccttaggt  1140 gcagcagtga tcaatggctc tcagcatcca tcatcatcgt cgtctgtcaa tgatgtgtct  1200
tcaatgtcaa cagatccgac tttggcctct gatacagaca gcagtctaga agcagcagct  1260
gggcctctgg gctgctgtag atga                                        1284
```

```
<210> SEQ ID NO 15
<211> LENGTH: 1446
<212> TYPE: DNA
<213> ORGANISM: Homo sapiens

<400> SEQUENCE: 15
atgggggcct tggccagagc cctgccgtcc atactgctgg cattgctgct tacgtccacc      60
ccagaggctc tgggtgccaa ccccggcttg gtcgccagga tcaccgacaa gggactgcag     120
tatgcggccc aggaggggct attagctctg cagagtgagc tgctcaggat cacgctgcct     180
gacttcaccg ggacttgag gatcccccac gtcggccgtg gcgctatga gttccacagc      240 ctgaacatcc acagctgtga gctgcttcac tctgcgctga ggcctgtccc tggccagggc     300
ctgagtctca gcatctccga ctcctccatc cgggtccagg gcaggtggaa ggtgcgcaag     360
tcattcttca aactacaggg ctcctttgat gtcagtgtca agggcatcag catttcggtc     420
aacctcctgt tgggcagcga gtcctccggg aggcccacag ttactgcctc agctgcagc      480 agtgacatcg ctgacgtgga ggtggacatg tcgggagact ggggtggct gttgaacctc      540 ttccacaacc agattgagtc caagttccag aaagtactgg agagcaggat ttgcgaaatg     600
atccagaaat cggtgtcctc cgatctacag cctatctcc aaactctgcc agttacaaca     660
gagattgaca gtttcgccga cattgattat agcttagtgg aagcccctcg ggcaacagcc     720
cagatgctgg aggtgatgtt taagggtgaa tctttcatc gtaaccaccg ttctccagtt      780
accctccttg ctgcagtcat gagccttcct gaggaacaca caaaatggt ctactttgcc      840 atctcggatt atgtcttcaa cacggccagc ctggtttatc atgaggaagg atatctgaac     900
ttctccatca cagatgacat gataccgcct gactctaata tccgactgac caccaagtcc     960
ttccgaccct tcgtcccacg gttagccagg ctctacccca acatgaacct ggaactccag    1020
ggatcagtgc cctctgctcc gctcctgaac ttcagccctg gaatctgtc tgtggacccc     1080 tatatggaga tagatgcctt tgtgctcctg cccagctcca gcaaggagcc tgtcttccgg    1140
ctcagtgtgg ccactaatgt gtccgccacc ttgaccttca ataccagcaa gatcactggg    1200
ttcctgaagc caggaaaggt aaaagtggaa ctgaaagaat ccaaagttgg actattcaat    1260
gcagagctgt tggaagcgct cctcaactat tacatcctta acaccctcta ccccaagttc    1320
aatgataagt tggccgaagg cttccccctt cctctgctga gcgtgttca gctctacgac     1380 cttgggctgc agatccataa ggacttcctg ttcttgggtg ccaatgtcca atacatgaga    1440
gtttga                                                              1446

<210> SEQ ID NO 16
<211> LENGTH: 1182
<212> TYPE: DNA
<213> ORGANISM: Homo sapiens

<400> SEQUENCE: 16
atgcccaaga agaagccgac gcccatccag ctgaacccgg ccccgacgg ctctgcagtt     60 aacgggacca gctctgcgga gaccaacttg gaggccttgc agaagaagct ggaggagcta    120
gagcttgatg agcagcagcg aaagcgcctt gaggcctttc ttacccagaa gcagaaggtg    180
ggagaactga aggatgacga ctttgagaag atcagtgagc tggggggctgg caatggcggt    240 gtggtgttca ggtctcccca caagccttct ggcctggtca tggccagaaa gctaattcat    300
ctggagatca aaccccaat ccggaaccag atcataaggg agctgcaggt tctgcatgag    360
tgcaactctc cgtacatcgt gggcttctat ggtgcgttct acagcgatgg cgagatcagt    420
```

```
atctgcatgg agcacatgga tggaggttct ctggatcaag tcctgaagaa agctggaaga      480
attcctgaac aaattttagg aaaagttagc attgctgtaa taaaaggcct gacatatctg      540
agggagaagc acaagatcat gcacagagat gtcaagccct ccaacatcct agtcaactcc      600
cgtggggaga tcaagctctg tgactttggg gtcagcgggc agctcatcga ctccatggcc      660
aactccttcg tgggcacaag gtcctacatg tcgccagaaa gactccaggg gactcattac      720
tctgtgcagt cagacatctg gagcatggga ctgtctctgg tagagatggc ggttgggagg      780
tatcccatcc ctcctccaga tgccaaggag ctggagctga tgtttgggtg ccaggtggaa      840
ggagatgcgg ctgagacccc acccaggcca aggaccccg ggaggcccct tagctcatac       900
ggaatggaca ccgacctcc catggcaatt tttgagttgt tggattacat agtcaacgag       960
cctcctccaa aactgcccag tggagtgttc agtctggaat tcaagatttt gtgaataaa      1020 tgcttaataa aaaccccgc agagagagca gatttgaagc aactcatggt tcatgctttt      1080
atcaagagat ctgatgctga ggaagtggat tttgcaggtt ggctctgctc caccatcggc      1140
cttaaccagc ccagcacacc aacccatgct gctggcgtct aa                        1182

<210> SEQ ID NO 17
<211> LENGTH: 1203
<212> TYPE: DNA
<213> ORGANISM: Homo sapiens

<400> SEQUENCE: 17
atgctggccc ggaggaagcc ggtgctgccg gcgctcacca tcaaccctac catcgccgag       60
ggcccatccc ctaccagcga gggcgcctcc gaggcaaacc tggtggacct gcagaagaag      120
ctggaggagc tggaacttga cgagcagcag aagaagcggc tggaagcctt tctcacccag      180
aaagccaagg tcggcgaact caaagacgat gacttcgaaa ggatctcaga gctgggcgcg      240
ggcaacggcg gggtggtcac caaagtccag cacagaccct cgggcctcat catgcccagg      300
aagctgatcc accttgagat caagccggcc atccggaacc agatcatccg cgagctgcag      360
gtcctgcacg aatgcaactc gccgtacatc gtgggcttct acggggcctt ctacagtgac      420
ggggagatca gcatttgcat ggaacacatg gacgcggct ccctggacca ggtgctgaaa       480
gaggccaaga ggattcccga ggagatcctg gggaaagtca gcatcgcggt tctccggggc      540
ttggcgtacc tccgagagaa gcaccagatc atgcaccgag atgtgaagcc ctccaacatc      600
ctcgtgaact ctagaggga gatcaagctg tgtgacttcg gggtgagcgg ccagctcatc      660
gactccatgg ccaactcctt cgtgggcacg cgctcctaca tggctccgga gcggttgcag      720
ggcacacatt actcggtgca gtcggacatc tggagcatgg gcctgtccct ggtggagctg      780
gccgtcggaa ggtaccccat cccccgccc gacgccaaag agctggaggc catctttggc       840
cggcccgtgg tcgacgggga agaaggagag cctcacagca tctcgcctcg gccgaggccc      900
cccgggcgcc ccgtcagcgg tcacgggatg gatagccggc tgccatggc catctttgaa       960 ctcctggact atattgtgaa cgagccacct cctaagctgc caacggtgt gttcacccc      1020 gacttccagg agtttgtcaa taatgcctc atcaagaacc cagcggagcg gcggacctg      1080 aagatgctca caaccacac cttcatcaag cggtccgagg tggaagaagt ggattttgcc      1140
ggctggttgt gtaaaaccct gcggctgaac cagcccggca cccacgcg caccgccgtg      1200 tga                                                                   1203

<210> SEQ ID NO 18
```

<211> LENGTH: 957
<212> TYPE: DNA
<213> ORGANISM: Homo sapiens

<400> SEQUENCE: 18

```
atgtccaagc cacccgcacc caaccccaca cccccccgga acctggactc ccggaccttc      60
atcaccattg gagacagaaa ctttgaggtg gaggctgatg acttggtgac catctcagaa     120
ctgggccgtg gagcctatgg ggtggtagag aaggtgcggc acgcccagag cggcaccatc     180
atggccgtga agcggatccg ggccaccgtg aactcacagg agcagaagcg gctgctcatg     240
gacctggaca tcaacatgcg cacggtcgac tgtttctaca ctgtcacctt ctacggggca     300
ctattcagag agggagacgt gtggatctgc atggagctca tggacacatc cttggacaag     360
ttctaccgga aggtgctgga taaaaacatg acaattccag aggacatcct tgggagatt      420
gctgtgtcta tcgtgcgggc cctggagcat ctgcacagca gctgtcggt gatccacaga      480
gatgtgaagc cctccaatgt ccttatcaac aaggagggcc atgtgaagat gtgtgacttt     540
ggcatcagtg gctacttggt ggactctgtg gccaagacga tggatgccgg ctgcaagccc     600
tacatggccc ctgagaggat caacccagag ctgaaccaga agggctacaa tgtcaagtcc     660
gacgtctgga gcctgggcat caccatgatt gagatggcca tcctgcggtt cccttacgag     720
tcctggggga ccccgttcca gcagctgaag caggtggtgg aggagccgtc cccccagctc     780
ccagccgacc gtttctcccc cgagtttgtg gacttcactg ctcagtgcct gaggaagaac     840
cccgcagagc gtatgagcta cctggagctg atggagcacc ccttcttcac cttgcacaaa     900
accaagaaga cggacattgc tgccttcgtg aaggagatcc tgggagaaga ctcatag        957
```

<210> SEQ ID NO 19
<211> LENGTH: 1005
<212> TYPE: DNA
<213> ORGANISM: Homo sapiens

<400> SEQUENCE: 19

```
atgtctcagt cgaaaggcaa gaagcgaaac cctggcctta aaattccaaa agaagcattt      60
gaacaacctc agaccagttc cacaccacct cgagatttag actccaaggc ttgcatttct     120
attggaaatc agaactttga ggtgaaggca gatgacctgg agcctataat ggaactggga     180
cgaggtgcgt acggggtggt ggagaagatg cggcacgtgc ccagcgggca gatcatggca     240
gtgaagcgga tccgagccac agtaaatagc caggaacaga aacggctact gatggatttg     300
gatatttcca tgaggacggt ggactgtcca ttcactgtca ccttttatgg cgcactgttt     360
cgggagggtg atgtgtggat ctgcatggag ctcatggata catcactaga taaattctac     420
aaacaagtta ttgataaagg ccagacaatt ccagaggaca tcttagggaa atagcagtt      480
tctattgtaa aagcattaga acatttacat agtaagctgt ctgtcattca cagagacgtc     540
aagccttcta atgtactcat caatgctctc ggtcaagtga gatgtgcga ttttggaatc      600
agtggctact tggtggactc tgttgctaaa acaattgatg caggttgcaa accatacatg     660
gcccctgaaa gaataaaccc agagctcaac cagaagggat acagtgtgaa gtctgacatt     720
tggagtctgg gcatcacgat gattgagttg gccatcctc gatttcccta tgattcatgg     780
ggaactccat ttcagcagct caaacaggtg gtagaggagc catcgccaca actcccagca     840
gacaagttct ctgcagagtt tgttgacttt acctcacagt gcttaagaa gaattccaaa      900
gaacggccta catacccaga gctaatgcaa catccatttt tcaccctaca tgaatccaaa     960
ggaacagatg tggcatcttt tgtaaaactg attcttggag actaa                    1005
```

<210> SEQ ID NO 20
<211> LENGTH: 4539
<212> TYPE: DNA
<213> ORGANISM: Homo sapeins

<400> SEQUENCE: 20

```
atggcggcgg cggcggggaa tcgcgcctcg tcgtcgggat cccgggcgc cagggctacg      60
agccctgagg caggcggcgg cggaggagcc ctcaaggcga gcagcgcgcc cgcggctgcc     120
gcgggactgc tgcgggaggc gggcagcggg ggccgcgagc gggcggactg cggcggcgg     180
cagctgcgca aagtgcggag tgtggagctg accagctgc ctgagcagcc gctcttcctt     240
gccgcctcac cgccggcctc ctcgacttcc ccgtcgccgg agcccgcgga cgcagcgggg     300
agtgggaccg gcttccagcc tgtggcggtg ccgccgcccc acggagccgc gagccgcggc     360
ggcgcccacc ttaccgagtc ggtggcggcg ccggacagcg gcgcctcgag tcccgcagcg     420
gccgagcccg gggagaagcg ggcgcccgcc gccgagccgt cctgcagc ggccccgcc       480
ggtcgtgaga tggagaataa agaaactctc aaagggttgc acaagatgga tgatcgtcca     540
gaggaacgaa tgatcaggga gaaactgaag gcaacctgta tgccagcctg gaagcacgaa     600
tggttggaaa ggagaaatag gcgagggcct gtggtggtaa accaatccc agttaaagga     660
gatggatctg aaatgaatca cttagcagct gagtctccag gagaggtcca ggcaagtgcg     720
gcttcaccag cttccaaagg ccgacgcagt ccttctcctg gcaactcccc atcaggtcgc     780
acagtgaaat cagaatctcc aggagtaagg agaaaaagag tttccccagt gcctttcag     840
agtggcagaa tcacaccacc ccgaagagcc ccttcaccag atggcttctc accatatagc     900
cctgaggaaa caaccgccg tgttaacaaa gtgatgcggg ccagactgta cttactgcag     960
cagataggg ctaactcttt cctgattgga ggagacagcc agacaataa ataccgggtg    1020
tttattgggc ctcagaactg cagctgtgca cgtggaacat tctgtattca tctgctattt    1080
gtgatgctcc gggtgtttca actagaacct tcagacccaa tgttatggag aaaaacttta    1140
aagaattttg aggttgagag tttgttccag aaatatcaca gtaggcgtag ctcaaggatc    1200
aaagctccat ctcgtaacac catccagaag tttgttttcac gcatgtcaaa ttctcataca    1260
ttgtcatcat ctagtacttc tacgtctagt tcagaaaaca gcataaagga tgaagaggaa    1320
cagatgtgtc ctatttgctt gttgggcatg cttgatgaag aaagtcttac agtgtgtgaa    1380
gacggctgca ggaacaagct gcaccaccac tgcatgtcaa tttgggcaga gagtgtaga    1440
agaaatagaa aacctttaat atgtccccctt tgtagatcta gtggagatc tcatgatttc    1500
tacagccacg agttgtcaag tcctgtggat cccccttctt ccctcagagc tgcacagcag    1560
caaaccgtac agcagcagcc tttggctgga tcacgaagga tcaagagag caatttaac    1620
cttactcatt atggaactca gcaaatccct cctgcttaca agatttagc tgagccatgg    1680
attcaggtgt ttgaatgga actcgttggc tgcttatttt ctagaaactg gaatgtgaga    1740
gagatggccc tcaggcgtct ttcccatgat gtcagtgggg ccctgctgtt ggcaaatggg    1800
gagagcactg gaaattctgg gggcagcagt ggaagcagcc cgagtggggg agccaccagt    1860
gggtcttccc agaccagtat ctcaggagat gtggtggagg catgctgcag cgttctgtca    1920
atggtctgtg ctgaccctgt ctacaaagtg tacgttgctg cttttaaaaac attgagagcc    1980
atgctggtat atactccttg ccacagttta gcggaaagaa tcaaacttca gagcttctc    2040
cagccagttg tagacaccat cctagtcaaa tgtgcagatg ccaatagccg cacaagtcag    2100
```

```
ctgtccatat caacactgtt ggaactgtgc aaaggccaag caggagagtt ggcagttggc   2160
agagaaatac taaaagctgg atccattggt attggtggtg ttgattatgt cttaaattgt   2220
attcttggaa accaaactga atcaaacaat tggcaagaac ttcttggccg cctttgtctt   2280
atagatagac tgttgttgga atttcctgct gaattttatc ctcatattgt cagtactgat   2340
gtttcacaag ctgagcctgt tgaaatcagg tataagaagc tgctgtccct cttaaccttt   2400
gctttgcagt ccattgataa ttcccactca atggttggca aactttccag aaggatctac   2460
ttgagttctg caagaatggt tactacagta ccccatgtgt tttcaaaact gttagaaatg   2520
ctgagtgttt ccagttccac tcacttcacc aggatgcgtc gccgtttgat ggctattgca   2580
gatgaggtgg aaattgccga agccatccag ttgggcgtag aagacacttt ggatggtcaa   2640
caggacagct tcttgcaggc atctgttccc aacaactatc tggaaaccac agagaacagt   2700
tcccctgagt gcacagtcca tttagagaaa actggaaaag gattatgtgc tacaaaattg   2760
agtgccagtt cagaggacat ttctgagaga ctggccagca tttcagtagg accttctagt   2820
tcaacaacaa caacaacaac aacaacagag caaccaaagc caatggttca aacaaaaggc   2880
agacccacag tcagtgtttt gaactcctct cctttatctc atcattccca attaatgttt   2940
ccagccttgt caacccccttc ttcttctacc ccatctgtac cagctggcac tgcaacagat   3000
gtctctaagc atagacttca gggattcatt ccctgcagaa taccttctgc atctcctcaa   3060
acacagcgca agttttctct acaattccac agaaactgtc ctgaaaacaa agactcagat   3120
aaactttccc cagtctttac tcagtcaaga cccttgccct ccagtaacat acacaggcca   3180
aagccatcta gacctacccc aggtaataca agtaaacagg gagatccctc aaaaaatagc   3240
atgacacttg atctgaacag tagttccaaa tgtgatgaca gctttggctg tagcagcaat   3300
agtagtaatg ctgttatacc cagtgacgag acagtgttca ccccagtaga ggagaaatgc   3360
agattagatg tcaatacaga gctcaactcc agtattgagg accttcttga agcatctatg   3420
ccttcaagtg atacaacagt aactttttaag tcagaagttg ctgtcctgtc tcctgaaaag   3480
gctgaaaatg atgatacccta caaagatgat gtgaatcata atcaaaagtg caaagagaag   3540
atggaagctg aagaagaaga agcttttagca attgccatgg caatgtcagc gtctcaggat   3600
gccctcccca tagttcctca gctgcaggtt gaaaatggag aagatatcat cattattcaa   3660
caggatacac cagagactct accaggacat accaaagcaa aacaaccgta tagaagagac   3720
actgaatggc tgaaaggtca acagataggc cttggagcat tttcttcttg ttatcaggct   3780
caagatgtgg gaactggaac tttaatggct gttaaacagg tgacttatgt cagaaacaca   3840
tcttctgagc aagaagaagt agtagaagca ctaagagaag agataagaat gatgagccat   3900
ctgaatcatc caaacatcat taggatgttg ggagccacgt gtgagaagag caattacaat   3960
ctcttcattg aatggatggc aggggatcg gtggctcatt gctgagtaa atatggagcc   4020 ttcaaagaat cagtagttat taactacact gaacagttac tccgtggcct ttcgtatctc   4080
catgaaaacc aaatcattca cagagatgtc aaaggtgcca atttgctaat tgacagcact   4140
ggtcagagac taagaattgc agattttgga gctgcagcca ggttggcatc aaaaggaact   4200
ggtgcaggag agtttcaggg acaattactg ggacaattg catttatggc acctgaggta   4260
ctaagaggtc aacagtatgg aaggagctgt gatgtatgga gtgttggctg tgctattata   4320
gaaatggctt gtgcaaaacc accatggaat gcagaaaaac actccaatca tcttgctttg   4380
atatttaaga ttgctagtgc aactactgct ccatcgatcc cttcacattt gtctcctggt   4440
ttacgagatg tggctcttcg ttgtttagaa cttcaacctc aggacagacc tccatcaaga   4500
```

| | |
|---|---|
| gagctactga agcatccagt ctttcgtact acatggtag | 4539 |

<210> SEQ ID NO 21
<211> LENGTH: 1974
<212> TYPE: DNA
<213> ORGANISM: Homo sapiens

<400> SEQUENCE: 21

| | |
|---|---|
| atggacgaac aggaggcatt gaactcaatc atgaacgatc tggtggccct ccagatgaac | 60 |
| cgacgtcacc ggatgcctgg atatgagacc atgaagaaca agacacagg tcactcaaat | 120 |
| aggcagaaaa aacacaacag cagcagctca gcccttctga acagccccac agtaacaaca | 180 |
| agctcatgtg caggggccag tgagaaaaag aaattttga gtgacgtcag aatcaagttc | 240 |
| gagcacaacg gggagaggcg aattatagcg ttcagccggc ctgtgaaata tgaagatgtg | 300 |
| gagcacaagg tgacaacagt atttggacaa cctcttgatc tacattacat gaacaatgag | 360 |
| ctctccatcc tgctgaaaaa ccaagatgat cttgataaag caattgacat tttagataga | 420 |
| agctcaagca tgaaaagcct taggatattg ctgttgtccc aggacagaaa ccataacagt | 480 |
| tcctctcccc actctggggt gtccagacag gtgcggatca aggcttccca gtccgcaggg | 540 |
| gatataaata ctatctacca gcccccgag cccagaagca ggcacctctc tgtcagctcc | 600 |
| cagaaccctg gccgaagctc acctcccct ggctatgttc ctgagcggca gcagcacatt | 660 |
| gcccggcagg ggtcctacac cagcatcaac agtgaggggg agttcatccc agagaccagc | 720 |
| gagcagtgca tgctggatcc cctgagcagt gcagaaaatt ccttgtctgg aagctgccaa | 780 |
| tccttggaca ggtcagcaga cagcccatcc ttccggaaat cacgaatgtc ccgtgcccag | 840 |
| agcttccctg acaacagaca ggaatactca gatcgggaaa ctcagcttta tgacaagggg | 900 |
| gtcaaaggtg aacctacccc cggcgctac cacgtgtctg tgcaccacaa ggactacagt | 960 |
| gatggcagaa gaacatttcc ccgaatacgc gtcatcaag caacttgtt caccctggtg | 1020 |
| ccctccagcc gctccctgag cacaaatggc gagaacatgg gtctggctgt gcaatacctg | 1080 |
| gaccccgtg ggcgcctgcg gagtgcggac agcgagaatg ccctctctgt gcaggagagg | 1140 |
| aatgtgccaa ccaagtctcc cagtgccccc atcaactggc gcggggaaa gctcctgggc | 1200 |
| cagggtgcct tcggcagggt ctatttgtgc tatgacgtgg acacgggacg tgaacttgct | 1260 |
| tccaagcagg tccaatttga tccagacagt cctgagacaa gcaaggaggt gagtgctctg | 1320 |
| gagtgcgaga tccagttgct aaagaacttg cagcatgagc gcatcgtgca gtactatggc | 1380 |
| tgtctgcggg accgcgctga aagaccctg accatcttca tggagtacat gccagggggc | 1440 |
| tcggtgaaag accagttgaa ggcttacggt gctctgacag agagcgtgac ccgaaagtac | 1500 |
| acgcggcaga tcctggaggg catgtcctac ctgcacagca acatgattgt tcaccgggac | 1560 |
| attaagggag ccaacatcct ccgagactct gctgggaatg taaagctggg ggactttggg | 1620 |
| gccagcaaac gcctgcagac gatctgtatg tcggggacgg catgcgctc cgtcactggc | 1680 |
| acaccctact ggatgagccc tgaggtgatc agcggcgagg gctatggaag gaaagcagac | 1740 |
| gtgtggagcc tgggctgcac tgtggtggag atgctgacag agaaaccacc gtgggcagag | 1800 |
| tatgaagcta tggccgccat cttcaagatt gccacccagc ccaccaatcc tcagctgccc | 1860 |
| tcccacatct ctgaacatgg ccgggacttc ctgaggcgca ttttgtgga ggctcgccag | 1920 |
| agaccttcag ctgaggagct gctcacacac cactttgcac agctcatgta ctga | 1974 |

<210> SEQ ID NO 22

<211> LENGTH: 4826
<212> TYPE: DNA
<213> ORGANISM: Homo sapiens

<400> SEQUENCE: 22

| | | | | | |
|---|---|---|---|---|---|
| atgagagaag | ccgctgccgc | gctggtccct | cctcccgcct | ttgccgtcac | gcctgccgcc | 60 |
| gccatggagg | agccgccgcc | accgccgccg | ccgccaccac | cgccaccgga | acccgagacc | 120 |
| gagtcagaac | ccgagtgctg | cttggcggcg | aggcaagagg | gcacattggg | agattcagct | 180 |
| tgcaagagtc | ctgaatctga | tctagaagac | ttctccgatg | aaacaaatac | agagaatctt | 240 |
| tatggtacct | ctccccccag | cacacctcga | cagatgaaac | gcatgtcaac | caaacatcag | 300 |
| aggaataatg | tggggaggcc | agccagtcgg | tctaatttga | agaaaaaat | gaatgcacca | 360 |
| aatcagcctc | cacataaaga | cactggaaaa | acagtggaga | atgtggaaga | atacagctat | 420 |
| aagcaggaga | aaagatccg | agcagctctt | agaacaacag | agcgtgatca | taaaaaaat | 480 |
| gtacagtgct | cattcatgtt | agactcagtg | ggtggatctt | tgccaaaaaa | atcaattcca | 540 |
| gatgtggatc | tcaataagcc | ttacctcagc | cttggctgta | gcaatgctaa | gcttccagta | 600 |
| tctgtgccca | tgcctatagc | cagacctgca | cgccagactt | ctaggactga | ctgtccagca | 660 |
| gatcgtttaa | agttttttga | aactttacga | cttttgctaa | agcttacctc | agtctcaaag | 720 |
| aaaaaagaca | gggagcaaag | aggacaagaa | aatacgtctg | gtttctggct | taaccgatct | 780 |
| aacgaactga | tctggttaga | gctacaagcc | tggcatgcag | acggacaat | taacgaccag | 840 |
| gacttctttt | tatatacagc | ccgtcaagcc | atcccagata | ttattaatga | aatccttact | 900 |
| ttcaaagtcg | actatgggag | cttcgccttt | gttagagata | gagctggttt | taatggtact | 960 |
| tcagtagaag | ggcagtgcaa | agccactcct | ggaacaaaga | ttgtaggtta | ctcaacacat | 1020 |
| catgagcatc | tccaacgcca | gagggtctca | tttgagcagg | taaaacggat | aatggagctg | 1080 |
| ctagagtaca | tagaagcact | ttatccatca | ttgcaggctc | ttcagaagga | ctatgaaaaa | 1140 |
| tatgctgcaa | agacttcca | ggacagggtg | caggcactct | gtttgtggtt | aaacatcaca | 1200 |
| aaagacttaa | atcagaaatt | aaggattatg | ggcactgttt | tgggcatcaa | gaatttatca | 1260 |
| gacattggct | ggccagtgtt | tgaaatccct | tcccctcgac | catccaaagg | taatgagccg | 1320 |
| gagtatgagg | gtgatgacac | agaaggagaa | ttaaggagt | tggaaagtag | tacggatgag | 1380 |
| agtgaagaag | aacaaatctc | tgatcctagg | gtaccggaaa | tcagacagcc | catagataac | 1440 |
| agcttcgaca | tccagtcgcg | ggactgcata | tccaagaagc | ttgagaggct | cgaatctgag | 1500 |
| gatgattctc | ttggctgggg | agcaccagac | tggagcacag | aagcaggctt | tagtagacat | 1560 |
| tgtctgactt | ctatttatag | accatttgta | gacaaagcac | tgaagcagat | ggggttaaga | 1620 |
| aagttaattt | taagacttca | caagctaatg | atggttcct | tgcaaagggc | acgtatagca | 1680 |
| ttggtaaaga | acgatcgtcc | agtggagttt | tctgaatttc | cagatccat | gtggggttca | 1740 |
| gattatgtgc | agttgtcaag | gacaccacct | tcatctgagg | gaaatgcag | tgctgtgtcg | 1800 |
| tgggaggagc | tgaaggccat | ggatttacct | tcattcgaac | ctgccttcct | agttctctgc | 1860 |
| cgagtccttc | tgaatgtcat | acatgagtgt | ctgaagttaa | gattggagca | gagacctgct | 1920 |
| ggagaaccat | ctctcttgag | tattaagcag | ctggtgagag | agtgtaagga | ggtcctgaag | 1980 |
| ggcggcctgc | tgatgaagca | gtactaccag | ttcatgctgc | aggaggttct | ggaggacttg | 2040 |
| gagaagcccg | actgcaacat | tgacgctttt | gaagaggatc | tacataaaat | gcttatggtg | 2100 |
| tatttttgatt | acatgagaag | ctggatccaa | atgctacagc | aattacctca | gcatcgcat | 2160 |
| agtttaaaaa | atctgttaga | agaagaatgg | aatttcacca | agaaataac | tcattacata | 2220 |

```
cggggaggag aagcacaggc cgggaagctt ttctgtgaca ttgcaggaat gctgctgaaa    2280
tctacaggaa gttttttaga atttggctta caggagagct gtgctgaatt ttggactagt    2340
gcggatgaca gcagtgcttc cgacgaaatc aggaggtctg ttatagagat cagtcgagcc    2400
ctgaaggagc tcttccatga agccagagaa agggcttcca agcacttgg atttgctaaa     2460 atgttgagaa aggacctgga aatagcagca gaattcaggc tttcagcccc agttagagac    2520
ctcctggatg ttctgaaatc aaaacagtat gtcaaggtgc aaattcctgg gttagaaaac    2580
ttgcaaatgt ttgttccaga cactcttgct gaggagaaga gtattatttt gcagttactc    2640
aatgcagctg caggaaagga ctgttcaaaa gattcagatg acgtactcat cgatgcctat    2700
ctgcttctga ccaagcacgg tgatcgagcc cgtgattcag aggacagctg gggcacctgg    2760
gaggcacagc ctgtcaaagt cgtgcctcag gtggagactg ttgacaccct gagaagcatg    2820
caggtggata atcttttact agttgtcatg cagtctgcgc atctcacaat tcagagaaaa    2880
gctttccagc agtccattga gggacttatg actctgtgcc aggagcagac atccagtcag    2940
ccggtcatcg ccaaagcttt gcagcagctg aagaatgatg cattggagct atgcaacagg    3000
ataagcaatg ccattgaccg cgtggaccac atgttcacat cagaatttga tgctgaggtt    3060
gatgaatctg aatctgtcac cttgcaacag tactaccgag aagcaatgat tcagggtac     3120 aattttggat ttgagtatca taaagaagtt gttcgtttga tgtctgggga gtttagacag    3180
aagataggag acaaatatat aagctttgcc cggaagtgga tgaattatgt cctgactaaa    3240
tgtgagagtg gtagaggtac aagacccagg tgggcgactc aaggatttga ttttctacaa    3300
gcaattgaac ctgcctttat ttcagctta ccagaagatg acttcttgag tttacaagcc     3360
ttgatgaatg aatgcattgg ccatgtcata ggaaaaccac acagtcctgt tacaggtttg    3420
taccttgcca ttcatcggaa cagcccccgt cctatgaagg tacctcgatg ccatagtgac    3480
cctcctaacc cacacctcat tatccccact ccagagggat tcagcactcg gagcatgcct    3540
tccgacgcgc ggagccatgg cagccctgct gctgctgctg ctgctgctgc tgctgctgtt    3600
gctgccagtc ggcccagccc ctctggtggt gactctgtgc tgcccaaatc catcagcagt    3660
gcccatgata ccagggggttc cagcgttcct gaaaatgatc gattggcttc catagctgct    3720
gaattgcagt ttaggtccct gagtcgtcac tcaagcccca cggaggagcg agatgaacca    3780
gcatatccaa gaggagattc aagtgggtcc acaagaagaa gttgggaact tcggacacta    3840
atcagccaga gtaaagatac tgcttctaaa ctaggaccca tagaagctat ccagaagtca    3900
gtccgattgt ttgaagaaaa gaggtaccga gaaatgagga gaaagaatat cattggtcaa    3960
gtttgtgata cgcctaagtc ctatgataat gttatgcacg ttggcttgag gaaggtgacc    4020
ttcaaatggc aaagaggaaa caaaattgga gaaggccagt atgggaaggt gtacacctgc    4080
atcagcgtcg acaccgggga gctgatggcc atgaaagaga ttcgatttca acctaatgac    4140
cataagacta tcaaggaaac tgcagacgaa ttgaaaatat tcgaaggcat caaacacccc    4200
aatctggttc ggtattttgg tgtggagctc catagagaag aaatgtacat cttcatggag    4260
tactgcgatg aggggacttt agaagaggtg tcaaggctgg acttcaggaa acatgtgatt    4320
aggctgtatt caaagcagat caccattgcg atcaacgtcc tccatgagca tggcatagtc    4380
caccgtgaca ttaaaggtgc caatatcttc cttacctcat ctggattaat caaactggga    4440
gattttggat gttcagtaaa gctcaaaaac aatgcccaga ccatgcctgg tgaagtgaac    4500
agcaccctgg ggacagcagc atacatggca cctgaagtca tcactcgtgc caaaggagag    4560
```

| | |
|---|---|
| ggccatgggc gtgcggccga catctggagt ctggggtgtg ttgtcataga gatggtgact | 4620 |
| ggcaagaggc cttggcatga gtatgagcac aactttcaaa ttatgtataa agtggggatg | 4680 |
| ggacataagc caccaatccc tgaaagatta agccctgaag gaaaggactt cctttctcac | 4740 |
| tgccttgaga gtgacccaaa gatgagatgg accgccagcc agctcctcga ccattcgttt | 4800 |
| gtcaaggttt gcacagatga agaatg | 4826 |

<210> SEQ ID NO 23
<211> LENGTH: 3867
<212> TYPE: DNA
<213> ORGANISM: Homo sapiens

<400> SEQUENCE: 23

| | |
|---|---|
| atggcgggc cgtgtccccg gtccggggcg gagcgcgccg gcagctgctg gcaggacccg | 60 |
| ctggccgtgg cgctgagccg gggccggcag ctcgcgcgc ccccgggccg gggctgcgcg | 120 |
| cggagccggc cgctcagcgt ggtctacgtg ctgacccggg agccgcagcc cgggctcgag | 180 |
| cctcgggagg gaaccgaggc ggagccgctg ccctgcgct gcctgcgcga ggcttgcgcg | 240 |
| caggtccccc ggccgcggcc gccccgcag ctgcgcagcc tgcccttcgg gacgctggag | 300 |
| ctaggcgaca ccgcggctct ggatgccttc tacaacgcgg atgtggtggt gctggaggtg | 360 |
| agcagctcgc tggtacagcc ctccctgttc taccaccttg gtgtgcgtga gagcttcagc | 420 |
| atgaccaaca atgtgctcct ctgctcccag gccgacctcc ctgacctgca ggccctgcgg | 480 |
| gaggatgttt tccagaagaa ctcggattgc gttggcagct acacactgat cccctatgtg | 540 |
| gtgacggcca ctggtcgggt gctgtgtggt gatgcaggcc ttctgcgggg cctggctgat | 600 |
| gggctggtac aggctggagt ggggaccgag gccctgctca ctcccctggt gggccggctt | 660 |
| gcccgcctgc tggaggccac acccacagac tcttgtggct atttccggga gaccattcgg | 720 |
| cgggacatcc ggcaggcgcg ggagcggttc agtgggccac agctgcggca ggagctggct | 780 |
| cgcctgcagc ggagactgga cagcgtggag ctgctgagcc ccgacatcat catgaacttg | 840 |
| ctgctctcct accgcgatgt gcaggactac tcggccatca ttgagctggt ggagacgctg | 900 |
| caggccttgc ccacctgtga tgtggccgag cagcataatg tctgcttcca ctacactttt | 960 |
| gccctcaacc ggaggaacag gcctggggac cgggcgaagg ccctgtctgt gctgctgccg | 1020 |
| ctggtacagc ttgagggctc tgtggcgccc gatctgtact gcatgtgtgg ccgtatctac | 1080 |
| aaggacatgt tcttcagctc gggttttccag gatgctgggc accgggagca ggcctatcac | 1140 |
| tggtatcgca aggcttttga cgtagagccc agccttcact caggcatcaa tgcagctgtg | 1200 |
| ctcctcattg ctgccgggca gcactttgag gattccaaag agctccggct aataggcatg | 1260 |
| aagctgggct gcctgctggc cgcaaaggc tgcgtggaga gatgcagta ttactgggat | 1320 |
| gtgggtttct acctgggagc ccagatcctc gccaatgacc ccacccaggt ggtgctggct | 1380 |
| gcagagcagc tgtataagct caatgccccc atatggtacc tggtgtccgt gatggagacc | 1440 |
| ttcctgctct accagcactt caggcccacg ccagagcccc tggagggcc accacgccgt | 1500 |
| gcccacttct ggctccactt cttgctacag tcctgccaac cattcaagac agcctgtgcc | 1560 |
| cagggcgacc agtgcttggt gctggtcctg agatgaaca aggtgctgct gcctgcaaag | 1620 |
| ctcgaggttc ggggtactga cccagtaagc acagtgaccc tgagcctgct ggagcctgag | 1680 |
| acccaggaca ttccctccag ctggaccttc ccagtcgcct ccatatgcgg agtcagcgcc | 1740 |
| tcaaagcgcg acgagcgctg ctgcttcctc tatgcactcc ccccggctca ggacgtccag | 1800 |
| ctgtgcttcc ccagcgtagg gcactgccag tggttctgcg gcctgatcca ggcctgggtg | 1860 |

```
acgaacccgg attccacggc gcccgcggag gaggcggagg gcgcggggga gatgttggag      1920
tttgattatg agtacacgga gacgggcgag cggctggtgc tgggcaaggg cacgtatggg      1980
gtggtgtacg cgggccgcga tcgccacacg agggtgcgca tcgccatcaa ggagatcccg      2040
gagcgggaca gcaggttctc tcagcccctg catgaagaga tcgctcttca cagacgcctg      2100
cgccacaaga acatagtgcg ctatctgggc tcagctagcc agggcggcta ccttaagatc      2160
ttcatggagg aagtgcctgg aggcagcctg tcctccttgc tgcggtcggt gtggggaccc      2220
ctgaaggaca acgagagcac catcagtttc tacacccgcc agatcctgca gggacttggc      2280
tacttgcacg acaaccacat cgtgcacagg gacataaaag gggacaatgt gctgatcaac      2340
accttcagtg ggctgctcaa gatttctgac ttcggcacct ccaagcggct ggcaggcatc      2400
acaccttgca ctgagacctt cacaggaact ctgcagtata tggccccaga aatcattgac      2460
cagggcccac gcgggtatgg aaagcagct gacatctggt cactgggctg cactgtcatt      2520
gagatggcca caggtcgccc ccccttccac gagctcggga gcccacaggc tgccatgttt      2580
caggtgggta tgtacaaggt ccatccgcca atgcccagct ctctgtcggc cgaggcccaa      2640
gcctttctcc tccgaacttt tgagccgac ccccgcctcc gagccagcgc ccagacactg      2700
ctgggggacc ccttcctgca gctgggaaa aggagccgca gccccagctc cccacgacat      2760
gctccacggc cctcagatgc ccctttctgcc agtcccactc cttcagccaa ctcaaccacc      2820
cagtctcaga cattcccgtg ccctcaggca ccctctcagc ccacccag ccccccgaag      2880 cgctgcctca gttatggggg caccagccag ctccgggtgc ccgaggagcc tgcggccgag      2940
gagcctgcgt ctccggagga gagttcgggg ctgagcctgc tgcaccagga gagcaagcgt      3000
cgggccatgc tggccgcagt attggagcag gagctgccag cgctggcgga gaatctgcac      3060
caggagcaga agcaagagca gggggcccgt ctgggcagaa accatgtgga agagctgctg      3120
cgctgcctcg gggcacacat ccacactccc aaccgccggc agctcgccca ggagctgcgg      3180
gcgctgcaag gacggctgag ggcccagggc cttgggcctg cgcttctgca cagaccgctg      3240
tttgccttcc cggatgcggt gaagcagatc ctccgcaagc gccagatccg tccacactgg      3300
atgttcgttc tggactcact gctcagccgt gctgtgcggg cagccctggg tgtgctagga      3360
ccggaggtgg agaaggaggc ggtctcaccg aggtcagagg agctgagtaa tgaaggggac      3420
tcccagcaga gcccaggcca gcagagcccg cttccggtgg agcccgagca gggccccgct      3480
cctctgatgg tgcagctgag cctcttgagg gcagagactg atcggctgcg cgaaatcctg      3540
gcggggaagg aacgggagta ccaggccctg gtgcagcggg ctctacagcg gctgaatgag      3600
gaagcccgga cctatgtcct ggccccagag cctccaactg ctctttcaac ggaccagggc      3660
ctggtgcagt ggctacagga actgaatgtg gattcaggca ccatccaaat gctgttgaac      3720
catagcttca ccctccacac tctgctcacc tatgccactc gagatgacct catctacacc      3780
cgcatcaggg gagggatggt atgccgcatc tggagggcca tcttggcaca gcgagcagga      3840
tccacaccag tcacctctgg accctga                                          3867
```

<210> SEQ ID NO 24
<211> LENGTH: 1740
<212> TYPE: DNA
<213> ORGANISM: Homo sapeins

<400> SEQUENCE: 24

```
atgtctacag cctctgccgc ctcctcctcc tcctcgtctt cggccggtga gatgatcgaa       60
```

| | |
|---|---|
| gcccttccc aggtcctcaa ctttgaagag atcgactaca aggagatcga ggtggaagag | 120 |
| gttgttggaa gaggagcctt tggagttgtt tgcaaagcta agtggagagc aaaagatgtt | 180 |
| gctattaaac aaatagaaag tgaatctgag aggaaagcgt ttattgtaga gcttcggcag | 240 |
| ttatcccgtg tgaaccatcc taatattgta aagctttatg gagcctgctt gaatccagtg | 300 |
| tgtcttgtga tggaatatgc tgaaggggc tctttatata atgtgctgca tggtgctgaa | 360 |
| ccattgccat attatactgc tgcccacgca atgagttggt gtttacagtg ttcccaagga | 420 |
| gtggcttatc ttcacagcat gcaacccaaa gcgctaattc acagggacct gaaaccacca | 480 |
| aacttactgc tggttgcagg ggggacagtt ctaaaaattt gtgattttgg tacagcctgt | 540 |
| gacattcaga cacacatgac caataacaag gggagtgctg cttggatggc acctgaagtt | 600 |
| tttgaaggta gtaattacag tgaaaaatgt gacgtcttca gctggggtat tattctttgg | 660 |
| gaagtgataa cgcgtcggaa acctttgat gagattggtg gcccagcttt ccgaatcatg | 720 |
| tgggctgttc ataatggtac tcgaccacca ctgataaaaa atttacctaa gcccattgag | 780 |
| agcctgatga ctcgttgttg gtctaaagat ccttcccagc gcccttcaat ggaggaaatt | 840 |
| gtgaaaataa tgactcactt gatgcggtac tttccaggag cagatgagcc attacagtat | 900 |
| ccttgtcagt attcagatga aggacagagc aactctgcca ccagtacagg ctcattcatg | 960 |
| gacattgctt ctacaaatac gagtaacaaa agtgacacta atatggagca agttcctgcc | 1020 |
| acaaatgata ctattaagcg cttagaatca aaattgttga aaaatcaggc aaagcaacag | 1080 |
| agtgaatctg gacgtttaag cttgggagcc tcccgtggga gcagtgtgga gagcttgccc | 1140 |
| ccaacctctg agggcaagag gatgagtgct gacatgtctg aaatagaagc taggatcgcc | 1200 |
| gcaaccacag gcaacggaca gccaagacgt agatccatcc aagacttgac tgtaactgga | 1260 |
| acagaacctg tcaggtgag cagtaggtca tccagtccca gtgtcagaat gattactacc | 1320 |
| tcaggaccaa cctcagaaaa gccaactcga agtcatccat ggacccctga tgattccaca | 1380 |
| gataccaatg gatcagataa ctccatccca atggcttatc ttacactgga tcaccaacta | 1440 |
| cagcctctag caccgtgccc aaactccaaa gaatctatgg cagtgtttga acagcattgt | 1500 |
| aaaatggcac aagaatatat gaaagttcaa acagaaattg cattgttatt acagagaaag | 1560 |
| caagaactag ttgcagaact ggaccaggat gaaaaggacc agcaaaatac atctcgcctg | 1620 |
| gtacaggaac ataaaaagct tttagatgaa aacaaaagcc tttctactta ctaccagcaa | 1680 |
| tgcaaaaaac aactagaggt catcagaagt cagcagcaga acgacaagg cacttcatga | 1740 |

<210> SEQ ID NO 25
<211> LENGTH: 1113
<212> TYPE: DNA
<213> ORGANISM: Homo sapiens

<400> SEQUENCE: 25

| | |
|---|---|
| atgctgtcca actcccaggg ccagagcccg ccggtgccgt tccccgcccc ggccccgccg | 60 |
| ccgcagcccc ccaccccctgc cctgccgcac cccccgcgc agccgccgcc gccgccccg | 120 |
| cagcagttcc cgcagttcca cgtcaagtcc ggcctgcaga tcaagaagaa cgccatcatc | 180 |
| gatgactaca aggtcaccag ccaggtcctg ggctgggca tcaacggcaa agttttgcag | 240 |
| atcttcaaca gaggacccca ggagaaattc gccctcaaaa tgcttcagga ctgccccaag | 300 |
| gcccgcaggg aggtggagct gcactggcgg gcctcccagt gcccgcacat cgtacggatc | 360 |
| gtggatgtgt acgagaatct gtacgcaggg aggaagtgcc tgctgattgt catggaatgt | 420 |
| ttggacggtg gagaactctt tagccgaatc caggatcgag agaccaggc attcacagaa | 480 |

| | |
|---|---|
| agagaagcat ccgaaatcat gaagagcatc ggtgaggcca tccagtatct gcattcaatc | 540 |
| aacattgccc atcgggatgt caagcctgag aatctcttat acacctccaa aaggcccaac | 600 |
| gccatcctga aactcactga ctttggcttt gccaaggaaa ccaccagcca caactctttg | 660 |
| accactcctt gttatacacc gtactatgtg gctccagaag tgctgggtcc agagaagtat | 720 |
| gacaagtcct gtgacatgtg gtccctgggt gtcatcatgt acatcctgct gtgtgggtat | 780 |
| ccccccttct actccaacca cggccttgcc atctctccgg gcatgaagac tcgcatccga | 840 |
| atgggccagt atgaatttcc caacccagaa tggtcagaag tatcagagga agtgaagatg | 900 |
| ctcattcgga atctgctgaa acagagccc acccagagaa tgaccatcac cgagtttatg | 960 |
| aaccacccctt ggatcatgca atcaacaaag gtccctcaaa ccccactgca caccagccgg | 1020 |
| gtcctgaagg aggacaagga gcggtgggag gatgtcaagg ggtgtcttca tgacaagaac | 1080 |
| agcgaccagg ccacttggct gaccaggttg tga | 1113 |

<210> SEQ ID NO 26
<211> LENGTH: 954
<212> TYPE: DNA
<213> ORGANISM: Homo sapiens

<400> SEQUENCE: 26

| | |
|---|---|
| atgcgacccg accgcgctga ggctccagga ccgcccgcca tggctgcagg aggtcccggc | 60 |
| gcggggtctg cggccccggt ctcctccaca tcctcccttc ccctggctgc tctcaacatg | 120 |
| cgagtgcggc gccgcctgtc tctgttcttg aacgtgcgga cacaggtggc ggccgactgg | 180 |
| accgcgctgg cggaggagat ggactttgag tacttggaga tccggcaact ggagacacaa | 240 |
| gcggacccca ctggcaggct gctggacgcc tggcagggac gccctggcgc ctctgtaggc | 300 |
| cgactgctcg agctgcttac caagctgggc cgcgacgacg tgctgctgga gctgggaccc | 360 |
| agcattgagg aggattgcca aaagtatatc ttgaagcagc agcaggagga ggctgagaag | 420 |
| cctttacagg tggccgctgt agacagcagt gtcccacgga cagcagagct ggcgggcatc | 480 |
| accacacttg atgacccccct ggggcatatg cctgagcgtt tcgatgcctt catctgctat | 540 |
| tgccccagcg acatccagtt tgtgcaggag atgatccggc aactgaacaa gacaaactat | 600 |
| cgactgaagt tgtgtgtgtc tgaccgcgat gtcctgcctg gcacctgtgt ctggtctatt | 660 |
| gctagtgagc tcatcgaaaa gaggttggct agaaggccac ggggtgggtg ccgccggatg | 720 |
| gtggtggttg tctctgatga ttacctgcag agcaaggaat gtgacttcca gaccaaattt | 780 |
| gcactcagcc tctctccagg tgcccatcag aagcgactga tccccatcaa gtacaaggca | 840 |
| atgaagaaag agttccccag catcctgagg ttcatcactg tctgcgacta caccaacccc | 900 |
| tgcaccaaat cttggttctg gactcgcctt gccaaggcct tgtccctgcc ctga | 954 |

<210> SEQ ID NO 27
<211> LENGTH: 2907
<212> TYPE: DNA
<213> ORGANISM: Homo sapiens

<400> SEQUENCE: 27

| | |
|---|---|
| atggcagaag atgatccata tttgggaagg cctgaacaaa tgtttcattt ggatccttct | 60 |
| ttgactcata caatatttaa tccagaagta tttcaaccac agatggcact gccaacagat | 120 |
| ggcccatacc ttcaaatatt agagcaacct aaacagagag gatttcgttt ccgttatgta | 180 |
| tgtgaaggcc catcccatgg tggactacct ggtgcctcta gtgaaaagaa caagaagtct | 240 |

-continued

| | |
|---|---|
| taccctcagg tcaaaatctg caactatgtg ggaccagcaa aggttattgt tcagttggtc | 300 |
| acaaatggaa aaaatatcca cctgcatgcc cacagcctgg tgggaaaaca ctgtgaggat | 360 |
| gggatctgca ctgtaactgc tggacccaag acatggtgg tcggcttcgc aaacctgggt | 420 |
| atacttcatg tgacaaagaa aaaagtattt gaaacactgg aagcacgaat gacagaggcg | 480 |
| tgtataaggg gctataatcc tggactcttg gtgcaccctg accttgccta tttgcaagca | 540 |
| gaaggtggag gggaccggca gctgggagat cgggaaaaag agctaatccg ccaagcagct | 600 |
| ctgcagcaga ccaaggagat ggacctcagc gtggtgcggc tcatgtttac agctttctct | 660 |
| ccggatagca ctggcagctt cacaaggcgc ctggaacccg tggtatcaga cgccatctat | 720 |
| gacagtaaag ccccccaatgc atccaacttg aaaattgtaa gaatggacag acagctgga | 780 |
| tgtgtgactg gaggggagga aatttatctt ctttgtgaca agttcagaa agatgacatc | 840 |
| cagattcgat tttatgaaga ggaagaaaat ggtggagtct gggaaggatt tggagatttt | 900 |
| tcccccacag atgttcatag acaatttgcc attgtcttca aaactccaaa gtataaagat | 960 |
| attaatatta caaaaccagc ctctgtgttt gtccagcttc ggaggaaatc tgacttggaa | 1020 |
| actagtgaac caaaaccttt cctctactat cctgaaatca agataaaga gaagtgcag | 1080 |
| aggaaacgtc agaagctcat gcccaatttt tcggatagtt tcggcggtgg tagtggtgct | 1140 |
| ggagctggag gcggaggcat gtttggtagt ggcggtggag gaggggcac tggaagtaca | 1200 |
| ggtccagggt atagcttccc acactatgga tttcctactt atggtgggat tactttccat | 1260 |
| cctggaacta ctaaatctaa tgctgggatg aagcatggaa ccatggacac tgaatctaaa | 1320 |
| aaggaccctg aaggttgtga caaaagtgat gacaaaaaca ctgtaaaacct ctttgggaaa | 1380 |
| gttattgaaa ccacagagca agatcaggag cccagcgagg ccaccgttgg aatggtgag | 1440 |
| gtcactctaa cgtatgcaac aggaacaaaa gaagagagtg ctggagttca ggataacctc | 1500 |
| tttctagaga aggctatgca gcttgcaaag aggcatgcca atgccctttt cgactacgcg | 1560 |
| gtgacaggag acgtgaagat gctgctggcc gtccagcgcc atctcactgc tgtgcaggat | 1620 |
| gagaatgggg acagtgtctt acacttagca atcatccacc ttcattctca acttgtgagg | 1680 |
| gatctactag aagtcacatc tggtttgatt tctgatgaca ttatcaacat gagaaatgat | 1740 |
| ctgtaccaga cgcccttgca cttggcagtg atcactaagc aggaagatgt ggtggaggat | 1800 |
| ttgctgaggg ctggggccga cctgagcctt tggaccgct tgggtaactc tgttttgcac | 1860 |
| ctagctgcca agaaggaca tgataaagtt ctcagtatct tactcaagca caaaaaggca | 1920 |
| gcactacttc ttgaccaccc caacggggac ggtctgaatg ccattcatct agccatgatg | 1980 |
| agcaatagcc tgccatgttt gctgctgctg gtggccgctg gggctgacgt caatgctcag | 2040 |
| gagcagaagt ccgggcgcac agcactgcac ctggctgtgg agcacgacaa catctcattg | 2100 |
| gcaggctgcc tgctcctgga gggtgatgcc catgtggaca gtactaccta cgatggaacc | 2160 |
| acacccctgc atatagcagc tgggagaggg tccaccaggc tggcagctct tctcaaagca | 2220 |
| gcaggagcag atcccctggt ggagaacttt gagcctctct atgacctgga tgactcttgg | 2280 |
| gaaaatgcag gagaggatga aggagttgtg cctggaacca cgcctctaga tatggccacc | 2340 |
| agctggcagg tatttgacat attaaatggg aaaccatatg agccagagtt tacatctgat | 2400 |
| gatttactag cacaaggaga catgaaacag ctggctgaag atgtgaagct gcagctgtat | 2460 |
| aagttactag aaattcctga tccagacaaa aactgggcta ctctggcgca gaaattaggt | 2520 |
| ctggggatac ttaataatgc cttccggctg agtcctgctc cttccaaaac acttatggac | 2580 |
| aactatgagg tctctggggg tacagtcaga gagctggtgg aggccctgag acaaatgggc | 2640 |

| tacaccgaag caattgaagt gatccaggca gcctccagcc cagtgaagac cacctctcag | 2700 |
| gcccactcgc tgcctctctc gcctgcctcc acaaggcaga aaatagacga gctccgagac | 2760 |
| agtgacagtg tctgcgacag cggcgtggag acatccttcc gcaaactcag ctttaccgag | 2820 |
| tctctgacca gtggtgcctc actgctaact ctcaacaaaa tgccccatga ttatgggcag | 2880 |
| gaaggacctc tagaaggcaa aatttag | 2907 |

<210> SEQ ID NO 28
<211> LENGTH: 2844
<212> TYPE: DNA
<213> ORGANISM: Homo sapiens

<400> SEQUENCE: 28

| atggcagtga tggaaatggc ctgcccaggt gcccctggct cagcagtggg gcagcagaag | 60 |
| gaactcccca agccaaggag aagacgccg ccactgggga agaaacagag ctccgtctac | 120 |
| aagcttgagg ccgtggagaa gagccctgtg ttctgcggaa agtgggagat cctgaatgac | 180 |
| gtgattacca agggcacagc caaggaaggc tccgaggcag ggccagctgc catctctatc | 240 |
| atcgcccagg ctgagtgtga aatagccaa gagttcagcc ccacctttc agaacgcatt | 300 |
| ttcatcgctg ggtccaaaca gtacagccag tccgagagtc ttgatcagat ccccaacaat | 360 |
| gtggcccatg ctacagaggg caaaatggcc cgtgtgtgtt ggaagggaaa gcgtcgcagc | 420 |
| aaagcccgga gaaacggaa gaagagagc tcaaagtccc tggctcatgc aggagtggcc | 480 |
| ttggccaaac ccctccccag gacccctgag caggagagct gcaccatccc agtgcaggag | 540 |
| gatgagtctc cactcggcgc cccatatgtt agaaacaccc cgcagttcac caagcctctg | 600 |
| aaggaaccag gccttgggca actctgtttt aagcagcttg gcgagggcct acggccggct | 660 |
| ctgcctcgat cagaactcca caaactgatc agccccttgc aatgtctgaa ccacgtgtgg | 720 |
| aaactgcacc accccagga cggaggcccc ctgcccctgc ccacgcaccc cttcccctat | 780 |
| agcagactgc ctcatccctt cccattccac cctctccagc cctggaaacc tcaccctctg | 840 |
| gagtccttcc tgggcaaact ggcctgtgta gacagccaga aacccttgcc tgacccacac | 900 |
| ctgagcaaac tggcctgtgt agacagtcca aagcccctgc tggcccacac cctggagccc | 960 |
| agctgcctgt ctcgtggtgc ccatgagaag ttttctgtgg aggaataccct agtgcatgct | 1020 |
| ctgcaaggca gcgtgagctc aggccaggcc cacagcctga ccagcctggc caagacctgg | 1080 |
| gcagcaaggg gctccagatc ccgggagccc agcccaaaa ctgaggacaa cgagggtgtc | 1140 |
| ctgctcactg agaaactcaa gccagtggat tatgagtacc gagaagaagt ccactgggcc | 1200 |
| acgcaccagc tccgcctggg cagaggctcc ttcggagagg tgcacaggat ggaggacaag | 1260 |
| cagactggct tccagtgcgc tgtcaaaaag gtgcggctgg aagtatttcg ggcagaggag | 1320 |
| ctgatggcat gtgcaggatt gacctcaccc agaattgtcc ctttgtatgg agctgtgaga | 1380 |
| gaagggcctt gggtcaacat cttcatggag ctgctggaag tggctccct gggccagctg | 1440 |
| gtcaaggagc agggctgtct cccagaggac cgggccctgt actacctggg ccaggccctg | 1500 |
| gagggtctgg aatacctcca ctcacgaagg attctgcatg gggacgtcaa agctgacaac | 1560 |
| gtgctcctgt ccagcgatgg gagccacgca gccctctgtg actttggcca tgctgtgtgt | 1620 |
| cttcaacctg atggcctggg aaagtccttg ctcacagggg actacatccc tggcacagag | 1680 |
| acccacatgg ctccggaggt ggtgctgggc aggagctgcg acgccaaggt ggatgtctgg | 1740 |
| agcagctgct gtatgatgct gcacatgctc aacggctgcc acccctggac tcagttcttc | 1800 |

| | |
|---|---:|
| cgagggccgc tctgcctcaa gattgccagc gagcctccgc ctgtgaggga gatcccaccc | 1860 |
| tcctgcgccc ctctcacagc ccaggccatc aagaggggc tgaggaaaga gcccatccac | 1920 |
| cgcgtgtctg cagcggagct gggagggaag gtgaaccggg cactacagca agtgggaggt | 1980 |
| ctgaagagcc cttggagggg agaatataaa gaaccaagac atccaccgcc aaatcaagcc | 2040 |
| aattaccacc agaccctcca tgcccagccg agagagcttt cgccaagggc cccagggccc | 2100 |
| cggccagctg aggagacaac aggcagagcc cctaagctcc agcctcctct cccaccagag | 2160 |
| cccccagagc caaacaagtc tcctcccttg actttgagca aggaggagtc tgggatgtgg | 2220 |
| gaacccttac ctctgtcctc cctggagcca gcccctgcca gaaacccag ctcaccagag | 2280 |
| cggaaagcaa ccgtcccgga gcaggaactg cagcagctgg aaatagaatt attcctcaac | 2340 |
| agcctgtccc agccatttc tctggaggag caggagcaaa ttctctcgtg cctcagcatc | 2400 |
| gacagcctct ccctgtcgga tgacagtgag aagaacccat caaaggcctc tcaaagctcg | 2460 |
| cgggacaccc tgagctcagg cgtacactcc tggagcagcc aggccgaggc tcgaagctcc | 2520 |
| agctggaaca tggtgctggc ccgggggcgg ccccaccgaca ccccaagcta tttcaatggt | 2580 |
| gtgaaagtcc aaatacagtc tcttaatggt gaacacctgc acatccggga gttccaccgg | 2640 |
| gtcaaagtgg agacatcgc cactggcatc agcagccaga tcccagctgc agccttcagc | 2700 |
| ttggtcacca agacgggca gcctgttcgc tacgacatgg aggtgccaga ctcgggcatc | 2760 |
| gacctgcagt gcacactggc ccctgatggc agcttcgcct ggagctggag ggtcaagcat | 2820 |
| ggccagctgg agaacaggcc ctaa | 2844 |

<210> SEQ ID NO 29
<211> LENGTH: 1083
<212> TYPE: DNA
<213> ORGANISM: Homo sapiens

<400> SEQUENCE: 29

| | |
|---|---:|
| atgtctcagg agaggcccac gttctaccgg caggagctga acaagacaat ctgggaggtg | 60 |
| cccgagcgtt accagaacct gtctccagtg ggctctggcg cctatggctc tgtgtgtgct | 120 |
| gcttttgaca caaaaacggg gttacgtgtg cagtgaagaa agctctccag accatttcag | 180 |
| tccatcattc atgcgaaaag aacctacaga gaactgcggt tacttaaaca tatgaaacat | 240 |
| gaaaatgtga ttggtctgtt ggacgttttt acacctgcaa ggtctctgga ggaattcaat | 300 |
| gatgtgtatc tggtgaccca tctcatgggg gcagatctga caacattgt gaaatgtcag | 360 |
| aagcttacag atgaccatgt tcagttcctt atctaccaaa ttctccgagg tctaaagtat | 420 |
| atacattcag ctgacataat tcacagggac ctaaaaccta gtaatctagc tgtgaatgaa | 480 |
| gactgtgagc tgaagattct ggattttgga ctggctcggc acacagatga tgaaatgaca | 540 |
| ggctacgtgg ccactaggtg gtacagggct cctgagatca tgctgaactg gatgcattac | 600 |
| aaccagacag ttgatatttg gtcagtggga tgcataatgg ccgagctgtt gactggaaga | 660 |
| acattgtttc ctggtacaga ccatattaac cagcttcagc agattatgcg tctgacagga | 720 |
| acacccccg cttatctcat taacaggatg ccaagccatg aggcaagaaa ctatattcag | 780 |
| tctttgactc agatgccgaa gatgaactt gcgaatgtat ttattggtgc caatcccctg | 840 |
| gctgtcgact tgctggagaa gatgcttgta ttggactcag ataagagaat tacagcggcc | 900 |
| caagcccttg cacatgccta ctttgctcag taccacgatc ctgatgatga accagtggcc | 960 |
| gatccttatg atcagtcctt tgaaagcagg gacctcctta tagatgagtg gaaaagcctg | 1020 |
| acctatgatg aagtcatcag ctttgtgcca ccaccccttg accaagaaga gatggagtcc | 1080 |

```
tga                                                         1083

<210> SEQ ID NO 30
<211> LENGTH: 1656
<212> TYPE: DNA
<213> ORGANISM: Homo sapiens

<400> SEQUENCE: 30
atggctggtg atctttcagc aggtttcttc atggaggaac ttaatacata ccgtcagaag     60
cagggagtag tacttaaata tcaagaactg cctaattcag gacctccaca tgataggagg    120
tttacatttc aagttataat agatggaaga gaatttccag aaggtgaagg tagatcaaag    180
aaggaagcaa aaaatgccgc agccaaatta gctgttgaga tacttaataa ggaaaagaag    240
gcagttagtc ctttattatt gacaacaacg aattcttcag aaggattatc catggggaat    300
tacataggcc ttatcaatag aattgcccag aagaaaagac taactgtaaa ttatgaacag    360
tgtgcatcgg gggtgcatgg gccagaagga tttcattata aatgcaaaat gggacagaaa    420
gaatatagta ttggtacagg ttctactaaa caggaagcaa acaattggc cgctaaactt     480 gcatatcttc agatattatc agaagaaacc tcagtgaaat ctgactacct gtcctctggt    540
tcttttgcta ctacgtgtga gtcccaaagc aactctttag tgaccagcac actcgcttct    600
gaatcatcat ctgaaggtga cttctcagca gatacatcag agataaattc taacagtgac    660
agtttaaaca gttcttcgtt gcttatgaat ggtctcagaa ataatcaaag gaaggcaaaa    720
agatctttgg cacccagatt tgaccttcct gacatgaaag aaacaaagta tactgtggac    780
aagaggtttg gcatggattt taagaaaata gaattaattg gctcaggtgg atttggccaa    840
gttttcaaag caaacacag aattgacgga aagacttacg ttattaaacg tgttaaatat     900
aataacgaga aggcggagcg tgaagtaaaa gcattggcaa acttgatca tgtaaatatt     960 gttcactaca tggctgttg ggatggattt gattatgatc ctgagaccag tgatgattct    1020
cttgagagca gtgattatga tcctgagaac agcaaaaata gttcaaggtc aaagactaag    1080
tgccttttca tccaaatgga attctgtgat aaagggacct ggaacaatg gattgaaaaa    1140 agaagaggcg agaaactaga caaagttttg gctttggaac tctttgaaca aataacaaaa    1200
ggggtggatt atatacattc aaaaaaatta attcatagag atcttaagcc aagtaatata    1260
ttcttagtag atacaaaaca gtaaagatt ggagactttg gacttgtaac atctctgaaa    1320
aatgatggaa agcgaacaag gagtaaggga acttttgcgat acatgagccc agaacagatt    1380
tcttcgcaag actatggaaa ggaagtggac ctctacgctt ggggctaat tcttgctgaa    1440 cttcttcatg tatgtgacac tgcttttgaa acatcaaagt ttttcacaga cctacgggat    1500
ggcatcatct cagatatatt tgataaaaaa gaaaaactc ttctacagaa attactctca    1560
aagaaacctg aggatcgacc taacacatct gaaatactaa ggaccttgac tgtgtggaag    1620
aaaagcccag agaaaatga acgacacaca tgttag                              1656

<210> SEQ ID NO 31
<211> LENGTH: 1443
<212> TYPE: DNA
<213> ORGANISM: Homo sapiens

<400> SEQUENCE: 31
atgagcgacg tggctattgt gaaggagggt tggctgcaca acgagggga gtacatcaag     60 acctggcggc cacgctactt cctcctcaag aatgatggca ccttcattgg ctacaaggag    120
```

| | |
|---|---|
| cggccgcagg atgtggacca acgtgaggct cccctcaaca acttctctgt ggcgcagtgc | 180 |
| cagctgatga agacggagcg gccccggccc aacaccttca tcatccgctg cctgcagtgg | 240 |
| accactgtca tcgaacgcac cttccatgtg gagactcctg aggagcggga ggagtggaca | 300 |
| accgccatcc agactgtggc tgacggcctc aagaagcagg aggaggagga gatggacttc | 360 |
| cggtcgggct cacccagtga caactcaggg gctgaagaga tggaggtgtc cctggccaag | 420 |
| cccaagcacc gcgtgaccat gaacgagttt gagtacctga agctgctggg caagggcact | 480 |
| ttcggcaagg tgatcctggt gaaggagaag gccacaggcc gctactacgc catgaagatc | 540 |
| ctcaagaagg aagtcatcgt ggccaaggac gaggtggccc acacactcac cgagaaccgc | 600 |
| gtcctgcaga actccaggca ccccttcctc acagccctga agtactcttt ccagacccac | 660 |
| gaccgcctct gctttgtcat ggagtacgcc aacggggggcg agctgttctt ccacctgtcc | 720 |
| cgggagcgtg tgttctccga ggaccgggcc cgcttctatg gcgctgagat tgtgtcagcc | 780 |
| ctggactacc tgcactcgga gaagaacgtg gtgtaccggg acctcaagct ggagaacctc | 840 |
| atgctggaca aggacgggca cattaagatc acagacttcg ggctgtgcaa ggaggggatc | 900 |
| aaggacggtg ccaccatgaa gacctttttgc ggcacacctg agtacctggc ccccgaggtg | 960 |
| ctggaggaca atgactacgg ccgtgcagtg gactggtggg gctgggcgt ggtcatgtac | 1020 |
| gagatgatgt gcggtcgcct gccccttctac aaccaggacc atgagaagct ttttgagctc | 1080 |
| atcctcatgg aggagatccg cttcccgcgc acgcttggtc ccgaggccaa gtccttgctt | 1140 |
| tcagggctgc tcaagaagga ccccaagcag aggcttggcg ggggctccga ggacgccaag | 1200 |
| gagatcatgc agcatcgctt ctttgccggt atcgtgtggc agcacgtgta cgagaagaag | 1260 |
| ctcagcccac ccttcaagcc ccaggtcacg tcggagactg acaccaggta ttttgatgag | 1320 |
| gagttcacgg cccagatgat caccatcaca ccacctgacc aagatgacag catggagtgt | 1380 |
| gtggacagcg agcgcaggcc ccacttcccc cagttctcct actcggccag cggcacggcc | 1440 |
| tga | 1443 |

<210> SEQ ID NO 32
<211> LENGTH: 2514
<212> TYPE: DNA
<213> ORGANISM: Homo sapiens

<400> SEQUENCE: 32

| | |
|---|---|
| atggctagca acgaaaatc tacaactcca tgcatggttc ggacatcaca agtagtagaa | 60 |
| caagatgtgc ccgaggaagt agacagggcc aaagagaaag gaatcggcac accacagcct | 120 |
| gacgtggcca aggacagttg ggcagcagaa cttgaaaact cttccaaaga aaacgaagtg | 180 |
| atagaggtga atctatggg ggaaagccag tccaaaaaac tccaaggtgg ttatgagtgc | 240 |
| aaatactgcc cctactccac gcaaaacctg aacgagttca cggagcatgt cgacatgcag | 300 |
| catcccaacg tgattctcaa ccccctctac gtgtgtgcag aatgtaactt cacaaccaaa | 360 |
| aagtacgact ccctatccga ccacaactcc aagttccatc ccggggaggc caacttcaag | 420 |
| ctgaagttaa ttaaacgcaa taatcaaact gtcttggaac agtccatcga aaccaccaac | 480 |
| catgtcgtgt ccatcaccac cagtggccct ggaactggtg acagtgattc tgggatctcg | 540 |
| gtgagtaaaa cccccatcat gaagcctgga aaaccaaaag cggatgccaa gaaggtgccc | 600 |
| aagaagcccg aggagatcac ccccgagaac cacgtggaag ggaccgcccg cctggtgaca | 660 |
| gacacagctg agatcctctc gagactcggc ggggtggagc cctccaagga cacattagga | 720 |
| cacgtcatgc cttctgtaca gctgccacca aatatcaacc ttgtgccaa ggtccctgtc | 780 |

```
ccactaaata ctaccaaata caactctgcc ctggatacaa atgccacgat gatcaactct    840
ttcaacaagt ttccttaccc gacccaggct gagttgtcct ggctgacagc tgcctccaaa    900
cacccagagg agcacatcag aatctggttt gccacccagc gcttaaagca tggcatcagc    960
tggtccccag aagaggtgga ggaggccagg aagaagatgt tcaacggcac catccagtca   1020
gtaccccgga ccatcactgt gctgcccgcc cagttggccc ccacaaaggt gacgcagccc   1080
atcctccaga cggctctacc gtgccagatc ctcggccaga ctagcctggt gctgactcag   1140
gtgaccagcg ggtcaacaac cgtctcttgc tcccccatca cacttgccgt ggcaggagtc   1200
accaaccatg ccagaagag acccttggtg actcccaag ctgcccccga acccaagcgt    1260
ccacacatcg ctcaggtgcc agagccccca cccaaggtgg ccaaccccc gctcacacca    1320 gccagtgacc gcaagaagac aaaggagcag atagcacatc tcaaggccag ctttctccag   1380
agccagttcc ctgacgatgc cgaggtttac cggctcatcg aggtgactgg ccttgccagg   1440
agcgagatca agaagtggtt cagtgaccac cgatatcggt gtcaaagggg catcgtccac   1500
atcaccagcg aatcccttgc caaagaccag ttggccatcg cggcctcccg acacggtcgc   1560
acgtatcatg cgtacccaga ctttgccccc cagaagttca aagagaaaac acagggtcag   1620
gttaaaatct tggaagacag cttttttgaaa agttcttttc ctacccaagc agaactggat   1680
cggctaaggg tggagaccaa gctgagcagg agagagatcg actcctggtt ctcggagagg   1740
cggaagcttc gagacagcat ggaacaagct gtcttggatt ccatggggtc tggcaaaaaa   1800
ggccaagatg tgggagcccc caatggtgct ctgtctcgac tcgaccagct ctccggtgcc   1860
cagttaacaa gttctctgcc cagcccttcg ccagcaattg caaaaagtca agaacaggtt   1920
catctcctga ggagcacgtt tgcaagaacc cagtggccta ctccccagga gtacgaccag   1980
ttagcggcca agactggcct ggtccgaact gagattgtgc gttggttcaa ggagaacaga   2040
tgcttgctga aaacgggaac cgtgaagtgg atggagcagt accagcacca gcccatggca   2100
gatgatcacg gctacgatgc cgtagcaagg aaagcaacaa acccatggc cgagagccca   2160 aagaacgggg gtgatgtggt tccacaatat tacaaggacc ccaaaaagct ctgcgaagag   2220
gacttggaga agttggtgac cagggtaaaa gtaggcagcg agccagcaaa agactgtttg   2280
ccagcaaagc cctcagaggc cacctcagac cggtcagagg gcagcagccg ggacggccag   2340
ggtagcgacg agaacgagga gtcgagcgtt gtggattacg tggaggtgac ggtcggggag   2400
gaggatgcga tctcagatag atcagatagc tggagtcagg ctgcggcaga aggtgtgtcg   2460
gaactggctg aatcagactc cgactgcgtc cctgcagagg ctggccaggc ctag         2514
```

<210> SEQ ID NO 33
<211> LENGTH: 567
<212> TYPE: DNA
<213> ORGANISM: Homo sapiens

<400> SEQUENCE: 33

```
atgactgaat ataaacttgt ggtagttgga gctggtggcg taggcaagag tgccttgacg     60
atacagctaa ttcagaatca ttttgtggac gaatatgatc caacaataga ggattcctac    120
aggaagcaag tagtaattga tgagaaaacc tgtctcttgg atattctcga cacagcaggt    180
caagaggagt acagtgcaat gagggaccag tacatgagga ctggggaggg ctttctttgt    240
gtatttgcca taaataatac taatcatttt gaagatattc accattatag agaacaaatt    300
aaaagagtta aggactctga agatgtacct atggtcctag taggaaataa atgtgatttg    360
```

```
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaaagatg agcaaagatg gtaaaaagaa gaaaaagaag    540
tcaaagacaa agtgtgtaat tatgtaa                                        567

<210> SEQ ID NO 34
<211> LENGTH: 570
<212> TYPE: DNA
<213> ORGANISM: Homo sapiens

<400> SEQUENCE: 34
atgactgagt acaaactggt ggtggttgga gcaggtggtg ttgggaaaag cgcactgaca     60
atccagctaa tccagaacca ctttgtagat gaatatgatc ccaccataga ggattcttac    120
agaaaacaag tggttataga tggtgaaacc tgtttgttgg acatactgga tacagctgga    180
caagaagagt acagtgccat gagagaccaa tacatgagga caggcgaagg cttcctctgt    240
gtatttgcca tcaataatag caagtcattt gcggatatta acctctacag ggagcagatt    300
aagcgagtaa aagactcgga tgatgtacct atggtgctag tgggaaacaa gtgtgatttg    360
ccaacaagga cagttgatac aaaacaagcc acgaactgg  ccaagagtta cgggattcca    420
ttcattgaaa cctcagccaa gaccagacag ggtgttgaag atgcttttta cacactggta    480
agagaaatac gccagtaccg aatgaaaaaa ctcaacagca tgatgatgg  gactcagggt    540 tgtatgggat tgccatgtgt ggtgatgtaa                                     570

<210> SEQ ID NO 35
<211> LENGTH: 2016
<212> TYPE: DNA
<213> ORGANISM: Homo sapiens

<400> SEQUENCE: 35
atgcaaccag acatgtcctt gaatgtcatt aagatgaaat ccagtgactt cctggagagt     60
gcagaactgg acagcggagg ctttgggaag gtgtctctgt gttttccacag aacccaggga    120 ctcatgatca tgaaaacagt gtacaagggg cccaactgca ttgagcacaa cgaggccctc    180
ttggaggagg cgaagatgat gaacagactg agacacagcc gggtggtgaa gctcctgggc    240
gtcatcatag aggaagggaa gtactccctg gtgatggagt acatggagaa gggcaacctg    300
atgcacgtgc tgaaagccga tgagtactac ccgctttctg taaaaggaag gataattttg    360
gaaatcattg aaggaatgtg ctacttacat ggaaaaggcg tgatacacaa ggacctgaag    420
cctgaaaata tccttgttga taatgacttc cacattaaga tcgcagacct cggccttgcc    480
tcctttaaga tgtggagcaa actgaataat aagagcacaa tgagctgag  ggaagtggac    540 ggcaccgcta agaagaatgg cggcaccctc tactacatgg cgcccgagca cctgaatgac    600
gtcaacgcaa agcccacaga gaagtcggat gtgtacagct ttgctgtagt actctgggcg    660
atatttgcaa ataaggagcc atatgaaaat gctatctgtg agcagcagtt gataatgtgc    720
ataaaatctg ggaacaggcc agatgtggat gacatcactg agtactgccc aagagaaatt    780
atcagtctca tgaagctctg ctgggaagcg aatccggaag ctcggccgac atttcctggc    840
attgaagaaa aatttaggcc ttttttattta agtcaattag aagaaagtgt agaagaggac    900
gtgaagagtt taaagaaaga gtattcaaac gaaaatgcag ttgtgaagag aatgcagtct    960
cttcaacttg attgtgtggc agtaccttca agccggtcaa attcagccac agaacagcct   1020
ggttcactgc acagttccca gggacttggg atgggtcctg tggaggagtc ctggtttgct   1080
```

```
ccttccctgg agcacccaca agaagagaat gagcccagcc tgcagagtaa actccaagac    1140
gaagccaact accatcttta tggcagccgc atggacaggc agacgaaaca gcagcccaga    1200
cagaatgtgg cttacaacag agaggaggaa aggagacgca gggtctccca tgacccttt     1260 gcacagcaaa gaccttacga gaattttcag aatacagagg gaaaaggcac tgcttattcc    1320
agtgcagcca gtcatggtaa tgcagtgcac cagccctcag ggctcaccag ccaacctcaa    1380
gtactgtatc agaacaatgg attatatagc tcacatggct ttggaacaag accactggat    1440
ccaggaacag caggtcccag agtttggtac aggccaattc caagtcatat gcctagtctg    1500
cataatatcc cagtgcctga gaccaactat ctaggaaata cacccaccat gccattcagc    1560
tccttgccac caacagatga atctataaaa tataccatat acaatagtac tggcattcag    1620
attggagcct acaattatat ggagattggt gggacgagtt catcactact agacagcaca    1680
aatacgaact tcaaagaaga gccagctgct aagtaccaag ctatctttga taataccact    1740
agtctgacgg ataaacacct ggacccaatc agggaaaatc tgggaaagca ctggaaaaac    1800
tgtgcccgta aactgggctt cacacagtct cagattgatg aaattgacca tgactatgag    1860
cgagatggac tgaaagaaaa ggtttaccag atgctccaaa agtgggtgat gagggaaggc    1920
ataaagggag ccacggtggg gaagctggcc caggcgctcc accagtgttc caggatcgac    1980
cttctgagca gcttgattta cgtcagccag aactaa                              2016

<210> SEQ ID NO 36
<211> LENGTH: 1569
<212> TYPE: DNA
<213> ORGANISM: Homo sapiens

<400> SEQUENCE: 36
atgagtctgc taaactgtga aaacagctgt ggatccagcc agtctgaaag tgactgctgt     60
gtggccatgg ccagctcctg tagcgctgta acaaaagatg atagtgtggg tggaactgcc    120
agcacgggga acctctccag ctcatttatg gaggagatcc agggatatga tgtagagttt    180
gacccacccc tggaaagcaa gtatgaatgc cccatctgct tgatggcatt acgagaagca    240
gtgcaaacgc catgcggcca taggttctgc aaagcctgca tcataaaatc aataagggat    300
gcaggtcaca aatgtccagt tgacaatgaa atactgctgg aaaatcaact atttccagac    360
aattttgcaa acgtgagatc tcttctctg atggtgaaat gtccaaatga aggttgtttg    420
cacaagatgg aactgagaca tcttgaggat catcaagcac attgtgagtt tgctcttatg    480
gattgtcccc aatgccagcg tcccttccaa aaattcccata ttaatattca cattctgaag    540
gattgtccaa ggagacaggt ttcttgtgac aactgtgctg catcaatggc atttgaagat    600
aaagagatcc atgaccagaa ctgtccttg gcaaatgtca tctgtgaata ctgcaatact    660
atactcatca gagaacagat gcctaatcat tatgatctag actgccctac agccccaatt    720
ccatgcacat tcagtacttt tggttgccat gaaaagatgc agaggaatca cttggcacgc    780
cacctacaag agaacaccca gtcacacatg agaatgttgg cccaggctgt tcatagtttg    840
agcgttatac ccgactctgg gtatatctca gaggtccgga atttccagga aactattcac    900
cagttagagg gtcgccttgt aagacaagac catcaaatcc gggagctgac tgctaaaatg    960
gaaactcaga gtatgtatgt aagtgagctc aaacgaacca ttcgaaccct gaggacaaa    1020 gttgctgaaa tcgaagcaca gcagtgcaat ggaatttata tttggaagat tggcaacttt    1080
ggaatgcatt tgaaatgtca agaagaggag aaacctgttg tgattcatag ccctggattc    1140
```

```
tacactggca aacccgggta caaactgtgc atgcgcttgc accttcagtt accgactgct    1200
cagcgctgtg caaactatat atcccttttt gtccacacaa tgcaaggaga atatgacagc    1260
cacctccctt ggcccttcca gggtacaata cgccttacaa ttcttgatca gtctgaagca    1320
cctgtaaggc aaaaccacga agagataatg gatgccaaac cagagctgct tgctttccag    1380
cgacccacaa tcccacggaa cccaaaaggt tttggctatg taacttttat gcatctggaa    1440
gccctaagac aaagaacttt cattaaggat gacacattat tagtgcgctg tgaggtctcc    1500
acccgctttg acatgggtag ccttcggagg gagggttttc agccacgaag tactgatgca    1560
ggggtatag                                                            1569

<210> SEQ ID NO 37
<211> LENGTH: 999
<212> TYPE: DNA
<213> ORGANISM: Homo sapiens

<400> SEQUENCE: 37
atggccaacc gttacaccat ggatctgact gccatctacg agagcctcct gtcgctgagc      60
cctgacgtgc ccgtgccatc cgaccatgga gggactgagt ccagcccagg ctggggctcc     120
tcgggaccct ggagcctgag ccccctccgac tccagcccgt ctggggtcac ctcccgcctg    180
cctggccgct ccaccagcct agtggagggc cgcagctgtg gctgggtgcc cccacccct     240 ggcttcgcac cgctggctcc ccgcctgggc cctgagctgt caccctcacc cacttcgccc    300
actgcaacct ccaccacccc ctcgcgctac aagactgagc tatgtcggac cttctcagag    360
agtgggcgct gccgctacgg ggccaagtgc cagtttgccc atggcctggg cgagctgcgc    420
caggccaatc gccaccccaa atacaagacg gaactctgtc acaagttcta cctccagggc    480
cgctgccccc acggctctcg ctgccacttc atccacaacc ctagcgaaga cctgcggcc     540 ccgggccacc ctcctgtgct tcgccagagc atcagcttct ccggcctgcc ctctggccgc    600
cggacctcac caccaccacc aggcctggcc ggcccttccc tgtcctccag ctccttctcg    660
ccctccagct ccccaccacc acctggggac cttccactgt caccctctgc cttctctgct    720
gcccctggca ccccctggc tcgaagagac cccaccccag tctgttgccc ctcctgccga    780
agggccactc ctatcagcgt ctgggggccc ttgggtggcc tggttcggac cccctctgta    840
cagtccctgg gatccgaccc tgatgaatat gccagcagcg gcagcagcct gggggctct    900 gactctcccg tcttcgaggc gggagttttt gcaccacccc agcccgtggc agccccccgg    960
cgactcccca tcttcaatcg catctctgtt tctgagtga                            999
```